(12) United States Patent
Basinger et al.

(10) Patent No.: US 9,708,334 B2
(45) Date of Patent: Jul. 18, 2017

(54) SUBSTITUTED 2,4,5,6-TETRAHYDROPYRROLO[3,4-C]PYRAZOLE AND 4,5,6,7-TETRAHYDRO-2H-PYRAZOLO[4,3-C]PYRIDINE COMPOUNDS AS GLYT1 INHIBITORS

(71) Applicant: DART NEUROSCIENCE (CAYMAN) LTD., Grand Cayman (KY)

(72) Inventors: Jillian Basinger, San Diego, CA (US); Brett Bookser, San Diego, CA (US); Mi Chen, San Diego, CA (US); DeMichael Chung, San Diego, CA (US); Varsha Gupta, Encinitas, CA (US); Andrew Hudson, San Diego, CA (US); Alan Kaplan, San Diego, CA (US); James Na, La Jolla, CA (US); Joel Renick, San Diego, CA (US); Vincent Santora, San Diego, CA (US)

(73) Assignee: Dart NeuroScience (Cayman) Ltd., Grand Cayman (KY)

( * ) Notice: Subject to any disclaimer, the term of this patent is extended or adjusted under 35 U.S.C. 154(b) by 0 days.

(21) Appl. No.: 15/306,064

(22) PCT Filed: Apr. 22, 2015

(86) PCT No.: PCT/US2015/027127
§ 371 (c)(1),
(2) Date: Oct. 21, 2016

(87) PCT Pub. No.: WO2015/164520
PCT Pub. Date: Oct. 29, 2015

(65) Prior Publication Data
US 2017/0044167 A1    Feb. 16, 2017

Related U.S. Application Data

(60) Provisional application No. 61/983,821, filed on Apr. 24, 2014.

(51) Int. Cl.
*C07D 471/04* (2006.01)
*C07D 487/04* (2006.01)
*C07D 519/00* (2006.01)

(52) U.S. Cl.
CPC ......... *C07D 487/04* (2013.01); *C07D 471/04* (2013.01); *C07D 519/00* (2013.01)

(58) Field of Classification Search
CPC combination set(s) only.
See application file for complete search history.

(56) References Cited

U.S. PATENT DOCUMENTS

| | | | |
|---|---|---|---|
| 4,938,949 A | 7/1990 | Borch et al. | |
| 6,710,071 B2 | 3/2004 | Lowe, III | |
| 7,189,850 B2 | 3/2007 | Ceccarelli et al. | |
| 7,220,744 B2 | 5/2007 | Jolidon et al. | |
| 7,319,099 B2 | 1/2008 | Jolidon et al. | |
| 7,427,612 B2 | 9/2008 | Alberati-Giani et al. | |
| 7,462,617 B2 | 12/2008 | Alberati-Giani et al. | |
| 7,538,114 B2 | 5/2009 | Hitchcock et al. | |
| 7,589,089 B2 | 9/2009 | Jolidon et al. | |
| 7,626,056 B2 | 12/2009 | Blackaby et al. | |
| 7,776,886 B2 | 8/2010 | Lindsley et al. | |

(Continued)

FOREIGN PATENT DOCUMENTS

| | | | | |
|---|---|---|---|---|
| DE | WO 2004056784 A1 * | 7/2004 | ........... | C07D 209/14 |
| DE | WO 2013037415 A1 * | 3/2013 | ........... | C07D 471/04 |
| DE | WO 2013037914 A1 * | 3/2013 | ........... | C07D 471/04 |
| WO | WO 2004/013144 A1 | 2/2004 | | |
| WO | WO 2005/040166 A1 | 5/2005 | | |
| WO | WO 2005/046601 | 5/2005 | | |
| WO | WO 2006/072436 A1 | 7/2006 | | |
| WO | WO 2006/094843 | 9/2006 | | |
| WO | WO 2010/010133 | 1/2010 | | |
| WO | WO 2010/010133 A1 | 1/2010 | | |

OTHER PUBLICATIONS

International Search Report and Written Opinion dated Sep. 3, 2015 for Application No. PCT/US2015/027127, filed Apr. 22, 2015.

*Primary Examiner* — Nyeemah A Grazier
(74) *Attorney, Agent, or Firm* — Knobbe Martens Olson & Bear LLP

(57) ABSTRACT

The invention provides a chemical entity of Formula (I), wherein $R^1$, $R^2$, $R^3$, $R^4$, $R^5$ and X have any of the values described herein, and compositions comprising such chemical entities; methods of making them; and their use in a wide range of methods, including metabolic and reaction kinetic studies; detection and imaging techniques; radioactive treatments; modulating and treating disorders mediated by GlyT1 activity; treating neurological disorders, CNS disorders, dementia, neurodegenerative diseases, and trauma-dependent losses of function; treating stroke, including cognitive and motor deficits during stroke rehabilitation; facilitating neuroprotection and neurorecovery; enhancing the efficiency of cognitive and motor training, including animal skill training; and treating other disorders, including pain and alcohol-dependence.

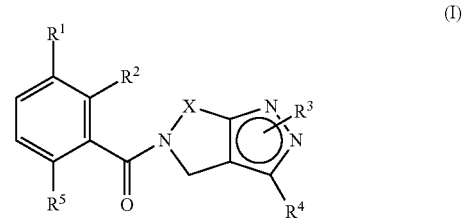

20 Claims, No Drawings

(56) References Cited

U.S. PATENT DOCUMENTS

| | | |
|---|---|---|
| 7,868,015 B2 | 1/2011 | Tully et al. |
| 7,947,731 B2 | 5/2011 | Tully et al. |
| 7,951,836 B2 | 5/2011 | Jolidon et al. |
| 8,124,639 B2 | 2/2012 | McHardy et al. |
| 2006/0135508 A1* | 6/2006 | Villa ................... A61K 31/415 514/215 |
| 2008/0188525 A1 | 8/2008 | Hallam et al. |
| 2008/0275052 A1* | 11/2008 | Dhar ................... C07D 487/04 514/249 |
| 2009/0053140 A1 | 2/2009 | Scott et al. |
| 2011/0190292 A1* | 8/2011 | Dhar ................... C07D 487/04 514/234.2 |

* cited by examiner

SUBSTITUTED 2,4,5,6-TETRAHYDROPYRROLO[3,4-C]PYRAZOLE AND 4,5,6,7-TETRAHYDRO-2H-PYRAZOLO[4,3-C]PYRIDINE COMPOUNDS AS GLYT1 INHIBITORS

CROSS REFERENCE TO RELATED APPLICATIONS

Any and all priority claims identified in the Application Data Sheet, or any correction thereto, are hereby incorporated by reference under 37 CFR 1.57. For example, this application is a U.S. National Phase of International Application No. PCT/US2015/027127, filed on Apr. 22, 2015 and published on Oct. 29, 2015 as WO 2015/164520, which claims the benefit of U.S. Provisional Application 61/983,821, filed on Apr. 24, 2014, which is incorporated herein by reference in its entirety.

BACKGROUND

Field

The present invention relates to certain substituted 2,4,5,6-tetrahydropyrrolo[3,4-c]pyrazole and 4,5,6,7-tetrahydro-2H-pyrazolo[4,3-c]pyridine compounds and derivatives of such compounds; pharmaceutical compositions containing them; methods of making them; and their use in various methods, including the inhibition of GlyT1, and the treatment of one or more disorders, including neurological disorders, psychotic disorders, dementia, and other conditions and diseases involving GlyT1.

Description of the Related Technology

The amino acid glycine has at least two important functions in the central nervous system (CNS). It acts as an inhibitory amino acid, binding to strychnine sensitive glycine receptors, and it also influences excitatory activity by acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One way to control synaptic concentrations of neurotransmitters is to influence their re-uptake at the synapses. By removing neurotransmitters from the extracellular space, transporters can control their extracellular lifetime and thereby modulate the magnitude of the synaptic transmission (Gainetdinov et al., Trends in Pharm. Sci. 2002, 23, 367-373).

Glycine transporters, which form part of the sodium and chloride family of neurotransmitter transporters, play an important role in the termination of post-synaptic glycinergic actions and maintenance of low extracellular glycine concentration by reuptake of glycine into presynaptic nerve terminals and surrounding fine glial processes.

Two distinct glycine transporter genes have been cloned (GlyT1 and GlyT2) from mammalian brain which give rise to two transporters with about 50% amino acid sequence homology. GlyT1 presents four isoforms arising from alternative splicing and alternative promoter usage (1a, 1b, 1c and 1d). Only two of these isoforms have been found in rodent brain (GlyT1a and GlyT1b). GlyT2 also presents some degree of heterogeneity. Two GlyT2 isoforms (2a and 2b) have been identified in rodent brains. GlyT1 is known to be located in CNS and in peripheral tissues, whereas GlyT2 is specific to the CNS. GlyT1 has a predominantly glial distribution and is found not only in areas corresponding to strychnine sensitive glycine receptors but also outside these areas, where it has been postulated to be involved in modulation of NMDA receptor function (Lopez-Corcurera et al., Mol. Mem. Biol. 2001, 18, 13-20). Thus, one strategy to enhance NMDA receptor activity is to elevate the glycine concentration in the local microenvironment of synaptic NMDA receptors by inhibition of the GlyT1 transporter (Bergereon et al., Proc. Mid Acad. Sci. USA 1998, 95, 15730-15734; Chen et al., J. Neurophysiol. 2003, 89, 691-703).

Glycine transporter inhibitors are suitable for the treatment of neurological and neuropsychiatric disorders. The majority of disease states implicated are psychoses, schizophrenia (Armer R. E. and Miller D. J., 2001, Exp. Opin. Ther. Patents, 11, 563-572), psychotic mood disorders such as severe major depressive disorder, mood disorders associated with psychotic disorders such as acute mania or depression associated with bipolar disorders and mood disorders associated with schizophrenia, (Pralong et al., Prog. Neurobiol., 2002, 67, 173-202), autistic disorders (Carlsson M. L., J. Neural Transm., 1998, 105, 525-535), cognitive disorders such as dementias, including age related dementia and senile dementia of the Alzheimer type, memory disorders in a mammal, including a human, attention deficit disorders and pain (Armer R. E. and Miller D. J., Exp. Opin. Ther. Patents 2001, 11, 563-572).

Thus, increasing activation of NMDA receptors via GlyT1 inhibition may lead to agents that treat psychosis, schizophrenia, dementia and other diseases in which cognitive processes are impaired, such as attention deficit disorders or Alzheimer's disease.

Glycine transport inhibitors are already known in the art, for example, as disclosed in: Intl. Pat. Appl. Publ. WO2010/010133 (Glaxo, Jan. 28, 2010) 2-Thia-1,3-diazaspirocyclic-substituted phenylacetamides; U.S. Pat. No. 7,589,089 (Hoffman-La Roche, Sep. 15, 2009) [(Arylcarbamoyl)methyl]arylamide derivatives; U.S. Pat. No. 7,538,114 (Amgen, May 26, 2009) Piperazineacetic acid derivatives; U.S. Pat. No. 7,951,836 (Hoffman-La Roche, May 31, 2011) Substituted phenyl methanone derivatives; U.S. Pat. No. 7,626,056 (Merck, Dec. 1, 2009) Cyclohexanesulfonyl derivatives; U.S. Pat. No. 8,124,639 (Pfizer, Feb. 28, 2012) Bicyclic [3.1.0] heteroaryl amides; Intl. Pat. Appl. Publ. WO2006/094843 (Glaxo, Sep. 14, 2006) N-benzoyl piperazines; U.S. Pat. No. 7,220,744 (Hoffman-La Roche, May 22, 2007) Benzoylpiperazine derivatives; U.S. Pat. No. 7,776,886 (Merck, Aug. 17, 2010) Cyclopropyl piperidine derivatives; Intl. Pat. Appl. Publ. WO2005/046601 (Merck, May 26, 2005) 4-Phenylpiperidine derivatives; U.S. Pat. No. 7,189,850 (Hoffman-La Roche, Mar. 13, 2007) Triaza-spiropiperidine derivatives; U.S. Pat. No. 7,462,617 (Hoffman-La Roche, Dec. 9, 2008) Acylpiperazine derivatives; U.S. Pat. No. 7,427,612 (Hoffman-La Roche, Sep. 23, 2008) 1-(2-Aminobenzoyl)-piperazine derivatives; U.S. Pat. No. 7,319,099 (Hoffman-La Roche, Jan. 15, 2008) Alkoxybenzoylpiperazines; and U.S. Pat. No. 6,710,071 (Pfizer, Mar. 23, 2004) Sarcosine difluoromethylene aromatic ether derivatives.

However, there remains a need for potent GlyT1 inhibitors with desirable pharmaceutical properties, such as those bearing on potency, specificity and side effect profiles. The present invention meets these and other needs in the art by disclosing substituted 2,4,5,6-tetrahydropyrrolo[3,4-c]pyrazole and 4,5,6,7-tetrahydro-2H-pyrazolo[4,3-c]pyridine compounds as potent and well-tolerated GlyT1 inhibitors.

SUMMARY

Some embodiments provide a chemical entity of Formula (I):

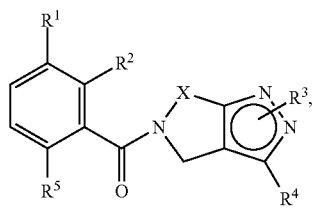

wherein $R^1$ is a member selected from the group consisting of: —$CO_2H$, —$C(O)N(R^a)_2$, —$SO_2(C_{1-4}alkyl)$, —$SO_2CH_2$ ($C_{3-6}$cycloalkyl), —CN,

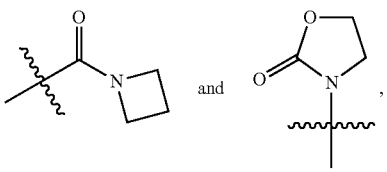

where each $R^a$ is a member independently selected from the group consisting of: —H, and —$C_{1-3}$alkyl;

$R^2$ is a member selected from the group consisting of: —H, halo, —$C_{1-3}$alkyl, —$C_{1-3}$haloalkyl, —$C_{1-3}$alkoxy, and —CN;

$R^3$ is a member selected from the group consisting of:
- (a) —H, —$C_{1-6}$alkyl, —$C_{1-6}$haloalkyl, —$(C_{1-3}alkyl)_{0-1}$ $C_{3-6}$cycloalkyl, or —$(C_{1-3}alkyl)_{0-1}$heterocycloalkyl;
- (b) benzyl or phenyl, wherein the phenyl is unsubstituted or substituted with one to three members each independently selected from the group consisting of: halo, —$C_{1-4}$alkyl, —$C_{1-4}$haloalkyl, —$C_{1-6}$alkoxy, and —CN; and
- (c) monocyclic five or six membered heteroaryl ring containing one to three nitrogen members, unsubstituted or substituted with one to three members each independently selected from the group consisting of: —$C_{1-6}$alkyl, —$C_{1-6}$haloalkyl, —$C_{1-3}$alkoxy, —$C_{1-3}$haloalkoxy, —$C_{3-6}$cycloalkyl, and —CN;

$R^4$ is a member selected from the group consisting of: —H, —F, —$C_{1-4}$alkyl, —$C_{1-4}$haloalkyl, —$C_{1-4}$alkoxy, —OH, phenyl, and 4-trifluoromethylphenyl;

$R^5$ is a member selected from the group consisting of:
- (a) —$C_{1-6}$alkyl, —$C_{1-6}$haloalkyl, —$OC_{1-6}$alkyl, or —$OC_{1-6}$haloalkyl;
- (b) —$(C_{1-3}alkyl)_{0-1}C_{3-6}$cycloalkyl, —$(C_{1-3}alkyl)_{0-1}$heterocycloalkyl, —$O(C_{1-3}alkyl)_{0-1}C_{3-6}$cycloalkyl, —$O(C_{1-3}alkyl)_{0-1}$heterocycloalkyl, or —$O(C_{1-3}haloalkyl)_{0-1}C_{3-6}$cycloalkyl, wherein each cycloalkyl member is optionally unsubstituted or substituted with one to three members each independently selected from the group consisting of: —H, -D, —F, —$OC_{1-4}$alkyl, and —$C_{1-4}$haloalkyl, wherein each heterocycloalkyl member is a four, five or six membered monocyclic ring, unsubstituted or substituted with one to three members each independently selected from the group consisting of: —H, —F, and —$C_{1-6}$alkyl; and
- (c) phenyl or pyridyl, each unsubstituted or substituted with one to three members each independently selected from the group consisting of: —H, halo, —$C_{1-6}$alkyl, and $C_{1-6}$haloalkyl;

X is —$(CR^b)_{1-2}$—; and $R^b$ is a member independently selected from the group consisting of: —H and —$C_{1-3}$alkyl.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I). In a specific aspect, the chemical entity is a compound of Formula (I), or a pharmaceutically acceptable salt thereof.

In certain embodiments, the compound of Formula (I) is a compound of Formula (Ia):

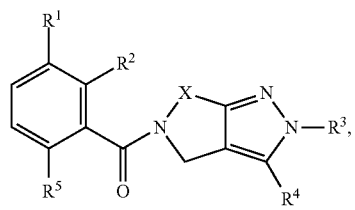

or a pharmaceutically acceptable salt thereof, wherein $R^1$, $R^2$, $R^3$, $R^4$, $R^5$ and X have any of the values described herein.

In certain embodiments, the compound of Formula (I) is a compound of Formula (Ib):

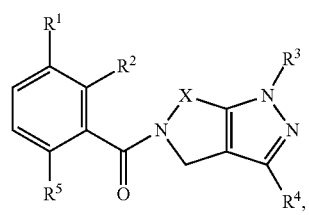

or a pharmaceutically acceptable salt thereof, wherein $R^1$, $R^2$, $R^3$, $R^4$, $R^5$ and X have any of the values described herein.

In certain embodiments, the compound of Formula (I) is a compound selected from those species described or exemplified in the detailed description below.

Some embodiments provide pharmaceutical compositions for treating a disease, disorder, or medical condition mediated by GlyT1 activity, comprising an effective amount of at least one chemical entity selected from compounds of Formula (1), pharmaceutically acceptable salts of compounds of Formula (I), pharmaceutically acceptable prodrugs of compounds of Formula (I), and pharmaceutically active metabolites of Formula (I).

Pharmaceutical compositions according to the embodiments may further comprise one or more pharmaceutically acceptable excipients.

Some embodiments provide a method of treating a subject suffering from or diagnosed with a disease, disorder, or medical condition mediated by GlyT1 activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

Chemical entities of compounds of Formula (I) are useful in wide range of methods, as described herein. Isotopically-labeled compounds and prodrugs can be used in metabolic and reaction kinetic studies, detection and imaging techniques and radioactive treatments. In certain embodiments, the chemical entities can be used to inhibit GlyT1, in particular; to treat a disorder mediated by GlyT1, in particular; to enhance neuronal plasticity; to treat neurological disorders, including neurodegenerative disorders, cognitive disorders, and cognitive deficits associated with CNS disorders; to confer neuroprotection; and to treat peripheral disorders, as disclosed herein. In certain embodiments, the chemical entities are also useful as augmenting agents to enhance the efficiency of cognitive and motor training, in stroke rehabilitation, to facilitate neurorecovery and neurorehabilitation, and to increase the efficiency of non-human animal training protocols. The invention is further directed to the general and specific embodiments defined, respectively, by the independent and dependent claims appended hereto, which are incorporated by reference herein.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

Abbreviations

The specification includes numerous abbreviations, whose meanings are listed in the following Table:

TABLE 1

| Abbreviation | Definition |
| --- | --- |
| ACN | Acetonitrile |
| AIBN | Azobisisobutyronitrile |
| BINAP | 2,2'-Bis(diphenylphosphino)-1,1'-binaphthyl |
| BOC | tert-butoxycarbonyl |
| CELITE ® | Diatomaceous earth |
| m-CPBA | meta-Chloroperoxybenzoic acid |
| DAST | Diethylaminosulfur trifluoride |
| DBU | 1,8-Diazabicyclo[5.4.0]undec-7-ene |

TABLE 1-continued

| Abbreviation | Definition |
| --- | --- |
| DCC | Dicyclohexylcarbodiimide |
| DCM | Dichloromethane |
| Deoxo-Fluor ® | Bis(2-methoxyethyl)aminosulfur trifluoride |
| DIPEA | N,N-Ethyl-diisopropylamine or N,N-Diisopropylethyl amine |
| DMA | N,N-Dimethylacetamide |
| DMAP | 4-Dimethylamino pyridine |
| DMF | N,N-Dimethylformamide |
| DMSO | Dimethylsulfoxide |
| DPEphos | Bis[(2-diphenylphosphino)phenyl] ether |
| dppf | 1,1'-Bis(diphenylphosphino)ferrocene |
| EDCI | N-(3-Dimethylaminopropyl)-N'-ethylcarbodiimide hydrochloride |
| EtOAc, or EA | Ethyl Acetate |
| EtOH | Ethanol |
| IPA | Isopropyl alcohol |
| HATU | (1-[Bis(dimethylamino)methylene]-1H-1,2,3-triazolo[4,5-b]pyridinium 3-oxid hexafluorophosphate) |
| HOAc or AcOH | Acetic Acid |
| HOAT | 1-Hydroxy-7-azabenzotriazole |
| HOBt | 1-Hydroxybenzotriazole |
| HPLC | High-performance liquid chromatography |
| LAH | Lithium aluminum hydride |
| LiHMDS, LHMDS | Lithium bis(trimethylsilyl)amide |
| LDA | Lithium diisopropylamide |
| LCMS, LC/MS | Liquid chromatography-mass spectrometry |
| MeOH | Methanol |
| MsCl | Methanesulfonyl chloride |
| NBS | N-Bromosuccinimide |
| NMP | 1-Methyl-2-pyrrolidinone |
| OTs | p-Toluenesulfonic acid |
| Pd/C | Palladium on activated carbon |
| $Pd_2(dba)_3$ | Tris(dibenzylideneacetone)dipalladium (0) |
| $PdCl_2(dppf)$—$Cl_2$ adduct | [1'1'-Bis(diphenylphosphino)ferrocene]palladium(II) dichloride dichloromethane adduct |
| $Pd(PPh_3)_4$ | Palladium-tetrakis(triphenylphosphine) |
| PyBroP | Bromotripyrrolidinophosphonium hexafluorophosphate |
| Selectfluor ® | 1-Chloromethyl-4-fluoro-1,4-diazoniabicyclo[2.2.2]octane |
| S-Phos | 2-Dicyclohexylphosphino-2',6'-dimethoxybiphenyl |
| TEA, $Et_3N$ | Triethylamine |
| TFA | Trifluoroacetic acid |
| THF | Tetrahydrofuran |
| TMEDA | Tetramethylethylenediamine |
| Xantphos | 4,5-Bis(diphenylphosphino)-9,9-dimethylxanthene |
| XtalFluor ® | Diethylaminodifluorosulfinium tetrafluoroborate |

Terms and Definitions

The use of subheadings such as "General," "Chemistry," "Compositions," "Formulations," etc., in this section, as well as in other sections of this application, are solely for convenience of reference and not intended to be limiting.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

Although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional," "traditional," "normal," "criterion," "known" and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to," or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemistry

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "▬"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, hydroxyl, alkoxy, thioalkoxy, amino, and aminoalkyl.

The term "alkenyl" refers to optionally substituted unsaturated aliphatic moieties having at least one carbon-carbon double bond and including E and Z isomers of said alkenyl moiety. Examples of alkenyl radicals include ethenyl, propenyl, butenyl, 1,4-butadienyl, cyclopentenyl, cyclohexenyl and the like.

The term "alkynyl" refers to an optionally substituted unsaturated aliphatic moieties having at least one carbon-carbon triple bond and includes straight and branched chain alkynyl groups. Examples of alkynyl radicals include ethynyl, propynyl, butynyl and the like.

The term "haloalkyl" refers to a straight- or branched-chain alkyl group having from 1 to 12 carbon atoms in the chain optionally substituting hydrogens with halogens. Examples of haloalkyl groups include, but are not limited to, —CF$_3$, —CHF$_2$, —CH$_2$F, —CH$_2$CF$_3$, —CH$_2$CHF$_2$, —CH$_2$CH$_2$F, —CH$_2$CH$_2$Cl, —CH$_2$CF$_2$CF$_3$ and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl," "thioalkyl," and "sulfonylalkyl" are analogous to alkoxy, replacing the terminal oxygen atom of alkoxy with, respectively, NH (or NR), S, and SO$_2$.

The term "haloalkoxy" refer to alkoxy groups optionally substituting hydrogens with halogens. Examples of haloalkoxy groups include, but are not limited to, —OCF$_3$, —OCH$_2$CF$_3$, —OCH$_2$CHF$_2$, —OCH$_2$CH$_2$Cl, —OCH$_2$CF$_2$CF$_3$, —OCH(CH$_3$)CHF$_2$ and other groups that in light of the ordinary skill in the art and the teachings provided herein, would be considered equivalent to any one of the foregoing examples.

The term "amino" refers to the —NH$_2$ group.

The term "alkylamino" refers to the —NRR' group, where R and R' are independently selected from hydrogen (however, R and R' cannot both be hydrogen), alkyl, and aryl groups; or R and R', taken together, can form a cyclic ring system. Examples of amino groups include, but are not limited to, —NH(CH$_3$), —N(CH$_3$)$_2$, —NPhenyl(CH$_3$), —NHPhenyl, —N(CH$_2$CH$_3$)(CH$_3$), and the like.

The term "cyano" refers to the group —CN.

The term "aryl" refers to a monocyclic, or fused or spiro polycyclic, aromatic carbocycle (ring structure having ring atoms that are all carbon), having from 3 to 12 ring atoms per ring (carbon atoms in aryl groups are sp2 hybridized). Illustrative examples of aryl groups include the following moieties:

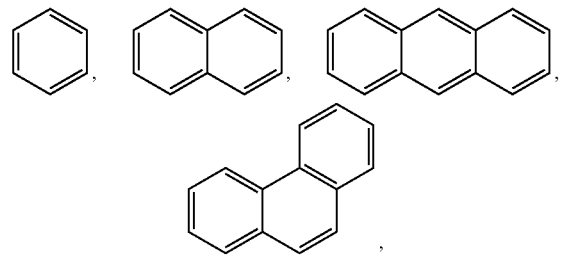

and the like.

The term "aryloxy" refers to a group having the formula, —O—R, wherein R is an aryl group.

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

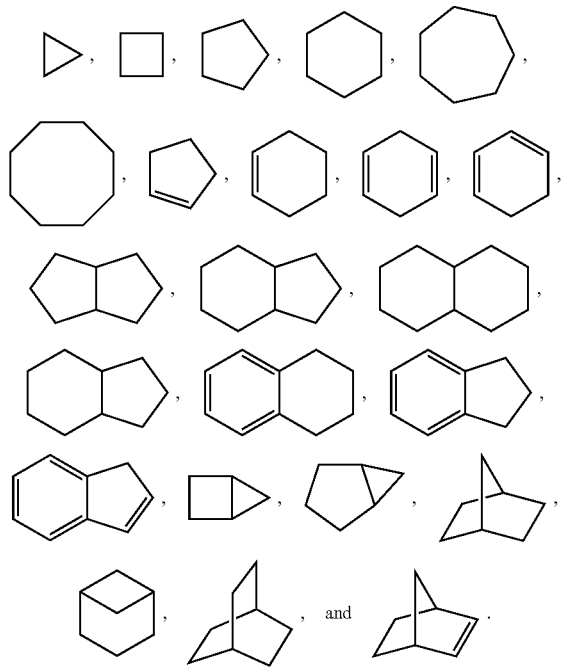

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

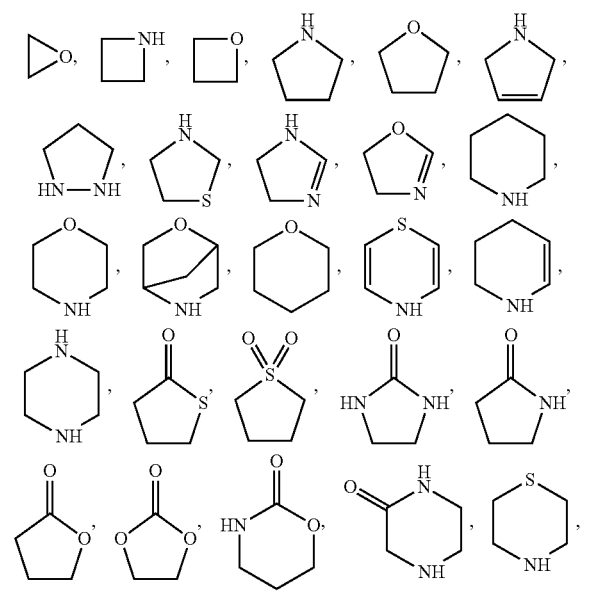

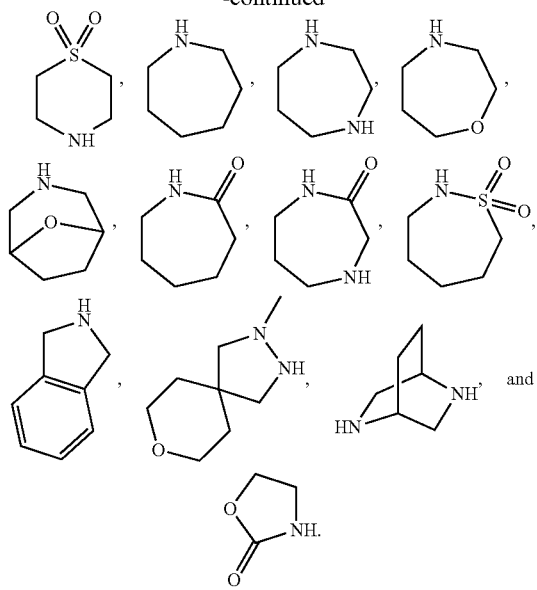

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

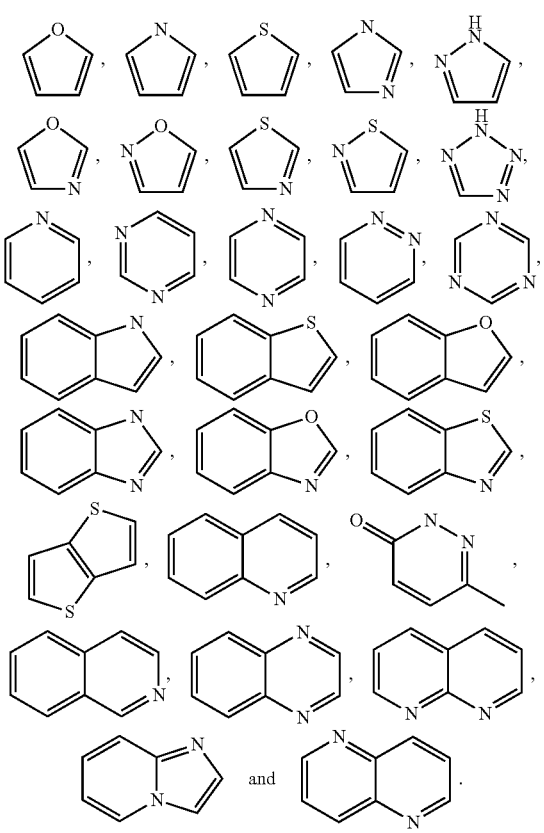

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

The term "substituted" means that the specified group or moiety bears one or more substituents. Where the term "substituted" is used to describe a structural system, unless specified otherwise, the substitution is meant to occur at any valency-allowed position on the system. The term "unsubstituted" means that the specified group bears no substituents.

Formulas

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols ▬ and ▬ are used as meaning the same spacial arrangement in chemical structures shown herein. Analogously, the symbols """ and ⋯⋯ are used as meaning the same spacial arrangement in chemical structures shown herein.

Compounds

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

As used herein, the term "chemical entity" collectively refers to a compound, along with the derivatives of the compound, including salts, chelates, solvates, conformers, non-covalent complexes, metabolites, and prodrugs.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I).

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in the same such medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological interest (ChEBI) dictionary of molecular entities. As is generally well known, a zwitterion or zwitterionic compound is a neutral compound that has formal unit charges of opposite sign. Sometimes these compounds are referred to by the term "inner salts". Other sources refer to these compounds as "dipolar ions," although the latter term is regarded by still other sources as a misnomer. As a specific example, aminoethanoic acid (the amino acid glycine) has the formula $H_2NCH_2COOH$, and exists in some media (in this case in neutral media) in the form of the zwitterion $+H_3NCH_2COO-$. Zwitterions, zwitterionic compounds, inner salts, and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Isotopes may be present in the compounds described. Each chemical element present in a compound either specifically or generically described herein may include any isotope of said element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S^2_{example}$ is one of $S_3$ and $S_4$ is accordingly used herein for the sake of brevity but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$ and X and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$ and $S_3$, the listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$ and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, and X and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with the total number N of carbon members in the chain that satisfies n≤N≤m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)).

A "pharmaceutically acceptable prodrug" is a prodrug that is preferably non-toxic, biologically tolerable, and otherwise biologically suitable for administration to the subject. Illustrative procedures for the selection and preparation of suitable prodrug derivatives are described, for example, in "Design of Prodrugs," ed. H. Bundgaard, Elsevier, 1985.

A "metabolite" means a pharmacologically active product of metabolism in the body of a compound of Formula (I) or salt thereof. Preferably, the metabolite is in an isolated form outside the body.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) and a pharmaceutically acceptable excipient.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal). An "effective amount" also means an amount or dose of a compound or composition effective to modulate activity of GlyT1 or an associated signaling pathway.

The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve, or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compounds

The present invention provides certain substituted 2,4,5,6-tetrahydropyrrolo[3,4-c]pyrazole and 4,5,6,7-tetrahydro-2H-pyrazolo[4,3-c]pyridine derivatives, which are useful, for example, as inhibitors of GlyT1 enzymatic activity. They are distinct from those described in U.S. Pat. No. 7,951,836 (Hoffman-La Roche, May 31, 2011) Substituted phenyl methanone derivatives; U.S. Pat. No. 7,427,612 (Hoffman- La Roche, Sep. 23, 2008) 1-(2-Aminobenzoyl)-piperazine derivatives; U.S. Pat. No. 7,319,099 (Hoffman-La Roche, Jan. 15, 2008) Alkoxybenzoylpiperazines; U.S. Pat. No. 7,462,617 (Hoffman-La Roche, Dec. 9, 2008) Acylpiperazine derivatives; and Intl. Pat. Appl. Publ. WO2006/094843 (Glaxo, Sep. 14, 2006) N-benzoyl piperazines.

In certain embodiments, of Formula (I), $R^1$ is —OCH$_3$, —CO$_2$H, —C(O)NH$_2$, —C(O)NHCH$_3$, —C(O)N(CH$_3$)$_2$, —SO$_2$CH$_3$, —SO$_2$CH$_2$CH$_3$, —SO$_2$CH(CH$_3$)$_2$, —SO$_2$CH$_2$cyclopropyl, —CN,

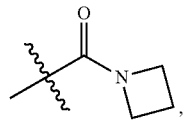 [SMILES: *C(=O)N1CCC1]

or oxazolidin-2-one.

In some of these embodiments, $R^1$ is —SO$_2$(C$_{1-4}$alkyl) or —CN.

In certain embodiments, $R^1$ is —SO$_2$CH$_3$ or —CN.

In certain embodiments, of Formula (I), $R^2$ is —H, —Cl, —F, or —OCH$_3$.

In some of these embodiments, $R^2$ is —H, —OCH$_3$, or —Cl.

In some embodiments, $R^3$ is —H, —CH$_3$, —CH(CH$_3$)$_2$, —CH$_2$CH(CH$_3$)$_2$, —CH$_2$CH$_2$CH$_2$OCH$_3$, (2S)-2-methylbutyl, —CH$_2$CF$_3$, —CH$_2$CF(CH$_3$)$_2$, (2,2-difluorocyclopropyl) methyl, 3,3-difluorocyclobutyl)methyl, cyclopentyl, cyclohexyl, cyclopropylmethyl, cyclobutylmethyl, cyclopentylmethyl, 4,4-difluorocyclohexyl, oxan-4-yl, oxan-4-ylmethyl, or oxolan-3-ylmethyl.

In some embodiments, $R^3$ is phenyl, benzyl, or pyridyl optionally unsubstituted or substituted with one to three members independently selected from the group consisting of halo, —C$_{1-4}$alkyl, —C$_{1-4}$haloalkyl, —C$_{1-4}$alkoxy, and —CN.

In some embodiments, $R^3$ is phenyl, benzyl, 2-fluorophenyl, 3-fluorophenyl, 4-fluorophenyl, 3-(trifluoromethyl)phenyl, 4-(trifluoromethyl)phenyl, 2,4-difluorophenyl, 2-methylphenyl, 3-methylphenyl, 3-methoxyphenyl, 4-methoxyphenyl, 4-cyanophenyl, 2,4-difluoro-3-methylphenyl, 2,5-difluorophenyl, 3,4-difluorophenyl, 3-(difluoromethyl)-4-fluorophenyl, 2-chloro-3-fluorophenyl, 5-chloro-2-fluorophenyl, 3-chloro-2-fluorophenyl, 2-fluoro-3-(trifluoromethyl)phenyl, 2-fluoro-3-methylphenyl, or 2-fluoro-5-methylphenyl.

In some embodiments, $R^3$ is phenyl, 2-fluorophenyl, 4-fluorophenyl, 3-methylphenyl, 2,5-difluorophenyl, 2-fluoro-3-(trifluoromethyl)phenyl, 2-fluoro-3-methylphenyl, 2-cyclopropylpyridin-4-yl, 2-methylpyridin-4-yl, 2-ethylpyridin-4-yl, 5-fluoropyridin-3-yl, 5-methylpyridin-2-yl, or 5-fluoropyridin-2-yl.

In some embodiments, $R^3$ is 1,2-dimethyl-1H-imidazol-4-yl, 1-methyl-1H-imidazol-4-yl, 1-methyl-1H-pyrazol-3-yl, 1-methyl-1H-pyrazol-4-yl, 2-(propan-2-yloxy)pyridin-4-yl, 2-(trifluoromethyl)pyridin-4-yl, 2,6-dimethylpyridin-4-yl, 2-cyclobutylpyridin-4-yl, 2-cyclopropylpyridin-4-yl, 2-ethoxypyridin-4-yl, 2-ethylpyridin-4-yl, 2-methoxypyridin-4-yl, 2-methylpyridin-4-yl, 3,5-difluoropyridin-2-yl, 3-fluoropyridin-2-yl, 3-fluoropyridin-4-yl, 3-methylpyridin-2-yl, 4-methylpyridin-2-yl, 5-(trifluoromethyl)pyridin-2-yl, 5-chloropyridin-2-yl, 5-fluoro-2-methoxypyridin-3-yl, 5-fluoro-2-methylpyridin-3-yl, 5-fluoro-3-methylpyridin-2-yl, 5-fluoro-4-methylpyridin-2-yl, 5-fluoro-4-methylpyridin-3-yl, 5-fluoro-6-methoxypyridin-3-yl, 5-fluoro-6-methylpyridin-2-yl, 5-fluoro-6-methylpyridin-3-yl, 5-fluoropyridin-2-yl, 5-fluoropyridin-3-yl, 5-methylpyridin-2-yl, 6-(trifluoromethyl)pyridin-3-yl, 6-methoxypyridin-2-yl, 6-methylpyridin-2-yl, 6-methylpyridin-3-yl, pyridazin-4-yl, pyridin-2-yl, pyridin-3-yl, pyridin-4-yl, pyridine-2-carbonitrile, or trimethyl-1H-pyrazol-4-yl.

In some embodiments, $R^3$ is phenyl, 2-fluorophenyl, 4-fluorophenyl, 3-methylphenyl, 2,5-difluorophenyl, 2-fluoro-3-(trifluoromethyl)phenyl, 2-fluoro-3-methylphenyl, 2-cyclopropylpyridin-4-yl, or 2-ethylpyridin-4-yl.

In some embodiments, $R^4$ is —H, —CH$_3$, —CF$_3$, —C$_{1-3}$alkoxy, phenyl, or 4-trifluoromethylphenyl.

In some embodiments, $R^4$ is —H.

In some embodiments, $R^5$ is —CH$_2$CH$_2$(CH$_3$)$_3$, —CF(CH$_2$CH$_3$)$_2$, —OCH$_2$C(CH$_3$)$_3$, —OCH(CH$_3$)$_2$, —OCH(CH$_2$CH$_3$)$_2$, —OCH$_2$CF$_3$, —OCH$_2$CHF$_2$, —OCH(CH$_3$)(CH$_2$F), —OCH(CH$_3$)(CHF$_2$), —OCH(CH$_3$)(CF$_3$), [(2S)-1,1,1-trifluoropropan-2-yl]oxy, —OC(CH$_3$)$_2$(CF$_3$), (3-methylbutan-2-yl)oxy, pentan-2-yloxy, —OCH$_2$cyclopropyl, (1-methylcyclopropyl)methoxy, 1-cyclopropylethoxy, 1-methylcyclopropoxy, cyclopentyloxy, (3-methyloxetan-3-yl)methoxy, oxetan-3-yloxy, or [1-(trifluoromethyl)cyclopropyl]methoxy.

In some embodiments, $R^5$ is —OCH(CH$_3$)$_2$, —OCH$_2$C(CH$_3$)$_3$, —OCH(CH$_3$)(CF$_3$), or [(2S)-1,1,1-trifluoropropan-2-yl]oxy.

In some embodiments, $R^5$ is cyclobutyl, cyclopentyl, 1-deuterocyclohexyl, 1-methoxycyclobutyl, 1-fluorocyclobutyl, 1-fluorocyclopentyl, or 1,4,4-trifluorocyclohexyl.

In some embodiments, $R^5$ is 3-fluorooxetan-3-yl, 4-fluorooxan-4-yl, azetidine, pyrrolidine, 3,3-difluoropyrrolidine, piperidine, 4,4-difluoropiperidin-1-yl, or morpholin-4-yl.

In some embodiments, $R^5$ is phenyl, 2-fluorophenyl, 3-fluorophenyl, 3-methylphenyl, 3-(trifluoromethyl)phenyl, 3,5-difluorophenyl, pyridine, 2-(trifluoromethyl)pyridine, or 5-fluoropyridin-3-yl.

In some embodiments, $R^5$ is —OCH(CH$_3$)$_2$, —OCH$_2$C(CH$_3$)$_3$, —OCH(CH$_3$)(CF$_3$), or [(2S)-1,1,1-trifluoropropan-2-yl]oxy, cyclopentyl or 3-fluorophenyl.

In some embodiments, X is —CH$_2$CH$_2$— or —CH$_2$(CH$_3$)$_2$—.

In some embodiments, X is —CH$_2$—.

In some embodiments, $R^1$ is —SO$_2$CH$_3$ or —CN, $R^2$ is H, and $R^5$ is —OCH(CH$_3$)$_2$, —OCH$_2$C(CH$_3$)$_3$, —OCH(CH$_3$)(CF$_3$), [(2S)-1,1,1-trifluoropropan-2-yl]oxy, cyclopentyl, or 3-fluorophenyl.

In some embodiments, $R^1$ is —SO$_2$(C$_{1-3}$alkyl) or —CN, $R^3$ is phenyl, or pyridyl optionally unsubstituted or substituted with one to three members independently selected from the group consisting of: halo, —C$_{1-4}$alkyl, —C$_{1-4}$haloalkyl, —C$_{1-4}$alkoxy, and —CN, $R^5$ is —OCH(CH$_3$)$_2$, —OCH$_2$C(CH$_3$)$_3$, —OCH(CH$_3$)(CF$_3$), [(2S)-1,1,1-trifluoropropan-2-yl]oxy, cyclopentyl, 3,5-difluorophenyl, or 3-fluorophenyl, and X is —CH$_2$—.

In certain embodiments, a compound, or pharmaceutically acceptable salt thereof, of Formula (I) is selected from the group consisting of Examples 1-577, as disclosed herein.

Further embodiments are provided by pharmaceutically acceptable salts of compounds of Formula (I), pharmaceutically acceptable prodrugs of compounds of Formula (I), and pharmaceutically active metabolites of compounds of Formula (I).

Isotopically-Labeled Compounds

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Compounds of the present invention (and derivatives of such compounds, such as pharmaceutically acceptable salts and prodrugs) that contain the aforementioned isotopes or other isotopes of other atoms are within the scope of the invention. Isotopically-labeled compounds of the present invention are useful in drug and substrate tissue distribution and target occupancy assays. For example, isotopically labeled compounds are particularly useful in SPECT (single photon emission computed tomography) and in PET (positron emission tomography), as discussed further herein.

Derivatives

The present invention also provides derivatives of a chemical entity of Formula (I), which include, but are not limited to, any salt, solvate, conformer, or crystalline form/polymorph.

Salts

Accordingly, in one embodiment the invention includes pharmaceutically acceptable salts of the compounds represented by Formula (I), and methods using such salts.

Examples of pharmaceutically acceptable salts include sulfates, pyrosulfates, bisulfates, sulfites, bisulfites, phosphates, monohydrogen -phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates , benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Solvates

In other embodiments, the invention provides a solvate of a compound of Formula (I), and the use of such solvates in methods of present invention. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. Hydrates include compounds formed by an incorporation of one or more water molecules.

Conformers and Crystalline Forms/Polymorphs

In other embodiments, the invention provides conformer and crystalline form of a compound of Formula (I), and the use of these derivatives in methods of present invention. A conformer is a structure that is a conformational isomer. Conformational isomerism is the phenomenon of molecules with the same structural formula but different conformations (conformers) of atoms about a rotating bond.

A polymorph is a composition having the same chemical formula, but a different solid state or crystal structure. In certain embodiments of the invention, compounds of Formula (I) were obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Prodrugs

The invention also relates to prodrugs of the compounds of Formula (I), and the use of such pharmaceutically acceptable prodrugs in methods of the present invention, particularly therapeutic methods. Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-6}$alkyl, $C_{1-6}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy) methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

The present invention also relates to a metabolite of a compound of Formula (I), as defined herein, and salts thereof. The present invention further relates to the use of such metabolites, and salts thereof, in methods of present invention, including therapeutic methods.

Metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, *Drug Dev. Res.* 1995, 34, 220-230; and Bodor, *Adv Drug Res.* 1984, 13, 224-231).

Compositions

In some embodiments compounds of Formula (I) and pharmaceutically acceptable salts thereof are used, alone or in combination with one or more additional active ingredients, to formulate pharmaceutical compositions. A pharmaceutical composition of the invention comprises: (a) an effective amount of at least one active agent in accordance with the invention; and (b) a pharmaceutically acceptable excipient.

Formulations and Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.),1980, 1553-1593.

Any suitable route of administration may be employed for providing an animal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose, aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring, such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

Preferably, the active ingredient should be administered to achieve peak plasma concentrations of the active compound of from about 0.5 to about 75 $\mu$M, preferably, about 1 to 50 $\mu$M, and more preferably, about 2 to about 30 $\mu$M. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

In one aspect, the present invention provides a method of using isotopically labeled compounds and prodrugs of the present invention in: (i) metabolic studies (preferably with $^{14}C$), reaction kinetic studies (with, for example $^2H$ or $^3H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the invention thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^2H$) may afford certain therapeutic advantages resulting from greater metabolic stability, for example increased in vivo half-life or reduced dosage requirements.

Therapeutic Methods

Generally

Chemical entities of the present invention are useful in methods (or in the manufacture of a medicament for use in such methods) of treating a disorder mediated by GlyT1 by administering to a subject in need thereof an effective amount of a chemical entity of the present invention. They are also useful in methods (or in the manufacture of a medicament for use in such methods) of enhancing cognitive or motor function mediated by GlyT1 by administering to a subject in need an effective amount of a chemical entity of the present invention.

In one embodiment the present invention provides a method of treating a subject suffering from or diagnosed with a disorder mediated by GlyT1 activity, comprising administering to a subject in need of such treatment an effective amount of at least one chemical entity of the present invention. In a further embodiment, the subject is diagnosed with a disorder mediated by GlyT1 activity.

Chemical entities of the present invention are also useful in enhancing neuronal plasticity—an essential property of the brain that can be augmented in healthy animals and impaired in numerous CNS disorders. Without being limited by mechanism, such chemical entities can enhance cyclic adenosine monophosphate (cAMP) response element binding protein (CREB) pathway function in cells, modulating transcription of multiple genes involved in synaptic plasticity. See, e.g., Tully et al., *Nat. Rev. Drug Discov.* 2003, 2, 267-277; Alberini, *Physiol. Rev.* 2009, 89, 121-145. Accordingly, the present invention provides a method of enhancing neuronal plasticity, comprising administering to a subject in need thereof an effective amount of a chemical entity of the present invention.

Chemical entities of the present invention are also useful as "agents" (also referred to as "augmenting agents") to augment the efficiency of training protocols, which facilitate functional reorganization in targeted "domains" (or "functions") in the brain. Training protocols can be directed to rehabilitating or enhancing a cognitive or motor function. The training protocol (cognitive or motor training) induces neuronal activity in specific brain regions and produces improved performance of a specific brain (cognitive or motor) function. Chemical entities of the present invention agents act as "augmenting agents," which shorten the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc., and a general administration of CREB pathway-enhancing drugs.

Neurological Disorders

Chemical entities of the present invention are useful in methods of treating a neurological disorder, comprising administering to a subject in need thereof an effective amount of a chemical entity of Formula (I). In a specific aspect, the methods are directed to a cognitive deficit ("cognitive impairment") or motor deficit ("motor impairment") associated with (or "due to") the neurological disorder.

A neurological disorder (or condition or disease) is any disorder of the body's nervous system. Neurological disorders can be categorized according to the primary location affected, the primary type of dysfunction involved, or the primary type of cause. The broadest division is between peripheral nervous system (PNS) disorders and central nervous system (CNS) disorders (such as mental and psychiatric disorders). Neurological disorders are well-known in the art, and they include, but are not limited to, the following mental and psychiatric disorders:

Neurodevelopmental (or "developmental" disorders), such as intellectual disability disorders (e.g., Rubinstein-Taybi syndrome, Down syndrome); communication disorders; autism-spectrum disorder; attention-deficit/hyperactivity disorder; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, and schizophreniform disorder, and other schizophrenia spectrum and psychotic disorders;

Bipolar and related disorders, such as Bipolar I and II disorders, cyclothymic disorder, and other bipolar and related disorders;

Depressive disorders, such as major depressive disorder, persistent depressive disorder (dysthymia), and other depressive disorders;

Anxiety disorders, such as specific phobias, social anxiety disorder (social phobia), panic disorder, generalized anxiety disorder (GAD), posttraumatic stress disorder (PTSD), and other anxiety disorders;

Obsessive-compulsive and related disorders, such as obsessive-compulsive disorder, body dysmorphic disorder, and other obsessive-compulsive and related disorders;

Dissociative disorders, such as dissociative identity disorder, dissociative amnesia, and other dissociative disorders;

Disruptive, impulse-control, and conduct disorders, such as conduct disorders, antisocial personality disorder, and other disruptive, impulse-control, and conduct disorders;

Trauma- and stressor-related disorders, such as posttraumatic stress disorder, adjustment disorders, and other trauma- and stressor-related disorders;

Feeding and eating disorders, such as anorexia, bulimia, binge-eating disorder, and other feeding and eating disorders;

Sleep-wake disorders, such as insomnia, narcolepsy, parasomnias, and other sleep-wake disorders;

Sexual disorders, such as arousal disorders, desire disorders, substance and medication-induced dysfunctions, and other sexual disorders;

Substance-related and addictive disorders, such as those involving alcohol, drugs, stimulants, opioids, tobacco, and non-substance-related disorders; and other substance-related and addictive disorders; and Personality disorders, such as paranoid personality disorder, antisocial personality disorders, borderline personality disorder, avoidance personality disorder, and other personality disorders; and In particular embodiments, the disorder is schizophrenia, an attention deficit disorder, or an anxiety disorder.

In other embodiments, the neurological disorder is an acquired disorder, in which the primary clinical feature is impaired cognition. In other words, it is a disorder in which the primary cognitive deficit has not been present since birth or very early life and therefore represents a decline from a previously attained level of functioning. Such disorders, which may be referred to herein as "cognitive disorders" or "neurocognitive disorders" include one or more of the following:

Delirium, such as substance-intoxication (or withdrawal) delirium, medication-induced delirium, and other forms of delirium;

Dementias and other cognitive impairments due to HIV infection or due to neurodegenerative diseases, such as Alzheimer's disease, Parkinson's disease, Huntington's disease, Lewy body disease, Pick's disease, a prion disease (e.g., Creutzfeldt-Jakob disease), Amyotrophic lateral sclerosis (ALS), multiple sclerosis, frontotemporal lobar degeneration, and corticobasal degeneration; dementia due to a vascular disease ("vascular disease"); and other dementias and neurodegenerative diseases;

Age-associated cognitive deficits, including age-associated memory impairment (AAMI), also referred to as age-related memory impairment (AMI) (See, e.g., Crook et al., *Devel. Neuropsychol.* 1986, 2, 261-276); and deficits affecting patients in early stages of cognitive decline, as in Mild Cognitive Impairment (MCI) (See, e.g., Arnáiz and Almkvist, *Acta Neurol. Scand. Suppl.* 2003, 179, 34-41), and;

Trauma-dependent losses of cognitive function, such as vascular diseases due to stroke (e.g., ischemic or hemorrhagic stroke) or ischemia; microvascular disease arising from diabetes or arthrosclerosis; traumatic brain injury (TBI), such as brain trauma, including subdural hematoma and brain tumor; head trauma (closed and penetrating); head injury; tumors, such as nervous system cancers, including cerebral tumors affecting the thalamic or temporal lobe; hypoxia; and viral infection (e.g., encephalitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such acquired disorders are not necessarily limited to cognitive impairments. For example, trauma related disorders, such as stroke, traumatic brain injury, head trauma, and head injury, may also include impairments in other neurological functions, such as impairments in motor functions.

As used herein, the terms "Neurodevelopment disorders," "Schizophrenia spectrum and other psychotic disorders," Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep-wake disorders," "Sexual disorders," "Substance-related and addictive disorders," "Personality disorders," "Delirium," "Neurocognitive disorders," "Delirium," "Dementias," and "Trauma" include treatment of those mental disorders as described in the Diagnostic and Statistical Manual of Mental Disorders (DSM-5; 5$^{th}$ ed., 2013, American Psychiatric Association). The skilled artisan will recognize that there are alternative nomenclatures and classification systems for mental disorders, and that these systems evolve with medical and scientific progress. Thus the terms described in this paragraph are intended to include like disorders that are described in other diagnostic sources.

In other embodiments, the neurological disorder is a movement or motor disorder, a group that includes, but is not limited to: kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor); chorea, such as that in Huntington's disease; myoclonus (including generalized myoclonus and focal myoclonus); tics (including simple tics, complex tics and symptomatic tics); dystonia; restless leg syndromes; Wilson's Disease; Hallerworden-Spatz disease; basal ganglia disorders; hyperkinetic, hypokinetic, and dyskinetic disorders; movement disorders induced by drugs; and other movement and motor disorders.

Augmented Training

In certain embodiments, chemical entities of the present invention provide augmenting agents to enhance the efficiency of training protocols, including cognitive training and motor training protocols. Such methods are known as "augmented training," and, more particularly, "augmented cognitive training" or "augmented motor training."

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol. (See, e.g., U.S. Pat. Nos. 7,868,015; 7,947,731; US 2008-0188525). When administered in combination with training protocols (or "training"), augmenting agents enhance functional reorganization in targeted domains (or "functions") in the brain.

Cognitive domains (or functions) that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory) memory, such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols

Training protocols (or "modules") are well known in the art and typically comprise a set of distinct exercises that can be process-specific or skill-based: See, e.g., Kim et al., *J. Phys. Ther. Sci.* 2014, 26, 1-6; Allen et al., *Parkinsons Dis.* 2012, 2012, 1-15; Jaeggi et al., *Proc. Natl. Acad. Sci. USA* 2011, 108, 10081-10086; Chein et al., *Psychon. Bull. Rev.* 2010, 17, 193-199; Klingberg, *Trends Cogn. Sci.* 2010, 14, 317-324; Owen et al., Nature 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of fact, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a GlyT1 inhibitor, and more particularly, is a chemical entity of the present invention, and is administered in conjunction with training. By "in conjunction" is meant that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a compound or composition of the present invention can be used as an augmenting agent in conjunction with any psychotherapeutic approach intended to modulate cognitive function in the brain, thereby enhancing the efficacy of such therapy by reducing the number of sessions necessary to attain benefits.

Stroke

In some embodiments, chemical entities and compositions of the present invention are useful in treating stroke, and in more specific embodiments, treating motor or cognitive impairments during post-stroke rehabilitation. Stroke care is a temporal continuum that includes immediate (acute) treatments and subsequent rehabilitative therapy.

Acute treatments directly target the initial damage, such as that triggered by ischemic or hemorrhagic stroke; they usually involve using agents to dissolve clots and restore blood flow to reduce tissue damage and stabilize the patient. The efficacy of acute treatments is typically limited to a short time window extending only a few hours from stroke onset.

The focus of stroke treatment shifts to rehabilitation after the patient has been medically stabilized. Rehabilitation (also referred to as "stroke rehabilitation" or "post-stroke rehabilitation") is directed to cognitive and motor deficits that persist after the initial stroke injury, the goal being to restore and recover neurological function as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; by problems with balance or coordination; deficits in gross motor skills such as gait and walking speed; deficits in fine motor skills or manual dexterity; and deficits in upper and lower extremity function.

Accordingly, the present invention provides the use of a GlyT1 inhibitor in the treatment of stroke, including post stroke rehabilitation. In certain embodiments, chemical entities of the present invention are useful during stroke rehabilitation to treat stroke deficits (or "post-stroke deficits") resulting from impaired neurological functions. In some embodiments, the present invention provides methods of treating a neurological deficit during post-stroke rehabilitation comprising: (a) administering to a subject in need thereof a GlyT1 inhibitor during recovery of the subject from stroke; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the GlyT1 inhibitor is a chemical entity of the present invention. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, said administering step (a) is in conjunction with said training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions of the present invention are useful in treating traumatic brain injury, and in more specific embodiments, treating motor or cognitive impairments during rehabilitation after the initial trauma. Like stroke care, Tramatic Brain Injury (TBI) is a temporal continuum that includes immediate (acute) treatments and subsequent rehabilitative therapy.

Accordingly, the present invention provides the use of a GlyT1 inhibitor in the treatment of TBI, including during TBI rehabilitation to treat TBI deficits (or "post-TBI deficits") resulting from impaired neurological functions. In some embodiments, the present invention provides methods of treating a neurological deficit during post-TBI rehabilitation comprising: (a) administering to a subject in need thereof a GlyT1 inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the GlyT1 inhibitor is a chemical entity of the present invention. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, said administering step (a) is in conjunction with said training step (b). In one aspect, the subject is a human. In another aspect, the subject has undergone neuronal stem cell manipulation. In other aspects, the compound is administered before and during each training session.

Schizophrenia

In particular embodiments, chemical entities of the present invention are useful in treating schizophrenia. Schizophrenia is a devastating neurological disorder, characterized by a combination of negative and positive symptoms. Negative symptoms can include flat affect (lack or decline in emotional response), alogia (lack or decline in speech), avolition (lack or decline in motivation), anhedonia (the inability to experience pleasure from activities usually found enjoyable), and asociality (lack of motivation to engage in social interaction, or a preference for solitary activities). Positive symptoms include paranoia, hallucinations, delusions, as well as impairments in cognitive functions, such as attention, memory, reasoning, and processing speed. See, e.g., Keefe, R S, and Harvey, P C, Cognitive Impairment in schizophrenia, 2012, Handb. Exp. Pharmacol. 213, 11-23.

Accordingly, the present invention provides a method of treating schizophrenia, comprising administering to a subject in need thereof an effective amount of a chemical entity of Formula (I). In particular embodiments, the treatment is directed to a positive symptom of schizophrenia. In other embodiments, treatment is directed to a negative symptom of schizophrenia, and more particularly, a cognitive deficit.

In other embodiments, present invention provides methods of treating pain or alcohol dependence, comprising administering to a subject in need thereof an effective amount of a chemical entity of Formula (I). See, e.g., Harvey and Yee, 2013, Nat. Rev. Drug. Discov. 12, 866-885.

In other embodiments, the present invention provides methods of treating pain or alcohol dependence, comprising administering to a subject in need thereof an effective amount of a chemical entity of Formula (I). See e.g., Harvey and Yee, 2013, Nat. Rev. Drug. Discov. 12, 866-885.

Animal Skill Training

In some embodiments, chemical entities of the present invention are used to enhance the efficiency of training protocols directed to cognitive and motor skills in an animal. Such augmented training reduces the time necessary to acquire or enhance a cognitive or motor skill in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a single drug in a service animal. In other embodiments, the training protocol may be directed to a complex set of skills, such as those underlying search and rescue training of a service animal; for a complex set of skills, training will therefore comprise more than one task.

Accordingly, in some embodiments, the present invention provides a method of teaching a non-human animal one or more skills, comprising (a) administering to a non-human animal in need thereof a GlyT1 inhibitor; (b) providing training to the animal under conditions sufficient to improve performance of said one or more skills; and (c) repeating steps (a) and (b) one or more times, whereby the amount of training sufficient to improve the performance is reduced compared to that produced by training alone.

EXAMPLES

The present disclosure will be further illustrated by the following non-limiting Examples. These Examples are understood to be exemplary only, and they are not to be construed as limiting the scope of the invention herein, and as defined by the appended claims.

Preparative Examples

Exemplary compounds useful in methods of the invention will now be described by reference to the illustrative synthetic schemes for their general preparation below and the specific examples to follow.

Synthetic Schemes

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

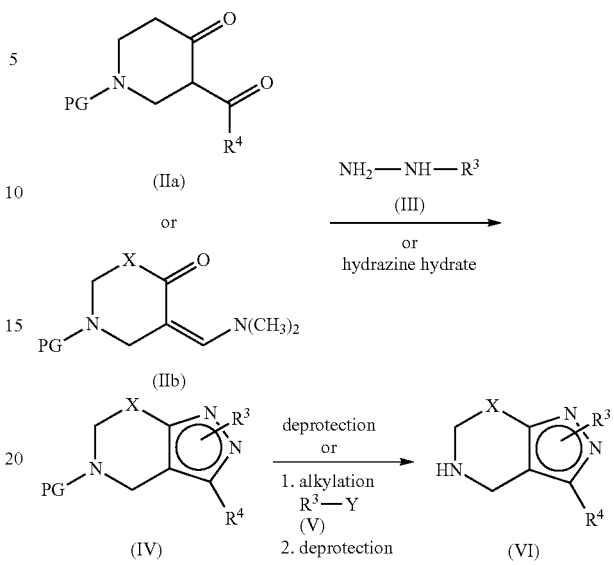

SCHEME A

The amine moiety of 4-oxopiperidine compounds of formula (II or IIb) are suitably protected, as an alkyl or benzyl amine, amide, carbamate or other groups such as those described in "Protecting Groups In Organic Synthesis," $3^{rd}$ ed; T. W. Greene and P. G. M. Wuts, John Wiley & Sons, 1999, as shown by substituent PG. A preferred protecting group is the tert-butyl carbamate (BOC) group. Synthetically accessible Intermediate compounds of formula (IIb) such as (Z)-tert-butyl 5-((dimethylamino)methylene)-3,3-dimethyl-4-oxopiperidine-1-carboxylate, are prepared by reaction of tert-butyl 3,3-dimethyl-4-oxopiperidine-1-carboxylate with N,N-dimethylformamide dimethyl acetal, at temperatures ranging from 100 to 120° C. for a period of 24 to 72 hrs.

According to Scheme A, condensation of commercially available or synthetically accessible aryl, heteroaryl, heterocycloalkyl or cycloalkyl hydrazine compounds of formula (III), with commercially available or synthetically accessible substituted 4-oxopiperidine compounds of formula (IIa or IIb), where $R^4$ is —H, —$CH_3$, —$CF_3$, —$OCH_3CH_3$, where X is —$CH_2$—, —$C(CH_3)_2$—, in a solvent such as MeOH, EtOH, isopropanol, tert-butyl alcohol, and the like, at temperatures ranging from 20 to 80° C., using conventional or microwave heating, for a period of 30 min to 24 h, provides compounds of formula (IV).

Intermediate compounds of formula (IV), where $R^4$ is —OH, are reacted with triflic anhydride, in the presence of a base such as TEA, and the like, in a solvent such as DCM and the like, a temperatures ranging from 0° C. to ambient temperature, for a period of 1 to 2 h, provides compounds of formula (IV), where $R^4$ is —$OSO_2CF_3$. Subsequent reduction of triflate compounds of formula (IV) under hydrogenation conditions known to one skilled in the art, provides compounds of formula (IV) were $R^4$ is —H.

Intermediate compounds of formula (IV), where $R^4$ is —OH, may be chlorinated with a chlorinating agent such as $POCl_3$, in a solvent such as toluene, at temperatures ranging from 0° C. to the reflux temperature of the solvent, for a period of 1 to 3 h, to provide Intermediate compounds of formula (IV), where $R^4$ is —Cl. Subsequent fluorination with a fluorinating agent such as potassium or sodium fluoride, in an appropriate solvent, at elevated temperatures, may provide Intermediate compounds of formula (IV), where $R^4$ is —F.

In an alternate method, substituted 4,5,6,7-tetrahydro-1H-pyrazolo[4,3-c]pyridine compounds of formula (IV), are prepared from compounds of formula (IIa or IIb) thru a reaction with hydrazine hydrate, followed by installation of the $R_3$ moiety thru an alkylation reaction. For example, treatment with a commercially available or synthetically accessible alkyl or aryl chloride, iodide, bromide, mesylate, triflate or tosylate of formula (V), in a solvent such as DMF, DMA, THF or EtOH, in the presence of a base such as $NaHCO_3$, $Na_2CO_3$, $K_2CO_3$, NaH, potassium tert-butoxide, or $Cs_2CO_3$, will afford compounds of formula (VI). One skilled in the art will recognize that alkylation of compounds of formula (IV) gives rise to regioisomers.

The protecting group on the nitrogen of compounds of formula (IV) was removed using generally accepted methods known to one skilled in the art, such as reaction of compounds of formula (IV) with an acid such as trifluoroacetic acid or hydrochloric acid, and the like, in a solvent such as DCM, EtOH, MeOH, dioxane, and the like, to provide compounds of formula (VI).

Referring to Scheme B, compounds of formula (X) are prepared from compounds of formula (VII), where X is —$CH_2$—, —$CH_2CH_2$—. The amine moiety in compounds of formula (VII) are suitably protected, shown by substitutent PG. A preferred protecting group is the tert-butyl carbamate (BOC) group. Coupling of aryl halides of formula (VIII) with nitrogen heterocycles of formula (VII), in the presence of a copper source such as CuI, CuCl, and the like, a base such as $K_3PO_4$, $Cs_2CO_3$, and the like, a ligand such as (1S,2S)-(+)-1,2-diaminocyclohexane, 1,3-propylenediamine, TMEDA, 1,2-phenylenediamine, and the like, in a solvent such as THF, dioxane, and the like, at temperatures ranging from 100 to 140° C., using conventional or microwave heating, for a period of 12 to 24 h, provides intermediates of formula (IX). The protecting group on the nitrogen of compounds of formula (IX) were removed according to methods previously described.

In an alternate method, amine compounds of formula (VII) are treated with a commercially available or synthetically accessible alkyl or aryl chloride, iodide, bromide, mesylate, triflate or tosylate of formula (VIII) (wherein Y is Cl, Br, I, F, OMs, OTs, or the like) in a solvent such as DMF, DMA, THF or ethanol, in the presence of a base such as $NaHCO_3$, $Na_2CO_3$, $K_2CO_3$, NaH, potassium tert-butoxide, or $Cs_2CO_3$, to afford compounds of formula (IX). One skilled in the art will recognize that alkylation of compounds of formula (VII) gives rise to regioisomers.

Substituted fluoroalkyl amine compounds of formula (X), where $R^3$ is a haloalkyl moiety, are prepared from amine compounds of formula (VII) in two steps. Reaction of compounds of amine compounds of formula (VII) with a base such as LHMDS and the like, 2,2-dimethyloxirane, in a solvent such as THF, at temperatures ranging from 0 to 80° C. Subsequent fluorination of hydroxyl compound of formula (IX), with a fluorinating agent such as DAST, and the like, followed by deprotection of the protecting group PG, provides fluoroalkyl compounds of formula (X).

SCHEME B

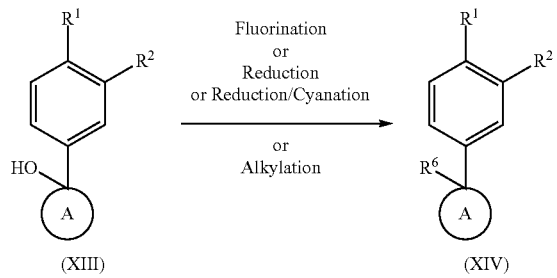

SCHEME C

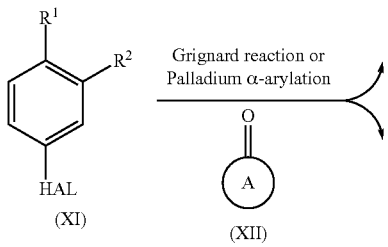

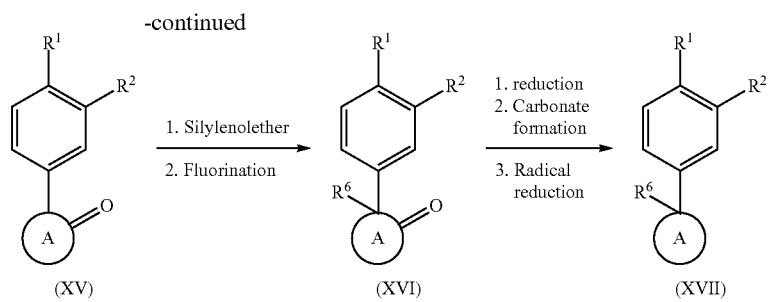

Intermediate compounds of formula (XIV) are readily prepared according to SCHEME C. Compounds of formula (XIII) are prepared by a Grignard reaction, for example, reaction of aryl halide compounds of formula (XI), where $R^1$ is —Br or —CN, $R^2$ is —H or —F, and HAL is —I, with an alkyl magnesium halide compound such as, isopropylmagnesium chloride, and the like, a suitable ketone of formula (XII), where A is an optionally substituted —$C_{4-8}$heterocycloalkyl or —$C_{4-8}$cycloalkyl ring, in a solvent such as THF and the like, at temperatures ranging from −20 to 100° C., to provide compounds of formula (XIII). Fluoro compounds of formula (XIV), where $R^6$ is —F, are prepared by reacting compounds of formula (XIII) with Deoxo-Fluor®, Xtal-Fluor®, DAST, and the like, in an appropriate solvent such as DCM, and the like, at room temperature, for a period of 1 to 24 h. In the advent that alkene by-products, which are difficult to separate from the desired product, are formed in the fluorination reaction, oxidation to the corresponding epoxides with an oxidizing agent such as m-CPBA facilitates separation from the desired fluoro compounds of formula (XIV). Compounds of formula (XIV), where $R^6$ is —H or -D, are prepared by reduction of tertiary alcohol compounds of formula (XIII), where $R^1$ is —Br or —CN and $R^2$ is —H or —F, with an organosilane such as triethylsilane, triethylsilane-d, and the like, and a strong acid such as boron trifluoride diethyl etherate, and the like, at temperatures ranging from −78 to 0° C., to provide compounds of formula (XIV), where $R^6$ is —H or -D. Compounds of formula (XIII), where $R^1$ is —Br, $R^2$ and $R^6$ are —H, are reacted with cyanide source such as, but not limited to KCN, NaCN, $Zn(CN)_2$, preferably $Zn(CN)_2$, a palladium catalyst such as $Pd_2(dba)_3$, $Pd(PPh_3)_4$, $Pd(dppf)Cl_2$, and the like, with or without the presence of additional ligand such as dppf, in a solvent such as DMF, ACN, THF, DMA, or a mixture thereof, at temperatures ranging from ambient temperature to 120° C., to provides benzonitrile compounds of formula (XIII), where $R^1$ is —CN, $R^2$ is —H and $R^6$ is —H. Compounds of formula (XIV), where $R^6$ is —$OCH_3$, are prepared by alkylating compounds of forumula (XIII), employing methods previously described, for example, reaction of compounds of formula (XIII) with a base such as NaH, and the like, in a solvent such as DMF, DMA, THF, and a suitable alkylhalide such as MeI, at temperatures ranging from 0° C. to room temperature, for a period of 5 min to 3 h.

Alternately, aryl bromides of formula (XI), where HAL is —Br, undergo a palladium-catalyzed α-arylation with carbonyl compounds of formula (XII) to provide compounds of formula (XV). For example, aryl bromide compounds of formula (XI), where $R^1$ is —CN, $R^2$ is —F, are reacted with a suitable carbonyl compound, such as cyclopentanone, and the like, a palladium catalyst such as $Pd(OAc)_2$, $Pd_2(dba)_3$, and the like, a ligand such as Xantphos, S-Phos®, BINAP, t-$Bu_3PHBF_4$, DPEphos, preferably Xantphos, a suitable base such as NaOt-Bu, $Cs_2CO_3$, $K_3PO_4$, and the like, in a suitable solvent such as ACN, THF, toluene, and the like, a temperatures ranging from 60 to 90° C., for a period of 12 to 19 h, to provide compounds of formula (XV). One skilled in the art will recognize that suitable carbonyl compounds employed in the palladium-catalyzed a-arylation reaction may also include unsubstituted or substituted —$C_{5-8}$cycloalkyl carbonyl and —$C_{6-10}$alkyl carbonyl compounds. Silylenolether are prepared from compounds of formula (XV), by reaction with NaI, a base such as TEA, in a solvent such as ACN, and a haloalkylsilane such as chlorotrimethylsilane. Subsequent fluorination of the silylenolether with a fluorinating agent such as Selectfluore, in a suitable solvent such as DMF, provides fluoro compounds of formula (XVI), where $R^6$ is —F. Reduction of compounds of formula (XVI) with a reducing agent such as $NaBH_4$, and the like, in a suitable solvent such as MeOH, at temperatures ranging from 0 to 23° C., provides the corresponding alcohol. Compounds of formula (XVIII) are prepared in two steps from the alcohol, first by formation of the thiocarbonate, second by a radical reduction. Thiocarbonate compounds are prepared employing methods known to one skilled in the art, for example, reaction of alcohol compounds with O-phenyl chlorothionoformate, in the presence of DMAP, in a solvent such as ACN, at temperatures ranging from 0 to 23° C. Radical reduction of thiocarbonate compounds with a reducing agent such as tributyltin hydride, a radical initiator such as AIBN, and the like, in a solvent such as toluene, employing microwave or conventional heating at temperatures ranging from 120 to 140° C., provides compounds of formula (XVII).

SCHEME D

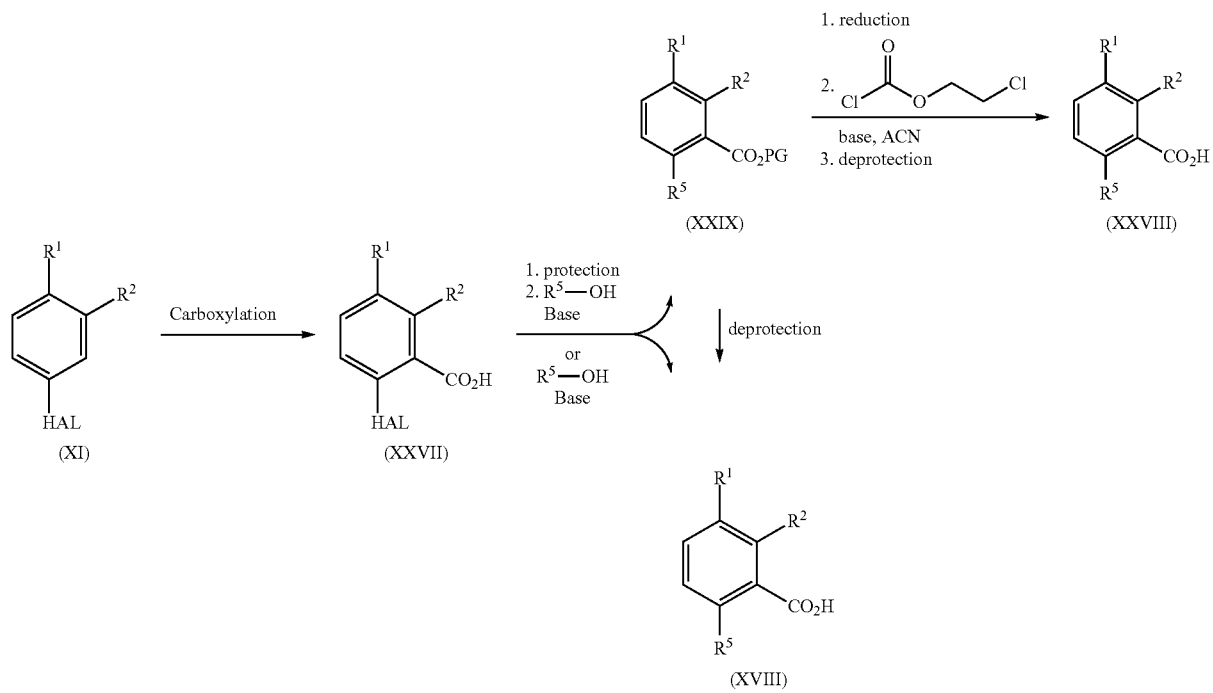

According to Scheme D, carboxy compounds of formula (XXVII) are commercially available or are synthetically accessible. For example, compounds of formula (XXVII) are prepared from compounds of formula (XI). Compounds of formula (XI), where $R^1$ is —CN, $R^2$ is —Cl, —F, or —OCH$_3$, and HAL is —F, are reacted with an organolithium base such as lithium diisopropylamide, and the like, in the presence of a CO$_2$ source such as dry ice or CO$_2$ (g), in a solvent such as THF, at temperatures ranging from —78 to 30° C. to provide compounds of formula (XXVII). Subsequent aromatic nucleophilic substitution reaction with a commercially available or synthetically accessible suitable alcohol of formula $R^5$, where $R^5$ is where $R^5$ is —OC$_{1-6}$alkyl, —OC$_{1-6}$haloalkyl, —O(C$_{1-3}$alkyl)$_{0-1}$C$_{3-6}$cycloalkyl, —O(C$_{1-3}$alkyl)$_{0-1}$heterocycloalkyl, or —O(C$_{1-3}$haloalkyl)$_{0-1}$C$_{3-6}$cycloalkyl, a suitable base such as K$_2$CO$_3$, Cs$_2$CO$_3$, and the like, in a suitable solvent such as THF, dioxane, and the like, at temperatures ranging from 80 to 120° C., provides compounds of formula (XVIII). Alternatively, compounds of formula (XXVII), are carboxylated employing methods previously described, and then protected with an appropriate carboxy protecting group, for example benzyl, prior to aromatic nucleophilic substitution with an appropriate alcohol of formula $R^5$, where $R^5$ is defined above. Deprotection affords compounds of formula (XVIII).

According to Scheme D, commercially available or synthetically accessible compounds of formula (XXVII), where $R^1$ is —NO$_2$ and —HAL is F, are reacted with a suitable alcohol of formula $R^5$—OH in an aromatic nucleophilic substitution reaction as previously described. Protection of the carboxy moiety with an appropriate carboxy protecting group, for example benzyl, followed by reduction of the nitro moiety employing methods known to one skilled in the art provides (XXIX). Reduction of the nitro moiety employing conditions known to one skilled in the art, for example, reduction with Iron, in HOAc/EtOH, at temperatures ranging from 50 to 75° C., for a period of 2-3 h, provides the corresponding aniline. Subsequent treatment with 2-chloroethylchloridocarbonate in the presence of a suitable base such as K$_2$CO$_3$, and the like, in a suitable solvent such as ACN, at or around ambient temperature, affords the corresponding oxazolidinone. Deprotection, employing known methods, affords compounds of formula (XXVIII).

SCHEME E

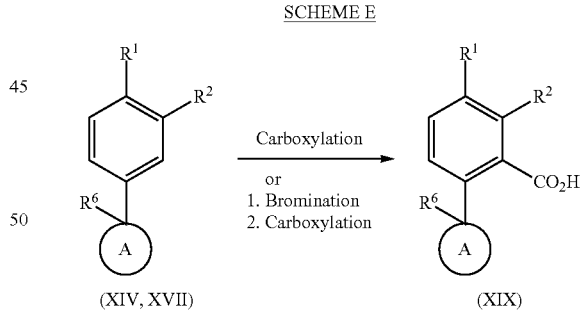

According to Scheme E, carboxylation of compounds of formula (XIV), where $R^1$ is —CN, and $R^2$ is —F, employing a lithiating agent such as n-BuLi, lithium diisopropylamide, and the like, a CO$_2$ source such as crushed solid CO$_2$, with or without a base such as diisopropylamine, 2,2,6,6-tetramethylpiperidine, and the like, in a solvent such as THF and the like, provides carboxy compounds of formula (XIX).

Carboxylic acid compounds of formula (XIX), where $R^1$ is —Br and $R^2$ is —F, are suitably protected (preferably benzyl), shown by substitutent PG, under conditions known to one skilled in the art. Cyanation, employing methods known to one skilled in the art provides benzonitrile compounds of formula (XIX), where $R^1$ is —CN and $R^2$ is —F. For example, reaction of compounds of formula (XIX), where $R^1$ is —Br and $R^2$ is —F, in the presence of a cyanide source such as, but not limited to KCN, NaCN, $Zn(CN)_2$, preferably $Zn(CN)_2$, a palladium catalyst such as $Pd_2(dba)_3$, $Pd(PPh_3)_4$, and the like, with or without the presence of additional ligand such as dppf, in a solvent such as DMF, ACN, THF, DMA, or a mixture thereof, at temperatures ranging from ambient temperature to 120° C., provides benzonitrile compounds of formula (XIX). Employing methods previously described, additional aromatic nucleophilic substitution reactions on compounds of formula (XIX), where $R^2$ is —F, under conditions known to one skilled in the art, provide compounds of formula (XIX), where $R^2$ is —$OC_{1-6}$alkyl.

According to Scheme E, compounds of formula (XIV), $R^1$ is —CN and $R^2$ is —H, are brominated, with a brominating agent such as NBS, and the like, in an aq. solution of $H_2SO_4$, at a suitable temperature such as room temperature, for a period of 12 to 24 h. Palladium catalyzed carboxylation of bromo compounds provides compounds of formula (XIX). For example, reaction with a palladium catalyst such as trans-bis(acetato)bis[o-(di-o-tolylphosphino)benzyl]dipalladium(II), and the like, insitu generation of $CO_2$ with molybdenumhexacarbonyl, a solvent such as water, a suitable base such as diisopropylethylamine, employing microwave irradiation at 150° C., for a period of about 10 min. provides carboxy compounds of formula (XIX), where $R^1$ is —CN and $R^2$ is —H.

accessible substituted benzoic acids of formula (XI). The carboxylic acid moiety of compounds of formula (XI), where $R^1$ is —$SO_2CH_3$, $R^2$ is H, and HAL is —Br, are suitably protected, (preferably a lower alkyl group such as methyl, ethyl, or tert-butyl), shown by substituent PG, under conditions known to one skilled in the art, to provide compounds of formula (XXI). For example, compounds of formula (XI), where HAL is —F, are reacted with a catalytic amount of an acid such as $H_2SO_4$, in a solvent such as MeOH, at temperatures ranging from room temperature to the reflux temperature of the solvent, for a period of 24 to 72 h, to provide ester compounds of formula (XXI), where PG is —$CH_3$. In an alternative method, compounds of formula (XI), where HAL is —Br, are alkylated, employing a base such as $K_2CO_3$ and the like, an alkyl halide such as iodomethane, in a suitable solvent such as DMF, to afford compounds of formula (XXI), where PG is —$CH_3$.

Esters of formula (XXI) are prepared from commercially available or synthetically accessible compounds of formula (XI), where $R^1$ is —H, $R^2$ is —F, and HAL is —F. Halosulfonation of compounds of formula (XI), by treatment with chlorosulfonic acid, at temperatures ranging from 65 to 150° C., for a period of 1 to 6 h, provides compounds of formula (XX). Reduction of sulfonyl chloride of formula (XX) with an aq. solution of $Na_2SO_3$, for a period of 1 to 3 h, provides the corresponding sulfinic acid. Subsequent alkylation, employing an alkyl halide such as methyl iodide, a mild base such as $K_2CO_3$, and the like, in a solvent such

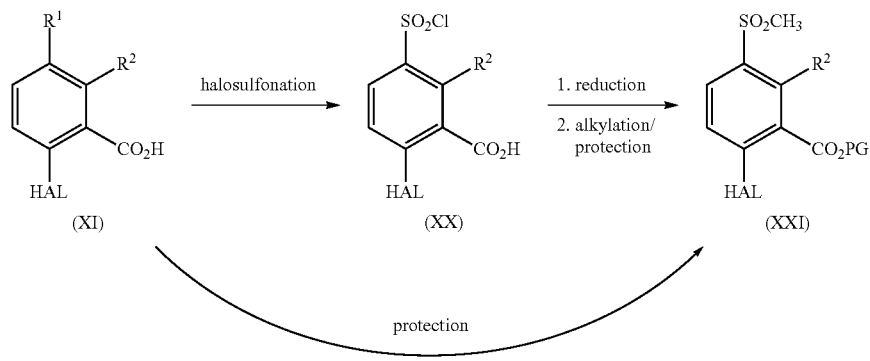

SCHEME F

According to Scheme F, compounds of formula (XXI) are prepared from commercially available or synthetically as DMF, DMA, THF and the like, delivers compounds of formula (XXI), where PG is —$CH_3$.

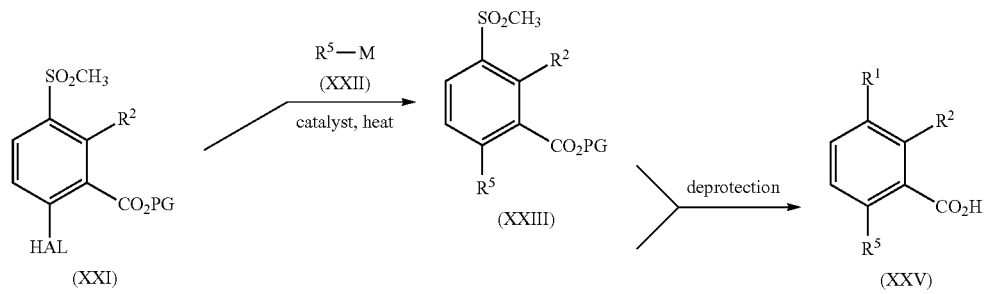

SCHEME G

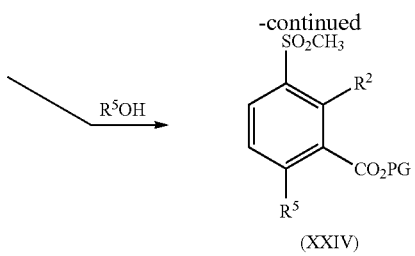

(XXIV)

According to Scheme G, compounds of formula (XXI), where HAL is —Br, are reacted under palladium or copper catalyzed coupling conditions such as but not limited to Suzuki reaction conditions. For example, reaction of bromo compounds of formula (XXI), with commercially available or synthetically accessible boronic acid or ester of formula (XXII), where $R^5$ is cycloalkenyl, and M is boron, in a solvent such as DME, ACN, toluene, EtOH, $H_2O$, or a mixture thereof, in the presence of a base such as, $NaHCO_3$, $Na_2CO_3$, $K_2CO_3$, $K_3PO_4$, $Cs_2CO_3$, and the like, and on organotransition metal catalyst such as $Pd_2(dba)_3$, $Pd(dppf)_2$, $Pd(PPh_3)_4$, and the like, employing conventional or microwave heating, at temperatures ranging from 80 to 120° C., to provide compounds of formula (XXIII), where $R^5$ is cycloalkenyl. Where the boronic acid reagent contains an alkenyl moiety, the coupled product is further reduced to the corresponding alkyl group or cycloalkyl group under hydrogenation conditions. Reduction of cycloalkenyl compounds of formula (XXIII), with a palladium catalyst such as $Pd(OH)_2$, Pd/C, and the like, in a suitable solvent such as MeOH, in the presence of $H_2$ (for example 55 psi), at temperatures ranging from 23 to 50° C. provides cycloalkyl compounds of formula (XXIII).

Compounds of formula (XXI), where $R^2$ is —F, HAL is —F, and compounds of formula (XI), where $R^1$ is —$SO_2CH_3$, and HAL is —F, are reacted with commercially available or synthetically accessible alcohol compounds of formula $R^5$—OH, in an aromatic nucleophilic substitution reaction. For example, compounds of formula (XXI) are reacted with racemic 1,1,1-trifluoropropan-2-ol, in a suitable solvent such as THF, dioxane, DMF, and the like, a base such as $Cs_2CO_3$, and the like, at temperatures ranging from 0 to 25° C., for a period of 12 to 24 h, to provide racemic compounds of formula (XXIV) where $R^5$ is —O—$C_{1-6}$haloalkyl. Additional aromatic nucleophilic substitution reactions on compounds of formula (XXIV), where $R^2$ is —F, under conditions known to one skilled in the art, provides compounds of formula (XXIV), where $R^2$ is —O—$C_{1-6}$alkyl. For example, reaction of compounds of formula (XXIV) with a base such as $NaHCO_3$, $Na_2CO_3$, $K_2CO_3$, NaH, potassium tert-butoxide, $Cs_2CO_3$, preferably NaH, in a solvent such as DMF, DMA, THF, preferably THF, and a suitable alcohol such as MeOH, at temperatures ranging from 0° C. to room temperature, for a period of 5 min to 2 h, to afford compounds of formula (XXIV), where $R^2$ is —$OCH_3$. Where chiral alcohol reagents are employed, chiral separation employing methods known to one skilled in the art, for example, supercritical fluid chromatography, affords the pure (R) and (S) enantiomers of compounds of formula (XXIV).

Hydrolysis of the ester moiety of compounds of formula (XXIII) and (XXIV), with a base such as NaOH, LiOH, and the like, in a solvent such as MeOH, and the like, at temperatures ranging from 50 to 80° C., for a period of 1 to 12 h, affords substituted benzoic acid compounds of formula (XXV).

SCHEME H

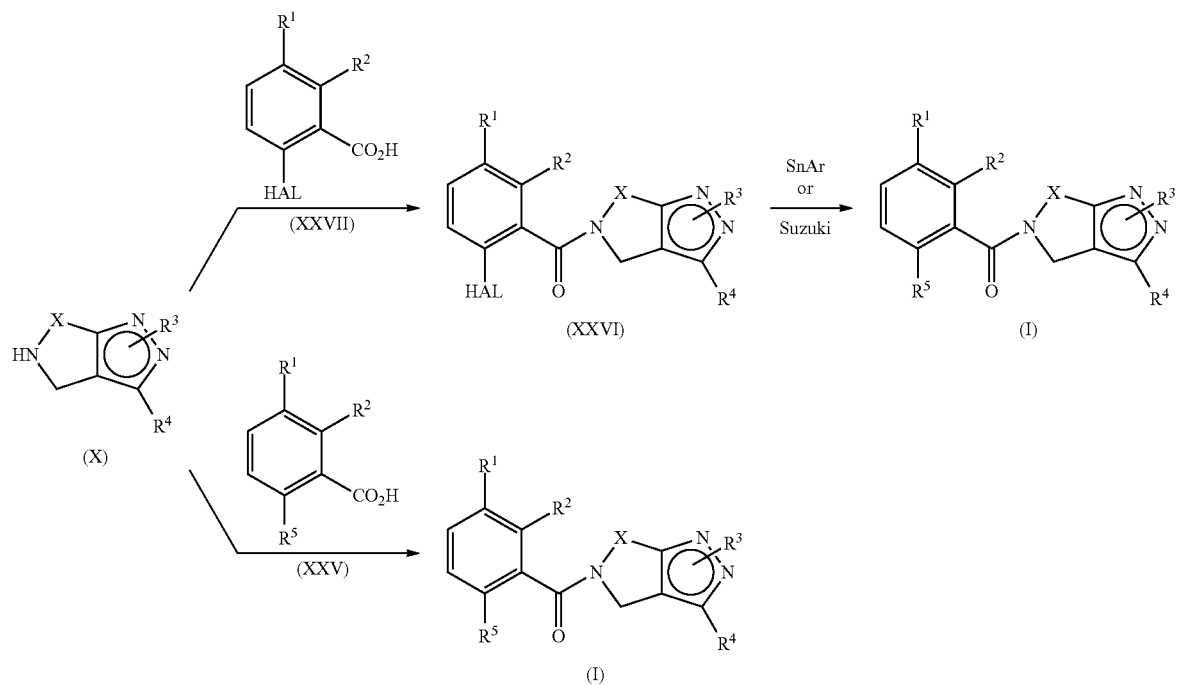

Coupling reactions are achieved by conventional amide bond forming techniques which are well known to those skilled in the art, as depicted in Scheme H. For example, an acyl halide (e.g. chloride) derivative of a compound of formula (XVIII), (XIX), (XXV), (XXVII) or (XXVIII) is reacted with a compound of formula (X), in the presence of an excess of a tertiary amine, such as TEA or pyridine, optionally in the presence of a suitable catalyst, such as DMAP, in a suitable solvent such as DCM or THF, at a temperature of about 0° C. to room temperature, to provide compounds of formula (XXVI) or Formula (I).

A variety of other amino acid coupling methodologies are used to couple the compounds of formulae (XVIII), (XIX), (XXV), (XXVII) or (XXVIII) with the compound of formula (X). For example, the acid of formula (XXV) or (XXVII) or a suitable salt thereof (e.g. sodium salt) are activated with an appropriate activating reagent, for example a carbodiimide, such as DCC or EDCI optionally in the presence of HOBt and/or a catalyst such as DMAP; a halotrisaminophosphonium salt such as PyBroP; a suitable pyridinium salt such as 2-chloro-1-methyl pyridinium chloride; or another suitable coupling agent such as HATU. Coupling reactions are conducted in a suitable solvent such as DCM, THF, DMF and the like, optionally in the presence of a tertiary amine such as N-methylmorpholine or N-ethyldiisopropylamine (for example when either the compound of formula (X), or the activating agent is presented in the form of an acid addition salt), at from about 0° C. to room temperature, to provide compounds of formula (XXVI) or Formula (I). Commmercially available or synthetically accessible compounds of formulae (XVIII), (XIX), (XXV), (XXVII) or (XXVIII), where $R^2$ is —$C_{1-3}$alkyl, —$C_{1-3}$haloalkyl, may be coupled with the compound of formula (X), according to methods previously described to provide compounds of Formula (I).

Compounds of formula (XXVI), where HAL is —F, are reacted with alcohols of formula $R^5$—OH, in an aromatic nucleophilic substitution reaction, employing methods previously described, to provide compounds of Formula (I).

Compounds of formula (XXVI), where HAL is —I, under Suzuki reaction conditions known to one skilled in the art, are reacted with commercially available or synthetically accessible aromatic or heteroaromatic boronic acids or esters, in a solvent such as ACN, toluene, EtOH, $H_2O$, or a mixture thereof, in the presence of a base such as, $NaHCO_3$, $Na_2CO_3$, $K_2CO_3$, $Cs_2CO_3$, and the like, and a palladium catalyst such as, pdopp02, $Pd(Ph_3)_4$, and the like, using conventional or microwave heating, at temperatures ranging from 80 to 120° C., provides compounds of Formula (I), where $R^5$ is an optionally unsubstituted or substituted aryl or heteroaryl group.

Compounds of Formula (I), where $R^2$ is —F, are reacted with a base such as sodium methoxide, and the like, and an alcohol such as MeOH, at temperatures ranging from room temperature to 50° C., for a period of 12 to 24 h, to provide compounds of Formula (I), where $R^2$ is —$OCH_3$.

Compounds of Formula (I), where $R^1$ is —CN, are hydrolyzed under basic conditions, for example, reacted with a base such as NaOH, in a solvent such as dioxane, at temperatures ranging from room temperature to 120° C., for a period of 12 to 24 h, to provide compounds of Formula (I), where $R^1$ is —$CO_2H$ or —$CONH_2$.

Compounds of Formula (I), where $R^1$ is —$CO_2H$, are coupled with alkylamines and heterocycloalkyls employing coupling conditions previously described, to provide compounds of Formula (I), where $R^1$ is —$C(O)N(R^a)_2$, where $R^a$ is

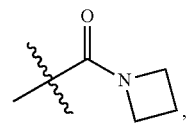

and independently selected from —H, and —$C_{1-3}$alkyl.

EXAMPLES

Chemistry:

In obtaining the compounds described in the examples below, and the corresponding analytical data, the following experimental and analytical protocols were followed unless otherwise indicated.

Unless otherwise stated, reaction mixtures were magnetically stirred at room temperature (rt) under nitrogen atmosphere. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on $SiO_2$ ($SiO_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Preparative HPLC was performed on a Waters Auotopurify system using a Waters XBridge OBD 30 mm×150 mm×5 μm (particle size) $C_{18}$ column with a 15 minute gradient of 10-100% acetonitrile in water and 0.1% trifluoroacetic acid added as a modifier to both phases. Elution profiles were monitored by UV at 254 and 220 nm and mass spectrometry.

Nuclear magnetic resonance (NMR) spectra were obtained in a Varian 400 MHz or Bruker 400 MHz NMR. Samples were analyzed in either deuterated acetone (($CD_3)_2CO$)), chloroform ($CDCl_3$), methanol-$d_4$ ($CD_3OD$), or dimethyl sulfoxide-$d_6$ (DMSO-$d_6$). For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMSO-$d_6$ the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, Mass.) or ChemAxon.

Intermediate 1: 2-(4-Fluorophenyl)-2,4,5,6-tetrahydropyrrolo[3,4-c]pyrazole.

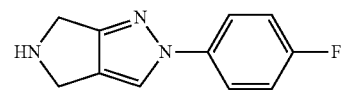 [SMILES: Fc1ccc(-n2cc3c(n2)CNC3)cc1]

Step A. tert-Butyl 2-(4-fluorophenyl)-4,6-dihydropyrrolo[3,4-c]pyrazole-5(2H)-carboxylate. To a 500 mL pressure vessel were added tert-butyl 4,6-dihydropyrrolo[3,4-c]pyrazole-5(2H)-carboxylate (9.0 g, 43.01 mmol) and 1-fluoro-4-iodobenzene (11.46 g, 51.61 mmol) in anhydrous THF (117 mL). Nitrogen gas was bubbled through the mixture for 5 minutes. Potassium phosphate (18.26 g, 86.02 mmol), CuI (1.64 g, 8.6 mmol) and (1S,2S)-(+)-1,2-diaminocyclohexane (0.982 g, 8.6 mmol) were then added. The reaction vessel was sealed and the mixture stirred at 120° C. for 16 hours. The reaction mixture was removed from heating and filtered while still hot. The filtrate was allowed to cool, diluted with ethyl acetate (250 mL) and washed with concentrated ammonium hydroxide (2×100 mL) and brine. The organic layer was dried ($MgSO_4$), filtered and evaporated and the resulting residue was purified by FCC (15% ethyl acetate/hexanes) to afford the title compound (7.4 g, 57%).

Step B. 2-(4-Fluorophenyl)-2,4,5,6-tetrahydropyrrolo[3,4-c]pyrazole HCl salt. A solution of tert-butyl 2-(4-fluorophenyl)-4,6-dihydropyrrolo[3,4-c]pyrazole-5(2H)-carboxylate (7.4 g, 24.4 mmol) in dioxane (60 mL) was treated with 4N HCl dioxane solution (61 mL, 244 mmol) and stirred at ambient temperature for 16 h. Solvents were removed under vacuum and the resulting solids treated with a minimum amount of methanol followed by excess diethyl ether. The title compound was filtered off and dried under reduced pressure (5.8 g, 99%). $^1$H NMR (400 MHz, DMSO-$d_6$) δ 10.40 (br s, 2H), 8.34 (s, 1H), 7.85-7.78 (m, 2H), 7.38-7.30 (m, 2H), 4.35 (d, J=5.1 Hz, 4H).

Intermediate 2: 2-(3,4-Difluorophenyl)-2,4,5,6-tetrahydropyrrolo[3,4-c]pyrazole HCl salt.

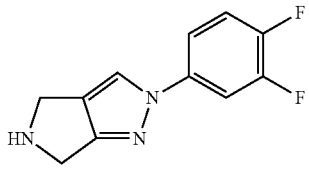 [SMILES: Fc1ccc(-n2cc3c(n2)CNC3)cc1F]

The title compound was prepared in a manner analogous to Intermediate 1. [M+H]=222.10

Intermediate 3: 4-(5,6-Dihydropyrrolo[3,4-c]pyrazol-1(4H)-yl)benzonitrile.

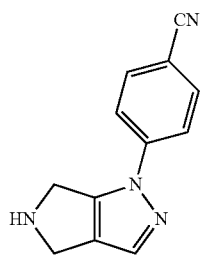 [SMILES: N#Cc1ccc(-n2ncc3c2CNC3)cc1]

The title compound was prepared in a manner analogous to Intermediate 1. [M+H]=211.10.

Intermediate 4: 2-(4-Fluorophenyl)-3-(trifluoromethyl)-4,5,6,7-tetrahydro-2H-pyrazolo[4,3-c]pyridine.

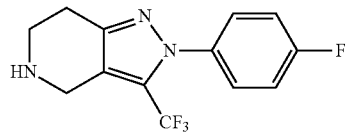

To a 20 mL microwave vial was added tert-butyl 4-oxo-3-(2,2,2-trifluoroacetyl)piperidine-1-carboxylate (0.2 g, 0.83 mmol) and (4-fluorophenyl)hydrazine hydrochloride (0.20 g, 1.24 mmol), and ethanol (2.8 mL). The reaction mixture was heated at 80° C. overnight. The crude material was purified via preparative HPLC on C-18 reverse-phase $SiO_2$, eluting with a gradient formed from acetonitrile: $H_2O$: 0.1%TFA (15-40%) to afford two regioisomers: fraction A (23.3 mg, 9.5%) and fraction B (21.4 mg, 9.3%). A 2 D NOESY experiment determined that fraction A was the title compound, 2-(4-fluorophenyl)-3-(trifluoromethyl)-4,5,6,7-tetrahydro-2H-pyrazolo[4,3-c]pyridine (Intermediate 4) and Fraction B was 1-(4-fluorophenyl)-3-(trifluoromethyl)-4,5,6,7-tetrahydro-1H-pyrazolo[4,3-c]pyridine HCl salt (Intermediate 5). The title compound, $^1$H NMR (400 MHz, $CDCl_3$) δ=8.03 (br s, 1H), 7.45-7.33 (m, 1H), 7.23-7.10 (m, 1H), 7.05 (dd, J=2.3, 9.8 Hz, 1H), 6.86 (dt, J=2.6, 9.0 Hz, 1H), 4.03 (br s, 1H), 3.85 (s, 1H), 3.32-3.09 (m, 2H), 2.77 (t, J=5.9 Hz, 2H).

Intermediate 5: 1-(4-Fluorophenyl)-3-(trifluoromethyl)-4,5,6,7-tetrahydro-1H-pyrazolo[4,3-c]pyridine HCl salt.

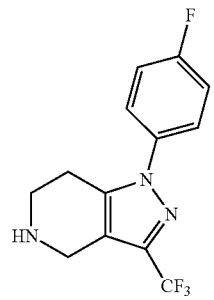 [SMILES: Fc1ccc(-n2nc(C(F)(F)F)c3c2CCNC3)cc1]

Intermediate 5 (21.4 mg, 9.3%) was isolated in the preparation of Intermediate 4.

Intermediate 6: 1-(4-Fluorophenyl)-4,5,6,7-tetrahydro-1H-pyrazolo[4,3-c]pyridine.

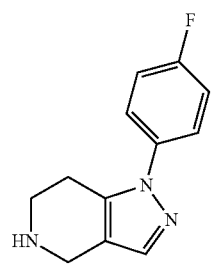 [SMILES: Fc1ccc(-n2ncc3c2CCNC3)cc1]

Step A. tert-Butyl 1-(4-fluorophenyl)-6,7-dihydro-1H-pyrazolo[4,3-c]pyridine-5(4H)-carboxylate. To a 20 mL microwave vial was added (Z)-tert-butyl 3-((dimethylamino)methylene)-4-oxopiperidine-1-carboxylate (0.2 g, 0.79 mmol) and (4-fluorophenyl)hydrazine hydrochloride (0.19 g, 1.18 mmol), and EtOH (1.9 mL). The reaction mixture was heated with microwave irradiation at 130° C. for 30 min. The crude was diluted with EtOAc, washed with saturated NaHCO$_3$, dried (MgSO$_4$), filtered, and concentrated under reduced pressure to afford the title compound as a black oil. Purification (FCC, SiO$_2$, 10% EtOAc:hexanes) afforded the title compound (84 mg, 34%). $^1$H NMR (400 MHz, CDCl$_3$) δ=7.47 (br s, 1H), 7.45-7.40 (m, 2H), 7.15-7.09 (m, 2H), 4.48 (br s, 2H), 3.67 (br s, 2H), 2.79-2.75 (m, 2H), 1.48 (s, 9H); [M+H]=318.27.

Step B. 1-(4-Fluorophenyl)-4,5,6,7-tetrahydro-1H-pyrazolo[4,3-c]pyridine HCl salt. The title compound was prepared in a manner analogous to Intermediate 1, Step B. [M+H]=218.09.

Intermediate 7: 1-(5-Fluoropyridin-2-yl)-4,5,6,7-tetrahydro-1H-pyrazolo[4,3-c]pyridine.

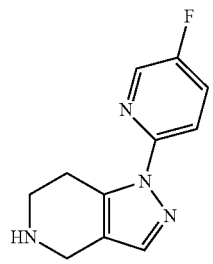 [SMILES: Fc1ccc(-n2ncc3c2CCNC3)nc1]

Step A. tert-Butyl 1-(5-fluoropyridin-2-yl)-6,7-dihydro-1H-pyrazolo[4,3-c]pyridine-5(4H)-carboxylate. To a 100 mL round-bottom flask were added tert-butyl 6,7-dihydro-2H-pyrazolo[4,3-c]pyridine-5(4H)-carboxylate (1.0 g, 4.48 mmol), 2,5-difluoropyridine (0.61 mL, 6.72 mmol), 60% sodium hydride in mineral oil (0.13 g, 5.38 mmol) and anhydrous DMF (22 mL). The mixture stirred at 50° C. overnight. The crude was diluted with EtOAc (50 mL), washed with H$_2$O (3×50 mL), dried (MgSO$_4$), filtered, and concentrated under reduced pressure. The crude material was purified with preparative HPLC on C-18 reverse-phase SiO$_2$, eluting with a gradient formed from acetonitrile: 20 mM aqueous ammonium acetate: 0.25% NH$_4$OH (60-95%) to afford the title compound: (100 mg, 7.0%).

Step B. 1-(5-Fluoropyridin-2-yl)-4,5,6,7-tetrahydro-1H-pyrazolo[4,3-c]pyridine HCl salt. The title compound was prepared in a manner analogous to Intermediate 1, Step B. [M+H]=219.09.

Intermediate 8: 2-Cyclopentyl-2,4,5,6-tetrahydropyrrolo[3,4-c]pyrazole.

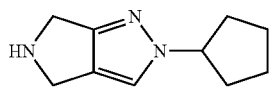

Step A. tert-Butyl 2-cyclopentyl-4,6-dihydropyrrolo[3,4-c]pyrazole-5(2H)-carboxylate. To a 25 mL round-bottom flask were added 60% sodium hydride in mineral oil (0.11 g, 2.87 mmol), anhydrous DMF (5.0 mL), and tert-butyl 4,6-dihydropyrrolo[3,4-c]pyrazole-5(2H)-carboxylate (0.5 g, 2.39 mmol). The mixture stirred at rt for 1 h. A solution of bromocyclopentane (0.53 g, 3.58 mmol) and DMF (7.5 mL) was then added drop-wise to the mixture and the mixture was stirred overnight at rt. The crude reaction mixture was quenched with water and then diluted with EtOAc (20 mL), washed with H$_2$O (3×50 mL), dried (MgSO$_4$), filtered, and concentrated under reduced pressure. The crude was purified (FCC, SiO$_2$, 20-30% EtOAc:hexanes) to afford the title compound as a solid (0.33 g, 50%). $^1$H NMR (400 MHz, CDCl$_3$) δ=7.16 (d, J=17.6 Hz, 1H), 4.62 (qd, J=7.0, 13.9 Hz, 1H), 4.52-4.34 (m, 4H), 2.23-2.10 (m, 2H), 2.07-1.93 (m, 2H), 1.93-1.79 (m, 2H), 1.77-1.59 (m, 2H), 1.52-1.43 (m, 9H).

Step B. 2-Cyclopentyl-2,4,5,6-tetrahydropyrrolo[3,4-c]pyrazole HCl salt. The title compound was prepared in a manner analogous to Intermediate 1, Step B. [M+H]=178.20.

Intermediate 9: 2-(2-Fluoro-2-methylpropyl)-2,4,5,6-tetrahydropyrrolo[3,4-c]pyrazole.

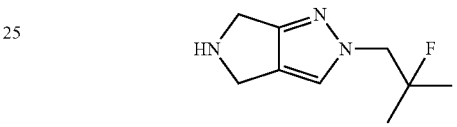

Step A. tert-Butyl 2-(2-hydroxy-2-methylpropyl)-4,6-dihydropyrrolo[3,4-c]pyrazole-5(2H)-carboxylate and tert-butyl 1-(2-hydroxy-2-methylpropyl)-4,6-dihydropyrrolo[3,4-c]pyrazole-5(1H)-carboxylate. To a stirred 0° C. solution of tert-butyl 4,6-dihydropyrrolo[3,4-c]pyrazole-5(2H)-carboxylate (100.00 mg, 0.48 mmol) was added lithium bis(trimethylsilyl)amide (1.00 mL, 1.00 mmol) in THF. The mixture was stirred at 0° C. for 30 min. 2,2-Dimethyloxirane (0.29 mL, 2.39 mmol) was added and the mixture was stirred at rt for 3 h and heated to 80° C. for 2 h under microwave irradiation. The crude material was diluted with EtOAc, washed with brine (3×30 mL), and concentrated under reduced pressure to a yellow oil. The yellow oil was absorbed onto silica and purified (FCC, SiO$_2$, 30-70% EtOAc:hexanes) to afford a 1:1 mixture of the title compounds: tert-butyl 2-(2-hydroxy-2-methylpropyl)-4,6-dihydropyrrolo[3,4-c]pyrazole-5(2H)-carboxylate and tert-butyl 1-(2-hydroxy-2-methylpropyl)-4,6-dihydropyrrolo[3,4-c]pyrazole-5(1H)-carboxylate (70 mg, 52%).

Step B. tert-Butyl 2-(2-fluoro-2-methylpropyl)-4,6-dihydropyrrolo[3,4-c]pyrazole-5(2H)-carboxylate and tert-butyl 1-(2-fluoro-2-methylpropyl)-4,6-dihydropyrrolo[3,4-c]pyrazole-5(1H)-carboxylate. To a dry flask filled with N$_2$ was added tert-butyl 2-(2-hydroxy-2-methylpropyl)-2H,4H,5H,6H-pyrrolo[3,4-c]pyrazole-5-carboxylate (0.07 g, 0.25 mmol) and dichloromethane (0.37 mL). This solution was cooled to −78° C. and then diethylaminosulfur trifluoride (0.18 mL, 1.37 mmol) was added slowly to this solution. The mixture was stirred at −78° C. for 1 h. The solution was quenched by dropwise addition of water (∼2 mL) at −78° C. The crude was warmed up to rt and then neutralized by adding saturated NaHCO$_3$ (∼1 mL). The resulting mixture was extracted with DCM (2×5 mL). The collected organic layers were dried (MgSO$_4$), filtered, and evaporated under reduced pressure. The residue was purified (FCC, SiO$_2$, 30-50% EtOAc:hexanes) to afford 2 separated regioisomers: $^1$H NMR (400 MHz, CDCl$_3$) δ=7.20 (d, J=12.9 Hz, 1H), 4.52-4.38 (m, 4H), 4.26-4.16 (m, 2H), 1.49 (s, 9H), 1.38-1.26 (m, 6H); MS 284.52, [M+H]$^+$.

Step C. 2-(2-Fluoro-2-methylpropyl)-2,4,5,6-tetrahydropyrrolo[3,4-c]pyrazole HCl salt. The title compound was prepared in a manner analogous to Intermediate 1, Step B. [M+H]=184.12.

Intermediate 10: 1-(2-Fluoro-2-methylpropyl)-1,4,5,6-tetrahydropyrrolo[3,4-c]pyrazole.

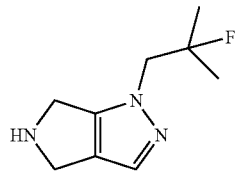

Step A. tert-Butyl 1-(2-fluoro-2-methylpropyl)-4,6-dihydropyrrolo[3,4-c]pyrazole-5(1H)-carboxylate. The title compound was isolated as a regioisomer from Intermediate 9, Step B, fraction B: $^1$H NMR (400 MHz, CDCl$_3$) δ=7.36-7.16 (m, 1H), 4.62-4.30 (m, 4H), 4.24-4.04 (m, 2H), 1.49 (d, J=1.2 Hz, 8H), 1.34 (d, J=23.9 Hz, 6H); [M+H]=284.52.

Step B. 1-(2-Fluoro-2-methylpropyl)-1,4,5,6-tetrahydropyrrolo[3,4-c]pyrazole HCl salt. The title compound was prepared in a manner analogous to Intermediate 1, Step B.

Intermediate 11: 1-(4-Fluorophenyl)-7,7-dimethyl-4,5,6,7-tetrahydro-1H-pyrazolo[4,3-c]pyridine hydrochloride.

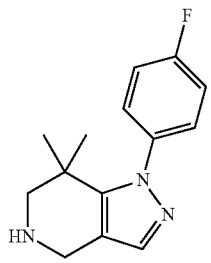

Step A. (Z)-tert-Butyl 5-((dimethylamino)methylene)-3,3-dimethyl-4-oxopiperidine-1-carboxylate. tert-Butyl 3,3-dimethyl-4-oxopiperidine-1-carboxylate (250 mg, 1.10 mmol) and N,N-dimethylformamide dimethyl acetal (1.25 mL, 9.35 mmol) were combined and stirred at 105° C. for 72 hour. The reaction mixture was cooled to rt, and diluted with ethyl acetate (50 mL) and washed with water (50 mL) and brine. The organic layer was dried (Na$_2$SO$_4$), filtered and concentrated under reduced pressure to afford the crude product as an orange oil (290 mg, 93%), which was taken forward without any additional purification.

Step B. tert-Butyl 1-(4-fluorophenyl)-7,7-dimethyl-6,7-dihydro-1H-pyrazolo[4,3-c]pyridine-5(4H)-carboxylate. A solution of (Z)-tert-butyl 5-((dimethylamino)methylene)-3,3-dimethyl-4-oxopiperidine-1-carboxylate (50 mg, 0.18 mmol), (4-fluorophenyl)hydrazine hydrochloride (43 mg, 0.26 mmol) in EtOH (0.89 mL) was stirred at room temperature for 5 hours, then heated to 45° C. for 15 hours. The reaction was cooled to room temperature and the solvent was removed under reduced pressure. The resulting residue was purified (FCC, SiO$_2$, 0-30% ethyl acetate/hexanes) to afford the title compound (50 mg, 82%).

Step C. 1-(4-Fluorophenyl)-7,7-dimethyl-4,5,6,7-tetrahydro-1H-pyrazolo[4,3-c]pyridine hydrochloride. A solution of tert-butyl 1-(4-fluorophenyl)-7,7-dimethyl-6,7-dihydro-1H-pyrazolo[4,3-c]pyridine-5(4H)-carboxylate (50 mg, 0.15 mmol) in dioxane (0.73 mL) was treated with 4N HCl/dioxane solution (0.2 mL, 0.86 mmol) and stirred at 40° C. for 16 hours, then at 60° C. for 24 h. Solvents were removed under vacuum and the resulting solids were dried under reduced pressure (36 mg, 99%). $^1$H NMR (400 MHz, CD$_3$OD) δ=7.63-7.59 (m, 1H), 7.53-7.44 (m, 2H), 7.37-7.27 (m, 2H), 4.31 (s, 2H), 3.65 (s, 2H), 1.22 (s, 6H), 1.18-1.14 (m, 1H); [M+H]=246.17.

Intermediate 12: 2-(4-Fluorophenyl)-7,7-dimethyl-4,5,6,7-tetrahydro-2H-pyrazolo[4,3-c]pyridine hydrochloride.

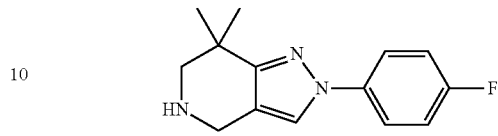

Step A. (Z)-tert-Butyl 5-((dimethylamino)methylene)-3,3-dimethyl-4-oxopiperidine-1-carboxylate. tert-Butyl 3,3-dimethyl-4-oxopiperidine-1-carboxylate (250 mg, 1.10 mmol) and N,N-dimethylformamide dimethyl acetal (1.25 mL, 9.35 mmol) were combined and stirred at 105° C. for 72 h. The reaction mixture was cooled to room temperature then diluted with ethyl acetate (50 mL), washed with water (50 mL), and washed with brine. The organic layer was dried (Na$_2$SO$_4$), filtered, and concentrated under reduced pressure to afford the crude product as an orange oil (290 mg, 93%), which was taken forward without any additional purification.

Step B. tert-Butyl 7,7-dimethyl-6,7-dihydro-2H-pyrazolo[4,3-c]pyridine-5(4H)-carboxylate. A solution of (Z)-tert-butyl 5-((dimethylamino)methylene)-3,3-dimethyl-4-oxopiperidine-1-carboxylate (225 mg, 0.80 mmol) and hydrazine hydrate (0.75 mL, 2.4 mmol) in EtOH (1.6 mL) was stirred at 45° C. for 18 h. The reaction was cooled to room temperature then the solvent was removed under reduced pressure. The resulting residue was taken forward in next reaction without any further purification.

Step C. tert-Butyl 2-(4-fluorophenyl)-7,7-dimethyl-6,7-dihydro-2H-pyrazolo[4,3-c]pyridine-5(4H)-carboxylate. To a vial was added tert-butyl 7,7-dimethyl-6,7-dihydro-2H-pyrazolo[4,3-c]pyridine-5(4H)-carboxylate (125 mg, 0.497 mmol), copper (I) iodide (27 mg, 0.14 mmol), potassium phosphate (382 mg, 1.80 mmol). The vial was purged with nitrogen then dioxane (2.5 mL) was added, followed by trans-amine and 1-fluoro-4-iodobenzene (0.69 mL, 0.60 mmol). The vial was heated to 100° C. for 5 hours. The reaction was cooled to room temperature then water and ethyl acetate were added. The layers were separated and the organics were washed with brine and dried (Na$_2$SO$_4$). Solvents were removed under vacuum and the resulting residue was purified was purified (FCC, SiO$_2$, 0-20% ethyl acetate/hexanes) to afford the title compound (75 mg, 44%).

Step D. 2-(4-Fluorophenyl)-7,7-dimethyl-4,5,6,7-tetrahydro-2H-pyrazolo[4,3-c]pyridine hydrochloride. A solution of tert-butyl 2-(4-fluorophenyl)-7,7-dimethyl-6,7-dihydro-2H-pyrazolo[4,3-c]pyridine-5(4H)-carboxylate (75 mg, 0.22 mmol) in dioxane (1.1 mL) was treated with 4N HCl/ dioxane solution (0.47 mL, 1.9 mmol) and stirred at 60° C. for 18 h. Solvents were removed under reduced pressure (61 mg, 99%). [M+H]=246.21.

Intermediate 13: 3-Ethoxy-2-(4-fluorophenyl)-4,5,6,7-tetrahydro-2H-pyrazolo[4,3-c]pyridine.

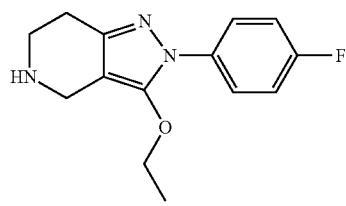 [SMILES: CCOc1c2c(nn1-c1ccc(F)cc1)CCNC2]

A solution of 1-tert-butyl 3-ethyl 4-oxopiperidine-1,3-dicarboxylate (350 mg, 1.29 mmol), (4-fluorophenyl)hydrazine hydrochloride (315 mg, 1.93 mmol) in EtOH (6.5 mL) was stirred at 100° C. for 5 h. The reaction was cooled to rt and diluted with water (75 mL) and ethyl acetate (75 mL). The organic layers were separated washed with brine (50 mL), dried (Na$_2$SO$_4$), filtered and concentrated under reduced pressure. Two products were observed, the title compound and 2-(4-fluorophenyl)-4,5,6,7-tetrahydro-2H-pyrazolo[4,3-c]pyridin-3-ol. Purification (FCC, SiO$_2$, 0-15% methanol/dichloromethane) provided the title compound (130 mg, 39%). $^1$H NMR (400 MHz, CD$_3$OD) δ=7.67-7.53 (m, 2H), 7.27-7.18 (m, 2H), 4.40 (s, 2H), 4.31-4.19 (m, 2H), 3.55 (t, J=6.3 Hz, 2H), 3.01 (t, J=6.5 Hz, 2H), 1.33 (t, J=7.0 Hz, 3H); [M+H]=262.20.

Intermediate 14: 2-(4-Fluorophenyl)-4,5,6,7-tetrahydro-2H-pyrazolo[4,3-c]pyridin-3-ol.

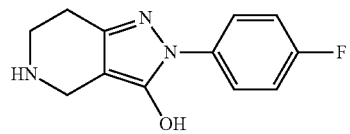 [SMILES: Oc1c2c(nn1-c1ccc(F)cc1)CCNC2]

2-(4-Fluorophenyl)-4,5,6,7-tetrahydro-2H-pyrazolo[4,3-c]pyridin-3-ol. The title compound was isolated from the above reaction (70 mg, 21%). $^1$H NMR (400 MHz, CD$_3$OD) δ=7.68-7.61 (m, 2H), 7.27-7.18 (m, 2H), 4.10 (s, 2H), 3.56 (t, J=6.3 Hz, 2H), 3.00 (t, J=6.3 Hz, 2H); [M+H]=234.16.

Intermediate 15: 2-(4-Methoxyphenyl)-4,5,6,7-tetrahydro-2H-pyrazolo[4,3-c]pyridine hydrochloride.

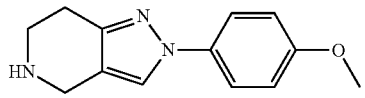 [SMILES: COc1ccc(-n2cc3c(n2)CCNC3)cc1]

Step A. tert-Butyl 3-hydroxy-2-(4-methoxyphenyl)-6,7-dihydro-2H-pyrazolo[4,3-c]pyridine-5(4H)-carboxylate. A solution of 1-tert-butyl 3-ethyl 4-oxopiperidine-1,3-dicarboxylate (500 mg, 1.84 mmol), (4-methoxyphenyl)hydrazine hydrochloride (483 mg, 2.76 mmol) and triethylamine (0.38 mL, 2.8 mmol), in EtOH (9.2 mL), was heated in a sealed vessel at 80° C. for 3 h. The reaction was cooled to room temperature and the solvent was removed under vacuum The resulting residue was purified (FCC, SiO$_2$ 0-15% methanol/dichloromethane) to afford the title compound (360 mg, 57%).

Step B. tert-Butyl 2-(4-methoxyphenyl)-3-(((trifluoromethypsulfonypoxy)-6,7-dihydro-2H-pyrazolo[4,3-c]pyridine-5(4H)-carboxylate. To a roundbottom flask under nitrogen was added tert-butyl 3-hydroxy-2-(4-methoxyphenyl)-6,7-dihydro-2H-pyrazolo[4,3-c]pyridine-5(4H)-carboxylate (360 mg, 1.04 mmol) followed by dichloromethane (2.0 mL) and TEA (0.43 mL, 3.1 mmol). The reaction mixture was cooled to 0° C. in an ice bath then trifluoromethanesulfonic anhydride (0.19 mL, 1.2 mmol) was added dropwise. The reaction mixture was allowed to warm slowly to room temperature then stirred for 1 h. Water and ethyl acetate were added to the reaction mixture. Layers were separated and organics were washed with brine then dried over sodium sulfate. Solvents were removed under vacuum and the resulting residue was purified (FCC, SiO$_2$, 0-50% ethyl acetate/hexanes) to afford the title compound (200 mg, 40%).

Step C. tert-Butyl 2-(4-methoxyphenyl)-6,7-dihydro-2H-pyrazolo[4,3-c]pyridine-5(4H)-carboxylate. To a roundbottom flask under nitrogen was added tert-butyl 2-(4-methoxyphenyl)-3-(((trifluoromethyl)sulfonyl)oxy)-6,7-dihydro-2H-pyrazolo[4,3-c]pyridine-5(4H)-carboxylate (200 mg, 0.42 mmol), 10 wt % palladium on carbon (20 mg), isopropyl alcohol (2.1 mL) and diethylamine (0.052 mL, 0.50 mmol). The reaction vessel was evacuated then purged with 1 atm of hydrogen and stirred at room temperature for three days. Solvents were removed under vacuum and resulting residue was purified (FCC, SiO$_2$, 0-50% ethyl acetate/hexanes) to afford the title compound (70 mg, 51%).

Step D. 2-(4-Methoxyphenyl)-4,5,6,7-tetrahydro-2H-pyrazolo[4,3-c]pyridine hydrochloride. The title compound was prepared in a manner analogous to Intermediate 1, Step B. [M+H]=230.18.

Intermediate 16: 2-(4,4-Difluorocyclohexyl)-2,4,5,6-tetrahydropyrrolo[3,4-c]pyrazole.

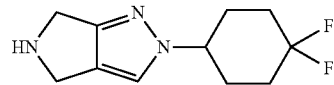 [SMILES: FC1(F)CCC(n2cc3c(n2)CNC3)CC1]

Step A. 4,4-Difluorocyclohexanol. To an ice-water bath cold solution of 4,4-difluorocyclohexanone (907 mg, 6.76 mmol) in MeOH (22 mL) was added NaBH$_4$ (460 mg, 12.17 mmol). The reaction mixture was stirred for 5 mm., allowed to warm to ambient temperature and stirred for 1 h. The reaction was quenched with water (11 mL) and stirred for 30 mm. The solvent was concentrated and the residue was partitioned between water (11 mL) and DCM (10 mL). The separated aqueous layer was washed with DCM (3×10 mL). The combined organic layers were dried (MgSO$_4$) and the solvent was concentrated to provide title compound (839 mg, 91%). $^1$H NMR (300 MHz, CDCl$_3$) δ=4.03-3.82 (m, 1H), 2.26-1.98 (m, 2H), 1.98-1.64 (m, 6H), 1.43 (d, J=3.6 Hz, 1H).

Step B. (4,4-Difluorocyclohexyl) 4-methylbenzenesulfonate. Tosyl chloride (1.70 g, 8.90 mmol) was added to an ice-water cold solution of 4,4-difluorocyclohexanol (1.01 g, 7.41 mmol) in pyridine (10 mL). The reaction mixture was stirred for 5 min., allowed to warm to ambient temperature and stirred for 24 h. The reaction was quenched with water (50 mL) and was extracted with EtOAc (3×30 mL). The combined organic layers were washed with a 0.5 M HCl solution (3×30 mL) and with water (30 mL). The organic layer was dried (MgSO$_4$) and the solvent was concentrated. Purification (FCC, SiO$_2$ using 10% of EtOAc in hexane) afforded the title compound (1.08 g, 50%). $^1$H NMR (500 MHz, CDCl$_3$) δ=7.83-7.77 (m, 2H), 7.35 (d, J=7.9 Hz, 2H), 4.72-4.66 (m, 1H), 2.46 (s, 3H), 2.13-1.98 (m, 2H), 1.92 (dd, J=24.7, 19.6 Hz, 4H), 1.84-1.76 (m, 2H).

Step C. tert-Butyl 2-(4,4-difluorocyclohexyl)-4,6-dihydropyrrolo[3,4-c]pyrazole-5-carboxylate. A flame-dried flask was charged with tert-butyl 4,6-dihydro-2H-pyrrolo[3,4-c]pyrazole-5-carboxylate (965 mg, 4.61 mmol) and cesium carbonate (2.25 g, 6.91 mmol) then purged with nitrogen. Degassed DMF (13 mL) was added, the reaction mixture was heated to 100° C. and (4,4-difluorocyclohexyl) 4-methylbenzenesulfonate (1.03 g, 3.54 mmol) was added by portion over 4 h. The reaction mixture was stirred for 18 h at 100° C. The solvent was concentrated, water (50 mL) was added and extracted with EtOAc (4×30 mL). The combined organic layers was washed with brine and dried over MgSO$_4$. The solvent was concentrated and the material and purified (FCC, SiO$_2$ using 25% EtOAc in hexanes) to provide 587 mg of 1.7:1 mixture of the linear and bent regioisomers. The material was recrystallized from EtOAc to give a ~9:1 mixture mixture of linear and bent regioisomers and a second recrystallization from MeOH to provide the title compound (70 mg, 6%). $^1$H NMR (500 MHz, CD$_3$OD) δ=7.38 (d, J=11.9 Hz, 1H), 4.44-4.38 (m, 4H), 4.38-4.30 (m, 1H), 2.23-2.09 (m, 6H), 2.09-2.01 (m, 1H), 2.01-1.92 (m, 1H), 1.51 (s, 9H); [M+H]=328.49.

Step D: 2-(4,4-Difluorocyclohexyl)-5,6-dihydro-4H-pyrrolo[3,4-c]pyrazole hydrochloride. A mixture of tert-butyl 2-(4,4-difluorocyclohexyl)-4,6-dihydropyrrolo[3,4-c]pyrazole-5-carboxylate (200 mg, 0.61 mmol) and HCl 4N in dioxane (12 mL) was stirred for 24 h at ambient temperature. The resulting precipitate was filtered and washed with small portions of cold ether. The resulting solid was highly hygroscopic and readily turned to a sticky heterogeneous paste. The product was dissolved in water (0.8 mL) and lyophilized to provide the title compound (131 mg, 94%). $^1$H NMR (500 MHz, DMSO-d$_6$) δ=10.30 (s, 2H), 7.71 (s, 1H), 4.93 (br s, 1H), 4.50-4.34 (m, 1H), 4.24 (t, J=5.3 Hz, 4H), 2.23-1.89 (m, 8H). [M+H]=228.4.

Intermediate 17: 2-[(3,3-Difluorocyclobutyl)methyl]-5,6-dihydro-4H-pyrrolo[3,4-c]pyrazole hydrochloride.

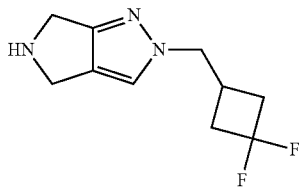 [SMILES: FC1(F)CC(Cn2cc3c(n2)CNC3)C1]

Step A: tert-Butyl 2-[(3,3-difluorocyclobutyl)methyl]-4,6-dihydropyrrolo[3,4-c]pyrazole-5-carboxylate. 3-(Bromomethyl)-1,1-difluoro-cyclobutane (505 mg, 2.73 mmol) was added dropwise over 15 min, to a mixture of tert-butyl 4,6-dihydro-2H-pyrrolo[3,4-c]pyrazole-5-carboxylate (560 mg, 2.67 mmol), cesium carbonate (1.39 g, 4.28 mmol) and DMF (5 mL) at 0° C. The reaction mixture was allowed to warm to ambient temperature and stirred for 18 h. The solvent was concentrated and the material was partitioned between water (50 mL) and EtOAc. The aqueous layer was washed with EtOAc (2×30 mL). The combined organic layers were washed with brine, dried (MgSO$_4$), and the solvent was concentrated. Purification (FCC, SiO$_2$ using ether) provided the title compound (344 mg, 41%). $^1$H NMR (300 MHz, CDCl$_3$) δ=7.10 (d, J=10.0 Hz, 1H), 4.50-4.37 (m, 4H), 4.18 (d, J=5.5 Hz, 2H), 2.78-2.56 (m, 3H), 2.47-2.25 (m, 2H), 1.50 (s, 9H); [M+H]=314.26.

Step B. 2-[(3,3-Difluorocyclobutypmethyl]-5,6-dihydro-4H-pyrrolo[3,4-c]pyrazole hydrochloride. A 4M HCl solution in dioxane (6.4 mL, 25 mmol) was added to a solution of tert-butyl 2-[(3,3-difluorocyclobutyl)methyl]-4,6-dihydropyrrolo[3,4-c]pyrazole-5-carboxylate (340 mg, 1.08 mmol) in dioxane (10 mL). The reaction mixture was stirred for 18 h and the solvent was concentrated. Ether (1.5 mL) was added to the gummy residue and the mixture was triturated. The process was repeated until a white powder suspension was obtained. The residual solvent was concentrated under reduced pressure to provide the title compound (260 mg, 99%). $^1$H NMR (300 MHz, CD$_3$OD) δ=7.59 (s, 1H), 4.41 (d, J=9.8 Hz, 4H), 4.27 (d, J=6.1 Hz, 2H), 2.75-2.52 (m, 3H), 2.51-2.26 (m, 2H); [M+H]=214.32.

TABLE 2

Amine Intermediates

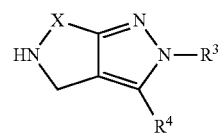

A

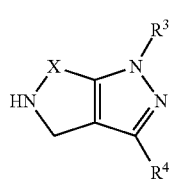

B

| R$^3$ | R$^4$ | X | —CH$_2$— | Prepared analogous to INT # | Regioisomer |
|---|---|---|---|---|---|
| ⟶⟨⟩—CN | —H | —CH$_2$— | 1 | A + B |
| —H | ⟶⟨⟩ | —(CH$_2$)$_2$— | 4 | A |

TABLE 2-continued
| Structure | | | | |
|---|---|---|---|---|
|  | —CF₃ | —(CH₂)₂— | 4 | A + B |
| 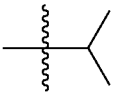 | —H | —CH₂— | 8<br>7 | A<br>B |
| 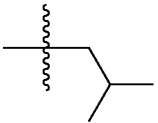 | —H | —CH₂— | 8<br>7 | A<br>B |
| 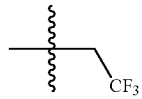 | —H | —CH₂— | 6 | B |
| 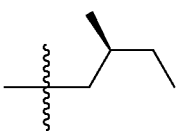 [SMILES: *C[C@@H](C)CC] | —H | —CH₂— | 8 | A |
| 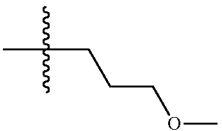 [SMILES: *CCCOC] | —H | —CH₂— | 8<br>7 | A<br>B |
| 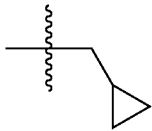 [SMILES: *CC1CC1] | —H | —CH₂— | 8<br>7 | A<br>B |
| 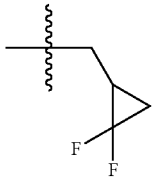 [SMILES: *CC1CC1(F)F] | —H | —CH₂— | 8<br>7 | A<br>B |
| 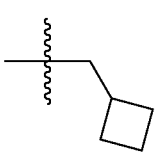 [SMILES: *CC1CCC1] | —H | —CH₂— | 8 | A |
| 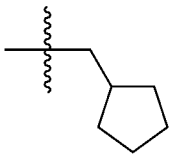 [SMILES: *CC1CCCC1] | —H | —CH₂— | 8 | A |
| 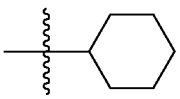 | —H | —CH₂— | 8 | A |

TABLE 2-continued
| | | | | |
|---|---|---|---|---|
| 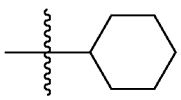 | —H | —(CH$_2$)$_2$— | 6 | B |
| 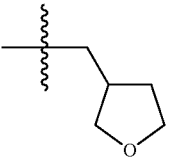 [SMILES: *CC1CCOC1] | —H | —CH$_2$— | 8 | A |
| 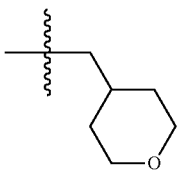 | —H | —CH$_2$— | 8<br>7 | A<br>B |
| 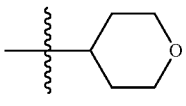 [SMILES: *C1CCOCC1] | —H | —(CH$_2$)$_2$— | 6 | B |
| 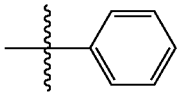 | —H | —CH$_2$— | 1 | A + B |
| 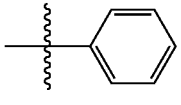 | —H | —(CH$_2$)$_2$— | 6 | A + B |
| 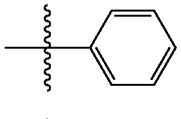 | —CH$_3$ | —(CH$_2$)$_2$— | 6 | A + B |
| 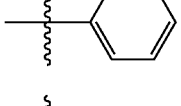 | —CF$_3$ | —(CH$_2$)$_2$— | 4 | B |
| 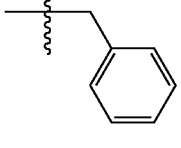 | —H | —CH$_2$— | 8 | A + B |
| 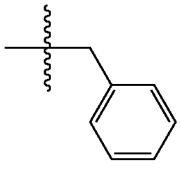 [SMILES: *Cc1ccccc1] | —H | —(CH$_2$)$_2$— | 7 | B |
| 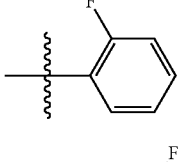 | —H | —CH$_2$— | 1 | A |
| 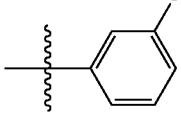 | —H | —CH$_2$— | 1 | A |

TABLE 2-continued

| Structure | R | Linker | n | Type |
|---|---|---|---|---|
| 4-F-phenyl | —CH₃ | —(CH₂)₂— | 4 | A + B |
| 4-F-phenyl | —H | —(CH₂)₂— | 1<br>6 | A<br>B |
| 4-F-phenyl | —H | —CH₂(CH₃)₂— | 11 | A + B |
| 4-F-phenyl | —CF₃ | —(CH₂)₂— | 4 | A + B |
| 2-methyl-phenyl | —H | —CH₂— | 1 | A |
| 3-methyl-phenyl | —H | —CH₂— | 1 | A |
| 3-CF₃-phenyl | —H | —CH₂— | 1 | A + B |
| 3-OMe-phenyl | —H | —(CH₂)₂— | 1 | A |
| 2,4-di-F-phenyl | —H | —CH₂— | 1 | A |
| 2,4-di-F-phenyl | —H | —(CH₂)₂— | 1<br>6 | A<br>B |
| 2,5-di-F-phenyl | —H | —CH₂— | 1 | A |

TABLE 2-continued
| | | | | |
|---|---|---|---|---|
| 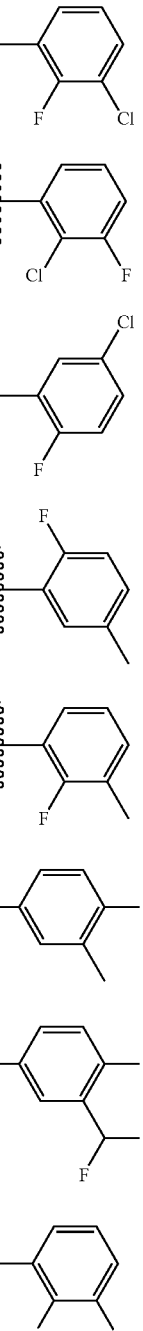 | —H | —CH$_2$— | 1 | A |
| 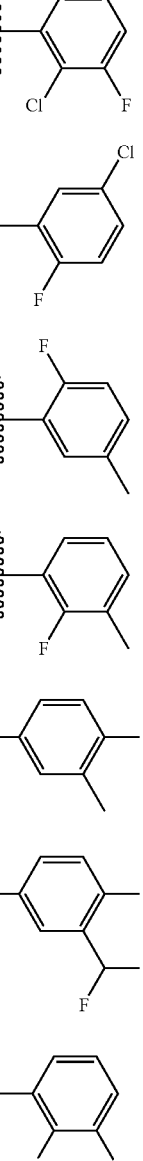 | —H | —CH$_2$— | 1 | A |
| 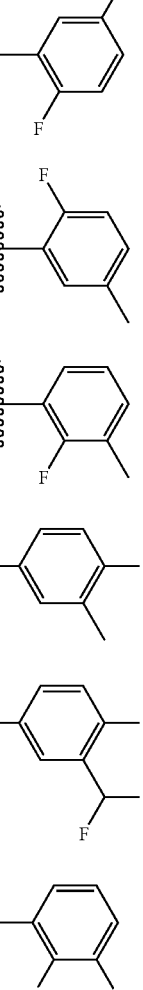 | —H | —CH$_2$— | 1 | A |
| 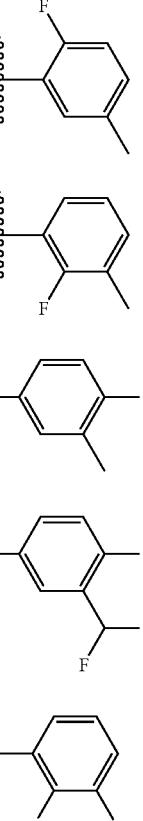 | —H | —CH$_2$— | 1 | A |
| 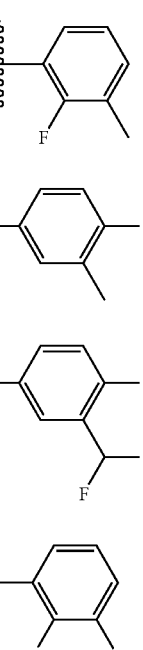 | —H | —CH$_2$— | 1 | A |
| 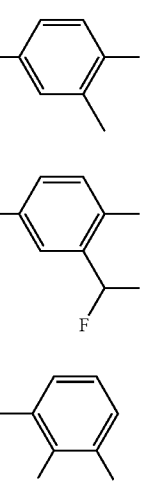 | —H | —CH$_2$— | 1 | A |
| 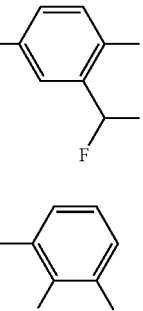 | —H | —CH$_2$— | 1 | A |
| 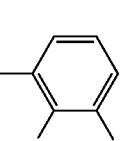 | —H | —CH$_2$— | 1 | A |
| | —H | —CH$_2$— | 1 | A |
| | —H | —CH$_2$— | 1 | A |

TABLE 2-continued
| Structure | | | | |
|---|---|---|---|---|
| 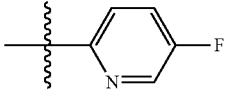 | —H | —CH$_2$— | 1 | A + B |
| 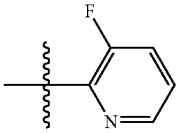 [SMILES: *c1ccccc1F] | —H | —CH$_2$— | 1 | A |
| 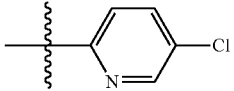 | —H | —(CH$_2$)$_2$— | 1 | A |
| 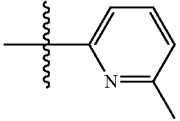 | —H | —CH$_2$— | 1 | A |
| 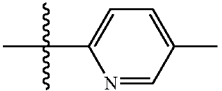 | —H | —CH$_2$— | 1 | A |
| 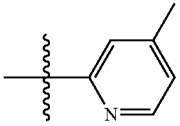 [SMILES: *c1cc(C)ccn1] | —H | —CH$_2$— | 1 | A |
| 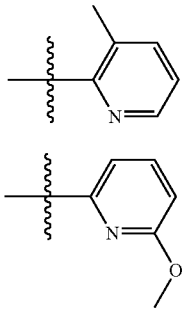 | —H | —CH$_2$— | 1 | A |
| 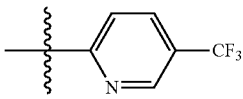 [SMILES: *c1ccc(C(F)(F)F)cn1] | —H | —CH$_2$— | 1 | A |
| 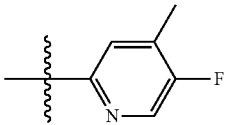 [SMILES: *c1cc(C)c(F)cn1] | —H | —CH$_2$— | 1 | A |
| 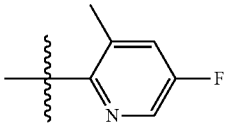 [SMILES: *c1ncc(F)cc1C] | —H | —CH$_2$— | 1 | A |
| 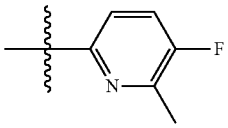 [SMILES: *c1ccc(F)c(C)n1] | —H | —CH$_2$— | 1 | A |
|  | —H | —CH$_2$— | 1 | A + B |

TABLE 2-continued

| Structure | R | Linker | n | Activity |
|---|---|---|---|---|
| 3-F, 5-F pyridin-2-yl | —H | —(CH$_2$)$_2$— | 8 | A |
| pyridin-3-yl | —H | —CH$_2$— | 1 | A |
| pyridin-3-yl | —H | —(CH$_2$)$_2$— | 1 | A + B |
| 5-F pyridin-3-yl | —H | —CH$_2$— | 1 | A |
| 5-F pyridin-3-yl | —H | —(CH$_2$)$_2$— | 1 | A |
| 5-methyl pyridin-3-yl | —H | —CH$_2$— | 1 | A |
| 6-methyl pyridin-3-yl | —H | —CH$_2$— | 1 | A |
| 6-CF$_3$ pyridin-3-yl | —H | —CH$_2$— | 1 | A |
| 6-CF$_3$ pyridin-3-yl | —H | —(CH$_2$)$_2$— | 1 | A |
| 4-methyl-5-F pyridin-3-yl | —H | —CH$_2$— | 1 | A |
| 5-F, 2-methyl pyridin-3-yl | —H | —CH$_2$— | 1 | A |
| 5-F, 2-methoxy pyridin-3-yl | —H | —CH$_2$— | 1 | A |

TABLE 2-continued

| Structure | R | Linker | n | Activity |
|---|---|---|---|---|
| 3-F, 2-OMe pyridin-5-yl | —H | —(CH$_2$)$_2$— | 1 | A |
| 3-F, 2-OMe pyridin-5-yl | —H | —CH$_2$— | 1 | A + B |
| 3-F, 2-Me pyridin-5-yl | —H | —CH$_2$— | 1 | A + B |
| 2-CN pyridin-5-yl | —H | —CH$_2$— | 1 | A + B |
| pyridin-4-yl | —H | —CH$_2$— | 1 | A |
| pyridin-4-yl | —H | —(CH$_2$)$_2$— | 1 | A |
| 2,6-diMe pyridin-4-yl | —H | —CH$_2$— | 1 | A |
| 2-Me pyridin-4-yl | —H | —CH$_2$— | 1 | A + B |
| 2-Me pyridin-4-yl | —H | —(CH$_2$)$_2$— | 1 | A |
| 2-CF$_3$ pyridin-5-yl | —H | —(CH$_2$)$_2$— | 1 | A |
| 3-F pyridin-4-yl | —H | —(CH$_2$)$_2$— | 1 | A |

TABLE 2-continued
| Structure | | | | |
|---|---|---|---|---|
| 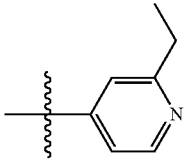 | —H | —CH$_2$— | 1 | A |
| 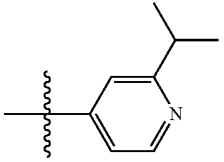 | —H | —CH$_2$— | 1 | A |
| 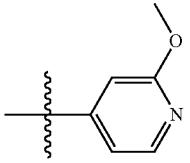 [SMILES: *c1ccnc(OC)c1] | —H | —CH$_2$— | 1 | A + B |
| 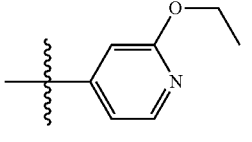 [SMILES: *c1ccnc(OCC)c1] | —H | —CH$_2$— | 1 | A |
| 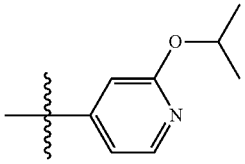 [SMILES: *c1ccnc(OC(C)C)c1] | —H | —CH$_2$— | 1 | A |
| 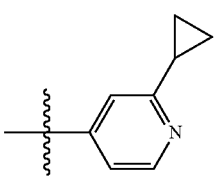 [SMILES: *c1ccnc(C2CC2)c1] | —H | —CH$_2$— | 1 | A |
| 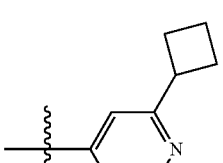 | —H | —CH$_2$— | 1 | A |
| 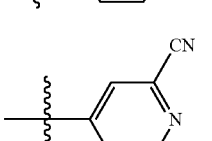 | —H | —CH$_2$— | 1 | A |
| 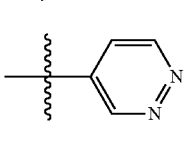 | —H | —CH$_2$— | 1 | A + B |
| 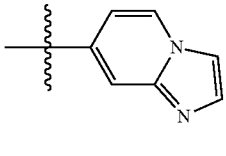 [SMILES: *c1ccn2ccnc2c1] | —H | —CH$_2$— | 1 | A |

TABLE 2-continued

| Structure | | | | |
|---|---|---|---|---|
| imidazo[1,2-a]pyridin-5-yl | —H | —CH₂— | 1 | B |
| 1-methyl-1H-pyrazol-4-yl | —H | —CH₂— | 1 | A |
| 1,2-dimethyl-1H-imidazol-5-yl | —H | —CH₂— | 1 | A + B |
| 1-methyl-1H-pyrazol-5-yl | —H | —CH₂— | 1 | A |
| 1-methyl-1H-imidazol-5-yl | —H | —CH₂— | 1 | A + B |
| 1,3,5-trimethyl-1H-pyrazol-4-yl | —H | —CH₂— | 1 | A |

Intermediate 18:
2-Isopropoxy-5-(methylsulfonyl)benzoic acid.

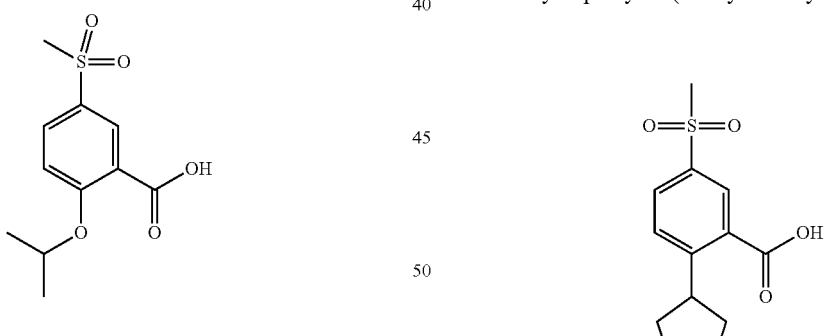

To a 500 mL round-bottomed flask were added sodium hydride (60% dispersion in mineral oil, 2.75 g, 68.7 mmol) and isopropanol (100 mL). The mixture was heated to 110° C. and stirred for 10 minutes. Then, the mixture was cooled to 70° C. and 2-fluoro-5-(methylsulfonyl)benzoic acid (3.0 g, 13.75 mmol) was added in one portion. Heating and stirring were continued for 7 h. Solvents were removed under reduced pressure and resulting solids were taken up in water (150 mL). The resulting aqueous mixture was acidified to pH 1 using conc. HCl and extracted with ethyl acetate (2×100 mL). The combined organic layers were dried over sodium sulfate, filtered and evaporated to afford the title compound (2.9 g, 82%). $^1$H NMR (400 MHz, DMSO-d$_6$) δ=13.00 (br s, 1H), 8.06 (d, J=2.7 Hz, 1H), 7.95 (dd, J=2.3, 9.0 Hz, 1H), 7.36 (d, J=9.0 Hz, 1H), 4.81 (td, J=6.1, 12.1 Hz, 1H), 3.18 (s, 3H), 1.29 (d, J=6.3 Hz, 6H).

Intermediate 19:
2-Cyclopentyl-5-(methylsulfonyl)benzoic acid.

Step A. Methyl 2-bromo-5-(methylsulfonyl)benzoate. A mixture of 2-bromo-5-(methylsulfonyl)benzoic acid (500 mg, 1.79 mmol), iodomethane (0.167 mL, 2.69 mmol), and K$_2$CO$_3$ (372 mg, 2.69 mmol) in DMF (9 mL) was stirred at 23° C. for 1 h. The reaction mixture was diluted with EtOAc, washed with water, brine, and dried (MgSO$_4$). The organic layer was concentrated under reduced pressure to provide the title compound (462 mg, 88%) as an amorphous solid. $^1$H NMR (400 MHz, DMSO-d$_6$) δ=8.27 (d, J=2 Hz, 1H), 8.08 (d, J=8 Hz, 1H), 7.99 (ddd, J=8, 2, 0.5 Hz, 1H), 3.91 (s, 6H); [M+H]=293.1/295.1.

Step B. Methyl 2-(cyclopent-1-en-1-yl)-5-(methylsulfonyl)benzoate. A mixture of methyl 2-bromo-5-(methylsulfonyl)benzoate (709 mg, 2.42 mmol), cyclopenten-1-ylboronic acid pinacol ester (704 mg, 3.63 mmol), Pd(dppf)Cl₂ (99 mg, 0.12 mmol), and K₂CO₃ (1.00 g, 7.26 mmol) in a combination of dioxane (6 mL), ethanol (4 mL) and water (2 mL) was stirred at 110° C. for 30 min. The reaction mixture was then diluted with EtOAc, washed with water, brine, dried (MgSO₄) and concentrated under reduced pressure. Purification (FCC, SiO₂, 10-40% EtOAc /hexanes) provided the title compound (590 mg, 87%) as a gum. $^1$H NMR (400 MHz, DMSO-d₆) δ=8.10 (d, J=2 Hz, 1H), 8.02 (dd, J=8, 2 Hz, 1H), 7.64 (d, J=8 Hz, 1H), 5.91 (t, J=2 Hz, 1H), 3.84 (s, 3H), 3.27 (s, 3H), 2.4-2.5 (m, 4H), 1.97 (m, 2H); [M+H]=281.2.

Step C. Methyl 2-cyclopentyl-5-(methylsulfonyl)benzoate. A mixture of methyl 2-(cyclopent-1-en-1-yl)-5-(methylsulfonyl)benzoate (590 mg, 2.10 mmol) and 10% Pd(OH)₂ on carbon (200 mg, 0.14 mmol) in methanol (20 mL) was shaken on a Parr hydrogenator under 55 psi H₂ at 23° C. for 16 h. The reaction was then filtered through CELITE®, and concentrated under reduced presssure to provide the title compound (530 mg, 89%) as an amorphous solid. $^1$H NMR (400 MHz, DMSO-d₆) δ=8.13 (d, J=2 Hz, 1H), 8.03 (dd, J=8, 2 Hz, 1H), 7.77 (d, J=8 Hz, 1H), 3.88 (s, 3H), 3.63 (quin, J=8 Hz, 1H), 3.25 (s, 3H), 2.0-2.1 (m, 2H), 1.7-1.9 (m, 2H), 1.5-1.7 (m, 4H); [M+H]=283.2.

Step D. 2-Cyclopentyl-5-(methylsulfonyl)benzoic acid. A mixture of methyl 2-cyclopentyl-5-(methylsulfonyl)benzoate (528 mg, 1.87 mmol), dioxane (11.2 mL), and of 0.5 M aq. NaOH (11.2 mL, 5.6 mmol) was stirred at 23° C. for 2 h. The reaction was then diluted with water, and extracted with EtOAc and this organic extract was discarded. The aqueous layer was acidified to pH 2 with 1 N HCl, and then extracted with EtOAc. The combined organic extracts were dried (MgSO₄) and concentrated under reduced pressure to provide the title compound (449 mg, 89%) as a white solid. $^1$H NMR (400 MHz, DMSO-d₆) δ 8.12 (d, J=2 Hz, 1H), 7.99 (dd, J=8, 2 Hz, 1H), 7.74 (d, J=8 Hz, 1H), 3.75 (quin, J=8 Hz, 1H), 3.24 (s, 3H), 2.0-2.1 (m, 2H), 1.8-1.9 (m, 2H), 1.6-1.7 (m, 4H).

Intermediate 20: (S)-2-Methoxy-3-(methylsulfonyl)-6-((1,1,1-trifluoropropan-2-yl)oxy)benzoic acid.

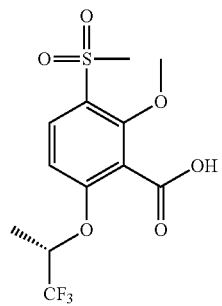 [SMILES: COc1c(S(C)(=O)=O)ccc(O[C@@H](C)C(F)(F)F)c1C(=O)O]

Step A. 3-(Chlorosulfonyl)-2,6-difluorobenzoic acid. 2,6-Difluorobenzoic acid (230 g, 1.455 mol) in ClSO₃H (700 mL, 10.2 mol) was stirred at 120° C. for 2 h. The mixture was poured into ice and stirred for 20 minutes. The slurry was filtered. The filter cake was dissolved with DCM, dried (Na₂SO₄) and concentrated under reduced pressure to give the title compound (200 g, 54%) as gray solid. $^1$H NMR (400 MHz, CD₃OD) δ=8.192-8.247 (m, 1H), 7.34-7.42 (m, 1 H).

Step B. 2,6-Difluoro-3-hydrosulfonylbenzoic acid. 3-(Chlorosulfonyl)-2,6-difluorobenzoic acid (122 g, 0.476 mol) was added to a solution of Na₂SO₃ (1420 g, 3.33 mol) in water (2 L) and stirred for 3 hours. The clear reaction mixture was then cooled to 0° C. and acidified by the addition of 20% sulfuric acid solution until reaching pH 2. Water was evaporated under vacuum, and then MeOH (60 mL) was added and stirred for 1 h. The suspension was filtered and the filtrate evaporated and dried under reduced pressure. The resulting title compound was used to the next step without further purification.

Step C. Methyl 2,6-difluoro-3-(methylsulfonyl)benzoate. To a solution of crude 2,6-difluoro-3-hydrosulfonylbenzoic acid (174 g) in DMF (1.75 L) was added MeI (83 mL, 1.3 mol) and K₂CO₃ (156 g, 1.13 mol), and the reaction was stirred at room temperature overnight. The mixture was poured into ice-water and stirred for 10 minutes. The slurry was filtered, washed with water and dried overnight under vacuum to afford the title compound (54 g, 57%) as white solid: $^1$H NMR (400 MHz, CDCl₃) δ 8.09-8.10 (m, 1H), 7.13-7.18 (m, 1H), 3.99 (s, 3H), 3.23 (s, 3H).

Step D. Methyl 2-fluoro-3-(methylsulfonyl)-6-((1,1,1-trifluoropropan-2-yl)oxy)benzoate. To a mixture of methyl 2,6-difluoro-3-(methylsulfonyl)benzoate (65 g, 0.26 mol) and Cs₂CO₃ (255 g, 0.78 mol) in THF (1.3 L) was added 1,1,1-trifluoropropan-2-ol (29.6 g, 0.26 mol) at 0° C. Then the resulting mixture was stirred at room temperature overnight. The mixture was poured into ice-water and extracted with EtOAc. The organic layers were separated and washed with brine, dried over Na₂SO₄, filtered, and concentrated to give the crude product. Purification (FCC, SiO₂) afforded the title compound (20 g, 22.4%) as brown oil. $^1$H NMR (400 MHz, CDCl₃) δ=7.89-7.93 (m, 1H), 6.85-6.87 (d, J=8.8 Hz, 1H), 4.71-4.80 (m, 1H), 3.88 (s, 3H), 3.13 (s, 3H), 1.48-1.49 (d, J=6.0 Hz, 3 H).

Step E. Methyl 2-methoxy-3-(methylsulfonyl)-6-((1,1,1-trifluoropropan-2-yl)oxy)benzoate. To a mixture of methyl 2-fluoro-3-(methylsulfonyl)-6-((1,1,1-trifluoropropan-2-yl)oxy)benzoate (25 g, 72.61 mmol) and MeOH (3.25 g, 101.65 mmol) in THF (250 mL) was added NaH (7 g, 174.3 mmol) at 0° C. Then the resulting mixture was stirred at 0° C. for 5 min. The mixture was poured into ice-water and extracted with EtOAc, the organic layer was separated and collected. The collected organic layers were washed with brine, dried (Na₂SO₄), filtered, and concentrated to give the crude product. The crude material was purified (FCC, SiO₂) to afford the title compound (20 g, 77%) as white solid. $^1$H NMR (400 MHz, CDCl₃) δ=8.01-8.03 (d, J=8.8 Hz, 1H), 6.83-6.86 (d, J=8.8 Hz, 1H), 4.74-4.83 (m, 1H), 4.05 (s, 3H), 3.97 (s, 3H), 3.32 (s, 3H), 1.55-1.56 (d, J=6.4 Hz 3H). Note: Methyl 2-methoxy-3-(methylsulfonyl)-6-((1,1,1-trifluoropropan-2-yl)oxy)benzoate was separated by SFC to (S)-methyl 2-methoxy-3-(methylsulfonyl)-6-((1,1,1-trifluoropropan-2-yl)oxy)benzoate and (R)-methyl 2-methoxy-3-(methylsulfonyl)-6-((1,1,1-trifluoropropan-2-yl)oxy)benzoate.

Step F. (S)-2-Methoxy-3-(methylsulfonyl)-6-((1,1,1-trifluoropropan-2-yl)oxy)benzoic acid. To a solution of (S)-methyl 2-methoxy-3-(methylsulfonyl)-6-((1,1,1-trifluoropropan-2-yl)oxy)benzoate (peak 2) (10 g, 28.1 mmol) in MeOH (100 mL) and H₂O (50 mL) was added LiOH a.q.(140 mL, 140 mmol). Then the mixture was stirred and heated to reflux overnight. Then the mixture was extracted with EtOAc, the aqueous phase was separated and acidified by the addition of diluted hydrochloric acid to pH=~2. Then the mixture was extracted with EtOAc, the organic layer was separated and collected. The collected organic layers were washed with brine, dried (Na₂SO₄), filtered, and concentrated to give the title compound (7 g, 73%) as white solid. ¹H NMR (400 MHz, CDCl₃) δ=8.03-8.05 (d, J=8.8 Hz, 1H), 6.86-6.89 (d, J=8.8 Hz, 1H), 4.77-4.86 (m, 1H), 4.11 (s, 3H), 3.22 (s, 3H), 1.56-1.57 (d, J=6.4 Hz 3 H).

Intermediate 21: (R)-2-Methoxy-3-(methylsulfonyl)-6-((1,1,1-trifluoropropan-2-yl)oxy)benzoic acid.

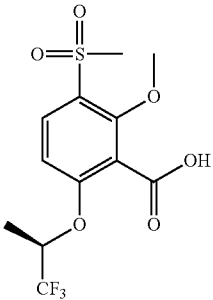 [SMILES: COc1c(S(C)(=O)=O)ccc(O[C@H](C)C(F)(F)F)c1C(=O)O]

The title compound was prepared in a manner analogous to Intermediate 20, substituting (R)-2-methoxy-3-(methylsulfonyl)-6-((1,1,1-trifluoropropan-2-yl)oxy)benzoic acid (peak1) in step F.

Intermediate 22: 3-Cyano-2-methoxy-6-(4-fluorotetrahydropyran-4-yl)benzoic acid.

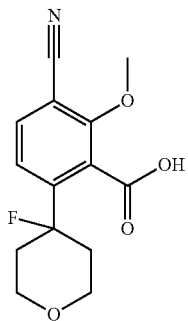 [SMILES: COc1c(C#N)ccc(C2(F)CCOCC2)c1C(=O)O]

Step A. 4-(4-Bromo-3-fluorophenyl)tetrahydro-2H-pyran-4-ol (2). To a solution of 4-bromo-3-fluoroiodobenzene (40.00 g, 133 mmol) in THF (400 mL) at −78° C. was added 2 M solution of i-PrMgCl in THF (73 mL, 146 mmol) and the mixture was stirred 40 min at −78° C. To this mixture was added via cannula needle over a period of about 5 minutes a solution of tetrahydro-4H-pyran-4-one (13.5 mL, 146 mmol) in THF (100 mL). The resulting mixture stirred for 30 min at −78° C. and then 1 h at 0° C. The resulting mixture was diluted with 1 M aq. NH₄Cl (200 mL) and extracted into EtOAc (2×300 mL). The organic extract was washed with brine, dried (MgSO₄) and concentrated under reduced pressure. Purification (FCC, SiO₂, 10-40% EtOAc/hexane) provided the title compound (18.9 g, 52%) as a tan solid. ¹H NMR (400 MHz, CDCl₃) δ=7.54 (dd, J=8.4, 7.2 Hz, 1H), 7.29 (dd, J=10, 2 Hz, 1H), 7.15 (dd, J=8.4, 2.4 Hz, 1H), 3.88-3.91 (m, 4H), 2.08-2.13 (m, 2H), 1.64 (dd, J=15, 1 Hz, 1H), 1.64 (s, 1H); ¹⁹F NMR (376 MHz, CDCl₃) δ=−106.76 (dd, J=10.2, 7.9 Hz, 1F).

Step B. 4-(4-Bromo-3-fluorophenyl)-4-fluorotetrahydro-2H-pyran. To XtalFluor-E (23.6 g, 103.1 mmol) in CH₂Cl₂ (170 mL) at 0° C. was added of triethylamine trihydrofluoride (22.5 mL, 137.4 mmol) and triethylamine (9.8 mL, 68.7 mmol) and the mixture stirred for 5 min at 0° C. when a homogeneous solution formed. This mixture was cooled to −78° C. and 4-(4-bromo-3-fluorophenyl)tetrahydro-2H-pyran-4-ol (18.9 g, 68.7 mmol) as a solution in DCM (170 mL) precooled to −78° C. was added via cannula needle. The resulting mixture was then stirred 1 h at 0° C. and then 1M aqueous NaHCO₃ (400 mL) was carefully added and stirred for 30 min until gas generation had ceased and pH was ≥6. The organic layer was separated and washed with 0.3 M NaClO₄ (400 mL) and brine (300 mL). The combined organics were dried (MgSO₄) and concentrated under reduced pressure to 300 mL. To this solution was added KHCO₃ (4.13 g, 41.2 mmol) and m-CPBA (5.93 g, 34.4 mmol) and the mixture stirred for 30 min at rt (conversion of alkene by-products to the corresponding epoxide for ease in purification). The mixture was washed with water, aqueous 1 M Na₂SO₃, and the combined organic layers were dried (MgSO₄), and concentrated under reduced pressure. Purification (FCC, SiO₂, 5-20% EtOAc/hexanes) provided the title compound (16.7 g, 88%) as a tan solid (HPLC purity 93%). ¹H NMR (400 MHz, CDCl₃) δ=7.56 (dt, J=7.8, 0.6 Hz, 1H), 7.18 (dd, J=9.6, 2.0 Hz, 1H), 7.04 (dd, J=8.4, 2.4 Hz, 1H), 3.95 (dd, J=11.6, 6 Hz, 2H), 3.85 (td, J=12, 2 Hz, 2H), 2.10 (dtd, J=40, 12, 5 Hz, 2H), 1.88 (dd, J=12.8, 10.8 Hz, 2H); ¹⁹F NMR (376 MHz, CDCl₃) δ=−106.42 (t, J=8.3 Hz, 1F), −160.53(tt, J=40, 9 Hz, 1F).

Step C. 3-Bromo-2-fluoro-6-(4-fluorotetrahydro-2H-pyran-4-yl)benzoic acid. To a solution of diisopropylamine (10.2 mL, 72.2 mmol) in THF (100 mL) was added 2.4 M n-butyllithium (27.6 mL, 66.2 mmol), the mixture stirred 1 min at −78° C. To this mixture at −78° C. was added 4-(4-bromo-3-fluorophenyl)-4-fluorotetrahydro-2H-pyran (16.7 g, 60.2 mmol) in THF (180 mL) chilled to −78° C. over 2 min via cannula needle. The resulting mixture stirred for 20 min at −78° C. To the resulting solution at −78° C. was added crushed solid CO₂ (8 g, 182 mmol). The reaction mixture was stirred for 10 min at −78° C. The mixture was diluted with water (500 mL) and extracted with EtOAc (2×400 mL). The aqueous layer was mixed with 4 N aq. HCl until pH 1 was obtained and then extracted EtOAc (2×200 mL). The combined organic layers were washed with brine, dried (MgSO₄), and evaporated under reduced pressure to provide the title compound (17.2 g, 89%). ¹H NMR (400 MHz, CDCl₃) δ=7.63 (ddd, J=8.4, 7.2, 1.2 Hz, 1H), 6.99 (d, J=8.4 Hz, 1H), 4.00 (dd, J=11.6, 5.2 Hz, 2H), 3.88 (td, J=12, 2 Hz, 2H), 2.23 (dtd, J=40, 12, 5 Hz, 2H), 2.10 (dd, J=12.8, 10.8 Hz, 2H); ¹⁹F NMR (376 MHz, CDCl₃) δ=108.39 (d, J=8.3 Hz, 1F), −156.43 (tt, J=40, 9 Hz, 1F).

Step D. Benzyl 3-bromo-2-fluoro-6-(4-fluorotetrahydro-2H-pyran-4-yl)benzoate. A mixture of 3-bromo-2-fluoro-6-(4-fluorotetrahydro-2H-pyran-4-yl)benzoic acid (17.2 g, 53.6 mmol), benzyl bromide (8.3 mL, 69.7 mmol) and triethylamine (11.5 mL, 80.5 mmol) in dioxane (270 mL) was stirred at rt for 96 h, then at 90° C. for 10 h. Additional benzyl bromide (2.2 mL, 19 mmol) and TEA (3.8 mL, 27 mmol) were added and the mixture heated at 90° C. for 16 h. Additional benzyl bromide (2.2 mL, 19 mmol) and TEA (3.8 mL, 27 mmol) were added and the mixture heated at 90° C. for 3 h. The mixture was diluted with EtOAc (300 mL) and washed with water (2×500 mL), and brine. The combined organics were dried (MgSO₄) and concentrated under reduced pressure. Purification (FCC, SiO₂, 10-33% EtOAc/hexanes) to provide the title compound (18.7 g, 85%) as a white solid. ¹H NMR (400 MHz, CDCl₃) δ=7.58 (ddd, J=8.4, 7.2, 1.6 Hz, 1H), 7.3-7.4 (m, 5H), 6.91 (dt, J=8.4, 1.2

Hz, 1H), 5.37 (s, 2H), 3.87 (dd, J=11.6, 5.6 Hz, 2H), 3.75 (td, J=12, 2.4 Hz, 2H), 2.12 (dtd, J=40, 12, 5 Hz, 2H), 2.00 (dd, J=12.8, 10.8 Hz, 2H); $^{19}$F NMR (376 MHz, CDCl$_3$) δ=−108.70 (d, J=6.4 Hz, 1F), −157.91 (tt, J=40, 9 Hz, 1F).

Step E. Benzyl 3-cyano-2-fluoro-6-(4-fluorotetrahydro-2H-pyran-4-yl)benzoate. A mixture of benzyl 3-bromo-2-fluoro-6-(4-fluorotetrahydro-2H-pyran-4-yl)benzoate (18.7 g, 45.5 mmol), Zn(CN)$_2$ (5.87 g, 50.1 mmol), Pd$_2$(dba)$_3$ (2.09 g, 2.28 mmol), and dppf (2.52 g, 4.55 mmol) in DMF/ACN (3:1, 200 mL) was bubbled with N$_2$ for 2 min, and then stirred for 16 h at 100° C. The mixture was diluted with EtOAc (300 mL) and water (1 L), and filtered. The organic layers were separated, the aqueous layer extracted with EtOAc. The combined organic layers washed with brine, dried (MgSO$_4$) and concentrated under reduced pressure. Purification (FCC, SiO$_2$, 10-50% EtOAc/hexanes) provided the title compound (7.95 g, 49%) as a gum. $^1$H NMR (400 MHz, CDCl$_3$) δ=7.67 (ddd, 1H, J=8.4, 7.2, 1.6 Hz), 7.3-7.4 (m, 5H), 7.15 (dd, 1H, J=8.0, 0.4 Hz), 5.38 (s, 2H), 3.89 (dd, 2H, J=11.6, 5.6 Hz), 3.75 (td, 2H, J=12, 2.4 Hz), 2.12 (dtd, 2H, J=40, 12, 5 Hz), 1.99 (dd, 2H, J=12.8, 10.8 Hz); $^{19}$F NMR (376 MHz, CDCl$_3$) δ=−108.26 (d, 1F, J=6.4 Hz), −157.98 (tt, 1F, J=40, 7.5 Hz); [M+H]=358.3.

Step F. 3-Cyano-2-fluoro-6-(4-fluorotetrahydro-2H-pyran-4-yl)benzoic acid. A mixture of benzyl 3-cyano-2-fluoro-6-(4-fluorotetrahydro-2H-pyran-4-yl)benzoate (7.95 g, 22.2 mmol) and 10% Pd/C (1.10 g) in EtOAc (90 mL) was subjected to 55 psi H$_2$ in a Parr shaker for 2.5 h. The resulting mixture was filtered through CELITE®, and the filtrate was concentrated under reduced pressure to provide (5.70 g, 96%) of the title compound as a white solid. $^1$H NMR (400 MHz, CDCl$_3$) δ=7.72 (ddd, J=8.4, 7.2, 1.6 Hz, 1H), 7.26 (t, J=8.4 Hz, 1H), 4.04 (dd, J=11.6, 5.6 Hz, 2H), 3.89 (td, J=12, 2.4 Hz, 2H), 2.30 (dtd, J=40, 12, 5 Hz, 2H), 2.09 (dd, J=12.8, 10.8 Hz, 2H); $^{19}$F NMR (376 MHz, CDCl$_3$) δ=−108.17 (d, J=6.4 Hz, 1F), −156.44 (tt, J=40, 7.5 Hz, 1F).

Step G. Preparation of 3-Cyano-2-methoxy-6-(4-fluorotetrahydropyran-4-yl)benzoic acid. To a solution of 3-cyano-2-fluoro-6-(4-fluorotetrahydro-2H-pyran-4-yl)benzoic acid (5.70 g, 21.3 mmol) in MeOH (50 mL) was added 25 weight % solution of sodium methoxide in MeOH (58 mL, 213 mmol) and the resulting solution stirred for 13 h at 65° C. The resulting mixture was cooled by ice-bath and 4 N aq. HCl (60 mL, 240 mmol) was added. Then the mixture was diluted with water (200 mL) and extracted with EtOAc (3×200 mL). The organic layers were combined, dried (MgSO$_4$), and concentrated under reduced pressure to provide the title compound (5.66 g, 95%) as a tan solid. $^1$H NMR (400 MHz, CDCl$_3$) δ=7.67 (dd, J=8, 1.6 Hz, 1H), 7.11 (dd, J=8, 1.6 Hz, 1H), 4.16 (s, 3H), 4.00 (dd, J=12, 5.2 Hz, 2H), 3.87 (td, J=12, 2.0 Hz, 2H), 2.13 (dtd, J=40, 12, 5 Hz, 2H), 2.08 (dd, J=12.8, 10.8 Hz, 2H); $^{19}$F NMR (376 MHz, CDCl$_3$) δ=−157.22 (tt, J=40, 10 Hz, 1F), [M−(HF)+H]=260.3.

Intermediate 23: 3-Cyano-2-methoxy-6-(1,4,4-trifluorocyclohexyl)benzoic acid.

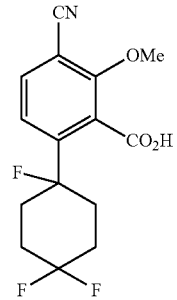

The title compound was prepared in a manner analogous to Intermediate 22, Steps A-G. $^1$H NMR (400 MHz, CDCl$_3$) δ=7.66 (dd, J=8.4, 1.6 Hz, 1H), 7.07 (dd, J=8.4, 0.8 Hz, 1H), 4.17 (s, 3H), 2.1-2.4 (m, 8H); $^{19}$F NMR (376 MHz, CDCl$_3$) δ=−93.49 (d, J=240 Hz, 1F), −104.91 (ddd, J=239, 21, 8 Hz, 1F), −158.66 (tt, J=40, 6 Hz, 1F), M−HF+H=294.3.

Intermediate 24: 3-Cyano-6-cyclobutyl-2-fluorobenzoic acid.

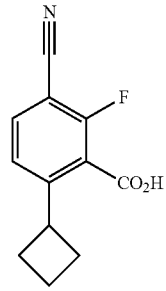 [SMILES: N#Cc1ccc(C2CCC2)c(C(=O)O)c1F]

Step A. 2-Fluoro-4-(1-hydroxycyclobutyl)benzonitrile. The title compound was prepared in a manner analogous to Intermediate 22, substituting 2-fluoro-4-iodobenzonitrile and cyclobutanone in Step A. $^1$H NMR (400 MHz, CDCl$_3$) δ=7.61 (t, J=8 Hz, 1H), 7.41 (dd, J=8, 1 Hz, 1H), 7.38 (dd, J=13, 1 Hz, 1H), 2.5-2.6 (m, 2H), 2.4-2.5 (m, 2H), 2.1-2.2 (m, 1H), 1.8-1.9 (m, 1H); [M+H]=192.1.

Step B. 2-Fluoro-4-cyclobutylbenzonitrile. To 2-Fluoro-4-(1-hydroxycyclobutyl)benzonitrile (800 mg, 4.2 mmol) in CH$_2$Cl$_2$ (10 mL) was added triethylsilane (0.8 mL, 5.02 mmol) and BF$_3$.Et$_2$O (0.65 mL, 5.23 mmol) at −78° C. After 30 min the reaction was warmed to 0° C. and stirred for 3 h. Additional triethylsilane (0.4 mL, 2.5 mmol) and BF$_3$.Et$_2$O (0.32 mL, 2.62 mmol) were added and stirring continued for 48 h at 0° C. The mixture was diluted with CH$_2$Cl$_2$ and washed with aq NaHCO$_3$. The combined organics were dried (MgSO$_4$), and concentrated under reduced pressure. Purification (FCC, SiO$_2$, 0-10% EtOAc/hexanes) provided the title compound (290 mg, 40%) as an oil. $^1$H NMR (400 MHz, CDCl$_3$) δ=7.52 (dd, J=8, 6 Hz, 1H), 7.07 (ddd, J=8, 1.2, 0.8 Hz, 1H), 7.03 (d, J=10 Hz, 1H), 3.59 (quin, J=8 Hz, 1H), 2.3-2.4 (m, 2H), 2.0-2.2 (m, 3H), 1.8-1.9 (m, 1H); [M+H]=176.1.

Step C. 3-Cyano-6-cyclobutyl-2-fluorobenzoic acid. The title compound was prepared in a manner analogous to Intermediate 22, Step C. ¹H NMR (400 MHz, CDCl₃) δ=7.95 (t, J=8 Hz, 1H), 7.44 (d, J=8 Hz, 1H), 3.73 (quin, J=8 Hz, 1H), 2.2-2.3 (m, 2H), 2.1-2.2 (m, 2H), 1.9-2.0 (m, 1H), 1.7-1.8 (m, 1H); [M+H]=220.1.

Intermediate 25: 3-Cyano-6-cyclobutylbenzoic acid.

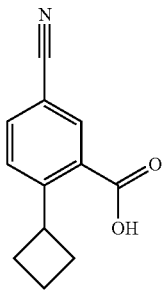 [SMILES: N#Cc1ccc(C2CCC2)c(C(=O)O)c1]

Step A. 1-(4-Bromophenyl)cyclobutanol. The title compound was prepared in a manner analogous to Intermediate 22, Step A, by substituting 1-bromo-4-iodobenzene for 4-bromo-3-fluoroiodobenzene and cyclobutanone for tetrahydro-4H-pyran-4-one.

Step B. 1-Bromo-4-cyclobutylbenzene. The title compound was prepared in a manner analogous to Intermediate 24, Step B.

Step C. 4-Cyclobutylbenzonitrile. A mixture of 1-bromo-4-cyclobutylbenzene (720 mg, 3.41 mmol), Zn(CN)₂ (600 mg, 5.12 mmol), and Pd(PPh₃)₄ (197 mg, 0.17 mmol) in DMF (10 mL) was stirred at 110° C. for 1 h. The reaction was diluted with ether, washed with water, brine, dried (MgSO₄) and concentrated under reduced pressure. Purification (SiO₂, 0-10% EtOAc/hexanes) provided the title compound (272 mg, 51%). ¹H NMR (400 MHz, CDCl₃) δ=7.57 (d, J=8 Hz, 1H), 7.29 (d, J=8 Hz, 1H), 3.59 (quin, J=8 Hz, 1H), 2.3-2.4 (m, 2H), 2.0-2.2 (m, 3H), 1.8-1.9 (m, 1H); [M+H]=158.2.

Step D. 3-Bromo-4-cyclobutylbenzonitrile. To a mixture of 4-cyclobutylbenzonitrile (272 mg, 1.73 mmol) in of 50% aqueous H₂SO₄ (4 mL) was added NBS (462 mg, 2.6 mmol) and the mixture stirred for 18 h at 23° C. The mixture was diluted with ether, washed with water, aq NaHCO₃, dried (MgSO₄) and concentrated under reduced pressure. Purification (SiO₂, 0-15% EtOAc/hexanes) provided the title compound (266 mg, 65%). ¹H NMR (400 MHz, CDCl₃) δ=7.79 (d, J=2 Hz, 1H), 7.58 (dd, J=8, 2 Hz, 1H), 7.40 (d, J=8 Hz, 1H), 3.77 (quin, J=9 Hz, 1H), 2.4-2.5 (m, 2H), 2.0-2.2 (m, 3H), 1.8-1.9 (m, 1H); [M+H]=236.0/238.0.

Step E. 3-Cyano-6-cyclobutylbenzoic acid. A mixture of 3-bromo-4-cyclobutylbenzonitrile (168 mg, 0.71 mmol), molybdenumhexacarbonyl (94 mg, 0.36 mmol), trans-bis (acetato)bis[o-(di-o-tolylphosphino)benzyl]dipalladium(II) (33 mg, 0.036 mmol), diisopropylethylamine (0.62 mL, 3.55 mmol) and water (7 mL) was microwave heated at 150° C. for 10 min. The reaction mixture was then filtered over CELITE®, diluted with 1 M aqueous NaHCO₃ (5 mL) and extracted with EtOAc. The pH of the aqueous layer was lowered to pH 1 with 1 M HCl and extracted with ether. The ether extract was washed with brine, dried (MgSO₄) and concentrated under reduced pressure to provide the title compound (73 mg, 51%) as a white solid. ¹H NMR (400 MHz, CDCl₃) δ=8.23 (d, J=2 Hz, 1H), 7.80 (dd, J=8, 2 Hz, 1H), 7.58 (d, J=8 Hz, 1H), 4.31 (quin, J=9 Hz, 1H), 2.4-2.5 (m, 2H), 2.0-2.2 (m, 3H), 1.8-1.9 (m, 1H); [M+H]=202.1.

Intermediate 26: 3-Cyano-6-(1-deuteriocyclopentyl)benzoic acid.

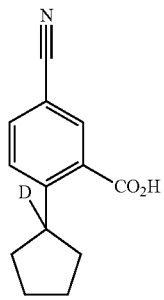 [SMILES: [2H]C1(c2ccc(C#N)cc2C(=O)O)CCCC1]

Step A. 1-(4-Bromophenyl)cyclopentanol. To a solution of 1-bromo-4-iodobenzene (10.00 g, 35.3 mmol) in THF (40 mL) at −78° C. was added 2 M solution of i-PrMgCl in THF (18.5 mL, 37.1 mmol) and the mixture was stirred 40 min at −78° C. To this mixture was added via cannula needle over a period of about 5 minutes a solution of cyclopentanone (3.3 mL, 37.1 mmol) in THF (10 mL). The resulting mixture stirred for 30 min at −78° C. and then 1 h at 0° C. The resulting mixture was diluted with 1 M aq. NH₄Cl and extracted into EtOAc. The organic extract was washed with brine, dried (MgSO₄) and concentrated under reduced pressure. Purification (FCC, SiO₂, 10-40% EtOAc/hexanes) provided the title compound (2.18 g, 20%) as an oil. ¹H NMR (400 MHz, DMSO-d₆) δ=7.48 (d, J=8 Hz, 1H), 7.42 (d, J=8 Hz, 1H), 4.88 (s, OH, confirmed by D₂O exchange, 1H), 1.7-1.9 (m, 8H), LCMS found M−H₂O+H =223/225.

Step B. 1-Bromo-4-(1-deuteriocyclopentyl)benzene. To 1-(4-bromophenyl)cyclopentanol (2.69 g, 11.2 mmol) in CH₂Cl₂ (45 mL) was added triethylsilane-d (2.0 mL, 12.9 mmol) and BF₃.Et₂O (1.7 mL, 14 mmol) at −78° C. The reaction mixture was stirred for 1 h at −78° C. The mixture was diluted with DCM and washed with aq NaHCO₃, dried (MgSO₄), and concentrated under reduced pressure. To the residue in CH₂Cl₂ (40 mL) at 0° C. was added KHCO₃ (1.7 g, 16.8 mmol) and m-CPBA (2.9 g, 16.8 mmol). Then the mixture was stirred at 23° C. for 1 h. [Note: this step converted alkene byproduct into an epoxide which was separated from the desired product by SiO₂ chromatography]. Then the mixture was washed with water, aqueous 1 M Na₂SO₃, 1 M NaHCO₃, dried (MgSO₄) and concentrated under reduced pressure. Purification (FCC, SiO₂, hexanes) provided the title compound (293 mg, 12%) as an oil. ¹H NMR (400 MHz, CDCl₃) δ=7.39 (d, J=8 Hz, 2H), 7.02 (d, J=8 Hz, 2H), 1.9-2.0 (m, 2H), 1.7-1.8 (m, 2H), 1.6-1.7 (m, 2H), 1.4-1.5 (m, 2H).

Step C. 3-Cyano-6-(1-deuteriocyclopentyl)benzoic acid. The title compound was prepared in a manner analogous to Intermediate 25, Steps C, D, and E from 1-bromo-4-(1-deuteriocyclopentyl)benzene.

Intermediate 27: 3-Cyano-2-fluoro-6-(1-methoxycyclobutyl)benzoic acid, and 2-Cyano-3-fluoro-5-(1-methoxycyclobutyl)benzoic acid.

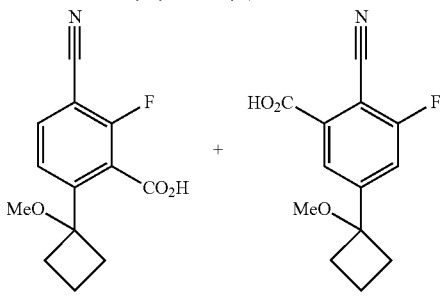

Step A. 2-Fluoro-4-(1-hydroxycyclobutyl)benzonitrile. The title compound was prepared in a manner analogous to Intermediate 22, substituting 2-fluoro-4-iodobenzonitrile and cyclobutanone in Step A.

Step B. 2-Fluoro-4-(1-methoxycyclobutyl)benzonitrile. 2-Fluoro-4-(1-hydroxycyclobutyl)benzonitrile (600 mg, 3.14 mmol) in DMF (8 mL) was added via cannula needle to sodium hydride (157 mg of a 60% suspension in oil, prewashed with hexanes and dried under vacuum, 3.92 mmol) suspended in DMF (8 mL) at 0° C. The reaction was stirred for 5 min and iodomethane (0.24 mL, 3.92 mmol) was added and stirred 3 h at 23° C. The mixture was diluted with EtOAc, washed with water and brine. The combined organics were dried (MgSO$_4$), and concentrated under reduced pressure. Purification (FCC, SiO$_2$, 0-10% EtOAc/hexanes) provided the title compound (376 mg, 59%) as an oil. $^1$H NMR (400 MHz, CDCl$_3$) δ=7.63 (dd, J=8 Hz, 6.4 Hz, 1H), 7.34 (dd, J=8, 1.6 Hz, 1H), 7.29 (dd, J=10, 1.6 Hz, 1H), 2.96 (s, 3H), 2.4-2.5 (m, 2H), 2.3-2.4 (m, 2H), 1.9-2.0 (m, 1H), 1.6-1.8 (m, 1H); [M−H]=206.2.

Step C. 3-Cyano-2-fluoro-6-(1-methoxycyclobutyl)benzoic acid and 2-Cyano-3-fluoro-5-(1-methoxycyclobutyl)benzoic acid. The title compounds were prepared from 2-fluoro-4-(1-methoxycyclobutyl)benzonitrile in a manner analogous to Intermediate 22, Step C, substituting 2,2,6,6-tetramethylpiperidine for diisopropylamine which provided a 1:1 mixture of compounds the title compounds. 3-Cyano-2-fluoro-6-(1-methoxycyclobutyl)benzoic acid. $^1$H NMR (400 MHz, CDCl$_3$) δ=7.73 (dd, J=8, 6 Hz, 1H), 7.38 (d, J=8 Hz, 1H), 3.04 (s, 3H), 2.5-2.6 (m, 3H), 2.3-2.4 (m, 1H), 1.9-2.1 (m, 1H), 1.7-1.8 (m, 1H); [M+H]=250.2. 2-Cyano-3-fluoro-5-(1-methoxycyclobutyl)benzoic acid: $^1$H NMR (400 MHz, CDCl$_3$) δ=8.12 (d, J=1.6 Hz, 1H), 7.57 (dd, J=9, 1.6 Hz, 1H), 3.01 (s, 3H), 2.5-2.6 (m, 3H), 2.3-2.4 (m, 1H), 1.9-2.1 (m, 1H), 1.7-1.8 (m, 1H).

Intermediate 28: 3-Cyano-6-(1-fluorocyclobutyl)-2-methoxybenzoic acid.

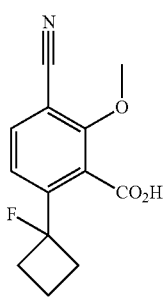

The title compound was prepared in a manner analogous to Intermediate 22, Steps A, B, C and G, substituting 2-fluoro-4-iodobenzonitrile and cyclobutanone in Step A. $^1$H NMR (400 MHz, CDCl$_3$) δ=7.70 (dd, J=8, 1.6 Hz, 1H), 7.27 (dd, J=8.4, 1.2 Hz, 1H), 2.6-2.8 (m, 4H), 2.1-2.2 (m, 1H), 1.7-1.9 (m, 1H); $^1$H NMR (376 MHz, CDCl$_3$) δ=−126.83 (ddd, J=39, 22, 17 Hz, 1F); [M+H]=192.1.

Intermediate 29: 3-Cyano-2-fluoro-6-(3-fluorooxetan-3-yl)benzoic acid.

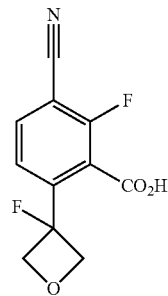 [SMILES: N#Cc1ccc(C2(F)COC2)c(C(=O)O)c1F]

Step A. 2-Fluoro-4-(3-hydroxyoxetan-3-yl)benzonitrile. The title compound was prepared in a manner analogous to Intermediate 22, Step A, from 2-fluoro-4-iodobenzonitrile and 3-oxetanone. $^1$H NMR (400 MHz, DMSO-d$_6$) δ=7.98 (t, J=8 Hz, 1H), 7.6-7.7 (m, 1H), 7.66 (d, J=8 Hz, 1H), 4.79 (d, J=6 Hz, 1H), 4.67 (d, J=6 Hz, 2H); [M+H]=194.1.

Step B. 2-Fluoro-4-(3-fluorooxetan-3-yl)benzonitrile. To 2-Fluoro-4-(3-hydroxyoxetan-3-yl)benzonitrile (770 mg, 4.0 mmol) in CH$_2$Cl$_2$ (40 mL) at −78° C. was added DAST (0.79 mL, 5.9 mmol). The mixture was stirred at −78° C. for 30 min and then at 0° C. for 1 h. The mixture was diluted with DCM and washed with aq 1 M NaHCO$_3$ for 5 min, then dried (MgSO$_4$) and concentrated under reduced pressure. Purification (FCC, SiO$_2$, 10-50% EtOAc/hexanes) provide the title compound (663 mg, 85%). $^1$H NMR (400 MHz, CDCl$_3$) δ=7.73 (dd, J=8, 6 Hz, 1H), 7.55 (dd, J=8, 2 Hz, 1H), 7.48 (dd, J=10, 2 Hz, 1H), 5.15 (dd, J=20, 8 Hz, 2H), 4.76 (dd, J=19, 8 Hz, 2H); [M+H]=196.1.

Step C. 3-Cyano-2-fluoro-6-(3-fluorooxetan-3-yl)benzoic acid. The title compound was in a manner analogous to Intermediate 22, Step C, from 2-fluoro-4-(3-fluorooxetan-3-yl)benzonitrile. $^1$H NMR (400 MHz, CDCl$_3$) δ=8.19 (t, J=8 Hz, 1H), 7.80 (dd, J=8, 2 Hz, 1H), 5.09 (dd, J=23, 9 Hz, 2H), 4.89 (dd, J=23, 9 Hz, 2H), 3.37 (br s, 1H); [M+H]=220.1.

Intermediate 30: 3-Cyano-2-fluoro-6-(1-fluorocyclopentyl)benzoic acid.

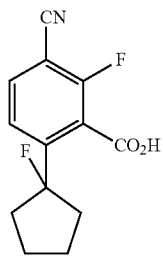 [SMILES: N#Cc1ccc(C2(F)CCCC2)c(C(=O)O)c1F]

Step A. 2-Fluoro-4-(2-oxocyclopentyl)benzonitrile. A mixture of 4-bromo-2-fluorobenzonitrile (4.52 g, 22.6 mmol), cyclopentanone (8 mL, 90.4 mmol), Pd$_2$(dba)$_3$ (103 mg, 0.113 mmol), Xantphos (144 mg, 0.249 mmol), K$_3$PO$_4$ (9.60 g, 45.2 mmol) in toluene (45 mL) was stirred at 80° C. for 19 h. The reaction mixture was diluted with EtOAc and water, layers separated and the organic layer washed with brine, dried (MgSO$_4$) and concentrated under reduced pressure. Purification (FCC, SiO$_2$, 10-40% EtOAc/hexanes) provided the title compound (1.90 g, 41%) as a white solid. $^1$H NMR (400 MHz, CDCl$_3$) δ=7.58 (dd, J=8, 6 Hz, 1H), 7.13 (dd, J=6, 2 Hz, 1H), 7.11 (dd, J=8, 2 Hz, 1H), 3.38 (dd, J=12, 8 Hz, 1H), 2.5-2.6 (m, 2H), 1.9-2.4 (m, 4H); [M+H]=204.1.

Step B. 2-Fluoro-4-(2-((trimethylsilyl)oxy)cyclopent-1-en-1-yl)benzonitrile. To a mixture of sodium iodide (2.07 g, 13.8 mmol) in acetonitrile (5 mL) was added a solution of 2-fluoro-4-(2-oxocyclopentyl)benzonitrile (1.87 g, 9.2 mmol) in acetonitrile (5 mL) and then triethylamine (2.0 mL, 13.8 mmol) added. The mixture was chilled to 0° C. and chlorotrimethylsilane (1.77 mL, 13.8 mmol) added and after stirring at 0° C. for 10 min and 23° C. for 1 h. The reaction mixture was extracted with hexanes, the hexane extract washed with ice-cold water and brine. The organics were dried (MgSO$_4$) and concentrated under reduced pressure to provide the title compound (2.1 g, 83%) as an oil. $^1$H NMR (400 MHz, CDCl$_3$) δ=7.48 (t, J=8 Hz, 1H), 7.50 (d, J=12 Hz. 1H), 7.37 (d, J=8 Hz, 1H), 2.5-2.6 (m, 4H), 1.96 (quin, J=7.5 Hz, 2H), 0.29 (s, 9H).

Step C. 2-Fluoro-4-(1-fluoro-2-oxocyclopentyl)benzonitrile. To a solution of 2-fluoro-4-(2-((trimethylsilyl)oxy)cyclopent-1-en-1-yl)benzonitrile (2.10 g, 7.6 mmol) in DMF (25 mL) at 0° C. was added Selectfluor (4.07 g, 11.5 mmol). The mixture stirred at 23° C. for 20 h. The reaction mixture was poured onto water, extracted with EtOAc, the organic extract washed with water, brine, dried (MgSO$_4$) and concentrated under reduced pressure. Purification (FCC, SiO$_2$, 10-40% EtOAc/hexanes) provided the title compound (950 mg, 57%) as a white crystalline solid. $^1$H NMR (400 MHz, CDCl$_3$) δ=7.66 (t, J=8 Hz, 1H), 7.27 (dd, J=10, 2 Hz, 1H), 7.22 (dd, J=8, 2 Hz, 1H), 2.5-2.8 (m, 2H), 2.2-2.5 (m, 3H), 2.1-2.2 (m, 1H); [M+H]=222.1.

Step D. 2-Fluoro-4-(1-fluoro-2-hydroxycyclopentyl)benzonitrile. A mixture of 2-fluoro-4-(1-fluoro-2-oxocyclopentyl)benzonitrile (950 mg, 4.3 mmol), and NaBH$_4$ (163 mg, 4.3 mmol) was combined in of methanol (17 mL) at 0° C. and then stirred at 23° C. for 1 h. The reaction mixture was diluted with DCM, washed with water, brine, dried (MgSO$_4$) and concentrated under reduced pressure to provide the title compound (940 mg, 98%) as a white solid. $^1$H NMR (400 MHz, CDCl$_3$) δ=7.64 (t, J=8 Hz, 1H), 7.2-7.3 (m, 2H), 4.17 (dt, J=22, 7.6 Hz, 1H), 1.8-2.4 (m, 6H); [M+H]=224.1.

Step E. O-(2-(4-Cyano-3-fluorophenyl)-2-fluorocyclopentyl) O-phenyl carbonothioate. To a solution of 2-fluoro-4-(1-fluoro-2-hydroxycyclopentyl)benzonitrile (940 mg, 4.22 mmol) and DMAP (1.031 g, 8.44 mmol) in acetonitrile (21 mL) at 0° C. was added O-phenyl chlorothionoformate (0.64 mL, 4.64 mmol). The mixture stirred at 23° C. for 1.5 h. The reaction was diluted with EtOAc, washed with 1 M HCl, water, 1 M NaHCO$_3$, dried (MgSO$_4$) and concentrated under reduced pressure. Purification (FCC, SiO$_2$, 0-20% EtOAc/hexanes) provided the title compound (1.28 g, 85%) as a white solid. $^1$H NMR (400 MHz, CDCl$_3$) δ=7.66 (t, J=8 Hz, 1H), 7.3-7.4 (m, 5H), 7.01 (dd, J=8, 2 Hz, 2H), 5.72 (dt, J=22, 8 Hz, 1H), 2.5-2.6 (m, 1H), 2.1-2.4 (m, 4H), 1.9-2.0 (m, 1H); [M+H]=360.2.

Step F. 2-Fluoro-4-(1-fluorocyclopentyl)benzonitrile. A mixture of O-(2-(4-cyano-3-fluorophenyl)-2-fluorocyclopentyl) O-phenyl carbonothioate (1230 mg, 3.42 mmol), tributyltin hydride (1.5 mL, 5.5 mmol) and 2,2'-azobis(2-methylpropionitrile) (112 mg, 0.68 mmol) in toluene (17 mL) was microwave heated to 140° C. for 10 min. The mixture was concentrated under reduced pressure and purified (FCC, SiO$_2$, O-20% EtOAc/hexanes) to provide (603 mg, 82%) of the title compound. $^1$H NMR (400 MHz, CDCl$_3$) δ=7.60 (t, J=8 Hz, 1H), 7.2-7.3 (m, 2H), 2.2-2.3 (m, 2H), 1.9-2.1 (m, 6H); [M+H]=208.1.

Step G. 3-Cyano-2-fluoro-6-(1-fluorocyclopentyl)benzoic acid. The title compound was prepared in a manner analogous to Intermediate 22, Step G, from 2-fluoro-4-(1-fluorocyclopentyl)benzonitrile. $^1$H NMR (400 MHz, CDCl$_3$) δ=7.67 (ddd, J=8, 6.4, 1.6 Hz, 1H), 7.19 (d, J=8 Hz, 1H), 5.09 (br s, 1H), 2.3-2.4 (m, 2H), 1.9-2.2 (m, 6H), [M–HF+H]=232.0.

Intermediate 31:
3-Cyano-6-fluoro-2-methoxybenzoic acid.

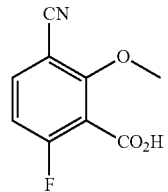

A solution of lithium diisopropylamide (18.20 mL, 36.39 mmol) in THF (25 mL) was stirred at –78° C. for ~10 minutes. A solution of 4-fluoro-2-methoxybenzonitrile (5.00 g, 33.08 mmol) in THF (15 mL) was added dropwise over 10 minutes and the resulting mixture was stirred at –78 for ~1 h. The reaction mixture was poured over dry ice (excess) and then allowed to warm to room temperature over several hours. After all the dry ice had evaporated the crude product was dissolved in DCM (125 mL) and extracted with saturated aqueous NaHCO$_3$ (2×70 mL). The combined aqueous extracts were acidified with conc. HCl to pH=~2, extracted with DCM (2×75 mL). The combined organic layers were dried (Na$_2$SO$_4$) and concentrated at reduced pressure to provide the product as a light yellow solid (4.5 g, 69%). $^1$H NMR (400 MHz, DMSO-d$_6$) δ=7.97 (dd, J=6.3, 8.6 Hz, 1H), 7.26 (t, J=8.8 Hz, 1H), 4.00 (s, 3H).

Intermediate 32:
3-Cyano-6-(2,2-difluoroethoxy)-2-methoxybenzoic acid.

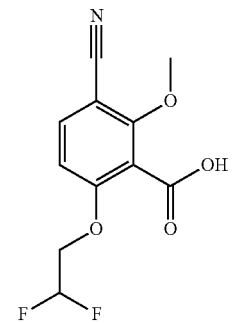

To a solution 3-cyano-6-fluoro-2-methoxybenzoic acid (0.78 g, 4.00 mmol) in dioxane (8 mL) was added 2,2-difluoroethan-1-ol (1.01 mL, 15.99 mmol), followed by cesium carbonate (5.21 g, 15.99 mmol). The mixture was heated at 80° C. for ~20 h then cooled to room temperature. The reaction mixture was dissolved in ice water (~100 mL), acidified to pH ~1 with conc. HCl, and extracted with EtOAc (2×75). The combined organics were dried ($Na_2SO_4$) and concentrated under reduced pressure to give crude product. Purification (FCC, $SiO_2$, 0-2% MeOH/DCM) provided the title compound as an off-white solid (0.82 g, 80%). $^1$H NMR (400 MHz, $CDCl_3$) δ=7.75-7.52 (m, 1H), 6.75 (d, J=8.6 Hz, 1H), 6.30-5.91 (m, 1H), 4.30 (dt, J=4.1, 12.6 Hz, 2H), 4.16 (d, J=0.8 Hz, 3H).

Intermediate 33: (S)-2-Chloro-3-cyano-6-((1,1,1-trifluoropropan-2-yl)oxy)benzoic acid.

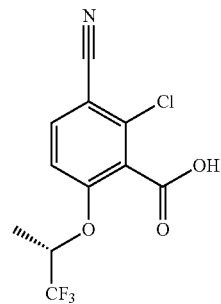 [SMILES: C[C@H](Oc1ccc(C#N)c(Cl)c1C(=O)O)C(F)(F)F]

Step A. 2-Chloro-3-cyano-6-fluorobenzoic acid. To a solution of 2-chloro-4-fluorobenzonitrile (50 g, 0.32 mol) in THF (2000 mL) was added LDA (160 mL, 0.32 mol) at −78° C. under $N_2$ atmosphere, after stirred at this temperature for 30 min. $CO_2$ was bubbled into the mixture at −78° C. Then the mixture was stirred for another 30 min at −78° C. and at rt overnight. The mixture was poured into ice-water and acidified to pH=2 with 1 M HCl at 0° C. Then the mixture was extracted with EtOAc, the organic layer was separated and washed with brine, dried ($Na_2SO_4$), and concentrated under reduced pressure to give the title compound (47 g, 73.3%) as a white solid. $^1$H NMR (400 MHz, DMSO-$d_6$) δ=8.12-8.16 (m, 1H), 7.56-7.61 (m, 1H).

Step B. Methyl 2-chloro-3-cyano-6-fluorobenzoate. To a solution of compound 2-chloro-3-cyano-6-fluorobenzoic acid (2 g, 0.01 mol) and $K_2CO_3$ (2.13 g, 0.015 mol) in DMF (50 mL) was added $CH_3I$ (0.62 mL, 0.015 mol) thereto at 0° C., the mixture was stirred at room temperature overnight. The mixture was poured into ice-water, the mixture was filtered and the filter cake was collected to give the title compound (2.14 g, 98.1%) as a white solid. $^1$H NMR (400 MHz, $CDCl_3$) δ=7.67-7.71 (m, 1H), 7.12-7.16 (m, 1H), 3.94 (s, 3H).

Step C. Methyl 2-chloro-3-cyano-6-((1,1,1-trifluoropropan-2-yl)oxy)benzoate. To a mixture of methyl 2-chloro-3-cyano-6-fluorobenzoate (85 g, 0.40 mol) and $Cs_2CO_3$ (130.32 g, 0.40 mol) in THF (850 mL) was added 1,1,1-trifluoropropan-2-ol (45.5 g, 0.40 mol) at 0° C. Then the resulting mixture was stirred at room temperature overnight. The mixture was poured into ice-water, the mixture was filtered and the filter cake was collected to give the title compound (80 g, 68.3%) as a white solid. $^1$H NMR (400 MHz, $CDCl_3$) δ=7.67-7.69 (d, J=8.8 Hz, 1H), 6.97-6.99 (d, J=8.8 Hz,1H), 4.74-4.77 (m, 1H), 3.93 (s, 3H), 1.51-1.52 (d, J=7.2 Hz, 3H).

Step D. 2-Chloro-3-cyano-6-((1,1,1-trifluoropropan-2-yl)oxy)benzoic acid. A solution of methyl 2-chloro-3-cyano-6-((1,1,1-trifluoropropan-2-yl)oxy)benzoate (100 g, 0.33 mol) and LiI (174 g, 1.29 mol) in pyridine (1000 mL) was refluxed for 2 hours. The solution was poured into ice-water and acidified to pH=2 with 1 M HCl at 0° C., then the mixture was extracted with EtOAc, the organic layer was separated and washed with brine, dried ($Na_2SO_4$) and concentrated under reduced pressure to give the title compound (87 g, 95%) as a white solid. $^1$H NMR (400 MHz, $CD_3OD$) δ=7.83-7.85 (d, J=8.8 Hz, 1H), 7.33-7.35 (d, J=9.2 Hz, 1H), 5.21-5.23 (m, 1H), 1.49-1.51 (d, J=6.4 Hz, 3H).

Step E. Benzyl 2-chloro-3-cyano-6-((1,1,1-trifluoropropan-2-yl)oxy)benzoate. To a mixture of 2-chloro-3-cyano-6-((1,1,1-trifluoropropan-2-yl)oxy)benzoic acid (86 g, 0.29 mol) and $K_2CO_3$ (92.75 g, 0.59 mol) in DMF (1500 mL) was added BnBr (55.2 g, 0.32 mol) at 0° C., then the resulting mixture was stirred at room temperature overnight. The mixture was poured into ice-water and extracted with EtOAc, the organic layer was separated and washed with brine, dried ($Na_2SO_4$), concentrated to give the title compound (85 g, 74.7%) as brown oil. The title compound was separated by SFC to give (S)-benzyl 2-chloro-3-cyano-6-((1,1,1-trifluoropropan-2-yl)oxy)benzoate (Peak 1) (63 g) and compound (R)-benzyl 2-chloro-3-cyano-6-((1,1,1-trifluoropropan-2-yl)oxy)benzoate (Peak 2) (66 g). Note: These series of compounds can only be separated by SFC at the ester stage.

Step F. (S)-2-Chloro-3-cyano-6-((1,1,1-trifluoropropan-2-yl)oxy)benzoic acid. To a solution of compound (S)-benzyl 2-chloro-3-cyano-6-((1,1,1-trifluoropropan-2-yl)oxy)benzoate (10 g, 26 mmol) in EtOAc (600 mL) and conc. HCl (60 mL) was added Pd/C (1 g) under $N_2$ atmosphere. After the addition, the mixture was stirred under $H_2$ balloon at rt overnight. Then the mixture was filtered and the filtrate was concentrated under reduced pressure to give the title compound (6 g, 81%) as a brown oil. $^1$H NMR (400 MHz, $CDCl_3$) δ=7.65-7.67 (d, 1H), 6.92-6.95 (d, 1H), 4.66-4.74 (m, 1H), 1.44-1.51 (s, 3H).

Intermediate 34: (R)-2-Chloro-3-cyano-6-((1,1,1-trifluoropropan-2-yl)oxy)benzoic acid.

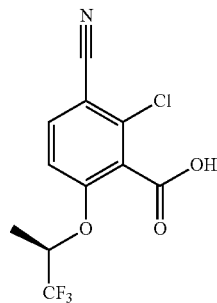 [SMILES: C[C@@H](Oc1ccc(C#N)c(Cl)c1C(=O)O)C(F)(F)F]

The title compound was prepared in a manner analogous to Intermediate 33, substituting (R)-benzyl 2-chloro-3-cyano-6-((1,1,1-trifluoropropan-2-yl)oxy)benzoate (Peak 2) in step F.

Intermediate 35: (S)-3-Cyano-2-methoxy-6-((1,1,1-trifluoropropan-2-yl)oxy)benzoic acid.

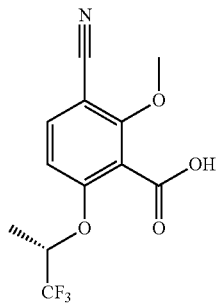 [SMILES: COc1c(C#N)ccc(O[C@@H](C)C(F)(F)F)c1C(=O)O]

Step A. 3-Cyano-2,6-difluorobenzoic acid. To a solution of 2,4-difluorobenzonitrile (100 g, 0.718 mol) in THF (2000 mL) was added LDA (360 mL, 0.718 mol) at −78° C. under N₂ atmosphere, after stirred at this temperature for 30 min. CO₂ was bubbled into the mixture at −78° C. Then the mixture was stirred at −78° C. for another 30 min and at room temperature overnight. The mixture was poured into ice-water and acidified to pH=~2 with 1 M HCl at 0° C. Then the mixture was extracted with EtOAc, the organic layer was separated and washed with brine, dried (Na₂SO₄) and concentrated under reduced pressure to give the title compound (84 g, 68%) as white solid. $^1$H NMR (400 MHz, CDCl₃) δ=8.14-8.19 (m, 1H), 7.44-7.49 (m, 1H).

Step B. Benzyl 3-cyano-2,6-difluorobenzoate. To a mixture of 3-cyano-2,6-difluorobenzoic acid (50 g, 0.27 mol) and K₂CO₃ (86 g, 0.54 mol) in DMF (1000 mL) was added BnBr (51 g, 0.29 mol) dropwise at 0° C. The resulting mixture was stirred at room temperature overnight. The mixture was poured into ice-water and extracted with EtOAc. The organic layers were combined and washed with brine and dried (Na₂SO₄), concentrated under reduced pressure to give the title compound (72 g, 97.7%) as brown oil. $^1$H NMR (400 MHz, CDCl₃) δ=7.70-7.75 (m, 1H), 7.36-7.44 (m, 5H), 7.06-7.11 (m, 1H), 5.41 (s, 2H).

Step C. Benzyl 3-cyano-2-fluoro-6-((1,1,1-trifluoropropan-2-yl)oxy)benzoate. To a mixture of benzyl 3-cyano-2,6-difluorobenzoate (350 g, 1.28 mol) and Cs₂CO₃ (1251 g, 3.84 mol) in THF (6000 mL) was added 1,1,1-trifluoropropan-2-ol (146 g, 1.28 mol) at 0° C. The resulting mixture was stirred at rt overnight. The mixture was poured into ice-water and extracted with EtOAc, the organic layer was separated and washed with brine, dried (Na₂SO₄), concentrated to give the crude product, which was purified by column chromatography to give the title compound (108 g, 37.9%) as yellow oil. The title compound was separated by SFC to give (S)-benzyl 3-cyano-2-fluoro-6-((1,1,1-trifluoropropan-2-yl)oxy)benzoate (peak 1) (79 g) and (R)-benzyl 3-cyano-2-fluoro-6-((1,1,1-trifluoropropan-2-yl)oxy)benzoate (peak2) (81 g). $^1$H NMR (400 MHz, CDCl₃) δ=7.65-7.69 (m, 1H), 7.39-7.44 (m, 5H), 6.86-6.88 (d, 1H), 5.40-5.41 (s, 2H), 4.75-4.78 (m, 1H), 1.47-1.49 (d, 3H). Note: These series of compounds can only be separated by SFC at ester stage.

Step D. (S)-3-Cyano-2-fluoro-6((1,1,1-trifluoropropan-2-yl)oxy)benzoic acid. To a solution of (S)-benzyl 3-cyano-2-fluoro-6-((1,1,1-trifluoropropan-2-yl)oxy)benzoate (peak 1) (10 g, 0.027 mol) in EtOAc (600 mL) was added Pd/C (1 g) under N₂ atmosphere. After the addition, the mixture was stirred under H₂ balloon at room temperature overnight. Then the mixture was filtered and the filtrate was concentrated under reduced pressure to give the title compound (6 g, 80%) as a brown oil. $^1$H NMR (400 MHz, DMSO-d₆) δ=8.01-8.05 (m, 1H), 7.38-7.40 (d, 1H), 5.52-5.55 (m, 1H), 1.41-1.43 (d, 3H).

Step E. (S)-3-Cyano-2-methoxy-6-((1,1,1-trifluoropropan-2-yl)oxy)benzoic acid. (S)-3-Cyano-2-fluoro-6-((1,1,1-trifluoropropan-2-yl)oxy)benzoic acid (12 g, 0.043 mol) and MeONa (46.8 g, 0.86 mol) was dissolved in ACN (120 mL) at room temperature for 5 min. Then the solution was poured into ice-water and acidified to pH=2 with 1 M HCl, and the mixture was extracted with EtOAc, the organic layer was separated and washed with brine, dried (Na₂SO₄) and concentrated under reduced pressure to give crude product. Purification (FCC, SiO₂) afforded the title compound (6.5 g, 52%) as a white solid: $^1$H NMR (400 MHz, CDCl₃) δ=7.63-7.65 (d, J=8.8 Hz, 1H), 6.77-6.80 (d, J=8.8 Hz, 1H), 4.74-4.76 (m, 1H), 4.16 (s, 3 H),1.54-1.56 (d, J=6.4 Hz, 3H).

Intermediate 36: (R)-3-Cyano-2-methoxy-6-((1,1,1-trifluoropropan-2-yl)oxy)benzoic acid.

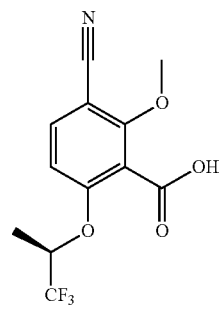 [SMILES: COc1c(C#N)ccc(O[C@H](C)C(F)(F)F)c1C(=O)O]

The title compound was prepared in a manner analogous to Intermediate 35, substituting (R)-benzyl 3-cyano-2-fluoro-6-((1,1,1-trifluoropropan-2-yl)oxy)benzoate (peak 2) in step D.

Intermediate 37: 3-Carbamoyl-2-chloro-6-((1,1,1-trifluoropropan-2-yl)oxy)benzoic acid.

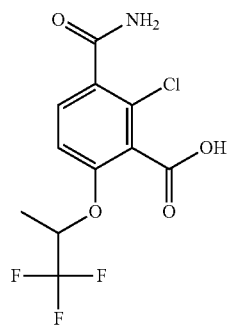 [SMILES: CC(Oc1ccc(C(N)=O)c(Cl)c1C(=O)O)C(F)(F)F]

To a scintillation vial was added methyl 2-chloro-3-cyano-6-((1,1,1-trifluoropropan-2-yl)oxy)benzoate (2.1 g, 7.0 mmol) and dioxane (70 mL) followed by a 1.0 M aqueous solution of NaOH (21 mL, 21 mmol). The reaction was stirred at 45° C. for 90 minutes. The reaction was cooled to room temperature then ethyl acetate and water were added. The layers were separated then the aqueous layer was acidified to about pH 3 and extracted with ethyl acetate. The organic layer was dried (Na₂SO₄), filtered and evaporated and the resulting residue was purified (FCC, SiO₂, 0-20% MeOH/DCM) to afford the title compound. [M+H]=312.09.

Intermediate 38:
3-Cyano-6-cyclopentyl-2-fluorobenzoic acid.

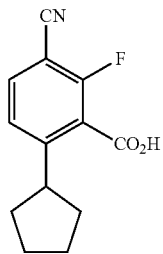 [SMILES: N#Cc1ccc(C2CCCC2)c(C(=O)O)c1F]

Step A. 6-Bromo-3-cyano-2-fluorobenzoic acid. The title compound was prepared in a manner analogous to Intermediate 35, Step A.

Step B. 3-Cyano-6-(cyclopent-1-en-1-yl)-2-fluorobenzoic acid. To a 100 mL flask was added 6-bromo-3-cyano-2-fluorobenzoic acid (2.0 g, 8.20 mmol), 2-(cyclopent-1-en-1-yl)-4,4,5,5-tetramethyl-1,3,2-dioxaborolane (2.60 mL, 2.39 mmol), Pd(dba)₂ (0.375 g, 0.41 mmol), di-tert-butyl (methyl)phosphoniumtetrafluoroborate salt (0.36 g, 1.23 mmol), potassium phosphate (5.22 g, 24.6 mmol), and THF:H₂O (41 mL, 4:1). The mixture was heated to 80° C. and stirred at that temperature for 1 h. The reaction mixture was basicified with 1 M NaOH and washed with EtOAc (2×100 mL). Then, the aqueous layer was acidified with 1 M HCl and extracted with EtOAc (3×25 mL). The organic layers were combined, dried (MgSO₄), filtered, and concentrated under reduced pressure. This material was taken forward without further purification.

Step C. 3-Cyano-6-cyclopentyl-2-fluorobenzoic acid. To a 150 mL pressure-vessel was added 3-cyano-6-(cyclopent-1-en-1-yl)-2-fluorobenzoic acid (1.89 g, 8.20 mmol), 10% Pd/C (0.38 g, 0.36 mmol), and 1:1 EtOAC:MeOH (82 mL). The reaction mixture was evacuate and backfilled with N₂ (3 times) and then evacuate and backfilled with H₂ (3 times). On the last refill, the hydrogen-pressure was adjusted to 30-35 psi. The mixture was shook under 40 psi of H₂ for 24 h. The crude material was used in the next step without further purification (0.67 g, 35%). [M+H]=234.1.

Intermediate 39: 5-cyano-2-cyclopentylbenzoic acid.

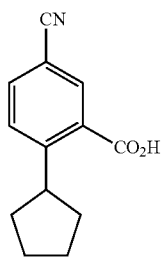

Step A. Methyl 2-bromo-5-cyanobenzoate. A solution of methyl 2-bromo-5-iodobenzoate (5.0 g, 14.7 mmol), Zn(CN)₂ (1.73 g, 14.7 mmol), Pd (PPh₃)₄ (1.7 g, 1.47 mmol) in DMF (150 mL) was heated to 55° C. for 7 h. The reaction mixture was cooled, and water and EtOAc was added. The reaction mixture was extracted with EtOAc, the combined organic layers were washed with brine, dried (Na₂SO₄), filtered and concentrated under reduced pressure. Purification (FCC, SiO₂, 0-20% EtOAc/hexanes) provided the title compound (2.6 g, 74%).

Step B. Methyl 5-cyano-2-(cyclopent-1-en-1-yl)benzoate. A solution of methyl 2-bromo-5-cyanobenzoate (1.4 g, 5.83 mmol), 2-(cyclopent-1-en-1-yl)-4,4,5,5-tetramethyl-1,3,2-dioxaborolane (1.7 g, 8.75 mmol), Pd(dppf)Cl₂ (95 mg, 0.117 mmol), K₂CO₃ (2.42 g, 17.5 mmol), dioxane (15 mL), EtOH (10 mL), and water (5 mL), was degassed and heated to 110° C. for 18 h. The reaction mixture was cooled, and water and EtOAc was added. The reaction mixture was extracted with EtOAc, the combined organic layers were washed with brine, dried (Na₂SO₄), filtered and concentrated under reduced pressure. Purification (FCC, SiO₂, 0-20% EtOAc/hexanes) provided the title compound (1.16 g, 88%).

Step C. 5-Cyano-2-(cyclopent-1-en-1-yl)benzoic acid. To a round bottom flask was added methyl 5-cyano-2-(cyclopent-1-en-1-yl)benzoate (800 mg, 3.52 mmol) followed by dioxane (22 mL), water (10 mL) and a 1.0 M solution of sodium hydroxide (10.7 mL, 10.7 mmol). The reaction was stirred at room temperature for 3 h. A solution of HCl (1.0 M) was added until the reaction mixture was acidic (pH 3) then ethyl acetate was added. Phases were separated and the organics were washed with brine, dried (Na₂SO₄), filtered and evaporated to afford the title compound as a beige solid, which was used without any further purification (750 mg, quantitative).

Step C. 5-Cyano-2-cyclopentylbenzoic acid. The title compound was prepared in a manner analogous to Intermediate 38, Step C. ¹H NMR (400 MHz, CDCl₃) δ 8.10 (br s, 1H), 7.71 (d, J=7.4 Hz, 1H), 7.53 (d, J=7.8 Hz, 1H), 3.99-3.83 (m, 1H), 2.27-2.02 (m, 2H), 1.83 (br s, 2H), 1.72 (br s, 2H), 1.56 (br s, 2H); [M+H]=216.22.

Intermediate 40:
3-Cyano-6-cyclopentyl-2-methoxy-benzoic acid.

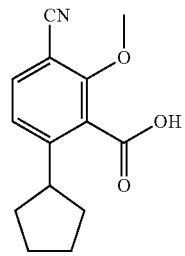 [SMILES: COc1c(C#N)ccc(C2CCCC2)c1C(=O)O]

Step A. 6-Bromo-3-cyano-2-fluoro-benzoic acid. Diisopropylamine (5.25 mL, 37 mmol) was slowly added to a solution of n-BuLi 2.5M in hexanes (14 mL, 35 mmol) and dry THF (50 mL) at 0° C. The reaction mixture was stirred at 0° C. for 15 min. and cooled to −78° C. A solution of 4-bromo-2-fluoro-benzonitrile (5.00 g, 25 mmol) in THF (20 mL) was added dropwise to the reaction mixture. The reaction mixture was stirred for 15 min. Dry-ice pellets were charged into a separated flask that was capped with an unfolded septum. The sublimating CO₂ was passed through a drierite laboratory gas drying unit, then added subsurface to the reaction mixture (bubbling) while the temperature was slowly allowed to reach 0° C. The reaction mixture was then allowed to warm to ambient temperature and stirred for 2 h. The reaction was quenched with water (20 mL) and the product was extracted with a 0.5 M NaOH solution (4×40 mL). The combined aqueous layers were washed with EtOAc (2×50 mL). The separated aqueous layer was acidified to pH 1 using a 2M HCl solution. The product was extracted using EtOAc (3×100 mL). The combined organic layers were washed with brine, dried (Na₂SO₄) and the solvent was removed under reduced pressure to provide the title compound (5.02 g, 82%) as a solid. The product was used for the next step without further purification. ¹H NMR (300 MHz, DMSO-d₆) δ 7.96 (dd, J=8.4, J=7.0 Hz, 1H), 7.80 (dd, J=8.4, J=0.8 Hz, 1H).

Step B. 6-Bromo-3-cyano-2-methoxy-benzoic acid. Sodium methoxide 25% in MeOH (40 mL, 175 mmol) was added to a solution of 6-bromo-3-cyano-2-fluoro-benzoic acid (5.02 g, 21 mmol) in MeOH (60 mL). The reaction mixture was heated to 65° C. and stirred for 18 h. The reaction mixture was allowed cool to ambient temperature and the solvent was concentrated under reduced pressure. The residue was recovered in HCl 0.5M (100 mL) and the mixture pH was adjusted to 1 using concentrated HCl. The product was extracted with EtOAc (3×75 mL). The combined organic layers were washed with brine, dried (Na₂SO₄) and the solvent was concentrated under reduced pressure to provide the title compound (4.65 g, 88%) as a solid. The product was used for the next step without further purification. ¹H NMR (300 MHz, DMSO-d₆) δ 7.81 (d, J=8.4 Hz, 1H), 7.62 (d, J=8.4 Hz, 1H), 4.00 (s, 3H).

Step C. 3-Cyano-6-(cyclopenten-1-yl)-2-methoxy-benzoic acid. Palladium acetate (0.48 g, 2.14 mmol) and PPh₃ (1.12 g, 4.29 mmol) were added to a degassed solution of DME (200 mL). The argon bubbling was continued for 30 min and the mixture was stirred until a dark-orange color appears (~20 min). Together was added 6-bromo-3-cyano-2-methoxy-benzoic acid (5.5 g, 21.4 mmol) and Cs₂CO₃ (17.5 g, 53.7 mmol) followed by degassed water (50 mL) and a solution of 2-(cyclopenten-1-yl)-4,4,5,5-tetramethyl-1,3,2-dioxaborolane (6.25 g, 32.2 mmol) in DME (3 mL). The reaction mixture was degassed with argon for 15 min. The reaction mixture was heated to 88° C. for 3 h. The reaction mixture was allowed to cool to ambient temperature and partitioned between HCl 0.5 M (300 mL) and EtOAc (300 mL). The separated aqueous layer was washed with EtOAc (3×100 mL). The combined organic layers were washed with brine and dried (Na₂SO₄). The solvent was concentrated under reduced pressure. Purification (FCC, SiO₂, 1% AcOH/1% MeOH/DCM) afforded the title compound (3.70 g, 70%) as yellow gum. ¹H NMR (300 MHz, CDCl₃) δ 7.59 (d, J=8.2 Hz, 1H), 7.15 (d, J=8.2 Hz, 1H), 6.15 (m, 1H), 4.13 (s, 3H), 2.70 (m, 2H), 2.54 (m, 2H), 2.02 (m, 2H); [M+H]⁻=244.2.

Step D. 3-Cyano-6-cyclopentyl-2-methoxy-benzoic acid. Hydrogen gas was passed through a stirred mixture of 10% Pd/C (710 mg, 0.66 mmol), EtOH (200 mL) and 3-cyano-6-(cyclopenten-1-yl)-2-methoxy-benzoic acid (3.70 g, 15.2 mmol) for 60 min. The reaction mixture was filtered over a CELITE® pad and the solvent was concentrated under reduced pressure. Purification (FCC, SiO₂, 1%AcOH/20% of EtOAc/hexanes) provided the title compound (3.09 g, 88%) as colorless gum. ¹H NMR (300 MHz, CDCl₃) δ 7.60 (d, J=8.3 Hz, 1H), 7.17 (d, J=8.3 Hz, 1H), 4.13 (s, 3H), 3.13 (m, 1H), 2.12 (m, 2H), 1.83 (m, 2H), 1.71 (m, 2H), 1.58 (m, 2H); [M−OH]=228.2.

Intermediate 41. 5-(2-oxooxazolidin-3-yl)-2-((1,1,1-trifluoropropan-2-yl)oxy)benzoic acid.

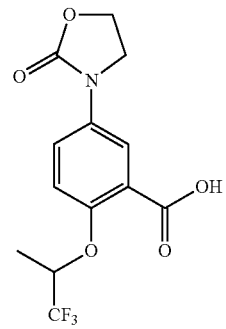 [SMILES: CC(Oc1ccc(N2CCOC2=O)cc1C(=O)O)C(F)(F)F]

Step A. 5-Nitro-2-((1,1,1-trifluoropropan-2-yl)oxy)benzoic acid. To a solution of 2-fluoro-5-nitrobenzoic acid (1.0 g, 5.4 mmol) in dioxane (20 mL) was added 1,1,1-trifluoropropan-2-ol (1.84 g, 16.2 mmol), and cesium carbonate (4.4 g, 13.5 mmol). The mixture was heated to 110° C. for 3.5 h. The crude mixture was poured into 1M HCl (100 mL) and was stirred for 20-30 min. The mixture was filtered to afford the title compound (0.89 g, 59%): ¹H NMR (400 MHz, DMSO-d₆) δ=13.42 (s, 1H), 8.45 (d, J=3.1 Hz, 1H), 8.38 (dd, J=2.9, 9.2 Hz, 1H), 7.56 (d, J=9.4 Hz, 1H), 5.56 (td, J=6.4, 12.6 Hz, 1H), 1.45 (d, J=6.3 Hz, 3H).

Step B. Benzyl 5-nitro-2-((1,1,1-trifluoropropan-2-yl)oxy)benzoate. To a solution of 5-nitro-2-((1,1,1-trifluoropropan-2-yl)oxy)benzoic acid (1.0 g, 5.4 mmol) in DMF (83 mL) was added potassium carbonate (4.6 g, 33.1 mmol), and (bromomethyl)benzene (2.8 g, 19.9 mmol). The mixture was stirred for 3 h before it was diluted with EtOAc (200 mL) and H₂O (200 mL) to form a bilayer. The bilayer was separated. The organic layer was washed with saturated NaHCO₃ (2×100 mL), H₂O (1×100 mL). The organic layer was dried (MgSO₄), filtered, and concentrated under reduced pressure. Purification (FCC, SiO₂, 0-100% EtOAc/hexanes) provided the title compound (1.14 g, 19%): ¹H NMR (400 MHz, DMSO-d₆) δ=8.50 (d, J=2.7 Hz, 1H), 8.46-8.39 (m, 1H), 7.61 (d, J=9.4 Hz, 1H), 7.48-7.42 (m, 2H), 7.42-7.27 (m, 3H), 5.61 (td, J=6.4, 12.6 Hz, 1H), 5.33 (s, 2H), 1.41 (d, J=6.3 Hz, 3H).

Step C. Benzyl 5-amino-2-((1,1,1-trifluoropropan-2-yl)oxy)benzoate. To a solution of benzyl 5-nitro-2-((1,1,1-trifluoropropan-2-yl)oxy)benzoate (1.1 g, 3.0 mmol) in acetic acid (30 mL) and ethanol (30 mL) was added iron (1.7 g, 30 mmol). The mixture was heated to 70° C. for 2 h. The mixture was filtered and the filtrate was concentrated down to near dryness. The crude was diluted with EtOAc (200 mL) and MeOH. The organic layer was washed saturated NaHCO₃ (2×100 mL). The organics were collected and concentrated under reduced pressure to provied the title compound (0.81 g, 80%), which was used in the next step without further purification: ¹H NMR (400 MHz, DMSO-d₆) δ=7.48-7.27 (m, 4H), 6.95 (d, J=8.6 Hz, 1H), 6.89 (d, J=2.7 Hz, 1H), 6.70 (dd, J=2.9, 8.8 Hz, 1H), 5.24 (s, 2H), 5.18-5.02 (m, 2H), 4.82 (td, J=6.5, 13.2 Hz, 1H), 1.27 (d, J=6.7 Hz, 3H).

Step D. Benzyl 5-(2-oxooxazolidin-3-yl)-2-((1,1,1-trifluoropropan-2-yl)oxy)benzoate. To a 0° C. solution of benzyl 5-amino-2-((1,1,1-trifluoropropan-2-yl)oxy)benzoate (0.81 g, 2.4 mmol), potassium carbonate (0.7 g, 5.3 mmol), and acetonitrile (12 mL) was slowly added 2-chloroethyl carbonochloridate (0.4 g, 2.9 mmol). The mixture was allowed to warm to rt over 1 h and then heated to reflux for 2 days. DMF (10 mL) was added to the mixture. The mixture was heated to 120° C. for 12 h. The crude material was diluted with EtOAc (200 mL), washed with $H_2O$ (3×200 mL), dried ($MgSO_4$), filtered, and concentrated under reduced pressure. The resulting residue was purified by chromatography (silica gel, 10-40% EtOAc/hexanes) to afford the title compound (0.67 g, 69%): $^1H$ NMR (400 MHz, $CDCl_3$) δ=7.99-7.91 (m, 1H), 7.75-7.68 (m, 1H), 7.48-7.41 (m, 2H), 7.41-7.30 (m, 3H), 7.05 (d, J=9.4 Hz, 1H), 5.35 (s, 2H), 4.63 (td, J=6.1, 12.4 Hz, 1H), 4.54-4.44 (m, 2H), 4.05 (t, J=7.8 Hz, 2H), 1.44 (d, J=6.3 Hz, 3H).

Step E. 5-(2—Oxooxazolidin-3-yl)-2-((1,1,1-trifluoropropan-2-yl)oxy)benzoic acid. A mixture of benzyl 5-(2-oxooxazolidin-3-yl)-2-((1,1,1-trifluoropropan-2-yl)oxy)benzoate (0.67 g, 1.6 mmol), 10% Pd/C (0.067 g, 0.06 mmol), and EtOH (16 mL) was charged with hydrogen gas and stirred for 1.5 h. The mixture was filtered through CELITE® and concentrated under reduced pressure to afford the title compound: $^1H$ NMR (400 MHz, DMSO-$d_6$) δ=12.99 (br s, 1H), 7.82 (d, J=3.1 Hz, 1H), 7.63 (dd, J=2.7, 9.0 Hz, 1H), 7.30 (d, J=9.0 Hz, 1H), 5.15 (td, J=6.5, 12.9 Hz, 1H), 4.41 (dd, J=6.8, 8.8 Hz, 2H), 4.04 (dd, J=7.0, 9.0 Hz, 2H), 1.39 (d, J=6.7 Hz, 3H).

Intermediate 42.
2-Cyclopentyl-5-(2-oxooxazolidin-3-yl)benzoic acid.

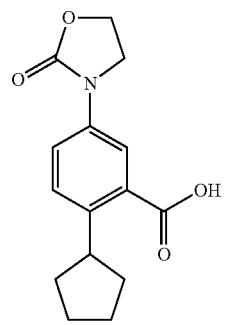 [SMILES: O=C(O)c1cc(N2CCOC2=O)ccc1C1CCCC1]

Step A. Methyl 2-(cyclopent-1-en-1-yl)-5-nitrobenzoate. To a solid mixture of methyl 2-bromo-5-nitrobenzoate (6.0 g, 23.1 mmol), Pd(dppf)$Cl_2$ (0.93 g, 1.14 mmol), and potassium carbonate (9.6 g, 69.3 mmol) was added dioxane:EtOH:$H_2O$ (115 mL, 3:2:1) solution and 2-(cyclopent-1-en-1-yl)-4,4,5,5-tetramethyl-1,3,2-dioxaborolane (6.72 g, 34.6 mmol). The reaction mixture was immediately heated to 110° C. for 30 mm. The crude was diluted with EtOAc (300 mL). The resulting organics was washed with brine (3×300 mL), dried ($MgSO_4$), filtered, and concentrated under reduced pressure. Purification (FCC, $SiO_2$, 0-10% EtOAc/hexanes) afforded the title compound (5.64 g, 99%): $^1H$ NMR (400 MHz, $CDCl_3$) δ=8.54 (d, J=2.3 Hz, 1H), 8.25 (dd, J=2.5, 8.4 Hz, 1H), 7.46 (d, J=8.6 Hz, 1H), 5.94-5.86 (m, 1H), 3.91 (s, 3H), 2.73-2.48 (m, 4H), 2.11-2.00 (m, 2H).

Step B. Methyl 5-amino-2-cyclopentylbenzoate. A solution of methyl 2-(cyclopent-1-en-1-yl)-5-nitrobenzoate (2.0 g, 8.1 mmol), palladium hydroxide (0.2 g, 0.14 mmol), and EtOH (80 mL) was shook overnight in a Parr-Shaker under hydrogen atmosphere (50 psi). The crude material was filtered through CELITE® and the filtrate was concentrated under reduced pressure to provided the title compound which was used without further purification: $^1H$ NMR (400 MHz, DMSO-$d_6$) δ=7.06 (d, J=8.2 Hz, 1H), 6.81 (d, J=2.7 Hz, 1H), 6.67 (dd, J=2.7, 8.6 Hz, 1H), 5.10 (s, 2H), 3.75 (s, 3H), 3.41-3.33 (m, 1H), 1.85 (br. s., 2H), 1.78-1.64 (m, 2H), 1.63-1.49 (m, 2H), 1.48-1.32 (m, 2H); (M+H)=220.27.

Step C. Methyl 2-cyclopentyl-5-(2-oxooxazolidin-3-yl)benzoate. To a 0° C. solution of methyl 5-amino-2-cyclopentylbenzoate (1.7 g, 7.6 mmol), potassium carbonate (3.1 g, 23 mmol), and ACN (76 mL) was slowly added 2-chloroethyl carbonochloridate (1.2 g, 8.3 mmol). The mixture was allowed to warm to rt over 1 h and then heated to 80° C. overnight. The crude material was diluted with EtOAc (200 mL), washed with $H_2O$ (3×200 mL), dried ($MgSO_4$), filtered, and concentrated under reduced pressure. Purification (FCC, $SiO_2$, 30-40% EtOAc/hexanes) provided the title compound (1.74 g, 77%): $^1H$ NMR (400 MHz, DMSO-$d_6$) δ=7.81 (d, J=2.7 Hz, 1H), 7.62 (dd, J=2.7, 8.6 Hz, 1H), 7.46 (d, J=8.6 Hz, 1H), 4.49-4.36 (m, 2H), 4.04 (dd, J=7.0, 9.0 Hz, 2H), 3.82 (s, 3H), 3.54-3.41 (m, 1H), 2.02-1.88 (m, 2H), 1.85-1.68 (m, 2H), 1.68-1.55 (m, 2H), 1.55-1.40 (m, 2H).

Step D. 2-Cyclopentyl-5-(2-oxooxazolidin-3-yl)benzoic acid. A solution of methyl 2-cyclopentyl-5-(2-oxooxazolidin-3-yl)benzoate (1.74 g, 6.0 mmol) in 1 M NaOH (9 mL, 9 mmol), and THF:$H_2O$ (30 mL, 4:1) was stirred overnight. The reaction mixture was diluted with EtOAc (100 mL) and saturated $NaHCO_3$ (100 mL) to form a bilayer. The layers were separated and the aqueous layer was collected. To the collected aqueous layer was added 1 M HCl to adjust the pH to 1. Then, the aqueous layer was extracted with EtOAc (4×100 mL). The combined organic layers were dried ($MgSO_4$), filtered, and concentrated reduced pressure to afford the title compound which was used without further purification (0.59 g, 36%).

TABLE 3

| $R^5$ | $R^1$ | $R^2$ | Prepared analogous to INT # |
|---|---|---|---|
| tetrahydropyran-4-yl (with F) | —CN | —F | 22 Steps A-G |
| 2-fluoropropan-2-yl | —CN | —$OCH_3$ | 22 |

TABLE 3-continued

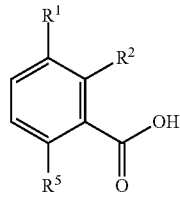

| R⁵ | R¹ | R² | Prepared analogous to INT # |
|---|---|---|---|
| 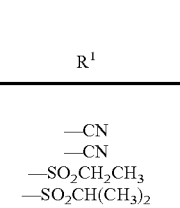 | —CN<br>—CN<br>—SO₂CH₂CH₃<br>—SO₂CH(CH₃)₂ | —H<br>—OCH₃<br>—H<br>—H | 18<br>32<br>18<br>32 |
| 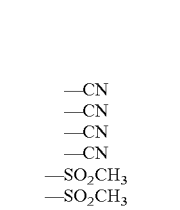 | —CN<br>—CN<br>—CN<br>—CN<br>—SO₂CH₃<br>—SO₂CH₃<br>—SO₂CH₂CH₃<br>—SO₂CH(CH₃)₂ | —H<br>—Cl<br>—F<br>—OCH₃<br>—H<br>—OCH₃<br>—H<br>—H | 32<br>33<br>35<br>35<br>32<br>20<br>32<br>32 |
| | 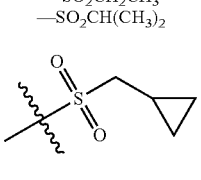 | —H | 18 |
| 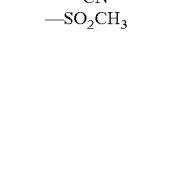 | —CN<br>—SO₂CH₃ | —OCH₃<br>—H | 32<br>32 |
| 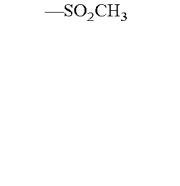 | —SO₂CH₃ | —H | 32 |
| 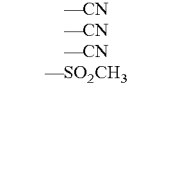 | —CN<br>—CN<br>—CN<br>—SO₂CH₃ | —H<br>—Cl<br>—OCH₃<br>—H | 32<br>33<br>35<br>32 |
| 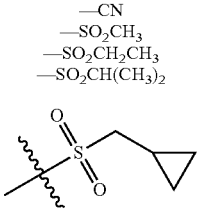 | —CN<br>—SO₂CH₃<br>—SO₂CH₂CH₃<br>—SO₂CH(CH₃)₂ | —H<br>—H<br>—H<br>—H | 32<br>32<br>32<br>32 |
| |  | —H | 32 |

TABLE 3-continued

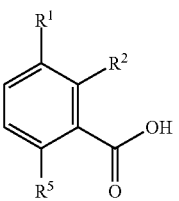

| R⁵ | R¹ | R² | Prepared analogous to INT # |
|---|---|---|---|
| 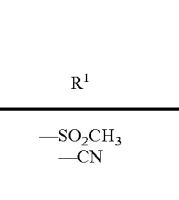 | —SO₂CH₃<br>—CN | —H<br>—OCH₃ | 32<br>32 |
| 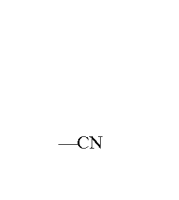 | —CN | —OCH₃ | 25 |

Example 1

(2-(4-Fluorophenyl)pyrrolo[3,4-c]pyrazol-5(2H,4H,6H)-yl)(2-isopropoxy-5-(methylsulfonyl)phenyl)methanone.

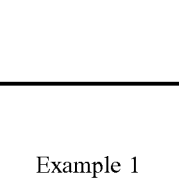

To a mixture of 2-(4-fluorophenyl)-2,4,5,6-tetrahydropyrrolo[3,4-c]pyrazole HCl salt (Intermediate 1, 51.2 mg, 0.21 mmol), 2-isopropoxy-5-(methylsulfonyl)benzoic acid (Intermediate 18, 46 mg, 0.18 mmol) and HATU (81.3 mg, 0.21 mmol) was added anhydrous DMF (828 µL) and triethylamine (124 µL, 0.89 mmol). The mixture was stirred at ambient temperature for 2 h. Purification (HPLC, 5-95% gradient ACN-H₂O using formic acid as modifier) afforded the title compound (63 mg, 80%). NMR (400 MHz, DMSO-d₆) δ=8.36-8.18 (m, 1H), 7.93 (dd, J=2.5, 8.8 Hz, 1H), 7.84-7.76 (m, 3H), 7.40-7.27 (m, 3H), 4.83 (dt, J=3.1, 6.1 Hz, 1H), 4.66 (d, J=6.3 Hz, 2H), 4.36 (d, J=17.6 Hz, 2H), 3.19 (s, 3H), 1.29-1.23 (m, 6H); [M+H]=444.3.

Example 2

(2-(3,4-Difluorophenyl)pyrrolo[3,4-c]pyrazol-5(2H,4H,6H)-yl)(2-isopropoxy-5-(methylsulfonyl)phenyl)methanone.

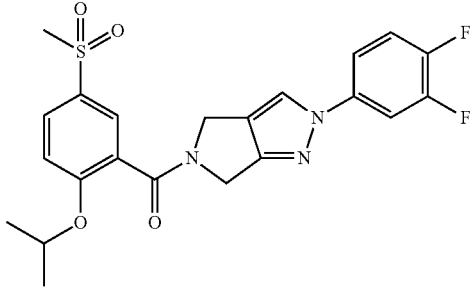 [SMILES: CC(C)Oc1ccc(S(C)(=O)=O)cc1C(=O)N1Cc2cn(-c3ccc(F)c(F)c3)nc2C1]

Step A. 2-Isopropoxy-5-(methylsulfonyl)benzoyl chloride. A mixture of 2-isopropoxy-5-(methylsulfonyl)benzoic acid (Intermediate 18, 40 mg, 0.14 mmol) in thionyl chloride (500 μL) heated at 70° C. for 45 min., then evaporated to dryness. The resulting residue was dissolved in ethyl acetate and evaporated to dryness and used without further purification.

Step B. (2-(3,4-Difluorophenyl)pyrrolo[3,4 c]pyrazol-5 (2H,4H,6H)-yl)(2-isopropoxy-5-(methylsulfonyl)phenyl)methanone. To a 25 mL round bottomed flask were added 2-(3,4-difluorophenyl)-2,4,5,6-tetrahydropyrrolo[3,4-c] pyrazole HCl salt (Intermediate 2, 37 mg, 0.14 mmol) and anhydrous DCM (2 mL). TEA (80 μL, 0.58 mmol) was added followed by a DCM solution (2 mL) of product from Step A and the reaction mixture was stirred at ambient temperature for 3 h. The reaction mixture was washed with water and the organic phase evaporated to dryness. Purification (HPLC, 30-95% gradient ACN-H$_2$O using formic acid as modifier) afforded the title compound (45 mg, 67%). $^1$H NMR (400 MHz, DMSO-d$_6$) δ=8.43-8.24 (m, 1H), 7.99-7.77 (m, 3H), 7.72-7.50 (m, 2H), 7.38 (dd, J=1.2, 9.0 Hz, 1H), 4.83 (dtd, J=3.5, 6.1, 12.1 Hz, 1H), 4.66 (d, J=6.7 Hz, 2H), 4.37 (d, J=17.6 Hz, 2H), 3.20 (s, 3H), 1.26 (dd, J=0.8, 6.3 Hz, 6H); [M+H]=462.1.

Example 3

3-(2-(2-Methylpyridin-4-yl)-2,4,5,6-tetrahydropyrrolo[3,4-c]pyrazole-5-carbonyl)-4-(neopentyloxy)benzonitrile

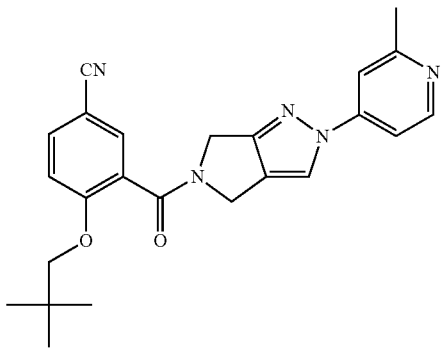 [SMILES: Cc1cc(-n2cc3c(n2)CN(C(=O)c2cc(C#N)ccc2OCC(C)(C)C)C3)ccn1]

Step A. 4-Fluoro-3-(2-(2-methylpyridin-4-yl)-2,4,5,6-tetrahydropyrrolo[3,4-c]pyrazole-5-carbonyl)benzonitrile. To mixture of 5-cyano-2-fluorobenzoic acid (300.00 mg, 1.82 mmol), 1-[bis(dimethylamino)methylene]-1H-1,2,3-triazolo[4,5-b]pyridinium 3-oxid hexafluorophosphate (829 mg, 2.2 mmol), and 2-(2-methylpyridin-4-yl)-4,5,6,7-tetrahydro-2H-pyrazolo[4,3-c]pyridine dihydrochloride (595.55 mg, 2.18 mmol) was added anhydrous DMF (5.4 mL) and TEA (1.27 mL, 9.08 mmol). The mixture was stirred at ambient temperature for 16 h. The reaction mixture was diluted with EtOAc, washed with saturated NaHCO$_3$, dried (MgSO$_4$), filtered, and concentrated under reduced pressure. Purification (FCC, SiO$_2$, 5-10% MeOH:EtOAc) afforded the title compound (60 mg, 9.51%) as a brownish powder. $^1$H NMR (400 MHz, DMSO-d$_6$) δ=8.58-8.39 (m, 2H), 8.18-8.03 (m, 2H), 7.83-7.55 (m, 3H), 4.76-4.68 (m, 2H), 4.57-4.45 (m, 2H), 2.51 (s, 3H); [M+H]=348.10.

Step B. 3-(2-(2-Methylpyridin-4-yl)-2,4,5,6-tetrahydropyrrolo[3,4-c]pyrazole-5-carbonyl)-4-(neopentyloxy)benzonitrile. To a mixture of 4-fluoro-3-{[2-(2-methylpyridin-4-yl)-2H,4H,5H,6H-pyrrolo[3,4-c]pyrazol-5-yl]carbonyl}benzonitrile (20.00 mg, 0.06 mmol), cesium carbonate (37.52 mg, 0.12 mmol), 2,2-dimethylpropan-1-ol (15.23 mg, 0.17 mmol), was added N-methylpyrrolidinone (0.35 ml). The mixture was heated to 80° C. for 2 h. The crude reaction mixture was diluted with MeOH and filtered. The filtrate was purified by HPLC (5-85% gradient ACN-H$_2$O using formic acid as modifier). The collected fraction was neutralized with NH$_4$OH, froze and lyophilized to afford the title compound (6 mg, 25%). $^1$H NMR (400 MHz, DMSO-d$_6$) δ=8.60-8.36 (m, 2H), 7.90 (dd, J=2.2, 8.8 Hz, 1H), 7.78 (dd, J=2.0, 5.9 Hz, 1H), 7.75-7.67 (m, 1H), 7.62 (ddd, J=2.2, 5.6, 14.6 Hz, 1H), 7.29 (dd, J=2.2, 8.8 Hz, 1H), 4.66 (d, J=7.8 Hz, 2H), 4.36 (d, J=16.8 Hz, 2H), 3.79 (d, J=3.5 Hz, 2H), 2.50 (d, J=2.3 Hz, 3H), 0.83 (d, J=8.2 Hz, 9H); [M+H]=416.2.

Example 4

3-(2-(4-Fluorophenyl)-4,5,6,7-tetrahydro-2H-pyrazolo[4,3-c]pyridine-5-carbonyl)-2-methoxy-4-((1,1,1-trifluoropropan-2-yl)oxy)benzonitrile

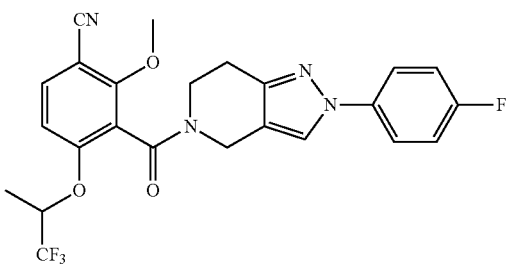 [SMILES: COc1c(C#N)ccc(OC(C)C(F)(F)F)c1C(=O)N1CCc2nn(-c3ccc(F)cc3)cc2C1]

Step A. 2-Fluoro-3-(2-(4-fluorophenyl)-4,5,6,7-tetrahydro-2H-pyrazolo[4,3-c]pyridine-5-carbonyl)-4-((1,1,1-trifluoropropan-2-yl)oxy)benzonitrile. The title compound was prepared in a manner analogous to Example 1, from 2-(4-fluorophenyl)-4,5,6,7-tetrahydro-2H-pyrazolo [4,3-c]pyridine and 3-cyano-2-fluoro-6-((1,1,1-trifluoropropan-2-yl)oxy)benzoic acid.

Step B. 3-(2-(4-Fluorophenyl)-4,5,6,7-tetrahydro-2H-pyrazolo[4,3-c]pyridine-5-carbonyl)-2-methoxy-4-((1,1,1-trifluoropropan-2-yl)oxy)benzonitrile. To a solution of 2-fluoro-3-(2-(4-fluorophenyl)-4,5,6,7-tetrahydro-2H-pyrazolo[4,3-c]pyridine-5-carbonyl)-4-((1,1,1-trifluoropropan-2-yl)oxy)benzonitrile (45.00 mg, 0.095 mmol) in MeOH (0.4 mL) was added 4.6 M of sodium methoxide (41 μL, 0.16 mmol). The mixture was heated to 50° C. overnight. The reaction mixture was diluted with EtOAc, washed with saturated NaHCO₃, dried (MgSO₄), filtered, and concentrated under reduced pressure. The crude was purified (FCC, SiO₂, 20-60% EtOAc:hexanes) to afford the title compound (29.6 mg). ¹H NMR (400 MHz, CDCl₃) δ=7.75-7.46 (m, 4H), 7.13 (q, J=8.0 Hz, 2H), 6.84-6.63 (m, 1H), 5.18-4.58 (m, 2H), 4.47-4.25 (m, 1H), 4.19-3.96 (m, 4H), 3.68-3.35 (m, 1H), 3.09-2.70 (m, 2H), 1.55-1.42 (m, 3 H); [M+H]=489.26.

Example 5

2-Chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzoic acid

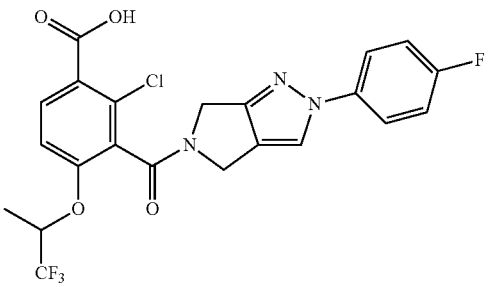 [SMILES: CC(Oc1ccc(C(=O)O)c(Cl)c1C(=O)N1Cc2cn(-c3ccc(F)cc3)nc2C1)C(F)(F)F]

Step A. 2-Chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzonitrile. The title compound was prepared in a manner analogous to Example 1, with the appropriate starting material substitutions.

Step B. 2-Chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzoic acid. To a solution of 2-chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzonitrile (0.05 g, 0.10 mmol) and dioxane (0.50 ml) was added sodium hydroxide (0.26 ml, 0.52 mmol), then, heated to 120° C. for overnight. The crude material was purified via preparative HPLC on C-18 reverse-phase SiO₂, eluting with a gradient formed from acetonitrile: H₂O: 0.1% TFA (15-40%) to afford the title compound (fraction A, 23.3 mg, 9.5%) and 2-chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzamide (fraction B, 21.4 mg, 9.3%).

Example 6

1-{2-Chloro-3-[2-(4-fluorophenyl)-2H 4H 5H 6H 7H-pyrazolo[4,3-c]pyridine-5-carbonyl]-4-[(1 1 1-trifluoropropan-2-yl)oxy]benzoyl}azetidine

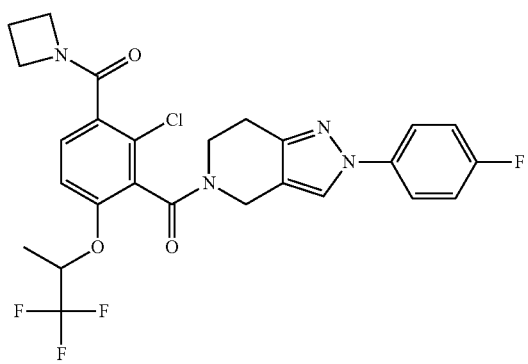 [SMILES: CC(Oc1ccc(C(=O)N2CCC2)c(Cl)c1C(=O)N1CCc2nn(-c3ccc(F)cc3)cc2C1)C(F)(F)F]

The title compound was prepared in a manner analogous to Example 1, from 2-chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzoic acid (Example 5) and azetidine.

Example 7

3-(2-(4-Fluorophenyl)-4,5,6,7-tetrahydro-2H-pyrazolo[4,3-c]pyridine-5-carbonyl)-4-((1,1,1-trifluoropropan-2-yl)oxy)benzamide

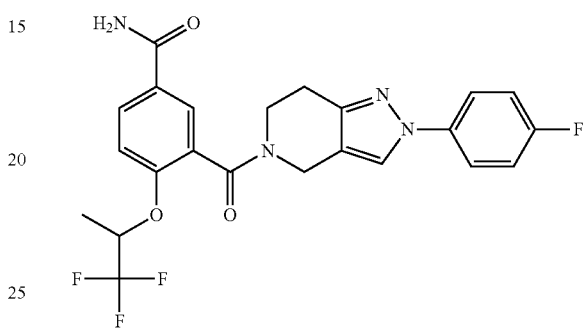

The title compound was prepared in a manner analogous to Example 5 with the appropriate reagent and starting material substitutions.

Example 8

4-(3-Fluorophenyl)-3-[2-(2-methylpyridin-4-yl)-2H 4H 5H 6H-pyrrolo[3,4-c]pyrazole-5-carbonyl]benzonitrile

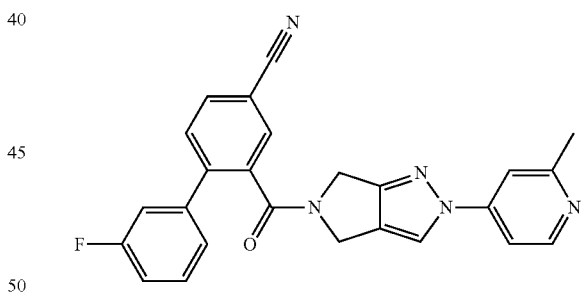

Step A. 5-Cyano-2-iodobenzoyl chloride. To a 30 mL vial was added 5-cyano-2-iodobenzoic acid (0.30 g, 1.10 mmol) and of thionyl chloride (5 mL). The vial was sealed and the mixture heated at 70° C. for ~1 h. After cooling to room temperature the mixture was evaporated under vacuum. The residue was diluted with EtOAc (10 mL) and the mixture evaporated to dryness and used without further purification.

Step B: 4-Iodo-3-(2-(2-methylpyridin-4-yl)-2,4,5,6-tetrahydropyrrolo[3,4-c]pyrazole-5-carbonyl)benzonitrile. To a 30 mL vial were added 2-(2-methylpyridin-4-yl)-2,4,5,6-tetrahydropyrrolo[3,4-c]pyrazole dihydrochloride (330 mg, 1.21 mmol) and DCM (5 mL). DIEA (0.77 mL, 4.40 mmol) was added and the mixture stirred at room temperature. The pyrazole/DIEA mixture was then added to a DCM (5 mL) solution of the acid chloride from Step A and the reaction was stirred for 4 h. The reaction mixture was washed with H₂O, dried (Na₂SO₄) then concentrated under reduced pressure. Purification (SiO₂, 0-3% MeOH/DCM) gave the title compound (0.42 g, 84%) as a pale yellow foam. ¹H NMR (400 MHz, DMSO-d₆) δ=8.57-8.40 (m, 2H), 8.15 (dd, J=1.2, 8.2 Hz, 1H), 7.91 (dd, J=2.2, 6.8 Hz, 1H), 7.70 (dd, J=2.0, 16.4 Hz, 1H), 7.67-7.57 (m, 2H), 4.70 (d, J=8.2 Hz, 2H), 4.32 (d, J=19.2 Hz, 2H), 3.31-3.31 (s, 3H); [M+H]=456.3.

Step C. 4-(3-Fluorophenyl)-3-[2-(2-methylpyridin-4-yl)-2H 4H 5H 6H-pyrrolo[3,4-c]pyrazole-5-carbonyl]benzonitrile. To a 30 mL vial were added 4-iodo-3-(2-(2-methylpyridin-4-yl)-2,4,5,6-tetrahydropyrrolo[3,4-c]pyrazole-5-carbonyl)benzonitrile (200.0 mg, 0.44 mmol) and (3-fluorophenyl)boronic acid (73.76 mg, 0.53 mmol) in CH₃CN (30 mL) and saturated aq. NaHCO₃ (7.5 mL) with stirring. Pd(dppf)₂Cl₂ catalyst (16.07 mg, 0.02 mmol) was added and the mixture was flushed with nitrogen for 2 minutes. The mixture was stirred at 50° C. for 6 h then cooled to room temperature and concentrated under reduced pressure. Purification (FCC, SiO₂, 0-3% MeOH/DCM) afforded the title compound (128.0 mg, 68.8%) as a tan solid. ¹H NMR (400 MHz, DMSO-d₆) δ=8.47-8.32 (m, 2H), 8.07-8.01 (m, 2H), 7.77-7.72 (m, 1H), 7.65 (dd, J=2.2, 15.5 Hz, 1H), 7.56 (ddd, J=2.0, 5.6, 12.0 Hz, 1H), 7.51-7.44 (m, 1H), 7.37-7.29 (m, 2H), 7.27-7.18 (m, 1H), 4.51 (d, J=11.3 Hz, 2H), 4.22 (d, J=14.1 Hz, 2H), 2.48 (s, 3H); [M+H]=424.4.

Example 9

4-((1,1-Difluoropropan-2-yl)oxy)-3-(2-(4-fluorophenyl)-2,4,5,6-tetrahydropyrrolo[3,4-c]pyrazole-5-carbonyl)benzonitrile

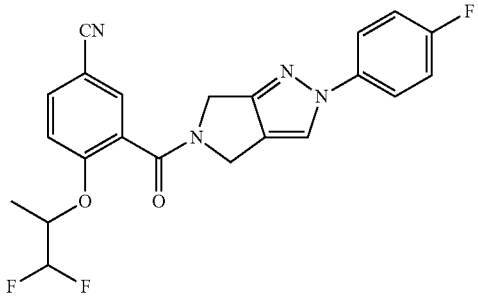 [SMILES: CC(Oc1ccc(C#N)cc1C(=O)N1Cc2cn(-c3ccc(F)cc3)nc2C1)C(F)F]

Step A. 4-Fluoro-3-(2-(4-fluorophenyl)-2,4,5,6-tetrahydropyrrolo[3,4-c]pyrazole-5-carbonyl)benzonitrile. The title compound was prepared in a manner analogous to Example 1, with the appropriate starting material substitutions.

Step B. 4-((1,1-Difluoropropan-2-yl)oxy)-3-(2-(4-fluorophenyl)-2,4,5,6-tetrahydropyrrolo[3,4-c]pyrazole-5-carbonyl)benzonitrile. To a 0° C. solution of 1,1-difluoropropan-2-one (100.00 mg, 1.06 mmol) and THF (5.00 mL) was added NaBH₄ (14.92 mg, 0.39 mmol). The mixture was allowed to reach rt overnight. The mixture was filtered and placed into a 50 mL flask along with 4-fluoro-3-(2-(4-fluorophenyl)-2,4,5,6-tetrahydropyrrolo[3,4-c]pyrazole-5-carbonyl)benzonitrile (50.00 mg, 0.14 mmol) and heated to 60° C. for 3 h. The crude material was filtered, diluted with MeOH, and purified via preparative HPLC on C-18 reverse-phase SiO₂, eluting with a gradient formed from acetonitrile:H₂O: 0.1% formic acid (15-85%) to afford the title compound (9 mg, 16%). ¹H NMR (400 MHz, DMSO-d₆) δ=8.39-8.17 (m, 1H), 7.93 (dd, J=2.2, 8.8 Hz, 1H), 7.88-7.74 (m, 3H), 7.48 (dd, J=1.2, 9.0 Hz, 1H), 7.39-7.22 (m, 2H), 6.41-5.79 (m, 1H), 5.04 (dd, J=3.1, 6.3 Hz, 1H), 4.64 (d, J=7.0 Hz, 2H), 4.47-4.23 (m, 2H), 1.28 (d, J=6.3 Hz, 3H); [M+H]=427.04.

Example 10

4-(3,3-Dimethylbutyl)-3-(2-(4-fluorophenyl)-2,4,5,6-tetrahydropyrrolo[3,4-c]pyrazole-5-carbonyl)-2-methoxybenzonitrile

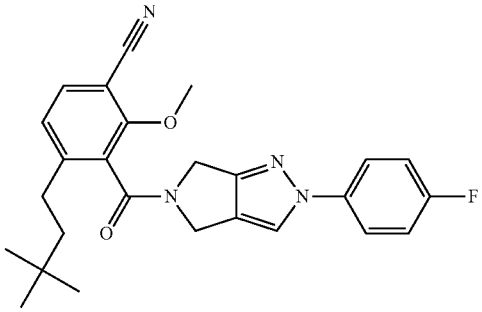 [SMILES: COc1c(C#N)ccc(CCC(C)(C)C)c1C(=O)N1Cc2cn(-c3ccc(F)cc3)nc2C1]

Step A. 4-[(1E)-3,3-Dimethylbut-1-en-1-yl]-3-{[2-(4-fluorophenyl)-2H,4H,5H,6H-pyrrolo[3,4-c]pyrazol-5-yl]carbonyl}-2-methoxybenzonitrile. The title compound was prepared in a manner analogous to Example 8, substituting (E)-(3,3-dimethylbut-1-en-1-yl)boronic acid for (3-fluorophenyl)boronic acid.

Step B. 4-(3,3-Dimethylbutyl)-3-(2-(4-fluorophenyl)-2,4,5,6-tetrahydropyrrolo[3,4-c]pyrazole-5-carbonyl)-2-methoxybenzonitrile. To a 150 mL pressure-vessel was added 4-[(1E)-3,3-dimethylbut-1-en-1-yl]-3-{[2-(4-fluorophenyl)-2H,4H,5H,6H-pyrrolo[3,4-c]pyrazol-5-yl]carbonyl}-2-methoxybenzonitrile (40.00 mg, 0.09 mmol), Pd/C (0.96 mg, 0.01 mmol), and MeOH (2.00 mL). The reaction mixture was evacuate and backfilled with N₂ (3 times) and then evacuate and backfilled with H₂ (3 times). On the last refill, the hydrogen-pressure was adjusted to 40 psi. The mixture was shook under 40 psi of H₂ for 2 h. The crude was filtered through CELITE®, concentrated under reduced pressure. Purification (FCC, SiO₂, 20-60% EtOAc/hexanes) afforded the title compound (24 mg, 59.7%). ¹H NMR (400 MHz, CDCl₃) δ=7.71-7.51 (m, 4H), 7.22-7.06 (m, 3H), 4.98-4.72 (m, 3H), 4.49 (dd, J=3.9, 13.3 Hz, 1H), 4.26-4.15 (m, 1H), 4.08 (d, J=3.5 Hz, 3H), 2.70-2.47 (m, 3H), 1.69-1.58 (m, 1H), 1.33 (ddt, J=2.7, 4.7, 12.9 Hz, 1H), 0.89 (d, J=2.0 Hz, 9H); [M+H]=447.25.

Example 11

4-[(1 1-Difluoropropan-2-yl)oxy]-3-[2-(4-fluorophenyl)-2H 4H 5H 6H-pyrrolo[3,4-c]pyrazole-5-carbonyl]-2-methoxybenzonitrile

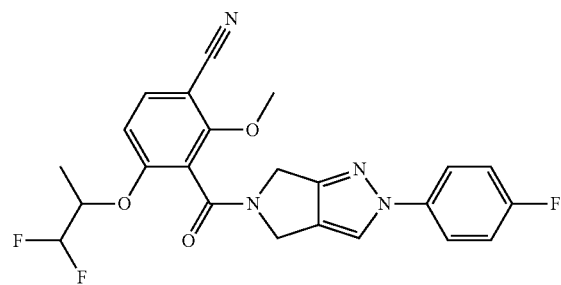 [SMILES: COc1c(C#N)ccc(OC(C)C(F)F)c1C(=O)N1Cc2cn(-c3ccc(F)cc3)nc2C1]

The title compound was prepared in a manner analogous to Example 9, with the appropriate starting material substitutions. $^1$H NMR (400 MHz, CDCl$_3$) δ=7.72-7.52 (m, 3H), 7.19-7.09 (m, 2H), 6.85-6.72 (m, 1H), 6.05-5.52 (m, 1H), 4.93-4.75 (m, 2H), 4.70-4.51 (m, 1H), 4.50-4.22 (m, 2H), 4.19-4.05 (m, 3H), 1.49-1.32 (m, 3H); [M+H]=457.32.

Examples 12-152 were prepared in a manner analogous to Example 2 with the appropriated starting material substitutions.

Example 12

3-[2-(5-Fluoropyridin-2-yl)-2H 4H 5H 6H 7H-pyrazolo[4,3-c]pyridine-5-carbonyl]-2-methoxy-4-(1 4 4-trifluorocyclohexyl)benzonitrile

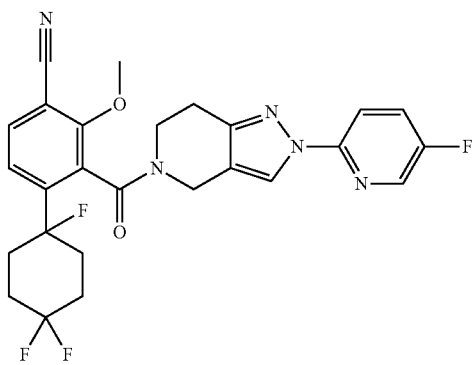 [SMILES: COc1c(C#N)ccc(C2(F)CCC(F)(F)CC2)c1C(=O)N1CCc2nn(-c3ccc(F)cn3)cc2C1]

$^1$H NMR (400 MHz, CDCl$_3$) δ=8.40-8.07 (m, 2H), 7.90 (td, J=4.5, 9.0 Hz, 1H), 7.61 (dd, J=3.9, 8.2 Hz, 1H), 7.56-7.45 (m, 1H), 7.09 (d, J=8.2 Hz, 1H), 5.14-4.20 (m, 2H), 4.13-3.83 (m, 4H), 3.67-3.32 (m, 1H), 3.08-2.73 (m, 2H), 2.63-1.73 (m, 8H); [M+H]=514.4.

Example 13

2-Methoxy-3-[2-(pyridin-3-yl)-2H 4H 5H 6H 7H-pyrazolo[4,3-c]pyridine-5-carbonyl]-4-(1 4 4-trifluorocyclohexyl)benzonitrile

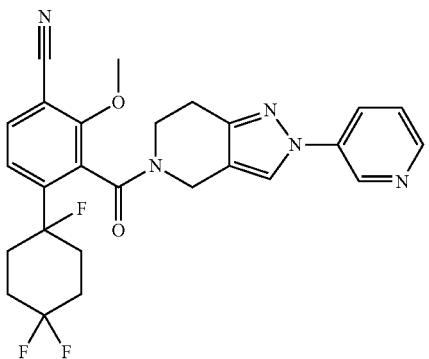 [SMILES: COc1c(C#N)ccc(C2(F)CCC(F)(F)CC2)c1C(=O)N1CCc2nn(-c3cccnc3)cc2C1]

$^1$H NMR (400 MHz, CDCl$_3$) δ=9.08-8.82 (m, 1H), 8.61-8.40 (m, 1H), 8.00 (d, J=8.2 Hz, 1H), 7.83 (s, 1H), 7.69-7.56 (m, 1H), 7.39 (td, J=4.3, 8.6 Hz, 1H), 7.10 (d, J=8.6 Hz, 1H), 5.15-4.27 (m, 2H), 4.25-3.91 (m, 4H), 3.66-3.36 (m, 1H), 3.09-2.73 (m, 2H), 2.68-1.71 (m, 8H); [M+H]=496.3.

Example 14

4-(4-Fluorooxan-4-yl)-3-[2-(5-fluoropyridin-2-yl)-2H 4H 5H 6H 7H-pyrazolo[4,3-c]pyridine-5-carbonyl]-2-methoxybenzonitrile

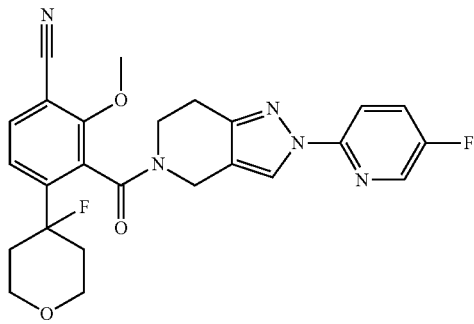 [SMILES: COc1c(C#N)ccc(C2(F)CCOCC2)c1C(=O)N1CCc2nn(-c3ccc(F)cn3)cc2C1]

$^1$H NMR (400 MHz, CDCl$_3$) δ=8.41-8.05 (m, 2H), 7.96-7.57 (m, 2H), 7.55-6.99 (m, 2H), 5.13-4.15 (m, 2H), 4.02 (d, J=15.7 Hz, 3H), 3.97-3.35 (m, 6H), 3.03-2.68 (m, 2H), 2.58-2.19 (m, 2H), 2.06-1.65 (m, 2H); [M+H]=480.4.

Example 15

3-[2-(5-Fluoropyridin-2-yl)-2H 4H 5H 6H-pyrrolo[3,4-c]pyrazole-5-carbonyl]-2-methoxy-4-(1 4 4-trifluorocyclohexyl)benzonitrile

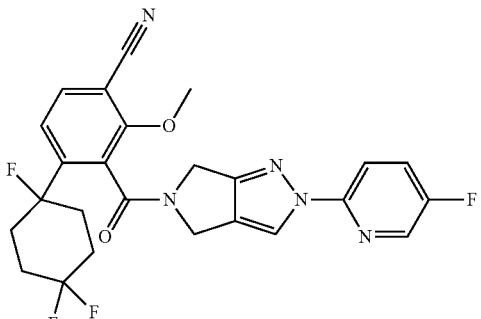

$^1$H NMR (400 MHz, CDCl$_3$) δ=8.40-8.09 (m, 2H), 8.01-7.76 (m, 1H), 7.69-7.61 (m, 1H), 7.59-7.44 (m, 1H), 7.12 (d, J=8.2 Hz, 1H), 4.93-4.68 (m, 2H), 4.46-4.22 (m, 2H), 4.18-4.06 (m, 3H), 2.72-1.78 (m, 8H); [M+H]=500.23.

Example 16

2-Chloro-3-[2-(2-methoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile

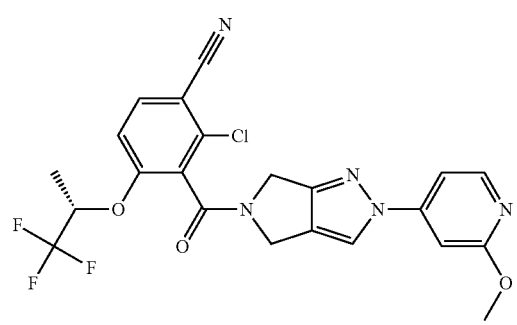 [SMILES: COc1cc(-n2cc3c(n2)CN(C(=O)c2c(O[C@@H](C)C(F)(F)F)ccc(C#N)c2Cl)C3)ccn1]

¹H NMR (400 MHz, DMSO-d₆) δ=8.61-8.39 (m, 1H), 8.20 (dd, J=2.3, 5.5 Hz, 1H), 8.17-8.09 (m, 1H), 7.57 (dd, J=4.5, 9.2 Hz, 1H), 7.53-7.40 (m, 1H), 7.27-7.14 (m, 1H), 5.57 (qd, J=6.1, 12.5 Hz, 1H), 4.86-4.51 (m, 2H), 4.49-4.14 (m, 2H), 3.90-3.81 (m, 3H), 1.49-1.23 (m, 3H); [M+H]=492.21.

Example 17

2-Chloro-3-[2-(2-methylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

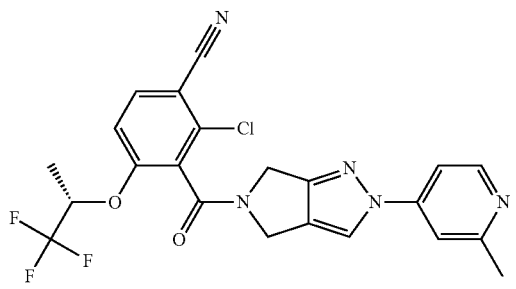 [SMILES: Cc1cc(-n2cc3c(n2)CN(C(=O)c2c(O[C@@H](C)C(F)(F)F)ccc(C#N)c2Cl)C3)ccn1]

¹H NMR (400 MHz, DMSO-d₆) δ=8.58-8.40 (m, 2H), 8.20-8.08 (m, 1H), 7.77-7.66 (m, 1H), 7.65-7.51 (m, 2H), 5.64-5.53 (m, 1H), 4.81-4.59 (m, 2H), 4.47-4.15 (m, 2H), 1.47-1.33 (m, 2H); [M+H]=476.32.

Example 18

2-Methoxy-3-[2-(2-methylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

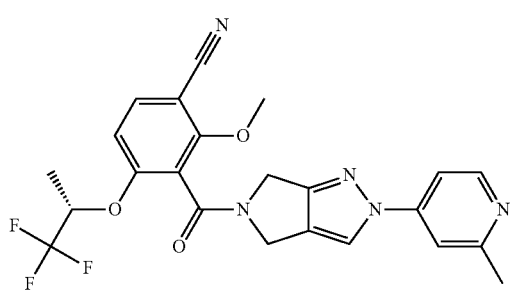 [SMILES: COc1c(C#N)ccc(O[C@@H](C)C(F)(F)F)c1C(=O)N1Cc2cn(-c3ccnc(C)c3)nc2C1]

¹H NMR (400 MHz, DMSO-d₆) δ=8.84-8.54 (m, 2H), 8.29-8.01 (m, 2H), 7.94 (td, J=2.4, 8.9 Hz, 1H), 7.26 (dd, J=4.9, 8.8 Hz, 1H), 5.57-5.43 (m, 1H), 4.89-4.18 (m, 4H), 4.02-3.92 (m, 3H), 2.68 (s, 3H), 1.47-1.27 (m, 3H); [M+H]=472.18.

Example 19

2-Chloro-3-[2-(6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

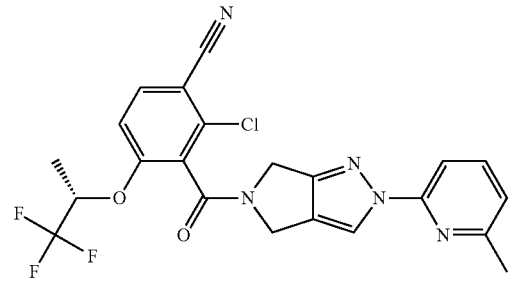 [SMILES: Cc1cccc(-n2cc3c(n2)CN(C(=O)c2c(O[C@@H](C)C(F)(F)F)ccc(C#N)c2Cl)C3)n1]

¹H NMR (400 MHz, DMSO-d₆) δ=8.51-8.30 (m, 1H), 8.20-8.09 (m, 1H), 7.84 (td, J=7.7, 9.2 Hz, 1H), 7.71-7.50 (m, 2H), 7.19 (d, J=8.2 Hz, 1H), 5.56 (dd, J=6.1, 11.2 Hz, 1H), 4.81-4.52 (m, 2H), 4.46-4.16 (m, 2H), 1.43-1.35 (m, 3H); [M+H]=476.21.

Example 20

4-(1-Fluorocyclobutyl)-2-methoxy-3-[2-(6-methyl-pyridin-2-yl)-2H 4H 5H 6H-pyrrolo[3,4-c]pyrazole-5-carbonyl]benzonitrile

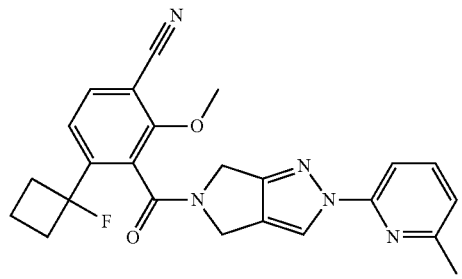 [SMILES: COc1c(C#N)ccc(C2(F)CCC2)c1C(=O)N1Cc2cn(-c3cccc(C)n3)nc2C1]

¹H NMR (400 MHz, DMSO-d₆) δ=8.51-8.23 (m, 1H), 7.96 (ddd, J=1.6, 3.5, 8.2 Hz, 1H), 7.89-7.74 (m, 1H), 7.71-7.55 (m, 1H), 7.49 (ddd, J=2.0, 6.3, 8.2 Hz, 1H), 7.18 (d, J=7.4 Hz, 1H), 4.77-4.53 (m, 3H), 4.35-4.10 (m, 3H), 4.03-3.90 (m, 3H), 2.94-2.74 (m, 1H), 2.52 (dd, J=2.7, 7.0 Hz, 2H), 2.13-1.87 (m, 1H), 1.83-1.62 (m, 1H); [M+H]=432.1.

Example 21

4-(4-Fluorooxan-4-yl)-2-methoxy-3-[2-(6-methyl-pyridin-2-yl)-2H 4H 5H 6H-pyrrolo[3,4-e]pyrazole-5-carbonyl]benzonitrile

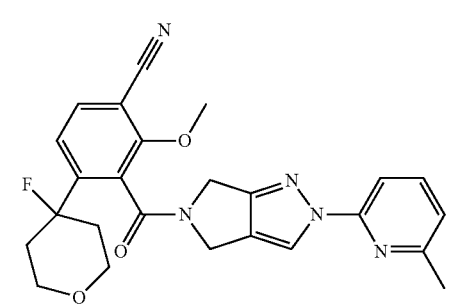 [SMILES: COc1c(C#N)ccc(C2(F)CCOCC2)c1C(=O)N1Cc2cn(-c3cccc(C)n3)nc2C1]

¹H NMR (400 MHz, DMSO-d₆) δ=8.51-8.23 (m, 1H), 7.93 (ddd, J=1.2, 4.6, 8.3 Hz, 1H), 7.83 (td, J=8.0, 10.3 Hz, 1H), 7.72-7.52 (m, 1H), 7.55-7.37 (m, 1H), 7.26-7.07 (m, 1H), 4.80-4.52 (m, 2H), 4.32-4.14 (m, 2H), 3.96 (d, J=3.5 Hz, 3H), 3.88-3.70 (m, 2H), 3.59 (q, J=11.7 Hz, 2H), 2.25-1.69 (m, 4H); [M+H]=462.2.

Example 22

2-Chloro-3-[2-(6-methylpyridin-2-yl)-2H 4H 5H 6H-pyrrolo[3,4-c]pyrazole-5-carbonyl]-4-(2 2 2-trifluoroethoxy)benzonitrile

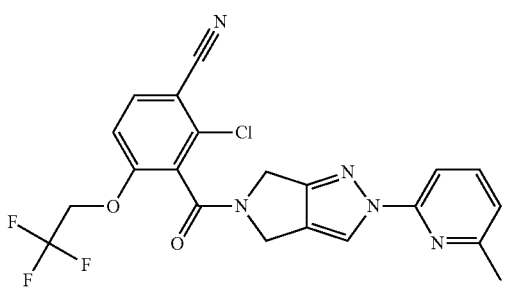 [SMILES: Cc1cccc(-n2cc3c(n2)CN(C(=O)c2c(OCC(F)(F)F)ccc(C#N)c2Cl)C3)n1]

¹H NMR (400 MHz, DMSO-d₆) δ=8.52-8.32 (m, 1H), 8.23-8.09 (m, 1H), 7.83 (td, J=7.8, 9.8 Hz, 1H), 7.71-7.56 (m, 1H), 7.48 (dd, J=7.6, 8.8 Hz, 1H), 7.19 (dd, J=0.8, 7.0 Hz, 1H), 5.13-4.94 (m, 2H), 4.81-4.55 (m, 3H), 4.44-4.20 (m, 3H); [M+H]=462.15.

Example 23

4-(1-Fluorocyclobutyl)-3-[2-(5-fluoropyridin-3-yl)-2H 4H 5H 6H-pyrrolo[3,4-c]pyrazole-5-carbonyl]-2-methoxybenzonitrile

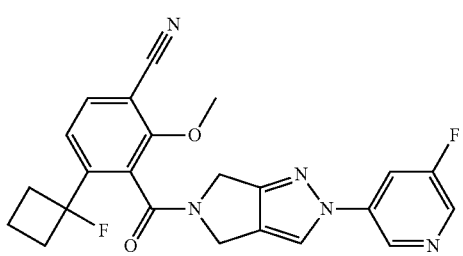 [SMILES: COc1c(C#N)ccc(C2(F)CCC2)c1C(=O)N1Cc2cn(-c3cncc(F)c3)nc2C1]

¹H NMR (400 MHz, DMSO-d₆) δ=9.01-8.90 (m, 1H), 8.57-8.33 (m, 2H), 8.18 (tdd, J=2.3, 10.4, 19.0 Hz, 1H), 7.96 (ddd, J=1.2, 2.3, 8.2 Hz, 1H), 7.49 (ddd, J=2.0, 3.5, 8.2 Hz, 1H), 4.83-4.55 (m, 2H), 4.39-4.10 (m, 5H), 3.99-3.89 (m, 3H), 2.99-2.70 (m, 1H), 2.59-2.34 (m, 8H), 2.15-1.90 (m, 1H), 1.83-1.62 (m, 1H); [M+H]=436.0.

Example 24

4-(4-Fluorooxan-4-yl)-3-[2-(5-fluoropyridin-3-yl)-2H 4H 5H 6H-pyrrolo[3,4-c]pyrazole-5-carbonyl]-2-methoxybenzonitrile

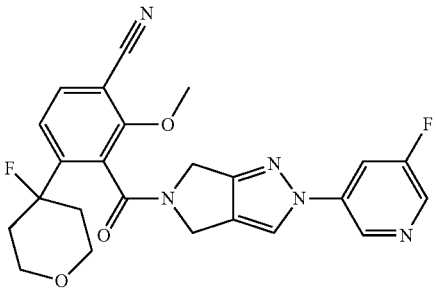 [SMILES: COc1c(C#N)ccc(C2(F)CCOCC2)c1C(=O)N1Cc2cn(-c3cncc(F)c3)nc2C1]

¹H NMR (400 MHz, DMSO-d₆) δ=9.04-8.91 (m, 1H), 8.61-8.33 (m, 2H), 8.29-8.10 (m, 1H), 7.93 (ddd, J=1.2, 2.9, 8.4 Hz, 1H), 7.46 (ddd, J=1.6, 4.5, 8.4 Hz, 1H), 4.82-4.55 (m, 2H), 4.37-4.14 (m, 2H), 3.96 (d, J=2.3 Hz, 3H), 3.87-3.70 (m, 2H), 3.69-3.41 (m, 2H), 2.75-2.53 (m, 1H), 2.20-1.74 (m, 3H); [M+H]=466.21.

Example 25

2-Chloro-3-[2-(5-fluoropyridin-3-yl)-2H 4H 5H 6H-pyrrolo[3,4-c]pyrazole-5-carbonyl]-4-(2 2 2-trifluoroethoxy)benzonitrile

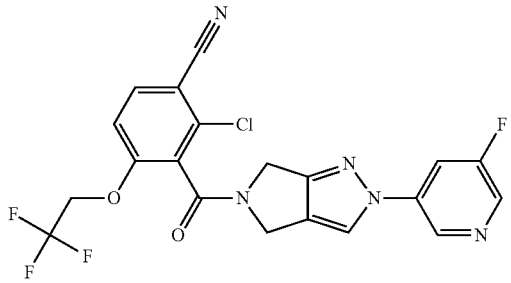 [SMILES: N#Cc1ccc(OCC(F)(F)F)c(C(=O)N2Cc3cn(-c4cncc(F)c4)nc3C2)c1Cl]

¹H NMR (400 MHz, DMSO-d₆) δ=8.98 (dd, J=1.2, 13.3 Hz, 1H), 8.57-8.39 (m, 2H), 8.24-8.12 (m, 2H), 7.47 (dd, J=6.3, 9.0 Hz, 1H), 5.15-4.94 (m, 2H), 4.84-4.60 (m, 2H), 4.54-4.22 (m, 2H); [M+H]=466.02.

Example 26

4-(1-Fluorocyclobutyl)-3-[2-(4-fluorophenyl)-2H 4H 5H 6H-pyrrolo[3,4-c]pyrazole-5-carbonyl]-2-methoxybenzonitrile

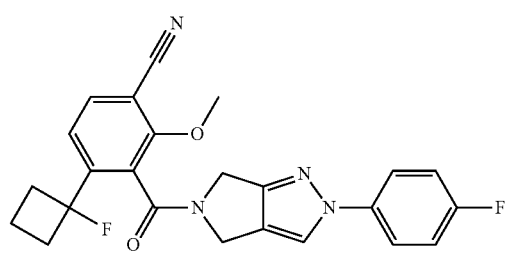 [SMILES: COc1c(C#N)ccc(C2(F)CCC2)c1C(=O)N1Cc2cn(-c3ccc(F)cc3)nc2C1]

¹H NMR (400 MHz, DMSO-d₆) δ=8.34-8.09 (m, 1H), 7.91 (td, J=1.8, 8.2 Hz, 1H), 7.83-7.67 (m, 2H), 7.60 (d, J=8.2 Hz, 1H), 7.44 (ddd, J=2.1, 3.2, 8.3 Hz, 1H), 7.34-7.19 (m, 2H), 4.73-4.48 (m, 2H), 4.33-4.07 (m, 2H), 3.97-3.83 (m, 3H), 2.89-2.70 (m, 1H), 2.68-2.54 (m, 1H), 2.41-2.31 (m, 2H), 2.08-1.82 (m, 1H), 1.82-1.41 (m, 1H); [M+H]=435.24.

Example 27

4-(4-Fluorooxan-4-yl)-3-[2-(4-fluorophenyl)-2H 4H 5H 6H-pyrrolo[3,4-c]pyrazole-5-carbonyl]-2-methoxybenzonitrile

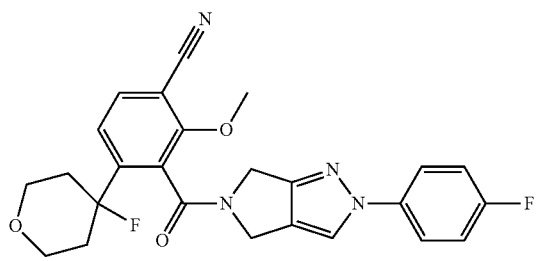 [SMILES: COc1c(C#N)ccc(C2(F)CCOCC2)c1C(=O)N1Cc2cn(-c3ccc(F)cc3)nc2C1]

¹H NMR (400 MHz, DMSO-d₆) δ=8.35-8.11 (m, 1H), 7.87 (ddd, J=1.2, 2.9, 8.3 Hz, 1H), 7.81-7.66 (m, 2H), 7.41 (ddd, J=1.3, 4.3, 8.4 Hz, 1H), 7.32-7.14 (m, 2H), 4.75-4.47 (m, 2H), 4.34-4.08 (m, 2H), 3.91 (d, J=2.6 Hz, 3H), 3.83-3.66 (m, 2H), 3.53 (q, J=11.8 Hz, 2H), 2.19-1.65 (m, 4H); [M+H]=465.26.

Example 28

2-Chloro-3-[2-(4-fluorophenyl)-2H 4H 5H 6H-pyrrolo[3,4-c]pyrazole-5-carbonyl]-4-(2 2 2-trifluoroethoxy)benzonitrile

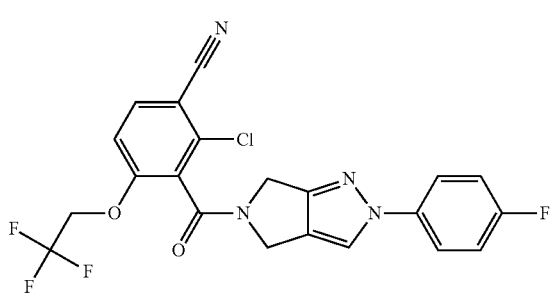 [SMILES: N#Cc1ccc(OCC(F)(F)F)c(C(=O)N2Cc3cn(-c4ccc(F)cc4)nc3C2)c1Cl]

¹H NMR (400 MHz, DMSO-d₆) δ=8.35-8.18 (m, 1H), 8.10 (dd, J=3.0, 8.8 Hz, 1H), 7.87-7.66 (m, 2H), 7.42 (dd, J=5.7, 9.0 Hz, 1H), 7.34-7.18 (m, 2H), 5.08-4.89 (m, 2H), 4.74-4.49 (m, 2H), 4.36-4.13 (m, 2H); [M+H]=465.07.

Example 29

3-[2-(4-Fluorophenyl)-2H 4H 5H 6H-pyrrolo[3,4-c]pyrazole-5-carbonyl]-2-methoxy-4-(2 2 2-trifluoroethoxy)benzonitrile

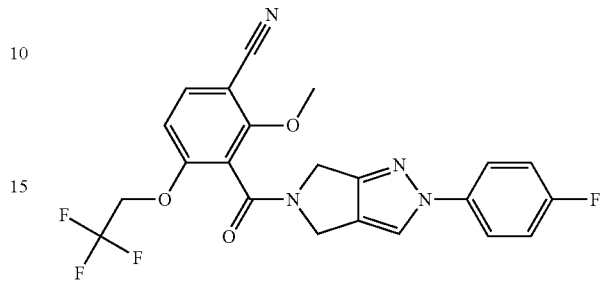

¹H NMR (400 MHz, DMSO-d₆) δ=8.33-8.14 (m, 1H), 7.88 (dd, J=2.9, 8.8 Hz, 1H), 7.83-7.67 (m, 2H), 7.35-7.20 (m, 2H), 7.10 (dd, J=6.9, 8.8 Hz, 1H), 4.93 (q, J=8.7 Hz, 2H), 4.74-4.45 (m, 3H), 4.45-4.12 (m, 2H), 3.99-3.78 (m, 3H); [M+H]=461.16.

Example 30

2-Chloro-3-[2-(5-fluoropyridin-3-yl)-2H 4H 5H 6H-pyrrolo[3,4-c]pyrazole-5-carbonyl]-4-{[(2R)-1 1 1-trifluoropropan-2-yl]oxy}benzonitrile

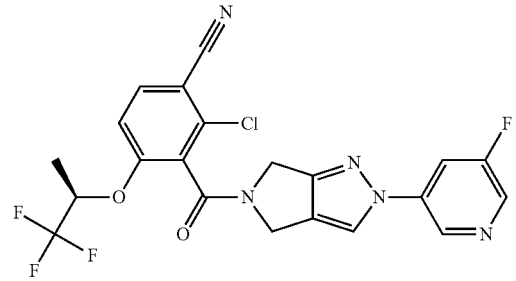 [SMILES: C[C@@H](Oc1ccc(C#N)c(Cl)c1C(=O)N1Cc2cn(-c3cncc(F)c3)nc2C1)C(F)(F)F]

¹H NMR (400 MHz, DMSO-d₆) δ=9.03-8.90 (m, 1H), 8.57-8.37 (m, 2H), 8.28-8.04 (m, 2H), 7.57 (dd, J=4.3, 9.0 Hz, 1H), 5.57 (qd, J=6.3, 12.5 Hz, 1H), 4.83-4.58 (m, 2H), 4.49-4.16 (m, 2H), 1.48-1.34 (m, 3H); [M+H]=480.20.

Example 31

2-Chloro-3-[2-(3-methylpyridin-2-yl)-2H 4H 5H 6H-pyrrolo[3,4-c]pyrazole-5-carbonyl]-4-{[(2R)-1 1 1-trifluoropropan-2-yl]oxy}benzonitrile

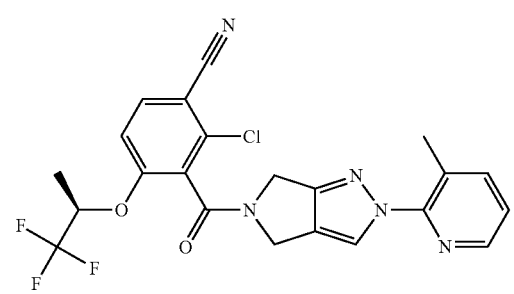 [SMILES: Cc1cccnc1-n1cc2c(n1)CN(C(=O)c1c(O[C@H](C)C(F)(F)F)ccc(C#N)c1Cl)C2]

¹H NMR (400 MHz, DMSO-d₆) δ=8.37-8.29 (m, 1H), 8.22-8.09 (m, 2H), 7.85 (tdd, J=0.8, 7.1, 8.0 Hz, 1H), 7.57 (t, J=9.2 Hz, 1H), 7.41-7.32 (m, 1H), 5.58 (qd, J=6.3, 12.5 Hz, 2H), 4.83-4.10 (m, 6H), 1.45-1.36 (m, 3H); [M+H]=476.1.

Example 32

2-Chloro-3-[2-(5-fluoropyridin-2-yl)-2H 4H 5H 6H-pyrrolo[3,4-c]pyrazole-5-carbonyl]-4-{[(2R)-1 1 1-trifluoropropan-2-yl]oxy}benzonitrile

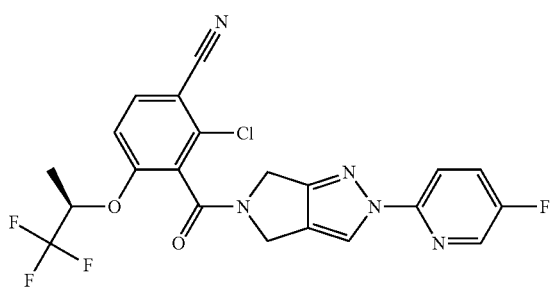 [SMILES: C[C@@H](Oc1ccc(C#N)c(Cl)c1C(=O)N1Cc2cn(-c3ccc(F)cn3)nc2C1)C(F)(F)F]

¹H NMR (400 MHz, DMSO-d₆) δ=8.50-8.39 (m, 1H), 8.37-8.29 (m, 1H), 8.20-8.07 (m, 1H), 7.99-7.78 (m, 2H), 7.64-7.51 (m, 1H), 5.71-5.46 (m, 1H), 4.84-4.53 (m, 2H), 4.49-4.10 (m, 2H), 1.52-1.25 (m, 3H); M+H =480.1.

Example 33

5-(5-Methanesulfonyl-2-{[(2S)-1 1 1-trifluoropropan-2-yl]Oxy}benzoyl)-2-(2-methylphenyl)-2H 4H 5H 6H-pyrrolo[3,4-c]pyrazole

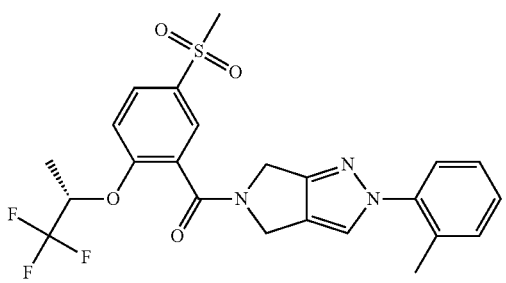

¹H NMR (400 MHz, DMSO-d₆) δ=8.02-7.97 (m, 1H), 7.93-7.76 (m, 2H), 7.59 (dd, J=3.1, 9.0 Hz, 1H), 7.41-7.28 (m, 4H), 5.54 (td, J=6.2, 12.7 Hz, 1H), 4.67 (s, 2H), 4.42-4.28 (m, 2H), 3.24 (s, 3H), 2.19 (d, J=7.0 Hz, 3H), 1.43 (d, J=6.3 Hz, 3H); [M+H]=494.3.

Example 34

5-(5-Methanesulfonyl-2-{[(2S)-1 1 1-trifluoropropan-2-yl]oxy}benzoyl)-2-(3-methylphenyl)-2H 4H 5H 6H-pyrrolo[3,4-c]pyrazole

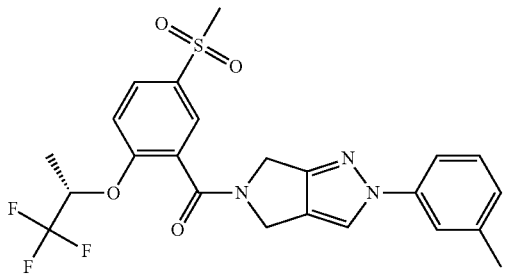 [SMILES: Cc1cccc(-n2cc3c(n2)CN(C(=O)c2cc(S(C)(=O)=O)ccc2O[C@@H](C)C(F)(F)F)C3)c1]

¹H NMR (400 MHz, DMSO-d₆) δ=8.36-8.20 (m, 2H), 8.00 (dd, J=2.3, 8.6 Hz, 1H), 7.90 (dd, J=2.3, 4.3 Hz, 1H), 7.65-7.49 (m, 4H), 7.34 (dt, J=2.0, 7.8 Hz, 1H), 7.09 (d, J=7.8 Hz, 1H), 5.54 (dq, J=3.9, 6.4 Hz, 1H), 4.66 (d, J=5.5 Hz, 2H), 4.39-4.30 (m, 2H), 3.24 (s, 3H), 2.35 (d, J=2.7 Hz, 3H), 1.42 (dd, J=2.0, 6.3 Hz, 3H); [M+H]=494.18.

Example 35

2-(3-Chloro-4-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

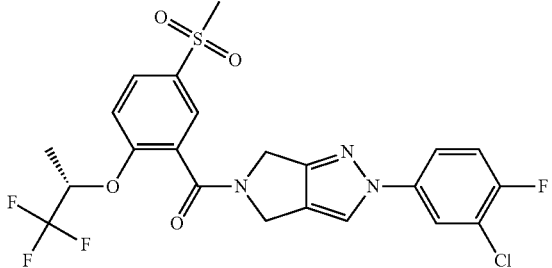

¹H NMR (400 MHz, DMSO-d₆) δ=8.44-8.28 (m, 1H), 8.08-7.88 (m, 3H), 7.81 (dddd, J=2.7, 4.3, 8.9, 13.0 Hz, 1H), 7.63-7.50 (m, 2H), 5.53 (dq, J=4.3, 6.3 Hz, 1H), 4.66 (d, J=6.3 Hz, 2H), 4.43-4.27 (m, 2H), 3.23 (s, 2H), 1.42 (dd, J=1.6, 6.3 Hz, 2H); [M+H]=532.19.

Example 36

2-(4-Fluoro-3-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole

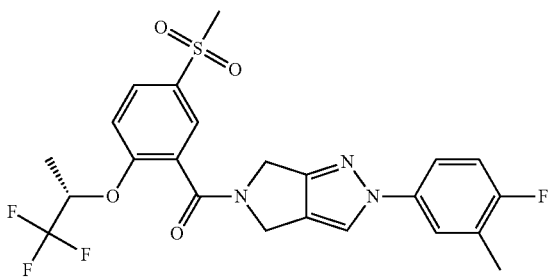

¹H NMR (400 MHz, DMSO-d₆) δ=8.33-8.17 (m, 2H), 8.00 (dd, J=2.5, 8.8 Hz, 1H), 7.90 (dd, J=2.3, 3.9 Hz, 1H), 7.72 (ddd, J=2.5, 6.6, 14.0 Hz, 1H), 7.65-7.54 (m, 2H), 7.24 (t, J=9.0 Hz, 1H), 5.59-5.49 (m, 1H), 4.65 (d, J=4.7 Hz, 2H), 4.42-4.27 (m, 3H), 3.23 (s, 2H), 2.27 (t, J=2.2 Hz, 3H), 1.42 (dd, J=1.6, 6.3 Hz, 3H); [M+H]=512.16.

Example 37

2-(3 4-Difluorophenyl)-5-(5-methanesulfonyl-2-{[(2S)-1 1 1-trifluoropropan-2-yl]oxy}benzoyl)-2H 4H 5H 6H-pyrrolo[3,4-e]pyrazole

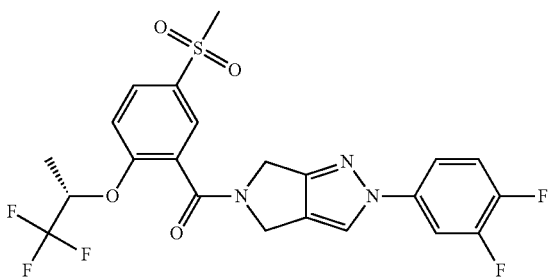 [SMILES: C[C@H](Oc1ccc(S(C)(=O)=O)cc1C(=O)N1Cc2cn(-c3ccc(F)c(F)c3)nc2C1)C(F)(F)F]

¹H NMR (400 MHz, DMSO-d₆) δ=8.42-8.25 (m, 1H), 8.03-7.85 (m, 3H), 7.70-7.51 (m, 3H), 5.58-5.49 (m, 1H), 4.66 (d, J=6.7 Hz, 2H), 4.44-4.27 (m, 2H), 3.23 (s, 2H), 1.42 (dd, J=1.8, 6.5 Hz, 2H); [M+H]=516.17.

Example 38

2-(2 4-Difluorophenyl)-5-(5-methanesulfonyl-2-{[(2S)-1 1 1-trifluoropropan-2-yl]oxy}benzoyl)-2H 4H 5H 6H-pyrrolo[3,4-e]pyrazole

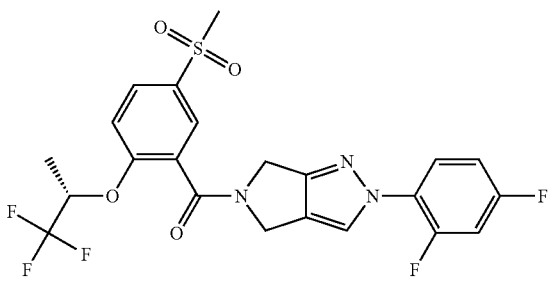 [SMILES: C[C@H](Oc1ccc(S(C)(=O)=O)cc1C(=O)N1Cc2cn(-c3ccc(F)cc3F)nc2C1)C(F)(F)F]

¹H NMR (400 MHz, DMSO-d₆) δ=8.05-7.97 (m, 1H), 7.90 (td, J=2.2, 4.3 Hz, 1H), 7.84-7.69 (m, 1H), 7.63-7.50 (m, 2H), 7.29-7.19 (m, 1H), 5.53 (td, J=6.3, 12.5 Hz, 1H), 4.67 (d, J=8.6 Hz, 2H), 4.44-4.27 (m, 2H), 3.23 (s, 2H), 1.43 (d, J=6.7 Hz, 3H); [M+H]=516.11.

Example 39

5-[5-Methanesulfonyl-2-(2-methylpropoxy)benzoyl]-2-(3-methylphenyl)-2H 4H 5H 6H-pyrrolo[3,4-e]pyrazole

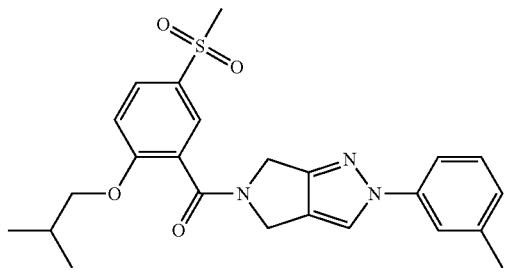

¹H NMR (400 MHz, DMSO-d₆) δ=8.36-8.18 (m, 1H), 7.95 (dd, J=2.3, 8.6 Hz, 1H), 7.82 (dd, J=2.3, 3.9 Hz, 1H), 7.64-7.50 (m, 2H), 7.39-7.06 (m, 3H), 4.66 (d, J=5.5 Hz, 2H), 4.36 (d, J=16.8 Hz, 2H), 3.94 (dd, J=3.9, 6.3 Hz, 2H), 3.20 (s, 3H), 2.35 (d, J=3.1 Hz, 2H), 2.03-1.90 (m, 1H), 0.86 (dd, J=1.6, 6.7 Hz, 5H); [M+H]=545.24.

Example 40

5-[5-(Ethanesulfonyl)-2-{[(2S)-1 1 1-trifluoropropan-2-yl]oxy}benzoyl]-2-phenyl-2H 4H 5H 6H-pyrrolo[3,4-e]pyrazole

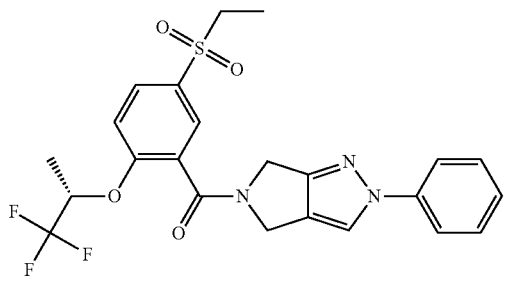 [SMILES: CCS(=O)(=O)c1ccc(O[C@@H](C)C(F)(F)F)c(C(=O)N2Cc3cn(-c4ccccc4)nc3C2)c1]

¹H NMR (400 MHz, DMSO-d₆) δ=8.39-8.22 (m, 1H), 7.99-7.93 (m, 1H), 7.86 (dd, J=2.3, 3.9 Hz, 1H), 7.81-7.74 (m, 2H), 7.60 (dd, J=1.6, 9.0 Hz, 1H), 7.50-7.43 (m, 2H), 7.32-7.25 (m, 1H), 5.54 (td, J=6.3, 12.8 Hz, 1H), 4.66 (d, J=6.7 Hz, 2H), 4.42-4.26 (m, 2H), 3.36-3.31 (m, 2H), 1.43 (dd, J=2.0, 6.3 Hz, 3H), 1.14-1.07 (m, 3H); [M+H]=494.22.

Example 41

5-[5-(Ethanesulfonyl)-2-{[(2S)-1 1 1-trifluoropropan-2-yl]oxy}benzoyl]-2-(4-fluorophenyl)-2H 4H 5H 6H-pyrrolo[3,4-c]pyrazole

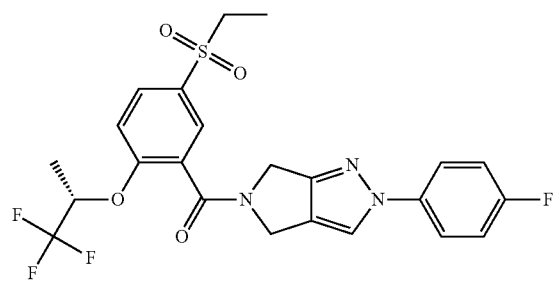 [SMILES: CCS(=O)(=O)c1ccc(O[C@@H](C)C(F)(F)F)c(C(=O)N2Cc3cn(-c4ccc(F)cc4)nc3C2)c1]

¹H NMR (400 MHz, DMSO-d₆) δ=8.36-8.20 (m, 1H), 7.99-7.93 (m, 1H), 7.86 (dd, J=2.3, 3.5 Hz, 1H), 7.84-7.76 (m, 2H), 7.60 (dd, J=1.6, 9.0 Hz, 1H), 7.36-7.28 (m, 2H), 5.54 (quind, J=6.3, 12.8 Hz, 1H), 4.66 (d, J=6.3 Hz, 2H), 4.42-4.26 (m, 2H), 3.37-3.31 (m, 2H), 1.42 (dd, J=1.6, 6.3 Hz, 3H), 1.11 (t, J=7.4 Hz, 3H); [M+H]=512.16.

Example 42

2-(2-Fluoro-3-methylphenyl)-5-(5-methanesulfonyl-2-{[(2S)-1 1 1-trifluoropropan-2-yl]oxy}benzoyl)-2H 4H 5H 6H-pyrrolo[3,4-e]pyrazole

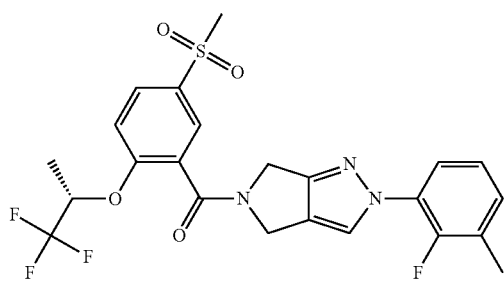 [SMILES: Cc1cccc(-n2cc3c(n2)CN(C(=O)c2cc(S(C)(=O)=O)ccc2O[C@@H](C)C(F)(F)F)C3)c1F]

¹H NMR (400 MHz, DMSO-d₆) δ=8.05-7.97 (m, 1H), 7.95-7.88 (m, 2H), 7.62-7.48 (m, 2H), 7.32-7.26 (m, 1H), 7.24-7.16 (m, 1H), 5.59-5.48 (m, 1H), 4.67 (d, J=7.8 Hz, 2H), 4.44-4.27 (m, 2H), 3.24 (s, 3H), 2.30 (t, J=2.0 Hz, 3H), 1.43 (d, J=6.3 Hz, 3H); [M+H]=512.12.

Example 43

2-[2-Fluoro-3-(trifluoromethyl)phenyl]-5-(5-methanesulfonyl-2-{[(2S)-1 1 1-trifluoropropan-2-yl]oxy}benzoyl)-2H 4H 5H 6H-pyrrolo[3,4-e]pyrazole

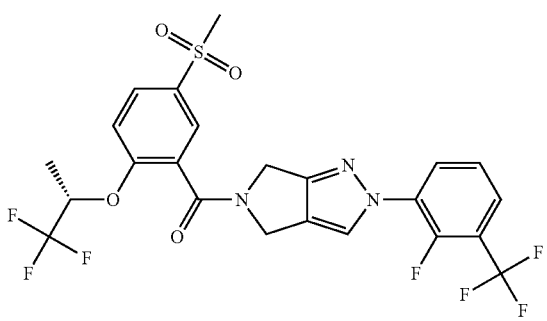 [SMILES: C[C@H](Oc1ccc(S(C)(=O)=O)cc1C(=O)N1Cc2cn(-c3cccc(C(F)(F)F)c3F)nc2C1)C(F)(F)F]

¹H NMR (400 MHz, DMSO-d₆) δ=8.18-8.03 (m, 2H), 8.00 (dd, J=2.2, 9.2 Hz, 1H), 7.91 (dd, J=2.3, 4.7 Hz, 1H), 7.79 (t, J=7.2 Hz, 1H), 7.63-7.51 (m, 2H), 5.54 (td, J=6.3, 12.5 Hz, 1H), 4.69 (d, J=11.3 Hz, 2H), 4.46-4.28 (m, 2H), 3.26-3.21 (m, 3H), 1.43 (d, J=6.3 Hz, 3H); [M+H]=566.12.

Example 44

5-(5-Methanesulfonyl-2-{[(2S)-1 1 1-trifluoropropan-2-yl]oxy}benzoyl)-2-[3-(trifluoromethyl)phenyl]-2H 4H 5H 6H-pyrrolo[3,4-c]pyrazole

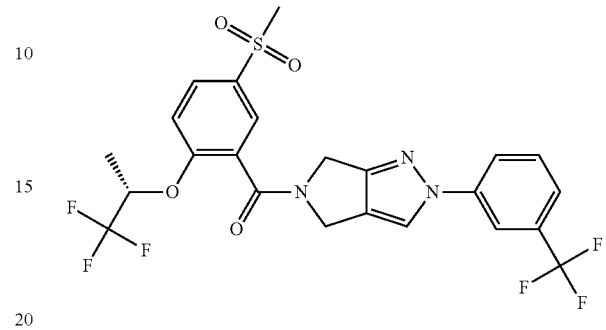

¹H NMR (400 MHz, DMSO-d₆) δ=8.58-8.40 (m, 1H), 8.17-8.08 (m, 2H), 8.05-7.98 (m, 1H), 7.91 (dd, J=2.3, 4.3 Hz, 1H), 7.76-7.68 (m, 1H), 7.66-7.57 (m, 2H), 5.54 (td, J=6.3, 12.5 Hz, 1H), 4.68 (d, J=7.8 Hz, 2H), 4.46-4.29 (m, 2H), 3.26-3.21 (m, 3H), 1.42 (dd, J=2.0, 6.3 Hz, 3H); [M+H]=548.15.

Example 45

5-[5-Methanesulfonyl-2-(propan-2-yloxy)benzoyl]-2-phenyl-2H 4H 5H 6H-pyrrolo[3,4-c]pyrazole

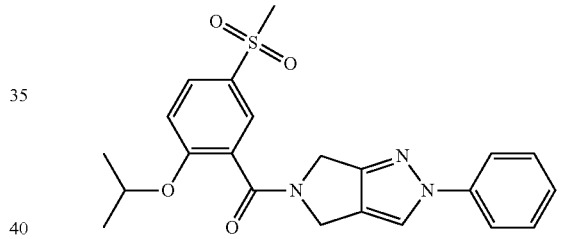

¹H NMR (400 MHz, DMSO-d₆) δ=8.39-8.21 (m, 1H), 7.93 (dd, J=2.3, 9.0 Hz, 1H), 7.83-7.73 (m, 3H), 7.50-7.43 (m, 2H), 7.38 (d, J=8.6 Hz, 1H), 7.32-7.23 (m, 1H), 4.88-4.79 (m, 1H), 4.67 (d, J=7.0 Hz, 2H), 4.37 (d, J=18.8 Hz, 2H), 3.20 (s, 3H), 1.29-1.23 (m, 6H); [M+H]=426.20.

Example 46

2-[2-Fluoro-3-(trifluoromethyl)phenyl]-5-[5-methanesulfonyl-2-(propan-2-yloxy)benzoyl]-2H 4H 5H 6H-pyrrolo[3,4-c]pyrazole

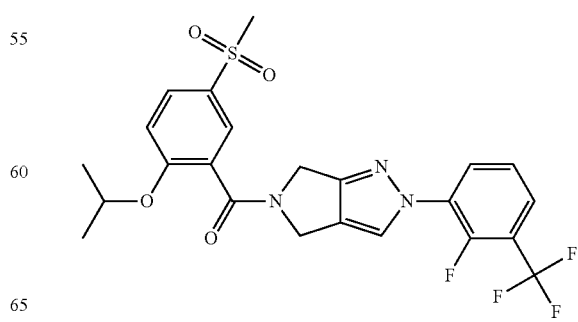

¹H NMR (400 MHz, DMSO-d₆) δ=8.18-8.02 (m, 2H), 7.96-7.90 (m, 1H), 7.83-7.75 (m, 2H), 7.54 (dt, J=4.7, 8.0 Hz, 1H), 7.38 (dd, J=1.6, 9.0 Hz, 1H), 4.84 (dtd, J=3.1, 6.1, 12.1 Hz, 1H), 4.69 (d, J=11.0 Hz, 2H), 4.45-4.34 (m, 2H), 3.23-3.17 (m, 3H), 1.27 (d, J=5.9 Hz, 6H); [M+H]=512.16.

Example 47

5-[5-Methanesulfonyl-2-(propan-2-yloxy)benzoyl]-2-[3-(trifluoromethyl)phenyl]-2H 4H 5H 6H-pyrrolo[3,4-c]pyrazole

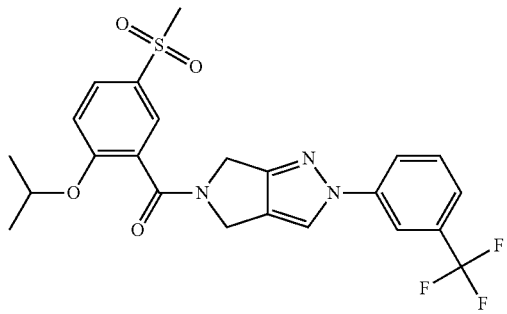 [SMILES: CC(C)Oc1ccc(S(C)(=O)=O)cc1C(=O)N1Cc2cn(-c3cccc(C(F)(F)F)c3)nc2C1]

¹H NMR (400 MHz, DMSO-d₆) δ=8.58-8.40 (m, 1H), 8.17-8.08 (m, 2H), 7.93 (dd, J=2.5, 8.8 Hz, 1H), 7.81 (dd, J=2.5, 4.1 Hz, 1H), 7.71 (t, J=8.0 Hz, 1H), 7.67-7.60 (m, 1H), 7.42-7.35 (m, 1H), 4.84 (dtd, J=2.7, 6.1, 12.1 Hz, 1H), 4.68 (d, J=7.8 Hz, 2H), 4.39 (d, J=18.8 Hz, 2H), 3.23-3.17 (m, 3H), 1.26 (dd, J=1.2, 5.9 Hz, 6H); [M+H]=494.18.

Example 48

5-[2-(2 2-Dimethylpropoxy)-5-methanesulfonylbenzoyl]-2-phenyl-2H 4H 5H 6H-pyrrolo[3,4-e]pyrazole

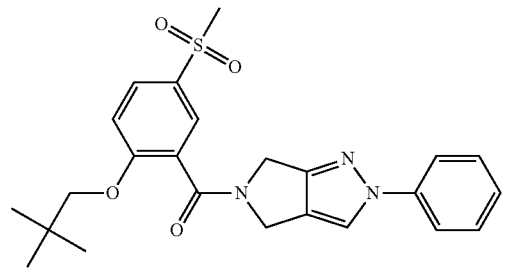 [SMILES: CC(C)(C)COc1ccc(S(C)(=O)=O)cc1C(=O)N1Cc2cn(-c3ccccc3)nc2C1]

¹H NMR (400 MHz, DMSO-d₆) δ=8.39-8.20 (m, 1H), 7.95 (dd, J=2.3, 8.6 Hz, 1H), 7.85-7.73 (m, 3H), 7.50-7.42 (m, 2H), 7.34 (dd, J=1.6, 8.6 Hz, 1H), 7.31-7.24 (m, 1H), 4.67 (d, J=6.3 Hz, 2H), 4.36 (d, J=17.6 Hz, 2H), 3.81 (d, J=4.3 Hz, 2H), 3.23-3.17 (m, 3H), 0.90-0.84 (m, 9H); [M+H]=454.36.

Example 49

5-[2-(2 2-Dimethylpropoxy)-5-methanesulfonylbenzoyl]-2-[2-fluoro-3-(trifluoromethyl)phenyl]-2H 4H 5H 6H-pyrrolo[3,4-c]pyrazole

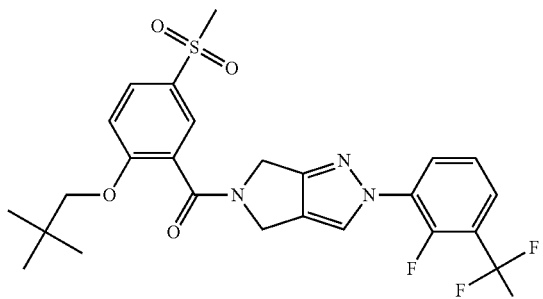

¹H NMR (400 MHz, DMSO-d₆) δ=8.18-8.01 (m, 2H), 7.95 (dd, J=2.3, 8.6 Hz, 1H), 7.83 (dd, J=2.5, 3.7 Hz, 1H), 7.78 (t, J=7.2 Hz, 1H), 7.53 (dt, J=5.1, 8.0 Hz, 1H), 7.34 (dd, J=2.3, 9.0 Hz, 1H), 4.69 (d, J=11.0 Hz, 2H), 4.44-4.34 (m, 2H), 3.81 (d, J=3.9 Hz, 2H), 3.22-3.17 (m, 3H), 0.87 (d, J=2.7 Hz, 9H); [M+H]=540.17.

Example 50

5-[2-(2 2-Dimethylpropoxy)-5-methanesulfonylbenzoyl]-2-[3-(trifluoromethyl)phenyl]-2H 4H 5H 6H-pyrrolo[3,4-c]pyrazole

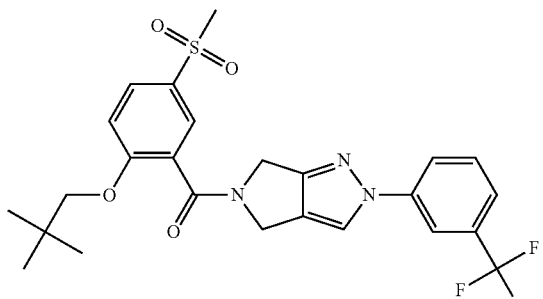

¹H NMR (400 MHz, DMSO-d₆) δ=8.59-8.39 (m, 1H), 8.18-8.06 (m, 2H), 7.96 (dd, J=2.3, 8.6 Hz, 1H), 7.83 (dd, J=2.3, 3.9 Hz, 1H), 7.75-7.67 (m, 1H), 7.66-7.59 (m, 1H), 7.34 (dd, J=1.6, 9.0 Hz, 1H), 4.69 (d, J=7.4 Hz, 2H), 4.38 (d, J=16.8 Hz, 2H), 3.81 (d, J=3.5 Hz, 2H), 3.23-3.16 (m, 3H), 0.89-0.84 (m, 9H); [M+H]=522.19.

Example 51

5-[5-Methanesulfonyl-2-(2-methylpropoxy)benzoyl]-2-phenyl-2H 4H 5H 6H-pyrrolo[3,4-c]pyrazole

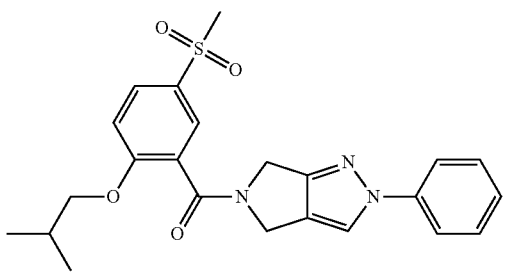 [SMILES: CC(C)COc1ccc(S(C)(=O)=O)cc1C(=O)N1Cc2cn(-c3ccccc3)nc2C1]

¹H NMR (400 MHz, DMSO-d₆) δ=8.41-8.20 (m, 1H), 7.99-7.92 (m, 1H), 7.85-7.73 (m, 3H), 7.51-7.43 (m, 2H), 7.35 (dd, J=1.2, 9.0 Hz, 1H), 7.31-7.23 (m, 1H), 4.67 (d, J=6.7 Hz, 2H), 4.37 (d, J=18.4 Hz, 2H), 3.94 (dd, J=3.9, 6.3 Hz, 2H), 3.23-3.17 (m, 3H), 1.97-1.89 (m, 3H), 0.87 (dd, J=1.4, 6.8 Hz, 6H); [M+H]=440.11.

Example 52

2-[2-Fluoro-3-(trifluoromethyl)phenyl]-5-[5-methanesulfonyl-2-(2-methylpropoxy)benzoyl]-2H 4H 5H 6H-pyrrolo[3,4-c]pyrazole

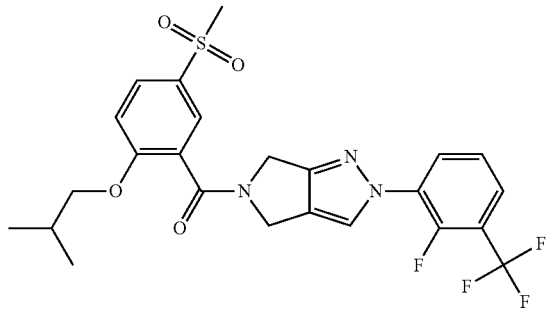 [SMILES: CC(C)COc1ccc(S(C)(=O)=O)cc1C(=O)N1Cc2cn(-c3cccc(C(F)(F)F)c3F)nc2C1]

¹H NMR (400 MHz, DMSO-d₆) δ=8.18-8.01 (m, 2H), 7.95 (dd, J=2.3, 9.0 Hz, 1H), 7.83 (dd, J=2.3, 3.5 Hz, 1H), 7.78 (t, J=7.0 Hz, 1H), 7.54 (dt, J=4.7, 8.0 Hz, 1H), 7.36 (dd, J=2.2, 8.8 Hz, 1H), 4.69 (d, J=11.3 Hz, 2H), 4.45-4.33 (m, 2H), 3.94 (dd, J=3.5, 6.7 Hz, 2H), 3.22-3.17 (m, 3H), 2.02-1.90 (m, 2H), 0.87 (dd, J=2.3, 6.7 Hz, 6H); [M+H]=526.22.

Example 53

5-[5-Methanesulfonyl-2-(2-methylpropoxy)benzoyl]-2-[3-(trifluoromethyl)phenyl]-2H 4H 5H 6H-pyrrolo[3,4-c]pyrazole

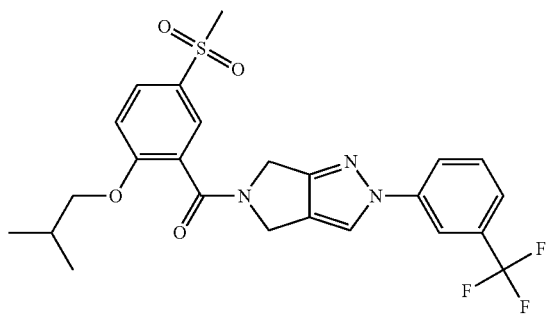 [SMILES: CC(C)COc1ccc(S(C)(=O)=O)cc1C(=O)N1Cc2cn(-c3cccc(C(F)(F)F)c3)nc2C1]

¹H NMR (400 MHz, DMSO-d₆) δ=8.58-8.39 (m, 1H), 8.17-8.07 (m, 2H), 7.95 (dd, J=2.5, 8.8 Hz, 1H), 7.82 (dd, J=2.5, 4.1 Hz, 1H), 7.71 (t, J=8.0 Hz, 1H), 7.67-7.60 (m, 1H), 7.36 (dd, J=1.6, 9.0 Hz, 1H), 4.69 (d, J=7.8 Hz, 2H), 4.39 (d, J=18.4 Hz, 2H), 3.94 (dd, J=2.7, 6.3 Hz, 2H), 3.23-3.16 (m, 3H), 2.03-1.91 (m, 2H), 0.86 (dd, J=1.8, 6.8 Hz, 6H); [M+H]=508.13.

Example 54

4 4-Difluoro-1-(4-methanesulfonyl-2-{2-phenyl-2H 4H 5H 6H-pyrrolo[3,4-c]pyrazole-5-carbonyl}phenyl)piperidine

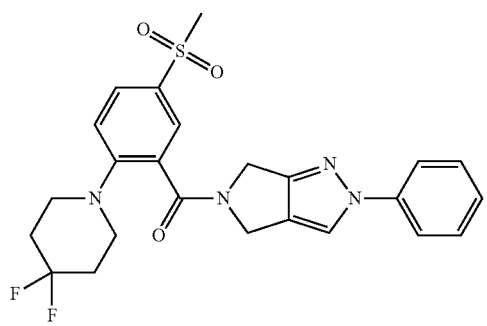 [SMILES: CS(=O)(=O)c1ccc(N2CCC(F)(F)CC2)c(C(=O)N2Cc3cn(-c4ccccc4)nc3C2)c1]

¹H NMR (400 MHz, DMSO-d₆) δ=8.42-8.20 (m, 1H), 7.90-7.84 (m, 1H), 7.82-7.73 (m, 3H), 7.47 (dt, J=2.3, 8.0 Hz, 2H), 7.35-7.24 (m, 2H), 4.72 (br s, 2H), 4.51 (br s, 2H), 3.37 (br s, 2H), 3.31-3.22 (m, 2H), 3.20 (d, J=1.2 Hz, 3H), 2.06-1.93 (m, 4H); [M+H]=487.19.

Example 55

4 4-Difluoro-1-(4-methanesulfonyl-2-{2-[3-(trifluoromethyl)phenyl]-2H 4H 5H 6H-pyrrolo[3,4-e]pyrazole-5-carbonyl}phenyl)piperidine

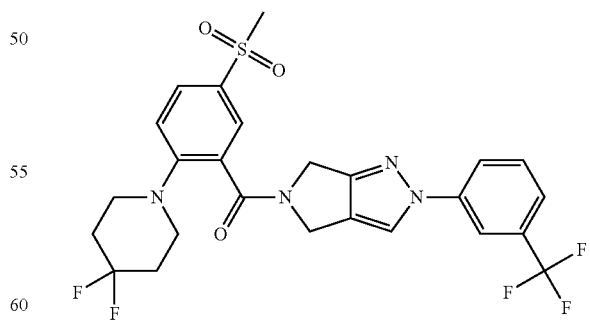

¹H NMR (400 MHz, DMSO-d₆) δ=8.60-8.39 (m, 1H), 8.17-8.08 (m, 2H), 7.88 (dd, J=2.3, 8.6 Hz, 1H), 7.78-7.61 (m, 3H), 7.33 (dd, J=1.2, 8.6 Hz, 1H), 4.74 (br s, 2H), 4.61-4.31 (m, 2H), 3.42-3.33 (m, 2H), 3.27 (br s, 2H), 3.20 (s, 3H), 2.06-1.93 (m, 4H); [M+H]=555.18.

Example 56

4 4-Difluoro-1-{2-[2-(4-fluorophenyl)-2H 4H 5H 6H-pyrrolo[3,4-c]pyrazole-5-carbonyl]-4-methanesulfonylphenyl}piperidine

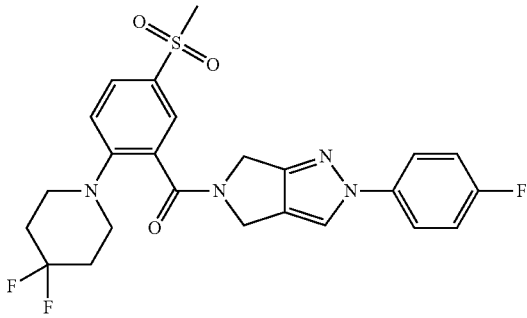 [SMILES: CS(=O)(=O)c1ccc(N2CCC(F)(F)CC2)c(C(=O)N2Cc3cn(-c4ccc(F)cc4)nc3C2)c1]

$^1$H NMR (400 MHz, DMSO-d$_6$) δ=8.39-8.16 (m, 1H), 7.91-7.73 (m, 4H), 7.36-7.29 (m, 3H), 4.71 (br s, 2H), 4.59-4.32 (m, 2H), 3.42-3.33 (m, 2H), 3.29 (br s, 2H), 3.19 (d, J=0.8 Hz, 3H), 2.06-1.92 (m, 4H); [M+H]=505.20.

Example 57

2-(2-Fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

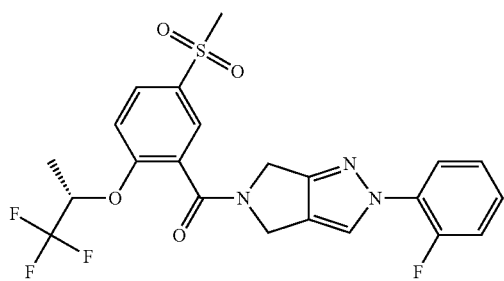

$^1$H NMR (400 MHz, DMSO-d$_6$) δ=8.10-7.88 (m, 3H), 7.81-7.68 (m, 1H), 7.60 (dd, J=2.0, 9.0 Hz, 1H), 7.50-7.28 (m, 3H), 5.60-5.50 (m, 1H), 4.67 (d, J=10.2 Hz, 2H), 4.45-4.27 (m, 2H), 3.24 (s, 3H), 1.45-1.40 (m, 3H); [M+H]=498.17.

Example 58

2-(2 4-Difluoro-3-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole

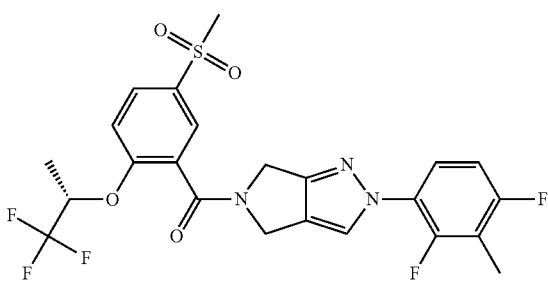

$^1$H NMR (400 MHz, DMSO-d$_6$) δ=8.03-7.87 (m, 3H), 7.65-7.50 (m, 2H), 7.26-7.16 (m, 1H), 5.54 (td, J=6.2, 12.2 Hz, 1H), 4.66 (d, J=7.0 Hz, 2H), 4.43-4.26 (m, 2H), 3.24 (s, 3H), 2.22 (d, J=1.6 Hz, 3H), 1.43 (d, J=6.3 Hz, 3H); [M+H]=530.17.

Example 59

2-(5-Chloro-2-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

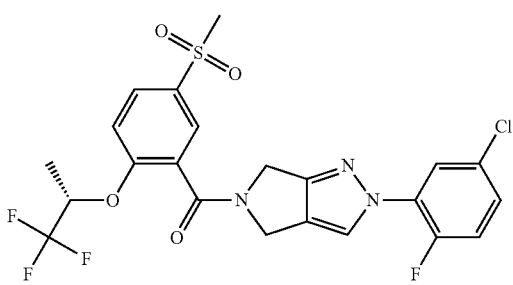 [SMILES: C[C@H](Oc1ccc(S(C)(=O)=O)cc1C(=O)N1Cc2cn(-c3cc(Cl)ccc3F)nc2C1)C(F)(F)F]

$^1$H NMR (400 MHz, DMSO-d$_6$) δ=8.15-7.97 (m, 2H), 7.93-7.77 (m, 2H), 7.64-7.43 (m, 3H), 5.60-5.48 (m, 1H), 4.67 (d, J=11.7 Hz, 2H), 4.47-4.26 (m, 2H), 3.27-3.15 (m, 3H), 1.43 (dd, J=1.6, 6.3 Hz, 3H); [M+H]=532.11.

Example 60

2-(2-Fluorophenyl)-5-[5-methanesulfonyl-2-(propan-2-yloxy)benzoyl]-2H 4H 5H 6H-pyrrolo[3,4-c]pyrazole

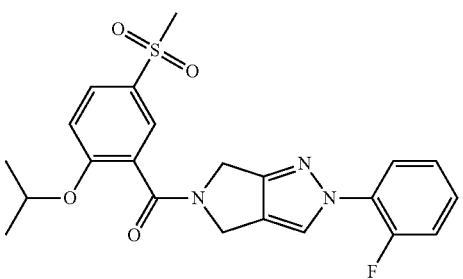 [SMILES: CC(C)Oc1ccc(S(C)(=O)=O)cc1C(=O)N1Cc2cn(-c3ccccc3F)nc2C1]

$^1$H NMR (400 MHz, DMSO-d$_6$) δ=8.09-7.89 (m, 2H), 7.82-7.68 (m, 2H), 7.50-7.29 (m, 4H), 4.88-4.79 (m, 1H), 4.68 (d, J=10.2 Hz, 2H), 4.43-4.33 (m, 2H), 3.20 (s, 3H), 1.27 (d, J=5.9 Hz, 6H); [M+H]=444.21.

Example 61

2-(2 4-Difluoro-3-methylphenyl)-5-[5-methanesulfonyl-2-(propan-2-yloxy)benzoyl]-2H 4H 5H 6H-pyrrolo[3,4-c]pyrazole

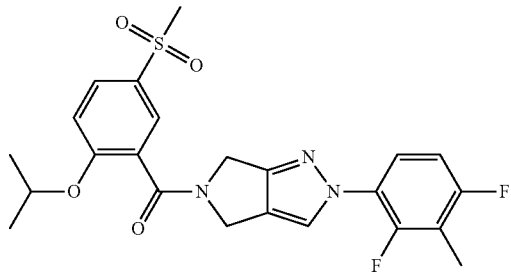 [SMILES: Cc1c(F)ccc(-n2cc3c(n2)CN(C(=O)c2cc(S(C)(=O)=O)ccc2OC(C)C)C3)c1F]

¹H NMR (400 MHz, DMSO-d₆) δ=8.04-7.86 (m, 2H), 7.80 (dd, J=2.3, 3.9 Hz, 1H), 7.65-7.50 (m, 1H), 7.38 (dd, J=1.6, 9.0 Hz, 1H), 7.20 (ddt, J=1.6, 5.2, 9.0 Hz, 1H), 4.88-4.79 (m, 1H), 4.67 (d, J=7.4 Hz, 2H), 4.36 (d, J=19.2 Hz, 2H), 3.20 (s, 3H), 2.22 (d, J=1.6 Hz, 3H), 1.27 (d, J=6.3 Hz, 6H); [M+H]=476.25.

Example 62

2-(5-Chloro-2-fluorophenyl)-5-[5-methanesulfonyl-2-(propan-2-yloxy)benzoyl]-2H 4H 5H 6H-pyrrolo[3,4-c]pyrazole

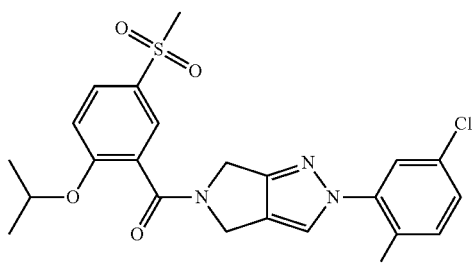

¹H NMR (400 MHz, DMSO-d₆) δ=8.15-7.97 (m, 1H), 7.96-7.83 (m, 2H), 7.82-7.76 (m, 1H), 7.59-7.44 (m, 2H), 7.38 (d, J=8.6 Hz, 1H), 4.90-4.78 (m, 1H), 4.67 (d, J=11.7 Hz, 2H), 4.43-4.31 (m, 2H), 3.23-3.16 (m, 3H), 1.30-1.23 (m, 6H); [M+H]=478.15.

Example 63

5-[2-(2 2-Dimethylpropoxy)-5-methanesulfonylbenzoyl]-2-(2-fluorophenyl)-2H 4H 5H 6H-pyrrolo[3,4-c]pyrazole

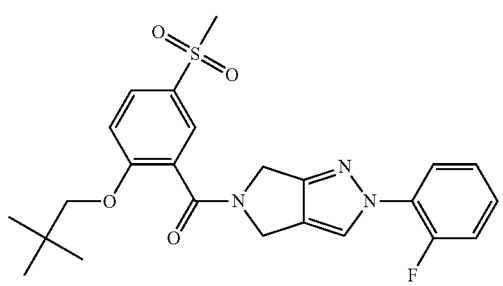 [SMILES: CC(C)(C)COc1ccc(S(C)(=O)=O)cc1C(=O)N1Cc2cn(-c3ccccc3F)nc2C1]

¹H NMR (400 MHz, DMSO-d₆) δ=8.09-7.91 (m, 2H), 7.85-7.66 (m, 2H), 7.49-7.37 (m, 2H), 7.37-7.28 (m, 2H), 4.68 (d, J=9.8 Hz, 2H), 4.43-4.33 (m, 2H), 3.81 (d, J=4.7 Hz, 2H), 3.20 (s, 3H), 0.88 (d, J=3.1 Hz, 9H); [M+H]=472.18.

Example 64

2-(2 4-Difluoro-3-methylphenyl)-5-[2-(2 2-dimethylpropoxy)-5-methanesulfonylbenzoyl]-2H 4H 5H 6H-pyrrolo[3,4-c]pyrazole

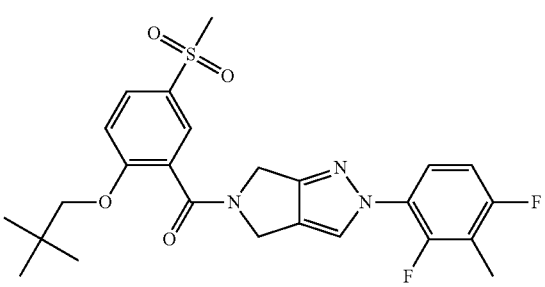 [SMILES: Cc1c(F)ccc(-n2cc3c(n2)CN(C(=O)c2cc(S(C)(=O)=O)ccc2OCC(C)(C)C)C3)c1F]

¹H NMR (400 MHz, DMSO-d₆) δ=8.04-7.79 (m, 4H), 7.68-7.49 (m, 2H), 7.34 (dd, J=2.2, 8.8 Hz, 1H), 7.19 (ddt, J=1.8, 5.5, 8.9 Hz, 1H), 4.67 (d, J=7.0 Hz, 2H), 4.36 (d, J=18.4 Hz, 2H), 3.81 (d, J=4.3 Hz, 2H), 3.20 (s, 3H), 2.21 (d, J=1.6 Hz, 3H), 0.87 (d, J=3.1 Hz, 9H); [M+H]=504.25.

Example 65

2-(5-Chloro-2-fluorophenyl)-5-[2-(2 2-dimethylpropoxy)-5-methanesulfonylbenzoyl]-2H 4H 5H 6H-pyrrolo[3,4-c]pyrazole

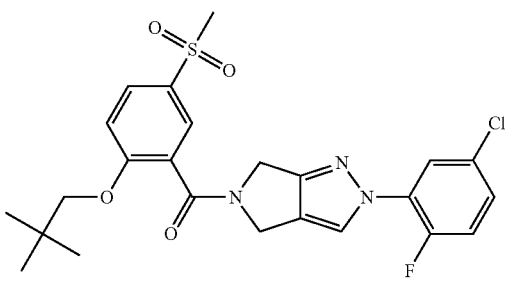 [SMILES: CC(C)(C)COc1ccc(S(C)(=O)=O)cc1C(=O)N1Cc2cn(-c3cc(Cl)ccc3F)nc2C1]

¹H NMR (400 MHz, DMSO-d₆) δ=8.16-7.93 (m, 3H), 7.88-7.75 (m, 2H), 7.57-7.44 (m, 2H), 7.34 (dd, J=1.8, 8.8 Hz, 1H), 4.68 (d, J=11.7 Hz, 2H), 4.42-4.32 (m, 2H), 3.81 (d, J=5.1 Hz, 2H), 3.23-3.18 (m, 3H), 0.87 (d, J=3.1 Hz, 9H); [M+H]=506.19.

Example 66

2-(2-Fluorophenyl)-5-[5-methanesulfonyl-2-(2-methylpropoxy)benzoyl]-2H 4H 5H 6H-pyrrolo[3,4-c]pyrazole

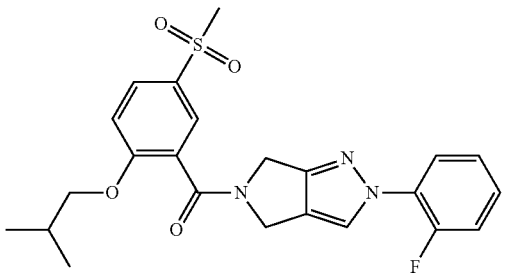 [SMILES: CC(C)COc1ccc(S(C)(=O)=O)cc1C(=O)N1Cc2cn(-c3ccccc3F)nc2C1]

¹H NMR (400 MHz, DMSO-d₆) δ=8.10-7.91 (m, 2H), 7.84-7.67 (m, 2H), 7.50-7.29 (m, 4H), 4.68 (d, J=10.6 Hz, 2H), 4.43-4.32 (m, 2H), 3.94 (dd, J=4.3, 6.3 Hz, 2H), 3.20 (s, 3H), 2.01-1.92 (m, 1H), 0.87 (dd, J=2.0, 6.7 Hz, 6H); [M+H]=458.27.

Example 67

2-(2 4-Difluoro-3-methylphenyl)-5-[5-methanesulfonyl-2-(2-methylpropoxy)benzoyl]-2H 4H 5H 6H-pyrrolo[3,4-c]pyrazole

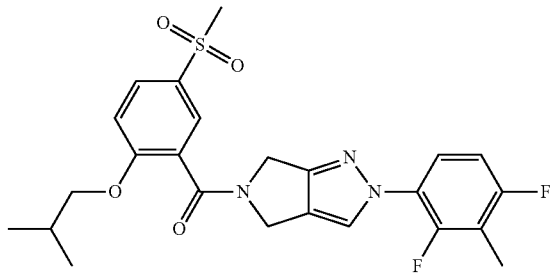 [SMILES: Cc1c(F)ccc(-n2cc3c(n2)CN(C(=O)c2cc(S(C)(=O)=O)ccc2OCC(C)C)C3)c1F]

¹H NMR (400 MHz, DMSO-d₆) δ=8.04-7.92 (m, 2H), 7.91-7.79 (m, 2H), 7.68-7.49 (m, 2H), 7.35 (dd, J=2.2, 8.8 Hz, 1H), 7.20 (ddt, J=1.8, 5.2, 8.9 Hz, 1H), 4.67 (d, J=7.4 Hz, 2H), 4.36 (d, J=19.2 Hz, 2H), 3.94 (dd, J=3.5, 6.3 Hz, 2H), 3.22-3.17 (m, 3H), 2.22 (d, J=2.0 Hz, 3H), 1.97 (td, J=6.7, 13.3 Hz, 1H), 0.87 (dd, J=2.3, 6.7 Hz, 6H); [M+H]=490.23.

Example 68

2-(5-Chloro-2-fluorophenyl)-5-[5-methanesulfonyl-2-(2-methylpropoxy)benzoyl]-2H 4H 5H 6H-pyrrolo[3,4-c]pyrazole

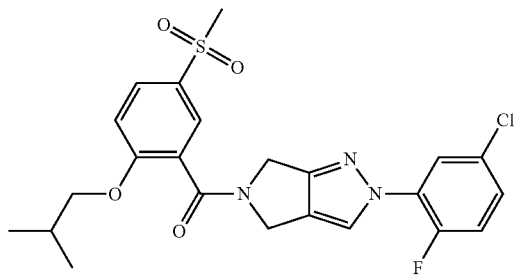 [SMILES: CC(C)COc1ccc(S(C)(=O)=O)cc1C(=O)N1Cc2cn(-c3cc(Cl)ccc3F)nc2C1]

¹H NMR (400 MHz, DMSO-d₆) δ=8.14-7.97 (m, 1H), 7.95 (dd, J=2.3, 9.0 Hz, 1H), 7.88-7.75 (m, 2H), 7.58-7.43 (m, 2H), 7.36 (dd, J=1.8, 8.8 Hz, 1H), 4.68 (d, J=12.1 Hz, 2H), 4.43-4.32 (m, 2H), 3.94 (dd, J=4.7, 6.3 Hz, 2H), 3.23-3.17 (m, 3H), 2.02-1.90 (m, 1H), 0.87 (dd, J=2.0, 6.7 Hz, 6H); [M+H]=492.21.

Example 69

4 4-Difluoro-1-{2-[2-(2-fluorophenyl)-2H 4H 5H 6H-pyrrolo[3,4-c]pyrazole-5-carbonyl]-4-methanesulfonylphenyl}piperidine

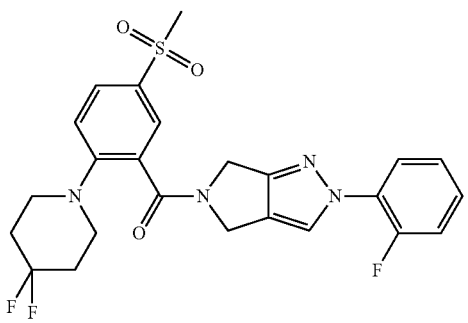 [SMILES: CS(=O)(=O)c1ccc(N2CCC(F)(F)CC2)c(C(=O)N2Cc3cn(-c4ccccc4F)nc3C2)c1]

¹H NMR (400 MHz, DMSO-d₆) δ=8.10-7.91 (m, 1H), 7.87 (ddd, J=1.2, 2.3, 8.6 Hz, 1H), 7.80-7.66 (m, 2H), 7.50-7.29 (m, 4H), 4.72 (d, J=11.3 Hz, 2H), 4.61-4.31 (m, 2H), 3.39-3.32 (m, 2H), 3.27 (br s, 2H), 3.19 (d, J=1.2 Hz, 3H), 2.07-1.94 (m, 4H); [M+H]=505.24.

Example 70

1-{2-[2-(2 4-Difluoro-3-methylphenyl)-2H 4H 5H 6H-pyrrolo[3,4-c]pyrazole-5-carbonyl]-4-methanesulfonylphenyl}-4 4-difluoropiperidine

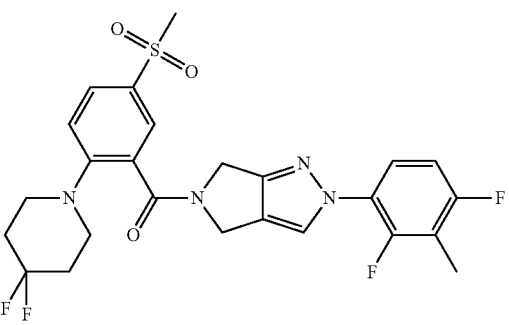 [SMILES: Cc1c(F)ccc(-n2cc3c(n2)CN(C(=O)c2cc(S(C)(=O)=O)ccc2N2CCC(F)(F)CC2)C3)c1F]

¹H NMR (400 MHz, DMSO-d₆) δ=8.06-7.73 (m, 3H), 7.63-7.49 (m, 1H), 7.32 (dd, J=1.6, 9.0 Hz, 1H), 7.20 (ddt, J=1.8, 4.4, 8.9 Hz, 1H), 4.72 (br s, 2H), 4.60-4.32 (m, 2H), 3.36 (br s, 2H), 3.31-3.25 (m, 5H), 3.19 (d, J=1.2 Hz, 3H), 2.22 (d, J=1.6 Hz, 3H), 2.08-1.93 (m, 4H); [M+H]=537.16.

Example 71

1-{2-[2-(5-Chloro-2-fluorophenyl)-2H 4H 5H 6H-pyrrolo[3,4-c]pyrazole-5-carbonyl]-4-methanesulfonylphenyl}-4 4-difluoropiperidine

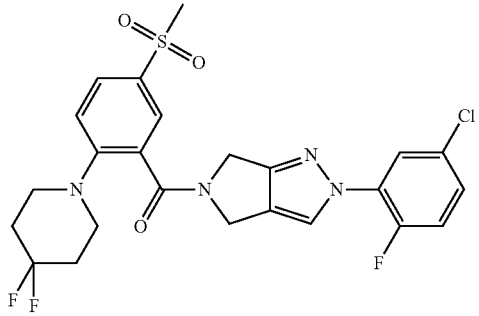 [SMILES: CS(=O)(=O)c1ccc(N2CCC(F)(F)CC2)c(C(=O)N2Cc3cn(-c4cc(Cl)ccc4F)nc3C2)c1]

¹H NMR (400 MHz, DMSO-d₆) δ=8.16-7.96 (m, 1H), 7.91-7.74 (m, 3H), 7.61-7.44 (m, 2H), 7.32 (dd, J=0.8, 8.6 Hz, 1H), 4.71 (d, J=14.9 Hz, 2H), 4.59-4.34 (m, 2H), 3.36 (br s, 2H), 3.30-3.24 (m, 2H), 3.21-3.17 (m, 3H), 2.07-1.93 (m, 4H); [M+H]=539.14.

Example 72

5-[5-(Ethanesulfonyl)-2-{[(2S)-1 1 1-trifluoropropan-2-yl]oxy}benzoyl]-2-(3-methylphenyl)-2H 4H 5H 6H-pyrrolo[3,4-c]pyrazole

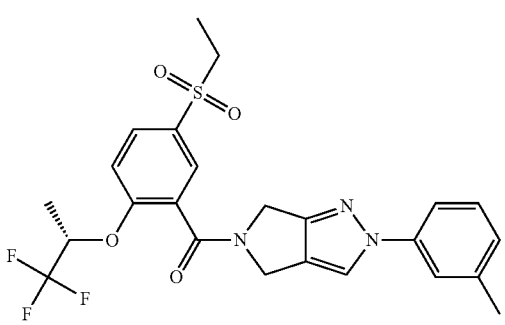 [SMILES: CCS(=O)(=O)c1ccc(O[C@@H](C)C(F)(F)F)c(C(=O)N2Cc3cn(-c4cccc(C)c4)nc3C2)c1]

¹H NMR (400 MHz, DMSO-d₆) δ=8.39-8.21 (m, 1H), 7.98 (dd, J=2.4, 8.8 Hz, 1H), 7.91-7.85 (m, 1H), 7.69-7.51 (m, 3H), 7.36 (dt, J=1.8, 7.8 Hz, 1H), 7.11 (d, J=7.4 Hz, 1H), 5.62-5.51 (m, 1H), 4.68 (d, J=5.3 Hz, 2H), 4.44-4.28 (m, 2H), 3.39-3.34 (m, 2H), 2.37 (d, J=2.8 Hz, 3H), 1.48-1.42 (m, 3H), 1.13 (t, J=7.3 Hz, 3H); [M+H]=508.21.

Example 73

5-[5-(Ethanesulfonyl)-2-(propan-2-yloxy)benzoyl]-2-phenyl-2H 4H 5H 6H-pyrrolo[3,4-c]pyrazole

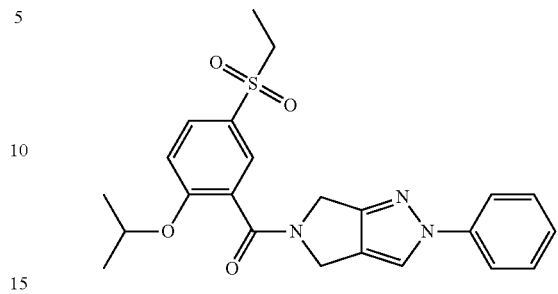

¹H NMR (400 MHz, DMSO-d₆) δ=8.42-8.22 (m, 1H), 7.90 (dd, J=2.4, 8.9 Hz, 1H), 7.84-7.73 (m, 3H), 7.53-7.45 (m, 2H), 7.41 (d, J=8.8 Hz, 1H), 7.35-7.27 (m, 1H), 4.90-4.81 (m, 1H), 4.69 (d, J=6.8 Hz, 2H), 4.38 (d, J=17.9 Hz, 2H), 3.31-3.25 (m, 2H), 1.28 (d, J=5.9 Hz, 6H), 1.12 (t, J=7.3 Hz, 3H); [M+H]=440.18.

Example 74

5-[5-(Ethanesulfonyl)-2-(propan-2-yloxy)benzoyl]-2-(2-fluorophenyl)-2H 4H 5H 6H-pyrrolo[3,4-c]pyrazole

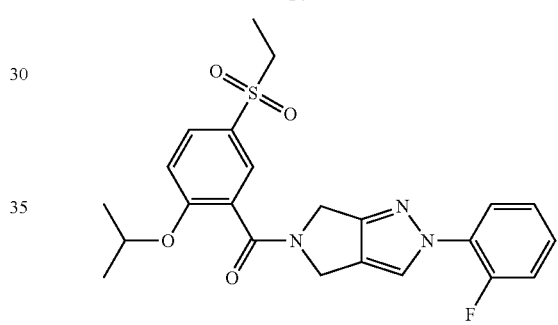

¹H NMR (400 MHz, DMSO-d₆) δ=8.12-7.94 (m, 1H), 7.90 (dd, J=2.4, 8.8 Hz, 1H), 7.82-7.70 (m, 2H), 7.52-7.31 (m, 4H), 4.86 (qd, J=6.1, 9.8 Hz, 1H), 4.69 (d, J=9.8 Hz, 2H), 4.43-4.33 (m, 2H), 3.31-3.25 (m, 2H), 1.29 (d, J=6.0 Hz, 6H), 1.11 (t, J=7.3 Hz, 3H); [M+H]=458.20.

Example 75

2-[3-(Difluoromethyl)-4-fluorophenyl]-5-(5-methanesulfonyl-2-{[(2S)-1 1 1-trifluoropropan-2-yl]oxy}benzoyl)-2H 4H 5H 6H-pyrrolo[3,4-c]pyrazole

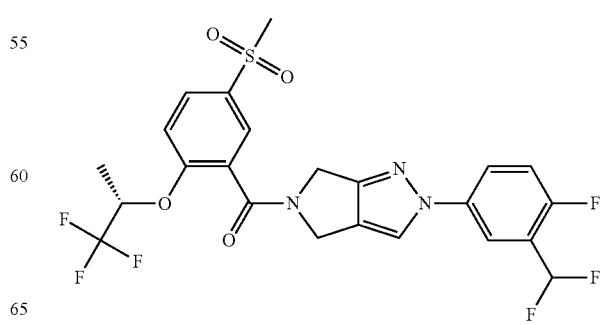

¹H NMR (400 MHz, DMSO-d₆) δ=8.48-8.30 (m, 1H), 8.09-7.96 (m, 3H), 7.90 (dd, J=2.3, 4.7 Hz, 1H), 7.60 (d, J=8.6 Hz, 1H), 7.52 (t, J=9.6 Hz, 1H), 7.41-7.09 (m, 2H), 5.54 (td, J=5.7, 12.1 Hz, 1H), 4.67 (d, J=7.4 Hz, 2H), 4.44-4.27 (m, 2H), 3.24 (s, 3H), 1.42 (dd, J=1.6, 6.3 Hz, 3H); [M+H]=548.11.

Example 76

2-[3-(Difluoromethyl)-4-fluorophenyl]-5-[5-methanesulfonyl-2-(propan-2-yloxy)benzoyl]-2H 4H 5H 6H-pyrrolo[3,4-c]pyrazole

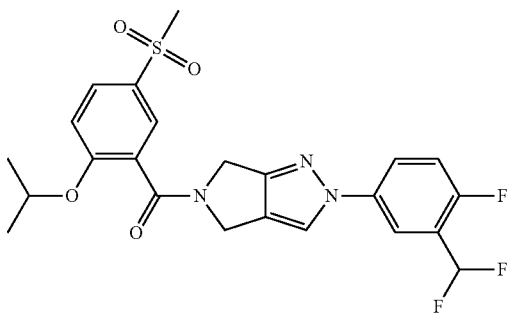 [SMILES: CC(C)Oc1ccc(S(C)(=O)=O)cc1C(=O)N1Cc2cn(-c3ccc(F)c(C(F)F)c3)nc2C1]

¹H NMR (400 MHz, DMSO-d₆) δ=8.47-8.29 (m, 1H), 8.09-7.97 (m, 2H), 7.96-7.90 (m, 1H), 7.80 (dd, J=2.3, 3.9 Hz, 1H), 7.51 (t, J=9.4 Hz, 1H), 7.42-7.09 (m, 3H), 4.84 (dtd, J=3.1, 6.1, 12.1 Hz, 1H), 4.67 (d, J=7.0 Hz, 2H), 4.38 (d, J=18.8 Hz, 2H), 3.20 (s, 3H), 1.26 (dd, J=0.8, 5.9 Hz, 6H); [M+H]=494.22.

Example 77

2-[3-(Difluoromethyl)-4-fluorophenyl]-5-[2-(2 2-dimethylpropoxy)-5-methanesulfonylbenzoyl]-2H 4H 5H 6H-pyrrolo[3,4-e]pyrazole

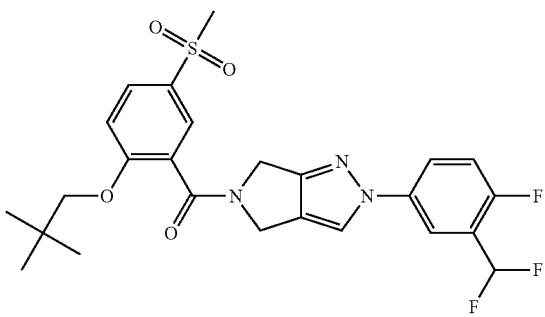 [SMILES: CC(C)(C)COc1ccc(S(C)(=O)=O)cc1C(=O)N1Cc2cn(-c3ccc(F)c(C(F)F)c3)nc2C1]

¹H NMR (400 MHz, DMSO-d₆) δ=8.48-8.27 (m, 1H), 8.10-7.92 (m, 3H), 7.82 (dd, J=2.5, 3.7 Hz, 1H), 7.51 (t, J=9.4 Hz, 1H), 7.41-7.08 (m, 3H), 4.68 (d, J=7.0 Hz, 2H), 4.37 (d, J=16.8 Hz, 2H), 3.81 (d, J=3.9 Hz, 2H), 3.20 (s, 3H), 0.90-0.82 (m, 9H); [M+H]=522.23.

Example 78

5-[5-(Ethanesulfonyl)-2-{[(2S)-1 1 1-trifluoropropan-2-yl]oxy}benzoyl]-2-(2-fluoro-3-methylphenyl)-2H 4H 5H 6H-pyrrolo[3,4-c]pyrazole

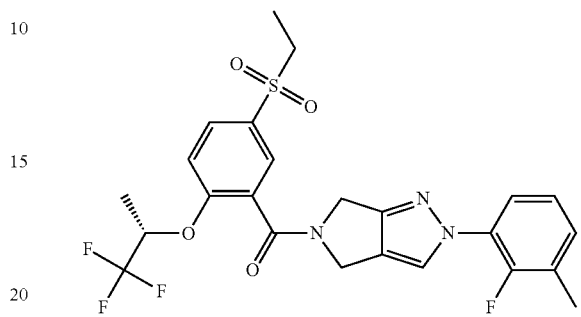

¹H NMR (400 MHz, DMSO-d₆) δ=8.06-7.90 (m, 2H), 7.86 (dd, J=2.3, 3.5 Hz, 1H), 7.63-7.46 (m, 2H), 7.34-7.26 (m, 1H), 7.24-7.16 (m, 1H), 5.54 (td, J=6.1, 12.4 Hz, 1H), 4.66 (d, J=7.8 Hz, 2H), 4.42-4.26 (m, 2H), 3.36-3.30 (m, 2H), 2.33-2.29 (m, 3H), 1.43 (d, J=6.3 Hz, 3H), 1.10 (t, J=7.2 Hz, 3H); [M+H]=526.14.

Example 79

2-[3-(Difluoromethyl)-4-fluorophenyl]-5-[5-(ethanesulfonyl)-2-{[(2S)-1 1 1-trifluoropropan-2-yl]oxy}benzoyl]-2H 4H 5H 6H-pyrrolo[3,4-c]pyrazole

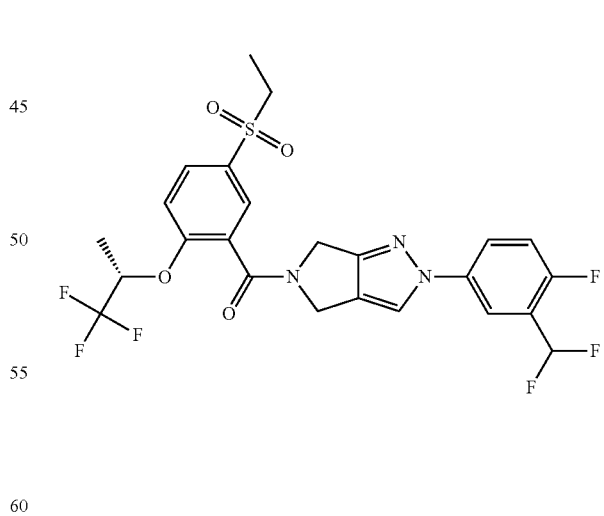

¹H NMR (400 MHz, DMSO-d₆) δ=8.47-8.29 (m, 1H), 8.09-7.93 (m, 3H), 7.86 (dd, J=2.3, 3.5 Hz, 1H), 7.64-7.57 (m, 1H), 7.51 (t, J=9.4 Hz, 1H), 7.40-7.08 (m, 2H), 5.54 (td, J=6.3, 12.8 Hz, 1H), 4.67 (d, J=7.4 Hz, 2H), 4.44-4.27 (m, 2H), 3.37-3.31 (m, 2H), 1.42 (d, J=6.3 Hz, 3H), 1.11 (t, J=7.4 Hz, 3H); [M+H]=562.13.

Example 80

5-[5-(Ethanesulfonyl)-2-{[(2S)-1 1 1-trifluoropropan-2-yl]oxy}benzoyl]-2-(2-fluorophenyl)-2H 4H 5H 6H-pyrrolo[3,4-c]pyrazole

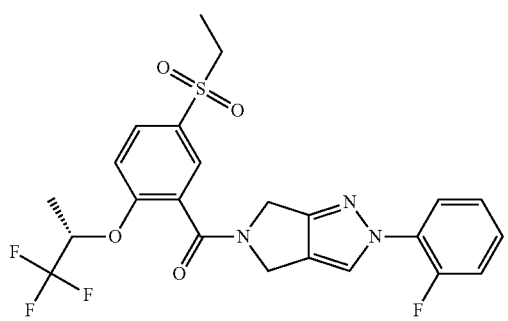 [SMILES: CCS(=O)(=O)c1ccc(O[C@@H](C)C(F)(F)F)c(C(=O)N2Cc3cn(-c4ccccc4F)nc3C2)c1]

¹H NMR (400 MHz, DMSO-d₆) δ=8.09-7.96 (m, 1H), 7.95 (dd, J=0.8, 2.3 Hz, 1H), 7.86 (dd, J=2.5, 3.3 Hz, 1H), 7.81-7.68 (m, 1H), 7.60 (dd, =2.0, 9.0 Hz, 1H), 7.50-7.29 (m, 3H), 5.54 (td, J=6.4, 12.6 Hz, 1H), 4.67 (d, J=9.8 Hz, 2H), 4.44-4.26 (m, 2H), 3.37-3.31 (m, 2H), 1.47-1.40 (m, 3H), 1.14-1.07 (m, 3H); [M+H]=512.16.

Example 81

2-(2 4-Difluorophenyl)-5-[5-(ethanesulfonyl)-2-(propan-2-yloxy)benzoyl]-2H 4H 5H 6H-pyrrolo[3,4-c]pyrazole

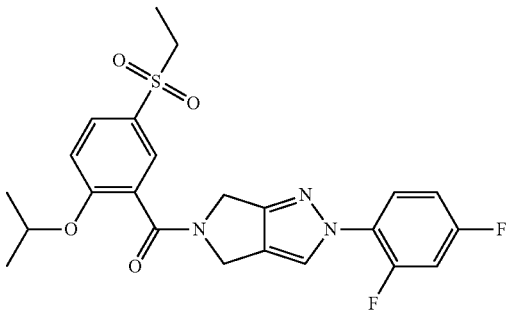 [SMILES: CCS(=O)(=O)c1ccc(OC(C)C)c(C(=O)N2Cc3cn(-c4ccc(F)cc4F)nc3C2)c1]

¹H NMR (400 MHz, DMSO-d₆) δ=8.06-7.85 (m, 2H), 7.83-7.69 (m, 2H), 7.55 (tdd, J=2.3, 9.0, 11.4 Hz, 1H), 7.39 (dd, J=1.6, 9.0 Hz, 1H), 7.24 (ddddd, J=1.4, 2.9, 5.2, 7.9, 9.2 Hz, 1H), 4.84 (dtd, J=3.5, 6.1, 12.0 Hz, 1H), 4.67 (d, J=9.0 Hz, 2H), 4.35 (d, J=20.0 Hz, 2H), 3.29-3.22 (m, 2H), 1.27 (d, J=5.9 Hz, 6H), 1.14-1.05 (m, 3H); [M+H]=476.25.

Example 82

2-[3-(Difluoromethyl)-4-fluorophenyl]-5-[5-(ethanesulfonyl)-2-(propan-2-yloxy)benzoyl]-2H 4H 5H 6H-pyrrolo[3,4-c]pyrazole

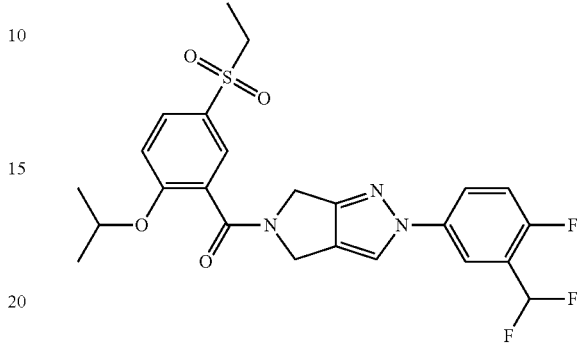

¹H NMR (400 MHz, DMSO-d₆) δ=8.48-8.27 (m, 1H), 8.09-7.96 (m, 2H), 7.88 (dd, J=2.3, 9.0 Hz, 1H), 7.79-7.72 (m, 1H), 7.51 (t, J=9.4 Hz, 1H), 7.42-7.09 (m, 3H), 4.84 (dtd, J=2.9, 6.0, 12.1 Hz, 1H), 4.67 (d, J=7.4 Hz, 2H), 4.36 (d, J=18.0 Hz, 2H), 3.29-3.23 (m, 2H), 1.26 (d, J=5.9 Hz, 6H), 1.10 (t, J=7.4 Hz, 3H); [M+H]=508.17.

Example 83

5-[5-(Ethanesulfonyl)-2-(propan-2-yloxy)benzoyl]-2-(3-methylphenyl)-2H 4H 5H 6H-pyrrolo[3,4-c]pyrazole

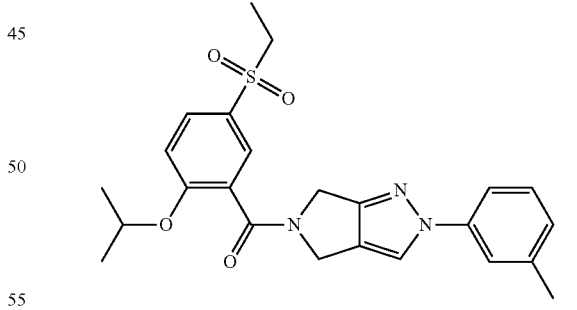

¹H NMR (400 MHz, DMSO-d₆) δ=8.37-8.17 (m, 1H), 7.88 (dd, J=2.3, 8.6 Hz, 1H), 7.75 (t, J=2.5 Hz, 1H), 7.66-7.51 (m, 2H), 7.43-7.29 (m, 2H), 7.09 (d, J=7.4 Hz, 2H), 4.84 (dtd, J=3.5, 6.1, 12.1 Hz, 1H), 4.66 (d, J=5.5 Hz, 2H), 4.35 (d, J=16.4 Hz, 2H), 3.29-3.22 (m, 2H), 2.35 (d, =3.1 Hz, 3H), 1.30-1.24 (m, 6H), 1.13-1.07 (m, 3H); [M+H]=454.28.

Example 84

5-[5-(Ethanesulfonyl)-2-(propan-2-yloxy)benzoyl]-2-(4-fluorophenyl)-2H 4H 5H 6H-pyrrolo[3,4-c]pyrazole

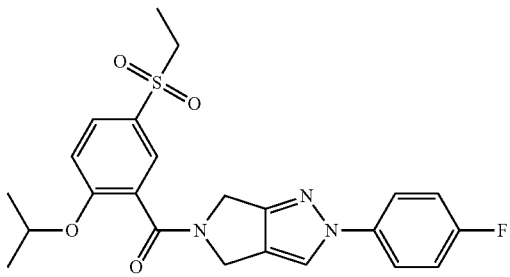 [SMILES: CCS(=O)(=O)c1ccc(OC(C)C)c(C(=O)N2Cc3cn(-c4ccc(F)cc4)nc3C2)c1]

$^1$H NMR (400 MHz, DMSO-d$_6$) δ=8.37-8.17 (m, 1H), 7.88 (dd, J=2.5, 8.8 Hz, 1H), 7.84-7.76 (m, 2H), 7.76-7.72 (m, 1H), 7.42-7.28 (m, 3H), 4.83 (dtd, J=3.1, 5.9, 12.1 Hz, 1H), 4.66 (d, J=6.7 Hz, 2H), 4.35 (d, J=17.6 Hz, 2H), 3.29-3.23 (m, 2H), 1.29-1.24 (m, 6H), 1.09 (t, J=7.2 Hz, 3H); [M+H]=458.23.

Example 85

5-[5-Methanesulfonyl-2-(propan-2-yloxy)benzoyl]-2-(3-methylphenyl)-2H 4H 5H 6H-pyrrolo[3,4-c]pyrazole

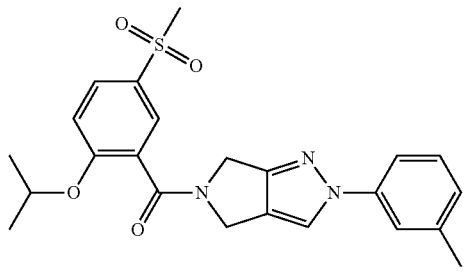 [SMILES: Cc1cccc(-n2cc3c(n2)CN(C(=O)c2cc(S(C)(=O)=O)ccc2OC(C)C)C3)c1]

$^1$H NMR (400 MHz, DMSO-d$_6$) δ=8.39-8.17 (m, 1H), 7.93 (dd, J=2.3, 8.6 Hz, 1H), 7.80 (dd, J=2.3, 3.9 Hz, 1H), 7.66-7.30 (m, 4H), 7.09 (d, =7.4 Hz, 1H), 4.83 (dtd, J=3.5, 6.1, 12.1 Hz, 1H), 4.66 (d, J=5.5 Hz, 2H), 4.36 (d, J=17.6 Hz, 2H), 3.20 (s, 3H), 2.35 (d, J=2.7 Hz, 3H), 1.26 (dd, =1.0, 6.1 Hz, 6H); [M+H]=440.07.

Example 86

2-[2-Fluoro-3-(trifluoromethyl)phenyl]-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

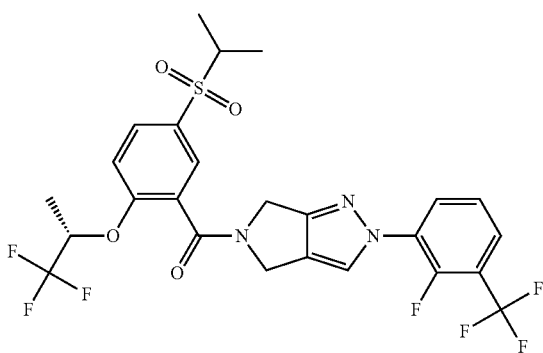 [SMILES: CC(C)S(=O)(=O)c1ccc(O[C@@H](C)C(F)(F)F)c(C(=O)N2Cc3cn(-c4cccc(C(F)(F)F)c4F)nc3C2)c1]

$^1$H NMR (400 MHz, DMSO-d$_6$) δ=8.19-8.02 (m, 2H), 7.93 (ddd, J=1.4, 2.3, 8.8 Hz, 1H), 7.86-7.82 (m, 1H), 7.79 (t, J=7.0 Hz, 1H), 7.64-7.50 (m, 2H), 5.54 (quind, J=6.1, 12.6 Hz, 1H), 4.68 (d, J=11.0 Hz, 2H), 4.44-4.26 (m, 2H), 3.45 (quind, J=6.9, 13.6 Hz, 1H), 1.43 (d, J=6.3 Hz, 3H), 1.16 (d, J=7.0 Hz, 6H); [M+H]=594.2.

Example 87

2-(2-Fluoro-3-methylphenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

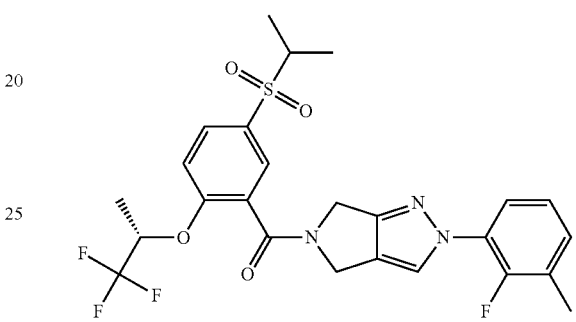

$^1$H NMR (400 MHz, DMSO-d$_6$) δ=8.05-7.90 (m, 2H), 7.83 (t, J=2.3 Hz, 1H), 7.64-7.47 (m, 2H), 7.33-7.26 (m, 1H), 7.24-7.16 (m, 1H), 5.60-5.48 (m, 1H), 4.66 (d, J=7.8 Hz, 2H), 4.42-4.26 (m, 2H), 3.45 (quind, J=6.8, 13.7 Hz, 1H), 2.30 (t, J=2.0 Hz, 3H), 1.43 (d, J=6.3 Hz, 3H), 1.16 (d, J=7.0 Hz, 6H); [M+H]=540.2.

Example 88

2-(2-Fluorophenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

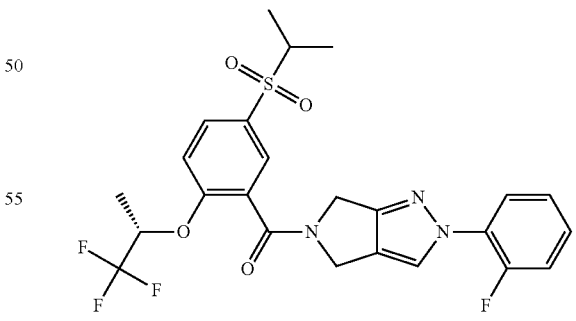

$^1$H NMR (400 MHz, DMSO-d$_6$) δ=8.09-7.90 (m, 2H), 7.86-7.81 (m, 1H), 7.81-7.68 (m, 1H), 7.60 (dd, J=2.3, 9.0 Hz, 1H), 7.50-7.29 (m, 3H), 5.54 (td, J=6.3, 12.8 Hz, 1H), 4.67 (d, J=9.8 Hz, 2H), 4.43-4.25 (m, 2H), 3.45 (quind, J=6.8, 13.7 Hz, 1H), 1.43 (d, J=6.3 Hz, 3H), 1.16 (d, J=7.0 Hz, 6H); [M+H]=526.26.

Example 89

2-(3-Methylphenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

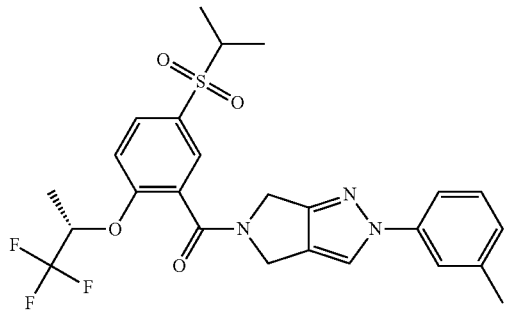 [SMILES: Cc1cccc(-n2cc3c(n2)CN(C(=O)c2cc(S(=O)(=O)C(C)C)ccc2O[C@@H](C)C(F)(F)F)C3)c1]

¹H NMR (400 MHz, DMSO-d₆) δ=8.36-8.18 (m, 1H), 7.93 (dd, J=2.3, 8.6 Hz, 1H), 7.85-7.80 (m, 1H), 7.65-7.52 (m, 3H), 7.33 (dt, J=2.0, 7.8 Hz, 1H), 7.13-7.06 (m, 1H), 5.54 (td, J=6.2, 12.2 Hz, 1H), 4.65 (d, J=5.5 Hz, 2H), 4.41-4.24 (m, 2H), 3.45 (quind, J=6.8, 13.7 Hz, 1H), 2.35 (d, =3.1 Hz, 3H), 1.43 (dd, J=1.4, 6.5 Hz, 3H), 1.16 (d, J=6.7 Hz, 6H); [M+H]=522.23.

Example 90

2-Phenyl-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

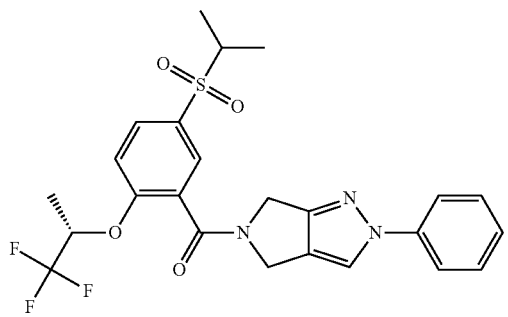 [SMILES: CC(C)S(=O)(=O)c1ccc(O[C@@H](C)C(F)(F)F)c(C(=O)N2Cc3cn(-c4ccccc4)nc3C2)c1]

¹H NMR (400 MHz, DMSO-d₆) δ=8.39-8.22 (m, 1H), 7.93 (ddd, J=1.0, 2.3, 8.8 Hz, 1H), 7.83 (t, J=2.3 Hz, 1H), 7.80-7.73 (m, 2H), 7.60 (dd, =1.6, 9.0 Hz, 1H), 7.51-7.43 (m, 2H), 7.32-7.24 (m, 1H), 5.60-5.48 (m, 1H), 4.66 (d, J=6.7 Hz, 2H), 4.42-4.25 (m, 2H), 3.45 (quind, J=6.8, 13.5 Hz, 1H), 1.43 (dd, J=1.6, 6.3 Hz, 3H), 1.16 (d, J=7.0 Hz, 6H); [M+H]=508.17.

Example 91

2-(4-Fluorophenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

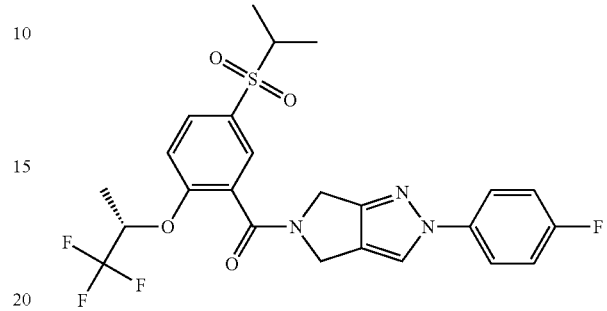

¹H NMR (400 MHz, DMSO-d₆) δ=8.37-8.19 (m, 1H), 7.93 (ddd, J=1.0, 2.3, 8.8 Hz, 1H), 7.85-7.75 (m, 3H), 7.60 (dd, J=2.0, 9.0 Hz, 1H), 7.37-7.27 (m, 2H), 5.60-5.48 (m, 1H), 4.65 (d, J=6.7 Hz, 2H), 4.41-4.24 (m, 2H), 3.45 (spt, J=6.8 Hz, 1H), 1.47-1.40 (m, 3H), 1.16 (d, J=6.7 Hz, 6H); [M+H]=526.22.

Example 92

2-(3 4-Difluorophenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole

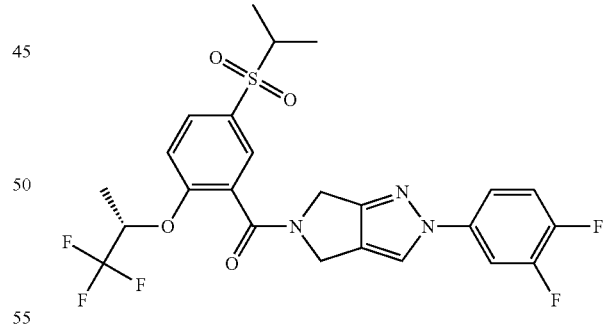

¹H NMR (400 MHz, DMSO-d₆) δ=8.42-8.25 (m, 1H), 7.96-7.85 (m, 2H), 7.84-7.80 (m, 1H), 7.70-7.51 (m, 3H), 5.54 (quind, J=6.4, 12.6 Hz, 1H), 4.65 (d, J=6.7 Hz, 2H), 4.41-4.25 (m, 2H), 3.50-3.39 (m, 1H), 1.42 (d, J=6.3 Hz, 3H), 1.16 (d, J=7.0 Hz, 6H); [M+H]=544.23.

Example 93

2-[2-Fluoro-3-(trifluoromethyl)phenyl]-5-[2-(propan-2-yloxy)-5-(propane-2-sulfonyl)benzoyl]-2H 4H 5H 6H-pyrrolo[3,4-c]pyrazole

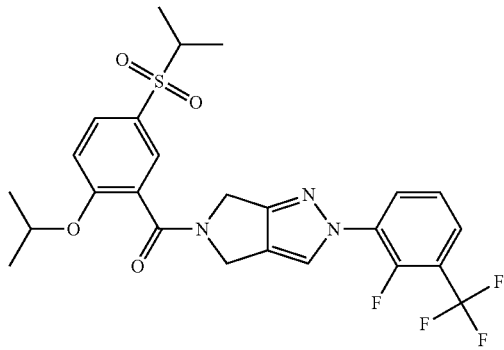 [SMILES: CC(C)Oc1ccc(S(=O)(=O)C(C)C)cc1C(=O)N1Cc2cn(-c3cccc(C(F)(F)F)c3F)nc2C1]

¹H NMR (400 MHz, DMSO-d₆) δ=8.18-8.00 (m, 2H), 7.89-7.83 (m, 1H), 7.79 (t, J=7.0 Hz, 1H), 7.72 (dd, J=1.2, 2.3 Hz, 1H), 7.59-7.50 (m, 1H), 7.40 (dd, J=2.0, 9.0 Hz, 1H), 4.84 (dtd, J=3.1, 6.1, 12.1 Hz, 1H), 4.68 (d, J=11.3 Hz, 2H), 4.44-4.31 (m, 2H), 3.39 (td, J=6.7, 13.6 Hz, 2H), 1.30-1.25 (m, 6H), 1.15 (d, J=7.0 Hz, 6H); [M+H]=540.24.

Example 94

2-(2-Fluoro-3-methylphenyl)-5-[2-(propan-2-yloxy)-5-(propane-2-sulfonyl)benzoyl]-2H 4H 5H 6H-pyrrolo[3,4-c]pyrazole

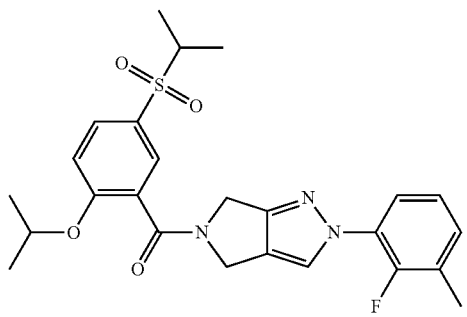 [SMILES: Cc1cccc(-n2cc3c(n2)CN(C(=O)c2cc(S(=O)(=O)C(C)C)ccc2OC(C)C)C3)c1F]

¹H NMR (400 MHz, DMSO-d₆) δ=8.05-7.89 (m, 2H), 7.85 (dd, J=2.5, 8.8 Hz, 1H), 7.71 (dd, J=1.2, 2.3 Hz, 1H), 7.59-7.47 (m, 1H), 7.39 (dd, =1.4, 9.2 Hz, 1H), 7.32-7.26 (m, 1H), 7.24-7.16 (m, 1H), 4.84 (dtd, J=3.9, 6.1, 12.1 Hz, 1H), 4.66 (d, J=7.8 Hz, 2H), 4.35 (d, J=18.8 Hz, 2H), 3.39 (td, J=6.8, 13.7 Hz, 2H), 2.34-2.28 (m, 3H), 1.27 (d, J=5.9 Hz, 6H), 1.15 (d, J=6.7 Hz, 6H); [M+H]=486.24.

Example 95

2-(2-Fluorophenyl)-5-[2-(propan-2-yloxy)-5-(propane-2-sulfonyl)benzoyl]-2H 4H 5H 6H-pyrrolo[3,4-c]pyrazole

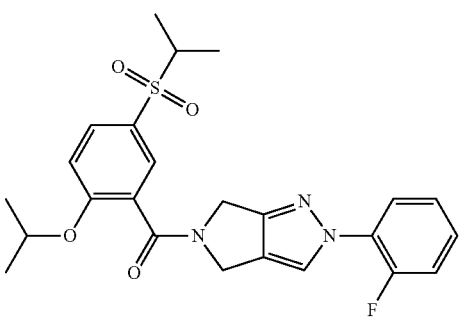 [SMILES: CC(C)Oc1ccc(S(=O)(=O)C(C)C)cc1C(=O)N1Cc2cn(-c3ccccc3F)nc2C1]

¹H NMR (400 MHz, DMSO-d₆) δ=8.09-7.91 (m, 2H), 7.85 (dd, J=2.5, 8.8 Hz, 1H), 7.80-7.68 (m, 2H), 7.49-7.29 (m, 5H), 4.89-4.80 (m, 1H), 4.67 (d, J=9.8 Hz, 2H), 4.41-4.30 (m, 2H), 3.44-3.37 (m, 1H), 1.27 (d, J=5.9 Hz, 6H), 1.15 (d, J=6.7 Hz, 6H); [M+H]=472.22.

Example 96

2-(3-Methylphenyl)-5-[2-(propan-2-yloxy)-5-(propane-2-sulfonyl)benzoyl]-2H 4H 5H 6H-pyrrolo[3,4-c]pyrazole

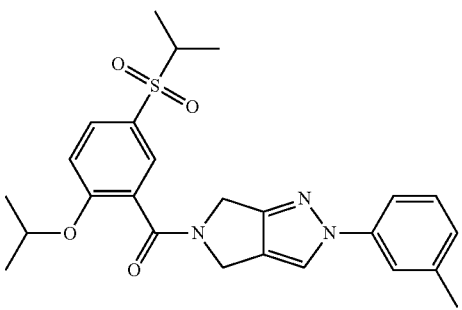

¹H NMR (400 MHz, DMSO-d₆) δ=8.37-8.17 (m, 2H), 7.85 (dd, J=2.5, 8.8 Hz, 1H), 7.71 (dd, J=1.6, 2.3 Hz, 1H), 7.65-7.52 (m, 2H), 7.43-7.30 (m, 2H), 7.13-7.07 (m, 1H), 4.89-4.79 (m, 1H), 4.66 (d, J=5.5 Hz, 2H), 4.34 (d, J=15.7 Hz, 2H), 3.39 (quin, J=6.7 Hz, 2H), 2.35 (d, J=2.7 Hz, 3H), 1.28-1.24 (m, 6H), 1.15 (d, J=6.7 Hz, 6H); [M+H]=468.27.

Example 97

2-Phenyl-5-[2-(propan-2-yloxy)-5-(propane-2-sulfonyl)benzoyl]-2H 4H 5H 6H-pyrrolo[3,4-c]pyrazole

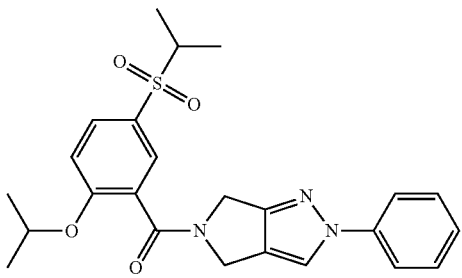 [SMILES: CC(C)Oc1ccc(S(=O)(=O)C(C)C)cc1C(=O)N1Cc2cn(-c3ccccc3)nc2C1]

$^1$H NMR (400 MHz, DMSO-d$_6$) δ=8.37-8.18 (m, 3H), 7.85 (dd, J=2.5, 8.8 Hz, 2H), 7.79-7.73 (m, 2H), 7.70 (dd, J=1.4, 2.5 Hz, 1H), 7.51-7.43 (m, 3H), 7.39 (d, J=8.6 Hz, 2H), 7.31-7.23 (m, 2H), 4.82 (dtd, J=3.7, 5.9, 12.2 Hz, 2H), 4.66 (d, J=6.7 Hz, 2H), 4.34 (d, J=17.2 Hz, 3H), 3.39-3.33 (m, 2H), 1.26 (d, J=5.9 Hz, 6H), 1.14 (d, J=7.0 Hz, 6H); [M+H]=454.17.

Example 98

2-(4-Fluorophenyl)-5-[2-(propan-2-yloxy)-5-(propane-2-sulfonyl)benzoyl]-2H 4H 5H 6H-pyrrolo[3,4-c]pyrazole

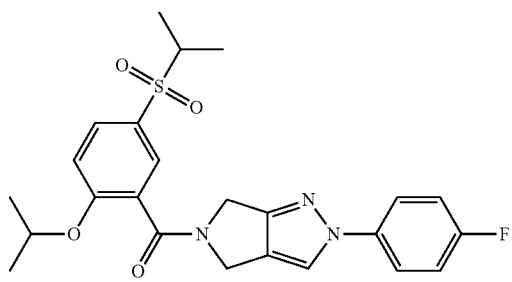 [SMILES: CC(C)Oc1ccc(S(=O)(=O)C(C)C)cc1C(=O)N1Cc2cn(-c3ccc(F)cc3)nc2C1]

$^1$H NMR (400 MHz, DMSO-d$_6$) δ=8.37-8.15 (m, 2H), 7.89-7.75 (m, 3H), 7.73-7.68 (m, 1H), 7.43-7.27 (m, 3H), 4.84 (tdd, J=2.8, 6.0, 9.1 Hz, 1H), 4.66 (d, J=6.7 Hz, 2H), 4.34 (d, J=17.2 Hz, 2H), 3.44-3.35 (m, 2H), 1.29-1.24 (m, 6H), 1.15 (d, J=7.0 Hz, 6H); [M+H]=472.18.

Example 99

2-(3 4-Difluorophenyl)-5-[2-(propan-2-yloxy)-5-(propane-2-sulfonyl)benzoyl]-2H 4H 5H 6H-pyrrolo[3,4-c]pyrazole

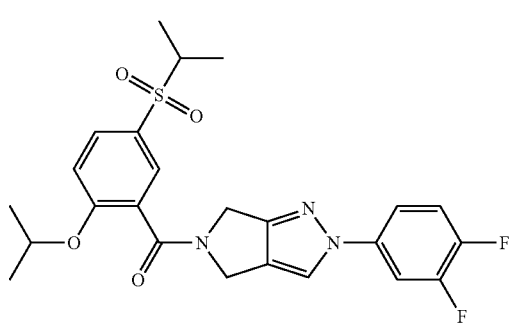 [SMILES: CC(C)Oc1ccc(S(=O)(=O)C(C)C)cc1C(=O)N1Cc2cn(-c3ccc(F)c(F)c3)nc2C1]

$^1$H NMR (400 MHz, DMSO-d$_6$) δ=8.41-8.23 (m, 2H), 7.97-7.82 (m, 2H), 7.73-7.69 (m, 1H), 7.69-7.61 (m, 1H), 7.60-7.50 (m, 1H), 7.39 (dd, J=1.4, 9.2 Hz, 1H), 4.83 (dtd, J=3.3, 6.0, 12.1 Hz, 1H), 4.66 (d, J=6.7 Hz, 2H), 4.35 (d, J=16.8 Hz, 2H), 3.44-3.35 (m, 2H), 1.26 (d, J=6.3 Hz, 6H), 1.15 (d, J=6.7 Hz, 5H); [M+H]=490.23.

Example 100

3-{5-[2-(4 4-Difluoropiperidin-1-yl)-5-methanesulfonylbenzoyl]-2H 4H 5H 6H-pyrrolo[3,4-c]pyrazol-2-yl}-5-fluoropyridine

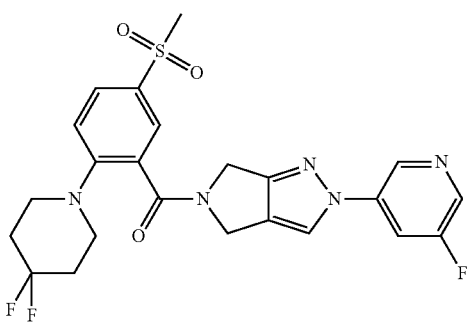 [SMILES: CS(=O)(=O)c1ccc(N2CCC(F)(F)CC2)c(C(=O)N2Cc3cn(-c4cncc(F)c4)nc3C2)c1]

$^1$H NMR (400 MHz, DMSO-d$_6$) δ=8.98 (dd, J=1.4, 11.9 Hz, 1H), 8.56-8.49 (m, 1H), 8.36 (s, 1H), 8.25-8.12 (m, 1H), 7.88 (dd, J=2.5, 8.8 Hz, 1H), 7.75 (dd, J=1.2, 2.3 Hz, 1H), 7.32 (dd, J=1.8, 8.8 Hz, 1H), 4.73 (d, J=11.3 Hz, 2H), 4.46 (br s, 2H), 3.38-3.30 (m, 4H), 3.22-3.15 (m, 3H), 2.08-1.92 (m, 4H); [M+H]=506.19.

Example 101

4-{5-[2-(4 4-Difluoropiperidin-1-yl)-5-methanesulfonylbenzoyl]-2H 4H 5H 6H-pyrrolo[3,4-c]pyrazol-2-yl}-2-methylpyridine

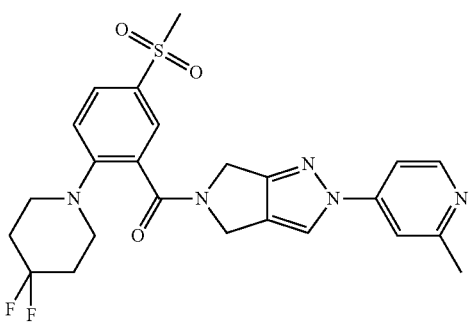 [SMILES: Cc1cc(-n2cc3c(n2)CN(C(=O)c2cc(S(C)(=O)=O)ccc2N2CCC(F)(F)CC2)C3)ccn1]

$^1$H NMR (400 MHz, DMSO-d$_6$) δ=8.55 (s, 0.5H), 8.46 (dd, J=1.6, 5.9 Hz, 1H), 8.37 (s, 0.5H), 7.92-7.85 (m, 1H), 7.75 (dd, J=1.6, 2.3 Hz, 1H), 7.69 (dd, J=2.2, 15.8 Hz, 1H), 7.60 (ddd, J=2.0, 5.5, 12.9 Hz, 1H), 7.32 (dd, J=1.0, 8.8 Hz, 1H), 4.72 (d, J=9.8 Hz, 2H), 4.61-4.34 (m, 2H), 3.44-3.32 (m, 3H), 3.19 (d, J=0.8 Hz, 3H), 2.49 (d, J=1.6 Hz, 3H), 1.99 (t, J=13.3 Hz, 4H); [M+H]=502.24.

Example 102

5-[5-Methanesulfonyl-2-(2 2 2-trifluoroethoxy)benzoyl]-2-phenyl-2H 4H 5H 6H-pyrrolo[3,4-c]pyrazole

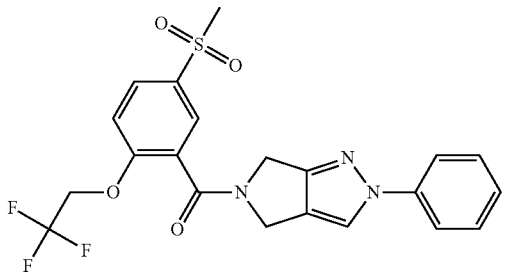 [SMILES: CS(=O)(=O)c1ccc(OCC(F)(F)F)c(C(=O)N2Cc3cn(-c4ccccc4)nc3C2)c1]

$^1$H NMR (400 MHz, DMSO-d$_6$) δ=8.40-8.23 (m, 1H), 8.02 (dd, J=2.3, 9.0 Hz, 1H), 7.90 (dd, J=2.3, 5.9 Hz, 1H), 7.82-7.74 (m, 2H), 7.53-7.43 (m, 3H), 7.32-7.24 (m, 1H), 5.03 (dq, J=1.4, 8.7 Hz, 2H), 4.67 (d, J=7.0 Hz, 2H), 4.38 (d, J=20.0 Hz, 2H), 3.24 (s, 3H); [M+H]=466.14.

Example 103

2-(4-Fluorophenyl)-5-[5-methanesulfonyl-2-(2 2 2-trifluoroethoxy)benzoyl]-2H 4H 5H 6H-pyrrolo[3,4-c]pyrazole

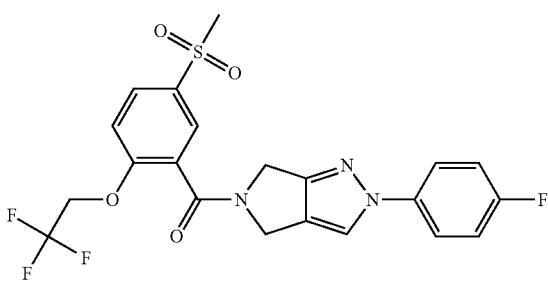 [SMILES: CS(=O)(=O)c1ccc(OCC(F)(F)F)c(C(=O)N2Cc3cn(-c4ccc(F)cc4)nc3C2)c1]

$^1$H NMR (400 MHz, DMSO-d$_6$) δ=8.36-8.21 (m, 1H), 8.02 (dd, J=2.5, 8.8 Hz, 1H), 7.90 (dd, J=2.3, 5.5 Hz, 1H), 7.85-7.76 (m, 2H), 7.50 (dd, =3.9, 9.0 Hz, 1H), 7.32 (dt, J=2.2, 8.9 Hz, 2H), 5.07-4.98 (m, 2H), 4.66 (d, J=6.7 Hz, 2H), 4.37 (d, J=18.8 Hz, 2H), 3.24 (s, 3H); [M+H]=484.19.

Example 104

2-(2-Fluorophenyl)-5-[5-methanesulfonyl-2-(2 2 2-trifluoroethoxy)benzoyl]-2H 4H 5H 6H-pyrrolo[3,4-c]pyrazole

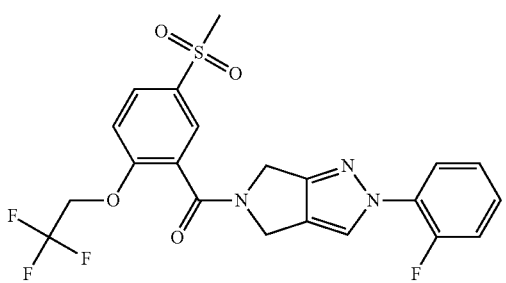 [SMILES: CS(=O)(=O)c1ccc(OCC(F)(F)F)c(C(=O)N2Cc3cn(-c4ccccc4F)nc3C2)c1]

$^1$H NMR (400 MHz, DMSO-d$_6$) δ=8.08-7.96 (m, 2H), 7.97-7.88 (m, 1H), 7.81-7.68 (m, 1H), 7.54-7.29 (m, 4H), 5.03 (dq, J=2.0, 8.7 Hz, 2H), 4.68 (d, J=10.2 Hz, 2H), 4.44-4.33 (m, 2H), 3.24 (s, 3H); [M+H]=484.11.

Example 105

5-[5-Methanesulfonyl-2-(2 2 2-trifluoroethoxy)benzoyl]-2-(3-methylphenyl)-2H 4H 5H 6H-pyrrolo[3,4-c]pyrazole

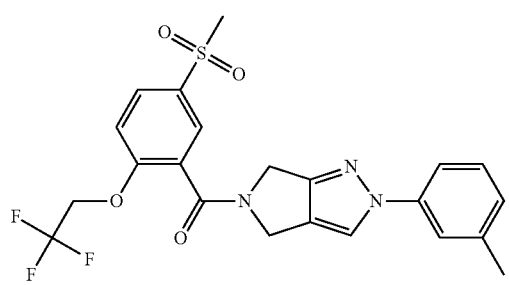 [SMILES: Cc1cccc(-n2cc3c(n2)CN(C(=O)c2cc(S(C)(=O)=O)ccc2OCC(F)(F)F)C3)c1]

$^1$H NMR (400 MHz, DMSO-d$_6$) δ=8.36-8.20 (m, 1H), 8.02 (dd, J=2.3, 8.6 Hz, 1H), 7.90 (dd, J=2.3, 5.1 Hz, 1H), 7.66-7.47 (m, 3H), 7.34 (dt, =2.0, 7.8 Hz, 1H), 7.13-7.06 (m, 1H), 5.03 (dq, J=2.0, 8.7 Hz, 2H), 4.66 (d, J=5.5 Hz, 2H), 4.37 (d, J=18.0 Hz, 2H), 3.24 (s, 3H), 2.35 (d, J=3.1 Hz, 3H); [M+H]=480.16.

Example 106

2-(2-Fluoro-3-methylphenyl)-5-[5-methanesulfonyl-2-(2 2 2-trifluoroethoxy)benzoyl]-2H 4H 5H 6H-pyrrolo[3,4-c]pyrazole

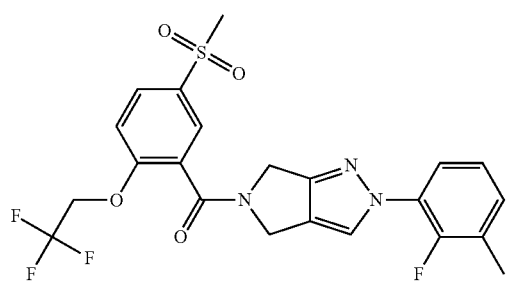 [SMILES: Cc1cccc(-n2cc3c(n2)CN(C(=O)c2cc(S(C)(=O)=O)ccc2OCC(F)(F)F)C3)c1F]

$^1$H NMR (400 MHz, DMSO-d$_6$) δ=8.05-7.88 (m, 3H), 7.59-7.47 (m, 2H), 7.32-7.26 (m, 1H), 7.24-7.16 (m, 1H), 5.03 (dq, J=2.0, 8.7 Hz, 2H), 4.67 (d, J=8.6 Hz, 2H), 4.42-4.33 (m, 2H), 3.23 (s, 3H), 2.33-2.28 (m, 3H); [M+H]=498.17.

Example 107

5-Fluoro-2-{5-[2-(3-fluorophenyl)-5-methanesulfonylbenzoyl]-2H 4H 5H 6H-pyrrolo[3,4-c]pyrazol-2-yl}pyridine

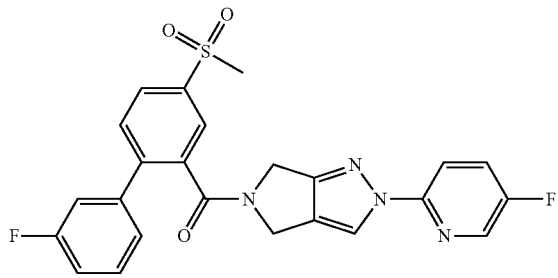 [SMILES: CS(=O)(=O)c1ccc(-c2cccc(F)c2)c(C(=O)N2Cc3cn(-c4ccc(F)cn4)nc3C2)c1]

$^1$H NMR (400 MHz, DMSO-$d_6$) δ=8.44 (dd, J=2.9, 7.6 Hz, 1H), 8.38-8.19 (m, 1H), 8.14-8.04 (m, 2H), 7.97-7.74 (m, 3H), 7.55-7.44 (m, 1H), 7.41-7.32 (m, 2H), 7.29-7.18 (m, 1H), 4.60-4.47 (m, 2H), 4.26-4.05 (m, 2H), 3.33 (s, 3H); [M+H]=481.4.

Example 108

3-Fluoro-5-{5-[2-(3-fluorophenyl)-5-methanesulfonylbenzoyl]-2H 4H 5H 6H-pyrrolo[3,4-c]pyrazol-2-yl}pyridine

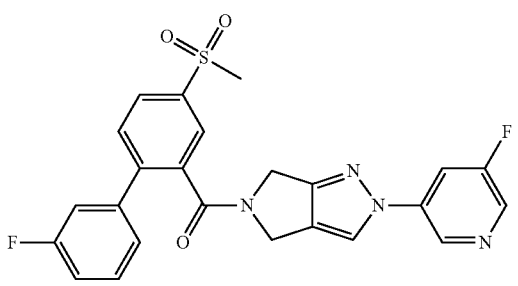 [SMILES: CS(=O)(=O)c1ccc(-c2cccc(F)c2)c(C(=O)N2Cc3cn(-c4cncc(F)c4)nc3C2)c1]

$^1$H NMR (400 MHz, DMSO-$d_6$) δ=8.93 (d, J=9.4 Hz, 1H), 8.53-8.48 (m, 1H), 8.46-8.28 (m, 1H), 8.19-8.12 (m, 1H), 8.12-8.05 (m, 2H), 7.83 (dd, J=4.7, 8.2 Hz, 1H), 7.53-7.45 (m, 1H), 7.41-7.32 (m, 2H), 7.28-7.21 (m, 1H), 4.54 (d, J=10.2 Hz, 2H), 4.19 (d, J=18.8 Hz, 2H), 3.33 (s, 3H); [M+H]=481.4.

Example 109

4-{5-[2-(3-Fluorophenyl)-5-methanesulfonylbenzoyl]-2H 4H 5H 6H-pyrrolo[3,4-c]pyrazol-2-yl}-2-methylpyridine

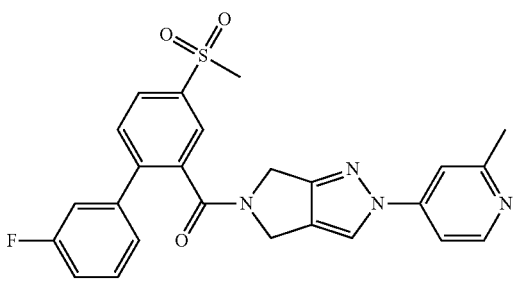 [SMILES: Cc1cc(-n2cc3c(n2)CN(C(=O)c2cc(S(C)(=O)=O)ccc2-c2cccc(F)c2)C3)ccn1]

$^1$H NMR (400 MHz, DMSO-$d_6$) δ=8.49-8.40 (m, 1H), 8.35-8.09 (m, 1H), 8.09-8.04 (m, 1H), 7.85-7.78 (m, 1H), 7.65 (d, J=13.3 Hz, 1H), 7.59-7.53 (m, 1H), 7.52-7.44 (m, 1H), 7.42-7.28 (m, 1H), 7.24 (t, J=8.6 Hz, 1H), 4.61-4.41 (m, 2H), 4.18 (d, J=17.6 Hz, 2H), 3.32 (d, J=1.6 Hz, 3H); [M+H]=477.5.

Example 110

4 4-Difluoro-1-{4-methanesulfonyl-2-[2-(3-methylphenyl)-2H 4H 5H 6H-pyrrolo[3,4-c]pyrazole-5-carbonyl]phenyl}piperidine

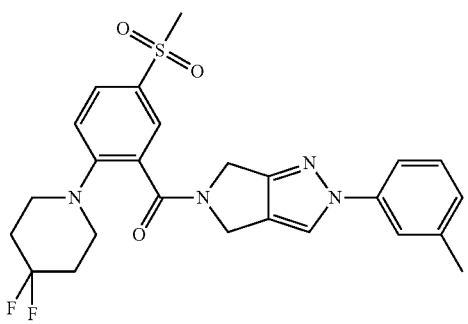

$^1$H NMR (400 MHz, DMSO-$d_6$) δ=8.38-8.16 (m, 1H), 7.87 (ddd, J=1.2, 2.3, 8.6 Hz, 1H), 7.75 (dd, J=1.2, 2.3 Hz, 1H), 7.65-7.29 (m, 4H), 7.09 (d, J=7.4 Hz, 1H), 4.71 (br s, 2H), 4.43 (br s, 2H), 3.19 (d, J=1.2 Hz, 3H), 2.35 (d, J=3.5 Hz, 3H), 2.07-1.94 (m, 4H); [M+H]=501.25.

Example 111

4-{5-[2-(4 4-Difluoropiperidin-1-yl)-5-(ethanesulfonyl)benzoyl]-2H 4H 5H 6H-pyrrolo[3,4-c]pyrazol-2-yl}-2-methylpyridine

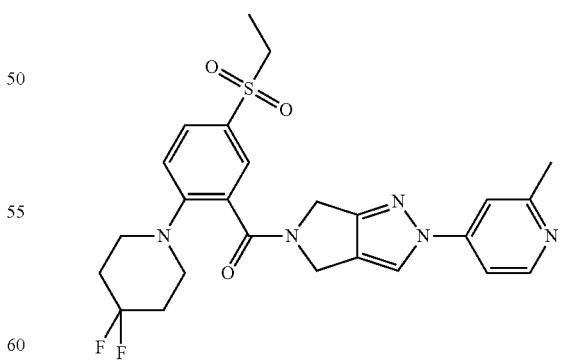

$^1$H NMR (400 MHz, DMSO-$d_6$) δ=8.64-8.42 (m, 2H), 7.93-7.68 (m, 4H), 7.33 (dd, J=1.6, 9.0 Hz, 1H), 4.78-4.68 (m, 2H), 4.60-4.32 (m, 2H), 3.26-3.21 (m, 2H), 2.56 (d, J=4.3 Hz, 2H), 2.07-1.92 (m, 4H), 1.15-1.05 (m, 3H); [M+H]=516.26.

Example 112

3-{5-[2-(4 4-Difluoropiperidin-1-yl)-5-(ethanesulfonyl)benzoyl]-2H 4H 5H 6H-pyrrolo[3,4-c]pyrazol-2-yl}-5-fluoropyridine

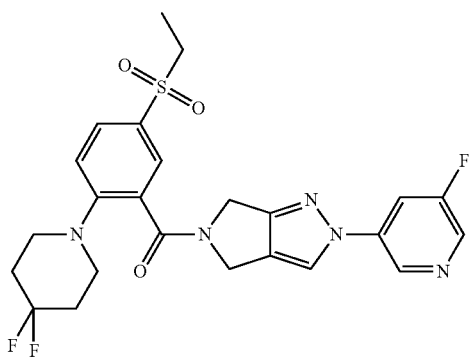 [SMILES: CCS(=O)(=O)c1ccc(N2CCC(F)(F)CC2)c(C(=O)N2Cc3cn(-c4cncc(F)c4)nc3C2)c1]

$^1$H NMR (400 MHz, DMSO-d$_6$) δ=8.98 (dd, J=1.4, 11.2 Hz, 1H), 8.56-8.35 (m, 2H), 8.19 (tdd, J=2.3, 10.2, 19.2 Hz, 1H), 7.83 (dd, J=2.3, 8.6 Hz, 1H), 7.70 (dd, J=0.8, 2.3 Hz, 1H), 7.32 (dd, J=1.8, 8.8 Hz, 1H), 4.76-4.68 (m, 2H), 4.61-4.33 (m, 2H), 3.28-3.21 (m, 2H), 2.07-1.92 (m, 4H), 1.13-1.05 (m, 3H); [M+H]=520.14.

Example 113

4-{5-[5-(Ethanesulfonyl)-2-{[(2S)-1 1 1-trifluoropropan-2-yl]oxy}benzoyl]-2H 4H 5H 6H-pyrrolo[3,4-c]pyrazol-2-yl}-2-methylpyridine

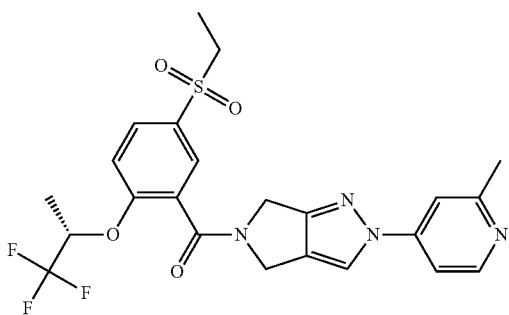 [SMILES: CCS(=O)(=O)c1ccc(O[C@@H](C)C(F)(F)F)c(C(=O)N2Cc3cn(-c4ccnc(C)c4)nc3C2)c1]

$^1$H NMR (400 MHz, DMSO-d$_6$) δ=8.77-8.58 (m, 2H), 8.25-8.05 (m, 2H), 8.02-7.94 (m, 1H), 7.90-7.83 (m, 1H), 7.62 (dd, J=2.3, 9.0 Hz, 1H), 5.55 (td, J=6.3, 12.5 Hz, 1H), 4.71 (d, J=12.9 Hz, 2H), 4.50-4.31 (m, 2H), 3.32 (q, J=7.3 Hz, 3H), 2.68 (d, J=2.0 Hz, 3H), 1.42 (d, J=6.3 Hz, 3H), 1.11 (dt, J=1.0, 7.3 Hz, 3H); [M+H]=509.19.

Example 114

3-{5-[5-(Ethanesulfonyl)-2-{[(2S)-1 1 1-trifluoropropan-2-yl]oxy}benzoyl]-2H 4H 5H 6H-pyrrolo[3,4-c]pyrazol-2-yl}-5-fluoropyridine

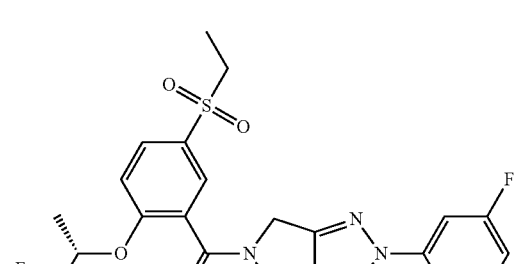

$^1$H NMR (400 MHz, DMSO-d$_6$) δ=9.02-8.93 (m, 1H), 8.54-8.37 (m, 2H), 8.24-8.14 (m, 1H), 7.96 (ddd, J=1.4, 2.4, 8.7 Hz, 1H), 7.86 (dd, =2.3, 3.1 Hz, 1H), 7.60 (dd, J=2.0, 9.0 Hz, 1H), 5.60-5.48 (m, 1H), 4.68 (d, J=9.0 Hz, 2H), 4.46-4.28 (m, 2H), 3.38-3.31 (m, 2H), 1.43 (dd, =1.6, 6.3 Hz, 3H), 1.11 (t, J=7.4 Hz, 3H); [M+H]=513.15.

Example 115

5-Fluoro-2-{5-[5-methanesulfonyl-2-(piperidin-1-yl)benzoyl]-2H 4H 5H 6H-pyrrolo[3,4-c]pyrazol-2-yl}pyridine

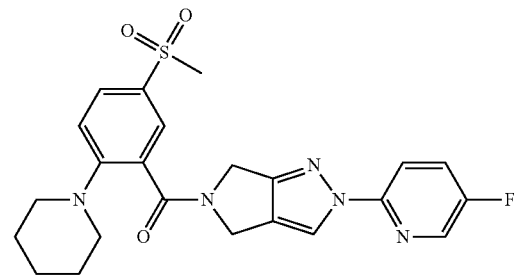 [SMILES: CS(=O)(=O)c1ccc(N2CCCCC2)c(C(=O)N2Cc3cn(-c4ccc(F)cn4)nc3C2)c1]

$^1$H NMR (400 MHz, CDCl$_3$) δ=8.39-8.14 (m, 2H), 7.99-7.81 (m, 3H), 7.59-7.48 (m, 1H), 7.14 (d, J=8.2 Hz, 1H), 4.90-4.77 (m, 2H), 4.66-4.47 (m, 2H), 3.32-3.15 (m, 4H), 3.05 (s, 3H), 1.67-1.60 (m, 6H); [M+H]=470.5.

Example 116

3-Fluoro-5-{5-[5-methanesulfonyl-2-(piperidin-1-yl)benzoyl]-2H 4H 5H 6H-pyrrolo[3,4-c]pyrazol-2-yl}pyridine

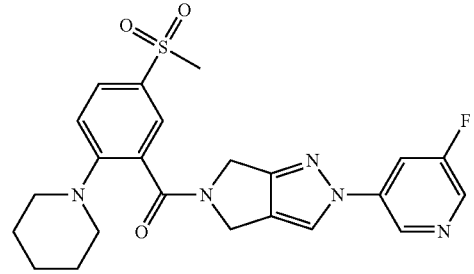 [SMILES: CS(=O)(=O)c1ccc(N2CCCCC2)c(C(=O)N2Cc3cn(-c4cncc(F)c4)nc3C2)c1]

¹H NMR (400 MHz, CDCl₃) δ=8.77 (br s, 1H), 8.41 (br s, 1H), 7.95-7.54 (m, 4H), 7.12-6.97 (m, 1H), 4.84 (d, J=13.7 Hz, 2H), 4.54 (br s, 2H), 3.22 (br s, 4H), 3.05 (d, J=2.7 Hz, 3H), 1.83-1.52 (m, 6H); [M+H]=470.5.

Example 117

4-{5-[5-Methanesulfonyl-2-(piperidin-1-yl)benzoyl]-2H 4H 5H 6H-pyrrolo[3,4-c]pyrazol-2-yl}-2-methylpyridine

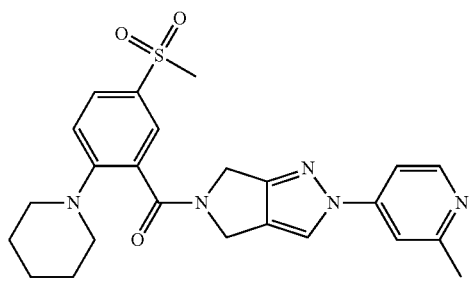 [SMILES: Cc1cc(-n2cc3c(n2)CN(C(=O)c2cc(S(C)(=O)=O)ccc2N2CCCCC2)C3)ccn1]

¹H NMR (400 MHz, DMSO-d₆) δ=8.62-8.38 (m, 2H), 7.85 (td, J=2.3, 8.6 Hz, 1H), 7.81-7.73 (m, 1H), 7.70 (d, J=2.3 Hz, 2H), 7.22 (d, J=8.6 Hz, 1H), 4.74 (br s, 4H), 3.25-2.90(m, 7H), 2.52 (d, J=3.1 Hz, 3H), 1.70-1.28 (m, 6H); [M+H]=466.6.

Example 118

5-[2-(Cyclopropylmethoxy)-5-methanesulfonylbenzoyl]-2-phenyl-2H 4H 5H 6H-pyrrolo[3,4-c]pyrazole

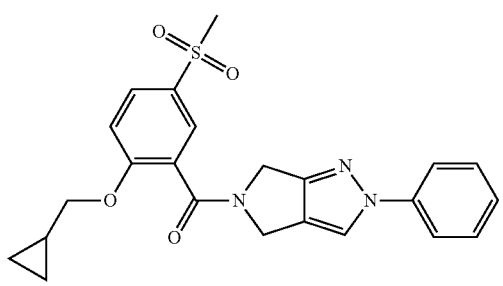

¹H NMR (400 MHz, DMSO-d₆) δ=8.38-8.22 (m, 1H), 7.94 (dd, J=2.3, 8.6 Hz, 1H), 7.83-7.74 (m, 3H), 7.50-7.43 (m, 2H), 7.36 (dd, J=2.0, 9.0 Hz, 1H), 7.31-7.24 (m, 1H), 4.68 (d, J=6.7 Hz, 2H), 4.42 (d, J=18.4 Hz, 2H), 4.06 (dd, J=2.7, 6.7 Hz, 2H), 3.20 (s, 3H), 1.18 (ddd, J=4.9, 7.6, 12.5 Hz, 1H), 0.52-0.44 (m, 2H), 0.31-0.25 (m, 2H); [M+H]=438.06.

Example 119

5-[2-(Cyclopropylmethoxy)-5-methanesulfonylbenzoyl]-2-(2-fluorophenyl)-2H 4H 5H 6H-pyrrolo[3,4-c]pyrazole

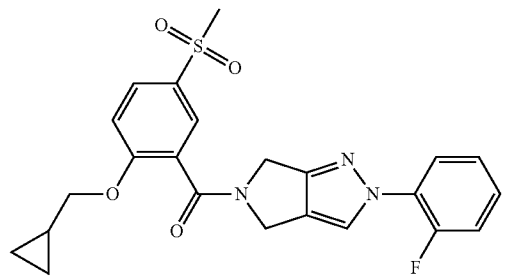 [SMILES: CS(=O)(=O)c1ccc(OCC2CC2)c(C(=O)N2Cc3cn(-c4ccccc4F)nc3C2)c1]

¹H NMR (400 MHz, DMSO-d₆) δ=8.08-7.91 (m, 2H), 7.83-7.68 (m, 2H), 7.49-7.29 (m, 4H), 4.69 (d, J=9.8 Hz, 2H), 4.49-4.36 (m, 2H), 4.06 (dd, J=3.7, 6.8 Hz, 2H), 3.20 (s, 3H), 1.25-1.14 (m, 1H), 0.53-0.45 (m, 2H), 0.31-0.25 (m, 2H); [M+H]=456.04.

Example 120

2-{5-[2-(4 4-Difluoropiperidin-1-yl)-5-methanesulfonylbenzoyl]-2H 4H 5H 6H-pyrrolo[3,4-c]pyrazol-2-yl}-5-fluoropyridine

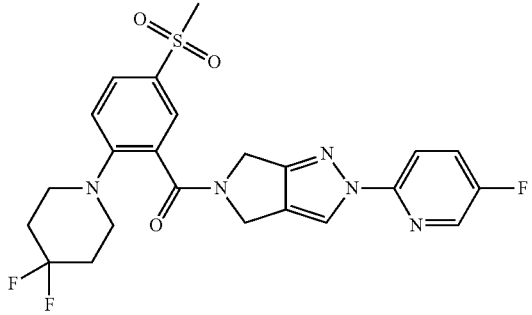 [SMILES: CS(=O)(=O)c1ccc(N2CCC(F)(F)CC2)c(C(=O)N2Cc3cn(-c4ccc(F)cn4)nc3C2)c1]

¹H NMR (400 MHz, DMSO-d₆) δ=8.49-8.27 (m, 2H), 7.95-7.81 (m, 3H), 7.75 (dd, J=1.2, 2.3 Hz, 1H), 7.32 (d, J=8.6 Hz, 1H), 4.75-4.65 (m, 2H), 4.46 (br s, 2H), 3.38-3.31 (m, 2H), 3.29-3.23 (m, 2H), 3.19 (s, 3H), 2.07-1.93 (m, 4H); [M+H]=506.24.

Example 121

2-(2 5-Difluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

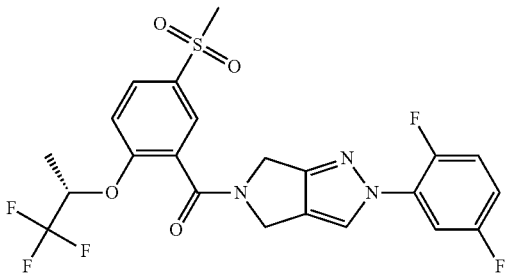 [SMILES: C[C@H](Oc1ccc(S(C)(=O)=O)cc1C(=O)N1Cc2cn(-c3cc(F)ccc3F)nc2C1)C(F)(F)F]

¹H NMR (400 MHz, DMSO-d₆) δ=8.14-7.88 (m, 3H), 7.70-7.47 (m, 3H), 7.30-7.22 (m, 1H), 5.54 (td, J=6.3, 12.8 Hz, 1H), 4.67 (d, J=11.7 Hz, 2H), 4.46-4.27 (m, 2H), 3.23 (s, 3H), 1.43 (dd, J=1.6, 6.3 Hz, 3H); [M+H]=516.01.

Example 122

2-(2-Fluoro-5-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole

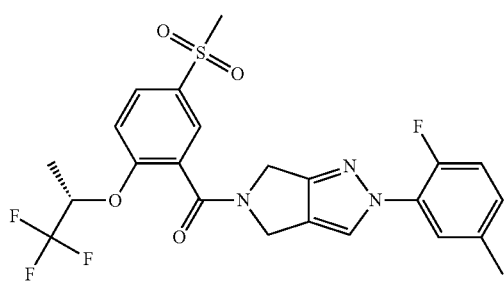 [SMILES: Cc1ccc(F)c(-n2cc3c(n2)CN(C(=O)c2cc(S(C)(=O)=O)ccc2O[C@@H](C)C(F)(F)F)C3)c1]

¹H NMR (400 MHz, DMSO-d₆) δ=8.05-7.88 (m, 3H), 7.62-7.49 (m, 2H), 7.32(ddd, J=2.3, 8.6, 11.3 Hz, 1H), 7.22-7.16 (m, 1H), 5.59-5.49 (m, 1H), 4.67 (d, J=9.0 Hz, 2H), 4.45-4.26 (m, 2H), 3.24 (d, J=1.2 Hz, 3H), 2.32 (d, J=6.3 Hz, 3H), 1.43 (dd, J=1.6, 6.3 Hz, 3H); [M+H]=512.09.

Example 123

1-{2-[2-(2 5-Difluorophenyl)-2H 4H 5H 6H-pyrrolo[3,4-c]pyrazole-5-carbonyl]-4-methanesulfonylphenyl}-4 4-difluoropiperidine

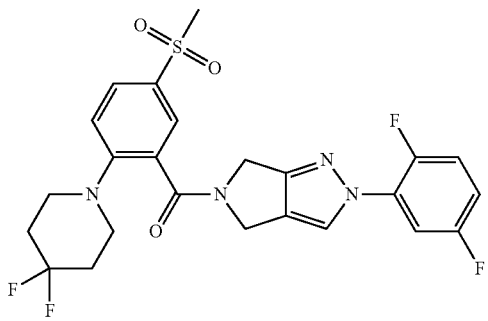 [SMILES: CS(=O)(=O)c1ccc(N2CCC(F)(F)CC2)c(C(=O)N2Cc3cn(-c4cc(F)ccc4F)nc3C2)c1]

¹H NMR (400 MHz, DMSO-d₆) δ=8.17-7.96 (m, 2H), 7.87 (ddd, J=1.2, 2.3, 8.6 Hz, 1H), 7.79-7.63 (m, 2H), 7.64-7.46 (m, 2H), 7.36-7.22 (m, 2H), 4.72 (d, J=15.7 Hz, 2H), 4.44 (br s, 2H), 3.40-3.33 (m, 2H), 3.27-3.22 (m, 2H), 3.19 (d, J=1.6 Hz, 3H), 2.07-1.93 (m, 4H); [M+H]=523.16.

Example 124

4 4-Difluoro-1-{2-[2-(2-fluoro-5-methylphenyl)-2H 4H 5H 6H-pyrrolo[3,4-c]pyrazole-5-carbonyl]-4-methanesulfonylphenyl}piperidine

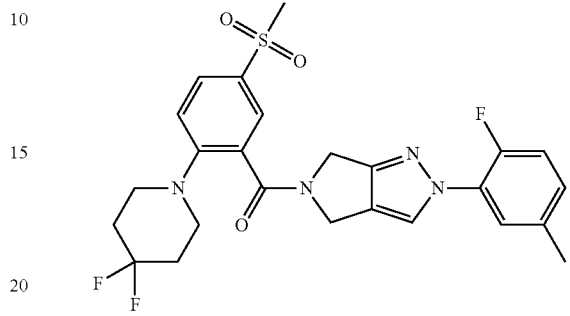

¹H NMR (400 MHz, DMSO-d₆) δ=8.06-7.84 (m, 2H), 7.76 (d, J=2.3 Hz, 1H), 7.61-7.49 (m, 1H), 7.36-7.28 (m, 2H), 7.20 (dd, J=2.3, 4.7 Hz, 1H), 4.71 (d, J=11.0 Hz, 2H), 4.58-4.29 (m, 2H), 3.36-3.30 (m, 2H), 3.30-3.24 (m, 2H), 3.19 (d, J=2.0 Hz, 3H), 2.32 (d, J=6.7 Hz, 3H), 2.07-1.89 (m, 4H); [M+H]=519.1.

Example 125

2-(2 5-Difluorophenyl)-5-[5-(ethanesulfonyl)-2-{[(2S)-1 1 1-trifluoropropan-2-yl]oxy}benzoyl]-2H 4H 5H 6H-pyrrolo[3,4-c]pyrazole

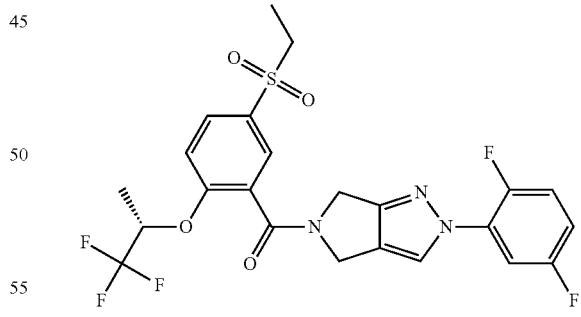

¹H NMR (400 MHz, DMSO-d₆) δ=8.14-7.92 (m, 2H), 7.86 (dd, J=2.3, 3.9 Hz, 1H), 7.70-7.48 (m, 3H), 7.31-7.22 (m, 1H), 5.54 (td, J=6.3, 12.8 Hz, 1H), 4.67 (d, J=11.7 Hz, 2H), 4.43-4.25 (m, 2H), 3.38-3.31 (m, 2H), 1.43 (dd, J=1.6, 6.3 Hz, 3H), 1.15-1.07 (m, 3H); [M+H]=530.08.

Example 126

5-[5-(Ethanesulfonyl)-2-{[(2S)-1 1 1-trifluoropropan-2-yl]oxy}benzoyl]-2-(2-fluoro-5-methylphenyl)-2H 4H 5H 6H-pyrrolo[3,4-c]pyrazole

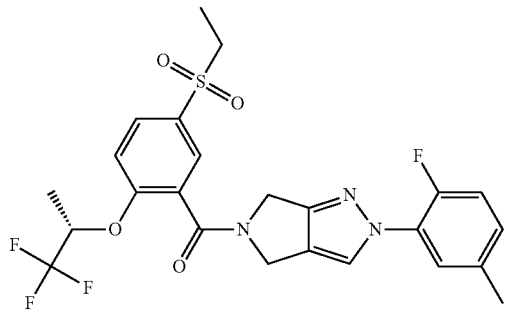 [SMILES: CCS(=O)(=O)c1ccc(O[C@@H](C)C(F)(F)F)c(C(=O)N2Cc3cn(-c4cc(C)ccc4F)nc3C2)c1]

¹H NMR (400 MHz, DMSO-d₆) δ=8.05-7.83 (m, 3H), 7.63-7.49 (m, 2H), 7.32 (ddd, J=2.3, 8.6, 11.3 Hz, 1H), 7.19 (ddd, J=2.3, 5.0, 7.9 Hz, 1H), 5.59-5.50 (m, 1H), 4.66 (d, J=9.0 Hz, 2H), 4.43-4.26 (m, 2H), 3.36-3.31 (m, 2H), 2.32 (d, J=6.7 Hz, 3H), 1.43 (dd, J=2.0, 6.3 Hz, 3H), 1.16-1.06 (m, 3H); [M+H]=526.11.

Example 127

1-{2-[2-(2 5-Difluorophenyl)-2H 4H 5H 6H-pyrrolo[3,4-c]pyrazole-5-carbonyl]-4-(ethanesulfonyl)phenyl}-4 4-difluoropiperidine

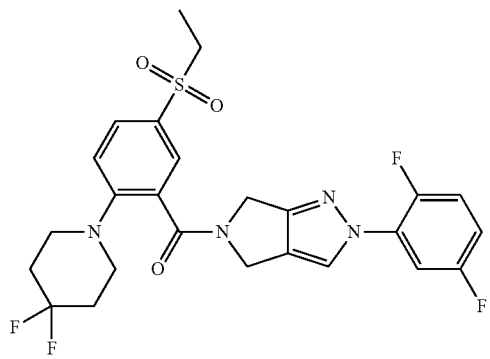 [SMILES: CCS(=O)(=O)c1ccc(N2CCC(F)(F)CC2)c(C(=O)N2Cc3cn(-c4cc(F)ccc4F)nc3C2)c1]

¹H NMR (400 MHz, DMSO-d₆) δ=8.16-7.96 (m, 2H), 7.87-7.69 (m, 2H), 7.68-7.47 (m, 2H), 7.35-7.21 (m, 2H), 4.71 (d, J=14.5 Hz, 2H), 4.61-4.37 (m, 2H), 3.29-3.22 (m, 4H), 2.09-1.93 (m, 4H), 1.09 (dt, J=1.2, 7.4 Hz, 3H); [M+H]=537.24.

Example 128

1-[4-(Ethanesulfonyl)-2-[2-(2-fluoro-5-methylphenyl)-2H 4H 5H 6H-pyrrolo[3,4-c]pyrazole-5-carbonyl]phenyl]-4 4-difluoropiperidine

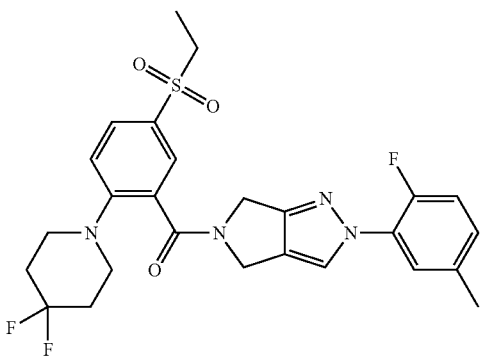 [SMILES: CCS(=O)(=O)c1ccc(N2CCC(F)(F)CC2)c(C(=O)N2Cc3cn(-c4cc(C)ccc4F)nc3C2)c1]

¹H NMR (400 MHz, DMSO-d₆) δ=8.07-7.87 (m, 1H), 7.85-7.68 (m, 2H), 7.61-7.48 (m, 1H), 7.36-7.27 (m, 2H), 7.19 (ddd, J=2.3, 4.9, 7.6 Hz, 1H), 4.76-4.67 (m, 2H), 4.61-4.34 (m, 2H), 3.28-3.22 (m, 2H), 2.32 (d, J=6.7 Hz, 3H), 2.07-1.94 (m, 4H), 1.09 (dt, J=1.4, 7.3 Hz, 3H); [M+H]=533.25.

Example 129

2-(2 5-Difluorophenyl)-5-[5-methanesulfonyl-2-(propan-2-yloxy)benzoyl]-2H 4H 5H 6H-pyrrolo[3,4-c]pyrazole

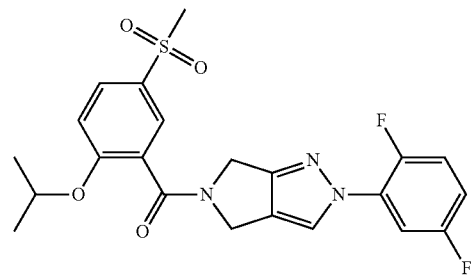 [SMILES: CC(C)Oc1ccc(S(C)(=O)=O)cc1C(=O)N1Cc2cn(-c3cc(F)ccc3F)nc2C1]

¹H NMR (400 MHz, DMSO-d₆) δ=8.14-7.97 (m, 1H), 7.93 (dd, J=2.5, 8.8 Hz, 1H), 7.80 (dd, J=2.3, 3.5 Hz, 1H), 7.70-7.48 (m, 2H), 7.38 (dd, =1.6, 9.0 Hz, 1H), 7.30-7.22 (m, 1H), 4.88-4.79 (m, 1H), 4.68 (d, J=11.7 Hz, 2H), 4.44-4.31 (m, 2H), 3.20 (s, 3H), 1.30-1.22 (m, 6H); [M+H]=462.03.

Example 130

2-(2-Fluoro-5-methylphenyl)-5-[5-methanesulfonyl-2-(propan-2-yloxy)benzoyl]-2H 4H 5H 6H-pyrrolo[3,4-c]pyrazole

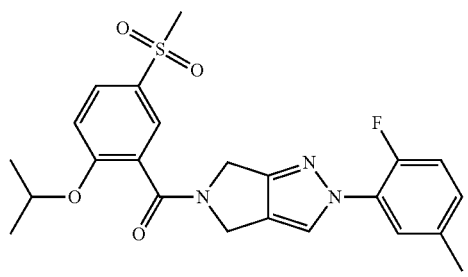 [SMILES: Cc1ccc(F)c(-n2cc3c(n2)CN(C(=O)c2cc(S(C)(=O)=O)ccc2OC(C)C)C3)c1]

$^1$H NMR (400 MHz, DMSO-$d_6$) δ=8.05-7.88 (m, 2H), 7.83-7.77 (m, 1H), 7.62-7.49 (m, 1H), 7.38 (d, J=9.0 Hz, 1H), 7.32 (ddd, J=2.3, 8.6, 11.3 Hz, 1H), 7.22-7.16 (m, 1H), 4.89-4.79 (m, 1H), 4.67 (d, J=9.0 Hz, 2H), 4.42-4.32 (m, 2H), 3.20 (d, J=0.8 Hz, 3H), 2.32 (d, J=6.7 Hz, 3H), 1.27 (dd, J=0.8, 6.3 Hz, 6H); [M+H]=458.23.

Example 131

4-{5-[2-(4 4-Difluoropiperidin-1-yl)-5-methanesulfonylbenzoyl]-2H 4H 5H 6H-pyrrolo[3,4-c]pyrazol-2-yl}-2-ethylpyridine

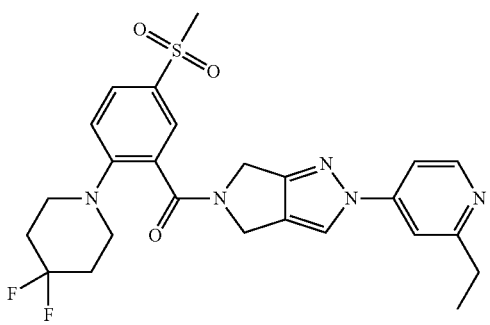 [SMILES: CCc1cc(-n2cc3c(n2)CN(C(=O)c2cc(S(C)(=O)=O)ccc2N2CCC(F)(F)CC2)C3)ccn1]

$^1$H NMR (400 MHz, DMSO-$d_6$) δ=8.59-8.38 (m, 2H), 7.88 (dd, J=2.0, 8.6 Hz, 1H), 7.77-7.73 (m, 1H), 7.69 (dd, J=2.0, 15.3 Hz, 1H), 7.62 (ddd, J=2.0, 5.7, 12.7 Hz, 1H), 7.32 (dd, J=1.2, 8.6 Hz, 1H), 4.77-4.67 (m, 2H), 4.59-4.37 (m, 2H), 3.30-3.24 (m, 4H), 3.19 (d, J=0.8 Hz, 3H), 2.78 (dq, J=3.5, 7.6 Hz, 2H), 2.07-1.92 (m, 4H), 1.24 (dt, J=2.9, 7.5 Hz, 3H); [M+H]=516.19.

Example 132

4-{5-[2-(4 4-Difluoropiperidin-1-yl)-5-(ethanesulfonyl)benzoyl]-2H 4H 5H 6H-pyrrolo[3,4-c]pyrazol-2-yl}-2-ethylpyridine

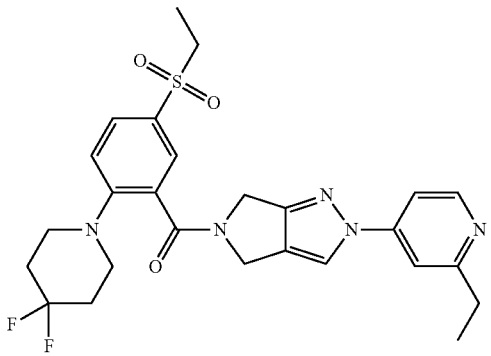 [SMILES: CCc1cc(-n2cc3c(n2)CN(C(=O)c2cc(S(=O)(=O)CC)ccc2N2CCC(F)(F)CC2)C3)ccn1]

$^1$H NMR (400 MHz, DMSO-$d_6$) δ=8.59-8.37 (m, 2H), 7.83 (dd, J=2.3, 9.0 Hz, 1H), 7.74-7.67 (m, 2H), 7.63 (ddd, J=2.2, 5.6, 12.2 Hz, 1H), 7.32 (dd, J=0.8, 8.6 Hz, 1H), 4.75-4.68 (m, 2H), 4.61-4.37 (m, 2H), 3.29-3.22 (m, 4H), 2.78 (dq, J=3.1, 7.6 Hz, 2H), 2.07-1.92 (m, 4H), 1.24 (dt, =3.1, 7.6 Hz, 3H), 1.09 (t, J=7.2 Hz, 3H); [M+H]=530.29.

Example 133

2-Ethyl-4-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]pyridine

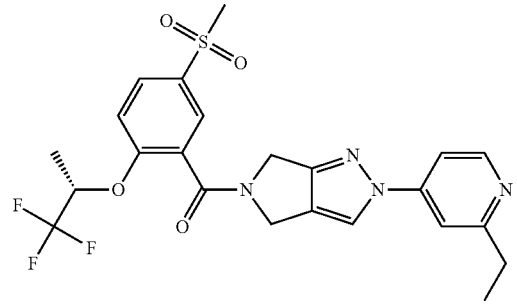 [SMILES: CCc1cc(-n2cc3c(n2)CN(C(=O)c2cc(S(C)(=O)=O)ccc2O[C@@H](C)C(F)(F)F)C3)ccn1]

$^1$H NMR (400 MHz, DMSO-$d_6$) δ=8.71-8.51 (m, 2H), 8.05-7.95 (m, 2H), 7.96-7.83 (m, 2H), 7.61 (dd, J=2.0, 9.0 Hz, 1H), 5.55 (td, J=6.3, 12.8 Hz, 1H), 4.70 (d, J=11.0 Hz, 2H), 4.49-4.32 (m, 2H), 3.24 (s, 3H), 2.89 (dq, J=3.3, 7.5 Hz, 2H), 1.42 (dd, J=2.0, 6.3 Hz, 3H), 1.28 (dt, =3.3, 7.5 Hz, 3H); [M+H]=509.19.

Example 134

4-{5-[5-(Ethanesulfonyl)-2-{[(2S)-1 1 1-trifluoropropan-2-yl]oxy}benzoyl]-2H 4H 5H 6H-pyrrolo[3,4-c]pyrazol-2-yl}-2-ethylpyridine

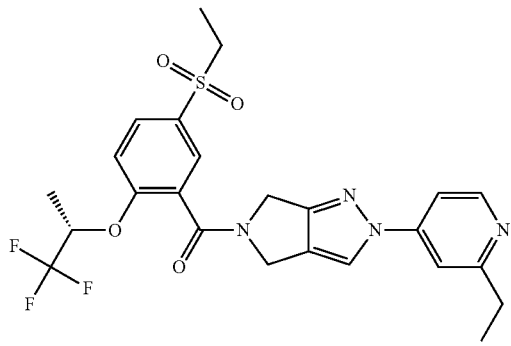 [SMILES: CCc1cc(-n2cc3c(n2)CN(C(=O)c2cc(S(=O)(=O)CC)ccc2O[C@@H](C)C(F)(F)F)C3)ccn1]

$^1$H NMR (400 MHz, DMSO-d$_6$) δ=8.64-8.46 (m, 2H), 8.01-7.93 (m, 1H), 7.88-7.71 (m, 3H), 7.61 (dd, J=2.0, 9.0 Hz, 1H), 5.54 (td, J=6.2, 12.7 Hz, 1H), 4.69 (d, J=9.8 Hz, 2H), 4.45-4.29 (m, 2H), 3.29 (br s, 4H), 3.28-3.26 (m, 2H), 2.83 (dq, J=3.9, 7.6 Hz, 2H), 1.42 (dd, J=1.8, 6.5 Hz, 3H), 1.26 (dt, J=3.3, 7.5 Hz, 3H), 1.11 (t, J=7.4 Hz, 3H); [M+H]=523.10.

Example 135

2-{5-[2-(4 4-Difluoropiperidin-1-yl)-5-(ethanesulfonyl)benzoyl]-2H 4H 5H 6H-pyrrolo[3,4-c]pyrazol-2-yl}-5-fluoropyridine

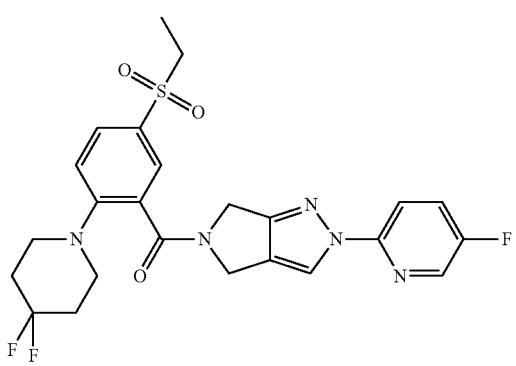 [SMILES: CCS(=O)(=O)c1ccc(N2CCC(F)(F)CC2)c(C(=O)N2Cc3cn(-c4ccc(F)cn4)nc3C2)c1]

$^1$H NMR (400 MHz, DMSO-d$_6$) δ=8.49-8.26 (m, 2H), 7.96-7.79 (m, 3H), 7.70 (d, J=2.3 Hz, 1H), 7.32 (d, J=8.6 Hz, 1H), 4.76-4.66 (m, 2H), 4.57-4.30 (m, 2H), 3.28-3.23 (m, 2H), 2.07-1.92 (m, 4H), 1.09 (t, J=7.4 Hz, 3H); [M+H]=520.22.

Example 136

5-[2-(Cyclopropylmethoxy)-5-methanesulfonylbenzoyl]-2-(2-fluoro-5-methylphenyl)-2H 4H 5H 6H-pyrrolo[3,4-c]pyrazole

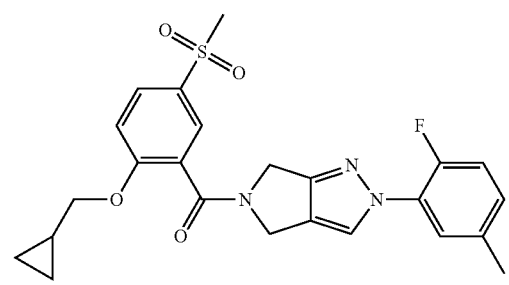 [SMILES: Cc1ccc(F)c(-n2cc3c(n2)CN(C(=O)c2cc(S(C)(=O)=O)ccc2OCC2CC2)C3)c1]

$^1$H NMR (400 MHz, DMSO-d$_6$) δ=8.05-7.89 (m, 2H), 7.83-7.80 (m, 1H), 7.62-7.50 (m, 1H), 7.38-7.28 (m, 2H), 7.23-7.17 (m, 1H), 4.68 (d, =9.0 Hz, 2H), 4.48-4.37 (m, 2H), 4.06 (dd, J=4.1, 6.8 Hz, 2H), 3.20 (d, J=0.8 Hz, 3H), 2.32 (d, J=5.9 Hz, 3H), 1.24-1.14 (m, 1H), 0.49 (td, =2.2, 8.1 Hz, 2H), 0.28 (d, J=5.5 Hz, 2H); [M+H]=470.04.

Example 137

5-[2-(Cyclopropylmethoxy)-5-methanesulfonylbenzoyl]-2-(2 5-difluorophenyl)-2H 4H 5H 6H-pyrrolo[3,4-c]pyrazole

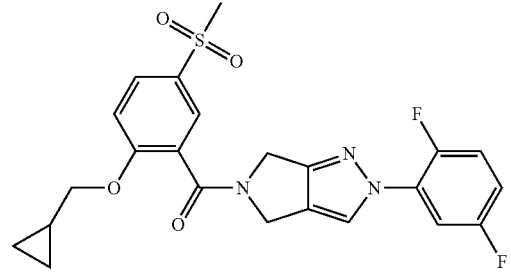 [SMILES: CS(=O)(=O)c1ccc(OCC2CC2)c(C(=O)N2Cc3cn(-c4cc(F)ccc4F)nc3C2)c1]

$^1$H NMR (400 MHz, DMSO-d$_6$) δ=8.14-7.98 (m, 1H), 7.94 (dd, J=2.3, 9.0 Hz, 1H), 7.82 (dd, J=2.5, 3.7 Hz, 1H), 7.70-7.48 (m, 2H), 7.36 (m, =2.7, 9.0 Hz, 1H), 7.31-7.23 (m, 1H), 4.69 (d, J=11.7 Hz, 2H), 4.48-4.37 (m, 2H), 4.06 (dd, J=3.7, 6.8 Hz, 2H), 3.20 (s, 3H), 1.24-1.14 (m, 1H), 0.52-0.44 (m, 2H), 0.31-0.25 (m, 2H); [M+H]=474.0.

Example 138

5-[2-(Cyclopropylmethoxy)-5-methanesulfonylbenzoyl]-2-[2-fluoro-3-(trifluoromethyl)phenyl]-2H 4H 5H 6H-pyrrolo[3,4-c]pyrazole

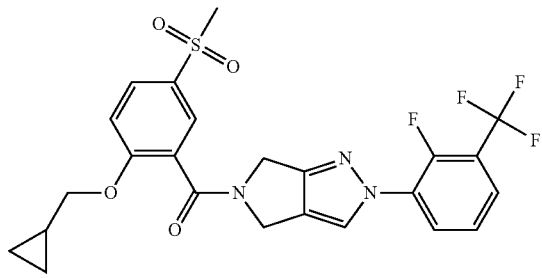 [SMILES: CS(=O)(=O)c1ccc(OCC2CC2)c(C(=O)N2Cc3cn(-c4cccc(C(F)(F)F)c4F)nc3C2)c1]

$^1$H NMR (400 MHz, DMSO-d$_6$) δ=8.18-8.02 (m, 2H), 7.94 (dd, J=2.5, 8.8 Hz, 1H), 7.84-7.76 (m, 2H), 7.55 (dt, J=3.9, 8.0 Hz, 1H), 7.36 (dd, =2.9, 8.8 Hz, 1H), 4.70 (d, J=11.3 Hz, 2H), 4.48-4.39 (m, 2H), 4.06 (dd, J=2.7, 7.0 Hz, 2H), 3.20 (s, 3H), 1.26-1.14 (m, 1H), 0.53-0.45 (m, 2H), 0.32-0.25 (m, 2H); [M+H]=524.0.

Example 139

5-[2-(Cyclopropylmethoxy)-5-methanesulfonylbenzoyl]-2-(2-fluoro-3-methylphenyl)-2H 4H 5H 6H-pyrrolo[3,4-c]pyrazole

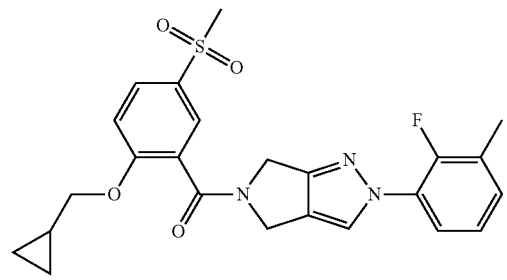 [SMILES: Cc1cccc(-n2cc3c(n2)CN(C(=O)c2cc(S(C)(=O)=O)ccc2OCC2CC2)C3)c1F]

$^1$H NMR (400 MHz, DMSO-d$_6$) δ=8.06-7.90 (m, 2H), 7.81 (dd, J=2.5, 3.7 Hz, 1H), 7.60-7.47 (m, 1H), 7.36 (dd, J=2.5, 8.8 Hz, 1H), 7.32-7.26 (m, 1H), 7.24-7.17 (m, 1H), 4.68 (d, J=7.8 Hz, 2H), 4.47-4.37 (m, 2H), 4.06 (dd, J=3.1, 7.0 Hz, 2H), 3.20 (s, 3H), 2.33-2.28 (m, 3H), 1.24-1.15 (m, 1H), 0.49 (ddd, J=2.0, 3.8, 7.9 Hz, 2H), 0.31-0.25 (m, 2H); [M+H]=470.18.

Example 140

5-[2-(Cyclopropylmethoxy)-5-methanesulfonylbenzoyl]-2-(3-methylphenyl)-2H 4H 5H 6H-pyrrolo[3,4-c]pyrazole

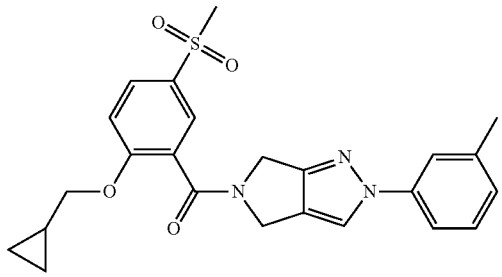

$^1$H NMR (400 MHz, DMSO-d$_6$) δ=8.37-8.19 (m, 1H), 7.96-7.79 (m, 2H), 7.66-7.53 (m, 2H), 7.40-7.31 (m, 2H), 7.09 (d, J=7.8 Hz, 1H), 4.67 (d, J=5.1 Hz, 2H), 4.41 (d, J=16.8 Hz, 2H), 4.06 (dd, J=2.5, 6.8 Hz, 2H), 3.20 (s, 3H), 2.35 (d, J=3.1 Hz, 3H), 1.23-1.14 (m, 1H), 0.48 (ddd, =2.2, 3.5, 8.0 Hz, 2H), 0.27 (d, J=5.9 Hz, 2H); [M+H]=452.12.

Example 141

3-{5-[2-(3-Fluorophenyl)-5-methanesulfonylbenzoyl]-2H 4H 5H 6H-pyrrolo[3,4-c]pyrazol-2-yl}pyridine

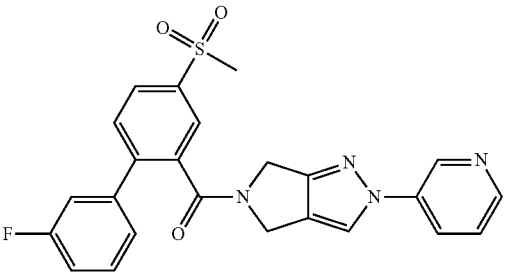 [SMILES: CS(=O)(=O)c1ccc(-c2cccc(F)c2)c(C(=O)N2Cc3cn(-c4cccnc4)nc3C2)c1]

$^1$H NMR (400 MHz, DMSO-d$_6$) δ=9.08 (br s, 1H), 8.54 (br s, 1H), 8.44-8.28 (m, 1H), 8.24 (dd, J=8.6, 13.7 Hz, 1H), 8.13-8.03 (m, 2H), 7.83 (dd, J=4.3, 8.2 Hz, 1H), 7.61 (br s, 1H), 7.53-7.45 (m, 1H), 7.41-7.32 (m, 2H), 7.29-7.20 (m, 1H), 4.54 (d, J=11.0 Hz, 2H), 4.27-4.11 (m, 2H), 3.38-3.23 (m, 3H); [M+H]=463.5.

Example 142

4-{5-[2-(3-Fluorophenyl)-5-methanesulfonylbenzoyl]-2H 4H 5H 6H-pyrrolo[3,4-c]pyrazol-2-yl}pyridine

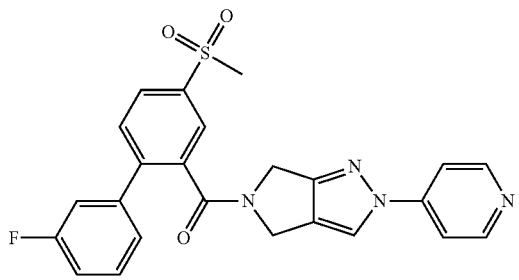 [SMILES: CS(=O)(=O)c1ccc(-c2cccc(F)c2)c(C(=O)N2Cc3cn(-c4ccncc4)nc3C2)c1]

$^1$H NMR (400 MHz, DMSO-d$_6$) δ=8.62-8.56 (m, 2H), 8.53-8.34 (m, 1H), 8.13-8.03 (m, 2H), 7.86-7.80 (m, 1H), 7.79-7.71 (m, 2H), 7.56-7.44 (m, 1H), 7.43-7.31 (m, 2H), 7.30-7.19 (m, 1H), 4.54 (d, J=11.7 Hz, 2H), 4.29-4.10 (m, 2H), 3.33 (s, 3H); [M+H]=463.5.

Example 143

2-Ethyl-4-{5-[2-(3-fluorophenyl)-5-methanesulfonylbenzoyl]-2H 4H 5H 6H-pyrrolo[3,4-c]pyrazol-2-yl}pyridine

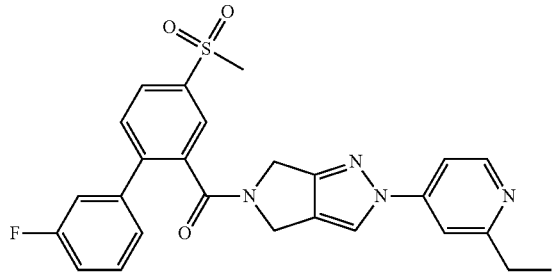 [SMILES: CCc1cc(-n2cc3c(n2)CN(C(=O)c2cc(S(C)(=O)=O)ccc2-c2cccc(F)c2)C3)ccn1]

$^1$H NMR (400 MHz, DMSO-d$_6$) δ=8.51-8.34 (m, 2H), 8.12-8.06 (m, 2H), 7.83 (dd, J=4.3, 7.8 Hz, 1H), 7.64 (dd, J=2.0, 12.5 Hz, 1H), 7.57 (ddd, J=2.2, 5.7, 9.8 Hz, 1H), 7.53-7.45 (m, 1H), 7.40-7.32 (m, 2H), 7.25 (t, J=8.6 Hz, 1H), 4.53 (d, J=9.4 Hz, 2H), 4.18 (d, J=15.3 Hz, 2H), 3.33 (hr s, 3H), 2.76 (dq, J=2.5, 7.6 Hz, 2H), 1.22 (dt, J=2.3, 7.6 Hz, 3H); [M+H]=491.5.

Example 144

5-(5-Cyclopropylmethanesulfonyl-2-{[(2S)-1 1 1-trifluoropropan-2-yl]oxy}benzoyl)-2-phenyl-2H 4H 5H 6H-pyrrolo[3,4-c]pyrazole

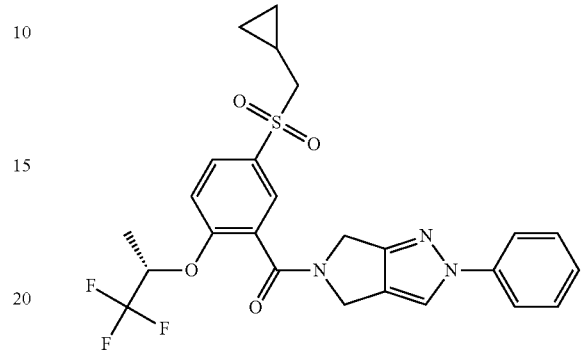

$^1$H NMR (400 MHz, DMSO-d$_6$) δ=8.38-8.23 (m, 1H), 7.99-7.93 (m, 1H), 7.85 (dd, J=2.3, 4.3 Hz, 1H), 7.81-7.74 (m, 2H), 7.60 (dd, J=1.2, 9.0 Hz, 1H), 7.51-7.42 (m, 2H), 7.32-7.25 (m, 1H), 5.60-5.50 (m, 1H), 4.67 (d, J=6.7 Hz, 2H), 4.42-4.27 (m, 2H), 3.28 (s, 2H), 1.43 (dd, J=1.6, 6.3 Hz, 3H), 0.92-0.82 (m, 1H), 0.47-0.41 (m, 2H), 0.12-0.06 (m, 2H); [M+H]=520.2.

Example 145

5-(5-Cyclopropylmethanesulfonyl-2-{[(2S)-1 1 1-trifluoropropan-2-yl]oxy}benzoyl)-2-(3-methylphenyl)-2H 4H 5H 6H-pyrrolo[3,4-c]pyrazole

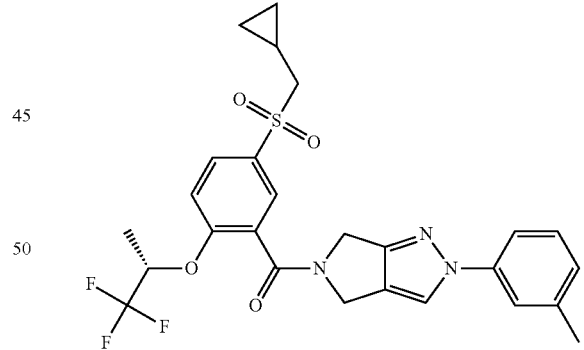

$^1$H NMR (400 MHz, DMSO-d$_6$) δ=8.36-8.20 (m, 1H), 7.96 (dd, J=2.3, 9.0 Hz, 1H), 7.85 (dd, J=2.3, 3.5 Hz, 1H), 7.64-7.50 (m, 3H), 7.34 (dt, =2.0, 7.8 Hz, 1H), 7.09 (d, J=7.4 Hz, 1H), 5.59-5.50 (m, 1H), 4.66 (d, J=5.5 Hz, 2H), 4.41-4.27 (m, 2H), 3.28 (s, 2H), 2.35 (d, J=2.7 Hz, 2H), 1.43 (dd, J=1.6, 6.3 Hz, 3H), 0.90-0.83 (m, 1H), 0.47-0.40 (m, 2H), 0.12-0.05 (m, 2H); [M+H]=534.2.

Example 146

2-(3-Chloro-2-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

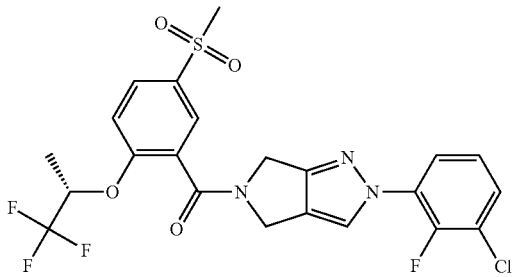 [SMILES: C[C@H](Oc1ccc(S(C)(=O)=O)cc1C(=O)N1Cc2cn(-c3cccc(Cl)c3F)nc2C1)C(F)(F)F]

¹H NMR (400 MHz, DMSO-d₆) δ=8.15-7.97 (m, 2H), 7.90 (dd, J=2.5, 4.5 Hz, 1H), 7.79-7.66 (m, 1H), 7.64-7.57 (m, 2H), 7.39-7.32 (m, 1H), 5.54 (td, J=6.4, 12.6 Hz, 1H), 4.68 (d, J=10.2 Hz, 2H), 4.45-4.28 (m, 2H), 3.26-3.21 (m, 3H), 1.43 (d, J=6.3 Hz, 3H); [M+H]=532.15.

Example 147

2-(2-Chloro-3-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

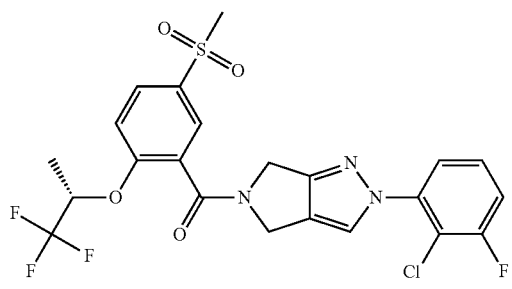 [SMILES: C[C@H](Oc1ccc(S(C)(=O)=O)cc1C(=O)N1Cc2cn(-c3cccc(F)c3Cl)nc2C1)C(F)(F)F]

¹H NMR (400 MHz, DMSO-d₆) δ=8.07-7.89 (m, 3H), 7.59 (dd, J=2.7, 9.0 Hz, 1H), 7.56-7.50 (m, 2H), 7.50-7.41 (m, 1H), 5.54 (td, J=6.2, 12.7 Hz, 1H), 4.68 (d, J=5.5 Hz, 2H), 4.44-4.28 (m, 2H), 3.26-3.21 (m, 3H), 1.43 (d, J=6.3 Hz, 3H); [M+H]=532.15.

Example 148

2-(3-Chloro-2-fluorophenyl)-5-[5-methanesulfonyl-2-(propan-2-yloxy)benzoyl]-2H 4H 5H 6H-pyrrolo[3,4-c]pyrazole

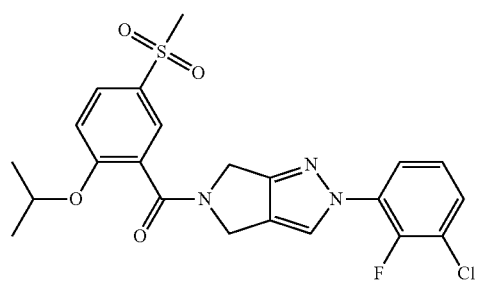 [SMILES: CC(C)Oc1ccc(S(C)(=O)=O)cc1C(=O)N1Cc2cn(-c3cccc(Cl)c3F)nc2C1]

¹H NMR (400 MHz, DMSO-d₆) δ=8.13-7.97 (m, 1H), 7.95-7.90 (m, 1H), 7.80 (dd, J=2.3, 3.1 Hz, 1H), 7.78-7.67 (m, 1H), 7.63-7.57 (m, 1H), 7.41-7.32 (m, 2H), 4.88-4.80 (m, 1H), 4.68 (d, J=10.2 Hz, 2H), 4.42-4.34 (m, 2H), 3.20 (s, 3H), 3.12-3.03 (m, 1H), 1.27 (d, J=6.3 Hz, 6H); [M+H]=478.2.

Example 149

2-(2-Chloro-3-fluorophenyl)-5-[5-methanesulfonyl-2-(propan-2-yloxy)benzoyl]-2H 4H 5H 6H-pyrrolo[3,4-c]pyrazole

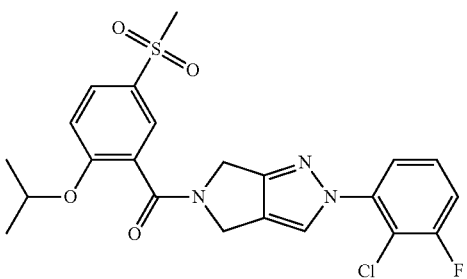 [SMILES: CC(C)Oc1ccc(S(C)(=O)=O)cc1C(=O)N1Cc2cn(-c3cccc(F)c3Cl)nc2C1]

¹H NMR (400 MHz, DMSO-d₆) δ=8.08-7.89 (m, 2H), 7.81 (dd, J=2.5, 3.7 Hz, 1H), 7.58-7.50 (m, 2H), 7.48-7.42 (m, 1H), 7.38 (dd, J=2.3, 9.0 Hz, 1H), 4.84 (dtd, J=2.9, 6.0, 12.1 Hz, 1H), 4.68 (d, J=5.1 Hz, 2H), 4.38 (d, J=17.2 Hz, 2H), 3.19 (s, 3H), 1.27 (d, J=6.3 Hz, 6H); [M+H]=479.19.

Example 150

2-(3-Chloro-2-fluorophenyl)-5-[5-(ethanesulfonyl)-2-{[(2S)-1 1 1-trifluoropropan-2-yl]oxy}benzoyl]-2H 4H 5H 6H-pyrrolo[3,4-c]pyrazole

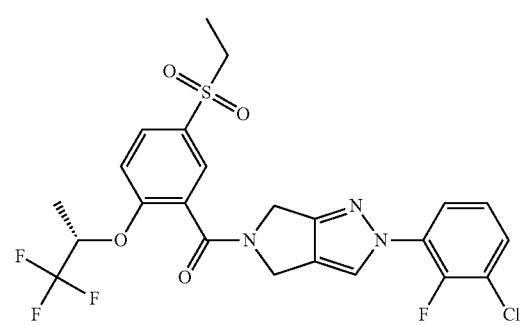 [SMILES: CCS(=O)(=O)c1ccc(O[C@@H](C)C(F)(F)F)c(C(=O)N2Cc3cn(-c4cccc(Cl)c4F)nc3C2)c1]

¹H NMR (400 MHz, DMSO-d₆) δ=8.15-7.91 (m, 2H), 7.86 (dd, J=2.3, 3.5 Hz, 1H), 7.78-7.66 (m, 1H), 7.64-7.56 (m, 2H), 7.39-7.31 (m, 1H), 5.54 (td, J=6.4, 12.6 Hz, 1H), 4.67 (d, J=9.8 Hz, 2H), 4.44-4.25 (m, 2H), 3.37-3.31 (m, 2H), 1.43 (d, J=6.3 Hz, 3H), 1.11 (t, J=7.4 Hz, 3H); [M+H]=546.13.

Example 151

2-(2-Chloro-3-fluorophenyl)-5-[5-(ethanesulfonyl)-2-{[(2S)-1 1 1-trifluoropropan-2-yl]oxy}benzoyl]-2H 4H 5H 6H-pyrrolo[3,4-c]pyrazole

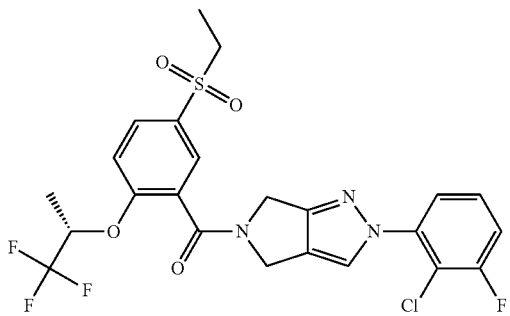 [SMILES: CCS(=O)(=O)c1ccc(O[C@@H](C)C(F)(F)F)c(C(=O)N2Cc3cn(-c4cccc(F)c4Cl)nc3C2)c1]

$^1$H NMR (400 MHz, DMSO-d$_6$) δ=8.07-7.92 (m, 2H), 7.87 (dd, J=2.3, 3.9 Hz, 1H), 7.60 (dd, J=2.9, 9.2 Hz, 1H), 7.56-7.50 (m, 2H), 7.49-7.42 (m, 1H), 5.54 (td, J=6.4, 12.6 Hz, 1H), 4.67 (d, J=5.5 Hz, 2H), 4.43-4.27 (m, 2H), 3.36-3.30 (m, 2H), 1.44 (d, J=6.3 Hz, 3H), 1.11 (t, J=7.4 Hz, 3H); [M+H]=546.09.

Example 152

2-{5-[2-(3-Fluorophenyl)-5-methanesulfonylbenzoyl]-2H 4H 5H 6H-pyrrolo[3,4-c]pyrazol-2-yl}pyridine

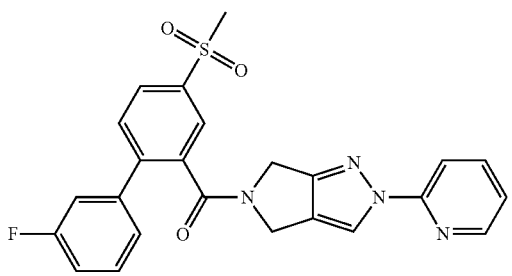 [SMILES: CS(=O)(=O)c1ccc(-c2cccc(F)c2)c(C(=O)N2Cc3cn(-c4ccccn4)nc3C2)c1]

$^1$H NMR (400 MHz, DMSO-d$_6$) δ=8.45-8.27 (m, 2H), 8.12-8.04 (m, 2H), 7.98-7.89 (m, 1H), 7.86-7.72 (m, 2H), 7.54-7.46 (m, 1H), 7.41-7.20 (m, 4H), 4.53 (d, J=18.8 Hz, 2H), 4.25-4.09 (m, 2H), 3.33 (s, 3H); [M+H]=463.5.

Examples 153-472 were prepared in a manner analogous to Example 1 with the appropriated starting material substitutions.

Example 153

2-Chloro-3-[2-(5-fluoropyridin-3-yl)-2H 4H 5H 6H 7H-pyrazolo[4,3-c]pyridine-5-carbonyl]-4-[(1 1 1-trifluoropropan-2-yl)oxy]benzonitrile

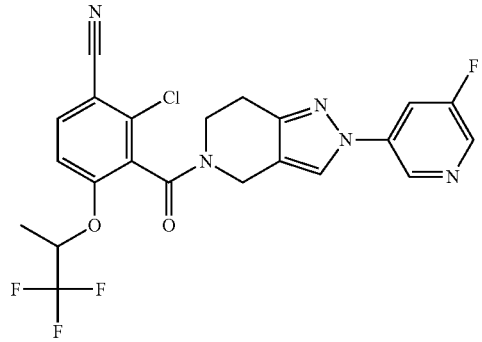 [SMILES: CC(Oc1ccc(C#N)c(Cl)c1C(=O)N1CCc2nn(-c3cncc(F)c3)cc2C1)C(F)(F)F]

$^1$H NMR (400 MHz, CDCl$_3$) δ=8.86-8.59 (m, 1H), 8.39 (d, .1 =3.9 Hz, 1H), 7.93-7.54 (m, 3H), 7.11-6.78 (m, 1H), 5.18-4.58 (m, 2H), 4.46-3.99 (m, 2H), 3.98-3.39 (m, 1H), 3.11-2.83 (m, 2H), 1.57-1.18 (m, 3H); [M+H]=494.26.

Example 154

3-[2-(5-Fluoropyridin-3-yl)-2H 4H 5H 6H 7H-pyrazolo[4,3-c]pyridine-5-carbonyl]-2-methoxy-4-[(1 1 1-trifluoropropan-2-yl)oxy]benzonitrile

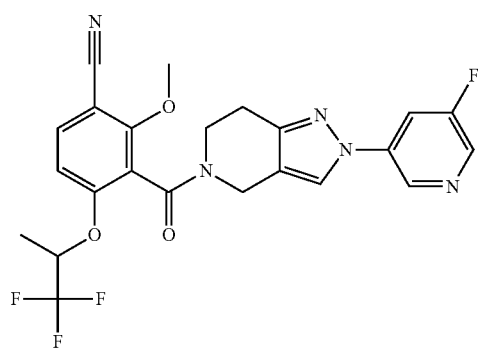 [SMILES: COc1c(C#N)ccc(OC(C)C(F)(F)F)c1C(=O)N1CCc2nn(-c3cncc(F)c3)cc2C1]

$^1$H NMR (400 MHz, CDCl$_3$) δ=8.84-8.64 (m, 1H), 8.39 (d, .1 =6.3 Hz, 1H), 7.89-7.73 (m, 2H), 7.69-7.52 (m, 1H), 6.85-6.59 (m, 1H), 5.18-4.59 (m, 2H), 4.47-4.27 (m, 1H), 4.22-3.98 (m, 3H), 3.97-3.86 (m, 1H), 3.71-3.39 (m, 1H), 3.11-2.66 (m, 2H), 1.53-1.44 (m, 2H), 1.31-1.21 (m, 1H); [M+H]=490.32.

Example 155

2-Chloro-3-[2-(pyridin-4-yl)-2H 4H 5H 6H 7H-pyrazolo[4,3-c]pyridine-5-carbonyl]-4-(2 2 2-trifluoroethoxy)benzonitrile

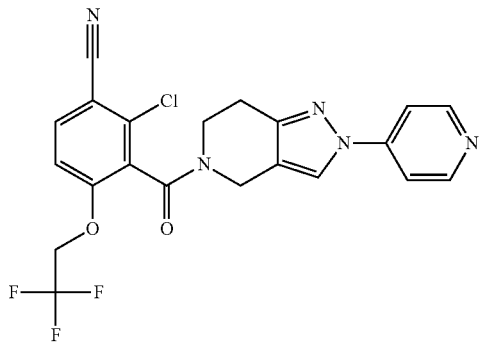 [SMILES: N#Cc1ccc(OCC(F)(F)F)c(C(=O)N2CCc3nn(-c4ccncc4)cc3C2)c1Cl]

$^1$H NMR (400 MHz, CDCl$_3$) δ=8.76-8.56 (m, 2H), 8.04-7.85 (m, 1H), 7.78-7.66 (m, 1H), 7.64-7.43 (m, 2H), 7.06-6.88 (m, 1H), 5.12-4.69 (m, 1H), 4.57-4.25 (m, 3H), 4.23-3.96 (m, 1H), 3.70-3.46 (m, 1H), 3.13-2.71 (m, 2H); [M+H]=426.26.

Example 156

2-Methoxy-3-[2-(pyridin-4-yl)-2H 4H 5H 6H 7H-pyrazolo[4,3-c]pyridine-5-carbonyl]-4-(2 2 2-trifluoroethoxy)benzonitrile

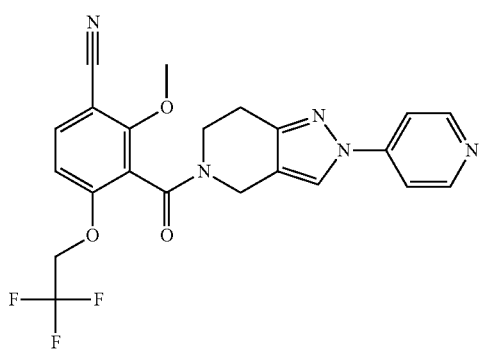 [SMILES: COc1c(C#N)ccc(OCC(F)(F)F)c1C(=O)N1CCc2nn(-c3ccncc3)cc2C1]

$^1$H NMR (400 MHz, CDCl$_3$) δ=8.73-8.57 (m, 2H), 7.89 (s, 1H), 7.74-7.46 (m, 3H), 6.80-6.66 (m, 1H), 5.11-4.73 (m, 1H), 4.54-4.27 (m, 3H), 4.19-3.98 (m, 4H), 3.65-3.43 (m, 1H), 3.07-2.74 (m, 2H); [M+H]=458.27.

Example 157

5-[2-(Cyclopropylmethoxy)-5-methanesulfonylbenzoyl]-1-methyl-1H 4H 5H 6H-pyrrolo[3,4-c]pyrazole

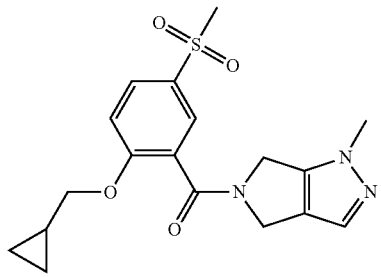 [SMILES: Cn1ncc2c1CN(C(=O)c1cc(S(C)(=O)=O)ccc1OCC1CC1)C2]

$^1$H NMR (400 MHz, DMSO-d$_6$) δ=7.94-7.86 (m, 1H), 7.75-7.64 (m, 1H), 7.51 (s, 1H), 7.33-7.27 (m, 1H), 4.63 (s, 1H), 4.28-4.11 (m, 1H), 4.06-3.82 (m, 3H), 3.73 (d, J=19.6 Hz, 3H), 3.19 (d, J=7.4 Hz, 3H), 2.67 (t, J=5.7 Hz, 1H), 1.13 (d, J=11.7 Hz, 1H), 0.93 (br s, 1H), 0.54-0.47 (m, 1H), 0.42 (br s, 1H), 0.28 (d, J=3.9 Hz, 1H), 0.15 (d, J=16.0 Hz, 1H); [M+H]=376.5.

Example 158

5-[2-(Cyclopropylmethoxy)-5-methanesulfonylbenzoyl]-1-methyl-1H 4H 5H 6H 7H-pyrazolo[4,3-c]pyridine

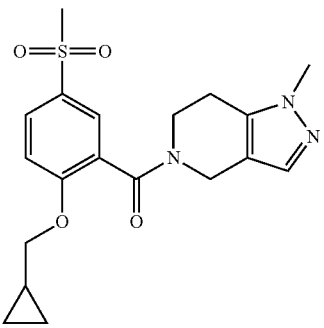 [SMILES: Cn1ncc2c1CCN(C(=O)c1cc(S(C)(=O)=O)ccc1OCC1CC1)C2]

$^1$H NMR (400 MHz, DMSO-d$_6$) δ=7.94-7.85 (m, 1H), 7.73-7.60 (m, 1H), 7.51 (s, 1H), 7.31-7.21 (m, 1H), 4.63 (s, 1H), 4.28-4.12 (m, 1H), 4.07-3.81 (m, 3H), 3.73 (d, J=19.6 Hz, 3H), 3.19 (d, J=7.4 Hz, 3H), 2.72-2.65 (m, 1H), 2.48 (d, J=1.6 Hz, 3H), 1.13 (d, J=11.7 Hz, 1H), 0.93 (br s, 1H), 0.54-0.46 (m, 1H), 0.42 (br s, 1H), 0.28 (d, J=3.9 Hz, 1H), 0.15 (s, 1H); [M+H]=390.4.

Example 159

5-[2-(Cyclopropylmethoxy)-5-methanesulfonylbenzoyl]-1-[3-(trifluoromethyl)phenyl]-1H 4H 5H 6H-pyrrolo[3,4-c]pyrazole

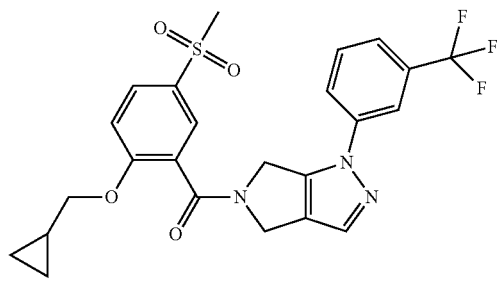 [SMILES: CS(=O)(=O)c1ccc(OCC2CC2)c(C(=O)N2Cc3cnn(-c4cccc(C(F)(F)F)c4)c3C2)c1]

$^1$H NMR (400 MHz, DMSO-$d_6$) δ=7.79 (br s, 1H), 7.74 (dd, J=2.5, 8.8 Hz, 2H), 7.63-7.59 (m, 1H), 7.58-7.43 (m, 3H), 7.39 (s, 1H), 7.17 (d,J =9.0 Hz, 1H), 4.92 (s, 1H), 4.67 (br s, 1H), 4.43 (br s, 1H), 4.16 (br s, 1H), 3.90-3.79 (m, 2H), 2.99 (d, J=2.7 Hz, 3H), 2.32-2.23 (m, 4H),1.04-0.92 (m, 1H), 1.02-0.92 (m, 1H), 1.04-0.90 (m, 2H), 0.37-0.26 (m, 1H), 0.18 (d, J=7.4 Hz, 1H), 0.11-0.05 (m, 1H), 0.05-0.04 (m, 1H); [M+H]=506.5.

Example 160

5-[2-(Cyclopropylmethoxy)-5-methanesulfonylbenzoyl]-1-[3-(trifluoromethyl)phenyl]-1H 4H 5H 6H 7H-pyrazolo[4,3-c]pyridine

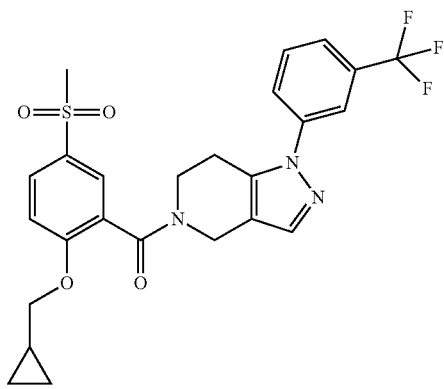

[M+H] = 520.3.

Example 161

5-{5-Methanesulfonyl-2-[(1 1 1-trifluoropropan-2-yl)oxy]benzoyl}-1-methyl-1H 4H 5H 6H 7H-pyrazolo[4,3-c]pyridine

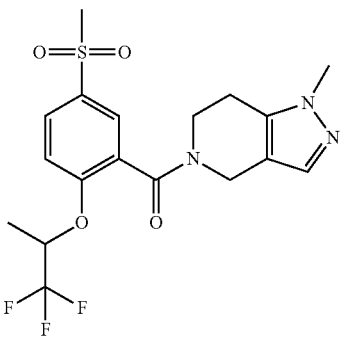 [SMILES: CC(Oc1ccc(S(C)(=O)=O)cc1C(=O)N1CCc2c(cnn2C)C1)C(F)(F)F]

$^1$H NMR (400 MHz, DMSO-$d_6$) δ=7.97 (br s, 1H), 7.77 (d, J=16.0 Hz, 1H), 7.56 (dd, J=8.8, 15.1 Hz, 1H), 7.31 (s, 1H), 5.59-5.41 (m, 2H), 4.76 (s, 1H), 4.50 (hr s, 1H), 4.16 (hr s, 1H), 3.76 (s, 1H), 3.70 (d, J=4.3 Hz, 1H), 3.23 (d, J=6.3 Hz, 3H), 2.69-2.61 (m, 1H), 2.53 (hr s, 1H), 1.44 (d, J=5.5 Hz, 1H), 1.36 (t, J=6.5 Hz, 1H), 1.26-1.21 (m, 1H), 1.16 (d, J=5.9 Hz, 1H); [M+H]=432.3.

Example 162

5-{5-Methanesulfonyl-2-[(1 1 1-trifluoropropan-2-yl)oxy]benzoyl}-1-[3-(trifluoromethyl)phenyl]-1H 4H 5H 6H 7H-pyrazolo[4,3-c]pyridine

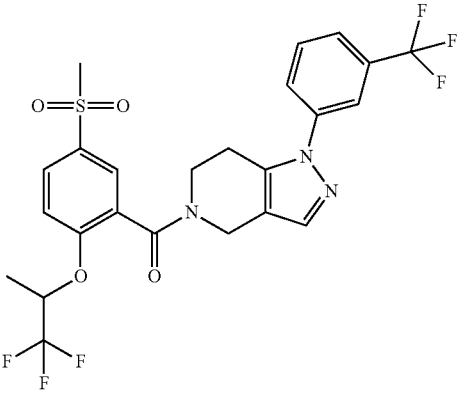

[M+H] = 562.2

Example 163

5-{5-Methanesulfonyl-2-[(1 1 1-trifluoropropan-2-yl)oxy]benzoyl}-2-phenyl-2H 4H 5H 6H 7H-pyrazolo[4,3-c]pyridine

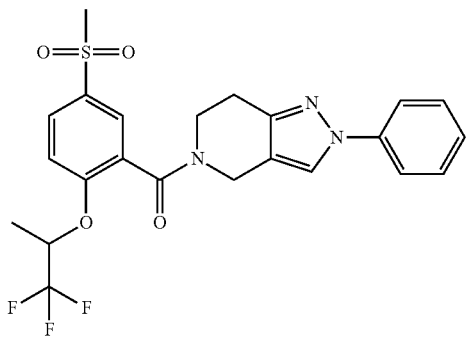 [SMILES: CC(Oc1ccc(S(C)(=O)=O)cc1C(=O)N1CCc2nn(-c3ccccc3)cc2C1)C(F)(F)F]

$^1$H NMR (400 MHz, CDCl$_3$) δ=8.05-7.84 (m, 2H), 7.78 (s, 1H), 7.70-7.52 (m, 2H), 7.50-7.37 (m, 2H), 7.31-7.21 (m, 1H), 7.20-7.03 (m, 1H), 5.17-4.91 (m, 1H), 4.87-4.66 (m, 1H), 4.49-4.19 (m, 1H), 3.98 (td, J=6.3, 12.8 Hz, 1H), 3.61-3.49 (m, 1H), 3.06 (s, 3H), 3.00 (t, J=5.9 Hz, 1H), 2.96-2.72 (m, 1H), 1.57 (d, J=6.7 Hz, 0.5H), 1.48 (dd, J=6.7, 12.1 Hz, 2H), 1.31 (d, J=6.7 Hz, 0.5H); [M+H]=494.3.

Example 164

5-{5-Methanesulfonyl-2-[(1 1 1-trifluoropropan-2-yl)oxy]benzoyl}-1-phenyl-1H 4H 5H 6H 7H-pyrazolo[4,3-c]pyridine

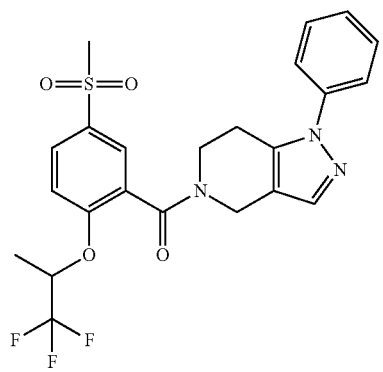 [SMILES: CC(Oc1ccc(S(C)(=O)=O)cc1C(=O)N1CCc2c(cnn2-c2ccccc2)C1)C(F)(F)F]

$^1$H NMR (400 MHz, CDCl$_3$) δ=8.10-7.83 (m, 2H), 7.62-7.43 (m, 4H), 7.41-7.29 (m, 2H), 7.21-6.99 (m, 1H), 5.15-4.68 (m, 2H), 4.48-4.29 (m, 1H), 3.94-3.65 (m, 1H), 3.55-3.39 (m, 1H), 3.15-3.04 (m, 3H), 2.98-2.81 (m, 2H), 1.55 (d, J=6.7 Hz, 1H), 1.52-1.45 (m, 0.4H), 1.31 (d, J=6.7 Hz, 0.6H); [M+H]=494.3.

Example 165

1-{4-Methanesulfonyl-2-[1-phenyl-3-(trifluoromethyl)-1H 4H 5H 6H 7H-pyrazolo[4,3-c]pyridine-5-carbonyl]phenyl}piperidine

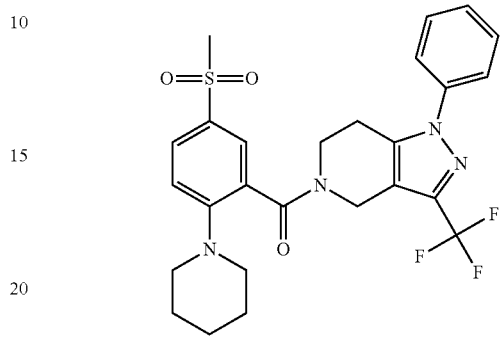

$^1$H NMR (400 MHz, DMSO-d$_6$) δ=7.85 (ddd, J=2.3, 8.7, 17.5 Hz, 1H), 7.67 (dd, J=2.3, 6.3 Hz, 1H), 7.60-7.45 (m, 5H), 7.21 (dd, J=8.6, 14.9 Hz, 1H), 5.07 (d, J=16.0 Hz, 1H), 4.55 (d, J=16.0 Hz, 1H), 4.39-4.30 (m, 2H), 4.23 (d, J=15.6 Hz, 1H), 3.67-3.58 (m, 1H), 3.48-3.42 (m, 1H), 3.18 (d, J=5.5 Hz, 3H), 3.11 (dd, J=5.9, 17.2 Hz, 2H), 3.00-2.91 (m, 2H), 2.85-2.76 (m, 2H), 2.68-2.66 (m, 1H), 1.35 (br s, 2H).

Example 166

1-(4-Methanesulfonyl-2-{3-methyl-1-phenyl-1H 4H 5H 6H 7H-pyrazolo[4,3-c]pyridine-5-carbonyl}phenyl)piperidine

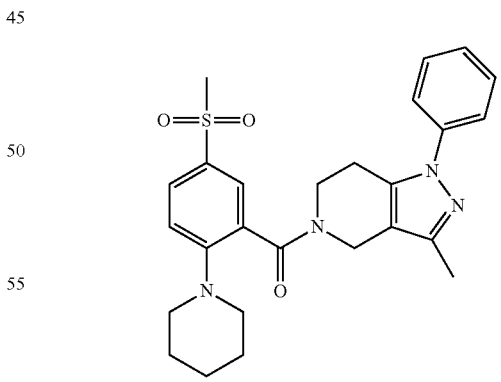

$^1$H NMR (400 MHz, DMSO-d$_6$) δ=7.90-7.78 (m, 1H), 7.70-7.59 (m, 1H), 7.59-7.39 (m, 4H), 7.37-7.27 (m, 1H), 7.19 (dd, J=4.7, 8.6 Hz, 1H), 4.84 (d, J=15.6 Hz, 1H), 4.42 (d, J=16.0 Hz, 1H), 4.32-4.16 (m, 1H), 4.11-3.97 (m, 1H), 3.62 (ddd, J=4.9, 7.6, 12.9 Hz, 1H), 3.24-3.05 (m, 5H), 3.03-2.78 (m, 5H), 2.74-2.68 (m, 1H), 2.22 (s, 1H), 2.00 (s, 1H), 1.64 (br s, 1H), 1.33 (br s, 3H).

Example 167

1-(4-Methanesulfonyl-2-{3-methyl-2-phenyl-2H 4H 5H 6H 7H-pyrazolo[4,3-c]pyridine-5-carbonyl}phenyl)piperidine

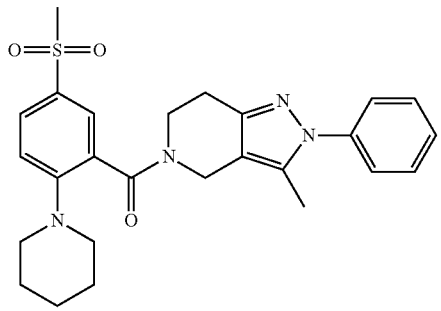 [SMILES: Cc1c2c(nn1-c1ccccc1)CCN(C(=O)c1cc(S(C)(=O)=O)ccc1N1CCCCC1)C2]

$^1$H NMR (400 MHz, CD$_3$OD) δ=7.95-7.89 (m, 1H), 7.77 (dd, J=2.3, 3.1 Hz, 1H), 7.57-7.37 (m, 6H), 7.25 (dd, J=4.9, 8.8 Hz, 1H), 4.71 (d, J=15.7 Hz, 1H), 4.54 (td, J=4.8, 13.1 Hz, 1H), 4.38 (d, J=15.3 Hz, 1H), 4.21 (d, J=15.3 Hz, 1H), 3.78-3.65 (m, 1H), 3.63-3.54 (m, 1H), 3.21-3.15 (m, 1H), 3.14-3.08 (m, 3H), 2.94-2.91 (m, 2H), 2.73-2.62 (m, 1H), 1.70-1.44 (m, 6H), 1.41-1.33 (m, 1H).

Example 168

5-{5-Methanesulfonyl-2-[(1 1 1-trifluoropropan-2-yl)oxy]benzoyl}-1-phenyl-3-(trifluoromethyl)-1H 4H 5H 6H 7H-pyrazolo[4,3-c]pyridine

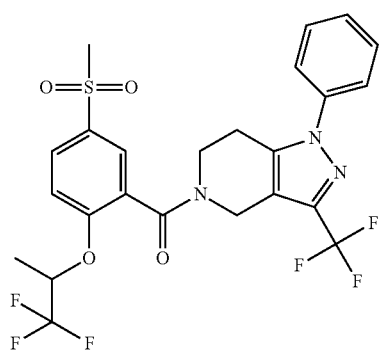 [SMILES: CC(Oc1ccc(S(C)(=O)=O)cc1C(=O)N1CCc2c(c(C(F)(F)F)nn2-c2ccccc2)C1)C(F)(F)F]

Example 169

4-Cyclopentyl-3-{2-phenyl-2H 4H 5H 6H 7H-pyrazolo[4,3-c]pyridine-5-carbonyl}benzonitrile

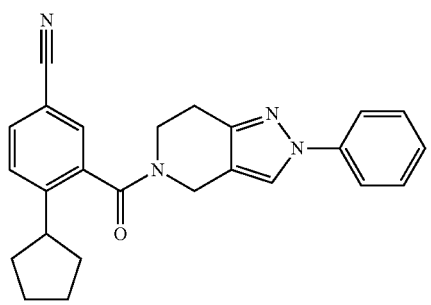 [SMILES: N#Cc1ccc(C2CCCC2)c(C(=O)N2CCc3nn(-c4ccccc4)cc3C2)c1]

$^1$H NMR (400 MHz, CDCl$_3$) δ=7.73 (s, 1H), 7.62-7.55 (m, 2H), 7.55-7.50 (m, 1H), 7.47-7.39 (m, 2H), 7.39-7.32 (m, 2H), 7.23 (t, J=8 Hz, 1H), 4.99 (d, J=12 Hz, 0.5H), 4.73 (t, J=12 Hz, 0.5H), 4.43-4.16 (m, 2H), 3.63-3.31 (m, 2H), 3.09-2.64 (m, 4H), 2.16-2.01 (m, 1H), 1.97-1.87 (m, 1H), 1.70-1.31 (m, 4H); [M+H]=397.33.

Example 170

5-(2-Cyclopentyl-5-methanesulfonylbenzoyl)-2-phenyl-2H 4H 5H 6H 7H-pyrazolo[4,3-c]pyridine

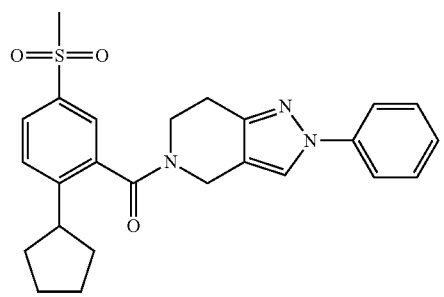 [SMILES: CS(=O)(=O)c1ccc(C2CCCC2)c(C(=O)N2CCc3nn(-c4ccccc4)cc3C2)c1]

$^1$H NMR (400 MHz, CDCl$_3$) δ=7.91 (dt, J=4, 10 Hz, 1H), 7.79 (s, 0.5H), 7.75 (dd, J=4, 8 Hz, 1H), 7.65-7.62 (m, 1H), 7.61-7.54 (m, 2.5H), 7.49-7.38 (m, 2H), 7.32-7.26 (m, 1H), 5.06-4.81 (m, 1H), 4.42-4.21 (m, 1H), 3.89-3.72 (m, 1H), 3.61-3.51 (m, 1H), 3.20-3.06 (m, 1H), 3.04 (s, 4H), 2.26-2.08 (m, 1H), 1.91-1.40 (m, 8H); [M+H]=450.31.

Example 171

3-(4-Cyclopentyl-3-{2-phenyl-2H 4H 5H 6H 7H-pyrazolo[4,3-c]pyridine-5-carbonyl}phenyl)-1 3-oxazolidin-2-one

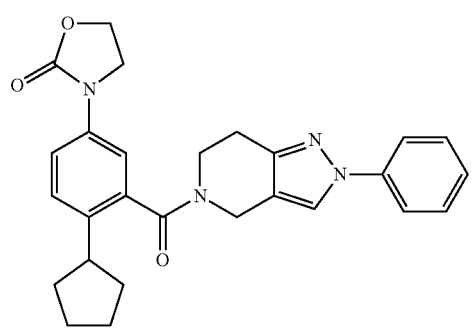 [SMILES: O=C(c1cc(N2CCOC2=O)ccc1C1CCCC1)N1CCc2nn(-c3ccccc3)cc2C1]

$^1$H NMR (400 MHz, CDCl$_3$) δ=7.78 (s, 0.6H), 7.69-7.53 (m, 3.4H), 7.48-7.33 (m, 3H), 7.31-7.14 (m, 2H), 5.18-4.64 (m, 1H), 4.54-4.42 (m, 2H), 4.01 (t, J=8.2 Hz, 2H), 3.91-3.44 (m, 2H), 3.01 (t, J=5.9 Hz, 1H), 2.86-2.71 (m, 1H), 2.17-1.90 (m, 2H), 1.88-1.34 (m, 8H); [M+H]=457.38.

Example 172

3-(3-{2-Phenyl-2H 4H 5H 6H 7H-pyrazolo[4,3-c]pyridine-5-carbonyl}-4-[(1 1 1-trifluoropropan-2-yl)oxy]phenyl)-1 3-oxazolidin-2-one

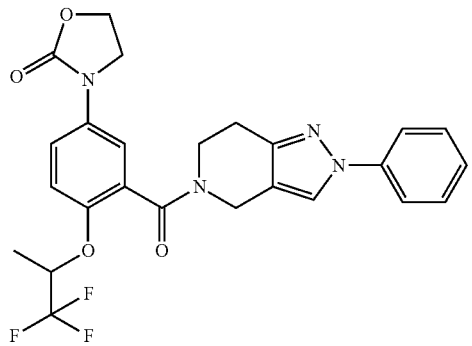 [SMILES: CC(Oc1ccc(N2CCOC2=O)cc1C(=O)N1CCc2nn(-c3ccccc3)cc2C1)C(F)(F)F]

$^1$H NMR (400 MHz, CDCl$_3$) δ=7.88-7.69 (m, 1H), 7.77 (s, 0.4H), 7.67-7.61 (m, 1H), 7.61-7.50 (m, 1.4H), 7.48-7.37 (m, 2H), 7.36-7.20 (m, 2H), 7.11-6.95 (m, 1H), 5.13-4.65 (m, 2H), 4.64-4.52 (m, 1H), 4.47 (q, J=8 Hz, 2H), 4.40-4.29 (m, 1H), 4.02 (q, J=8 Hz, 2H), 3.64-3.52 (m, 1H), 3.05-2.96 (m, 1H), 2.84-2.67 (m, 1H), 1.51-1.30 (m, 3H); [M+H]=501.36.

Example 173

4-[(1-$^2$H)Cyclopentyl]-3-{2-phenyl-2H 4H 5H 6H 7H-pyrazolo[4,3-c]pyridine-5-carbonyl}benzonitrile

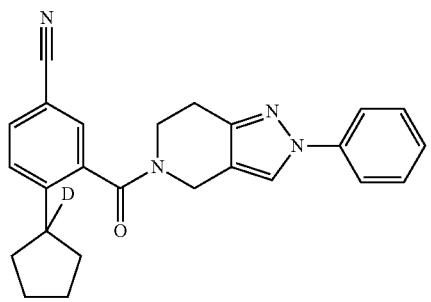 [SMILES: [2H]C1(c2ccc(C#N)cc2C(=O)N2CCc3nn(-c4ccccc4)cc3C2)CCCC1]

$^1$H NMR (400 MHz, CDCl$_3$) δ=7.80 (s, 1H), 7.70-7.60 (m, 2H), 7.59 (d, J=3.5 Hz, 1H), 7.54-7.38 (m, 4H), 7.33-7.27 (m, 1H), 5.06 (d, J=16.0 Hz, 1H), 4.80 (d, J=16.0 Hz, 1H), 4.52-4.19 (m, 1H), 3.88 (td, J=6.5, 13.2 Hz, 1H), 3.67-3.41 (m, 1H), 3.04 (t, J=5.9 Hz, 1H), 2.91-2.72 (m, 1H), 2.25-1.93 (m, 1H), 1.91-1.37 (m, 6 H), M+H=398.4.

Example 174

4-Cyclobutyl-3-{2-phenyl-2H 4H 5H 6H 7H-pyrazolo[4,3-c]pyridine-5-carbonyl}benzonitrile

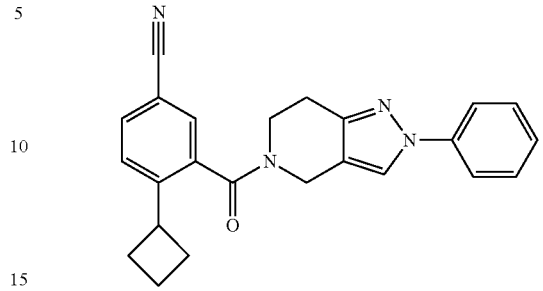

$^1$H NMR (400 MHz, CDCl$_3$) δ=7.80 (s, 1H), 7.72-7.51 (m, 4H), 7.51-7.37 (m, 3H), 7.33-7.27 (m, 1H), 5.17-4.61 (m, 1H), 4.48-3.78 (m, 2H), 3.76-3.35 (m, 2H), 3.04 (t, J=5.9 Hz, 1H), 2.83 (d, J=5.5 Hz, 1H), 2.45-1.55 (m, 6 H); M+H=383.3.

Example 175

4-Cyclopentyl-2-fluoro-3-{2-phenyl-2H 4H 5H 6H 7H-pyrazolo[4,3-c]pyridine-5-carbonyl}benzonitrile

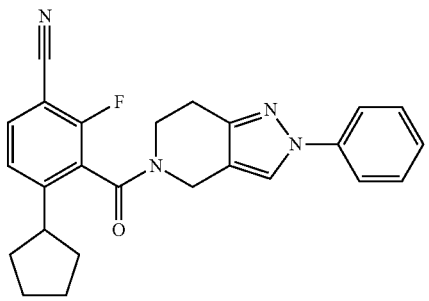 [SMILES: N#Cc1ccc(C2CCCC2)c(C(=O)N2CCc3nn(-c4ccccc4)cc3C2)c1F]

$^1$H NMR (400 MHz, CDCl$_3$) δ=7.69 (d, J=8.6 Hz, 1H), 7.30 (s, 1H), 7.07 (d, J=8.6 Hz, 1H), 5.38-4.72 (m, 1H), 4.51-4.31 (m, 3H), 4.27-3.93 (m, 2H), 3.68-3.29 (m, 2H), 3.15-2.84 (m, 2H), 2.10-1.61 (m, 4 H); [M+H]=415.28.

Example 176

2-Methoxy-3-{2-phenyl-2H 4H 5H 6H 7H-pyrazolo[4,3-c]pyridine-5-carbonyl}-4-[(1 1 1-trifluoropropan-2-yl)oxy]benzonitrile

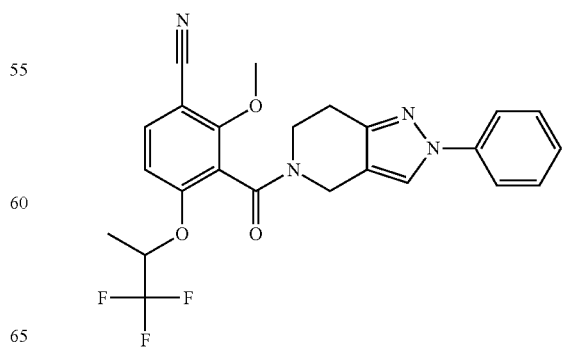

¹H NMR (400 MHz, CDCl₃) δ=7.78 (s, 1H), 7.68-7.53 (m, 3H), 7.50-7.37 (m, 2H), 7.33-7.26 (m, 1H), 6.83-6.64 (m, 1H), 5.19-4.95 (m, 1H), 4.95-4.59 (m, 2H), 4.44-4.27 (m, 1H), 4.13-3.97 (m, 3H), 3.64-3.43 (m, 1H), 3.10-2.96 (m, 1H), 2.86-2.75 (m, 1H), 1.54-1.13 (m, 3H); [M+H]=471.28.

Example 177

2-Chloro-3-[2-(4-fluorophenyl)-2H 4H 5H 6H 7H-pyrazolo[4,3-c]pyridine-5-carbonyl]-4-[(1 1 1-trifluoropropan-2-yl)oxy]benzonitrile

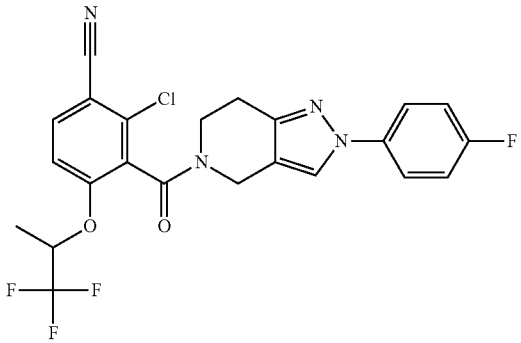

¹H NMR (400 MHz, CDCl₃) δ=7.75-7.64 (m, 2H), 7.64-7.47 (m, 2H), 7.13 (q, J=7.7 Hz, 2H), 7.05-6.90 (m, 1H), 5.15-4.63 (m, 2H), 4.47-3.80 (m, 2H), 3.69-3.36 (m, 1H), 3.00 (br s, 1H), 2.92-2.71 (m, 1H), 1.54-1.45 (m, 3H); [M+H]=493.24.

Example 178

2-Fluoro-4-(3-fluorooxetan-3-yl)-3-{2-phenyl-2H 4H 5H 6H 7H-pyrazolo[4,3-c]pyridine-5-carbonyl}benzonitrile

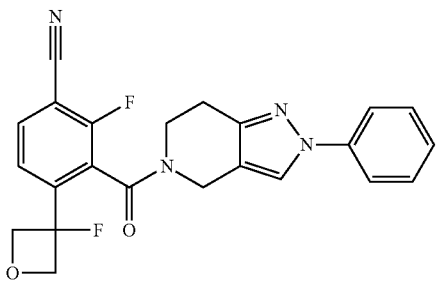 [SMILES: N#Cc1ccc(C2(F)COC2)c(C(=O)N2CCc3nn(-c4ccccc4)cc3C2)c1F]

¹H NMR (400 MHz, DMSO-d₆) δ=8.46-7.97 (m, 2H), 7.88-7.58 (m, 3H), 7.45 (q, J=8.5 Hz, 2H), 7.25 (q, J=7.6 Hz, 1H), 5.48-5.20 (m, 1H), 4.98-4.62 (m, 4H), 4.52-4.19 (m, 1H), 3.73-3.45 (m, 2H), 2.91-2.61 (m, 2H); [M+H]=421.3.

Example 179

2-Chloro-3-[1-(2 4-difluorophenyl)-1H 4H 5H 6H 7H-pyrazolo[4,3-c]pyridine-5-carbonyl]-4-[(1 1 1-trifluoropropan-2-yl)oxy]benzonitrile

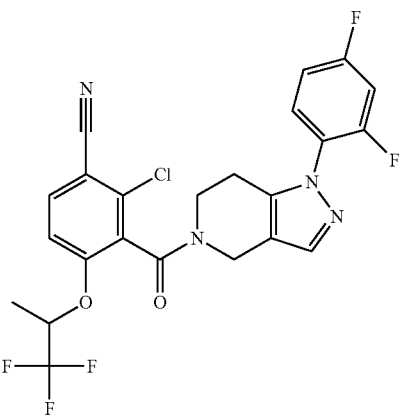 [SMILES: CC(Oc1ccc(C#N)c(Cl)c1C(=O)N1CCc2c(cnn2-c2ccc(F)cc2F)C1)C(F)(F)F]

¹H NMR (400 MHz, CDCl₃) δ=7.71 (dd, J=3.5, 9.0 Hz, 1H), 7.65-7.37 (m, 2H), 7.11-6.82 (m, 3H), 5.02-4.60 (m, 2H), 4.41-4.18 (m, 2H), 3.97-3.78 (m, 1H), 3.60-3.28 (m, 1H), 2.94-2.46 (m, 2H), 1.56-1.45 (m, 3 H); [M+H]=511.19.

Example 180

4-Cyclobutyl-2-fluoro-3-{2-phenyl-2H 4H 5H 6H 7H-pyrazolo[4,3-c]pyridine-5-carbonyl}benzonitrile

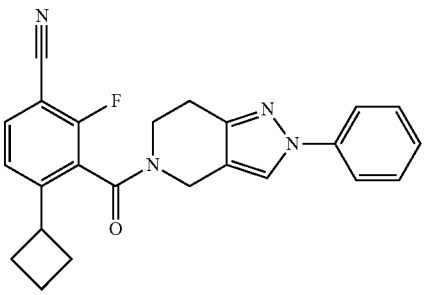 [SMILES: N#Cc1ccc(C2CCC2)c(C(=O)N2CCc3nn(-c4ccccc4)cc3C2)c1F]

¹H NMR (400 MHz, CDCl₃) δ=7.80 (s, 1H), 7.71-7.56 (m, 3H), 7.45 (q, J=8.5 Hz, 2H), 7.30 (dd, J=7.8, 12.9 Hz, 1H), 5.13-4.24 (m, 3H), 3.87-3.45 (m, 3H), 3.12-2.75 (m, 2H), 2.51-2.19 (m, 2H), 2.15-1.71 (m, 4 H), [M+H]=401.3.

Example 181

3-[2-(4-Fluorophenyl)-2H 4H 5H 6H 7H-pyrazolo[4,3-c]pyridine-5-carbonyl]-4-[(1 1 1-trifluoropropan-2-yl)oxy]benzonitrile

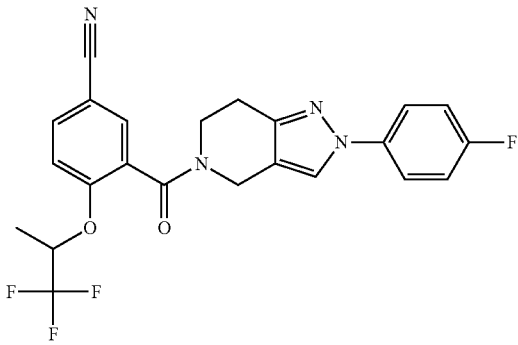 [SMILES: CC(Oc1ccc(C#N)cc1C(=O)N1CCc2nn(-c3ccc(F)cc3)cc2C1)C(F)(F)F]

$^1$H NMR (400 MHz, CDCl$_3$) δ=7.76-7.46 (m, 5H), 7.19-6.94 (m, 3H), 5.18-4.61 (m, 2H), 4.28-3.87 (m, 1H), 3.68-3.39 (m, 1H), 3.09-2.95 (m, 1H), 2.94-2.68 (m, 2H), 1.48 (dd, J=6.5, 14.3 Hz, 3 H); [M+H]=459.24.

Example 182

2-Chloro-3-[1-methyl-3-(trifluoromethyl)-1H 4H 5H 6H 7H-pyrazolo[4,3-c]pyridine-5-carbonyl]-4-[(1 1 1-trifluoropropan-2-yl)oxy]benzonitrile

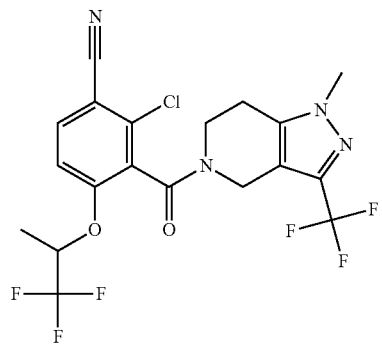 [SMILES: CC(Oc1ccc(C#N)c(Cl)c1C(=O)N1CCc2c(c(C(F)(F)F)nn2C)C1)C(F)(F)F]

$^1$H NMR (400 MHz, CDCl$_3$) δ=7.77-7.67 (m, 1H), 7.08-6.78 (m, 1H), 5.09-4.52 (m, 2H), 4.47-4.04 (m, 1H), 3.99-3.73 (m, 5H), 3.72-3.33 (m, 1H), 2.98-2.58 (m, 1H), 1.48 (dd, J=16.43, 6.26 Hz, 3 H); [M+H]=481.20.

Example 183

2-Chloro-3-{1H 4H 5H 6H 7H-pyrazolo[4,3-c]pyridine-5-carbonyl}-4-[(1 1 1-trifluoropropan-2-yl)oxy]benzonitrile

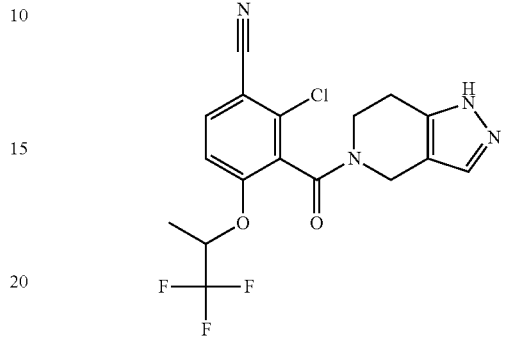

$^1$H NMR (400 MHz, CDCl$_3$) δ=7.70 (t, J=8.41 Hz, 1H), 7.09-6.92 (m, 1H), 5.48-5.27 (m, 1H), 5.11-4.90 (m, 1H), 4.74 (d, J=17.22 Hz, 1H), 4.37-4.19 (m, 1H), 3.58-3.36 (m, 1H), 2.92 (br s, 1H), 2.80 (br s, 1H), 1.53-1.46 (m, 1 H); [M+H]=399.15.

Example 184

2-Chloro-3-[3-ethoxy-2-(4-fluorophenyl)-2H 4H 5H 6H 7H-pyrazolo[4,3-c]pyridine-5-carbonyl]-4-[(1 1 1-trifluoropropan-2-yl)oxy]benzonitrile

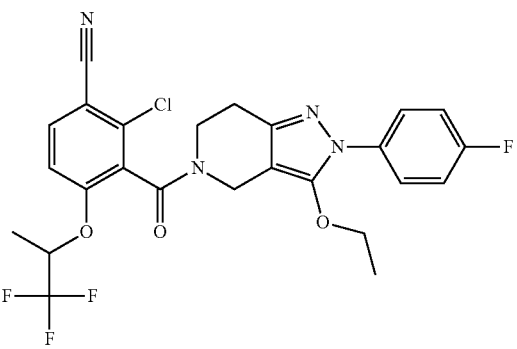 [SMILES: CCOc1c2c(nn1-c1ccc(F)cc1)CCN(C(=O)c1c(OC(C)C(F)(F)F)ccc(C#N)c1Cl)C2]

$^1$H NMR (400 MHz, CDCl$_3$) δ=7.77-7.67 (m, 1H), 7.66-7.51 (m, 2H), 7.16-7.06 (m, 2H), 7.05-6.91 (m, 1H), 5.23-4.98 (m, 1H), 4.90-4.68 (m, 2H), 4.34-4.23 (m, 2H), 3.64-3.35 (m, 2H), 2.92-2.70 (m, 2H), 1.55-1.49 (m, 2H), 1.38 (t, J=7.0 Hz, 2H), 1.30-1.21 (m, 1H), 1.21-1.14 (m, 1H); [M+H]=537.26.

Example 185

2-Chloro-3-[1-(4-fluorophenyl)-7 7-dimethyl-1H 4H 5H 6H 7H-pyrazolo[4,3-c]pyridine-5-carbonyl]-4-[(1 1 1-trifluoropropan-2-yl)oxy]benzonitrile

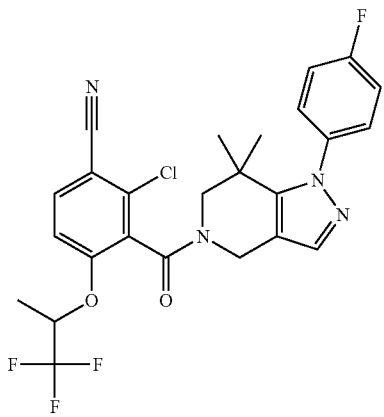 [SMILES: CC(Oc1ccc(C#N)c(Cl)c1C(=O)N1Cc2cnn(-c3ccc(F)cc3)c2C(C)(C)C1)C(F)(F)F]

¹H NMR (400 MHz, CDCl₃) δ=7.77-7.67 (m, 1H), 7.51 (s, 0.4H), 7.40-7.32 (m, 2H), 7.30 (s, 0.6H), 7.21-7.10 (m, 2H), 7.01 (d, J=9.0 Hz, 1H), 4.84-4.73 (m, 1H), 4.36-4.18 (m, 1H), 3.89-3.59 (m, 1H), 1.58 (s, 3H), 1.52 (d, J=6.3 Hz, 3H), 1.29-1.21 (m, 1H), 1.17 (d, J=4.7 Hz, 4H); [M+H]=521.24.

Example 186

2-Chloro-3-[2-methyl-3-(trifluoromethyl)-2H 4H 5H 6H 7H-pyrazolo[4,3-c]pyridine-5-carbonyl]-4-[(1 1 1-trifluoropropan-2-yl)oxy]benzonitrile

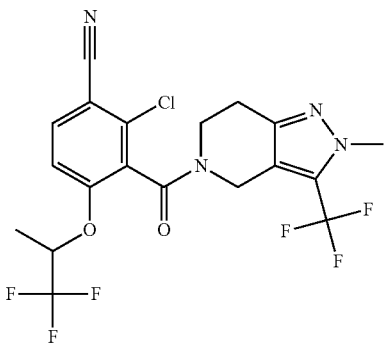 [SMILES: CC(Oc1ccc(C#N)c(Cl)c1C(=O)N1CCc2nn(C)c(C(F)(F)F)c2C1)C(F)(F)F]

¹H NMR (400 MHz, CDCl₃) δ=7.71 (dd, J=3.3, 8.8 Hz, 1H), 7.06-6.81 (m, 1H), 5.18-4.61 (m, 2H), 4.50-4.17 (m, 1H), 4.00-3.87 (m, 3H), 3.87-3.33 (m, 2H), 2.89 (t, J=5.7 Hz, 1H), 2.82-2.56 (m, 1H), 1.54-1.42 (m, 3 H); [M+H]=481.20.

Example 187

2-Fluoro-4-(1-fluorocyclopentyl)-3-{2-phenyl-2H 4H 5H 6H 7H-pyrazolo[4,3-c]pyridine-5-carbonyl}benzonitrile

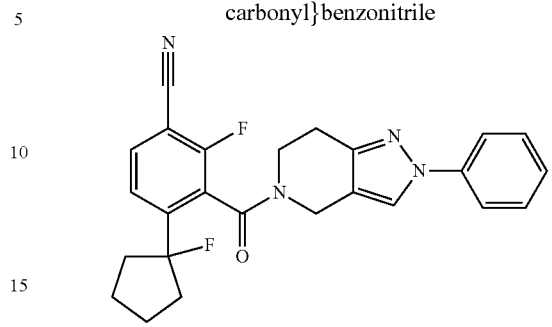

¹H NMR (400 MHz, CDCl₃) δ=7.82-7.54 (m, 4H), 7.52-7.38 (m, 3H), 7.36-7.29 (m, 1H), 5.09-4.67 (m, 1H), 4.55-4.20 (m, 1H), 3.95-3.42 (m, 2H), 3.10-2.76 (m, 2H), 2.71-2.38 (m, 2H), 2.34-2.02 (m, 3H), 2.02-1.69 (m, 3H); [M+H]=433.3.

Example 188

2-Fluoro-4-(1-fluorocyclopentyl)-3-[2-(4-fluorophenyl)-2H 4H 5H 6H 7H-pyrazolo[4,3-c]pyridine-5-carbonyl]benzonitrile

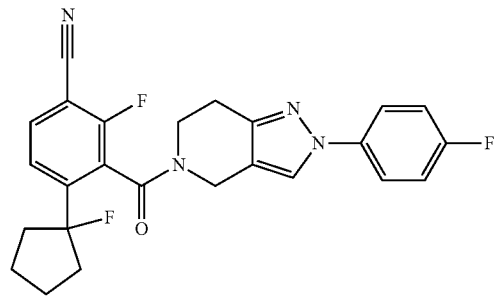 [SMILES: N#Cc1ccc(C2(F)CCCC2)c(C(=O)N2CCc3nn(-c4ccc(F)cc4)cc3C2)c1F]

¹H NMR (400 MHz, CDCl₃) δ=7.77-7.29 (m, 3H), 7.27-7.02 (m, 4H), 5.10-4.63 (m, 1H), 4.41-4.15 (m, 1H), 3.91 (td, J=6.4, 13.1Hz, 1H), 3.69-3.39 (m, 1H), 3.08-2.81 (m, 2H), 2.69-2.03 (m, 4H), 2.01-1.72 (m, 4H); [M+H]=451.3.

Example 189

2-Chloro-3-[2-(4-fluorophenyl)-3-methyl-2H 4H 5H 6H 7H-pyrazolo[4,3-c]pyridine-5-carbonyl]-4-[(1 1 1-trifluoropropan-2-yl)oxy]benzonitrile

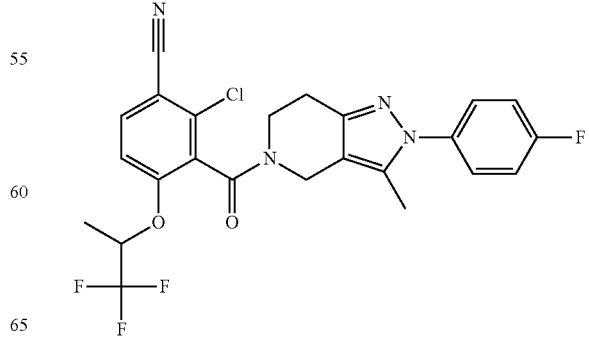

¹H NMR (400 MHz, CDCl₃) δ=8.13-7.64 (m, 1H), 7.50-7.31 (m, 1H), 7.26-7.08 (m, 2H), 7.08-6.74 (m, 2H), 5.26-4.54 (m, 3H), 4.53-4.05 (m, 2H), 3.76-3.36 (m, 1H), 3.15-2.71 (m, 2H), 2.27 (s, 1H), 2.06 (d, J=10.2 Hz, 1H), 1.60-1.19 (m, 3H); [M+H]=507.24.

Example 190

2-Chloro-3-[1-(4-fluorophenyl)-3-methyl-1H 4H 5H 6H 7H-pyrazolo[4,3-c]pyridine-5-carbonyl]-4-[(1 1 1-trifluoropropan-2-yl)oxy]benzonitrile

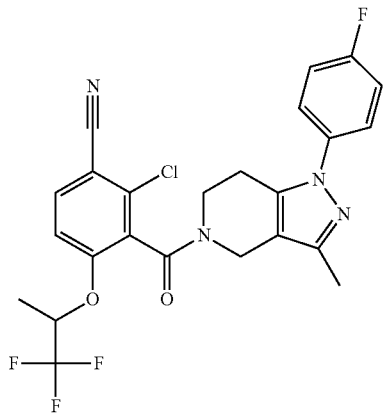 [SMILES: Cc1nn(-c2ccc(F)cc2)c2c1CN(C(=O)c1c(OC(C)C(F)(F)F)ccc(C#N)c1Cl)CC2]

¹H NMR (400 MHz, CDCl₃) δ=8.77-8.33 (m, 1H), 7.91-7.59 (m, 1H), 7.45-7.27 (m, 2H), 7.16-6.88 (m, 2H), 5.00-4.45 (m, 2H), 4.25-3.96 (m, 1H), 3.53-3.25 (m, 1H), 2.88-2.59 (m, 1H), 2.25 (s, 1H), 1.98 (s, 1H), 1.73-1.38 (m, 3H), 1.26-1.11 (m, 3H); [M+H]=507.24.

Example 191

2-Chloro-3-[2-(4-fluorophenyl)-7 7-dimethyl-2H 4H 5H 6H 7H-pyrazolo[4,3-c]pyridine-5-carbonyl]-4-[(1 1 1-trifluoropropan-2-yl)oxy]benzonitrile

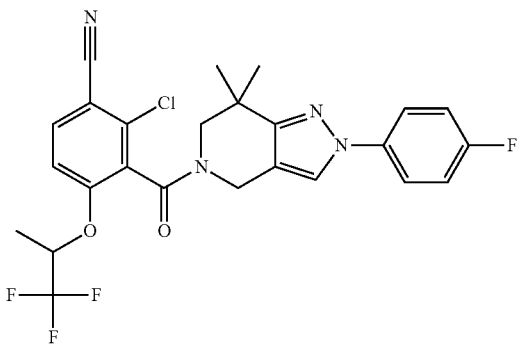 [SMILES: CC(Oc1ccc(C#N)c(Cl)c1C(=O)N1Cc2cn(-c3ccc(F)cc3)nc2C(C)(C)C1)C(F)(F)F]

¹H NMR (400 MHz, CDCl₃) δ=7.76-7.68 (m, 1H), 7.66 (s, 0.4H), 7.64-7.58 (m, 1H), 7.58-7.52 (m, 1H), 7.45 (s, 0.6H), 7.18-7.06 (m, 2H), 7.05-6.94 (m, 1H), 5.03-4.84 (m, 1H), 4.83-4.70 (m, 1H), 4.40-4.23 (m, 1H), 3.90-3.74 (m, 1H), 3.24-3.16 (m, 1H), 1.53-1.41 (m, 6H), 1.31-1.24 (m, 3H); [M+H]=521.24.

Example 192

3-[2-(4-Fluorophenyl)-7 7-dimethyl-2H 4H 5H 6H 7H-pyrazolo[4,3-c]pyridine-5-carbonyl]-2-methoxy-4-[(1 1 1-trifluoropropan-2-yl)oxy]benzonitrile

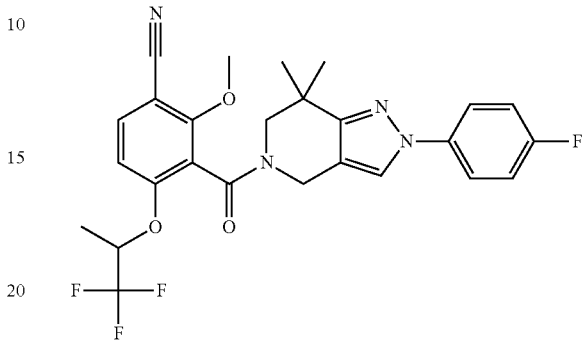

¹H NMR (400 MHz, CDCl₃) δ=7.70-7.39 (m, 4H), 7.11 (q, J=8 Hz, 2H), 6.82-6.68 (m, 1H), 5.14-4.59 (m, 3H), 4.35-4.27 (m, 1H), 4.13-4.05 (m, 3H), 3.95-3.70 (m, 1H), 1.55-1.47 (m, 2H), 1.44 (s, 3H), 1.37 (d, J=6.3 Hz, 1H), 1.27-1.21 (m, 3H); [M+H]=517.33.

Example 193

2-Chloro-3-{2-phenyl-2H 4H 5H 6H 7H-pyrazolo[4,3-c]pyridine-5-carbonyl}-4-[(1 1 1-trifluoropropan-2-yl)oxy]benzonitrile

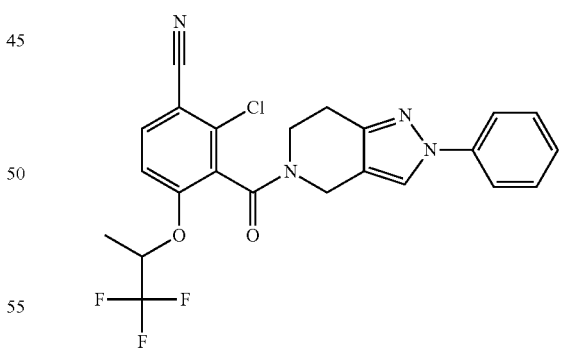

¹H NMR (400 MHz, CDCl₃) δ=7.80 (s, 1H), 7.76-7.54 (m, 3H), 7.45 (q, J=7.8 Hz, 2H), 7.34-7.22 (m, 1H), 7.10-6.87 (m, 1H), 5.16-4.64 (m, 2H), 4.53-4.23 (m, 1H), 4.21-4.03 (m, 1H), 3.71-3.45 (m, 1H), 3.03 (d, J=2.3 Hz, 1H), 2.94-2.82 (m, 1H), 1.56-1.46 (m, 3H); [M+H]=475.23.

Example 194

3-[2-(2 4-Difluorophenyl)-2H 4H 5H 6H 7H-pyrazolo[4,3-c]pyridine-5-carbonyl]-2-methoxy-4-[(1 1 1-trifluoropropan-2-yl)oxy]benzonitrile

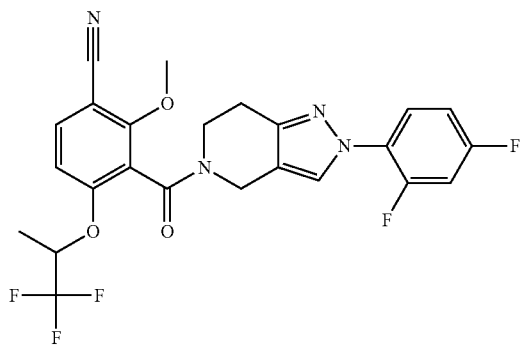 [SMILES: COc1c(C#N)ccc(OC(C)C(F)(F)F)c1C(=O)N1CCc2nn(-c3ccc(F)cc3F)cc2C1]

$^1$H NMR (400 MHz, CDCl$_3$) δ=7.81-7.64 (m, 2H), 7.60-7.45 (m, 1H), 7.02-6.85 (m, 2H), 6.76-6.58 (m, 1H), 5.11-4.52 (m, 2H), 4.41-4.16 (m, 1H), 4.12-3.88 (m, 4H), 3.61-3.36 (m, 1H), 2.96-2.75 (m, 2H), 1.49-1.35 (m, 3H); [M+H]=507.24.

Example 195

3-{1-Benzyl-1H 4H 5H 6H 7H-pyrazolo[4,3-c]pyridine-5-carbonyl}-2-chloro-4-[(1 1 1-trifluoropropan-2-yl)oxy]benzonitrile

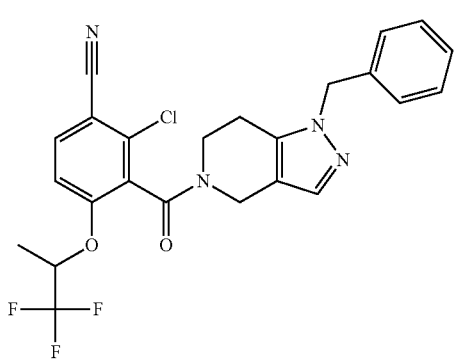 [SMILES: CC(Oc1ccc(C#N)c(Cl)c1C(=O)N1CCc2c(cnn2Cc2ccccc2)C1)C(F)(F)F]

$^1$H NMR (400 MHz, CDCl$_3$) δ=7.68 (dd, J=2.35, 8.61 Hz, 1H), 7.47-7.18 (m, 4H), 7.18-7.03 (m, 2H), 7.02-6.84 (m, 1H), 5.33-5.13 (m, 2H), 5.04-4.49 (m, 2H), 4.32-3.86 (m, 2H), 3.66-3.23 (m, 1H), 2.87-2.45 (m, 2H), 1.52-1.34 (m, 3H); [M+H]=489.23.

Example 196

2-Chloro-3-[2-(4-fluorophenyl)-2H 4H 5H 6H 7H-pyrazolo[4,3-c]pyridine-5-carbonyl]-4-[(1 1 1-trifluoropropan-2-yl)oxy]benzamide

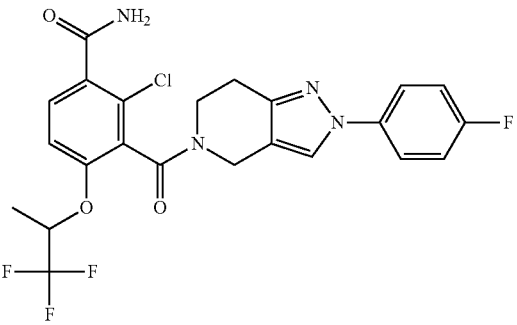 [SMILES: CC(Oc1ccc(C(N)=O)c(Cl)c1C(=O)N1CCc2nn(-c3ccc(F)cc3)cc2C1)C(F)(F)F]

$^1$H NMR (400 MHz, CDCl$_3$) δ=7.90-7.68 (m, 1H), 7.63-7.48 (m, 3H), 7.13 (q, J=7.96 Hz, 2H), 7.04-6.90 (m, 1H), 6.42-5.77 (m, 2H), 5.18-4.63 (m, 2H), 4.40-4.26 (m, 1H), 4.26-4.01 (m, 1H), 3.70-3.42 (m, 1H), 2.99 (br s, 1H), 2.90-2.82 (m, 1H), 1.53-1.41 (m, 3H); [M+H]=511.22.

Example 197

2-Chloro-3-[2-(4-fluorophenyl)-3-hydroxy-2H 4H 5H 6H 7H-pyrazolo[4,3-c]pyridine-5-carbonyl]-4-[(1 1 1-trifluoropropan-2-yl)oxy]benzonitrile

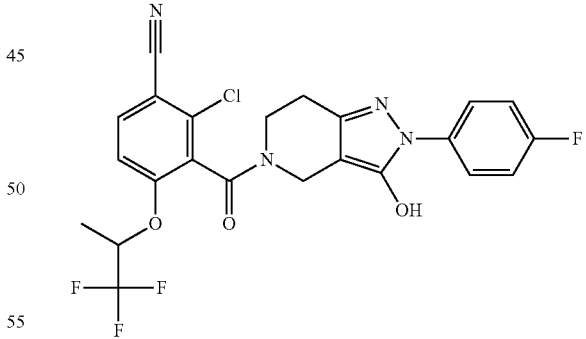

$^1$H NMR (400 MHz, CD$_3$OD) δ=8.02-7.86 (m, 2H), 7.86-7.47 (m, 2H), 7.47-7.26 (m, 1H), 7.26-7.13 (m, 1H), 5.42-5.16 (m, 1H), 4.78-3.43 (m, 6H), 2.84-2.79 (m, 3H); [M+H]=509.2.

Example 198

2-(4-Fluorophenyl)-5-{3-methanesulfonyl-2-methoxy-6-[(1 1 1-trifluoropropan-2-yl)oxy]benzoyl}-2H 4H 5H 6H 7H-pyrazolo[4,3-c]pyridine

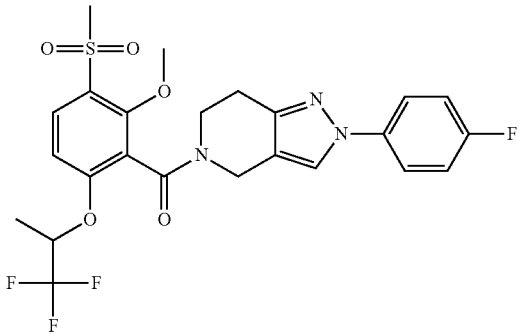 [SMILES: COc1c(S(C)(=O)=O)ccc(OC(C)C(F)(F)F)c1C(=O)N1CCc2nn(-c3ccc(F)cc3)cc2C1]

¹H NMR (400 MHz, CDCl₃) δ=8.06-7.93 (m, 1H), 7.78-7.07 (m, 6H), 6.93-6.72 (m, 1H), 5.21-4.67 (m, 2H), 4.52-4.33 (m, 1H), 4.22-3.84 (m, 3H), 3.73-3.47 (m, 1H), 3.22 (d, J=4.3 Hz, 3H), 3.07-2.84 (m, 2H), 1.62-1.28 (m, 3H); [M+H]=542.27.

Example 199

2-Fluoro-4-(4-fluorooxan-4-yl)-3-[2-(4-fluorophenyl)-2H 4H 5H 6H 7H-pyrazolo[4,3-c]pyridine-5-carbonyl]benzonitrile

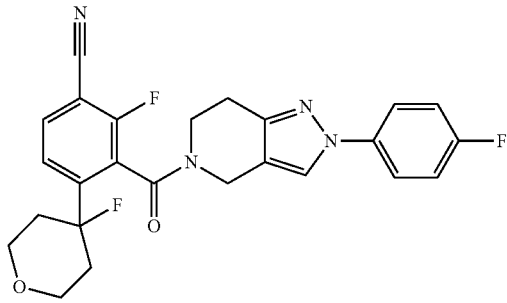 [SMILES: N#Cc1ccc(C2(F)CCOCC2)c(C(=O)N2CCc3nn(-c4ccc(F)cc4)cc3C2)c1F]

¹H NMR (400 MHz, CDCl₃) δ=7.84-7.42 (m, 3H), 7.26-7.06 (m, 4H), 5.07-4.67 (m, 1H), 4.51-4.25 (m, 1H), 4.09-3.43 (m, 6H), 3.11-2.85 (m, 2H), 2.62-2.23 (m, 2H), 2.08-1.70 (m, 2H); [M+H]=467.3.

Example 200

2-Chloro-3-[2-(4-fluorophenyl)-2H 4H 5H 6H 7H-pyrazolo[4,3-c]pyridine-5-carbonyl]-N N-dimethyl-4-[(1 1 1-trifluoropropan-2-yl)oxy]benzamide

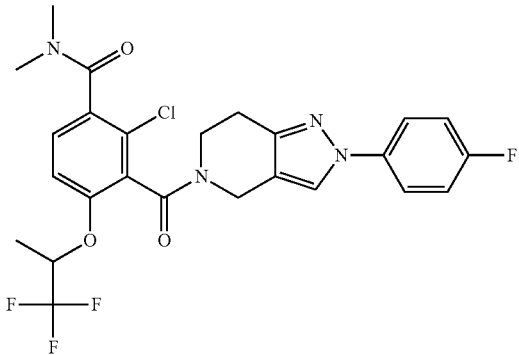 [SMILES: CC(Oc1ccc(C(=O)N(C)C)c(Cl)c1C(=O)N1CCc2nn(-c3ccc(F)cc3)cc2C1)C(F)(F)F]

¹H NMR (400 MHz, CDCl₃) δ=7.75-7.45 (m, 3H), 7.33 (t, J=8.02 Hz, 1H), 7.18-7.08 (m, 2H), 7.03-6.89 (m, 1H), 5.13-4.55 (m, 2H), 4.44-4.26 (m, 1H), 4.13 (t, J=5.87), 3.66-3.46 (m, 1H), 3.20-3.08 (m, 3H), 2.99 (br s, 1H), 2.94-2.88 (m, 3H), 2.85 (d, J=5.48 Hz, 1H), 1.48 (d, J=6.26 Hz, 3H); [M+H]=539.29.

Example 201

2-Chloro-3-[2-(5-fluoropyridin-2-yl)-2H 4H 5H 6H 7H-pyrazolo[4,3-c]pyridine-5-carbonyl]-4-[(1 1 1-trifluoropropan-2-yl)oxy]benzonitrile

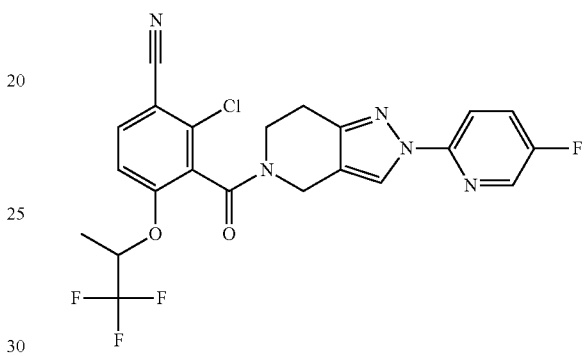

¹H NMR (400 MHz, CDCl₃) δ=8.09-8.39 (m, 1H), 7.96-7.83 (m, 1H), 7.76-7.65 (m, 1H), 7.52 (t, J=7.24 Hz, 1H), 7.12-6.83 (m, 1H), 5.15-4.62 (m, 2H), 4.52-4.23 (m, 1H), 4.21-4.02 (m, 1H), 3.92-3.43 (m, 1H), 3.09-2.71 (m, 2H), 1.58-1.16 (m, 4H); [M+H]=494.24.

Example 202

3-[2-(5-Fluoropyridin-2-yl)-2H 4H 5H 6H 7H-pyrazolo[4,3-c]pyridine-5-carbonyl]-2-methoxy-4-[(1 1 1-trifluoropropan-2-yl)oxy]benzonitrile

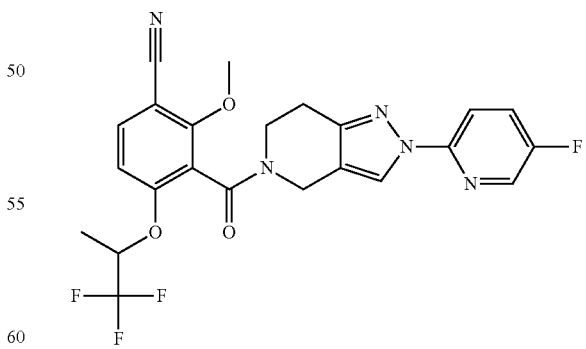

¹H NMR (400 MHz, CDCl₃) δ=8.36-8.06 (m, 2H), 7.89 (dq, J=4.27, 8.71 Hz, 1H), 7.65-7.57 (m, 1H), 7.56-7.45 (m, 1H), 6.92-6.58 (m, 1H), 5.17-4.55 (m, 2H), 4.49-4.27 (m, 1H), 4.20-3.92 (m, 4H), 3.89-3.42 (m, 1H), 3.09-2.81 (m, 2H), 1.55-1.16 (m, 3H); [M+H]=490.26.

Example 203

2-Chloro-3-{2-methyl-2H 4H 5H 6H 7H-pyrazolo[4,3-c]pyridine-5-carbonyl}-4-[(1 1 1-trifluoropropan-2-yl)oxy]benzonitrile

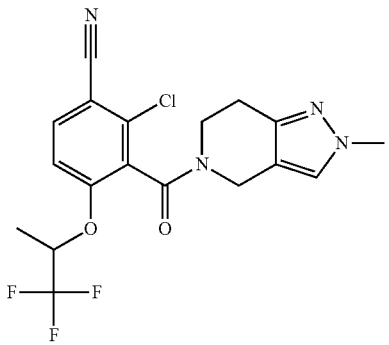 [SMILES: CC(Oc1ccc(C#N)c(Cl)c1C(=O)N1CCc2nn(C)cc2C1)C(F)(F)F]

$^1$H NMR (400 MHz, CDCl$_3$) δ=7.69 (t, J=9.00 Hz, 1H), 7.22 (s, 1H), 7.09-6.91 (m, 1H), 5.06-4.52 (m, 2H), 4.31-4.16 (m, 1H), 4.15-3.98 (m, 1H), 3.86 (d, J=16.43 Hz, 3H), 3.59-3.34 (m, 1H), 3.00-2.65 (m, 2H). 1.49 (t, J=6.06 Hz, 3H); [M+H]=413.19.

Example 204

2-Methoxy-3-{2-methyl-2H 4H 5H 6H 7H-pyrazolo[4,3-c]pyridine-5-carbonyl}-4-[(1 1 1-trifluoropropan-2-yl)oxy]benzonitrile

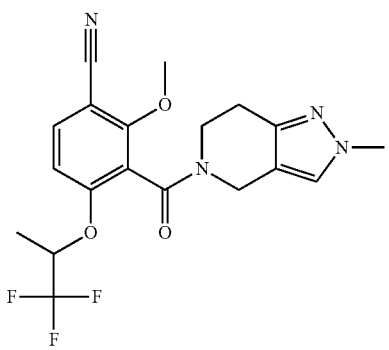 [SMILES: COc1c(C#N)ccc(OC(C)C(F)(F)F)c1C(=O)N1CCc2nn(C)cc2C1]

$^1$H NMR (400 MHz, CDCl$_3$) δ=7.67-7.45 (m, 1H), 7.33-7.18 (m, 1H), 6.84-6.63 (m, 1H), 5.10-4.50 (m, 2H), 4.36-3.71 (m, 7H), 3.62-3.29 (m, 1H), 2.96-2.63 (m, 3H), 1.60-1.05 (m, 3H); [M+H]=409.21.

Example 205

2-Chloro-3-[2-(3-methoxyphenyl)-2H 4H 5H 6H 7H-pyrazolo[4,3-c]pyridine-5-carbonyl]-4-[(1 1 1-trifluoropropan-2-yl)oxy]benzonitrile

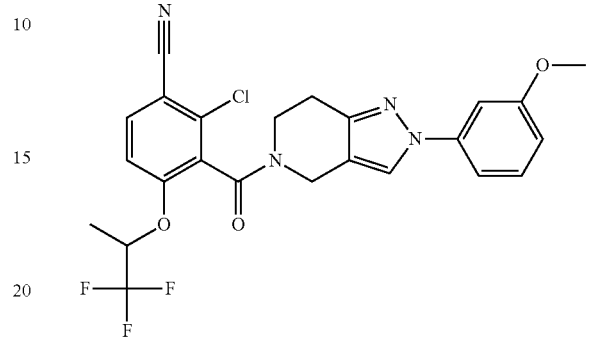

$^1$H NMR (400 MHz, CDCl$_3$) δ=7.83-7.53 (m, 2H), 7.33 (q, J=8.74 Hz, 1H), 7.24-7.08 (m, 2H), 7.05-6.89 (m, 1H), 6.82 (t, J=6.06 Hz, 1H), 5.16-4.56 (m, 2H), 4.43-4.05 (m, 1H), 3.87 (d, J=4.30 Hz, 3H), 3.81-3.43 (m, 2H), 3.08-2.84 (m, 2H), 1.55-1.19 (m, 3H); [M+H]=505.15.

Example 206

2-Chloro-3-[2-(4-methoxyphenyl)-2H 4H 5H 6H 7H-pyrazolo[4,3-c]pyridine-5-carbonyl]-4-[(1 1 1-trifluoropropan-2-yl)oxy]benzonitrile

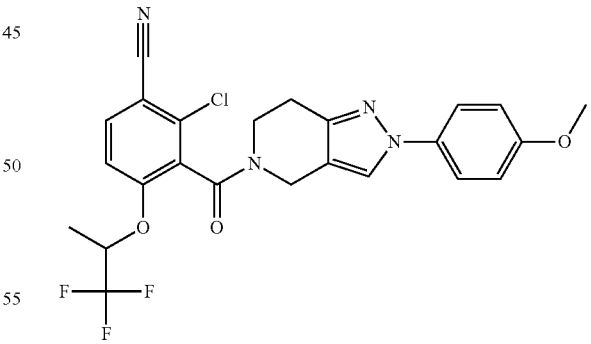

$^1$H NMR (400 MHz, CDCl$_3$) δ=7.76-7.61 (m, 2H), 7.57-7.44 (m, 2H), 7.07-6.85 (m, 3H), 4.90-4.61 (m, 2H), 4.38-4.24 (m, 1H), 4.21-4.01 (m, 1H), 3.88-3.77 (m, 3H), 3.62-3.45 (m, 1H), 3.05-2.84 (m, 2H), 1.57-1.36 (m, 3H); [M+H]=505.22.

Example 207

2-Methoxy-3-[2-(4-methoxyphenyl)-2H 4H 5H 6H 7H-pyrazolo[4,3-c]pyridine-5-carbonyl]-4-[(1 1 1-trifluoropropan-2-yl)oxy]benzonitrile

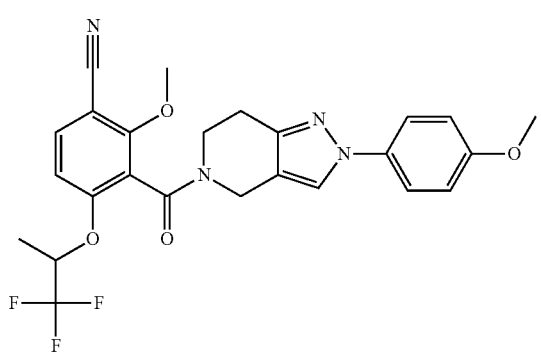 [SMILES: COc1ccc(-n2cc3c(n2)CCN(C(=O)c2c(OC(C)C(F)(F)F)ccc(C#N)c2OC)C3)cc1]

¹H NMR (400 MHz, CDCl₃) δ=7.74-7.44 (m, 4H), 7.05-6.89 (m, 2H), 6.81-6.66 (m, 1H), 5.22-4.93 (m, 1H), 4.88-4.59 (m, 2H), 4.40-4.29 (m, 1H), 4.13-3.99 (m, 3H), 3.90-3.75 (m, 3H), 3.63-3.43 (m, 1H), 2.98 (br s, 1H), 2.84 (br s, 1H), 1.53-1.44 (m, 1.5H), 1.29-1.21 (m, 1.5H); [M+H]=501.27.

Example 208

4-(3-Fluoropentan-3-yl)-3-[2-(4-fluorophenyl)-2H 4H 5H 6H 7H-pyrazolo[[4,3-c]pyridine-5-carbonyl]-2-methoxybenzonitrile

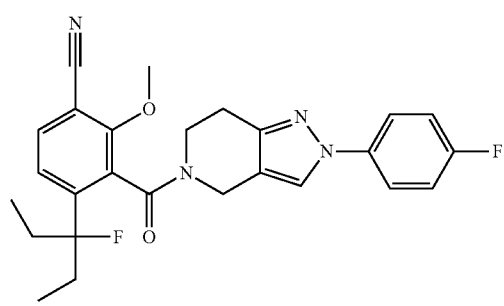 [SMILES: CCC(F)(CC)c1ccc(C#N)c(OC)c1C(=O)N1CCc2nn(-c3ccc(F)cc3)cc2C1]

¹H NMR (400 MHz, CDCl₃) δ=7.73-7.39 (m, 4H), 7.12 (q, J=8.3 Hz, 2H), 6.97 (d, J=8.2 Hz, 1H), 5.19-4.57 (m, 1H), 4.37-4.19 (m, 1H), 4.16-3.98 (m, 3H), 3.96-3.31 (m, 2H), 3.04-2.69 (m, 2H), 2.13-1.83 (m, 4H), 0.98-0.57 (m, 6H); [M+H]=465.2.

Example 209

3-[1-(5-Fluoropyridin-2-yl)-1H 4H 5H 6H 7H-pyrazolo[4,3-c]pyridine-5-carbonyl]-2-methoxy-4-[(1 1 1-trifluoropropan-2-yl)oxy]benzonitrile

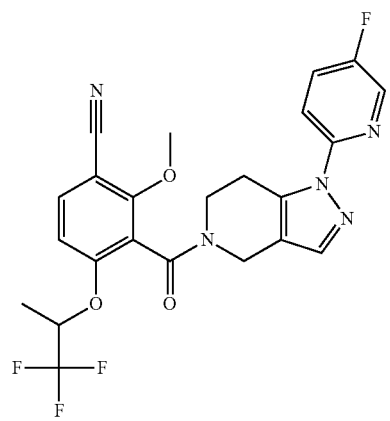 [SMILES: COc1c(C#N)ccc(OC(C)C(F)(F)F)c1C(=O)N1CCc2c(cnn2-c2ccc(F)cn2)C1]

¹H NMR (400 MHz, CDCl₃) δ=8.33-8.09 (m, 1H), 7.94 (ddt, J=4.11, 4.11, 8.80, 17.41, 1H), 7.70-7.29 (m, 3H), 6.88-6.59 (m, 1H), 5.13-4.57 (m, 2H), 4.51-4.19 (m, 2H), 4.09-3.98 (m, 3H), 3.82-3.17 (m, 3H), 1.54-1.40 (m ,2H), 1.21 (d, J=6.26 Hz, 1H); [M+H]=490.19.

Example 210

2-Chloro-3-[1-(5-fluoropyridin-2-yl)-1H 4H 5H 6H 7H-pyrazolo[4,3-c]pyridine-5-carbonyl]-4-[(1 1 1-trifluoropropan-2-yl)oxy]benzonitrile

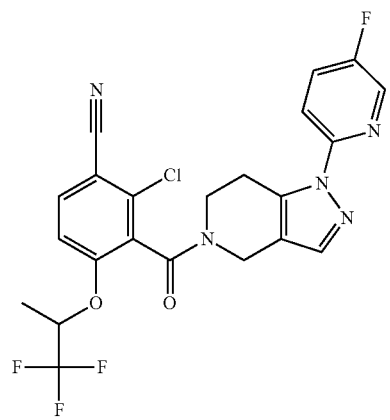

¹H NMR (400 MHz, CDCl₃) δ=8.29-8.11 (m, 1H), 8.03-7.85 (m, 1H), 7.77-7.64 (m, 1H), 7.60-7.34 (m, 2H), 7.10-6.85 (m, 1H), 5.11-4.61 (m, 2H), 4.54-4.41 (m, 1H), 4.38-4.17 (m, 1H), 3.60-3.38 (m, 2H), 3.30 (d, J=4.70 Hz, 1H), 1.54-1.45 (m, 2H), 1.21 (d, J=6.26 Hz, 1H); [M+H]=494.17.

Example 211

2-Chloro-3[2-(pyridin-3-yl)-2H 4H 5H 6H 7H-pyrazolo[4,3-c]pyridine-5-carbonyl]-4-[(1 1 1-trifluoropropan-2-yl)oxy]benzonitrile

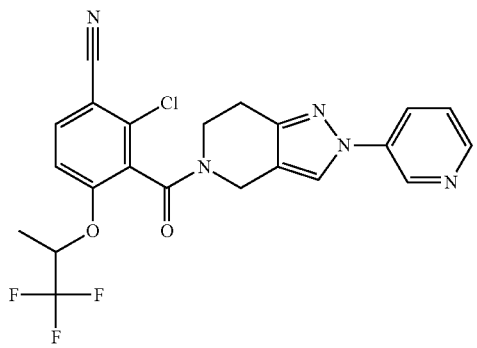

¹H NMR (400 MHz, CDCl₃) δ=8.98-8.70 (m, 1H), 8.54-7.85 (m, 2H), 7.81-7.53 (m, 2H), 7.41-7.23 (m, 1H), 7.09-6.73 (m, 1H), 5.12-4.56 (m, 2H), 4.40-3.96 (m, 2H), 3.60-3.36 (m, 1H), 3.02-2.66 (m, 2H), 1.56-1.34 (m, 3H); [M+H]=476.15.

Example 212

4-(1-Fluorocyclobutyl)-3-[2-(5-fluoropyridin-2-yl)-2H 4H 5H 6H 7H-pyrazolo[4,3-c]pyridine-5-carbonyl]-2-methoxybenzonitrile

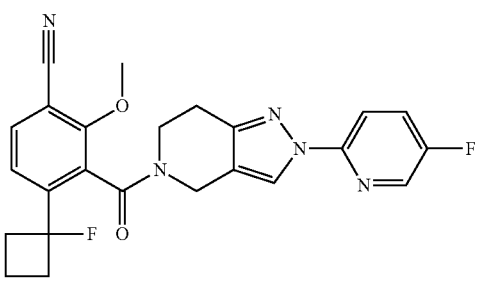

¹H NMR (400 MHz, CDCl₃) δ=8.40-8.04 (m, 2H), 7.89 (dd, J=3.9, 9.0 Hz, 1H), 7.65 (ddd, J=1.0, 5.2, 7.9 Hz, 1H), 7.56-7.44 (m, 1H), 7.26-7.15 (m, 1H), 5.19-4.59 (m, 1H), 4.36-4.20 (m, 1H), 4.14-3.92 (m, 4H), 3.65-3.35 (m, 1H), 3.04-2.69 (m, 2H), 2.66-2.36 (m, 4H), 2.16-1.97 (m, 1H), 1.86-1.54 (m, 1H); [M+H]=450.2.

Example 213

2-Methoxy-3-[2-(pyridin-3-yl)-2H 4H 5H 6H 7H-pyrazolo[4,3-c]pyridine-5-carbonyl]-4-[(1 1 1-trifluoropropan-2-yl)oxy]benzonitrile

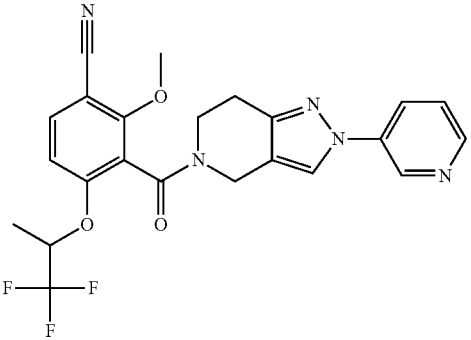 [SMILES: COc1c(C#N)ccc(OC(C)C(F)(F)F)c1C(=O)N1CCc2nn(-c3cccnc3)cc2C1]

¹H NMR (400 MHz, CDCl₃) δ =9.03-8.80 (m, 1H), 8.53 (t, J=4.7 Hz, 1H), 7.98 (br s, 1H), 7.82 (s, 1H), 7.69-7.52 (m, 2H), 7.45-7.33 (m, 1H), 6.90-6.63 (m, 1H), 5.16-4.52 (m, 2H), 4.45-4.25 (m, 1H), 4.19-3.97 (m, 4H), 3.96-3.45 (m, 1H), 3.05-2.82 (m, 2H), 1.53-1.39 (m, 2H); [M+H]=472.24.

Example 214

2-Chloro-3-{1-cyclohexyl-1H 4H 5H 6H 7H-pyrazolo[4,3-c]pyridine-5-carbonyl}-4-[(1 1 1-trifluoropropan-2-yl)oxy]benzonitrile.

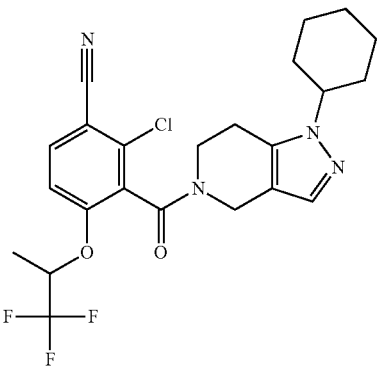 [SMILES: CC(Oc1ccc(C#N)c(Cl)c1C(=O)N1CCc2c(cnn2C2CCCCC2)C1)C(F)(F)F]

¹H NMR (400 MHz, CDCl₃) δ=7.76-7.54 (m, 1H), 7.41-7.12 (m, 1H), 7.05-6.80 (m, 1H), 5.04-4.55 (m, 2H), 4.33-4.05 (m, 2H), 4.03-3.77 (m, 1H), 3.61-3.37 (m, 1H), 2.95-2.58 (m, 2H), 1.99-1.80 (m, 6H), 1.71 (br s, 1H), 1.55-1.05 (m, 6H); [M+H]=481.30.

Example 215

3-{1-Cyclohexyl-1H 4H 5H 6H 7H-pyrazolo[4,3-c]pyridine-5-carbonyl}-2-methoxy-4-[(1 1 1-trifluoropropan-2-yl)oxy]benzonitrile

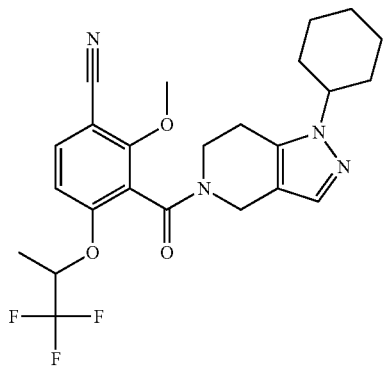 [SMILES: COc1c(C#N)ccc(OC(C)C(F)(F)F)c1C(=O)N1CCc2c(cnn2C2CCCCC2)C1]

$^1$H NMR (400 MHz, CDCl$_3$) δ=7.64-7.49 (m, 1H), 7.40-7.10 (m, 1H), 6.83-6.55 (m, 1H), 5.06-4.47 (m, 2H), 4.33-4.08 (m, 2H), 4.08-3.94 (m, 3H), 3.94-3.77 (m, 1H), 3.58-3.34 (m, 1H), 2.98-2.56 (m, 2H), 1.90 (d, J=9.4 Hz, 6H), 1.78-1.72 (m, 1H), 1.54-1.04 (m, 6H); [M+H]=477.35.

Example 216

2-Chloro-3-[2-(pyridin-2-yl)-2H 4H 5H 6H 7H-pyrazolo[4,3-c]pyridine-5-carbonyl]-4-[(1 1 1-trifluoropropan-2-yl)oxy]benzonitrile

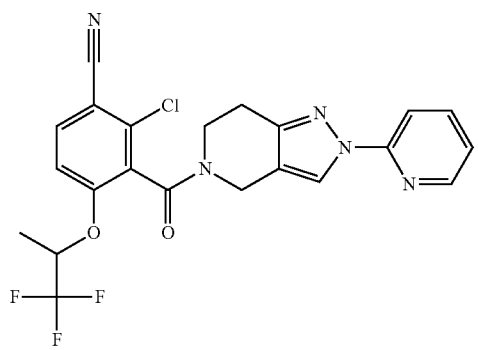

$^1$H NMR (400 MHz, CDCl$_3$) δ=8.42 (s, 0.5H), 8.41-8.31 (m, 1H), 8.23 (s, 0.5H), 7.93-7.85 (m, 1H), 7.83-7.74 (m, 1H), 7.73-7.64 (m, 1H), 7.21-7.11 (m, 1H), 7.08-6.91 (m, 1H), 5.07 (d, J=16.4 Hz, 1H), 4.84-4.73 (m, 1H), 4.37-4.30 (m, 1H), 4.19-4.11 (m, 1H), 3.62-3.45 (m, 1H), 3.00 (q, J=5.7 Hz, 1H), 2.88 (q, J=8Hz, 1H), 1.58-1.42 (m, 3H); [M+H]=476.25.

Example 217

2-Methoxy-3-[2-(pyridin-2-yl)-2H 4H 5H 6H 7H-pyrazolo[4,3-c]pyridine-5-carbonyl]-4-[(1 1 1-trifluoropropan-2-yl)oxy]benzonitrile

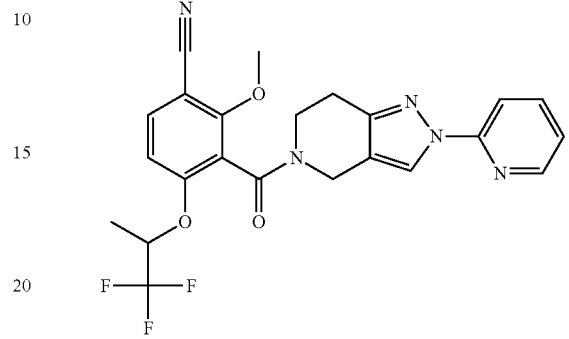

$^1$H NMR (400 MHz, CDCl$_3$) δ=8.41 (s, 0.5H), 8.40-8.32 (m, 1H), 8.22 (s, 0.5H), 7.93-7.84 (m, 1H), 7.83-7.73 (m, 1H), 7.65-7.52 (m, 1H), 7.20-7.09 (m, 1H), 6.84-6.64 (m, 1H), 5.25-4.98 (m, 1H), 4.85-4.60 (m, 2H), 4.39-4.30 (m, 1H), 4.11-3.97 (m, 3H), 3.62-3.45 (m, 1H), 3.08-2.92 (m, 1H), 2.89-2.82 (m, 1H), 1.49 (q, J=6.9 Hz, 3H); [M+H]=472.31.

Example 218

2-Methoxy-3-[1-(pyridin-3-yl)-1H 4H 5H 6H 7H-pyrazolo[4,3-c]pyridine-5-carbonyl]-4-[(1 1 1-trifluoropropan-2-yl)oxy]benzonitrile

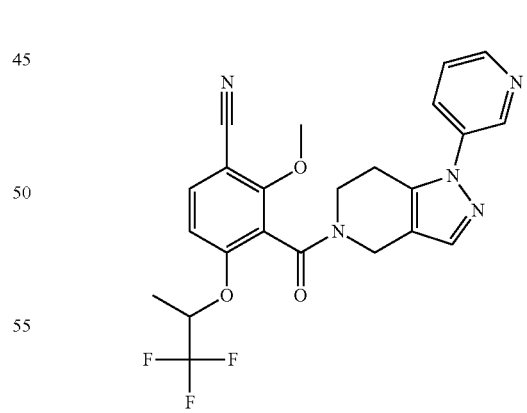

$^1$H NMR (400 MHz, CDCl$_3$) δ=8.87-8.44 (m, 1H), 7.78 (br s, 1H), 7.62-7.44 (m, 1H), 7.38 (s, 1H), 6.83-6.56 (m, 1H), 5.04-4.48 (m, 2H), 4.34-4.09 (m, 1H), 4.07-3.97 (m, 3H), 3.94-3.26 (m, 2H), 3.13-2.60 (m, 2H), 1.48-1.07 (m, 5H); [M+H]=472.31.

Example 219

2-Chloro-3-[2-(pyridin-4-yl)-2H 4H 5H 6H 7H-pyrazolo[4,3-c]pyridine-5-carbonyl]-4-[(1 1 1-trifluoropropan-2-yl)oxy]benzonitrile

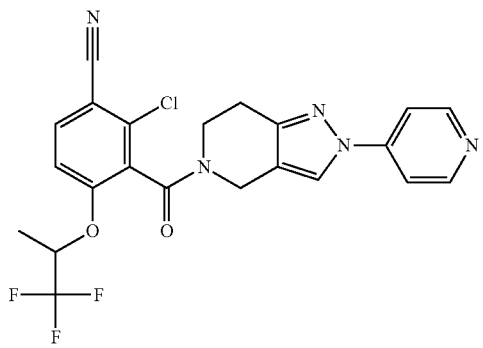 [SMILES: CC(Oc1ccc(C#N)c(Cl)c1C(=O)N1CCc2nn(-c3ccncc3)cc2C1)C(F)(F)F]

¹H NMR (400 MHz, CDCl₃) δ=8.71-8.57 (m, 2H), 7.97-7.64 (m, 2H), 7.56 (dd, J=6.3, 19.6 Hz, 2H), 7.14-6.81 (m, 1H), 5.15-4.62 (m, 2H), 4.45-4.25 (m, 1H), 4.23-4.02 (m, 1H), 3.68-3.39 (m, 1H), 3.10-2.84 (m, 2H), 1.56-1.36 (m, 3H); [M+H]=476.22.

Example 220

2-Methoxy-3-[2-(pyridin-4-yl)-2H 4H 5H 6H 7H-pyrazolo[4,3-c]pyridine-5-carbonyl]-4-[(1 1 1-trifluoropropan-2-yl)oxy]benzonitrile

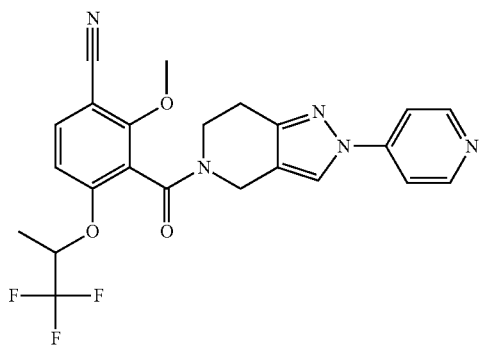

¹H NMR (400 MHz, CDCl₃) δ=8.70-8.53 (m, 2H), 7.94-7.47 (m, 4H), 6.88-6.57 (m, 1H), 5.18-4.54 (m, 2H), 4.46-4.26 (m, 1H), 4.16-3.98 (m, 3H), 3.72-3.41 (m, 1H), 3.07-2.82 (m, 2H), 1.57-1.36 (m, 3H), 1.32-1.19 (m, 1H); [M+H]=472.27.

Example 221

2-Methoxy-3-[1-(oxan-4-yl)-1H 4H 5H 6H 7H-pyrazolo[4,3-c]pyridine-5-carbonyl]-4-[(1 1 1-trifluoropropan-2-yl)oxy]benzonitrile

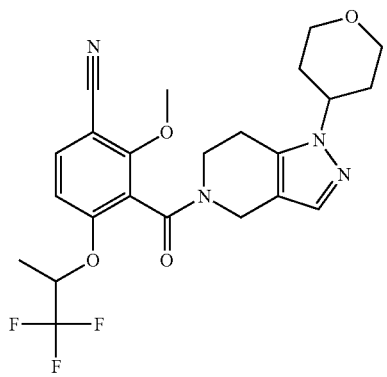 [SMILES: COc1c(C#N)ccc(OC(C)C(F)(F)F)c1C(=O)N1CCc2c(cnn2C2CCOCC2)C1]

¹H NMR (400 MHz, CDCl₃) δ=7.81-7.69 (m, 1H), 7.45-7.18 (m, 1H), 7.18-6.93 (m, 1H). 5.35-5.01 (m, 1H), 4.77-4.45 (m, 1H), 4.40-4.16 (m, 2H), 4.14-3.81 (m, 5H), 3.71-3.44 (m, 3H), 3.02-2.62 (m, 2H), 2.35-2.05 (m, 2H), 1.92-1.71 (m, 2H), 1.57-1.38 (m, 2H), 1.37-1.18 (m, 1H), 1.08 (d, J=6.3 Hz, 1H); [M+H]=479.34.

Example 222

2-Chloro-3-[2-(5-fluoropyridin-2-yl)-2H 4H 5H 6H 7H-pyrazolo[4,3-c]pyridine-5-carbonyl]-4-{[(2S)-1 1 1-trifluoropropan-2-yl]oxy}benzonitrile

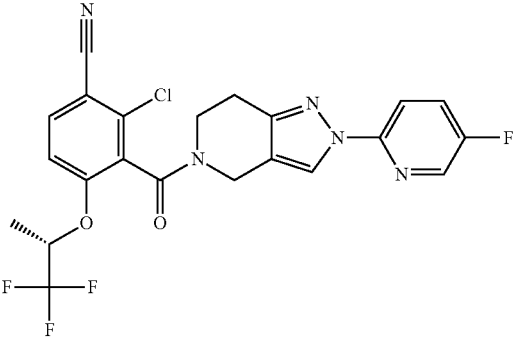

¹H NMR (400 MHz, CDCl₃) δ=8.44-8.30 (m, 1H), 8.17 (s, 1H), 8.05 (dd, J=5.1, 9.0 Hz, 1H), 7.82 (d, J=5.1 Hz, 2H), 7.59-7.37 (m, 1H), 5.64-5.28 (m, 1H), 4.89-4.47 (m, 1H), 4.38-4.12 (m, 1H), 4.11-3.73 (m, 1H), 3.65-3.30 (m, 1H), 2.89-2.53 (m, 2H), 1.39-0.89 (m, 3H); [M+H]=494.30.

Example 223

2-Chloro-3-[2-(4-fluorophenyl)-2H 4H 5H 6H 7H-pyrazolo[4,3-c]pyridine-5-carbonyl]-4-(2 2 2-tri-fluoroethoxy)benzonitrile

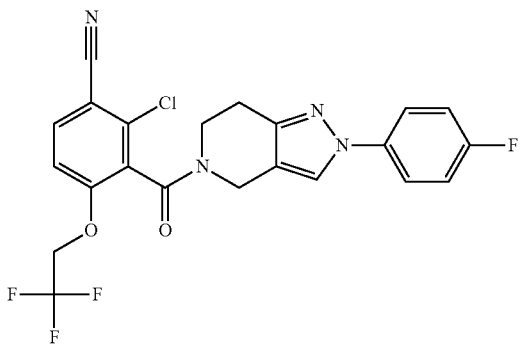 [SMILES: N#Cc1ccc(OCC(F)(F)F)c(C(=O)N2CCc3nn(-c4ccc(F)cc4)cc3C2)c1Cl]

¹H NMR (400 MHz, CDCl₃) δ=7.80-7.66 (m, 2H), 7.65-7.47 (m, 2H), 7.13 (q, J=8.0 Hz, 2H), 7.04-6.90 (m, 1H), 5.10-4.78 (m, 1H), 4.59-4.37 (m, 2H), 4.37-4.27 (m, 1H), 4.13 (quin, J=7.0 Hz, 1H), 3.65-3.43 (m, 1H), 3.09-2.71 (m, 2H); [M+H]=479.22.

Example 224

2-Chloro-3-[2-(5-fluoropyridin-2-yl)-2H 4H 5H 6H 7H-pyrazolo[4,3-c]pyridine-5-carbonyl]-4-(2 2 2-tri-fluoroethoxy)benzonitrile

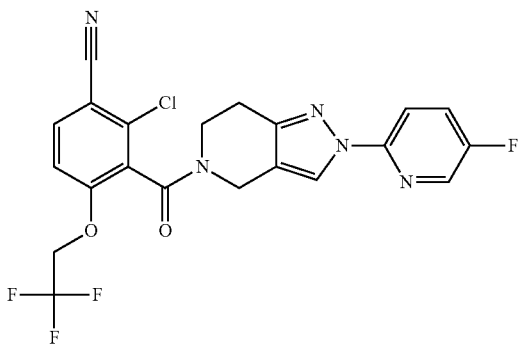

¹H NMR (400 MHz, CDCl₃) δ=8.43-8.04 (m, 2H), 7.98-7.84 (m, 1H), 7.73 (t, J=7.8 Hz, 1H), 7.60-7.41 (m, 1H), 6.96 (dd, J=8.8, 19.8 Hz, 1H), 5.12-4.76 (m, 1H), 4.58-4.26 (m, 3H), 4.25-4.02 (m, 1H), 3.69-3.43 (m, 1H), 3.00 (t, J=5.3 Hz, 1H), 2.93-2.73 (m, 1H); [M+H]=480.23.

Example 225

3-[2-(5-Fluoropyridin-2-yl)-2H 4H 5H 6H 7H-pyra-zolo[4,3-c]pyridine-5-carbonyl]-2-methoxy-4-{[(2S)-1 1 1-trifluoropropan-2-yl]oxy}benzonitrile

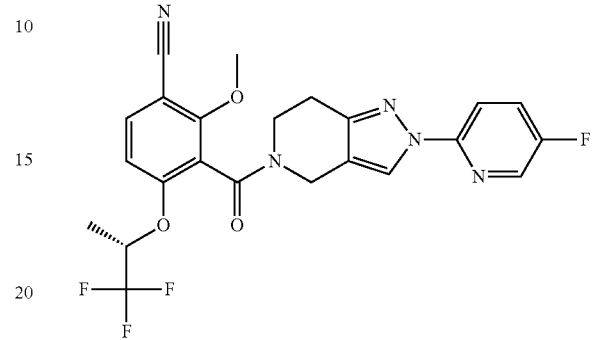

¹H NMR (400 MHz, CDCl₃) δ=8.45-8.32 (m, 1H), 8.19 (s, 1H), 7.90-7.76 (m, 3H), 7.23-7.08 (m, 1H), 5.50-5.23 (m, 1H), 4.83-4.55 (m, 1H), 4.38-4.12 (m, 1H), 4.09-3.95 (m, 1H), 3.90-3.73 (m, 3H), 3.64-3.33 (m, 1H), 2.87-2.55 (m, 2H), 1.41-1.20 (m, 2H), 0.95 (d, J=6.3 Hz, 1H); [M+H]=490.24.

Example 226

2-Chloro-3-[2-(2-methylpyridin-4-yl)-2H 4H 5H 6H 7H-pyrazolo[4,3-c]pyridine-5-carbonyl]-4-[(1 1 1-trifluoropropan-2-yl)oxy]benzonitrile

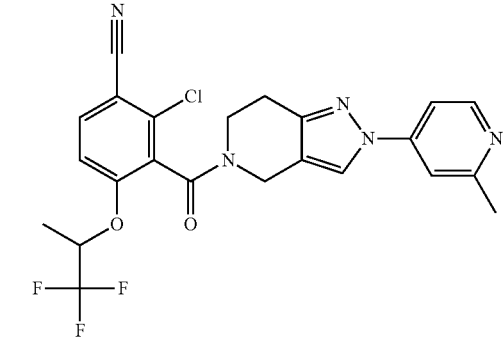 [SMILES: Cc1cc(-n2cc3c(n2)CCN(C(=O)c2c(OC(C)C(F)(F)F)ccc(C#N)c2Cl)C3)ccn1]

¹H NMR (400 MHz, CDCl₃) δ=8.51 (dd, J=5.9. 9.0 Hz, 1H), 7.93-7.64 (m, 2H), 7.48 (d, J=11.7 Hz, 1H), 7.39-7.28 (m, 1H), 7.00 (dd, J=9.0, 18.4 Hz, 1H), 5.13-4.66 (m, 2H), 4.47-4.24 (m, 1H), 4.23-4.00 (m, 1H), 3.71-3.30 (m, 1H), 3.13-2.81 (m, 2H), 2.61 (d, J=5.9 Hz, 3H), 1.53-1.41 (m, 3H); [M+H]=490.28.

Example 227

2-Methoxy-3-[2-(2-methylpyridin-4-yl)-2H 4H 5H 6H 7H-pyrazolo[4,3-c]pyridine-5-carbonyl]-4-[(1 1 1-trifluoropropan-2-yl)oxy]benzonitrile

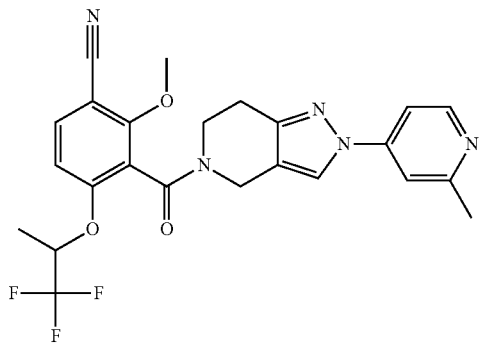 [SMILES: COc1c(C#N)ccc(OC(C)C(F)(F)F)c1C(=O)N1CCc2nn(-c3ccnc(C)c3)cc2C1]

¹H NMR (400 MHz, CDCl₃) δ=8.50 (dd, J=5.7. 8.8 Hz, 1H), 7.92-7.65 (m, 1H), 7.64-7.55 (m, 1H), 7.48 (d, J=11.7 Hz, 1H), 7.39-7.27 (m, 1H), 6.86-6.62 (m, 1H), 5.16-4.59 (m, 2H), 4.47-4.24 (m, 1H), 4.19-3.97 (m, 4H), 3.67-3.41 (m, 1H), 3.04-2.79 (m, 2H), 2.61 (d, J=6.3 Hz, 3H), 1.56-1.17 (m, 3H); [M+H]=486.37.

Example 228

2-Chloro-3-[2-(5-chloropyridin-2-yl)-2H 4H 5H 6H 7H-pyrazolo[4,3-c]pyridine-5-carbonyl]-4-[(1 1 1-trifluoropropan-2-yl)oxy]benzonitrile

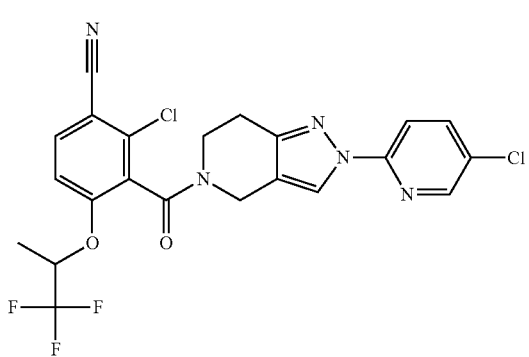 [SMILES: CC(Oc1ccc(C#N)c(Cl)c1C(=O)N1CCc2nn(-c3ccc(Cl)cn3)cc2C1)C(F)(F)F]

¹H NMR (400 MHz, CDCl₃) δ=8.44-8.12 (m, 2H), 7.93-7.81 (m, 1H), 7.79-7.63 (m, 2H), 7.11-6.86 (m, 1H), 5.15-4.60 (m, 2H), 4.53-4.23 (m, 1H), 4.22-3.34 (m, 2H), 3.09-2.72 (m, 2H), 1.57-1.08, [M+H]=510.21.

Example 229

3-[2-(5-Chloropyridin-2-yl)-2H 4H 5H 6H 7H-pyrazolo[4,3-c]pyridine-5-carbonyl]-2-methoxy-4-[(1 1 1-trifluoropropan-2-yl)oxy]benzonitrile

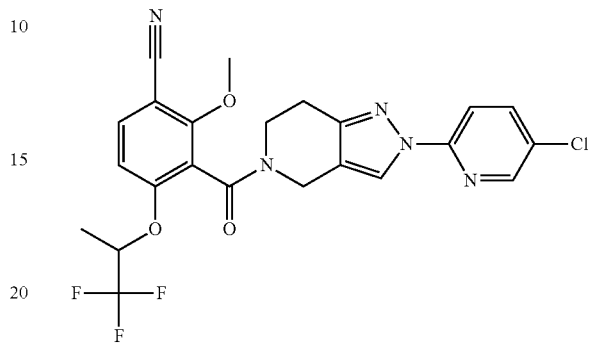

¹H NMR (400 MHz, CDCl₃) δ=8.42-8.09 (m, 2H), 7.94-7.67 (m, 2H), 7.67-7.50 (m, 1H), 6.90-6.47 (m, 1H), 5.18-4.58 (m, 2H), 4.50-4.25 (m, 1H), 4.22-3.92 (m, 4H), 3.87-3.35 (m, 1H), 3.17-2.66 (m, 2H), 1.56-1.15 (m, 3H); [M+H]=506.26.

Example 230

2-Chloro-3-[2-(5-fluoro-2-methoxypyridin-3-yl)-2H 4H 5H 6H 7H-pyrazolo[4,3-c]pyridine-5-carbonyl]-4-[(1 1 1-trifluoropropan-2-yl)oxy]benzonitrile

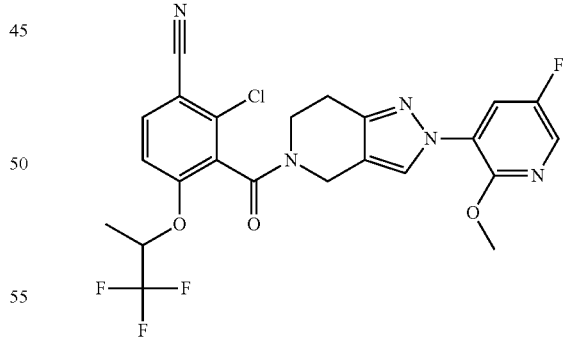

¹H NMR (400 MHz, CDCl₃) δ=8.24-8.03 (m, 1H), 8.02-7.87 (m, 2H), 7.70 (t, J=9.4 Hz, 1H), 7.11-6.87 (m, 1H), 5.15-4.63 (m, 2H), 4.50-4.23 (m, 1H), 4.17-4.09 (m, 1H), 4.09-3.92 (m, 3H), 3.68-3.32 (m, 1H), 3.08-2.75 (m, 2H), 1.50 (q, J=6.0, Hz, 3H); [M+H]=524.36.

Example 231

3-[2-(5-Fluoro-2-methoxypyridin-3-yl)-2H 4H 5H 6H 7H-pyrazolo[4,3-c]pyridine-5-carbonyl]-2-methoxy-4-[(1 1 1-trifluoropropan-2-yl)oxy]benzonitrile

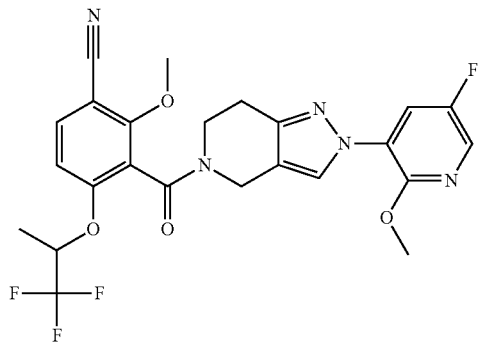 [SMILES: COc1ncc(F)cc1-n1cc2c(n1)CCN(C(=O)c1c(OC(C)C(F)(F)F)ccc(C#N)c1OC)C2]

¹H NMR (400 MHz, CDCl₃) δ=8.24-8.02 (m, 1H), 8.02-7.82 (m, 2H), 7.60 (t, J=8.6 Hz, 1H), 6.88-6.55 (m, 1H), 5.18-4.58 (m, 2H), 4.46-4.27 (m, 1H), 4.20-3.92 (m, 6H), 3.72-3.36 (m, 1H), 3.04-2.72 (m, 2H), 1.49 (q, J=6.8 Hz, 2H), 1.30-1.18 (m, 2H); [M+H]=520.33.

Example 232

2-Chloro-3-[2-(3 5-difluoropyridin-2-yl)-2H 4H 5H 6H 7H-pyrazolo[4,3-c]pyridine-5-carbonyl]-4-[(1 1 1-trifluoropropan-2-yl)oxy]benzonitrile

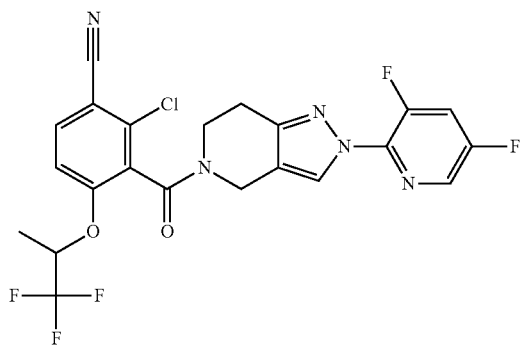 [SMILES: CC(Oc1ccc(C#N)c(Cl)c1C(=O)N1CCc2nn(-c3ncc(F)cc3F)cc2C1)C(F)(F)F]

¹H NMR (400 MHz, CDCl₃) δ=8.11 (d, J=13.3 Hz, 1H), 7.84-7.63 (m, 2H), 7.49 (s, 1H), 7.00 (dd, J=8.8, 18.6 Hz, 1H), 4.99-4.55 (m, 2H), 4.41-4.04 (m, 1H), 3.94-3.68 (m, 1H), 3.49 (q, J=5.5 Hz, 1H), 2.98-2.61 (m, 2H), 1.53-1.44 (m, 2H), 1.26 (d, J=6.3 Hz, 1H); [M+H]=512.24.

Example 233

3-[2-(3 5-Difluoropyridin-2-yl)-2H 4H 5H 6H 7H-pyrazolo[4,3-c]pyridine-5-carbonyl]-2-methoxy-4-[(1 1 1-trifluoropropan-2-yl)oxy]benzonitrile

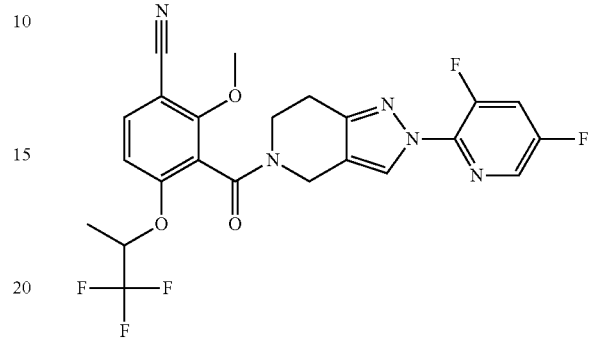

¹H NMR (400 MHz, CDCl₃) δ=8.13-7.97 (m, 1H), 7.81-7.65 (m, 1H), 7.64-7.37 (m, 2H), 6.81-6.48 (m, 1H), 4.96-4.45 (m, 2H), 4.37-4.12 (m, 1H), 4.11-3.92 (m, 3H), 3.89-3.30 (m, 2H), 2.93-2.51 (m, 2H), 1.49-1.35 (m, 2H), 1.29-1.13 (m, 1H); [M+H]=508.34.

Example 234

3-[2-(5-Fluoropyridin-2-yl)-2H 4H 5H 6H-pyrrolo[3,4-c]pyrazole-5-carbonyl]-2-methoxy-4-[(1 1 1-trifluoropropan-2-yl)oxy]benzonitrile

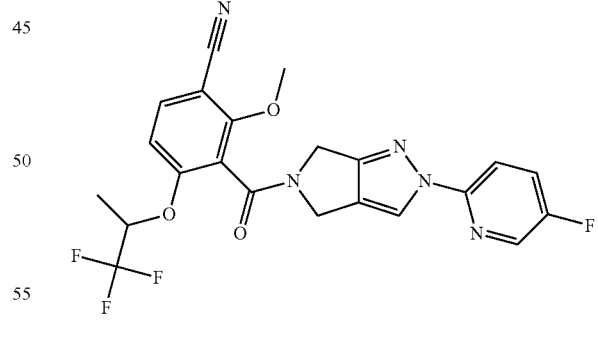

¹H NMR (400 MHz, CDCl₃) δ=8.33 (s, 1H), 8.26-8.18 (m, 1H), 7.97-7.81 (m, 1H), 7.62 (dd, J=2.7, 8.6 Hz, 1H), 7.58-7.44 (m, 1H), 6.85-6.73 (m, 1H), 4.93-4.68 (m, 3H), 4.46-4.26 (m, 2H), 4.12 (s, 3H), 1.55-1.44 (m, 3H); [M+H]=476.17.

Example 235

2-Chloro-3-[2-(5-fluoropyridin-2-yl)-2H 4H 5H 6H-pyrrolo[3,4-c]pyrazole-5-carbonyl]-4-[(1 1 1-trifluoropropan-2-yl)oxy]benzonitrile

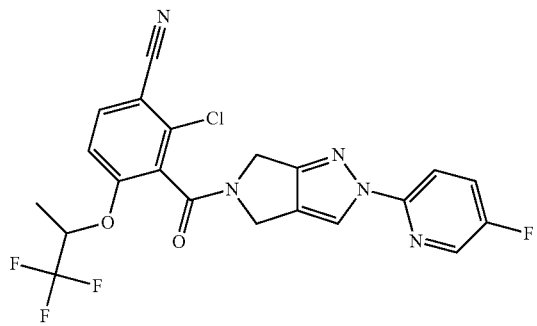 [SMILES: CC(Oc1ccc(C#N)c(Cl)c1C(=O)N1Cc2cn(-c3ccc(F)cn3)nc2C1)C(F)(F)F]

¹H NMR (400 MHz, CDCl₃) δ=8.35 (s, 1H), 8.23 (t, J=4.9 Hz, 1H), 7.98-7.80 (m, 1H), 7.73 (dd, J=3.1, 9.0 Hz, 1H), 7.61-7.43 (m, 1H), 7.09-6.97 (m, 1H), 4.98-4.70 (m, 3H), 4.44-4.29 (m, 2H), 1.56-1.48 (m, 3H); [M+H]=480.16.

Example 236

3-[1-(5-Fluoropyridin-2-yl)-1H 4H 5H 6H-pyrrolo[3,4-c]pyrazole-5-carbonyl]-2-methoxy-4-[(1 1 1-trifluoropropan-2-yl)oxy]benzonitrile

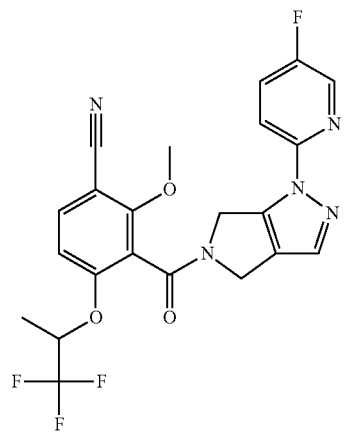 [SMILES: COc1c(C#N)ccc(OC(C)C(F)(F)F)c1C(=O)N1Cc2cnn(-c3ccc(F)cn3)c2C1]

¹H NMR (400 MHz, CDCl₃) δ=8.28-8.08 (m, 1H), 7.99-7.87 (m, 1H), 7.70-7.36 (m, 3H), 6.86-6.70 (m, 1H), 5.29-5.11 (m, 1H), 4.83-4.58 (m, 2H), 4.44-4.22 (m, 2H), 4.12 (d, J=2.0 Hz, 3H), 1.54-1.45 (m, 3H); [M+H]=476.17.

Example 237

2-Methoxy-3-[2-(pyridin-3-yl)-2H 4H 5H 6H 7H-pyrazolo[4,3-c]pyridine-5-carbonyl]-4-{[(2S)-1 1 1-trifluoropropan-2-yl]oxy}benzonitrile

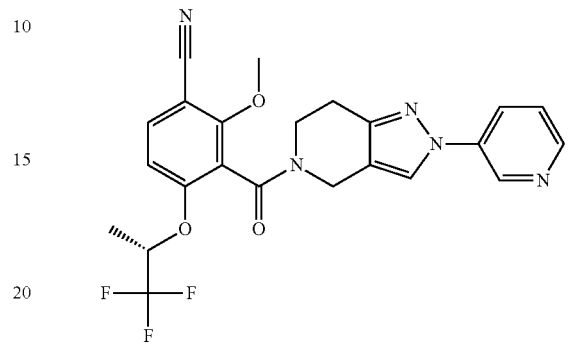

¹H NMR (400 MHz, CDCl₃) δ=9.00-8.78 (m, 1H), 8.57-8.41 (m, 1H), 8.05-7.88 (m, 1H), 7.84-7.51 (m, 2H), 7.40-7.30 (m, 1H), 6.83-6.64 (m, 1H), 5.19-4.54 (m, 2H), 4.45-4.23 (m, 1H), 4.18-3.95 (m, 3H), 3.94-3.40 (m, 1H), 3.04-2.79 (m, 3H), 1.58-1.34 (m, 3H); [M+H]=472.18.

Example 238

2-Methoxy-3-{2-[6-(trifluoromethyl)pyridin-3-yl]-2H 4H 5H 6H 7H-pyrazolo[4,3-c]pyridine-5-carbonyl}-4-{[(2S)-1 1 1-trifluoropropan-2-yl]oxy}benzonitrile

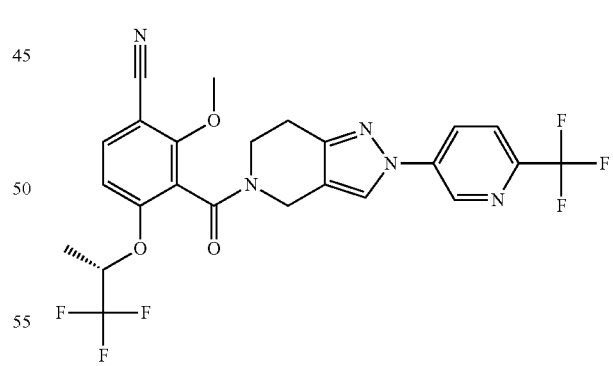

¹H NMR (400 MHz, CDCl₃) δ=9.09-8.92 (m, 1H), 8.24-7.81 (m, 1H), 7.81-7.65 (m, 2H), 7.61 (t, .1 =8.4 Hz, 1H), 6.85-6.63 (m, 1H), 5.20-4.59 (m, 2H), 4.50-4.27 (m, 1H), 4.26-3.98 (m, 4H), 3.98-3.42 (m, 1H), 3.13-2.71 (m, 2H), 1.54-1.20 (m, 3H); [M+H]=540.27.

Example 239

2-Chloro-3-{2-[6-(trifluoromethyl)pyridin-3-yl]-2H 4H 5H 6H 7H-pyrazolo[4,3-c]pyridine-5-carbonyl}-4-{[(2S)-1 1 1-trifluoropropan-2-yl]oxy}benzonitrile

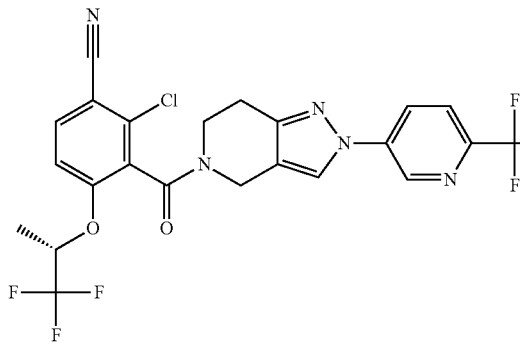

¹H NMR (400 MHz, CDCl₃) δ=9.08-8.89 (m, 1H), 8.16 (d, .1 =2.7 Hz, 1H), 7.96-7.63 (m, 3H), 7.09-6.87 (m, 1H), 5.18-4.65 (m, 2H), 4.50-3.83 (m, 2H), 3.69-3.44 (m, 1H), 3.16-2.76 (m, 2H), 1.57-1.17 (m, 3H); [M+H]=544.18.

Example 240

2-Chloro-3-{2-[2-(trifluoromethyl)pyridin-4-yl]-2H 4H 5H 6H 7H-pyrazolo[4,3-c]pyridine-5-carbonyl}-4-{[(2S)-1 1 1-trifluoropropan-2-yl]oxy}benzonitrile

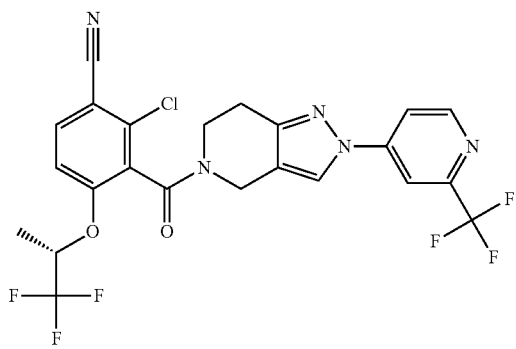 [SMILES: C[C@H](Oc1ccc(C#N)c(Cl)c1C(=O)N1CCc2nn(-c3ccnc(C(F)(F)F)c3)cc2C1)C(F)(F)F]

¹H NMR (400 MHz, CDCl₃) δ=8.73-8.60 (m, 1H), 8.01-7.86 (m, 2H), 7.73-7.57 (m, 2H), 7.03-6.84 (m, 1H), 5.08-4.58 (m, 2H), 4.42-3.81 (m, 2H), 3.63-3.38 (m, 1H), 3.05-2.69 (m, 2H), 1.50-1.37 (m, 3H); [M+H]=544.12.

Example 241

2-Methoxy-3-{2-[2-(trifluoromethyl)pyridin-4-yl]-2H 4H 5H 6H 7H-pyrazolo[4,3-c]pyridine-5-carbonyl}-4-{[(2S)-1 1 1-trifluoropropan-2-yl]oxy}benzonitrile

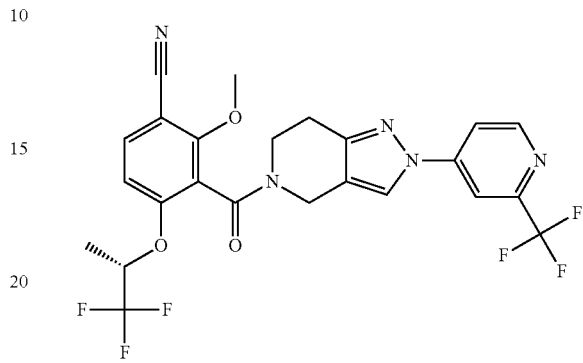

¹H NMR (400 MHz, CDCl₃) δ=8.67 (d, J=5.5 Hz, 1H), 7.98-7.84 (m, 2H), 7.71-7.58 (m, 1H), 7.58-7.48 (m, 1H), 6.78-6.57 (m, 1H), 5.10-4.54 (m, 2H), 4.40-4.19 (m, 1H), 4.17-3.93 (m, 4H), 3.91-3.38 (m, 1H), 3.00-2.73 (m, 2H), 1.48-1.36 (m, 2H), 1.27-1.13 (m, 1H); [M+H]=540.20.

Example 242

2-Chloro-3-[2-(5-fluoropyridin-2-yl)-2H 4H 5H 6H-pyrrolo[3,4-c]pyrazole-5-carbonyl]-4-{[(2S)-1 1 1-trifluoropropan-2-yl]oxy}benzonitrile

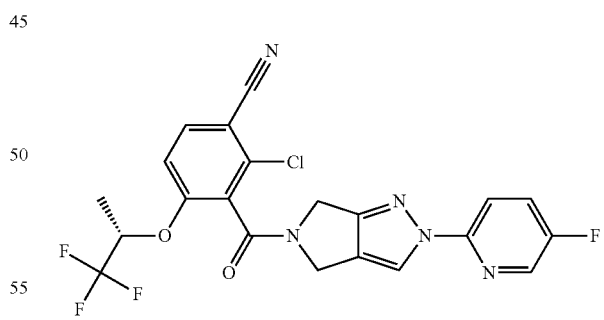

¹H NMR (400 MHz, DMSO-d₆) δ=8.50-8.30 (m, 2H), 8.17-8.09 (m, 1H), 7.98-.79 (m, 2H), 7.57 (dd, J=4.1, 8.8 Hz, 1H), 5.64-5.49 (m, 1H), 4.81-4.53 (m, 2H), 4.49-4.09 (m, 2H), 1.46-1.33 (m, 3H); [M+H]=480.16.

Example 243

3-[2-(5-Flouropyridin-2-yl)-2H 4 H 5H 6H-pyrrolo
[3,4-c]pyrazole-5-carbonyl]-2-methoxy-4-{[(2S)-1 1
1-trifluoropropan-2-yl]oxy}benzonitrile

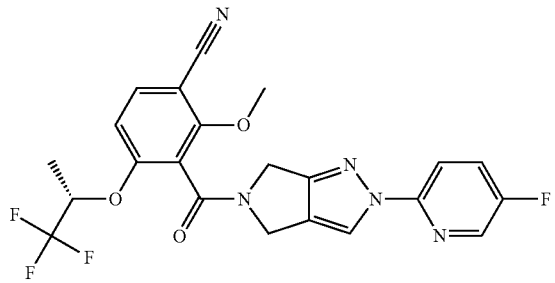

$^1$H NMR (400 MHz, DMSO-d$_6$) δ=8.51-8.27 (m, 2H), 8.00-7.77 (m, 3H), 7.24 (dd, J =4.7, 9.0 Hz, 1H), 5.55-5.41 (m, 1H), 4.82-4.11 (m, 4H), 3.95 (d, J=2.7 Hz, 3H), 1.41-1.32 (m, 3H); [M+H]=476.20.

Example 244

2-Chloro-3-[2-(3-fluoropyridin-4-yl)-2H 4H 5H 6H
7H-pyrazolo[4,3-c]pyridine-5-carbonyl]-4-{[(2S)-1
1 1-trifluoropropan-2-yl]oxy}benzonitrile

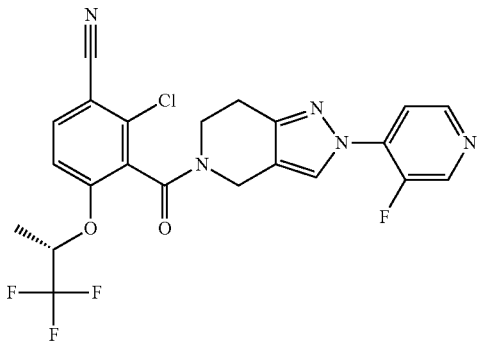 [SMILES: C[C@H](Oc1ccc(C#N)c(Cl)c1C(=O)N1CCc2nn(-c3ccncc3F)cc2C1)C(F)(F)F]

$^1$H NMR (400 MHz, CDCl$_3$) δ=8.56 (dd, J=3.3, 15.1 Hz, 1H), 8.44 (d, J=5.1 Hz, 1H), 8.10-7.84 (m, 2H), 7.70 (t, J=9.2 Hz, 1H), 7.07-6.89 (m, 1H), 5.14-4.64 (m, 2H), 4.48-4.26 (m, 1H), 4.25-4.01 (m, 1H), 3.92-3.44 (m, 1H), 3.09-2.77 (m, 2H), 1.57-1.42 (m, 2H), 1.31-1.19 (m, 1H); [M+H]=494.10.

Example 245

3-[2-(3-Fluoropyridin-4-yl)-2H 4H 5H 6H 7H-pyra-
zolo[4,3-c]pyridine-5-carbonyl]-2-methoxy-4-
{[(2S)-1 1 1-trifluoropropan-2-yl]oxy}benzonitrile

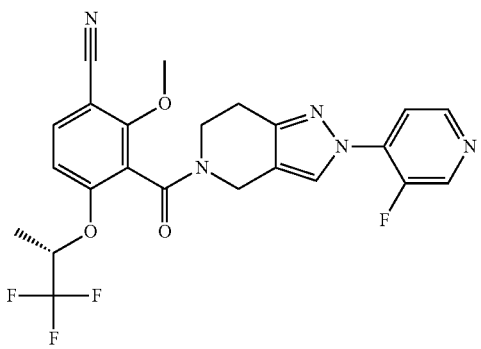 [SMILES: COc1c(C#N)ccc(O[C@@H](C)C(F)(F)F)c1C(=O)N1CCc2nn(-c3ccncc3F)cc2C1]

$^1$H NMR (400 MHz, CDCl$_3$) δ=8.64-8.36 (m, 2H), 8.10-7.82 (m, 2H), 7.60 (t, J=8.4 Hz, 1H), 6.84-6.64 (m, 1H), 5.15-4.98 (m, 1H), 4.89-4.58 (m, 1H), 4.46-4.30 (m, 1H), 4.24-3.98 (m, 3H), 3.94-3.77 (m, 1H), 3.68-3.43 (m, 1H), 3.06-2.75 (m, 2H), 1.55-1.41 (m, 2H), 1.29-1.17 (m, 1H); [M+H]=490.30.

Example 246

2-Methoxy-3-[2-(pyridin-3-yl)-2H 4H 5H 6H-pyr-
rolo[3,4-c]pyrazole-5-carbonyl]-4-{[(2S)-1 1 1-trif-
luoropropan-2-yl]oxy}benzonitrile

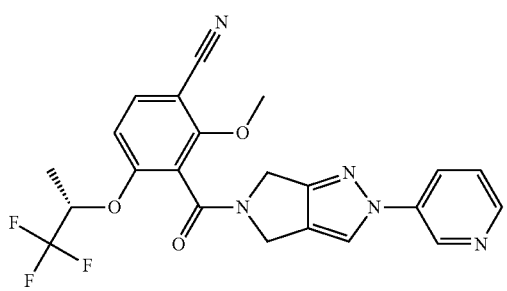

$^1$H NMR (400 MHz, CDCl$_3$) δ=8.94 (br s, 1H), 8.55 (br s, 1H), 8.09-7.91 (m, 1H), 7.84-7.66 (m, 1H), 7.63 (dd, J=2.5, 8.8 Hz, 1H), 7.49-7.33 (m, 1H), 6.86-6.74 (m, 1H), 4.95-4.70 (m, 3H), 4.49-4.27 (m, 2H), 4.18-4.07 (m, 3H), 1.52 (dd, J=6.7, 10.6 Hz, 3H); [M+H]=458.16.

Example 247

2-Chloro-342-(pyridin-3-yl)-2H 4H 5H 6H-pyrrolo
[3,4-c]pyrazole-5-carbonyl]-4-{[(2S)-1 1 1-trifluoro-
propan-2-yl]oxy}benzonitrile

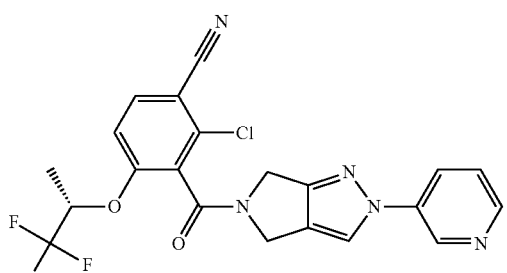

$^1$H NMR (400 MHz, CDCl$_3$) δ=8.94 (br s, 1H), 8.56 (br s, 1H), 8.01 (dd, J=7.6, 19.0 Hz, 1H), 7.85-7.63 (m, 2H), 7.50-7.35 (m, 1H), 7.05 (d, J=9.0 Hz, 1H), 5.00-4.65 (m, 3H), 4.50-4.24 (m, 2H), 1.58-1.49 (m, 3H); [M+H]=462.07.

Example 248

3-[2-(4-Fluorophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile

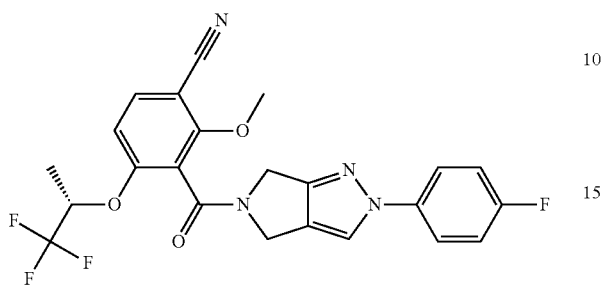

$^1$H NMR (400 MHz, CDCl$_3$) δ=7.66-7.45 (m, 4H), 7.14-6.99 (m, 2H), 6.79-6.63 (m, 1H), 4.88-4.64 (m, 3H), 4.42-4.20 (m, 2H), 4.05 (d, J=1.8 Hz, 3H), 1.51-1.38 (m, 3H); [M+H]=275.30.

Example 249

2-Chloro-3-[2-(4-fluorophenyl)-2H 4H 5H 6H-pyrrolo[3,4-c]pyrazole-5-carbonyl]-4-{[(2S)-1 1 1-trifluoropropan-2-yl]oxy}benzonitrile

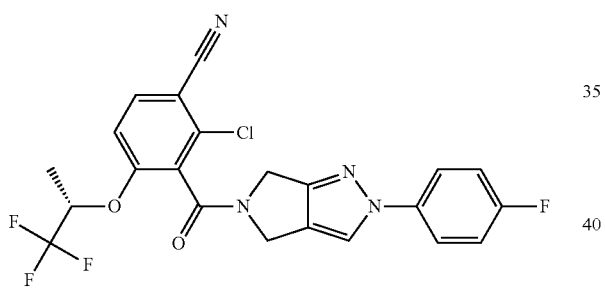

$^1$H NMR (400 MHz, CDCl$_3$) δ=7.71-7.44 (m, 4H), 7.14-7.03 (m, 2H), 7.02-6.89 (m, 1H), 4.91-4.66 (m, 3H), 4.40-4.22 (m, 2H), 1.52-1.41 (m, 3H); [M+H]=479.19.

Example 250

3-[2-(5-Flouropyridin-3-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile

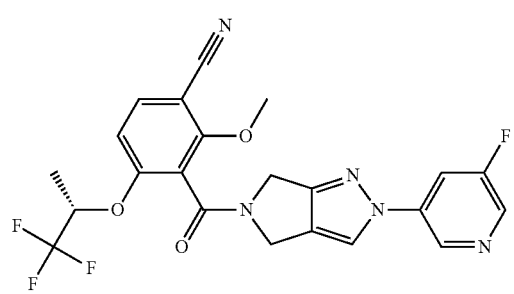 [SMILES: COc1c(C#N)ccc(O[C@@H](C)C(F)(F)F)c1C(=O)N1Cc2cn(-c3cncc(F)c3)nc2C1]

$^1$H NMR (400 MHz, DMSO-d$_6$) δ=9.04-8.91 (m, 1H), 8.52 (d, J=2.3 Hz, 1H), 8.47-8.36 (m, 1H), 8.19 (qdd, J=2.1, 10.3, 18.2 Hz, 1H), 8.01-7.87 (m, 1H), 7.30-7.16 (m, 1H), 5.63-5.39 (m, 1H), 4.86-4.58 (m, 2H), 4.62-4.12 (m, 3H), 3.99-3.92 (m, 3H), 1.46-1.25 (m, 3H); [M+H]=476.21.

Example 251

3-[2-(5 4H 5H 6H-pyrrolo[3,4-c]pyrazole-5-carbonyl]-4-[(1 1 1-trifluoropropan-2-yl)oxy]benzonitrile

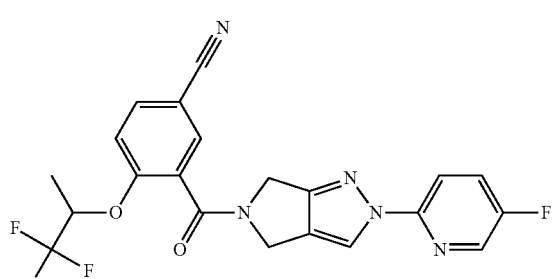

$^1$H NMR (400 MHz, CDCl$_3$) δ=8.29-8.08 (m, 2H), 7.90-7.73 (m, 1H), 7.69-7.59 (m, 2H), 7.46 (dddd, J=2.9, 7.6, 9.1, 14.1 Hz, 1H), 7.04 (d, J=8.7 Hz, 1H), 4.85-4.64 (m, 3H), 4.46-4.25 (m, 2H), 1.45 (d, J=6.4 Hz, 3H); [M+H]=446.00.

Example 252

2-Chloro-3-[2-(5-fluoropyridin-3-yl)-2H 4H 5H 6H-pyrrolo[3,4-c]pyrazole-5-carbonyl]-4-{[(2S)-1 1 1-trifluoropropan-2-yl]oxy}benzonitrile

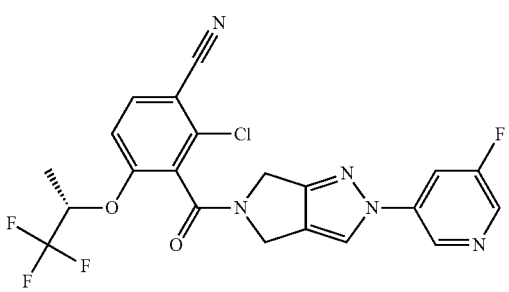 [SMILES: C[C@H](Oc1ccc(C#N)c(Cl)c1C(=O)N1Cc2cn(-c3cncc(F)c3)nc2C1)C(F)(F)F]

$^1$H NMR (400 MHz, CDCl$_3$) δ=8.77 (s, 1H), 8.50-8.39 (m, 1H), 7.90-7.75 (m, 1H), 7.70 (s, 1H), 7.66 (dd, J=3.0, 8.8 Hz, 1H), 6.88-6.73 (m, 1H), 5.00-4.68 (m, 3H), 4.55-4.28 (m, 2H), 4.22-4.04 (m, 3H), 1.60-1.47 (m, 3H); [M+H]=480.10.

Example 253

2-Methoxy-342-(6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

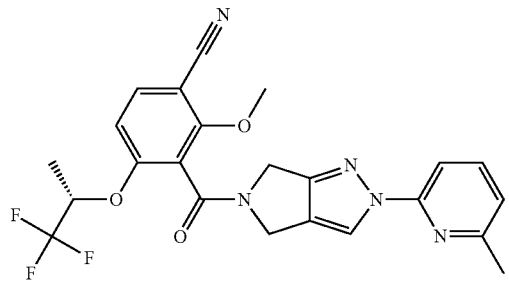 [SMILES: COc1c(C#N)ccc(O[C@@H](C)C(F)(F)F)c1C(=O)N1Cc2cn(-c3cccc(C)n3)nc2C1]

$^1$H NMR (400 MHz, CDCl$_3$) δ=8.52-8.21 (m, 1H), 7.76-7.47 (m, 3H), 7.10-6.92 (m, 1H), 6.88-6.70 (m, 1H), 4.96-4.67 (m, 3H), 4.51-4.25 (m, 2H), 4.13 (s, 3H), 2.59-2.43 (m, 3H), 1.57-1.44 (m, 3H); [M+H]=472.6.

Example 254

2-Methoxy-3-{2-[6-(trifluoromethyppyridin-3-yl]-2H 4H 5H 6H-pyrrolo[3,4-c]pyrazole-5-carbonyl}-4-{[(2S)-1 1 1-trifluoropropan-2-yl]oxy}benzonitrile

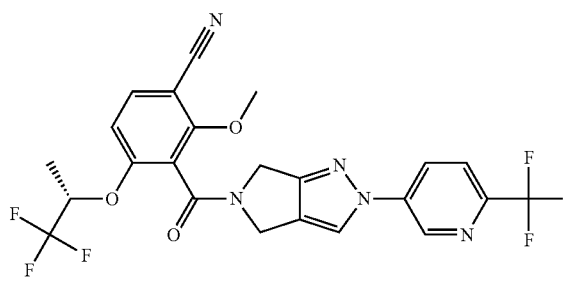

$^1$H NMR (400 MHz, CDCl$_3$) δ=9.14-8.34 (m, 2H), 8.29-8.05 (m, 1H), 7.93-7.70 (m, 2H), 7.64 (dd, J=2.3, 8.6 Hz, 1H), 7.47 (dd, J=4.5, 8.4 Hz, 1H), 6.97-6.72 (m, 1H), 4.97-4.70 (m, 2H), 4.52-4.37 (m, 1H), 4.36-4.06 (m, 3H), 1.74-1.46 (m, 3H); [M+H]=525.99.

Example 255

2-Chloro-3-{3-[4-(trifluoromethyl)phenyl]-1H 4H 5H 6H 7H-pyrazolo[4,3-c]pyridine-5-carbonyl}-4-{[(2S)-1 1 1-trifluoropropan-2-yl]oxy}benzonitrile

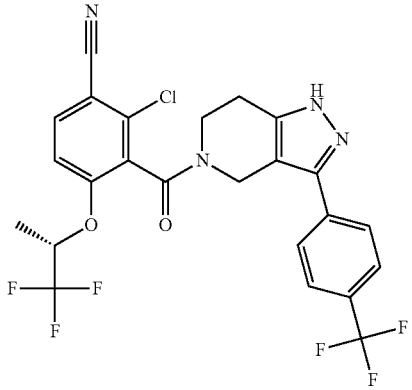 [SMILES: C[C@H](Oc1ccc(C#N)c(Cl)c1C(=O)N1CCc2[nH]nc(-c3ccc(C(F)(F)F)cc3)c2C1)C(F)(F)F]

$^1$H NMR (400 MHz, CDCl$_3$) δ=7.82-7.58 (m, 5H), 7.53-7.43 (m, 1H), 7.09-6.76 (m, 1H), 5.32-4.85 (m, 1H), 4.85-4.65 (m, 1H), 4.63-3.95 (m, 1H), 3.67-3.38 (m, 2H), 3.07-2.70 (m, 2H), 1.57-1.41 (m, 3H); [M+H]=543.05.

Example 256

2-Chloro-3-{2-[6-(trifluoromethyl)pyridin-3-yl]-2H 4H 5H 6H-pyrrolo[3,4-c]pyrazole-5-carbonyl}-4-{[(2S)-1 1 1-trifluoropropan-2-yl]oxy}benzonitrile

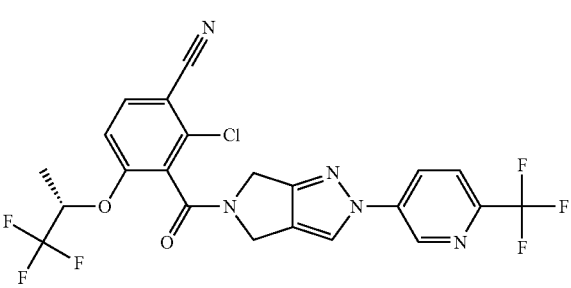 [SMILES: C[C@H](Oc1ccc(C#N)c(Cl)c1C(=O)N1Cc2cn(-c3ccc(C(F)(F)F)nc3)nc2C1)C(F)(F)F]

$^1$H NMR (400 MHz, CDCl$_3$) δ=9.04 (t, J=2.5 Hz, 1H), 8.25-8.08 (m, 1H), 7.94-7.68 (m, 3H), 7.10-6.96 (m, 1H), 4.99-4.74 (m, 3H), 4.49-4.31 (m, 2H), 1.60-1.45 (m, 3H); [M+H]=530.13.

Example 257

2-Methoxy-3-{3[4-(trifluoromethyl)phenyl]-1H 4H 5H 6H 7H-pyrazolo[4,3-c]pyridine-5-carbonyl}-4-{[(2S)-1 1 1-trifluoropropan-2-yl]oxy}benzonitrile

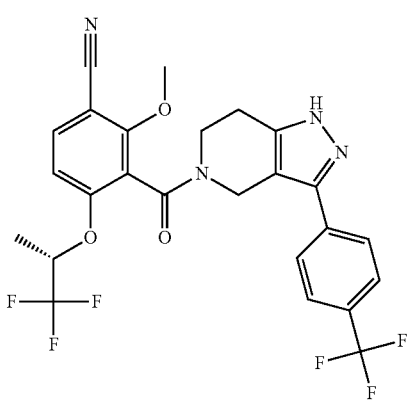 [SMILES: COc1c(C#N)ccc(O[C@@H](C)C(F)(F)F)c1C(=O)N1CCc2[nH]nc(-c3ccc(C(F)(F)F)cc3)c2C1]

$^1$H NMR (400 MHz, CDCl$_3$) δ=7.87-7.67 (m, 3H), 7.66-7.44 (m, 2H), 6.87-6.65 (m, 1H), 5.39-5.10 (m, 1H), 5.01-4.63 (m, 2H), 4.19-3.94 (m, 4H), 3.71-3.35 (m, 2H), 3.05-2.67 (m, 2H), 1.60-1.40 (m, 3H); [M+H]=539.18.

Example 258

4-(1-Fluorocyclobutyl)-3-[2-(5-fluoropyridin-2-yl)-2H 4H 5H 6H-pyrrolo[3,4-c]pyrazole-5-carbonyl]-2-methoxybenzonitrile

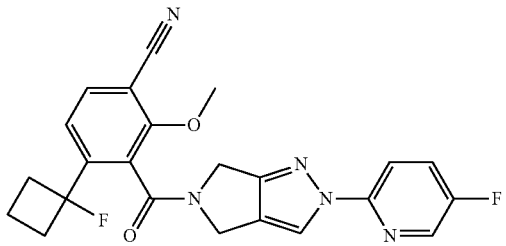 [SMILES: COc1c(C#N)ccc(C2(F)CCC2)c1C(=O)N1Cc2cn(-c3ccc(F)cn3)nc2C1]

¹H NMR (400 MHz, CDCl₃) δ=8.34-8.14 (m, 2H), 7.96-7.79 (m, 1H), 7.67 (d, J=8.2 Hz, 1H), 7.59-7.44 (m, 1H), 7.28 (d, J=1.2 Hz, 1H), 4.92-4.68 (m, 2H), 4.44-4.25 (m, 2H), 4.10 (s, 3H), 2.90-2.45 (m, 4H), 2.24-2.01 (m, 1H), 1.95-1.59 (m, 1H); [M+H]=436.2.

Example 259

4-(4-Fluorooxan-4-yl)-3-[2-(5-fluoropyridin-2-yl)-2H 4H 5H 6H-pyrrolo[3,4-c]pyrazole-5-carbonyl]-2-methoxybenzonitrile

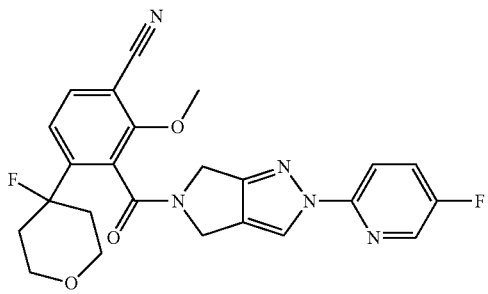 [SMILES: COc1c(C#N)ccc(C2(F)CCOCC2)c1C(=O)N1Cc2cn(-c3ccc(F)cn3)nc2C1]

¹H NMR (400 MHz, CDCl₃) δ=8.38-8.16 (m, 2H), 7.98-7.79 (m, 1H), 7.70-7.62 (m, 1H), 7.53 (dddd, J=2.9, 7.7, 9.0, 14.8 Hz, 1H), 7.14 (d, J=8.2 Hz, 1H), 4.83 (d, J=16.0 Hz, 2H), 4.45-4.34 (m, 1H), 4.34-4.23 (m, 1H), 4.11 (d, J=1.6 Hz, 3H), 4.01-3.69 (m, 4H), 2.62-2.27 (m, 2H), 2.10-1.77 (m, 2H); [M+H]=466.3.

Example 260

3-[2-(5-Fluoropyridin-2-yl)-2H 4H 5H 6H-pyrrolo[3,4-c]pyrazole-5-carbonyl]-2-methoxy-4-(2 2 2-trifluoroethoxy)benzonitrile

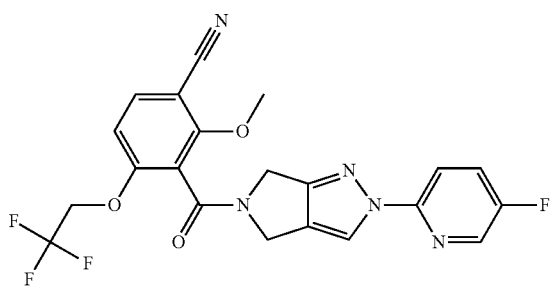 [SMILES: COc1c(C#N)ccc(OCC(F)(F)F)c1C(=O)N1Cc2cn(-c3ccc(F)cn3)nc2C1]

¹H NMR (400 MHz, CDCl₃) δ=8.38-8.14 (m, 2H), 7.99-7.80 (m, 1H), 7.65 (dd, J=2.3, 8.6 Hz, 1H), 7.61-7.42 (m, 1H), 6.77 (d, J=9.0 Hz, 1H), 4.95-4.73 (m, 2H), 4.56-4.28 (m, 4H), 4.12 (s, 3H); [M+H]=461.96.

Example 261

3-[2-(3 4H 5H 6H-pyrrolo[3,4-c]pyrazole-5-carbonyl]-2-methoxy-4-{[(2S)-1 1 1-trifluoropropan-2-yl]oxy}benzonitrile

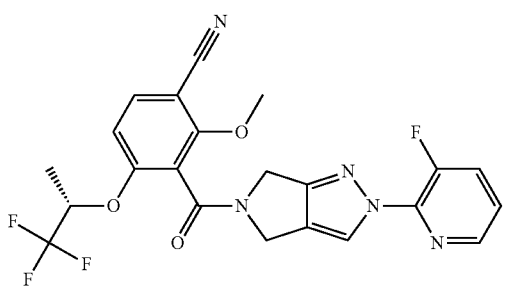 [SMILES: COc1c(C#N)ccc(O[C@@H](C)C(F)(F)F)c1C(=O)N1Cc2cn(-c3ncccc3F)nc2C1]

¹H NMR (400 MHz, CDCl₃) δ=8.37-8.00 (m, 2H), 7.74-7.50 (m, 2H), 7.39-7.21 (m, 1H), 6.91-6.68 (m, 1H), 4.96-4.66 (m, 3H), 4.53-4.27 (m, 2H), 4.12 (s, 3H), 1.57-1.39 (m, 3H); [M+H]=476.21.

Example 262

2-Chloro-3-[2-(3-fluoropyridin-2-yl)-2H 4H 5H 6H-pyrrolo[3,4-c]pyrazole-5-carbonyl]-4-{[(2S)-1 1 1-trifluoropropan-2-yl]oxy}benzonitrile

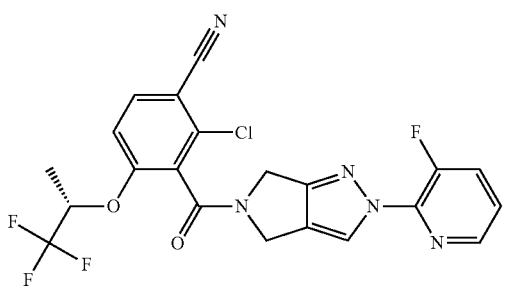 [SMILES: C[C@H](Oc1ccc(C#N)c(Cl)c1C(=O)N1Cc2cn(-c3ncccc3F)nc2C1)C(F)(F)F]

¹H NMR (400 MHz, CDCl₃) δ=8.37-7.99 (m, 2H), 7.78-7.70 (m, 1H), 7.70-7.56 (m, 1H), 7.33-7.26 (m, 1H), 7.07-6.97 (m, 1H), 5.00-4.69 (m, 3H), 4.50-4.25 (m, 2H), 1.57-1.48 (m, 3H); [M+H]=480.2.

Example 263

2-Methoxy-3-[2-(pyridin-2-yl)-2H 4H 5H 6H-pyrrolo[3,4-c]pyrazole-5-carbonyl]-4-{[(2S)-1 1 1-trifluoropropan-2-yl]oxy}benzonitrile

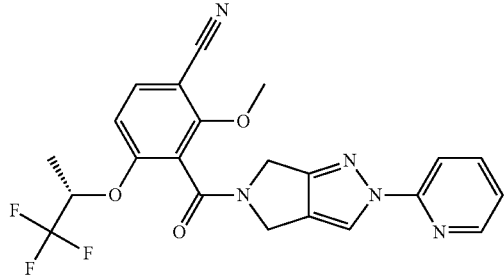 [SMILES: COc1c(C#N)ccc(O[C@@H](C)C(F)(F)F)c1C(=O)N1Cc2cn(-c3ccccn3)nc2C1]

$^1$H NMR (400 MHz, CDCl$_3$) δ=8.49-8.24 (m, 2H), 7.98-7.74 (m, 2H), 7.62 (dd, J=2.7, 9.0 Hz, 1H), 7.22-7.10 (m, 1H), 6.89-6.67 (m, 1H), 4.99-4.64 (m, 3H), 4.51-4.22 (m, 2H), 4.13 (s, 3H), 1.58-1.40 (m, 3H); [M+H]=458.16.

Example 264

2-Chloro-342-(pyridin-2-yl)-2H 4H 5H 6H-pyrrolo[3,4-c]pyrazole-5-carbonyl]-4-{[(2S)-1 1 1-trifluoropropan-2-yl]oxy}benzonitrile

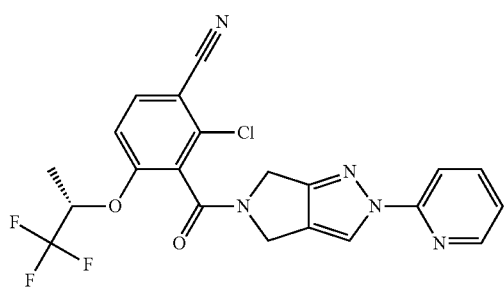 [SMILES: C[C@H](Oc1ccc(C#N)c(Cl)c1C(=O)N1Cc2cn(-c3ccccn3)nc2C1)C(F)(F)F]

$^1$H NMR (400 MHz, CDCl$_3$) δ=8.55-8.26 (m, 2H), 8.00-7.64 (m, 3H), 7.24-7.14 (m, 1H), 7.11-6.94 (m, 1H), 4.99-4.65 (m, 3H), 4.46-4.23 (m, 2H), 1.61-1.47 (m, 3H); [M+H]=462.22.

Example 265

2-Chloro-3-[2-(6-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile

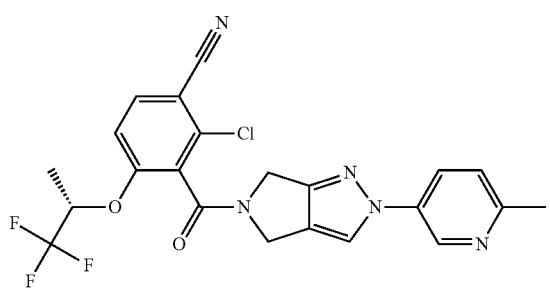 [SMILES: Cc1ccc(-n2cc3c(n2)CN(C(=O)c2c(O[C@@H](C)C(F)(F)F)ccc(C#N)c2Cl)C3)cn1]

$^1$H NMR (400 MHz, CDCl$_3$) δ=8.84-8.72 (m, 1H), 7.98-7.81 (m, 1H), 7.79-7.59(m, 2H), 7.33-7.18 (m, 1H), 7.09-6.92 (m, 1H), 4.99-4.73 (m, 3H), 4.47-4.27 (m, 2H), 2.61 (d, J=2.3 Hz, 3H), 1.61-1.45 (m, 3H); [M+H]=476.13.

Example 266

2-Methoxy-3-[2-(6-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile

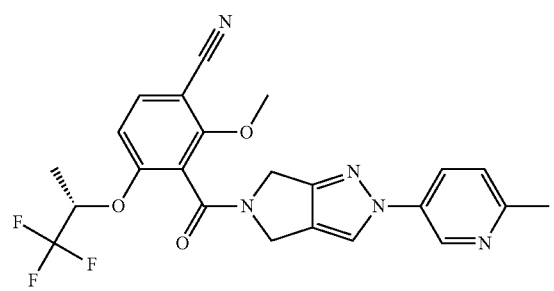 [SMILES: COc1c(C#N)ccc(O[C@@H](C)C(F)(F)F)c1C(=O)N1Cc2cn(-c3ccc(C)nc3)nc2C1]

$^1$H NMR (400 MHz, CDCl$_3$) δ=8.83-8.73 (m, 1H), 7.95-7.80 (m, 1H), 7.75 (d, J=1.6 Hz, 1H), 7.67-7.57 (m, 1H), 7.34-7.19 (m, 1H), 6.93-6.68 (m, 1H), 4.95-4.71 (m, 3H), 4.47-4.27 (m, 2H), 4.11 (d, J=1.6 Hz, 3H), 2.60 (d, J=2.3 Hz, 3H), 1.57-1.43 (m, 3H); [M+H]=472.18.

Example 267

2-Chloro-3-[2-(3-fluorophenyl)-2H 4H 5H 6H-pyrrolo[3,4-c]pyrazole-5-carbonyl]-4-{[(2S)-1 1 1-trifluoropropan-2-yl]oxy}benzonitrile

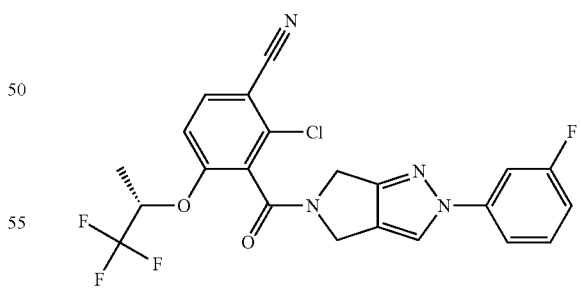

$^1$H NMR (400 MHz, CDCl$_3$) δ=7.80-7.62 (m, 2H), 7.45-7.35 (m, 3H), 7.11-6.91 (m, 2H), 5.03-4.68 (m, 3H), 4.56-4.16 (m, 2H), 1.58-1.47 (m, 3H); [M+H]=479.10.

Example 268

3-[2-(3-Fluorophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile

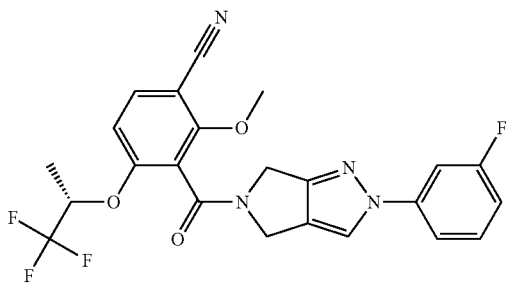 [SMILES: COc1c(C#N)ccc(O[C@@H](C)C(F)(F)F)c1C(=O)N1Cc2cn(-c3cccc(F)c3)nc2C1]

¹H NMR (400 MHz, CDCl₃) δ=7.78-7.58 (m, 2H), 7.48-7.34 (m, 3H), 7.06-6.92 (m, 1H), 6.87-6.70 (m, 1H), 4.99-4.64 (m, 3H), 4.49-4.24 (m, 2H), 4.12 (d, J=2.0 Hz, 3H), 1.58-1.46 (m, 3H); [M+H]=475.22.

Example 269

2-Chloro-3-[2-(2-fluorophenyl)-2H 4H 5H 6H-pyrrolo[3,4-c]pyrazole-5-carbonyl]-4-{[(2S)-1 1 1-trifluoropropan-2-yl]oxy}benzonitrile

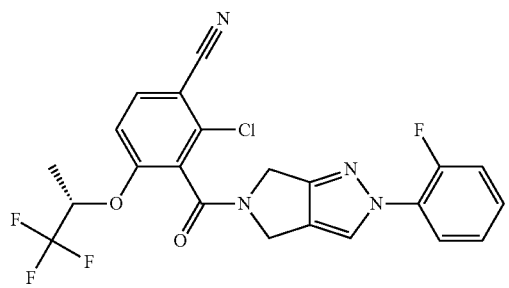 [SMILES: C[C@H](Oc1ccc(C#N)c(Cl)c1C(=O)N1Cc2cn(-c3ccccc3F)nc2C1)C(F)(F)F]

¹H NMR (400 MHz, CDCl₃) δ=7.94-7.65 (m, 4H), 7.37-7.18 (m, 1H), 7.12-6.89 (m, 2H), 5.00-4.60 (m, 4H), 4.48-4.24 (m, 3H), 1.55-1.49 (m, 3H); [M+H]=478.6.

Example 270

3-[2-(2-Fluorophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile

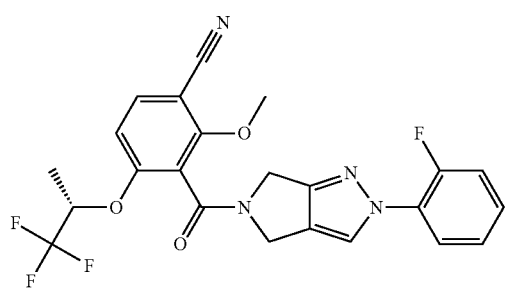 [SMILES: COc1c(C#N)ccc(O[C@@H](C)C(F)(F)F)c1C(=O)N1Cc2cn(-c3ccccc3F)nc2C1]

¹H NMR (400 MHz, CDCl₃) δ=7.92-7.75 (m, 2H), 7.73-7.57 (m, 2H), 7.38-7.15 (m, 1H), 6.89-6.58 (m, 2H), 5.02-4.69 (m, 3H), 4.53-4.27 (m, 2H), 4.21-4.06 (m, 3H), 1.55-1.48 (m, 3H); [M+H]=475.1.

Example 271

2-Chloro-3-[2-(3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

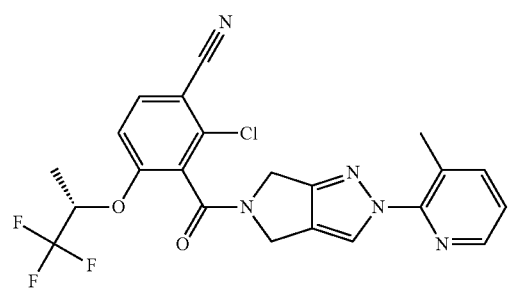 [SMILES: Cc1cccnc1-n1cc2c(n1)CN(C(=O)c1c(O[C@@H](C)C(F)(F)F)ccc(C#N)c1Cl)C2]

¹H NMR (400 MHz, CDCl₃) δ=8.31 (br s, 1H), 8.08-7.92 (m, 1H), 7.75-7.62 (m, 2H), 7.25-6.98 (m, 2H), 5.01-4.69 (m, 3H), 4.58-4.25 (m, 2H), 2.63-2.39 (m, 3H), 1.70-1.38 (m, 3H); [M+H]=476.1.

Example 272

2-Methoxy-3-[2-(3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

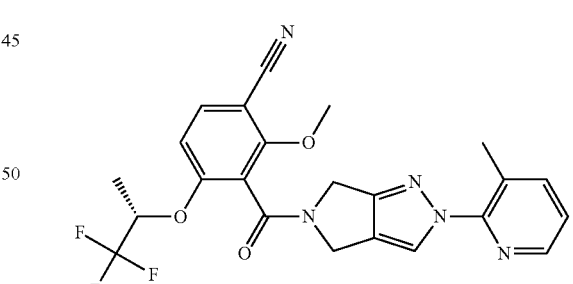

¹H NMR (400 MHz, CDCl₃) δ=8.42-8.20 (m, 1H), 8.11-7.83 (m, 1H), 7.67 (tt, J=0.9, 8.3 Hz, 1H), 7.61 (d, J=9.0 Hz, 1H), 7.25-7.14 (m, 1H), 6.79 (ddd, J=2.5, 8.9, 12.0 Hz, 1H), 4.97-4.69 (m, 3H), 4.51-4.26 (m, 2H), 2.62-2.41 (m, 3H), 1.64-1.41 (m, 3H); [M+H]=472.18.

Example 273

2-Chloro-3-[2-(4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

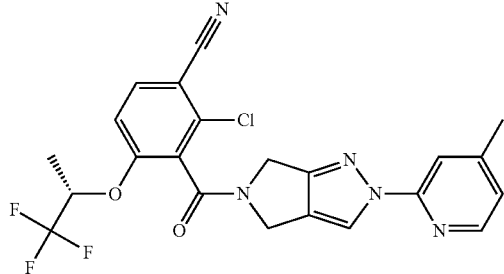 [SMILES: Cc1ccnc(-n2cc3c(n2)CN(C(=O)c2c(O[C@@H](C)C(F)(F)F)ccc(C#N)c2Cl)C3)c1]

$^1$H NMR (400 MHz, CDCl$_3$) δ=8.44-8.28 (m, 1H), 8.24 (dd, J=4.9, 7.2 Hz, 1H), 7.81-7.64 (m, 2H), 7.54-7.39 (m, 1H), 7.09-6.95 (m, 2H), 5.06-4.65 (m, 3H), 4.49-4.13 (m, 2H), 2.42 (d, J=9.4 Hz, 3H), 1.59-1.41 (m, 3H); [M+H]=476.21.

Example 274

2-Methoxy-3-[2-(4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

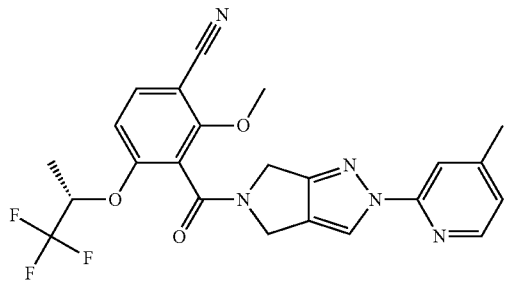 [SMILES: COc1c(C#N)ccc(O[C@@H](C)C(F)(F)F)c1C(=O)N1Cc2cn(-c3cc(C)ccn3)nc2C1]

$^1$H NMR (400 MHz, DMSO-d$_6$) δ=8.51-8.33 (m, 1H), 8.28 (dd, J=5.1, 9.0 Hz, 1H), 7.98-7.88 (m, 1H), 7.77-7.61 (m, 1H), 7.30-7.11 (m, 2H), 5.60-5.41 (m, 1H), 4.78-4.55 (m, 2H), 4.50-4.31 (m, 1H), 4.31-4.13 (m, 1H), 3.99-3.93 (m, 3H), 2.38 (d, J=7.4 Hz, 3H), 1.43-1.29 (m, 3H); [M+H]=472.22.

Example 275

2-Methoxy-3-[2-(6-methoxypyridin-2-yl)-2H 4H 5H 6H-pyrrolo[3,4-c]pyrazole-5-carbonyl]-4-{[(2S)-1 1 1-trifluoropropan-2-yl]oxy}benzonitrile

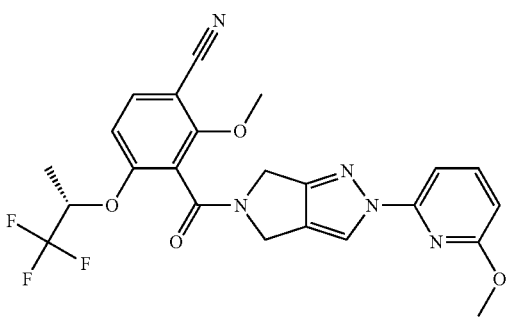 [SMILES: COc1cc(-n2cc3c(n2)CN(C(=O)c2c(O[C@@H](C)C(F)(F)F)ccc(C#N)c2OC)C3)ccn1]

$^1$H NMR (400 MHz, DMSO-d$_6$) δ=8.58-8.29 (m, 1H), 7.92 (ddd, J=2.0, 3.7, 8.8 Hz, 1H), 7.88-7.78 (m, 1H), 7.48-7.30 (m, 1H), 7.32-7.18 (m, 1H), 6.73 (dd, J=2.0, 8.2 Hz, 1H), 5.62-5.34 (m, 2H), 4.81-4.54 (m, 2H), 4.50-4.18 (m, 2H), 4.06-3.85 (m, 6H), 1.48-1.27 (m, 3H); [M+H]=488.18.

Example 276

2-Chloro-3-[2-(6-methoxypyridin-2-yl)-2H 4H 5H 6H-pyrrolo[3,4-c]pyrazole-5-carbonyl]-4-{[(2S)-1 1 1-trifluoropropan-2-yl]oxy}benzonitrile

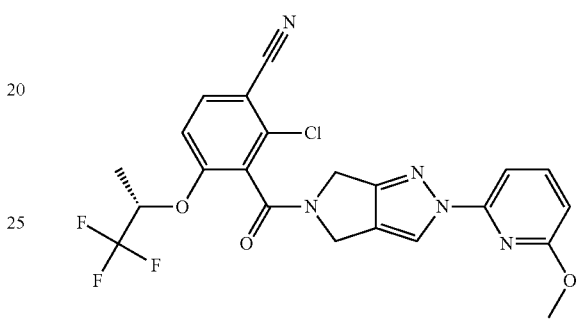

$^1$H NMR (400 MHz, DMSO-d$_6$) δ=8.56-8.34 (m, 1H), 8.19-8.05 (m, 1H), 7.91-7.74 (m, 1H), 7.57 (dd, J=7.0, 9.0 Hz, 1H), 7.48-7.30 (m, 1H), 6.76-6.73 (m, 1H), 5.69-5.44 (m, 1H), 4.82-4.61 (m, 2H), 4.49-4.09 (m, 2H), 3.91 (d, J=10.2 Hz, 3H), 1.54-1.30 (m, 3H); [M+H]=492.17.

Example 277

2-Methoxy-3-[2-(2-methoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile

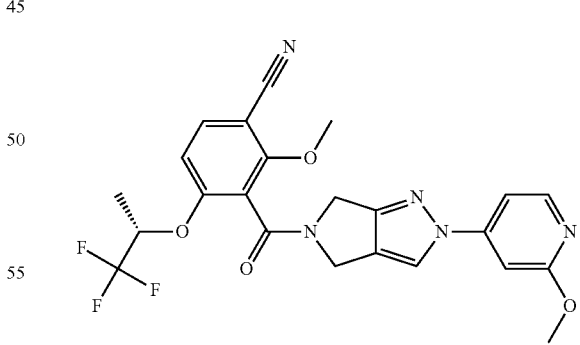

$^1$H NMR (400 MHz, DMSO-d$_6$) δ=8.61-8.37 (m, 1H), 8.20 (dd, J=2.5, 6.1 Hz, 1H), 7.96-7.82 (m, 1H), 7.51-7.38 (m, 1H), 7.31-7.08 (m, 1H), 5.58-5.41 (m, 1H), 4.79-4.52 (m, 2H), 4.53-4.14 (m, 2H), 4.00-3.83 (m, 3H), 1.40-1.33 (m, 2H); [M+H]=488.22.

Example 278

2-Methoxy-3-[2-(5-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

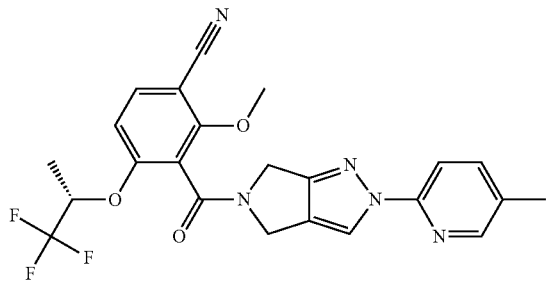 [SMILES: COc1c(C#N)ccc(O[C@@H](C)C(F)(F)F)c1C(=O)N1Cc2cn(-c3ccc(C)cn3)nc2C1]

$^1$H NMR (400 MHz, CDCl$_3$) δ=8.42-8.12 (m, 2H), 7.86-7.53 (m, 3H), 6.88-6.70 (m, 1H), 4.94-4.68 (m, 3H), 4.47-4.26 (m, 2H), 4.12 (s, 3H), 2.36 (s, 3H), 1.58-1.41 (m, 3H); [M+H]=472.26.

Example 279

2-Chloro-3-[2-(1-methyl-1H-pyrazol-4-yl)-2H 4H 5H 6H-pyrrolo[3,4-c]pyrazole-5-carbonyl]-4-{[(2S)-1 1 1-trifluoropropan-2-yl]oxy}benzonitrile

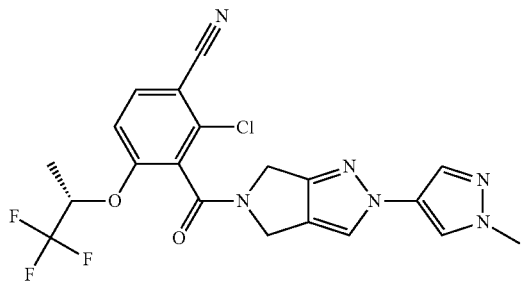 [SMILES: C[C@H](Oc1ccc(C#N)c(Cl)c1C(=O)N1Cc2cn(-c3cnn(C)c3)nc2C1)C(F)(F)F]

$^1$H NMR (400 MHz, DMSO-d$_6$) δ=8.17-8.06 (m, 2H), 8.02-7.87 (m, 1H), 7.83-7.72 (m, 1H), 7.56 (dd, J=3.7, 9.2 Hz, 1H), 5.69-5.45 (m, 2H), 4.77-4.49 (m, 3H), 4.44-4.11 (m, 3H), 3.84 (d, J=2.0 Hz, 4H), 1.50-1.19 (m, 3H); [M+H]=465.34.

Example 280

3-[2-(1 2-Dimethyl-1H-imidazol-4-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile

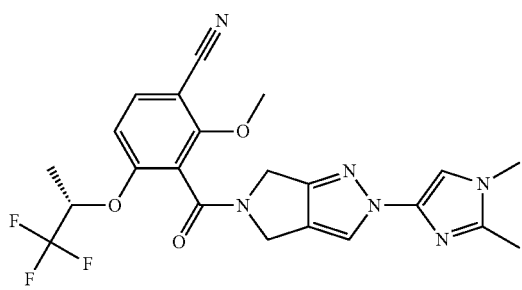 [SMILES: COc1c(C#N)ccc(O[C@@H](C)C(F)(F)F)c1C(=O)N1Cc2cn(-c3cn(C)c(C)n3)nc2C1]

$^1$H NMR (400 MHz, DMSO-d$_6$) δ=7.98-7.83 (m, 2H), 7.29-7.16 (m, 2H), 5.55-5.42 (m, 1H), 4.73-4.50 (m, 2H), 4.45-4.13 (m, 2H), 3.95 (dd, J=1.2, 2.7 Hz, 3H), 3.57 (d, J=4.3 Hz, 3H), 2.34-2.27 (m, 3H), 1.43-1.27 (m, 3H); [M+H]=475.0.

Example 281

3-[1-(1 2-Dimethyl-1H-imidazol-4-yl)-1H 4H 5H 6H-pyrrolo[3,4-c]pyrazole-5-carbonyl]-2-methoxy-4-{[(2S)-1 1 1-trifluoropropan-2-yl]oxy}benzonitrile

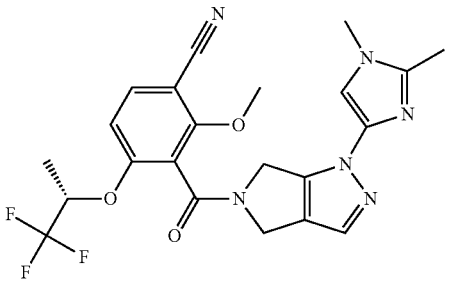 [SMILES: COc1c(C#N)ccc(O[C@@H](C)C(F)(F)F)c1C(=O)N1Cc2cnn(-c3cn(C)c(C)n3)c2C1]

$^1$H NMR (400 MHz, DMSO-d$_6$) δ=7.98-7.87 (m, 1H), 7.53-7.35 (m, 1H), 7.30-7.16 (m, 2H), 5.57-5.41 (m, 1H), 4.96-4.71 (m, 2H), 4.66-4.38 (m, 3H), 4.34-4.08 (m, 5H), 3.99-3.91 (m, 3H), 3.61-3.44 (m, 3H), 2.40-2.12 (m, 3H), 1.46-1.28 (m, 3H); [M+H]=475.1.

Example 282

2-Chloro-3-[2-(1 2-dimethyl-1H-imidazol-4-yl)-2H 4H 5H 6H-pyrrolo[3,4-c]pyrazole-5-carbonyl]-4-{[(2S)-1 1 1-trifluoropropan-2-yl]oxy}benzonitrile

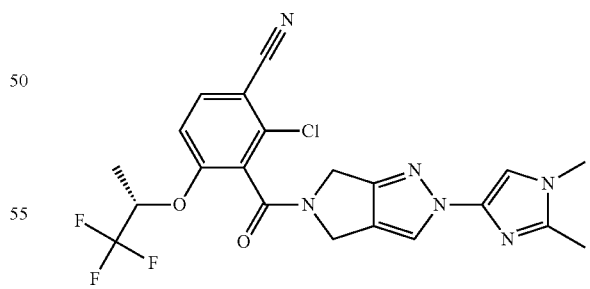

$^1$H NMR (400 MHz, DMSO-d$_6$) δ=8.17-8.07 (m, 1H), 8.01-7.86 (m, 1H), 7.56 (dd, J=2.7, 9.0 Hz, 1H), 7.31-7.16 (m, 1H), 5.57 (td, J=6.3, 12.5 Hz, 1H), 4.72-4.55 (m, 2H), 4.40-4.10 (m, 2H), 3.58 (d, J=4.7 Hz, 3H), 2.35-2.25 (m, 3H), 1.46-1.28 (m, 3H); [M+H]=479.2.

Example 283

3-[2-(4-Cyanophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile

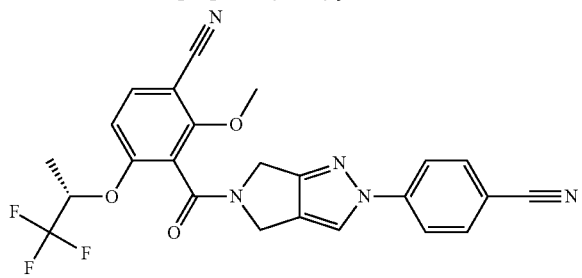

$^1$H NMR (400 MHz, DMSO-d$_6$) δ=8.56-8.51 (m, 1H), 8.45-8.40 (m, 1H), 8.07-7.85 (m, 4H), 7.35-7.16 (m, 1H), 5.63-5.37 (m, 1H), 4.81-4.55 (m, 2H), 4.52-4.20 (m, 2H), 4.06-3.88 (m, 3H), 1.49-1.27 (m, 3H); [M+H]=482.2.

Example 284

3-[1-(4-Cyanophenyl)-1H 4H 5H 6H-pyrrolo[3,4-c]pyrazole-5-carbonyl]-2-methoxy-4-{[(2S)-1 1 1-trifluoropropan-2-yl]oxy}benzonitrile

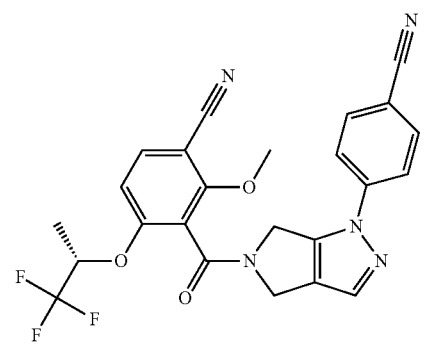 [SMILES: COc1c(C#N)ccc(O[C@@H](C)C(F)(F)F)c1C(=O)N1Cc2cnn(-c3ccc(C#N)cc3)c2C1]

$^1$H NMR (400 MHz, DMSO-d$_6$) δ=8.01-7.82 (m, 4H), 7.78-7.60 (m, 2H), 7.29-7.17 (m, 1H), 5.57-5.41 (m, 1H), 5.24-4.87 (m, 2H), 4.73-4.12 (m, 2H), 4.01-3.91 (m, 3H), 1.41-1.33 (m, 3H); [M+H]=482.2.

Example 285

2-Methoxy-3-{2-[5-(trifluoromethyl)pyridin-2-yl]-2H 4H 5H 6H-pyrrolo[3,4-apyrazole-5-carbonyl}-4-{1(2S)-1 1 1-trifluoropropan-2-yl]oxy}benzonitrile

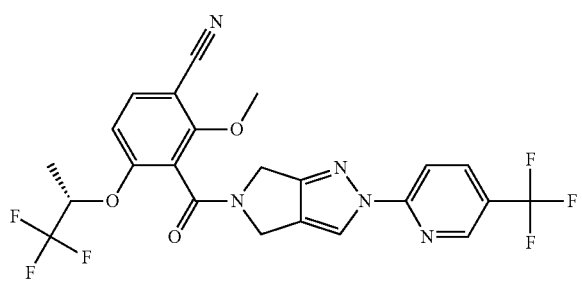

$^1$H NMR (400 MHz, DMSO-d$_6$) δ=8.86 (td, J=1.3, 9.2 Hz, 1H), 8.59-8.41 (m, 1H), 8.41-8.30 (m, 1H), 8.13-7.96 (m, 1H), 7.95-7.86 (m, 1H), 7.25 (dd, J=5.3, 9.2 Hz, 1H), 5.58-5.41 (m, 1H), 4.82-4.18 (m, 4H), 4.01-3.90 (m, 3H), 1.49-1.25 (m, 3H); [M+H]=526.18.

Example 286

2-Chloro-3-{2-[5-(trifluoromethyppyridin-2-yl]-2H 4H 5H 6H-pyrrolo[3,4-c]pyrazole-5-carbonyl}-4-{[(2S)-1 1 1-trifluoropropan-2-yl]oxy}benzonitrile

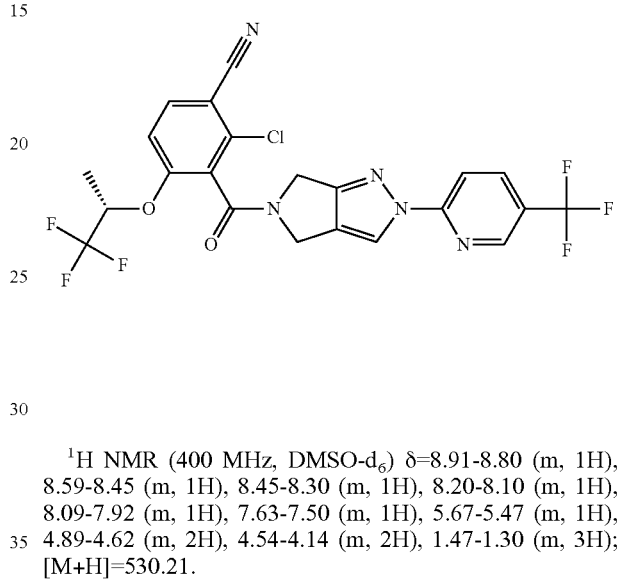

$^1$H NMR (400 MHz, DMSO-d$_6$) δ=8.91-8.80 (m, 1H), 8.59-8.45 (m, 1H), 8.45-8.30 (m, 1H), 8.20-8.10 (m, 1H), 8.09-7.92 (m, 1H), 7.63-7.50 (m, 1H), 5.67-5.47 (m, 1H), 4.89-4.62 (m, 2H), 4.54-4.14 (m, 2H), 1.47-1.30 (m, 3H); [M+H]=530.21.

Example 287

2-Chloro-3-[2-(2-methylpyridin-4-yl)-2H 4H 5H 6H-pyrrolo[3,4-c]pyrazole-5-carbonyl]-4-{[(2R)-1 1 1-trifluoropropan-2-yl]oxy}benzonitrile

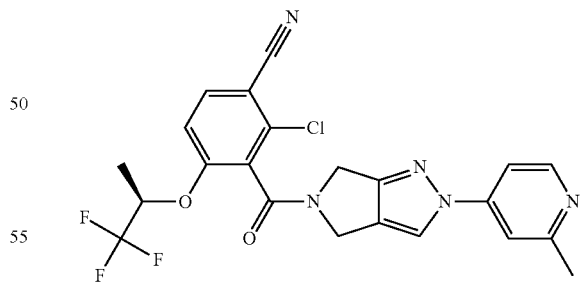

$^1$H NMR (400 MHz, DMSO-d$_6$) δ=8.84-8.57 (m, 2H), 8.34-7.99 (m, 3H), 7.60 (dd, J=4.3, 9.0 Hz, 1H), 5.60 (td, J=6.1, 12.4 Hz, 1H), 4.86-4.68 (m, 2H), 4.59-4.16 (m, 5H), 2.69 (s, 3H), 1.52-1.32 (m, 3H); [M+H]=476.2.

Example 288

2-Methoxy-3-[2-(2-methylpyridin-4-yl)-2H 4H 5H 6H-pyrrolo[3,4-c]pyrazole-5-carbonyl]-4-{[(2R)-1 1 1-trifluoropropan-2-yl]oxy}benzonitrile

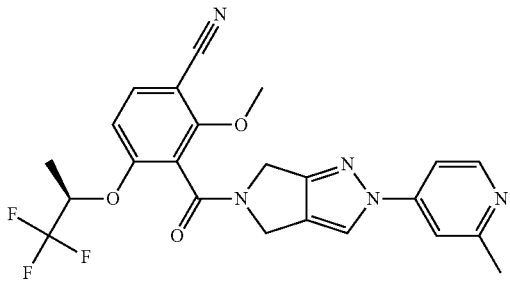 [SMILES: COc1c(C#N)ccc(O[C@H](C)C(F)(F)F)c1C(=O)N1Cc2cn(-c3ccnc(C)c3)nc2C1]

¹H NMR (400 MHz, CD₃OD) δ=8.84-8.58 (m, 2H), 8.32-8.04 (m, 2H), 8.01-7.87 (m, 1H), 7.27 (dd, J=5.1, 8.6 Hz, 1H), 5.65-5.40 (m, 2H), 4.91-4.63 (m, 3H), 4.61-4.16 (m, 4H), 4.06-3.92 (m, 3H), 2.69 (s, 3H), 1.39 (t, J=5.5 Hz, 3H); [M+H]=472.1.

Example 289

3-[2-(5 4H 5H 6H-pyrrolo[3,4-c]pyrazole-5-carbonyl]-2-methoxy-4-{[(2R)-1 1 1-trifluoropropan-2-yl]oxy}benzonitrile

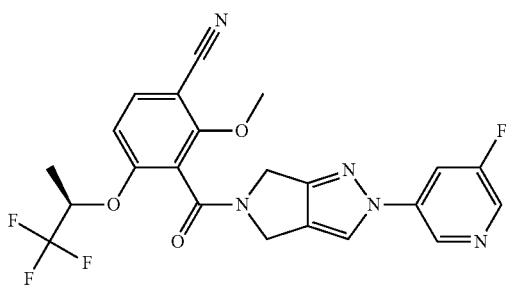 [SMILES: COc1c(C#N)ccc(O[C@H](C)C(F)(F)F)c1C(=O)N1Cc2cn(-c3cncc(F)c3)nc2C1]

¹H NMR (400 MHz, DMSO-d₆) δ=9.04-8.90 (m, 1H), 8.59-8.36 (m, 2H), 8.29-8.09 (m, 1H), 7.97-7.78 (m, 1H), 7.32-7.14 (m, 1H), 5.57-5.39 (m, 1H), 4.82-4.58 (m, 2H), 4.52-4.25 (m, 2H), 3.98-3.92 (m, 3H), 1.44-1.29 (m, 3H); [M+H]=476.21.

Example 290

3-[2-(5 4H 5H 6H-pyrrolo[3,4-c]pyrazole-5-carbonyl]-2-methoxy-4-{[(2R)-1 1 1-trifluoropropan-2-yl]oxy}benzonitrile

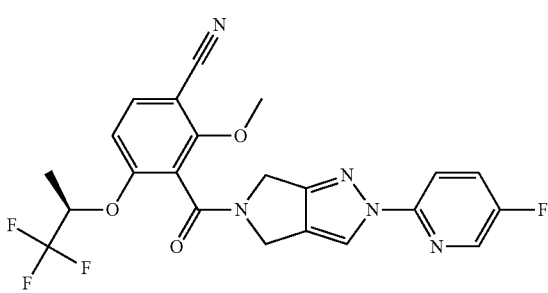 [SMILES: COc1c(C#N)ccc(O[C@H](C)C(F)(F)F)c1C(=O)N1Cc2cn(-c3ccc(F)cn3)nc2C1]

¹H NMR (400 MHz, DMSO-d₆) δ=8.51-8.24 (m, 2H), 8.00-7.78 (m, 3H), 7.25 (d, J=5.9 Hz, 1H), 5.49 (d, J=6.7 Hz, 1H), 4.78-4.53 (m, 2H), 4.51-4.18 (m, 2H), 3.96 (br s, 3H), 1.38 (d, J=5.9 Hz, 3H); [M+H]=476.02.

Example 291

2-Methoxy-3-[2-(1-methyl-1H-pyrazol-3-yl)-2H 4H 5H 6H-pyrrolo[3,4-c]pyrazole-5-carbonyl]-4-{[(2S)-1 1 1-trifluoropropan-2-yl]oxy}benzonitrile

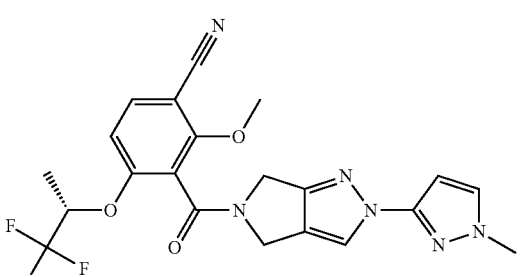

¹H NMR (400 MHz, DMSO-d₆) δ=8.09-7.86 (m, 2H), 7.74 (dd, J=2.3, 4.3 Hz, 1H), 7.30-7.17 (m, 1H), 6.40-6.34 (m, 1H), 5.49 (dd, J=6.3, 12.5 Hz, 1H), 4.74-4.53 (m, 2H), 4.45-4.14 (m, 2H), 3.98-3.86 (m, 3H), 3.82 (d, J=3.1 Hz, 3H), 1.48-1.29 (m, 3H); [M+H]=461.24.

Example 292

2-Chloro-3-[2-(1-methyl-1H-imidazol-4-yl)-2H 4H 5H 6H-pyrrolo[3,4-c]pyrazole-5-carbonyl]-4-{[(2S)-1 1 1-trifluoropropan-2-yl]oxy}benzonitrile

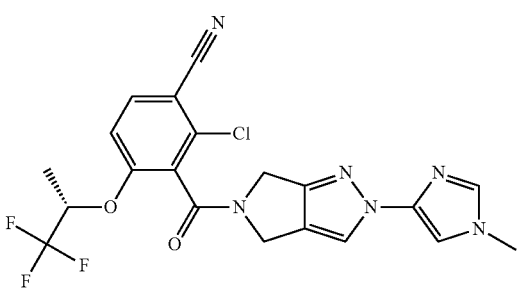 [SMILES: C[C@H](Oc1ccc(C#N)c(Cl)c1C(=O)N1Cc2cn(-c3cn(C)cn3)nc2C1)C(F)(F)F]

¹H NMR (400 MHz, DMSO-d₆) δ=8.19-8.06 (m, 1H), 8.03-7.85 (m, 1H), 7.66-7.45 (m, 2H), 7.27 (d, J=11.3 Hz, 1H), 5.57 (td, J=6.3, 12.5 Hz, 1H), 4.80-4.52 (m, 2H), 4.42-4.12 (m, 2H), 3.67 (d, J=5.5 Hz, 3H), 1.61-1.18 (m, 3H); [M+H]=465.2.

Example 293

2-Chloro-3-[2-(1-methyl-1H-pyrazol-3-yl)-2H 4H 5H 6H-pyrrolo[3,4-c]pyrazole-5-carbonyl]-4-{[(2S)-1 1 1-trifluoropropan-2-yl]oxy}benzonitrile

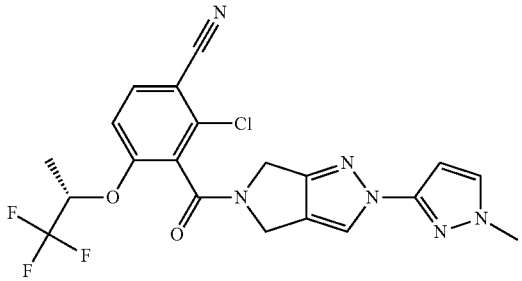 [SMILES: C[C@H](Oc1ccc(C#N)c(Cl)c1C(=O)N1Cc2cn(-c3ccn(C)n3)nc2C1)C(F)(F)F]

$^1$H NMR (400 MHz, DMSO-d$_6$) δ=8.17-8.11 (m, 1H), 8.09-7.92 (m, 1H), 7.76 (dd, J=2.3, 4.7 Hz, 1H), 7.58 (dd, J=2.7, 9.0 Hz, 1H), 6.45-6.32 (m, 1H), 5.59 (td, J=6.4, 12.6 Hz, 1H), 4.80-4.54 (m, 2H), 4.41-4.14 (m, 2H), 3.84 (d, J=3.1 Hz, 3H), 1.46-1.37 (m, 3H); [M+H]=465.3.

Example 294

2-Chloro-3-[1-(1-methyl-1H-imidazol-4-yl)-1H 4H 5H 6H-pyrrolo[3,4-c]pyrazole-5-carbonyl]-4-{[(2S)-1 1 1-trifluoropropan-2-yl]oxy}benzonitrile

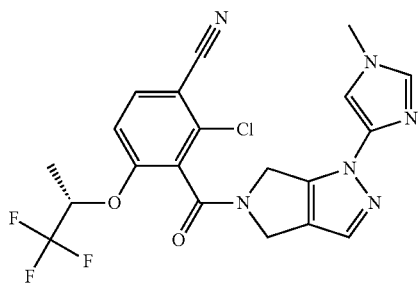 [SMILES: C[C@H](Oc1ccc(C#N)c(Cl)c1C(=O)N1Cc2cnn(-c3cn(C)cn3)c2C1)C(F)(F)F]

$^1$H NMR (400 MHz, DMSO-d$_6$) δ=8.14 (dd, J=7.4, 9.0 Hz, 1H), 7.67-7.26 (m, 4H), 5.69-5.47 (m, 1H), 4.92-4.59 (m, 2H), 4.30-4.08 (m, 2H), 3.72-3.61 (m, 3H), 1.47-1.32 (m, 3H); [M+H]=465.2.

Example 295

2-Chloro-3-[2-(5-fluoro-6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

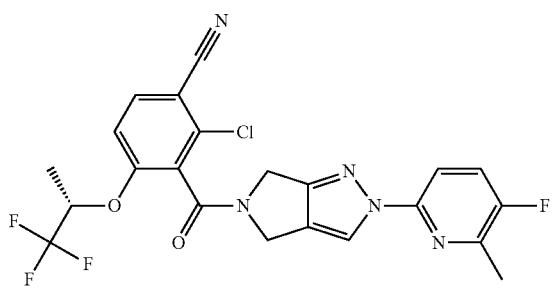 [SMILES: Cc1nc(-n2cc3c(n2)CN(C(=O)c2c(O[C@@H](C)C(F)(F)F)ccc(C#N)c2Cl)C3)ccc1F]

$^1$H NMR (400 MHz, DMSO-d$_6$) δ=8.47-8.27 (m, 1H), 8.18-8.07 (m, 1H), 7.87-7.61 (m, 2H), 7.57 (dd, J=5.5, 9.0 Hz, 1H), 5.63-5.51 (m, 1H), 4.80-4.58 (m, 2H), 4.49-4.15 (m, 2H), 2.46 (dd, J=2.9, 6.1 Hz, 2H), 1.44-1.35 (m, 3H); [M+H]=494.3.

Example 296

3-[2-(5-Fluoro-6-methylpyridin-2-yl)-2H 4H 5H 6H-pyrrolo[3,4-c]pyrazole-5-carbonyl]-2-methoxy-4-{[(2 S)-1 1 1-trifluoropropan-2-yl]oxy}benzonitrile

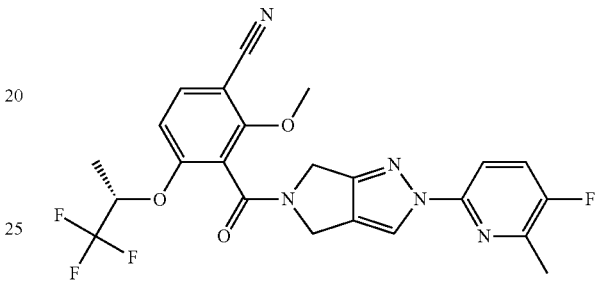

$^1$H NMR (400 MHz, DMSO-d$_6$) δ=8.42-8.26 (m, 1H), 7.96-7.88 (m, 1H), 7.85-7.59 (m, 2H), 7.25 (dd, J=6.7, 9.4 Hz, 1H), 5.56-5.44 (m, 1H), 4.79-4.55 (m, 2H), 4.48-4.16 (m, 2H), 4.02-3.88 (m, 3H), 2.45 (dd, J=3.1, 6.3 Hz, 3H), 1.44-1.32 (m, 3H); [M+H]=490.23.

Example 297

3-[1-(5-Fluoro-6-methylpyridin-2-yl)-1H 4H 5H 6H-pyrrolo[3,4-c]pyrazole-5-carbonyl]-2-methoxy-4-{[(2S)-1 1 1-trifluoropropan-2-yl]oxy}benzonitrile

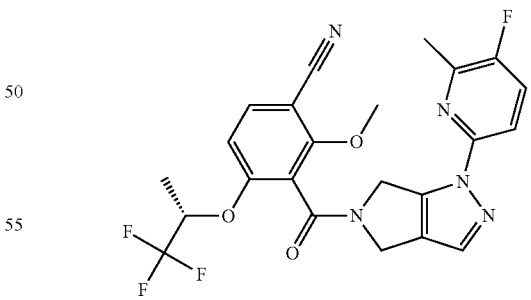

$^1$H NMR (400 MHz, DMSO-d$_6$) δ=7.99-7.88 (m, 1H), 7.87-7.77 (m, 1H), 7.77-7.63 (m, 1H), 7.56 (d, J=1.6 Hz, 1H), 7.32-7.12 (m, 1H), 5.63-5.40 (m, 1H), 5.11-4.87 (m, 1H), 4.76-4.50 (m, 1H), 4.39-4.13 (m, 2H), 4.01-3.90 (m, 3H), 2.30-2.15 (m, 1H), 1.46-1.28 (m, 2H); [M+H]=490.27.

Example 298

3-[2-(5-Fluoro-3-methylpyridin-2-yl)-2H 4H 5H 6H-pyrrolo[3,4-c]pyrazole-5-carbonyl]-2-methoxy-4-{[(2 S)-1 1 1-trifluoropropan-2-yl]oxy}benzonitrile

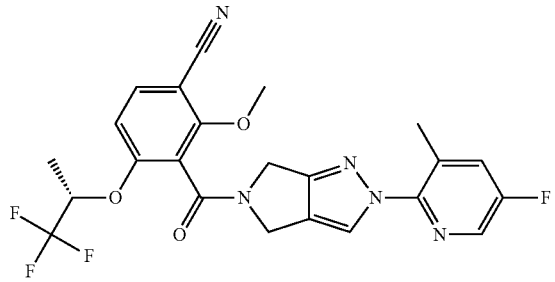 [SMILES: COc1c(C#N)ccc(O[C@@H](C)C(F)(F)F)c1C(=O)N1Cc2cn(-c3ccc(F)c(C)n3)nc2C1]

$^1$H NMR (400 MHz, DMSO-d$_6$) δ=1.34-1.43 (m, 3 H) 2.35-2.46 (m, 3 H) 3.95-4.00 (m, 3 H) 4.18-4.47 (m, 2 H) 4.58-4.76 (m, 2 H) 5.42-5.58 (m, 1 H) 7.16-7.33 (m, 1H) 7.81-7.97 (m, 2 H) 7.99-8.17 (m, 1 H) 8.35 (dd, J=7.04, 3.13 Hz, 1 H); [M+H]=490.27.

Example 299

2-Chloro-3-[2-(5-fluoro-3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

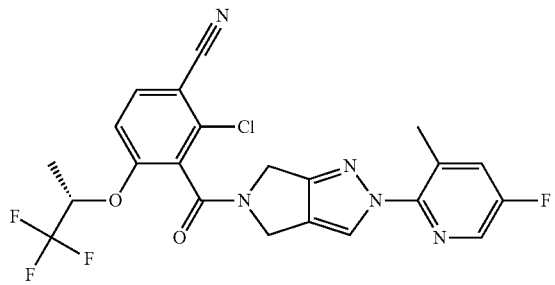 [SMILES: Cc1cc(F)cnc1-n1cc2c(n1)CN(C(=O)c1c(O[C@@H](C)C(F)(F)F)ccc(C#N)c1Cl)C2]

$^1$H NMR (400 MHz, DMSO-d$_6$) δ=1.38-1.44 (m, 3 H) 2.36-2.46 (m, 3 H) 4.15-4.45 (m, 2 H) 4.59-4.83 (m, 2 H) 5.51-5.65 (m, 1 H) 7.49-7.64 (m, 1 H) 7.82-7.95 (m, 1H) 8.02-8.18 (m, 2 H) 8.35 (dd, J=6.65, 2.74 Hz, 1 H); [M+H]=494.22.

Example 300

2-(4-Fluorophenyl)-5-(3-methanesulfonyl-2-methoxy-6-{[(2S)-1 1 1-trifluoropropan-2-yl]oxy}benzoyl)-2H 4H 5H 6H-pyrrolo[3,4-c]pyrazole

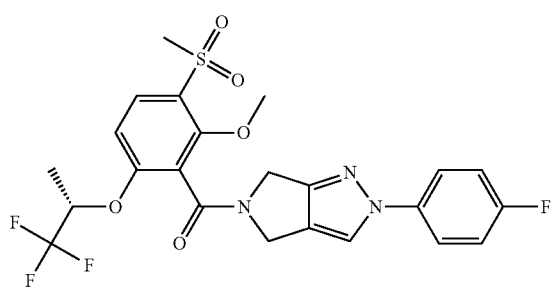 [SMILES: COc1c(S(C)(=O)=O)ccc(O[C@@H](C)C(F)(F)F)c1C(=O)N1Cc2cn(-c3ccc(F)cc3)nc2C1]

$^1$H NMR (400 MHz, DMSO-d$_6$) δ=8.43-8.20 (m, 1H), 7.92-7.86 (m, 1H), 7.85-7.75 (m, 2H), 7.68 (dd, J=4.5, 8.4 Hz, 1H), 7.41-7.25 (m, 3H), 5.56-5.42 (m, 1H), 4.80-4.56 (m, 2H), 4.52-4.12 (m, 2H), 4.04-3.76 (m, 3H), 1.53-1.27 (m, 3H); [M+H]=528.42.

Example 301

5-Fluoro-2-[5-(3-methanesulfonyl-2-methoxy-6-{[(2S)-1 1 1-trifluoropropan-2-yl]oxy}benzoyl)-2H 4H 5H 6H-pyrrolo[3,4-c]pyrazol-2-yl]pyridine

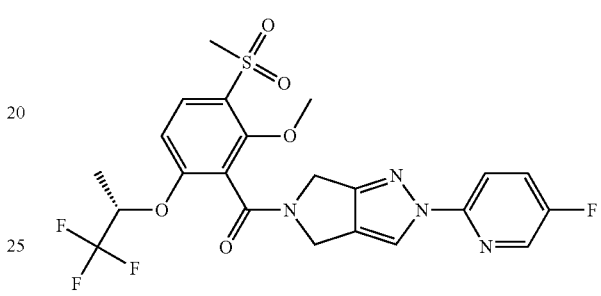

$^1$H NMR (400 MHz, DMSO-d$_6$) δ=8.53-8.26 (m, 2H), 8.04-7.77 (m, 3H), 7.39-7.24 (m, 1H), 5.64-5.35 (m, 1H), 4.85-4.19 (m, 4H), 3.95-3.83 (m, 3H), 1.48-1.24 (m, 3H); [M+H]=529.30.

Example 302

5-Fluoro-2-(5-{5-methanesulfonyl-2-[(1 1 1-trifluoropropan-2-yl)oxy]benzoyl}-2H 4H 5H 6H-pyrrolo[3,4-c]pyrazol-2-yl)pyridine

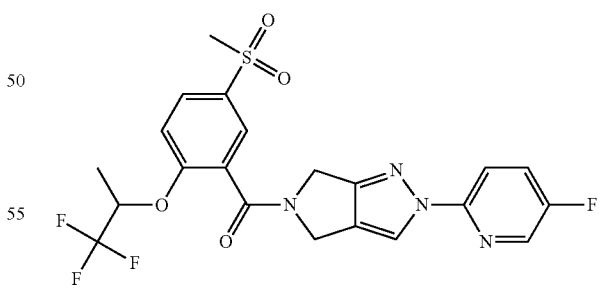

$^1$H NMR (400 MHz, DMSO-d$_6$) δ=8.51-8.28 (m, 2H), 8.08-7.79 (m, 3H), 7.59 (d, J=9.0 Hz, 1H), 5.53 (td, J=6.4, 12.6 Hz, 1H), 4.67 (d, J=16.0 Hz, 3H), 4.55-4.21 (m, 4H), 1.42 (dd, J=2.7, 6.3 Hz, 3H); [M+H]=499.3.

Example 303

2-(4-Fluorophenyl)-5-{5-methanesulfonyl-2-[(1 1 1-trifluoropropan-2-yl)oxy]benzoyl}-2H 4H 5H 6H-pyrrolo[3,4-c]pyrazole

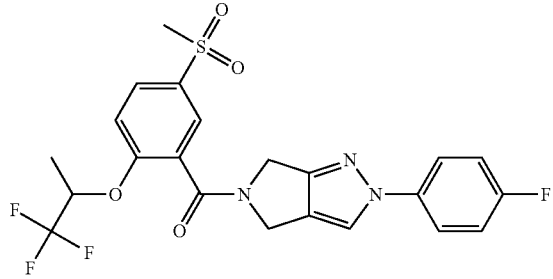 [SMILES: CC(Oc1ccc(S(C)(=O)=O)cc1C(=O)N1Cc2cn(-c3ccc(F)cc3)nc2C1)C(F)(F)F]

¹H NMR (400 MHz, DMSO-d₆) δ=8.38-8.16 (m, 1H), 8.00 (dd, J=2.2, 9.2 Hz, 1H), 7.90 (dd, J=2.3, 4.7 Hz, 1H), 7.88-7.69 (m, 2H), 7.59 (dd, J=1.6, 9.0 Hz, 1H), 7.40-7.18 (m, 2H), 5.53 (td, J=6.4, 12.6 Hz, 1H), 4.66 (d, J=6.3 Hz, 3H), 4.45-4.21 (m, 4H), 1.42 (dd, J=2.0, 6.3 Hz, 3H); [M+H]=498.2.

Example 304

2-Chloro-3-[2-(5-fluoro-4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

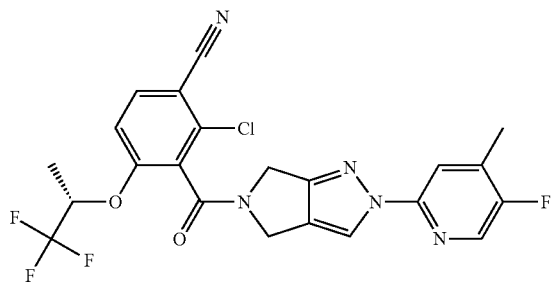 [SMILES: Cc1cc(-n2cc3c(n2)CN(C(=O)c2c(O[C@@H](C)C(F)(F)F)ccc(C#N)c2Cl)C3)ncc1F]

¹H NMR (400 MHz, DMSO-d₆) δ=8.46-8.26 (m, 2H), 8.18-8.09 (m, 1H), 7.90-7.74 (m, 1H), 7.57 (dd, J=2.0, 9.0 Hz, 1H), 5.57 (qd, J=6.1, 12.2 Hz, 1H), 4.79-4.57 (m, 2H), 4.48-4.14 (m, 2H), 2.41-2.30 (m, 3H), 1.47-1.32 (m, 3H); [M+H]=494.22.

Example 305

3-[2-(5-Fluoro-4-methylpyridin-2-yl)-2H 4H 5H 6H-pyrrolo[3,4-c]pyrazole-5-carbonyl]-2-methoxy-4-{[(2 S)-1 1 1-trifluoropropan-2-yl]oxy}benzonitrile

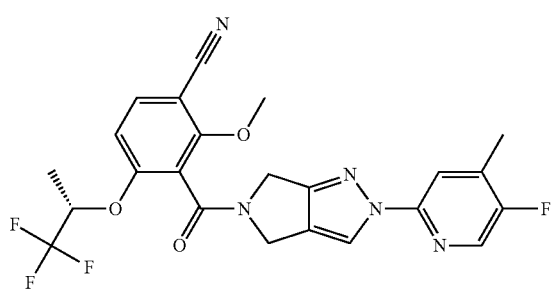

¹H NMR (400 MHz, DMSO-d₆) δ=8.44-8.26 (m, 2H), 7.95-7.89 (m, 1H), 7.88-7.74 (m, 1H), 7.29-7.17 (m, 1H), 5.57-5.43 (m, 1H), 4.76-4.55 (m, 2H), 4.50-4.16 (m, 2H), 3.98-3.94 (m, 3H), 2.39-2.30 (m, 3H), 1.43-1.29 (m, 3H); [M+H]=490.23.

Example 306

2-Methoxy-4-{[(2S)-1 1 1-trifluoropropan-2-yl]oxy}-3-[2-(trimethyl-1H-pyrazol-4-yl)-2H 4H 5H 6H-pyrrolo[3,4-c]pyrazole-5-carbonyl]benzonitrile

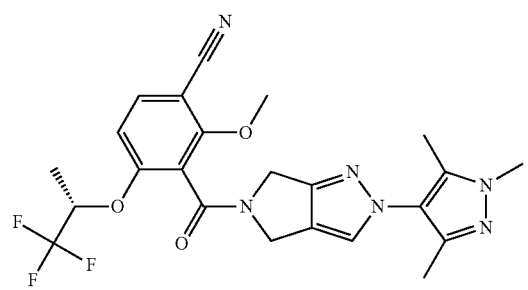 [SMILES: COc1c(C#N)ccc(O[C@@H](C)C(F)(F)F)c1C(=O)N1Cc2cn(-c3c(C)nn(C)c3C)nc2C1]

¹H NMR (400 MHz, DMSO-d₆) δ=7.96-7.86 (m, 1H), 7.70 (d, J=3.9 Hz, 1H), 7.58 (s, 1H), 7.29-7.16 (m, 1H), 5.49 (qd, J=6.4, 12.8 Hz, 1H), 4.74-4.53 (m, 2H), 4.43-4.16 (m, 2H), 3.98-3.94 (m, 3H), 3.68 (d, J=2.3 Hz, 3H), 2.12 (dd, J=2.5, 5.7 Hz, 3H), 2.01 (dd, J=2.5, 4.9 Hz, 3H), 1.38 (d, J=6.3 Hz, 3H); [M+H]=489.24.

Example 307

2-Chloro-4-{[(2S)-1 1 1-trifluoropropan-2-yl]oxy}-3-[2-(trimethyl-1H-pyrazol-4-yl)-2H 4H 5H 6H-pyrrolo[3,4-c]pyrazole-5-carbonyl]benzonitrile

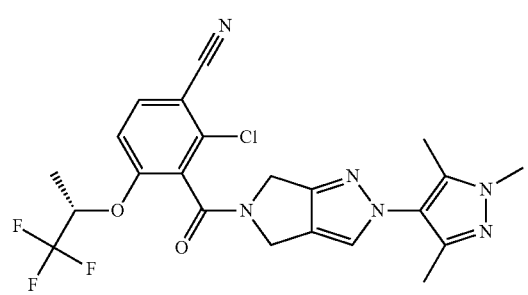 [SMILES: Cc1nn(C)c(C)c1-n1cc2c(n1)CN(C(=O)c1c(O[C@@H](C)C(F)(F)F)ccc(C#N)c1Cl)C2]

¹H NMR (400 MHz, DMSO-d₆) δ=8.17-8.07 (m, 1H), 7.73-7.52 (m, 2H), 5.62-5.51 (m, 1H), 4.72-4.59 (m, 2H), 4.40-4.13 (m, 2H), 3.68 (d, J=2.3 Hz, 3H), 2.18-1.97 (m, 6H), 1.41 (d, J=6.3 Hz, 3H); [M+H]=493.20.

Example 308

2-Methoxy-3-[2-(2-methylpyridin-4-yl)-2H 4H 5H 6H-pyrrolo[3,4-c]pyrazole-5-carbonyl]-4-(2 2 2-trifluoroethoxy)benzonitrile

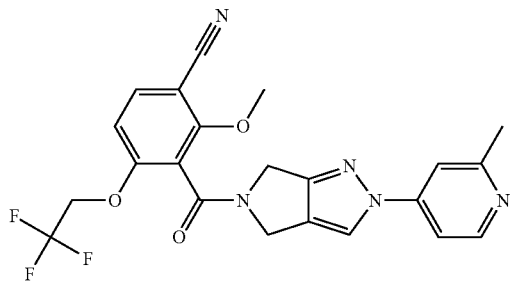 [SMILES: COc1c(C#N)ccc(OCC(F)(F)F)c1C(=O)N1Cc2cn(-c3ccnc(C)c3)nc2C1]

$^1$H NMR (400 MHz, DMSO-d$_6$) δ=3.88-4.00 (m, 3 H) 4.27-4.49 (m, 2 H) 4.57-4.81 (m, 2H) 4.97 (q, J=8.74 Hz, 2H) 7.15 (dd, J=8.80, 6.85 Hz, 1H) 7.54-7.75 (m, 2H) 7.93 (dd, J=9.00, 2.35 Hz, 1H) 8.36-8.58 (m, 2 H);[M+H]=458.2.

Example 309

2-Methoxy-3-[1-(2-methylpyridin-4-yl)-1H 4H 5H 6H-pyrrolo[3,4-c]pyrazole-5-carbonyl]-4-{[(2 S)-1 1 1-trifluoropropan-2-yl]oxy}benzonitrile

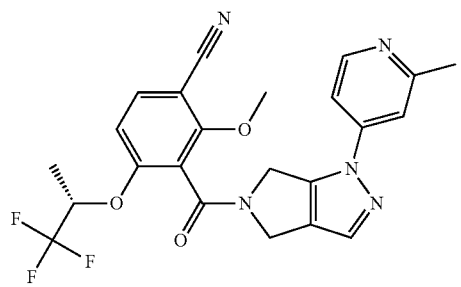 [SMILES: COc1c(C#N)ccc(O[C@@H](C)C(F)(F)F)c1C(=O)N1Cc2cnn(-c3ccnc(C)c3)c2C1]

$^1$H NMR (400 MHz, CD$_3$OD) δ=1.39-1.54 (m, 3H) 2.50-2.65 (m, 3 H) 4.09 (dd, J=6.06, 2.54 Hz, 3H) 4.21-4.47 (m, 2H) 4.88-5.35 (m, 3H) 7.15 (dt, J=9.00, 1.76 Hz, 1H) 7.26-7.55 (m, 2H) 7.56-7.62 (m, 1H) 7.69-7.83 (m, 1H) 8.34-8.53 (m, 1H); [M+H]=472.2.

Example 310

2-Chloro-3-[1-(2-methylpyridin-4-yl)-1H 4H 5H 6H-pyrrolo[3,4-c]pyrazole-5-carbonyl]-4-{[(2S)-1 1 1-trifluoropropan-2-yl]oxy}benzonitrile

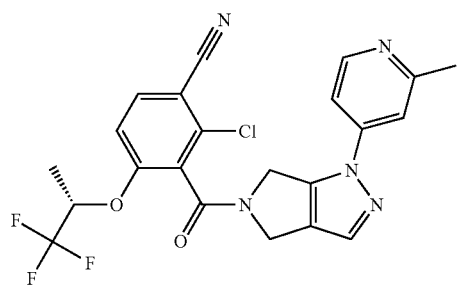 [SMILES: Cc1cc(-n2ncc3c2CN(C(=O)c2c(O[C@@H](C)C(F)(F)F)ccc(C#N)c2Cl)C3)ccn1]

$^1$H NMR (400 MHz, DMSO-d$_6$) δ=1.32-1.46 (m, 3H) 2.53 (s, 3H) 4.11-4.36 (m, 1H) 4.46-4.69 (m, 1H) 4.82-5.02 (m, 1H) 5.07-5.27 (m, 1H) 5.49-5.65 (m, 1H) 7.19 (dd, J=5.87, 1.96 Hz, 1H) 7.44-7.52 (m, 1H) 7.54-7.61 (m, 1H) 7.61-7.80 (m, 1H) 8.09-8.18 (m, 1H) 8.38-8.53 (m, 1H); [M+H]=476.2.

Example 311

3-[2-(5-Fluoropyridin-3-yl)-2H 4H 5H 6H-pyrrolo[3,4-c]pyrazole-5-carbonyl]-2-methoxy-4-(2 2 2-trifluoroethoxy)benzonitrile

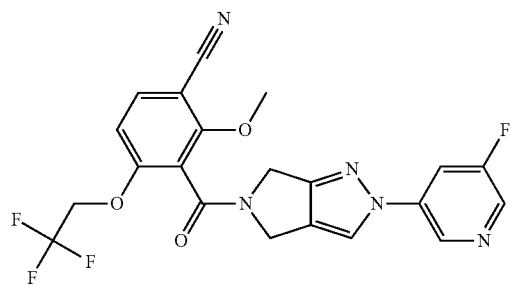 [SMILES: COc1c(C#N)ccc(OCC(F)(F)F)c1C(=O)N1Cc2cn(-c3cncc(F)c3)nc2C1]

$^1$H NMR (400 MHz, CDCl$_3$) δ=8.80-8.37 (m, 2H), 7.90-7.72 (m, 1H), 7.66 (dd, J=2.9, 8.8 Hz, 1H), 6.78 (dd, J=2.5, 8.8 Hz, 1H), 4.97-4.77 (m, 2H), 4.58-4.29 (m, 4H), 4.13 (d, J=2.3 Hz, 3H); [M+H]=462.1.

Example 312

3-[2-(3-Fluoropyridin-2-yl)-2H 4H 5H 6H-pyrrolo[3,4-c]pyrazole-5-carbonyl]-2-methoxy-4-(2 2 2-trifluoroethoxy)benzonitrile

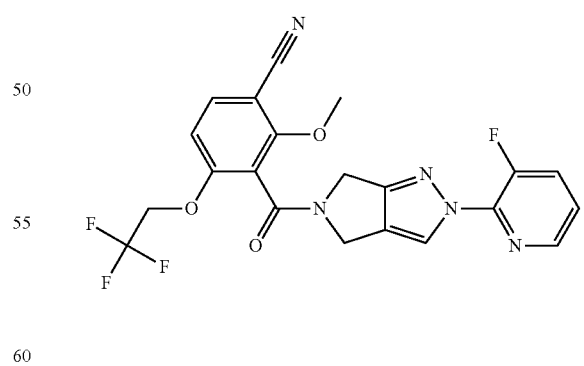

$^1$H NMR (400 MHz, CDCl$_3$) δ=8.36-8.00 (m, 2H), 7.73-7.57 (m, 2H), 7.36-7.27 (m, 1H), 6.77 (dd, J=4.3, 9.0 Hz, 1H), 4.99-4.78 (m, 2H), 4.54-4.32 (m, 4H), 4.13 (d, J=1.2 Hz, 3H); [M+H]=462.2.

Example 313

3-[2-(5-Fluoro-2-methoxypyridin-3-yl)-2H 4H 5H 6H-pyrrolo[3,4-c]pyrazole-5-carbonyl]-2-methoxy-4-{[(2 S)-1 1 1-trifluoropropan-2-yl]oxy}benzonitrile

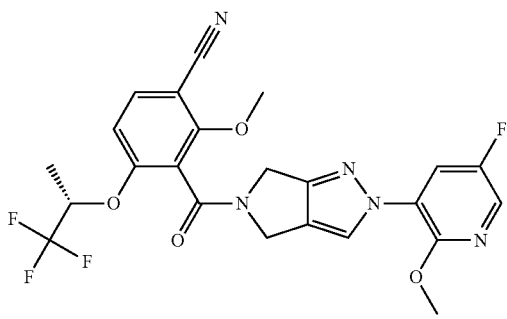 [SMILES: COc1ncc(F)cc1-n1cc2c(n1)CN(C(=O)c1c(O[C@@H](C)C(F)(F)F)ccc(C#N)c1OC)C2]

¹H NMR (400 MHz, CDCl₃) δ=8.20-8.03 (m, 1H), 8.02-7.89 (m, 2H), 7.67-7.59 (m, 1H), 6.87-6.74 (m, 1H), 4.95-4.70 (m, 3H), 4.49-4.23 (m, 2H), 4.12 (d, J=2.0 Hz, 3H), 4.06 (d, J=13.3 Hz, 3H), 1.55-1.47 (m, 3H); [M+H]=506.1.

Example 314

2-Chloro-3-[2-(5-fluoro-2-methoxypyridin-3-yl)-2H 4H 5H 6H-pyrrolo[3,4-c]pyrazole-5-carbonyl]-4-{[(2S)-1 1 1-trifluoropropan-2-yl]oxy}benzonitrile

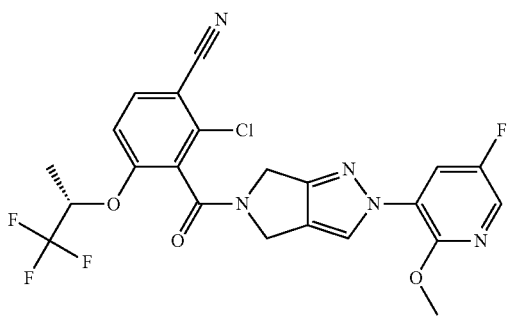 [SMILES: COc1ncc(F)cc1-n1cc2c(n1)CN(C(=O)c1c(O[C@@H](C)C(F)(F)F)ccc(C#N)c1Cl)C2]

¹H NMR (400 MHz, CDCl₃) δ=8.23-8.03 (m, 1H), 8.03-7.85 (m, 2H), 7.80-7.69 (m, 1H), 7.12-6.94 (m, 1H), 4.98-4.73 (m, 3H), 4.47-4.29 (m, 2H), 4.06 (d, J=13.3 Hz, 3H), 1.56-1.47 (m, 3H); [M+H]=510.1.

Example 315

3-[1-(5-Fluoro-6-methoxypyridin-3-yl)-1H 4H 5H 6H-pyrrolo[3,4-c]pyrazole-5-carbonyl]-2-methoxy-4-{[(2 S)-1 1 1-trifluoropropan-2-yl]oxy}benzonitrile

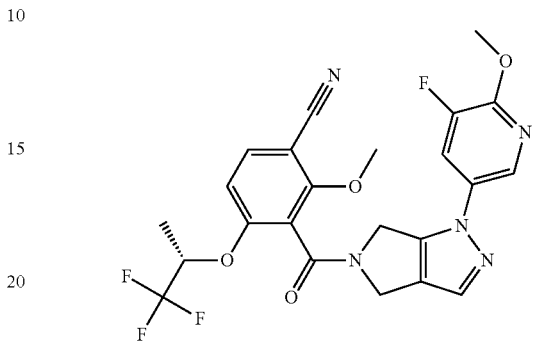

¹H NMR (400 MHz, CDCl₃) δ=8.14 (d, J=2.3 Hz, 1H), 7.83-7.73 (m, 1H), 7.70-7.40 (m, 2H), 6.89-6.76 (m, 1H), 5.13-4.95 (m, 1H), 4.89-4.69 (m, 2H), 4.66-4.45 (m, 1H), 4.43-4.23 (m, 1H), 4.22-3.91 (m, 6H), 1.53-1.48 (m, 3H); [M+H]=506.27.

Example 316

3-[2-(5-Fluoro-6-methoxypyridin-3-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile

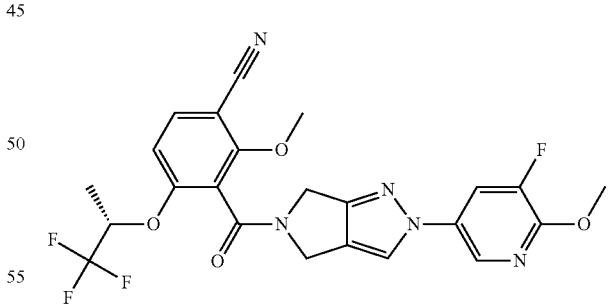

¹H NMR (400 MHz, CDCl₃) δ=8.23-8.14 (m, 1H), 7.79-7.68 (m, 1H), 7.68-7.52 (m, 2H), 6.85-6.74 (m, 1H), 4.94-4.72 (m, 3H), 4.47-4.27 (m, 2H), 4.12 (d, J=2.3 Hz, 3H), 4.06 (s, 3H), 1.54-1.48 (m, 3H); [M+H]=506.00.

Example 317

4-(Cyclopropylmethoxy)-3-[2-(4-fluorophenyl)-2H 4H 5H 6H-pyrrolo[3,4-c]pyrazole-5-carbonyl]-2-methoxybenzonitrile

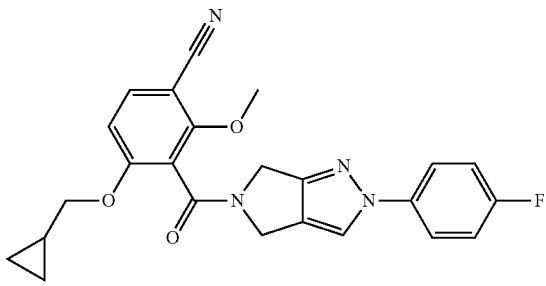

$^1$H NMR (400 MHz, CDCl$_3$) δ=7.72-7.51 (m, 4H), 7.14 (dt, J=2.9, 8.5 Hz, 2H), 6.73 (dd, J=1.8, 8.8 Hz, 1H), 4.86 (d, J=18.4 Hz, 2H), 4.50-4.34 (m, 2H), 4.09 (d, J=2.0 Hz, 3H), 3.94 (d, J=6.7 Hz, 2H), 1.27-1.14 (m, 1H), 0.65-0.49 (m, 2H), 0.39-0.18 (m, 2H); [M+H]=433.23.

Example 318

4-(Cyclopropylmethoxy)-3-[2-(5-fluoropyridin-2-yl)-2H 4H 5H 6H-pyrrolo[3,4-c]pyrazole-5-carbonyl]-2-methoxybenzonitrile

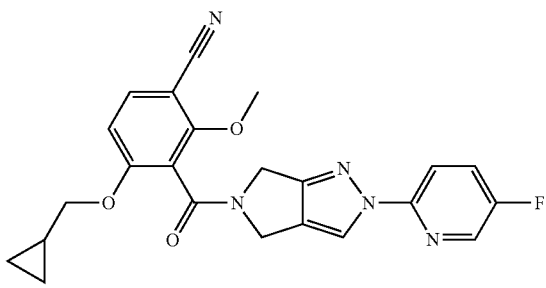 [SMILES: COc1c(C#N)ccc(OCC2CC2)c1C(=O)N1Cc2cn(-c3ccc(F)cn3)nc2C1]

$^1$H NMR (400 MHz, CDCl$_3$) δ=8.37-8.17 (m, 2H), 8.00-7.76 (m, 1H), 7.66-7.46 (m, 2H), 6.73 (dd, J=1.4, 8.8 Hz, 1H), 4.96-4.74 (m, 2H), 4.49-4.31 (m, 2H), 4.10 (s, 3H), 3.94 (d, J=6.7 Hz, 2H), 1.28-1.13 (m, 1H), 0.62-0.46 (m, 2H), 0.37-0.22 (m, 2H); [M+H]=434.22.

Example 319

4-(Cyclopropylmethoxy)-3-[2-(5-fluoropyridin-3-yl)-2H 4H 5H 6H-pyrrolo[3,4-c]pyrazole-5-carbonyl]-2-methoxybenzonitrile

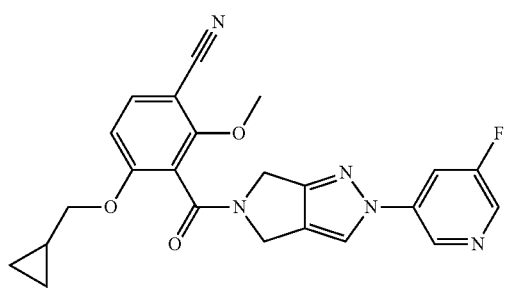 [SMILES: COc1c(C#N)ccc(OCC2CC2)c1C(=O)N1Cc2cn(-c3cncc(F)c3)nc2C1]

$^1$H NMR (400 MHz, CDCl$_3$) δ=8.82-8.36 (m, 2H), 7.86-7.63 (m, 2H), 7.59 (dd, J=2.9, 8.8 Hz, 1H), 6.74 (dd, J=2.2, 8.8 Hz, 1H), 4.87 (d, J=16.0 Hz, 2H), 4.51-4.35 (m, 2H), 4.10 (d, J=2.0 Hz, 3H), 3.94 (d, J=6.7 Hz, 2H), 1.31-1.13 (m, 1H), 0.66-0.49 (m, 2H), 0.39-0.23 (m, 2H); [M—HH]=434.14.

Example 320

4-(2 2-Dimethylpropoxy)-3-[2-(5-fluoropyridin-2-yl)-2H 4H 5H 6H-pyrrolo[3,4-c]pyrazole-5-carbonyl]-2-methoxybenzonitrile

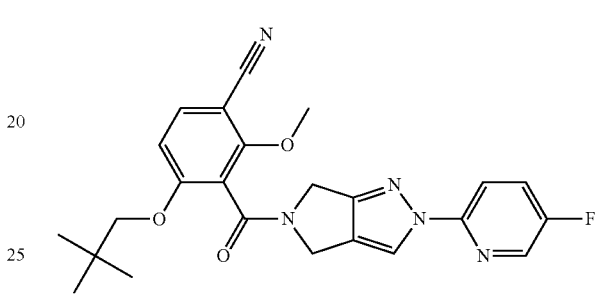

$^1$H NMR (400 MHz, CDCl$_3$) δ=8.37-8.16 (m, 2H), 7.97-7.80 (m, 1H), 7.65-7.48 (m, 2H), 6.72 (dd, J=1.6, 8.6 Hz, 1H), 4.95-4.75 (m, 2H), 4.47-4.31 (m, 2H), 4.11 (s, 3H), 3.72-3.59 (m, 2H), 0.93 (d, J=1.6 Hz, 9H); [M+H]=450.37.

Example 321

4-(2 2-Dimethylpropoxy)-3-[2-(5-fluoropyridin-3-yl)-2H 4H 5H 6H-pyrrolo[3,4-c]pyrazole-5-carbonyl]-2-methoxybenzonitrile

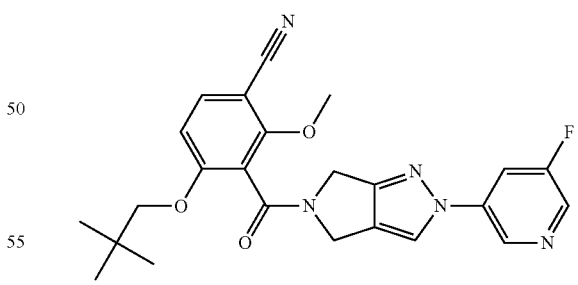

$^1$H NMR (400 MHz, CDCl$_3$) δ=8.75 (s, 1H), 8.47-8.37 (m, 1H), 7.87-7.64 (m, 2H), 7.64-7.53 (m, 1H), 6.73 (dd, J=2.3, 8.6 Hz, 1H), 5.07-4.70 (m, 2H), 4.57-4.24 (m, 2H), 4.11 (d, J=2.0 Hz, 3H), 3.72-3.62 (m, 2H), 0.94 (d, J=3.5 Hz, 9H); [M+H]=450.0.

Example 322

2-Methoxy-3-{2-phenyl-2H 4H 5H 6H-pyrrolo[3,4-c]pyrazole-5-carbonyl}-4-{[(2S)-1 1 1-trifluoropropan-2-yfloxy}benzonitrile

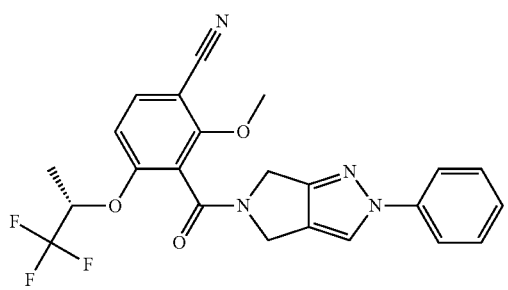 [SMILES: COc1c(C#N)ccc(O[C@@H](C)C(F)(F)F)c1C(=O)N1Cc2cn(-c3ccccc3)nc2C1]

$^1$H NMR (400 MHz, CDCl$_3$) δ=7.80-7.57 (m, 4H), 7.53-7.42 (m, 2H), 7.36-7.27 (m, 1H), 6.89-6.67 (m, 1H), 4.97-4.70 (m, 3H), 4.55-4.27 (m, 2H), 4.13 (d, J=1.6 Hz, 3H), 1.58-1.40 (m, 3H); [M+H]=457.1.

Example 323

2-Methoxy-3-{2-phenyl-2H 4H 5H 6H-pyrrolo[3,4-c]pyrazole-5-carbonyl}-4-(propan-2-yloxy)benzonitrile

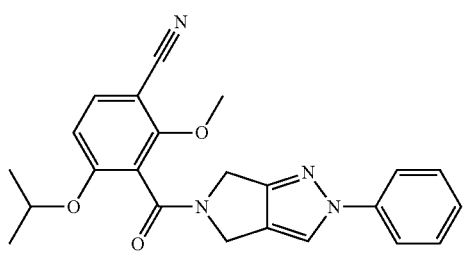 [SMILES: COc1c(C#N)ccc(OC(C)C)c1C(=O)N1Cc2cn(-c3ccccc3)nc2C1]

$^1$H NMR (400 MHz, CDCl$_3$) δ=7.79-7.49 (m, 4H), 7.49-7.27 (m, 3H), 6.74 (dd, J=2.3, 8.6 Hz, 1H), 4.98-4.77 (m, 2H), 4.64 (td, J=6.0, 11.8 Hz, 1H), 4.48-4.25 (m, 2H), 4.16-3.99 (m, 3H), 1.44-1.24 (m, 6H); [M+H]=403.09.

Example 324

3-[2-(5-Fluoropyridin-2-yl)-2H 4H 5H 6H-pyrrolo[3,4-c]pyrazole-5-carbonyl]-2-methoxy-4-(propan-2-yloxy)benzonitrile

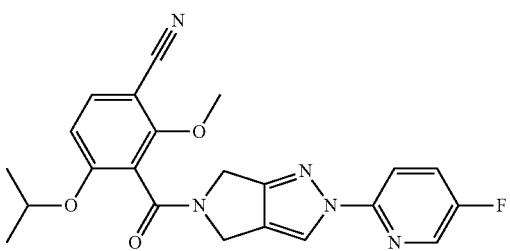

$^1$H NMR (400 MHz, CDCl$_3$) δ=8.38-8.16 (m, 2H), 8.02-7.80 (m, 1H), 7.61-7.46 (m, 2H), 6.74 (d, J=8.6 Hz, 1H), 4.92-4.76 (m, 2H), 4.64 (td, J=5.9, 12.0 Hz, 1H), 4.49-4.25 (m, 2H), 4.10 (s, 3H), 1.40-1.25 (m, 6H); [M+H]=422.21.

Example 325

3-[2-(5-Fluoropyridin-3-yl)-2H 4H 5H 6H-pyrrolo[3,4-c]pyrazole-5-carbonyl]-2-methoxy-4-(propan-2-yloxy)benzonitrile

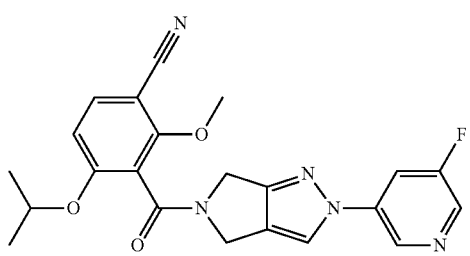 [SMILES: COc1c(C#N)ccc(OC(C)C)c1C(=O)N1Cc2cn(-c3cncc(F)c3)nc2C1]

$^1$H NMR (400 MHz, CDCl$_3$) δ=8.81-8.38 (m, 2H), 7.88-7.65 (m, 2H), 7.58 (dd, J=3.1, 9.0 Hz, 1H), 6.87-6.63 (m, 1H), 4.95-4.78 (m, 2H), 4.65 (dtd, J=2.5, 6.1, 12.2 Hz, 1H), 4.50-4.28 (m, 2H), 4.10 (d, J=2.0 Hz, 3H), 1.34 (ddd, J=1.6, 6.1, 9.2 Hz, 6H); [M+H]=422.1.

Example 326

2-Methoxy-3-[2-(6-methylpyridin-2-yl)-2H 4H 5H 6H-pyrrolo[3,4-c]pyrazole-5-carbonyl]-4-(propan-2-yloxy)benzonitrile

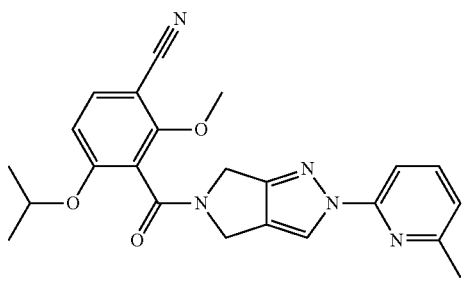 [SMILES: COc1c(C#N)ccc(OC(C)C)c1C(=O)N1Cc2cn(-c3cccc(C)n3)nc2C1]

$^1$H NMR (400 MHz, CDCl$_3$) δ=8.49-8.24 (m, 1H), 7.74-7.49 (m, 3H), 7.10-6.97 (m, 1H), 6.74 (d, J=9.0 Hz, 1H), 4.93-4.78 (m, 2H), 4.64 (td, J=6.1, 12.1 Hz, 1H), 4.50-4.24 (m, 2H), 4.10 (s, 3H), 2.54 (d, J=4.3 Hz, 3H); [M+H]=418.14.

Example 327

2-Chloro-3-{2-phenyl-2H 4H 5H 6H-pyrrolo[3,4-c]pyrazole-5-carbonyl}-4-{[(2S)-1 1 1-trifluoropropan-2-yl]oxy}benzonitrile

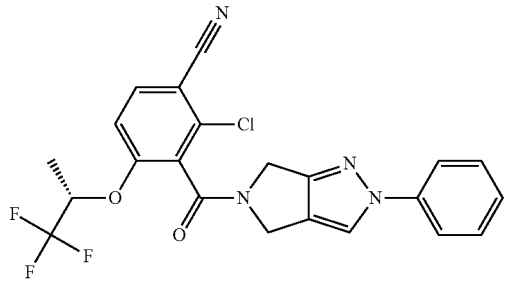 [SMILES: C[C@H](Oc1ccc(C#N)c(Cl)c1C(=O)N1Cc2cn(-c3ccccc3)nc2C1)C(F)(F)F]

¹H NMR (400 MHz, CDCl₃) δ=7.81-7.59 (m, 4H), 7.51-7.27 (m, 3H), 7.11-6.96 (m, 1H), 5.02-4.66 (m, 3H), 4.51-4.25 (m, 2H), 1.58-1.48 (m, 3H); [M+H]=461.20.

Example 328

2-Methoxy-3-[2-(2-methylpyridin-4-yl)-2H 4H 5H 6H-pyrrolo[3,4-c]pyrazole-5-carbonyl]-4-(propan-2-yloxy)benzonitrile

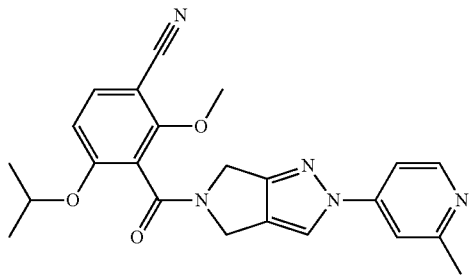 [SMILES: COc1c(C#N)ccc(OC(C)C)c1C(=O)N1Cc2cn(-c3ccnc(C)c3)nc2C1]

¹H NMR (400 MHz, CDCl₃) δ=8.53 (dd, J=2.0, 5.9 Hz, 1H), 7.90-7.70 (m, 2H), 7.62-7.55 (m, 1H), 7.55-7.46 (m, 1H), 7.46-7.37 (m, 1H), 6.75 (dd, J=1.2, 9.0 Hz, 1H), 4.94-4.76 (m, 2H), 4.72-4.59 (m, 1H), 4.48-4.29 (m, 2H), 4.11-4.08 (m, 3H), 2.67 (d, J=2.7 Hz, 3H), 1.41-1.30 (m, 6H); [M+H]=418.14.

Example 329

4-(2 2-Difluoroethoxy)-2-methoxy-3-{2-phenyl-2H 4H 5H 6H-pyrrolo{3,4-c]pyrazole-5-carbonyl}benzonitrile

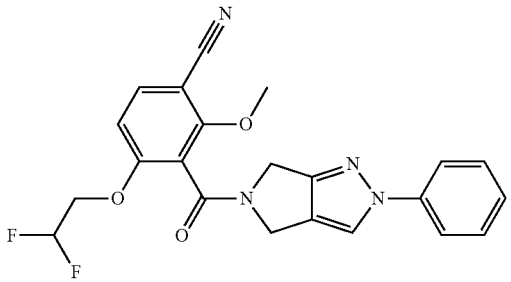 [SMILES: COc1c(C#N)ccc(OCC(F)F)c1C(=O)N1Cc2cn(-c3ccccc3)nc2C1]

¹H NMR (400MHz, CDCl₃) δ=7.79-7.57 (m, 4H), 7.52-7.27 (m, 3H), 6.76 (d, J=9.0 Hz, 1H), 6.25-5.85 (m, 1H), 4.94-4.78 (m, 2H), 4.49-4.23 (m, 4H), 4.21-4.01 (m, 3H); [M+H]=425.1.

Example 330

4-(2 2-Difluoroethoxy)-3-[2-(5-fluoropyridin-2-yl)-2H 4H 5H 6H-pyrrolo[3,4-c]pyrazole-5-carbonyl]-2-methoxybenzonitrile

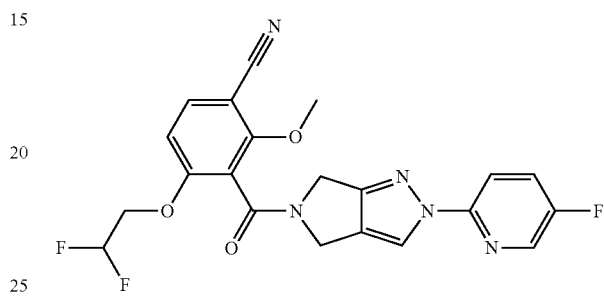

¹H NMR (400 MHz, CDCl₃) δ=8.39-8.18 (m, 2H), 7.98-7.79 (m, 1H), 7.64 (dd, J=2.5, 8.8 Hz, 1H), 7.53 (dddd, J=2.7, 7.6, 9.0, 13.5 Hz, 1H), 6.76 (dd, J=1.2, 8.6 Hz, 1H), 6.23-5.84 (m, 1H), 4.84 (dd, J=2.2, 15.5 Hz, 2H), 4.49-4.23 (m, 4H), 4.11 (s, 3H); [M+H]=444.1.

Example 331

4-(2 2-Difluoroethoxy)-3-[2-(5-fluoropyridin-3-yl)-2H 4H 5H 6H-pyrrolo[3,4-c]pyrazole-5-carbonyl]-2-methoxybenzonitrile

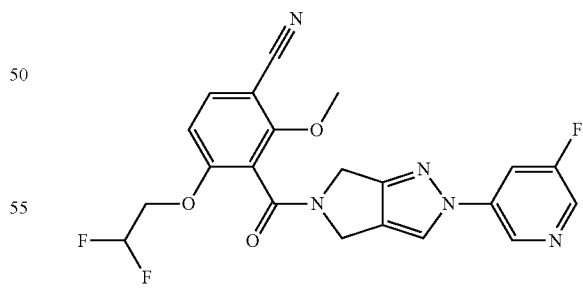

¹H NMR (400MHz, CDCl₃) δ=8.84-8.36 (m, 2H), 7.90-7.60 (m, 3H), 6.77 (d, J=9.0 Hz, 1H), 6.28-5.85 (m, 1H), 4.86 (dd, J=3.1, 15.7 Hz, 2H), 4.57-4.21 (m, 4H), 4.21-4.03 (m, 3H); [M+H]=444.2.

Example 332

4-(2 2-Difluoroethoxy)-2-methoxy-3-[2-(6-methyl-pyridin-2-yl)-2H 4H 5H 6H-pyrrolo[3,4-c]pyrazole-5-carbonyl]benzonitrile

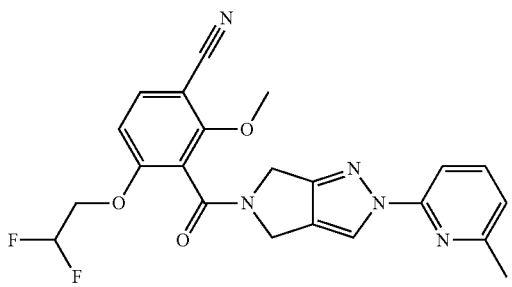 [SMILES: COc1c(C#N)ccc(OCC(F)F)c1C(=O)N1Cc2cn(-c3cccc(C)n3)nc2C1]

¹H NMR (400 MHz, CDCl₃) δ=8.48-8.29 (m, 1H), 7.76-7.58 (m, 3H), 7.10-6.98 (m, 1H), 6.76 (d, J=9.0 Hz, 1H), 6.26-5.85 (m, 2H), 4.92-4.75 (m, 2H), 4.51-4.21 (m, 4H), 4.16-4.01 (m, 3H), 2.54 (d, J=3.9 Hz, 3H); [M+H]=440.07.

Example 333

4-(2 2-Difluoroethoxy)-2-methoxy-3-[2-(2-methyl-pyridin-4-yl)-2H 4H 5H 6H-pyrrolo[3,4-c]pyrazole-5-carbonyl]benzonitrile

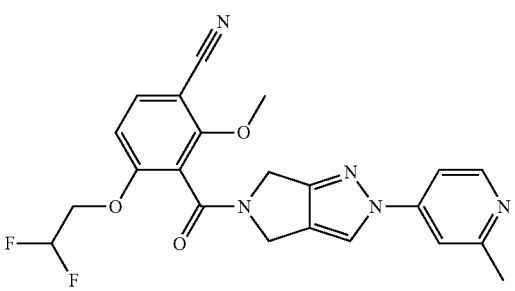 [SMILES: COc1c(C#N)ccc(OCC(F)F)c1C(=O)N1Cc2cn(-c3ccnc(C)c3)nc2C1]

¹H NMR (400MHz, CDCl₃) δ=8.55 (br s, 1H), 7.96-7.70 (m, 1H), 7.69-7.48 (m, 3H), 6.78 (d, J=8.6 Hz, 1H), 6.23-5.83 (m, 2H), 4.96-4.74 (m, 2H), 4.55-4.20 (m, 4H), 4.12 (dd, J=2.0, 3.1 Hz, 3H), 2.73 (d, J=3.5 Hz, 3H); [M+H]=439.99.

Example 334

3-{2-Phenyl-2H 4H 5H 6H-pyrrolo[3,4-c]pyrazole-5-carbonyl}-4-(propan-2-yloxy)benzonitrile

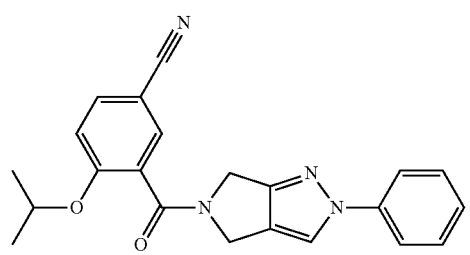 [SMILES: CC(C)Oc1ccc(C#N)cc1C(=O)N1Cc2cn(-c3ccccc3)nc2C1]

¹H NMR (400MHz, CDCl₃) δ=7.80-7.28 (m, 8H), 7.03 (d, .1 =8.6 Hz, 1H), 4.85 (d, J=19.6 Hz, 2H), 4.75-4.60 (m, 1H), 4.45 (d, J=12.9 Hz, 2H), 1.36 (d, J=5.9 Hz, 6H); [M+H]=373.22.

Example 335

3-[2-(5-Fluoropyridin-2-yl)-2H 4H 5H 6H-pyrrolo[3,4-c]pyrazole-5-carbonyl]-4-(propan-2-yloxy)benzonitrile

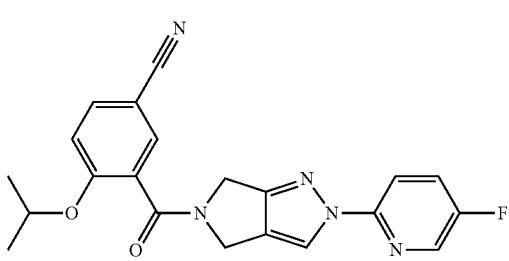 [SMILES: CC(C)Oc1ccc(C#N)cc1C(=O)N1Cc2cn(-c3ccc(F)cn3)nc2C1]

¹H NMR (400MHz, CDCl₃) δ=8.42-8.13 (m, 2H), 8.02-7.80 (m, 1H), 7.76-7.61 (m, 2H), 7.60-7.45 (m, 1H), 7.02 (d, J=8.6 Hz, 1H), 4.83 (d, J=15.3 Hz, 2H), 4.77-4.61 (m, 1H), 4.44 (br s, 2H), 1.35 (dd, J=2.3, 5.9 Hz, 6H); [M+H]=392.15.

Example 336

3-[2-(5-Fluoropyridin-3-yl)-2H 4H 5H 6H-pyrrolo[3,4-c]pyrazole-5-carbonyl]-4-(propan-2-yloxy)benzonitrile

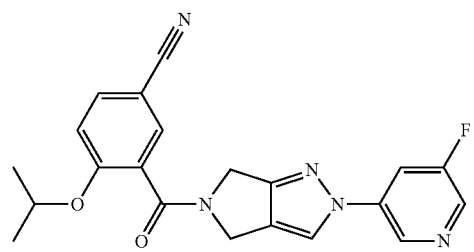 [SMILES: CC(C)Oc1ccc(C#N)cc1C(=O)N1Cc2cn(-c3cncc(F)c3)nc2C1]

¹H NMR (400MHz, CDCl₃) δ=8.75 (d, J=5.5 Hz, 1H), 8.41 (br s, 1H), 7.90-7.73 (m, 2H), 7.74-7.57 (m, 2H), 7.03 (d, J=8.6 Hz, 1H), 4.85 (d, J=14.9 Hz, 2H), 4.70 (qd, J=5.8, 11.5 Hz, 1H), 4.47 (d, J=11.3 Hz, 2H), 1.44-1.29 (m, 6H); [M+H]=392.33.

Example 337

3-[2-(2-Methylpyridin-4-yl)-2H 4H 5H 6H-pyrrolo[3,4-c]pyrazole-5-carbonyl]-4-(propan-2-yloxy)benzonitrile

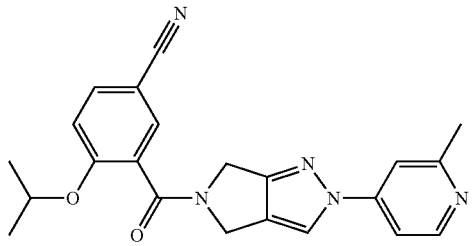 [SMILES: Cc1cc(-n2cc3c(n2)CN(C(=O)c2cc(C#N)ccc2OC(C)C)C3)ccn1]

¹H NMR (400MHz, CDCl₃) δ=8.54 (d, .1 =5.9 Hz, 1H), 7.96-7.76 (m, 1H), 7.74-7.58 (m, 2H), 7.59-7.41 (m, 2H), 7.04 (dd, J=1.2, 8.6 Hz, 1H), 4.85 (d, J=15.3 Hz, 2H), 4.76-4.62 (m, 1H), 4.47 (d, J=11.0 Hz, 2H), 2.68 (d, J=7.0 Hz, 3H), 1.36 (dd, J=2.0, 6.3 Hz, 6H); [M+H]=388.2.

Example 338

3-[2-(6-Methylpyridin-2-yl)-2H 4H 5H 6H-pyrrolo[3,4-c]pyrazole-5-carbonyl]-4-(propan-2-yloxy)benzonitrile

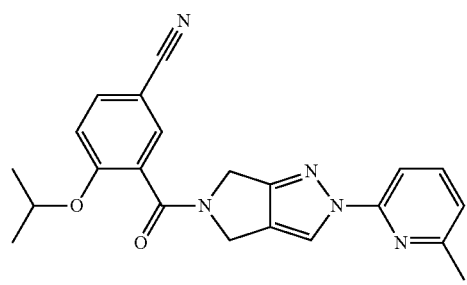 [SMILES: Cc1cccc(-n2cc3c(n2)CN(C(=O)c2cc(C#N)ccc2OC(C)C)C3)n1]

¹H NMR (400MHz, CDCl₃) δ=8.49-8.29 (m, 1H), 7.74-7.58 (m, 4H), 7.10-6.94 (m, 2H), 4.83 (d, J=18.4 Hz, 2H), 4.69 (td, J=6.1, 12.1 Hz, 1H), 4.44 (d, J=12.9 Hz, 2H), 2.54 (d, J=5.1 Hz, 3H), 1.35 (dd, J=3.3, 6.1 Hz, 6H); [M+H]=388.16.

Example 339

3-[2-(5-Fluoro-6-methylpyridin-2-yl)-2H 4H 5H 6H-pyrrolo[3,4-c]pyrazole-5-carbonyl]-4-(propan-2-yloxy)benzonitrile

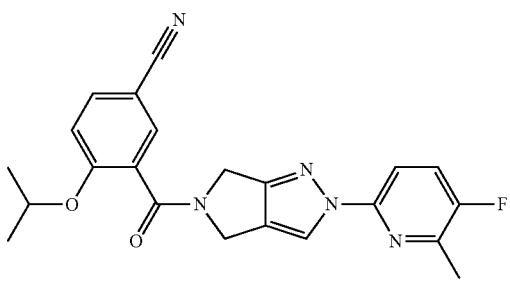 [SMILES: Cc1nc(-n2cc3c(n2)CN(C(=O)c2cc(C#N)ccc2OC(C)C)C3)ccc1F]

¹H NMR (400 MHz, CDCl₃) δ=8.42-8.18 (m, 1H), 7.79-7.59 (m, 3H), 7.43 (td, J=8.6, 13.7 Hz, 1H), 7.02 (d, J=8.6 Hz, 1H), 4.83 (d, J=16.4 Hz, 2H), 4.69 (td, J=5.9, 11.7 Hz, 1H), 4.44 (d, J=10.6 Hz, 2H), 2.51 (dd, J=2.9, 5.3 Hz, 3H), 1.35 (dd, J=2.9, 6.1 Hz, 6H); [M+H]=406.13.

Example 340

2-(4-Fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole

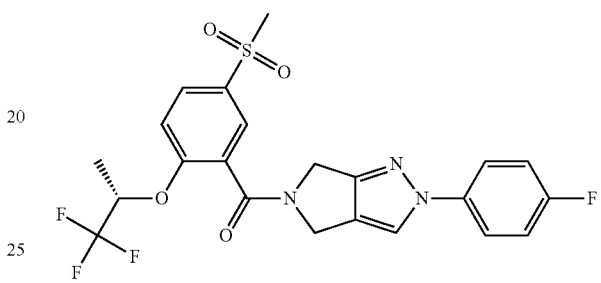

Rotamers observed: ¹H NMR (400 MHz, DMSO-d₆) δ=8.36-8.20 (m, 1H), 8.00 (dd, J=2.2, 9.2 Hz, 1H), 7.90 (dd, J=2.5, 4.5 Hz, 1H), 7.84-7.76 (m, 2H), 7.59 (dd, J=1.4, 9.2 Hz, 1H), 7.36-7.27 (m, 2H), 5.53 (td, J=6.5, 12.4 Hz, 1H), 4.66 (d, J=6.3 Hz, 2H), 4.43-4.26 (m, 2H), 3.23 (s, 3H), 1.42 (dd, J=1.6, 6.3 Hz, 3H); [M+H]=498.21.

Example 341

5-[2-(2 2-Dimethylpropoxy)-5-methanesulfonylbenzoyl]-2-(4-fluorophenyl)-2H 4H 5H 6H-pyrrolo[3,4-c]pyrazole

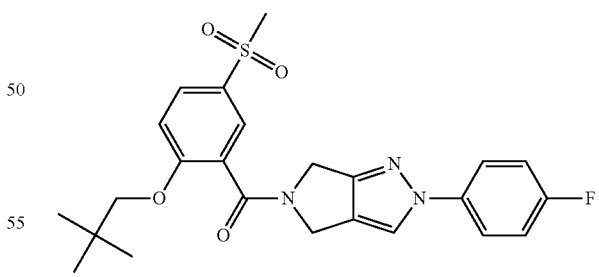

¹H NMR (400 MHz, DMSO-d₆) δ=8.37-8.18 (m, 1H), 7.95 (dd, J=2.5, 8.8 Hz, 1H), 7.86-7.75 (m, 3H), 7.38-7.27 (m, 3H), 4.67 (d, J=5.9 Hz, 2H), 4.36 (d, J=16.4 Hz, 2H), 3.81 (d, J=4.3 Hz, 2H), 3.20 (s, 3H), 0.87 (d, J=2.3 Hz, 9H); [M+H]=472.4.

Example 342

3-[2-(5-Fluoropyridin-2-yl)-2H 4H 5H 6H-pyrrolo[3,4-c]pyrazole-5-carbonyl]-4-{[(2S)-1 1 1-trifluoropropan-2-yl]oxy}benzonitrile

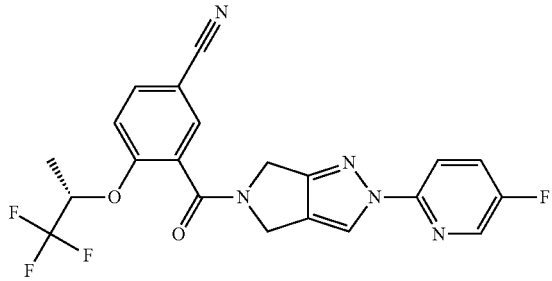 [SMILES: C[C@H](Oc1ccc(C#N)cc1C(=O)N1Cc2cn(-c3ccc(F)cn3)nc2C1)C(F)(F)F]

$^1$H NMR (400 MHz, DMSO-d$_6$) δ=8.48-8.44 (m, 1H), 8.43-8.30 (m, 1H), 8.00-7.82 (m, 3H), 7.54 (dd, J=1.6, 9.0 Hz, 1H), 5.52 (td, J=6.4, 12.6 Hz, 1H), 4.64 (d, J=16.8 Hz, 2H), 4.46-4.20 (m, 2H), 1.40 (dd, J=1.6, 6.3 Hz, 3H); [M+H]=446.04.

Example 343

3-[2-(5 4H 5H 6H-pyrrolo[3,4-c]pyrazole-5-carbonyl]-4-{[(2S)-1 1 1-trifluoropropan-2-yl]oxy}benzonitrile

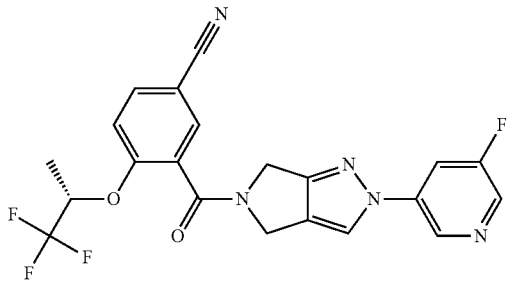 [SMILES: C[C@H](Oc1ccc(C#N)cc1C(=O)N1Cc2cn(-c3cncc(F)c3)nc2C1)C(F)(F)F]

$^1$H NMR (400 MHz, DMSO-d$_6$) δ=8.97 (dd, J=1.6, 10.6 Hz, 1H), 8.55-8.32 (m, 2H), 8.19 (tdd, J=2.3, 10.2, 16.4 Hz, 1H), 7.98 (dd, J=2.0, 9.0 Hz, 1H), 7.88 (dd, J=2.0, 7.0 Hz, 1H), 7.54 (dd, J=2.3, 9.0 Hz, 1H), 5.52 (td, J=6.4, 12.6 Hz, 1H), 4.66 (d, J=9.0 Hz, 2H), 4.49-4.25 (m, 2H), 1.40 (d, J=6.7 Hz, 3H); [M+H]=445.96.

Example 344

3-[2-(6-Methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

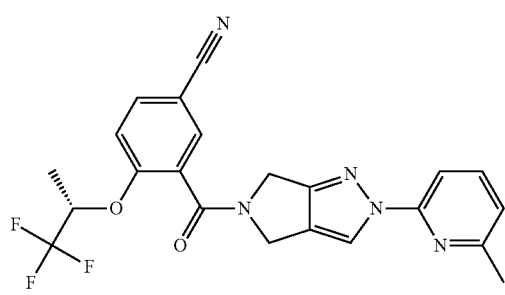 [SMILES: Cc1cccc(-n2cc3c(n2)CN(C(=O)c2cc(C#N)ccc2O[C@@H](C)C(F)(F)F)C3)n1]

$^1$H NMR (400 MHz, DMSO-d$_6$) δ=8.48-8.31 (m, 1H), 8.03-7.94 (m, 1H), 7.89 (dd, J=2.2, 11.5 Hz, 1H), 7.87-7.78 (m, 1H), 7.68-7.57 (m, 1H), 7.54 (dd, J=3.1, 9.0 Hz, 1H), 7.18 (d, J=7.4 Hz, 1H), 5.52 (td, J=6.4, 12.6 Hz, 1H), 4.73-4.56 (m, 2H), 4.47-4.21 (m, 2H), 1.40 (dd, J=1.8, 6.5 Hz, 3H); [M+H]=442.7.

Example 345

3-[2-(5-Fluoro-6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

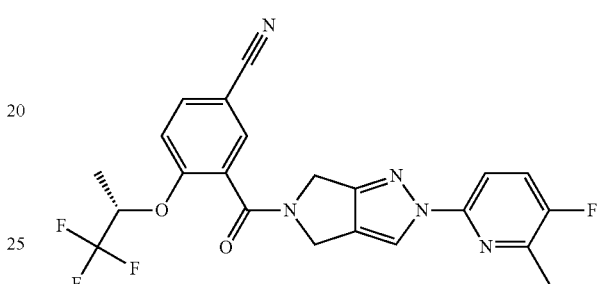

$^1$H NMR (400MHz, DMSO-d$_6$) δ=8.42-8.24 (m, 1H), 8.01-7.95 (m, 1H), 7.89 (dd, J=2.3, 11.0 Hz, 1H), 7.84-7.62 (m, 2H), 7.54 (dd, J=3.1, 9.0 Hz, 1H), 5.58-5.45 (m, 1H), 4.68-4.57 (m, 2H), 4.44-4.22 (m, 2H), 2.45 (dd, J=2.9, 6.5 Hz, 3H), 1.40 (dd, J=1.6, 6.3 Hz, 3H); [M+H]=460.5.

Example 346

3-[2-(5-Fluoro-3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

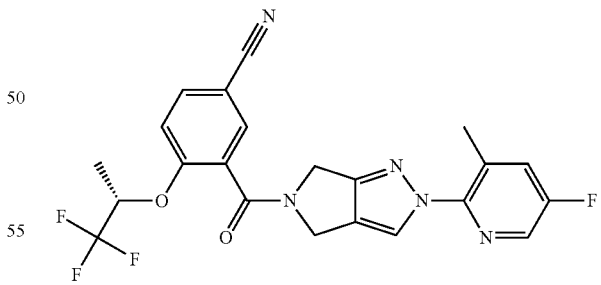

$^1$H NMR (400 MHz, DMSO-d$_6$) δ=8.34 (dd, J=2.7, 6.7 Hz, 1H), 8.12-8.00 (m, 1H), 8.00-7.94 (m, 1H), 7.92-7.84 (m, 2H), 7.54 (dd, J=5.5, 9.0 Hz, 1H), 5.61-5.45 (m, 1H), 4.64 (d, J=5.9 Hz, 2H), 4.46-4.20 (m, 2H), 2.46-2.35 (m, 3H), 1.41 (d, J=6.7 Hz, 3H); [M+H]=460.48.

Example 347

3-[2-(4-Methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile

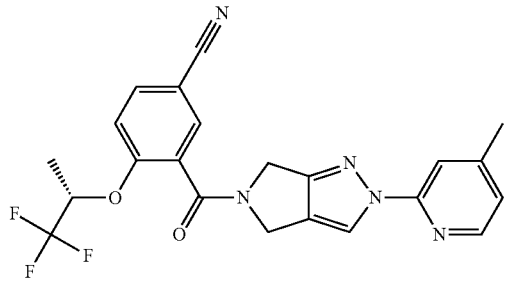 [SMILES: Cc1ccnc(-n2cc3c(n2)CN(C(=O)c2cc(C#N)ccc2O[C@@H](C)C(F)(F)F)C3)c1]

$^1$H NMR (400 MHz, DMSO-d$_6$) δ=8.48-8.33 (m, 1H), 8.28 (dd, J=5.3, 8.8 Hz, 1H), 8.02-7.94 (m, 1H), 7.89 (dd, J=2.3, 7.8 Hz, 1H), 7.76-7.64 (m, 1H), 7.54 (d, J=9.0 Hz, 1H), 7.20-7.07 (m, 1H), 5.53 (qd, J=6.5, 10.2 Hz, 1H), 4.72-4.58 (m, 2H), 4.46-4.22 (m, 2H), 2.38 (d, J=7.8 Hz, 3H), 1.40 (d, J=6.7 Hz, 3H); [M+H]=442.2.

Example 348

3-[2-(5-Fluoro-4-methylpyridin-2-yl)-2H 4H 5H 6H-pyrrolo[3,4-c]pyrazole-5-carbonyl]-4-{[(2 S)-1 1 1-trifluoropropan-2-yl]oxy}benzonitrile

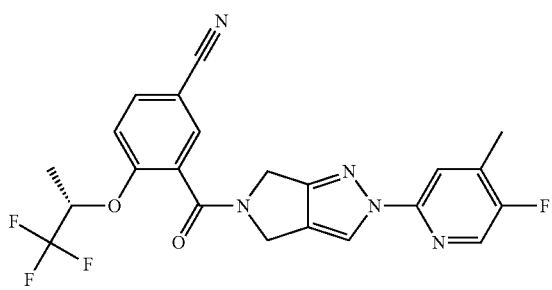 [SMILES: Cc1cc(-n2cc3c(n2)CN(C(=O)c2cc(C#N)ccc2O[C@@H](C)C(F)(F)F)C3)ncc1F]

$^1$H NMR (400 MHz, DMSO-d$_6$) δ=8.43-8.26 (m, 2H), 8.00-7.95 (m, 1H), 7.92-7.76 (m, 2H), 7.54 (d, J=9.0 Hz, 1H), 5.52 (qd, J=6.3, 10.2 Hz, 1H), 4.64 (d, J=15.3 Hz, 2H), 4.46-4.15 (m, 2H), 2.35 (dd, J=1.2, 7.8 Hz, 3H), 1.40 (d, J=6.3 Hz, 3H); [M+H]=460.17.

Example 349

3-[2-(Pyridin-2-yl)-2H 4H 5H 6H-pyrrolo[3,4-c]pyrazole-5-carbonyl]-4-{[(2 S)-1 1 1-trifluoropropan-2-yl]oxy}benzonitrile

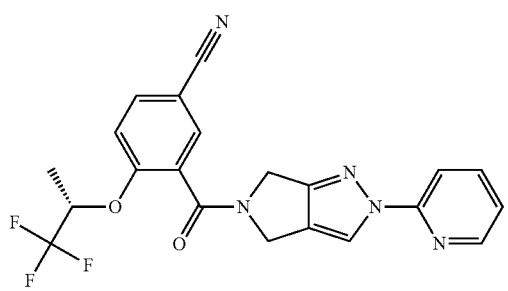 [SMILES: C[C@H](Oc1ccc(C#N)cc1C(=O)N1Cc2cn(-c3ccccn3)nc2C1)C(F)(F)F]

$^1$H NMR (400 MHz, DMSO-d$_6$) δ=8.54-8.35 (m, 2H), 8.07-7.73 (m, 4H), 7.54 (dd, J=1.6, 9.0 Hz, 1H), 7.40-7.25 (m, 1H), 5.52 (td, J=6.4, 12.6 Hz, 1H), 4.78-4.50 (m, 2H), 4.47-4.17 (m, 2H), 1.40 (dd, J=1.2, 6.3 Hz, 3H); [M+H]=428.59.

Example 350

5-(2-Cyclopentyl-5-methanesulfonylbenzoyl)-2-(4-fluorophenyl)-2H 4H 5H 6H-pyrrolo[3,4-c]pyrazole

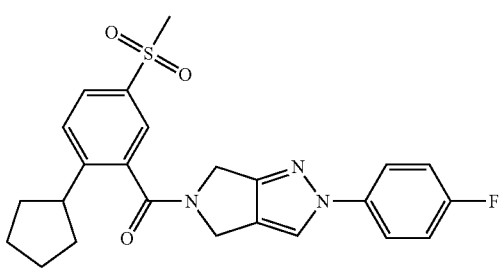 [SMILES: CS(=O)(=O)c1ccc(C2CCCC2)c(C(=O)N2Cc3cn(-c4ccc(F)cc4)nc3C2)c1]

Rotamers observed; $^1$H NMR (400 MHz, DMSO-d$_6$) δ=8.38-8.17 (m, 2H), 7.95-7.86 (m, 2H), 7.85-7.76 (m, 2H), 7.72 (dd, J=1.6, 8.2 Hz, 1H), 7.36-7.27 (m, 2H), 4.72 (d, J=7.8 Hz, 2H), 4.40-4.25 (m, 2H), 3.26-3.23 (m, 3H), 3.08 (d, J=8.6 Hz, 1H), 1.98 (br s, 2H), 1.77 (br s, 2H), 1.59 (br s, 4H); [M+H]=454.28.

Example 351

3-[2-(5-Fluoro-6-methylpyridin-3-yl)-2H 4H 5H 6H-pyrrolo[3,4-c]pyrazole-5-carbonyl]-4-{[(2 S)-1 1 1-trifluoropropan-2-yl]oxy}benzonitrile

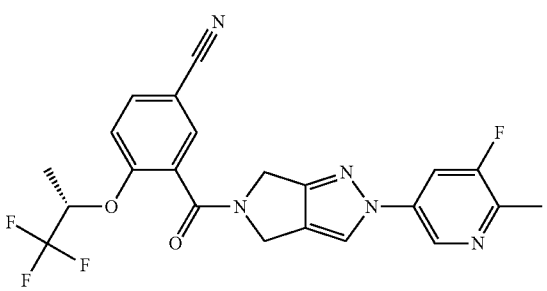 [SMILES: Cc1ncc(-n2cc3c(n2)CN(C(=O)c2cc(C#N)ccc2O[C@@H](C)C(F)(F)F)C3)cc1F]

$^1$H NMR (400 MHz, DMSO-d$_6$) δ=8.82 (dd, J=2.0, 11.3 Hz, 1H), 8.50-8.31 (m, 1H), 8.10 (ddd, J=2.2, 10.7, 16.1 Hz, 1H), 8.01-7.95 (m, 1H), 7.88 (dd, J=2.0, 7.4 Hz, 1H), 7.54 (dd, J=2.3, 9.0 Hz, 1H), 7.22-6.89 (m, 1H), 5.53 (td, J=6.4, 12.6 Hz, 1H), 4.65 (d, J=8.6 Hz, 2H), 4.47-4.22 (m, 2H), 2.45 (dd, J=1.6, 2.7 Hz, 3H), 1.40 (d, J=6.3 Hz, 3H); [M+H]=460.11.

Example 352

3-[2-(5-Fluoro-4-methylpyridin-3-yl)-2H 4H 5H 6H-pyrrolo[3,4-c]pyrazole-5-carbonyl]-4-{[(2 S)-1 1 1-trifluoropropan-2-yl]oxy}benzonitrile

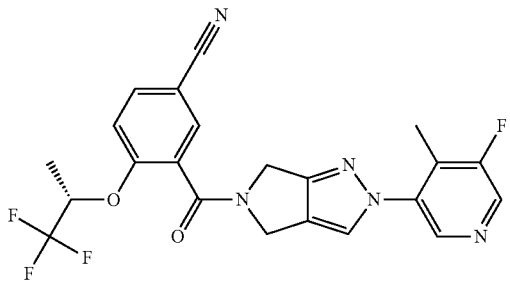 [SMILES: Cc1c(F)cncc1-n1cc2c(n1)CN(C(=O)c1cc(C#N)ccc1O[C@@H](C)C(F)(F)F)C2]

$^{1}$H NMR (400 MHz, DMSO-d$_{6}$) δ=8.60 (s, 1H), 8.49 (d, J=1.6 Hz, 1H), 8.09-7.94 (m, 2H), 7.89 (dd, J=2.2, 7.6 Hz, 1H), 7.54 (dd, J=4.7, 9.0 Hz, 1H), 5.62-5.45 (m, 1H), 4.66 (d, J=5.5 Hz, 2H), 4.45-4.22 (m, 2H), 2.22 (dd, J=2.2, 8.8 Hz, 3H), 1.41 (d, J=6.3 Hz, 3H); [M+H]=460.06.

Example 353

3-[2-(2-Methylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

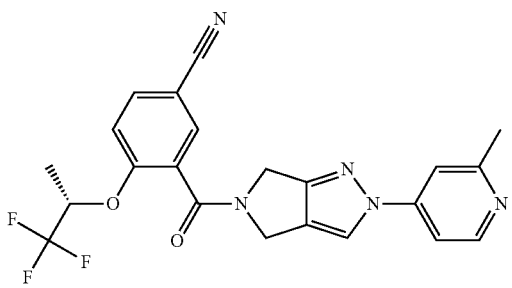 [SMILES: Cc1cc(-n2cc3c(n2)CN(C(=O)c2cc(C#N)ccc2O[C@@H](C)C(F)(F)F)C3)ccn1]

$^{1}$H NMR (400MHz, DMSO-d$_{6}$) δ=8.73-8.48 (m, 2H), 8.14-7.83 (m, 4H), 7.55 (dd, J=2.3, 9.0 Hz, 1H), 5.53 (td, J=6.0, 12.3 Hz, 1H), 4.79-4.60 (m, 2H), 4.48-4.28 (m, 2H), 2.62 (d, J=2.3 Hz, 3H), 1.40 (d, J=6.3 Hz, 3H); [M+H]=442.05.

Example 354

3-[2-(5-Fluoro-2-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile

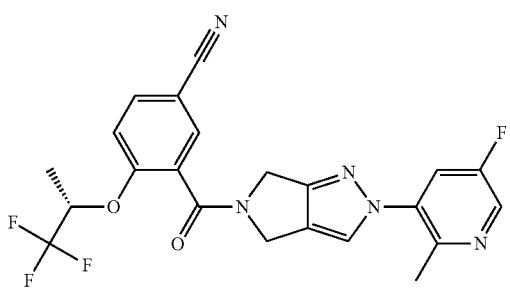 [SMILES: Cc1ncc(F)cc1-n1cc2c(n1)CN(C(=O)c1cc(C#N)ccc1O[C@@H](C)C(F)(F)F)C2]

$^{1}$H NMR (400 MHz, DMSO-d$_{6}$) δ=8.56 (d, J=2.3 Hz, 1H), 8.06 (s, 1H), 8.00-7.94 (m, 1H), 7.92-7.85 (m, 2H), 7.57-7.51 (m, 1H), 5.59-5.47 (m, 1H), 4.66 (d, J=4.7 Hz, 2H), 4.46-4.25 (m, 2H), 2.43 (dd, J=0.8, 7.8 Hz, 3H), 1.41 (d, J=6.3 Hz, 3H); [M+H]=460.6.

Example 355

5-(5-Methanesulfonyl-2-{[(2S)-1 1 1-trifluoropropan-2-yl]oxy}benzoyl)-2-phenyl-2H 4H 5H 6H-pyrrolo[3,4-c]pyrazole

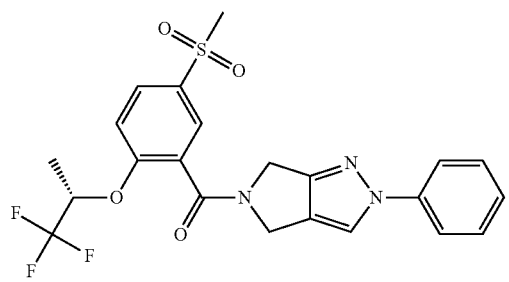

$^{1}$H NMR (400 MHz, CDCl$_{3}$) δ=8.04-7.97 (m, 2H), 7.76 (s, 1H), 7.67-7.60 (m, 2H), 7.50-7.42 (m, 2H), 7.33-7.27 (m, 1H), 7.19 (dd, J=1.6, 8.6 Hz, 1H), 4.90-4.78 (m, 3H), 4.53-4.36 (m, 2H), 3.07 (d, J=1.2 Hz, 3H), 1.54 (d, J=6.3 Hz, 3H); [M+H]=480.16.

Example 356

4-[5-(5-Methanesulfonyl-2-{[(2S)-1 1 1-trifluoropropan-2-yl]oxy}benzoyl)-2H 4H 5H 6H-pyrrolo[3,4-c]pyrazol-2-yl]-2-methylpyridine

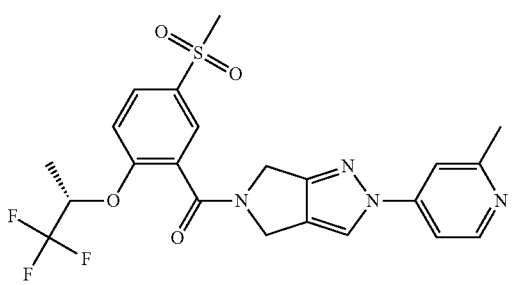 [SMILES: Cc1cc(-n2cc3c(n2)CN(C(=O)c2cc(S(C)(=O)=O)ccc2O[C@@H](C)C(F)(F)F)C3)ccn1]

$^{1}$H NMR (400 MHz, CDCl$_{3}$) δ=8.53 (dd, J=2.7, 5.9 Hz, 1H), 8.05-7.96 (m, 2H), 7.93-7.76 (m, 1H), 7.57 (dd, J=2.0, 18.0 Hz, 1H), 7.48 (ddd, J=2.3, 6.0, 8.1 Hz, 1H), 7.19 (d, J=8.6 Hz, 1H), 4.91-4.77 (m, 3H), 4.54-4.36 (m, 2H), 3.07 (s, 3H), 2.68 (d, J=3.1 Hz, 3H), 1.54 (d, J=6.3 Hz, 3H); [M+H]=495.13.

Example 357

2-[5-(5-Methanesulfonyl-2-{[(2S)-1 1 1-trifluoropropan-2-yl]oxy}benzoyl)-2H 4H 5H 6H-pyrrolo[3,4-c]pyrazol-2-yl]-4-methylpyridine

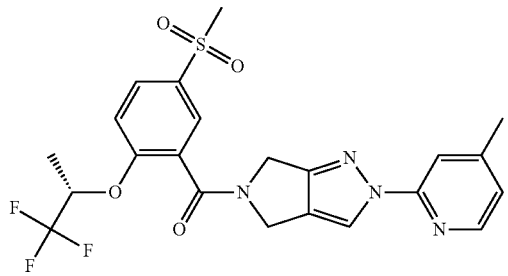 [SMILES: Cc1ccnc(-n2cc3c(n2)CN(C(=O)c2cc(S(C)(=O)=O)ccc2O[C@@H](C)C(F)(F)F)C3)c1]

¹H NMR (400 MHz, CDCl₃) δ=8.46-8.30 (m, 1H), 8.24 (dd, J=5.3, 6.8 Hz, 1H), 8.05-7.96 (m, 2H), 7.81-7.66 (m, 1H), 7.18 (d, J=8.6 Hz, 1H), 7.05-6.99 (m, 1H), 4.91-4.76 (m, 3H), 4.53-4.35 (m, 2H), 3.07 (s, 3H), 2.42 (d, J=10.6 Hz, 3H), 1.54 (d, J=6.7 Hz, 3H); [M+H]=495.13.

Example 358

3-Fluoro-5-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]pyridine

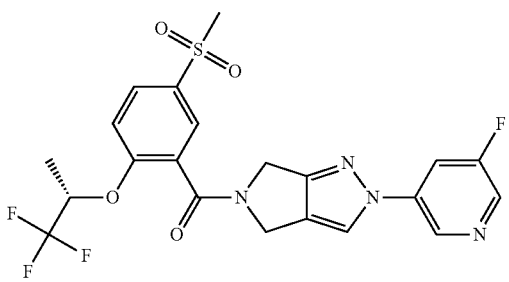 [SMILES: C[C@H](Oc1ccc(S(C)(=O)=O)cc1C(=O)N1Cc2cn(-c3cncc(F)c3)nc2C1)C(F)(F)F]

¹H NMR (400 MHz, CDCl₃) δ=8.77 (d, J=1.6 Hz, 1H), 8.44-8.40 (m, 1H), 8.06-7.96 (m, 2H), 7.90-7.78 (m, 2H), 7.69 (s, 1H), 7.19 (d, J=9.0 Hz, 1H), 4.93-4.78 (m, 3H), 4.54-4.38 (m, 2H), 3.08 (s, 3H), 1.55 (d, J=6.7 Hz, 3H); [M+H]=499.12.

Example 359

5-Fluoro-2-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]-4-methylpyridine

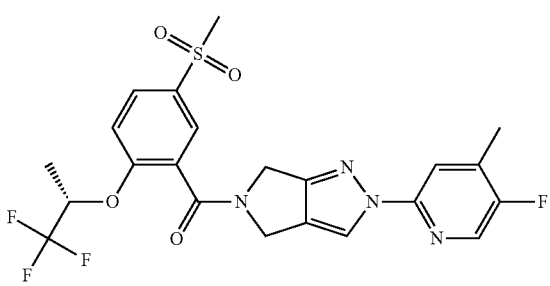 [SMILES: Cc1cc(-n2cc3c(n2)CN(C(=O)c2cc(S(C)(=O)=O)ccc2O[C@@H](C)C(F)(F)F)C3)ncc1F]

Rotamers observed: ¹H NMR (400 MHz, CDCl₃) δ=8.36-8.19 (m, 1H), 8.12 (d, J=7.0 Hz, 1H), 8.05-7.96 (m, 2H), 7.84-7.69 (m, 1H), 7.18 (d, J=8.6 Hz, 1H), 4.89-4.76 (m, 3H), 4.51-4.35 (m, 2H), 3.07 (s, 3H), 2.42-2.34 (m, 3H), 1.54 (d, J=6.7 Hz, 3H); [M−H]=513.18.

Example 360

2-[5-(5-Methanesulfonyl-2-{[(2S)-1 1 1-trifluoropropan-2-yl]oxy}benzoyl)-2H 4H 5H 6H-pyrrolo[3,4-c]pyrazol-2-yl]-6-methylpyridine

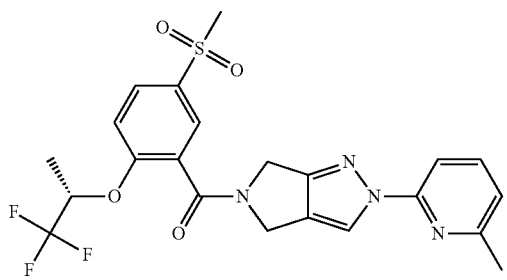 [SMILES: Cc1cccc(-n2cc3c(n2)CN(C(=O)c2cc(S(C)(=O)=O)ccc2O[C@@H](C)C(F)(F)F)C3)n1]

Rotamers observed: ¹H NMR (400 MHz, CDCl₃) δ=8.60-8.43 (m, 1H), 8.07-7.97 (m, 2H), 7.77-7.63 (m, 2H), 7.18 (d, J=8.6 Hz, 1H), 7.09-7.02 (m, 1H), 4.91-4.76 (m, 3H), 4.52-4.36 (m, 2H), 3.07 (d, J=2.0 Hz, 3H), 2.58 (d, J=3.1 Hz, 3H), 1.54 (d, J=6.3 Hz, 3H); [M+H]=495.21.

Example 361

5-Fluoro-2-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]-3-methylpyridine

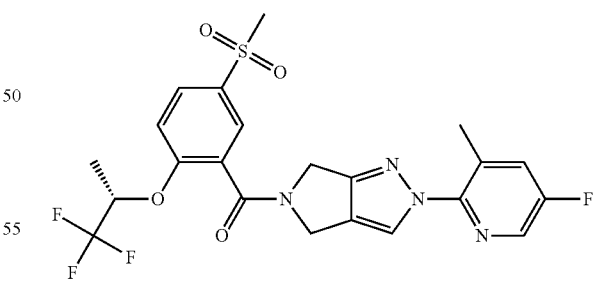

Rotamers observed: ¹H NMR (400 MHz, CDCl₃) δ=8.18-8.13 (m, 1H), 8.04-7.81 (m, 3H), 7.47-7.38 (m, 1H), 7.18 (dd, J=1.6, 8.6 Hz, 1H), 4.93-4.79 (m, 3H), 4.53-4.37 (m, 2H), 3.07 (d, J=0.8 Hz, 3H), 2.60-2.47 (m, 3H), 1.55 (d, J=6.3 Hz, 3H); [M+H]=513.15.

Example 362

3-Fluoro-6-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]-2-methylpyridine

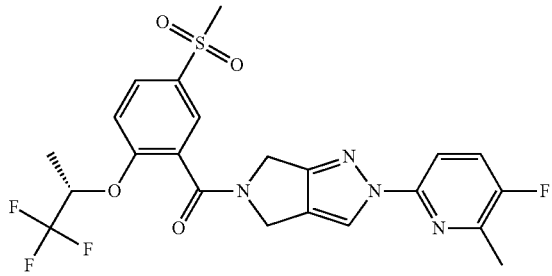 [SMILES: Cc1nc(-n2cc3c(n2)CN(C(=O)c2cc(S(C)(=O)=O)ccc2O[C@@H](C)C(F)(F)F)C3)ccc1F]

Rotamers observed: ¹H NMR (400 MHz, CDCl₃) δ=8.41-8.22 (m, 1H), 8.05-7.96 (m, 2H), 7.77-7.61 (m, 1H), 7.43 (td, J=8.6, 13.3 Hz, 1H), 7.18 (d, J=9.0 Hz, 1H), 4.90-4.77 (m, 3H), 4.51-4.35 (m, 2H), 3.07 (d, J=2.0 Hz, 3H), 2.51 (dd, J=3.1, 4.7 Hz, 3H), 1.54 (d, J=6.7 Hz, 3H); [M+H]=513.15.

Example 363

1-{2-[2-(4-Fluorophenyl)-2H 4H 5H 6H-pyrrolo[3,4-c]pyrazole-5-carbonyl]-4-methanesulfonylphenyl}piperidine

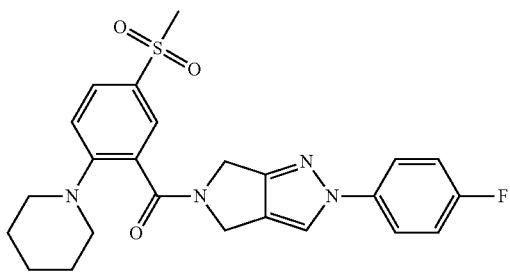 [SMILES: CS(=O)(=O)c1ccc(N2CCCCC2)c(C(=O)N2Cc3cn(-c4ccc(F)cc4)nc3C2)c1]

Rotamers observed: ¹H NMR (400 MHz, DMSO-d₆) δ=8.37-8.19 (m, 2H), 7.86-7.77 (m, 2H), 7.69 (d, J=2.3 Hz, 1H), 7.32 (dt, J=2.0, 8.8 Hz, 2H), 7.23-7.18 (m, 1H), 4.70 (br s, 3H), 4.38-4.19 (m, 2H), 3.16 (d, J=1.2 Hz, 2H), 3.08 (br s, 2H), 1.47 (br s, 3H); [M+H]=469.44.

Example 364

3-[2-(2-Methoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile

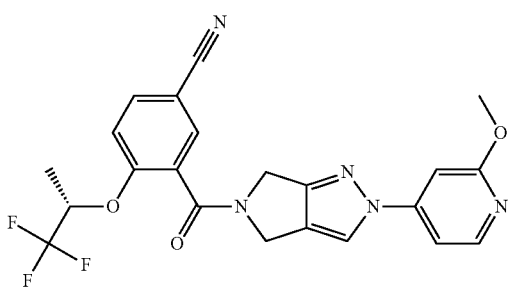 [SMILES: COc1cc(-n2cc3c(n2)CN(C(=O)c2cc(C#N)ccc2O[C@@H](C)C(F)(F)F)C3)ccn1]

¹H NMR (400 MHz, DMSO-d₆) δ=8.60-8.41 (m, 1H), 8.20 (dd, J=2.3, 5.9 Hz, 1H), 8.03-7.94 (m, 1H), 7.92-7.82 (m, 1H), 7.58-7.50 (m, 1H), 7.49-7.40 (m, 1H), 7.21 (d, J=2.0 Hz, 1H), 5.52 (s, 1H), 4.65 (d, J=9.8 Hz, 2H), 4.33 (br s, 2H), 3.87 (d, J=2.0 Hz, 3H), 1.40 (d, J=6.7 Hz, 3H); [M+H]=458.4.

Example 365

3-[1-(2-Methoxypyridin-4-yl)-1H 4H 5H 6H-pyrrolo[3,4-c]pyrazole-5-carbonyl]-4-{[(2S)-1 1 1-trifluoropropan-2-yl]oxy}benzonitrile

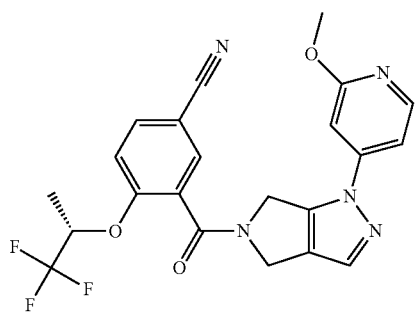 [SMILES: COc1cc(-n2ncc3c2CN(C(=O)c2cc(C#N)ccc2O[C@@H](C)C(F)(F)F)C3)ccn1]

¹H NMR (400 MHz, DMSO-d₆) δ=8.30-8.12 (m, 1H), 8.05-7.94 (m, 1H), 7.92-7.82 (m, 1H), 7.79-7.58 (m, 1H), 7.55 (d, J=9.0 Hz, 1H), 7.28 (dd, J=2.0, 5.5 Hz, 1H), 7.11 (dd, J=2.0, 5.9 Hz, 1H), 6.99-6.75 (m, 1H), 5.68-5.38 (m, 1H), 5.08 (s, 1H), 4.97-4.65 (m, 1H), 4.57 (s, 1H), 4.37-4.13 (m, 1H), 4.00-3.72 (m, 3H), 1.40 (dd, J=3.9, 6.3 Hz, 3H); [M+H]=458.12.

Example 366

3-[1-(2-Methoxypyridin-4-yl)-1H 4H 5H 6H-pyrrolo[3,4-c]pyrazole-5-carbonyl]-4-(propan-2-yloxy)benzonitrile

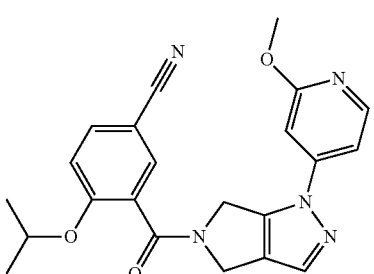

¹H NMR (400 MHz, DMSO-d₆) δ=8.28-8.14 (m, 1H), 7.88 (ddd, J=2.2, 4.4, 8.7 Hz, 1H), 7.78-7.59 (m, 2H), 7.34 (dd, J=2.5, 8.8 Hz, 1H), 7.29-7.09 (m, 1H), 6.98-6.77 (m, 1H), 5.08 (s, 1H), 4.82 (quin, J=6.1 Hz, 2H), 4.57 (s, 1H), 4.27 (s, 1H), 3.97-3.79 (m, 3H), 1.34-1.09 (m, 6H); [M+H]=404.08.

Example 367

3-[2-(2-Ethylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

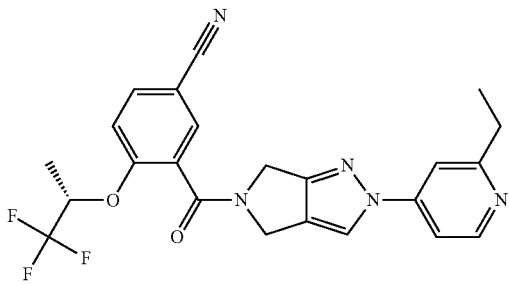 [SMILES: CCc1cc(-n2cc3c(n2)CN(C(=O)c2cc(C#N)ccc2O[C@@H](C)C(F)(F)F)C3)ccn1]

¹H NMR (400 MHz, DMSO-d₆) δ=8.63-8.39 (m, 2H), 8.03-7.82 (m, 2H), 7.75-7.50 (m, 3H), 5.52 (td, J=6.1, 12.4 Hz, 1H), 4.66 (d, J=8.6 Hz, 2H), 4.48-4.18 (m, 3H), 2.77 (dq, J=2.0, 7.6 Hz, 2H), 1.40 (d, J=6.3 Hz, 3H), 1.24 (dt, J=2.7, 7.6 Hz, 3H); [M+H]=456.03.

Example 368

3-[2-(2-Ethylpyridin-4-yl)-2H 4H 5H 6H-pyrrolo[3,4-c]pyrazole-5-carbonyl]-4-(propan-2-yloxy)benzonitrile

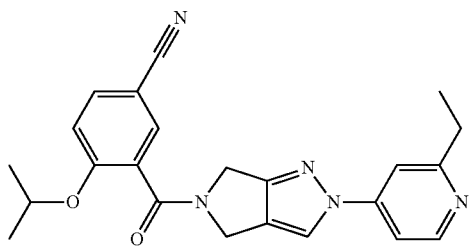 [SMILES: CCc1cc(-n2cc3c(n2)CN(C(=O)c2cc(C#N)ccc2OC(C)C)C3)ccn1]

¹H NMR (400 MHz, DMSO-d₆) δ=8.59-8.38 (m, 2H), 7.88 (dd, J=2.2, 8.8 Hz, 1H), 7.80-7.55 (m, 3H), 7.33 (dd, J=1.6, 9.0 Hz, 1H), 4.82 (dtd, J=3.1, 6.1, 12.1 Hz, 1H), 4.66 (d, J=8.2 Hz, 2H), 4.36 (d, J=18.8 Hz, 2H), 2.77 (dq, J=2.2, 7.6 Hz, 2H), 1.31-1.14 (m, 9H); [M+H]=402.12.

Example 369

3-[2-(2-Methoxypyridin-4-yl)-2H 4H 5H 6H-pyrrolo[3,4-c]pyrazole-5-carbonyl]-4-(propan-2-yloxy)benzonitrile

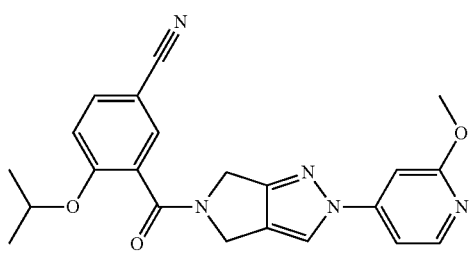

¹H NMR (400 MHz, DMSO-d₆) δ=8.57-8.41 (m, 1H), 8.20 (dd, J=2.3, 5.9 Hz, 1H), 7.88 (dd, J=2.2, 8.8 Hz, 1H), 7.75 (dd, J=2.2, 6.5 Hz, 1H), 7.45 (ddd, J=2.0, 5.7, 11.2 Hz, 1H), 7.33 (dd, J=2.0, 9.0 Hz, 1H), 7.20 (dd, J=1.6, 10.2 Hz, 1H), 4.82 (dtd, J=2.5, 6.0, 12.1 Hz, 1H), 4.65 (d, J=9.8 Hz, 2H), 4.35 (d, J=20.0 Hz, 2H), 3.87 (d, J=1.6 Hz, 3H), 1.23 (d, J=5.9 Hz, 6H); [M+H]=404.23.

Example 370

3-[2-(2-Ethoxypyridin-4-yl)-2H 4H 5H 6H-pyrrolo[3,4-c]pyrazole-5-carbonyl]-4-(propan-2-yloxy)benzonitrile

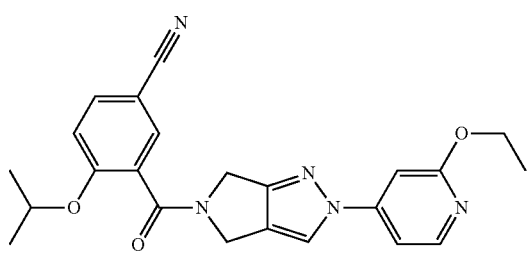 [SMILES: CCOc1cc(-n2cc3c(n2)CN(C(=O)c2cc(C#N)ccc2OC(C)C)C3)ccn1]

¹H NMR (400 MHz, DMSO-d₆) δ=8.59-8.37 (m, 1H), 8.18 (dd, J=3.1, 5.9 Hz, 1H), 7.87 (dd, J=2.2, 8.8 Hz, 1H), 7.75 (dd, J=2.2, 5.7 Hz, 1H), 7.43 (ddd, J=2.0, 5.9, 12.5 Hz, 1H), 7.33 (dd, J=1.2, 9.0 Hz, 1H), 7.24-7.12 (m, 1H), 4.81 (dtd, J=2.9, 6.0, 12.1 Hz, 1H), 4.65 (d, J=9.8 Hz, 2H), 4.44-4.27 (m, 4H), 1.35-1.28 (m, 3H), 1.23 (d, J=6.3 Hz, 6H); [M+H]=418.56.

Example 371

3-[2-(2-Ethoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile

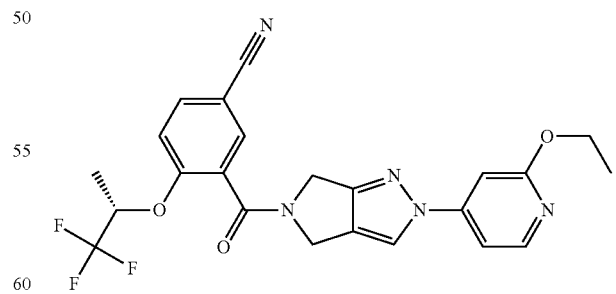

¹H NMR (400 MHz, CDCl₃) δ=8.18 (dd, J=3.9, 5.9 Hz, 1H), 7.87-7.65 (m, 3H), 7.29-7.19 (m, 1H), 7.12 (d, J=8.6 Hz, 1H), 7.02 (dd, J=1.6, 14.5 Hz, 1H), 4.95-4.73 (m, 3H), 4.59-4.30 (m, 4H), 1.53 (d, J=6.7 Hz, 3H), 1.43 (dt, J=3.9, 7.0 Hz, 3H); [M+H]=472.26.

Example 372

3-{2-[2-(Propan-2-yloxy)pyridin-4-yl]-2H 4H 5H 6H-pyrrolo[3,4-c]pyrazole-5-carbonyl}-4-{[(2S)-1 1 1-trifluoropropan-2-yl]oxy}benzonitrile

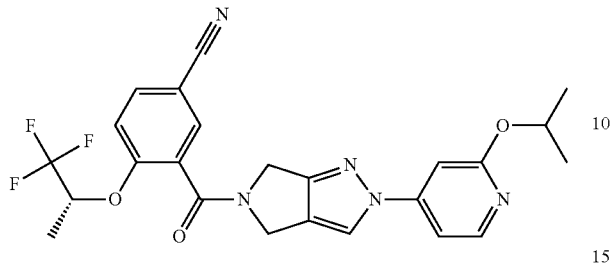

$^1$H NMR (400 MHz, DMSO-d$_6$) δ=8.56-8.41 (m, 1H), 8.17 (dd, J=3.9, 5.9 Hz, 1H), 7.98 (dd, J=2.2, 8.8 Hz, 1H), 7.87 (dd, J=2.3, 5.5 Hz, 1H), 7.54 (dd, J=1.2, 9.0 Hz, 1H), 7.40 (ddd, J=2.0, 5.7, 14.3 Hz, 1H), 7.14 (dd, J=2.0, 11.0 Hz, 1H), 5.52 (td, J=6.3, 12.5 Hz, 1H), 5.26 (spt, J=6.2 Hz, 1H), 4.65 (d, J=9.8 Hz, 2H), 4.46-4.20 (m, 3H), 1.40 (d, J=6.3 Hz, 3H), 1.34-1.23 (m, 6H); [M+H]=486.24.

Example 373

4-(Propan-2-yloxy)-3-{2-[2-(propan-2-yloxy)pyridin-4-yl]-2H 4H 5H 6H-pyrrolo[3,4-c]pyrazole-5-carbonyl}benzonitrile

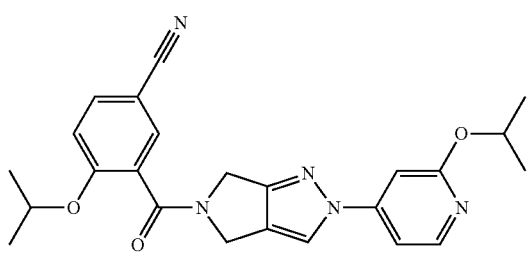

$^1$H NMR (400 MHz, DMSO-d$_6$) δ=8.57-8.38 (m, 1H), 8.17 (dd, J=3.7, 5.7 Hz, 1H), 7.91-7.82 (m, 1H), 7.75 (dd, J=2.2, 4.9 Hz, 1H), 7.40 (ddd, J=2.0, 5.5, 12.9 Hz, 1H), 7.32 (d, J=8.6 Hz, 1H), 7.13 (dd, J=1.6, 9.0 Hz, 1H), 5.26 (spt, J=6.1 Hz, 1H), 4.81 (dtd, J=3.1, 6.1, 12.1 Hz, 1H), 4.65 (d, J=9.8 Hz, 2H), 4.35 (d, J=19.6 Hz, 2H), 1.36-1.15 (m, 12H); [M+H]=432.24.

Example 374

3-{2-[2-(Propan-2-yl)pyridin-4-yl]-2H 4H 5H 6H-pyrrolo[3,4-c]pyrazole-5-carbonyl}-4-(propan-2-yloxy)benzonitrile

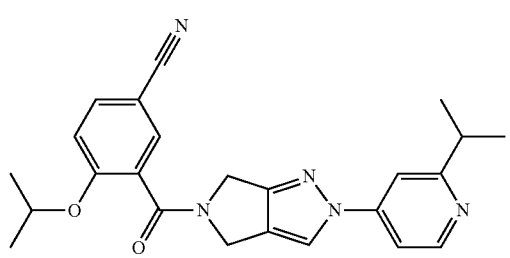 [SMILES: CC(C)Oc1ccc(C#N)cc1C(=O)N1Cc2cn(-c3ccnc(C(C)C)c3)nc2C1]

$^1$H NMR (400 MHz, DMSO-d$_6$) δ=8.62-8.40 (m, 2H), 7.88 (dd, J=2.2, 8.8 Hz, 1H), 7.76 (dd, J=2.2, 7.2 Hz, 1H), 7.68 (dd, J=2.0, 12.5 Hz, 1H), 7.64-7.58 (m, 1H), 7.33 (dd, J=1.8, 8.8 Hz, 1H), 4.82 (dtd, J=2.3, 6.1, 12.1 Hz, 1H), 4.66 (d, J=9.0 Hz, 2H), 4.36 (d, J=18.8 Hz, 2H), 3.05 (dtd, J=3.3, 6.9, 13.8 Hz, 1H), 1.32-1.14 (m, 12H); [M+H]=416.77.

Example 375

3-{2-[2-(Propan-2-yl)pyridin-4-yl]-2H 4H 5H 6H-pyrrolo[3,4-c]pyrazole-5-carbonyl}-4-{[(2S)-1 1 1-trifluoropropan-2-yl]oxy}benzonitrile

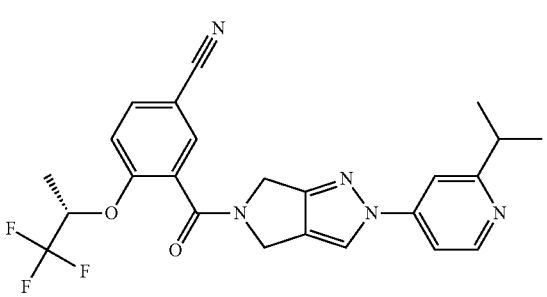 [SMILES: CC(C)c1cc(-n2cc3c(n2)CN(C(=O)c2cc(C#N)ccc2O[C@@H](C)C(F)(F)F)C3)ccn1]

$^1$H NMR (400 MHz, DMSO-d$_6$) δ=8.61-8.43 (m, 2H), 7.98 (dd, J=2.2, 8.8 Hz, 1H), 7.88 (dd, J=2.2, 7.6 Hz, 1H), 7.68 (dd, J=2.2, 13.9 Hz, 1H), 7.61 (ddd, J=2.2, 5.6, 10.7 Hz, 1H), 7.54 (dd, J=2.0, 9.0 Hz, 1H), 5.62-5.42 (m, 1H), 4.66 (d, J=8.6 Hz, 2H), 4.48-4.20 (m, 2H), 3.05 (dtd, J=2.9, 6.9, 13.7 Hz, 1H), 1.45-1.11 (m, 9H); [M+H]=470.00.

Example 376

4-(1-Fluorocyclopentyl)-2-methoxy-3-[2-(2-methylpyridin-4-yl)-2H 4H 5H 6H-pyrrolo[3,4-c]pyrazole-5-carbonyl]benzonitrile

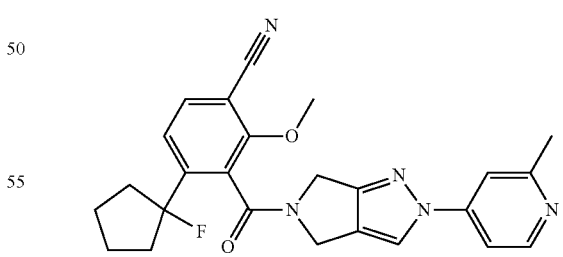

$^1$H NMR (400 MHz, CDCl$_3$) δ=8.53 (dd, J=2.7, 5.9 Hz, 1H), 7.89-7.65 (m, 1H), 7.62 (td, J=1.2, 8.2 Hz, 1H), 7.54 (d, J=16.0 Hz, 1H), 7.43 (br s, 1H), 7.15 (t, J=8.2 Hz, 1H), 4.93-4.67 (m, 2H), 4.47-4.27 (m, 2H), 4.17-4.02 (m, 3H), 2.58-1.77 (m, 8H); [M+H]=446.4.

Example 377

4-(1-Fluorocyclopentyl)-3-[2-(5-fluoropyridin-3-yl)-2H 4H 5H 6H-pyrrolo[3,4-c]pyrazole-5-carbonyl]-2-methoxybenzonitrile

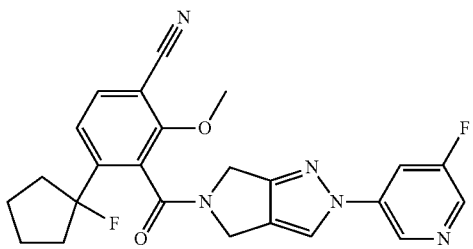 [SMILES: COc1c(C#N)ccc(C2(F)CCCC2)c1C(=O)N1Cc2cn(-c3cncc(F)c3)nc2C1]

$^1$H NMR (400 MHz, CDCl$_3$) δ=8.81-8.35 (m, 2H), 7.87-7.73 (m, 2H), 7.69-7.51 (m, 1H), 7.15 (t, J=8.2 Hz, 1H), 4.96-4.71 (m, 2H), 4.49-4.26 (m, 2H), 4.10 (dd, J=1.2, 3.5 Hz, 3H), 2.66-1.76 (m, 8H); [M+H]=450.14.

Example 378

3-[2-(2-Fluoro-2-methylpropyl)-2H 4H 5H 6H-pyrrolo[3,4-c]pyrazole-5-carbonyl]-4-{[(2S)-1 1 1-trifluoropropan-2-yl]oxy}benzonitrile

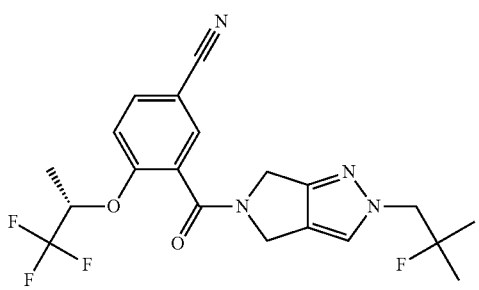 [SMILES: C[C@H](Oc1ccc(C#N)cc1C(=O)N1Cc2cn(CC(C)(C)F)nc2C1)C(F)(F)F]

$^1$H NMR (400 MHz, DMSO-d$_6$) δ=7.96 (dd, J=2.2, 8.8 Hz, 1H), 7.87 (dd, J=2.0, 7.8 Hz, 1H), 7.57-7.38 (m, 2H), 5.57-5.44 (m, 1H), 4.54 (s, 2H), 4.33-4.13 (m, 4H), 1.38 (d, J=6.3 Hz, 3H), 1.32-1.17 (m, 6H); [M+H]=425.0.

Example 379

3-[1-(2-Fluoro-2-methylpropyl)-1H 4H 5H 6H-pyrrolo[3,4-c]pyrazole-5-carbonyl]-4-{[(2S)-1 1 1-trifluoropropan-2-yl]oxy}benzonitrile

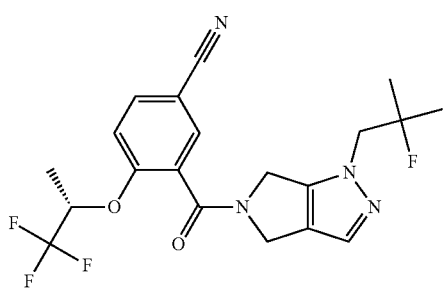 [SMILES: C[C@H](Oc1ccc(C#N)cc1C(=O)N1Cc2cnn(CC(C)(C)F)c2C1)C(F)(F)F]

$^1$H NMR (400 MHz, DMSO-d$_6$) δ=7.96 (ddd, J=2.2, 4.3, 8.8 Hz, 1H), 7.92-7.85 (m, 1H), 7.52 (dd, J=5.1, 9.0 Hz, 1H), 7.38-7.15 (m, 1H), 5.50 (dtd, J=3.5, 6.4, 12.6 Hz, 1H), 4.67-4.43 (m, 2H), 4.39-4.10 (m, 4H), 1.38 (dd, J=2.7, 6.3 Hz, 3H), 1.33-1.15 (m, 6H); [M+H]=425.48.

Example 380

3-[2-(2 6-Dimethylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

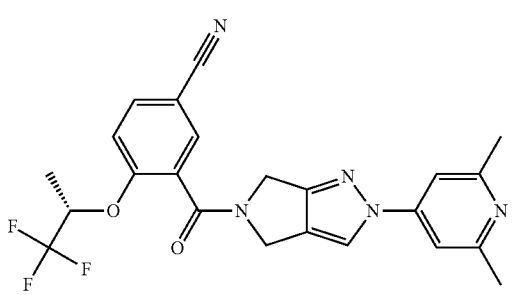

$^1$H NMR (400 MHz, DMSO-d$_6$) δ=8.52-8.34 (m, 1H), 7.98 (dd, J=2.2, 8.8 Hz, 1H), 7.88 (dd, J=2.3, 7.0 Hz, 1H), 7.57-7.46 (m, 3H), 5.65-5.42 (m, 1H), 4.65 (d, J=6.3 Hz, 2H), 4.45-4.19 (m, 2H), 2.44 (d, J=1.6 Hz, 6H), 1.40 (d, J=6.3 Hz, 3H); [M+H]=456.6.

Example 381

3-[2-(2 6-Dimethylpyridin-4-yl)-2H 4H 5H 6H-pyrrolo[3,4-c]pyrazole-5-carbonyl]-4-(propan-2-yloxy)benzonitrile

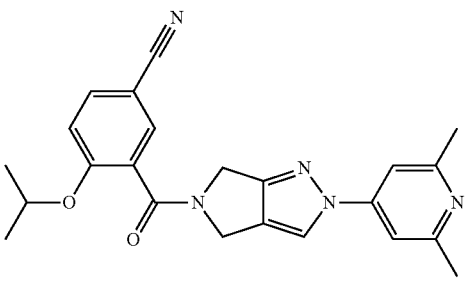 [SMILES: Cc1cc(-n2cc3c(n2)CN(C(=O)c2cc(C#N)ccc2OC(C)C)C3)cc(C)n1]

$^1$H NMR (400 MHz, DMSO-d$_6$) δ=8.51-8.33 (m, 1H), 7.88 (dd, J=2.2, 8.8 Hz, 1H), 7.76 (dd, J=2.3, 6.3 Hz, 1H), 7.49 (d, J=12.5 Hz, 2H), 7.33 (d, J=9.0 Hz, 1H), 4.89-4.75 (m, 1H), 4.65 (d, J=6.3 Hz, 2H), 4.35 (d, J=16.8 Hz, 2H), 2.44 (d, J=1.6 Hz, 6H), 1.23 (d, J=5.9 Hz, 6H); [M+H]=402.68.

Example 382

3-{2-Benzyl-2H 4H 5H 6H-pyrrolo[3,4-c]pyrazole-5-carbonyl}-4-{[(2S)-1 1 1-trifluoropropan-2-yl]oxy}benzonitrile

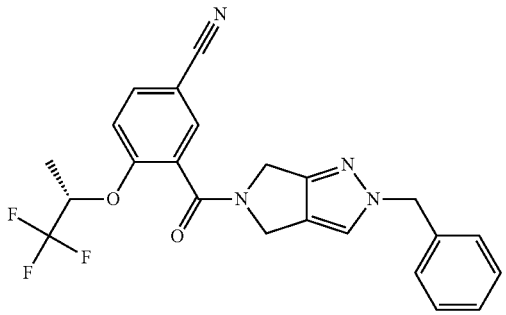 [SMILES: C[C@H](Oc1ccc(C#N)cc1C(=O)N1Cc2cn(Cc3ccccc3)nc2C1)C(F)(F)F]

¹H NMR (400 MHz, DMSO-d₆) δ=7.95 (td, J=2.0, 9.0 Hz, 1H), 7.85 (dd, J=2.2, 9.6 Hz, 1H), 7.72-7.59 (m, 1H), 7.51 (dd, J=3.3, 8.8 Hz, 1H), 7.38-7.15 (m, 5H), 5.50 (td, J=6.1, 12.4 Hz, 1H), 5.29 (s, 2H), 4.53 (d, J=5.9 Hz, 2H), 4.34-4.06 (m, 2H), 1.38 (d, J=6.7 Hz, 3H); [M+H]=441.39.

Example 383

3-{1-Benzyl-1H 4H 5H 6H-pyrrolo[3,4-c]pyrazole-5-carbonyl}-4-{[(2S)-1 1 1-trifluoropropan-2-yl]oxy}benzonitrile

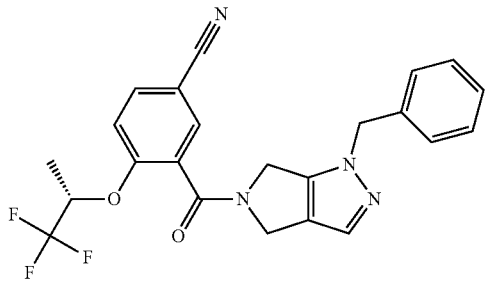 [SMILES: C[C@H](Oc1ccc(C#N)cc1C(=O)N1Cc2cnn(Cc3ccccc3)c2C1)C(F)(F)F]

¹H NMR (400 MHz, DMSO-d₆) δ=7.95 (ddd, J=2.2, 6.1, 8.6 Hz, 1H), 7.84 (t, J=2.5 Hz, 1H), 7.50 (d, J=9.0 Hz, 1H), 7.42-7.08 (m, 6H), 5.47 (qd, J=6.4, 16.4 Hz, 1H), 5.35-5.26 (m, 1H), 5.26-5.11 (m, 1H), 4.53-4.32 (m, 2H), 4.24-4.05 (m, 2H), 1.40-1.27 (m, 3H); [M+H]=441.39.

Example 384

3-[1-(Propan-2-yl)-1H 4H 5H 6H-pyrrolo[3,4-e]pyrazole-5-carbonyl]-4-{[(2S)-1 1 1-trifluoropropan-2-yl]oxy}benzonitrile

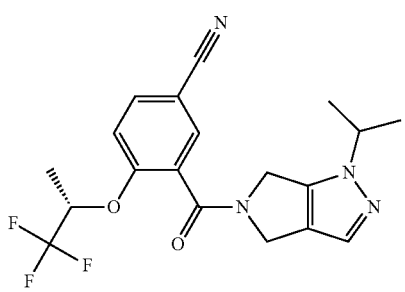 [SMILES: CC(C)n1ncc2c1CN(C(=O)c1cc(C#N)ccc1O[C@@H](C)C(F)(F)F)C2]

¹H NMR (400 MHz, DMSO-d₆) δ=7.96 (ddd, J=2.2, 4.7, 8.8 Hz, 1H), 7.85 (dd, J=1.2, 2.0 Hz, 1H), 7.53 (dd, J=3.1, 9.0 Hz, 1H), 7.32-7.08 (m, 1H), 5.52 (qd, J=6.3, 12.5 Hz, 1H), 4.73 (s, 1H), 4.57-4.28 (m, 3H), 4.22-4.04 (m, 1H), 1.43-1.34 (m, 6H), 1.25 (dd, J=4.3, 6.7 Hz, 3H); [M+H]=396.36.

Example 385

3-[2-(Propan-2-yl)-2H 4H 5H 6H-pyrrolo[3,4-c]pyrazole-5-carbonyl]-4-{[(2 S)-1 1 1-trifluoropropan-2-yl]oxy}benzonitrile

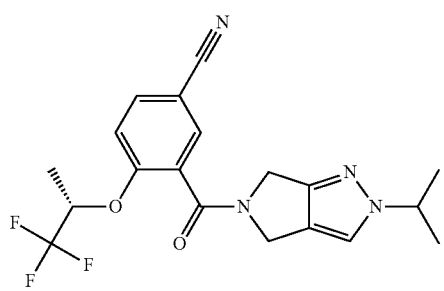 [SMILES: CC(C)n1cc2c(n1)CN(C(=O)c1cc(C#N)ccc1O[C@@H](C)C(F)(F)F)C2]

¹H NMR (400 MHz, DMSO-d₆) δ=7.99-7.92 (m, 1H), 7.85 (dd, J=2.2, 6.8 Hz, 1H), 7.65-7.46 (m, 2H), 5.57-5.36 (m, 1H), 4.52 (s, 2H), 4.46 (dtd, J=2.3, 6.7, 13.3 Hz, 1H), 4.28-4.09 (m, 2H), 1.43-1.33 (m, 9H); [M+H]=393.36.

Example 386

3-[2-(2-Methylpropyl)-2H 4H 5H 6H-pyrrolo[3,4-c]pyrazole-5-carbonyl]-4-{[(2S)-1 1 1-trifluoropropan-2-yl]oxy}benzonitrile

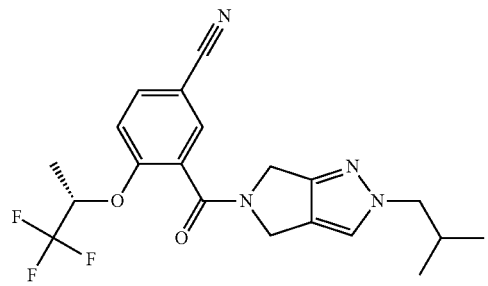 [SMILES: CC(C)Cn1cc2c(n1)CN(C(=O)c1cc(C#N)ccc1O[C@@H](C)C(F)(F)F)C2]

¹H NMR (400 MHz, DMSO-d₆) δ=7.96 (dd, J=2.2, 8.8 Hz, 1H), 7.86 (dd, J=2.0, 8.2 Hz, 1H), 7.58-7.44 (m, 2H), 5.59-5.43 (m, 1H), 4.52 (d, J=2.0 Hz, 2H), 4.33-4.09 (m, 2H), 3.87 (dd, J=1.2, 7.0 Hz, 2H), 2.05 (td, J=6.7, 8.6 Hz, 1H), 1.38 (d, J=6.3 Hz, 3H), 0.87-0.72 (m, 6H); [M+H]=407.08.

Example 387

3-[1-(2-Methylpropyl)-1H 4H 5H 6H-pyrrolo[3,4-c]pyrazole-5-carbonyl]-4-{[(2S)-1 1 1-trifluoropropan-2-yl]oxy}benzonitrile

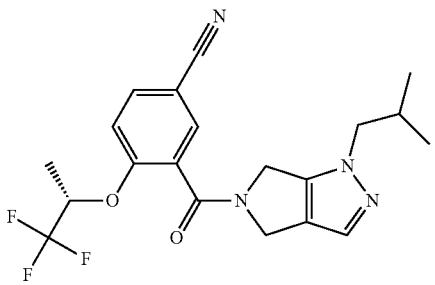 [SMILES: CC(C)Cn1ncc2c1CN(C(=O)c1cc(C#N)ccc1O[C@@H](C)C(F)(F)F)C2]

¹H NMR (400 MHz, DMSO-d₆) δ=8.01-7.93 (m, 1H), 7.88 (dd, J=0.8, 2.3 Hz, 1H), 7.53 (t, J=8.8 Hz, 1H), 7.32-7.14 (m, 1H), 5.51 (qd, J=6.2, 12.0 Hz, 1H), 4.71-4.47 (m, 2H), 4.44-4.04 (m, 3H), 3.92-3.63 (m, 2H), 2.12-1.86 (m, 1H), 1.38 (d, J=5.9 Hz, 3H), 0.83 (dd, J=0.8, 6.7 Hz, 3H), 0.74 (dd, J=2.0, 6.7 Hz, 3H); [M+H]=407.54.

Example 388

3-{1-Cyclopentyl-1H 4H 5H 6H-pyrrolo[3,4-c]pyrazole-5-carbonyl}-4-{[(2 S)-1 1 1-trifluoropropan-2-yl]oxy}benzonitrile

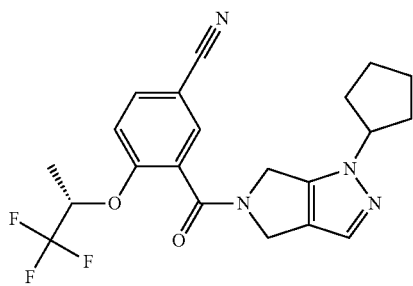 [SMILES: C[C@H](Oc1ccc(C#N)cc1C(=O)N1Cc2cnn(C3CCCC3)c2C1)C(F)(F)F]

¹H NMR (400 MHz, CDCl₃) δ=7.83-7.54 (m, 2H), 7.29-6.98 (m, 2H), 4.92-4.55 (m, 4H), 4.52-4.20 (m, 2H), 2.33-1.59 (m, 8H), 1.52 (d, J=6.3 Hz, 3H); [M+H]=419.1.

Example 389

3-{2-Cyclopentyl-2H 4H 5H 6H-pyrrolo[3,4-c]pyrazole-5-carbonyl}-4-{[(2S)-1 1 1-trifluoropropan-2-yl]oxy}benzonitrile

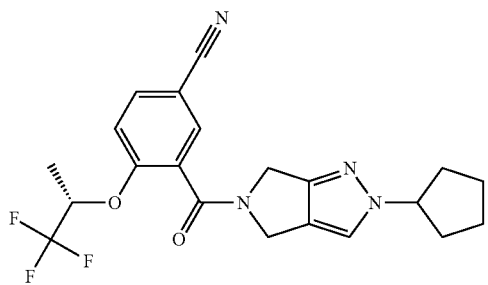 [SMILES: C[C@H](Oc1ccc(C#N)cc1C(=O)N1Cc2cn(C3CCCC3)nc2C1)C(F)(F)F]

¹H NMR (400 MHz, CDCl₃) δ=7.71 (ddd, J=2.3, 4.1, 8.8 Hz, 1H), 7.65 (d, J=2.0 Hz, 1H), 7.17-7.04 (m, 2H), 4.87-4.67 (m, 3H), 4.62 (dt, J=2.7, 7.2 Hz, 1H), 4.47-4.19 (m, 2H), 2.27-2.09 (m, 2H), 2.07-1.94 (m, 2H), 1.94-1.81 (m, 2H), 1.78-1.61 (m, 2H), 1.51 (d, J=6.3 Hz, 3H); [M+H]=419.21.

Example 390

3-[2-(2 4-Difluorophenyl)-2H 4H 5H 6H-pyrrolo[3,4-c]pyrazole-5-carbonyl]-4-(propan-2-yloxy)benzonitrile

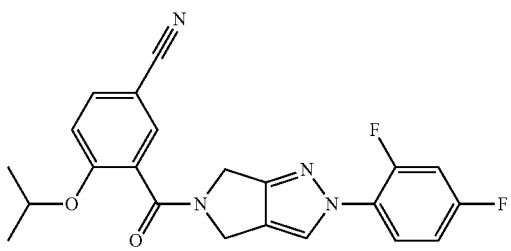

¹H NMR (400 MHz, CDCl₃) δ=7.87-7.71 (m, 2H), 7.70-7.57 (m, 2H), 7.07-6.93 (m, 3H), 4.85 (d, J=16.0 Hz, 2H), 4.69 (dt, J=3.1, 6.1 Hz, 1H), 4.45 (d, J=11.3 Hz, 2H), 1.36 (d, J=5.9 Hz, 6H); [M+H]=409.10.

Example 391

3-[2-(2 4-Difluorophenyl)-2H 4H 5H 6H-pyrrolo[3,4-c]pyrazole-5-carbonyl]-4-{[(2S)-1 1 1-trifluoropropan-2-yl]oxy}benzonitrile

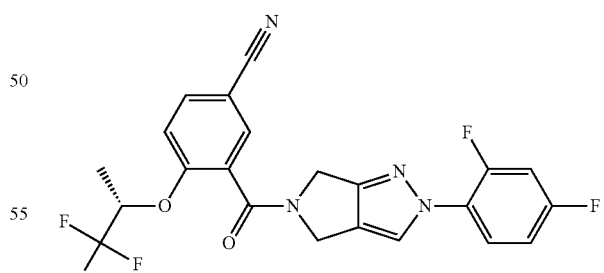

¹H NMR (400 MHz, CDCl₃) δ=7.87-7.58 (m, 4H), 7.12 (d, J=8.6 Hz, 1H), 7.07-6.91 (m, 2H), 4.96-4.70 (m, 3H), 4.59-4.32 (m, 2H), 1.53 (d, J=6.7 Hz, 3H); [M+H]=463.14.

Example 392

3-[1-(3-Methoxypropyl)-1H 4H 5H 6H-pyrrolo[3,4-c]pyrazole-5-carbonyl]-4-{[(2S)-1 1 1-trifluoropropan-2-yl]oxy}benzonitrile

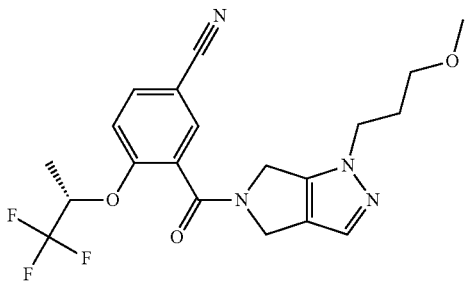 [SMILES: COCCCn1ncc2c1CN(C(=O)c1cc(C#N)ccc1O[C@@H](C)C(F)(F)F)C2]

$^1$H NMR (400 MHz, CDCl$_3$) δ=7.76-7.69 (m, 1H), 7.68-7.62 (m, 1H), 7.36-7.24 (m, 1H), 7.17-7.04 (m, 1H), 4.84-4.65 (m, 3H), 4.41-4.23 (m, 2H), 4.16 (t, J=6.7 Hz, 1H), 4.02 (t, J=6.8 Hz, 1H), 3.35-3.21 (m, 5H), 2.19-1.96 (m, 2H), 1.51 (d, J=6.7 Hz, 3H); [M+H]=423.04.

Example 393

3-[2-(3-Methoxypropyl)-2H 4H 5H 6H-pyrrolo[3,4-c]pyrazole-5-carbonyl]-4-{[(2S)-1 1 1-trifluoropropan-2-yl]oxy}benzonitrile

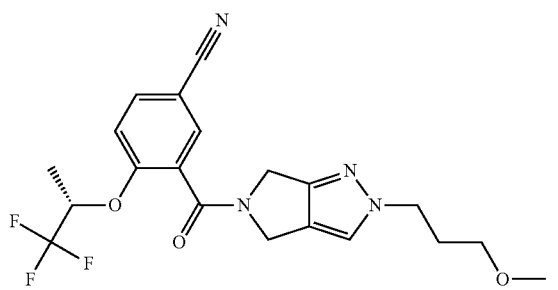 [SMILES: COCCCn1cc2c(n1)CN(C(=O)c1cc(C#N)ccc1O[C@@H](C)C(F)(F)F)C2]

$^1$H NMR (400 MHz, CDCl$_3$) δ=7.70 (ddd, J=2.2, 4.5, 8.6 Hz, 1H), 7.66 (d, J=2.0 Hz, 1H), 7.23-7.07 (m, 2H), 4.86-4.64 (m, 3H), 4.45-4.24 (m, 2H), 4.20 (dt, J=2.9, 6.7 Hz, 2H), 3.38-3.21 (m, 5H), 2.17-1.98 (m, 2H), 1.50 (d, J=6.3 Hz, 3H); [M+H]=423.04.

Example 394

3-[1-(Oxan-4-ylmethyl)-1H 4H 5H 6H-pyrrolo[3,4-c]pyrazole-5-carbonyl]-4-{[(2S)-1 1 1-trifluoropropan-2-yl]oxy}benzonitrile

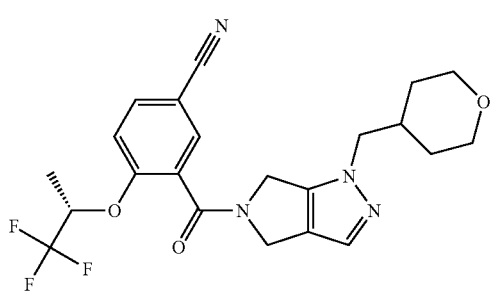 [SMILES: C[C@H](Oc1ccc(C#N)cc1C(=O)N1Cc2cnn(CC3CCOCC3)c2C1)C(F)(F)F]

$^1$H NMR (400 MHz, DMSO-d$_6$) δ=8.03-7.92 (m, 1H), 7.88 (dd, J=2.2, 4.9 Hz, 1H), 7.53 (dd, J=9.0, 11.7 Hz, 1H), 7.33-7.15 (m, 1H), 5.52 (qd, J=6.3, 15.5 Hz, 1H), 4.72-4.44 (m, 2H), 4.42-4.03 (m, 2H), 3.96 (d, J=7.0 Hz, 1H), 3.89-3.64 (m, 3H), 3.28-3.11 (m, 2H), 2.12-1.75 (m, 2H), 1.39 (dd, J=4.3, 6.3 Hz, 3H), 1.32-1.04 (m, 3H); [M+H]=449.2.

Example 395

3-[2-(2-Fluoro-3-methylphenyl)-2H 4H 5H 6H-pyrrolo[3,4-c]pyrazole-5-carbonyl]-4-{1(2S)-1 1 1-trifluoropropan-2-yl]oxy}benzonitrile

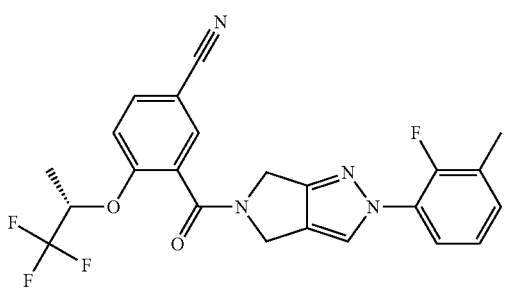 [SMILES: Cc1cccc(-n2cc3c(n2)CN(C(=O)c2cc(C#N)ccc2O[C@@H](C)C(F)(F)F)C3)c1F]

$^1$H NMR (400 MHz, DMSO-d$_6$) δ=8.06-7.91 (m, 2H), 7.89 (dd, J=2.0, 8.2 Hz, 1H), 7.61-7.45 (m, 2H), 7.35-7.25 (m, 1H), 7.24-7.14 (m, 1H), 5.53 (td, J=6.3, 12.8 Hz, 1H), 4.65 (d, J=8.6 Hz, 2H), 4.48-4.14 (m, 2H), 2.40-2.19 (m, 3H), 1.41 (d, J=6.7 Hz, 3H); [M+H]=459.22.

Example 396

3-[2-(Oxan-4-ylmethyl)-2H 4H 5H 6H-pyrrolo[3,4-c]pyrazole-5-carbonyl]-4-{[(2S)-1 1 1-trifluoropropan-2-yl]oxy}benzonitrile

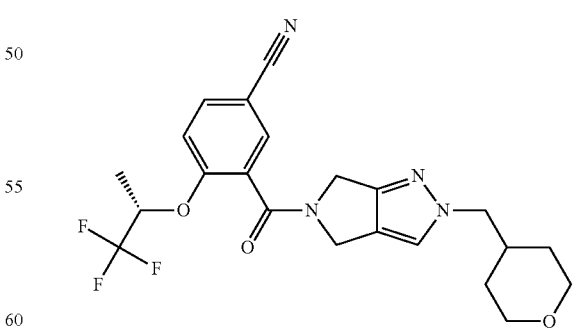

$^1$H NMR (400 MHz, DMSO-d$_6$) δ=8.01-7.78 (m, 2H), 7.64-7.37 (m, 2H), 5.50 (td, J=6.4, 12.6 Hz, 1H), 4.52 (s, 2H), 4.32-4.08 (m, 2H), 3.96 (d, J=7.0 Hz, 2H), 3.88-3.63 (m, 2H), 3.28-3.13 (m, 2H), 2.09-1.90 (m, 1H), 1.42-1.30 (m, 4H), 1.26-1.12 (m, 2H); [M+H]=449.23.

Example 397

3-[2-(2-Fluorophenyl)-2H 4H 5H 6H-pyrrolo[3,4-c]pyrazole-5-carbonyl]-4-{[(2S)-1 1 1-trifluoropropan-2-yl]oxy}benzonitrile

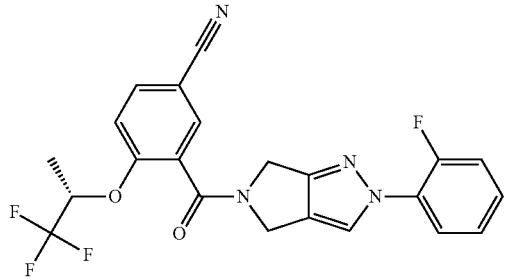 [SMILES: C[C@H](Oc1ccc(C#N)cc1C(=O)N1Cc2cn(-c3ccccc3F)nc2C1)C(F)(F)F]

$^1$H NMR (400 MHz, DMSO-d$_6$) δ=8.10-7.93 (m, 2H), 7.89 (dd, J=2.2, 7.6 Hz, 1H), 7.82-7.64 (m, 1H), 7.54 (dd, J=2.5, 8.8 Hz, 1H), 7.51-7.23 (m, 3H), 5.53 (td, J=6.4, 12.6 Hz, 1H), 4.65 (d, J=10.6 Hz, 2H), 4.48-4.19 (m, 2H), 1.41 (d, J=6.3 Hz, 3H); [M+H]=445.16.

Example 398

2-Benzyl-5-(5-methanesulfonyl-2-{[(2S)-1 1 1-trifluoropropan-2-yl]oxy}benzoyl)-2H 4H 5H 6H-pyrrolo[3,4-c]pyrazole

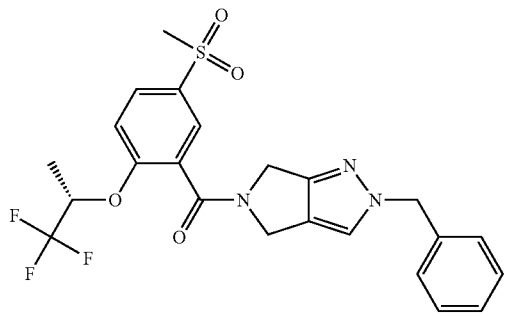 [SMILES: C[C@H](Oc1ccc(S(C)(=O)=O)cc1C(=O)N1Cc2cn(Cc3ccccc3)nc2C1)C(F)(F)F]

$^1$H NMR (400 MHz, DMSO-d$_6$) δ=8.00-7.94 (m, 1H), 7.86 (dd, J=2.3, 7.0 Hz, 1H), 7.74-7.59 (m, 1H), 7.57 (dd, J=3.1, 9.0 Hz, 1H), 7.38-7.15 (m, 5H), 5.58-5.47 (m, 1H), 5.29 (s, 2H), 4.55 (d, J=5.9 Hz, 2H), 4.35-4.14 (m, 2H), 3.22 (d, J=1.2 Hz, 3H), 1.40 (d, J=6.3 Hz, 3H); [M+H]=494.22.

Example 399

5-(5-Methanesulfonyl-2-{[(2S)-1 1 1-trifluoropropan-2-yl]oxy}benzoyl)-2-(2-methylpropyl)-2H 4H 5H 6H-pyrrolo[3,4-c]pyrazole

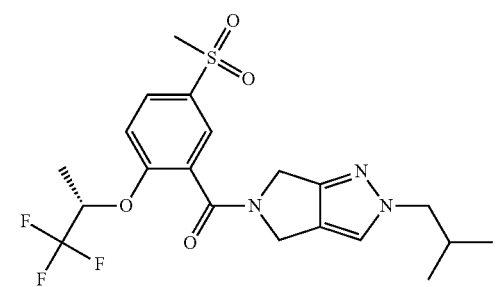 [SMILES: CC(C)Cn1cc2c(n1)CN(C(=O)c1cc(S(C)(=O)=O)ccc1O[C@@H](C)C(F)(F)F)C2]

$^1$H NMR (400 MHz, DMSO-d$_6$) δ=7.97 (dd, J=2.3, 9.0 Hz, 1H), 7.87 (dd, J=2.5, 4.9 Hz, 1H), 7.61-7.53 (m, 1H), 5.51 (dt, J=3.1, 6.3 Hz, 1H), 4.55 (d, J=2.0 Hz, 2H), 4.33-4.13 (m, 2H), 3.87 (dd, J=1.6, 7.0 Hz, 2H), 3.22 (d, J=1.2 Hz, 3H), 2.05 (qd, J=7.0, 15.9 Hz, 1H), 1.40 (d, J=6.7 Hz, 3H), 0.87-0.74 (m, 6H); [M+H]=460.21.

Example 400

5-[5-Methanesulfonyl-2-(propan-2-yloxy)benzoyl]-2-(2-methylpropyl)-2H 4H 5H 6H-pyrrolo[3,4-c]pyrazole

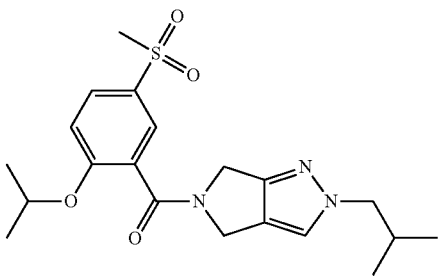 [SMILES: CC(C)Cn1cc2c(n1)CN(C(=O)c1cc(S(C)(=O)=O)ccc1OC(C)C)C2]

$^1$H NMR (400 MHz, DMSO-d$_6$) δ=7.94-7.86 (m, 1H), 7.77 (dd, J=2.5, 3.7 Hz, 1H), 7.60-7.42 (m, 1H), 7.36 (d, J=8.6 Hz, 1H), 4.92-4.71 (m, 1H), 4.55 (d, J=2.3 Hz, 2H), 4.24 (d, J=9.0 Hz, 2H), 3.87 (dd, J=1.6, 7.0 Hz, 2H), 3.18 (d, J=1.2 Hz, 3H), 2.19-1.93 (m, 2H), 1.24 (d, J=6.3 Hz, 6H), 0.81 (dd, J=3.5, 6.7 Hz, 6H); [M+H]=406.10.

Example 401

3-[2-(Cyclobutylmethyl)-2H 4H 5H 6H-pyrrolo[3,4-c]pyrazole-5-carbonyl]-4-{[(2S)-1 1 1-trifluoropropan-2-yl]oxy}benzonitrile

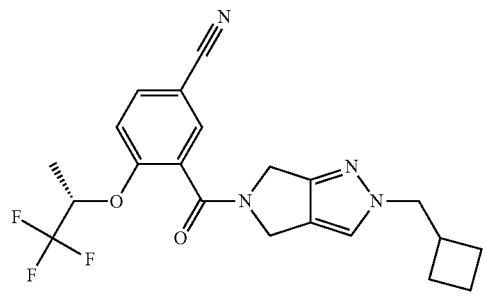 [SMILES: C[C@H](Oc1ccc(C#N)cc1C(=O)N1Cc2cn(CC3CCC3)nc2C1)C(F)(F)F]

$^1$H NMR (400 MHz, DMSO-d$_6$) δ=7.95 (dd, J=2.2, 8.8 Hz, 1H), 7.85 (dd, J=2.2, 7.6 Hz, 1H), 7.60-7.39 (m, 2H), 5.62-5.39 (m, 1H), 4.51 (d, J=2.3 Hz, 2H), 4.30-4.12 (m, 2H), 4.08 (dd, J=2.0, 7.0 Hz, 2H), 2.69 (qd, J=7.5, 14.6 Hz, 1H), 2.05-1.86 (m, 2H), 1.85-1.55 (m, 4H), 1.38 (d, J=6.3 Hz, 3H); [M+H]=419.05.

Example 402

3-{2-Cyclohexyl-2H 4H 5H 6H-pyrrolo[3,4-c]pyrazole-5-carbonyl}-4-{[(2S)-1 1 1-trifluoropropan-2-yl]oxy}benzonitrile

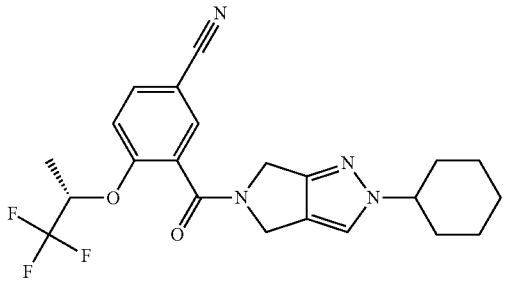 [SMILES: C[C@H](Oc1ccc(C#N)cc1C(=O)N1Cc2cn(C3CCCCC3)nc2C1)C(F)(F)F]

¹H NMR (400 MHz, DMSO-d₆) δ=7.95 (dd, J=2.2, 8.8 Hz, 1H), 7.84 (dd, J=2.2, 6.5 Hz, 1H), 7.64-7.47 (m, 2H), 5.50 (td, J=6.2, 12.7 Hz, 1H), 4.52 (s, 2H), 4.30-4.00 (m, 3H), 1.96 (d, J=12.1 Hz, 2H), 1.83-1.55 (m, 5H), 1.47-1.07 (m, 6H); [M+H]=433.19.

Example 403

2-Cyclohexyl-5-[5-methanesulfonyl-2-(propan-2-yloxy)benzoyl]-2H 4H 5H 6H-pyrrolo[3,4-c]pyrazole

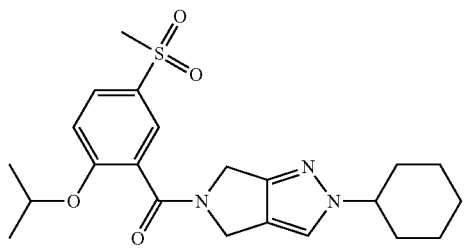 [SMILES: CC(C)Oc1ccc(S(C)(=O)=O)cc1C(=O)N1Cc2cn(C3CCCCC3)nc2C1]

¹H NMR (400 MHz, DMSO-d₆) δ=7.90 (dd, J=2.5, 8.8 Hz, 1H), 7.75 (dd, J=2.3, 3.1 Hz, 1H), 7.65-7.45 (m, 1H), 7.36 (d, J=9.0 Hz, 1H), 4.92-4.73 (m, 1H), 4.54 (s, 2H), 4.23 (d, J=9.8 Hz, 2H), 3.18 (d, J=1.2 Hz, 3H), 1.95 (d, J=12.1 Hz, 2H), 1.84-1.55 (m, 4H), 1.45-1.00 (m, 8H); [M+H]=432.24.

Example 404

3-[2-(2-Cyclopropylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

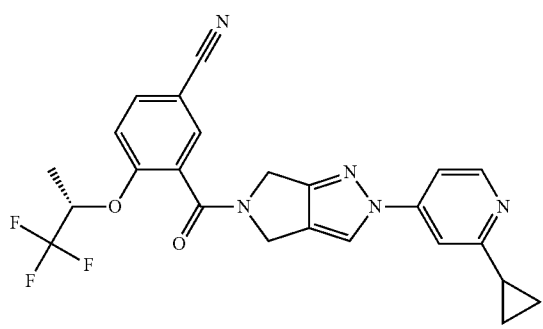 [SMILES: C[C@H](Oc1ccc(C#N)cc1C(=O)N1Cc2cn(-c3ccnc(C4CC4)c3)nc2C1)C(F)(F)F]

¹H NMR (400 MHz, DMSO-d₆) δ=8.57-8.37 (m, 2H), 8.02-7.85 (m, 2H), 7.72 (dd, J=2.0, 12.5 Hz, 1H), 7.62-7.46 (m, 2H), 5.52 (td, J=6.4, 12.6 Hz, 1H), 4.66 (d, J=8.2 Hz, 2H), 4.45-4.24 (m, 2H), 2.21-2.04 (m, 1H), 1.40 (d, J=6.3 Hz, 3H), 1.00-0.90 (m, 4H); [M+H]=468.23.

Example 405

3-[2-(2-Cyclopropylpyridin-4-yl)-2H 4H 5H 6H-pyrrolo[3,4-c]pyrazole-5-carbonyl]-4-(propan-2-yloxy)benzonitrile

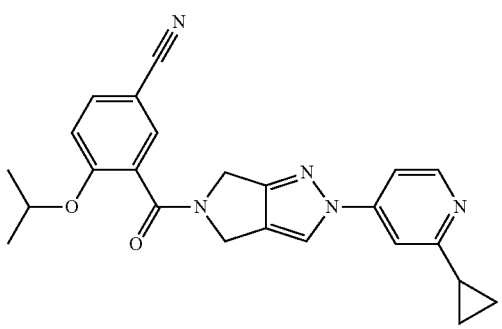 [SMILES: CC(C)Oc1ccc(C#N)cc1C(=O)N1Cc2cn(-c3ccnc(C4CC4)c3)nc2C1]

¹H NMR (400 MHz, DMSO-d₆) δ=8.58-8.36 (m, 2H), 7.88 (dd, J=2.2, 8.8 Hz, 1H), 7.79-7.68 (m, 2H), 7.53 (ddd, J=2.2, 5.7, 10.2 Hz, 1H), 7.33 (dd, J=2.0, 9.0 Hz, 1H), 4.82 (dt, J=3.1, 6.1 Hz, 1H), 4.66 (d, J=8.2 Hz, 2H), 4.36 (d, J=18.4 Hz, 2H), 2.23-2.05 (m, 1H), 1.24 (d, J=5.9 Hz, 6H), 1.04-0.85 (m, 4H); [M+H]=414.09.

Example 406

2-Cyclopentyl-5-[5-methanesulfonyl-2-(propan-2-yloxy)benzoyl]-2H 4H 5H 6H-pyrrolo[3,4-c]pyrazole

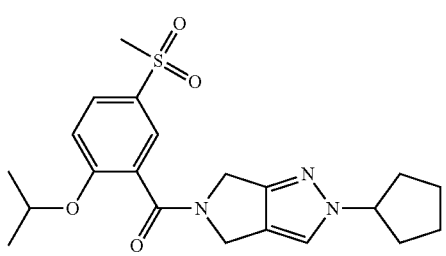 [SMILES: CC(C)Oc1ccc(S(C)(=O)=O)cc1C(=O)N1Cc2cn(C3CCCC3)nc2C1]

¹H NMR (400 MHz, DMSO-d₅) δ=7.90 (dd, J=2.5, 8.8 Hz, 1H), 7.75 (dd, J=2.5, 4.1 Hz, 1H), 7.66-7.47 (m, 1H), 7.36 (dd, J=1.2, 9.4 Hz, 1H), 4.92-4.73 (m, 1H), 4.65 (dd, J=6.5, 8.0 Hz, 1H), 4.54 (s, 2H), 4.23 (d, J=10.6 Hz, 2H), 3.18 (s, 3H), 2.11-1.95 (m, 2H), 1.93-1.68 (m, 4H), 1.68-1.44 (m, 2H), 1.25 (dd, J=1.0, 6.1 Hz, 6H); [M+H]=418.18.

Example 407

2-Cyclopentyl-5-(5-methanesulfonyl-2-{[(2S)-1 1 1-trifluoropropan-2-yl]oxy}benzoyl)-2H 4H 5H 6H-pyrrolo[3,4-c]pyrazole

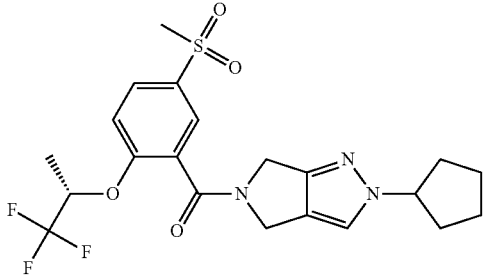 [SMILES: C[C@H](Oc1ccc(S(C)(=O)=O)cc1C(=O)N1Cc2cn(C3CCCC3)nc2C1)C(F)(F)F]

$^1$H NMR (400 MHz, DMSO-$d_6$) δ=8.03-7.92 (m, 1H), 7.86 (dd, J=2.5, 4.9 Hz, 1H), 7.65-7.49 (m, 2H), 5.52 (td, J=6.6, 12.7 Hz, 1H), 4.65 (quin, J=7.1 Hz, 2H), 4.54 (s, 2H), 4.35-4.08 (m, 3H), 3.22 (s, 3H), 2.14-1.94 (m, 3H), 1.86 (br s, 2H), 1.81-1.67 (m, 2H), 1.66-1.50 (m, 2H), 1.41 (dd, J=2.2, 6.5 Hz, 3H); [M+H]=472.18.

Example 408

3-[2-(Oxan-4-yl)-2H 4H 5H 6H-pyrrolo[3,4-c]pyrazole-5-carbonyl]-4-(propan-2-yloxy)benzonitrile

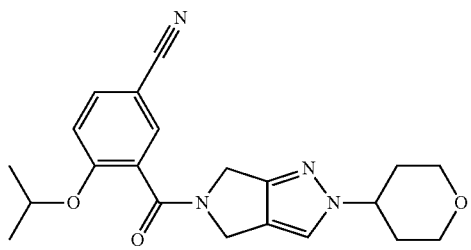 [SMILES: CC(C)Oc1ccc(C#N)cc1C(=O)N1Cc2cn(C3CCOCC3)nc2C1]

$^1$H NMR (400 MHz, CDCl$_3$) δ=7.71-7.53 (m, 2H), 7.36-7.11 (m, 1H), 7.08-6.95 (m, 1H), 4.91-4.60 (m, 3H), 4.48-4.21 (m, 3H), 4.09 (dd, J=3.3, 11.5 Hz, 2H), 3.61-3.34 (m, 2H), 2.22-1.75 (m, 4H), 1.42-1.23 (m, 6H); [M+H]=381.13.

Example 409

2-(Cyclobutylmethyl)-5-(5-methanesulfonyl-2-{[(2S)-1 1 1-trifluoropropan-2-yl]oxy}benzoyl)-2H 4H 5H 6H-pyrrolo[3,4-c]pyrazole

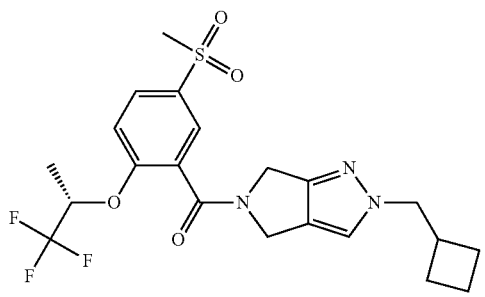 [SMILES: C[C@H](Oc1ccc(S(C)(=O)=O)cc1C(=O)N1Cc2cn(CC3CCC3)nc2C1)C(F)(F)F]

$^1$H NMR (400 MHz, DMSO-$d_6$) δ=7.97 (dd, J=2.3, 8.6 Hz, 1H), 7.92-7.82 (m, 1H), 7.64-7.38 (m, 2H), 5.63-5.42 (m, 1H), 4.53 (br s, 2H), 4.31-4.14 (m, 2H), 4.08 (dd, J=2.2, 7.2 Hz, 2H), 3.22 (d, J=1.2 Hz, 3H), 2.68 (dd, J=7.6, 15.1 Hz, 1H), 2.07-1.62 (m, 6H), 1.40 (d, J=5.9 Hz, 3H); [M+H]=472.14.

Example 410

2-(Cyclobutylmethyl)-5-[5-methanesulfonyl-2-(propan-2-yloxy)benzoyl]-2H 4H 5H 6H-pyrrolo[3,4-c]pyrazole

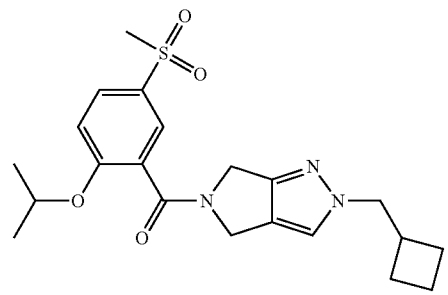 [SMILES: CC(C)Oc1ccc(S(C)(=O)=O)cc1C(=O)N1Cc2cn(CC3CCC3)nc2C1]

$^1$H NMR (400 MHz, DMSO-$d_6$) δ=7.90 (dd, J=2.5, 8.8 Hz, 1H), 7.76 (dd, J=2.5, 3.7 Hz, 1H), 7.61-7.42 (m, 1H), 7.36 (d, J=9.0 Hz, 1H), 4.90-4.74 (m, 1H), 4.53 (br s, 2H), 4.23 (d, J=9.4 Hz, 2H), 4.08 (dd, J=2.2, 7.2 Hz, 2H), 3.18 (s, 3H), 2.69 (dd, J=7.6, 15.1 Hz, 1H), 2.03-1.59 (m, 6H), 1.24 (d, J=5.9 Hz, 6H); [M+H]=418.22.

Example 411

3-[2-(Cyclobutylmethyl)-2H 4H 5H 6H-pyrrolo[3,4-c]pyrazole-5-carbonyl]-4-(propan-2-yloxy)benzonitrile

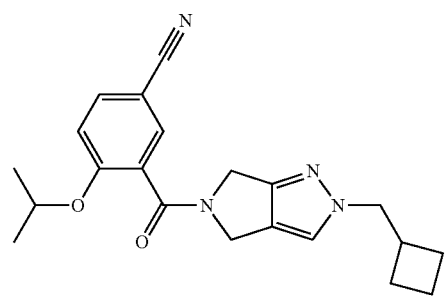 [SMILES: CC(C)Oc1ccc(C#N)cc1C(=O)N1Cc2cn(CC3CCC3)nc2C1]

$^1$H NMR (400 MHz, DMSO-$d_6$) δ=7.85 (dd, J=2.2, 8.8 Hz, 1H), 7.73 (dd, J=2.2, 6.5 Hz, 1H), 7.61-7.39 (m, 1H), 7.36-7.23 (m, 1H), 4.79 (dtd, J=3.9, 6.1, 12.1 Hz, 1H), 4.51 (s, 2H), 4.20 (d, J=8.2 Hz, 2H), 4.08 (dd, J=1.8, 7.2 Hz, 2H), 2.69 (dd, J=7.2, 14.7 Hz, 1H), 2.03-1.60 (m, 6H), 1.22 (d, J=5.9 Hz, 6H); [M+H]=365.13.

Example 412

3-[2-(Oxan-4-yl)-2H 4H 5H 6H-pyrrolo[3,4-c]pyrazole-5-carbonyl]-4-{[(2S)-1 1 1-trifluoropropan-2-yl]oxy}benzonitrile

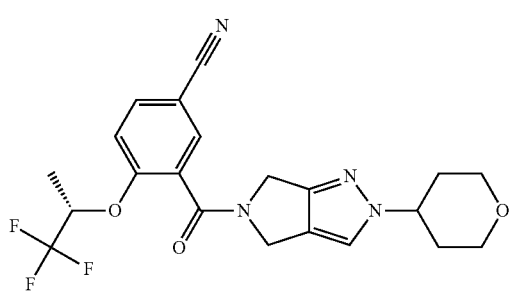 [SMILES: C[C@H](Oc1ccc(C#N)cc1C(=O)N1Cc2cn(C3CCOCC3)nc2C1)C(F)(F)F]

¹H NMR (400 MHz, DMSO-d₆) δ=7.95 (dd, J=1.8, 8.4 Hz, 1H), 7.84 (dd, J=2.0, 7.0 Hz, 1H), 7.72-7.54 (m, 1H), 7.52 (dd, J=1.8, 8.8 Hz, 1H), 5.50 (td, J=6.3, 12.8 Hz, 1H), 4.53 (s, 2H), 4.45-4.31 (m, 1H), 4.30-4.07 (m, 2H), 4.01-3.83 (m, 2H), 3.50-3.34 (m, 2H), 2.07-1.74 (m, 4H), 1.39 (d, J=6.7 Hz, 3H); [M+H]=435.1.

Example 413

2-(Cyclopentylmethyl)-5-(5-methanesulfonyl-2-{[(2S)-1 1 1-trifluoropropan-2-yl]oxy}benzoyl)-2H 4H 5H 6H-pyrrolo[3,4-c]pyrazole

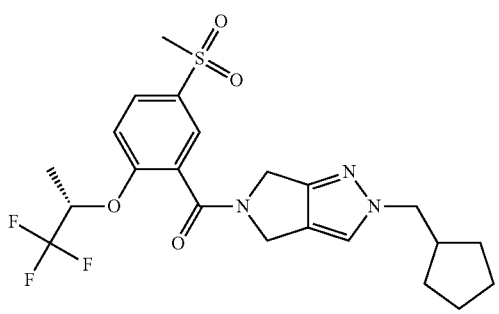 [SMILES: C[C@H](Oc1ccc(S(C)(=O)=O)cc1C(=O)N1Cc2cn(CC3CCCC3)nc2C1)C(F)(F)F]

¹H NMR (400 MHz, DMSO-d₆) δ=7.97 (dd, J=2.3, 9.0 Hz, 1H), 7.87 (dd, J=2.5, 4.5 Hz, 1H), 7.63-7.44 (m, 2H), 5.51 (dtd, J=3.1, 6.4, 12.7 Hz, 1H), 4.54 (s, 2H), 4.36-4.12 (m, 2H), 3.97 (dd, J=1.6, 7.4 Hz, 2H), 3.22 (d, J=0.8 Hz, 3H), 2.32 (qd, J=7.5, 15.3 Hz, 1H), 1.68-1.42 (m, 6H), 1.40 (d, J=6.7 Hz, 3H), 1.33-1.07 (m, 2H); [M+H]=486.28.

Example 414

3-[2-(Cyclopentylmethyl)-2H 4H 5H 6H-pyrrolo[3,4-c]pyrazole-5-carbonyl]-4-{[(2S)-1 1 1-trifluoropropan-2-yl]oxy}benzonitrile

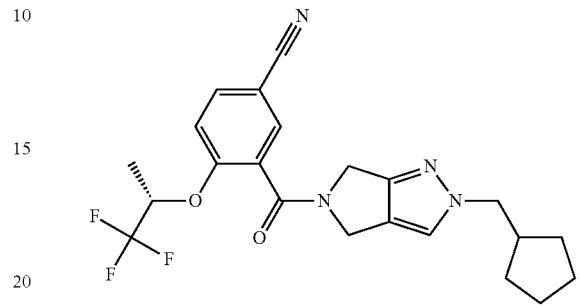

¹H NMR (400 MHz, DMSO-d₆) δ=7.95 (dd, J=2.3, 8.6 Hz, 1H), 7.86 (dd, J=2.2, 7.6 Hz, 1H), 7.63-7.42 (m, 2H), 5.59-5.44 (m, 1H), 4.52 (s, 2H), 4.28-4.12 (m, 2H), 3.97 (d, J=7.4 Hz, 2H), 2.31 (qd, J=7.4, 15.0 Hz, 1H), 1.66-1.42 (m, 6H), 1.38 (d, J=6.3 Hz, 3H), 1.30-1.07 (m, 2H); [M+H]=433.1.

Example 415

2-Cyclopentyl-5-[5-(ethanesulfonyl)-2-(propan-2-yloxy)benzoyl]-2H 4H 5H 6H-pyrrolo[3,4-c]pyrazole

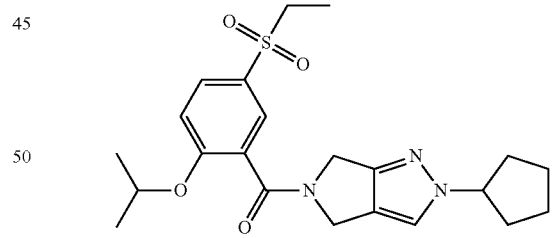

¹H NMR (400 MHz, DMSO-d₆) δ=7.86 (dd, J=2.3, 9.0 Hz, 1H), 7.70 (t, J=2.3 Hz, 1H), 7.65-7.45 (m, 1H), 7.36 (dd, J=1.2, 9.0 Hz, 1H), 4.81 (dtd, J=2.5, 6.1, 12.2 Hz, 1H), 4.71-4.59 (m, 1H), 4.54 (s, 2H), 4.22 (d, J=10.2 Hz, 2H), 3.45-3.18 (m, 2H), 2.09-1.96 (m, 2H), 1.94-1.80 (m, 2H), 1.80-1.67 (m, 2H), 1.67-1.50 (m, 2H), 1.33-1.16 (m, 6H), 1.08 (t, J=7.2 Hz, 3H); [M+H]=432.24.

Example 416

3-{2-[(2S)-2-Methylbutyl]-2H 4H 5H 6H-pyrrolo[3,4-c]pyrazole-5-carbonyl}-4-(propan-2-yloxy)benzonitrile

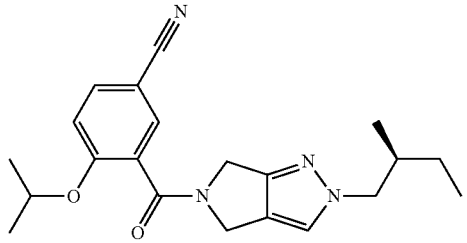 [SMILES: CC[C@H](C)Cn1cc2c(n1)CN(C(=O)c1cc(C#N)ccc1OC(C)C)C2]

$^1$H NMR (400 MHz, DMSO-d$_6$) δ=7.85 (dd, J=2.2, 8.8 Hz, 1H), 7.74 (dd, J=2.3, 6.3 Hz, 1H), 7.59-7.43 (m, 1H), 7.30 (dd, J=1.2, 9.0 Hz, 1H), 4.79 (dtd, J=3.5, 5.9, 12.0 Hz, 1H), 4.53 (d, J=2.7 Hz, 2H), 4.21 (d, J=7.8 Hz, 2H), 4.02-3.92 (m, 1H), 3.90-3.81 (m, 1H), 1.95-1.78 (m, 1H), 1.39-1.16 (m, 7H), 1.15-1.00 (m, 1H), 0.84 (dt, J=4.3, 7.4 Hz, 3H), 0.77 (dd, J=3.1, 6.7 Hz, 3H); [M+H]=367.18.

Example 417

2-Cyclopentyl-5-[5-(ethanesulfonyl)-2-{[(2S)-1 1 1-trifluoropropan-2-yl]oxy}benzoyl]-2H 4H 5H 6H-pyrrolo[3,4-c]pyrazole

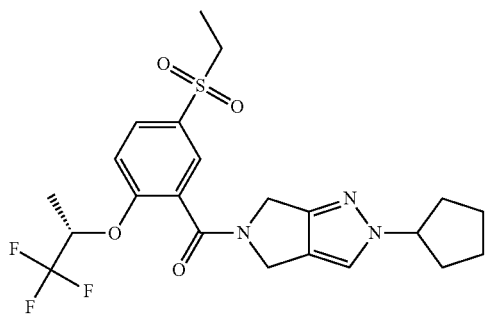 [SMILES: CCS(=O)(=O)c1ccc(O[C@@H](C)C(F)(F)F)c(C(=O)N2Cc3cn(C4CCCC4)nc3C2)c1]

$^1$H NMR (400 MHz, DMSO-d$_6$) δ=7.93 (ddd, J=1.2, 2.4, 8.9 Hz, 1H), 7.85-7.76 (m, 1H), 7.67-7.48 (m, 2H), 5.61-5.40 (m, 1H), 4.65 (quin, J=7.2 Hz, 1H), 4.54 (s, 2H), 4.33-4.11 (m, 2H), 3.43-3.09 (m, 2H), 2.11-1.94 (m, 2H), 1.93-1.69 (m, 4H), 1.69-1.53 (m, 2H), 1.51-1.30 (m, 3H), 1.16-1.05 (m, 3H); [M+H]=486.20.

Example 418

3-{2-[(2S)-2-Methylbutyl]-2H 4H 5H 6H-pyrrolo[3,4-c]pyrazole-5-carbonyl}-4-{[(2S)-1 1 1-trifluoropropan-2-yl]oxy}benzonitrile

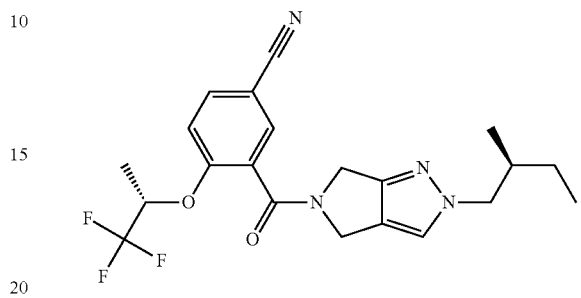

$^1$H NMR (400 MHz, DMSO-d$_6$) δ=7.95 (dd, J=2.2, 8.8 Hz, 1H), 7.86 (dd, J=2.3, 7.8 Hz, 1H), 7.61-7.41 (m, 2H), 5.56-5.40 (m, 1H), 4.52 (d, J=2.3 Hz, 2H), 4.32-4.08 (m, 2H), 4.05-3.90 (m, 1H), 3.85 (dd, J=7.6, 13.5 Hz, 1H), 1.95-1.77 (m, 1H), 1.38 (d, J=6.3 Hz, 3H), 1.34-1.18 (m, 1H), 1.15-0.99 (m, 1H), 0.83 (dt, J=4.7, 7.4 Hz, 3H), 0.76 (dd, J=3.1, 6.7 Hz, 3H); [M+H]=421.14.

Example 419

3-[2-(Oxolan-3-ylmethyl)-2H 4H 5H 6H-pyrrolo[3,4-c]pyrazole-5-carbonyl]-4-{[(2S)-1 1 1-trifluoropropan-2-yl]oxy}benzonitrile

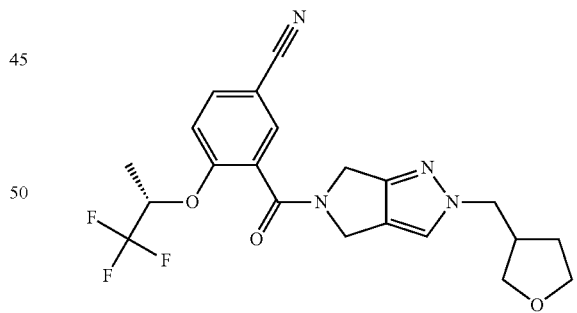

$^1$H NMR (400MHz, DMSO-d$_6$) δ=7.95 (dd, J=2.2, 8.8 Hz, 1H), 7.86 (dd, J=2.2, 7.6 Hz, 1H), 7.70-7.43 (m, 2H), 5.59-5.37 (m, 2H), 4.52 (s, 2H), 4.29-4.13 (m, 2H), 4.06 (d, J=7.4 Hz, 2H), 3.77-3.68 (m, 1H), 3.66-3.55 (m, 2H), 3.47-3.38 (m, 1H), 2.74-2.59 (m, 1H), 1.96-1.75 (m, 1H), 1.65-1.49 (m, 1H), 1.38 (d, J=6.3 Hz, 3H); [M+H]=435.28.

Example 420

3-[2-(Oxolan-3-ylmethyl)-2H 4H 5H 6H-pyrrolo[3,4-c]pyrazole-5-carbonyl]-4-(propan-2-yloxy)benzonitrile

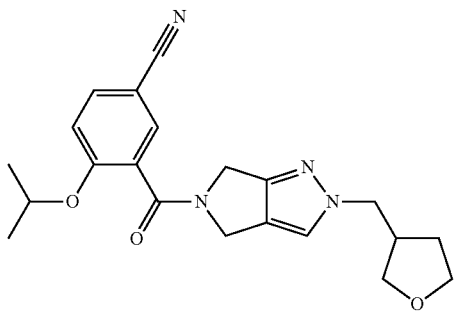 [SMILES: CC(C)Oc1ccc(C#N)cc1C(=O)N1Cc2cn(CC3CCOC3)nc2C1]

¹H NMR (400 MHz, DMSO-d₆) δ=7.85 (dd, J=2.3, 8.6 Hz, 1H), 7.73 (dd, J=2.2, 6.1 Hz, 1H), 7.66-7.48 (m, 1H), 7.38-7.22 (m, 1H), 4.80 (dtd, J=3.5, 6.1, 12.1 Hz, 1H), 4.53 (s, 2H), 4.22 (d, J=9.4 Hz, 2H), 4.06 (d, J=7.4 Hz, 2H), 3.72 (ddt, J=2.9, 5.5, 8.1 Hz, 1H), 3.66-3.55 (m, 2H), 3.43 (ddd, J=3.1, 5.5, 8.6 Hz, 1H), 2.72-2.61 (m, 1H), 1.95-1.79 (m, 1H), 1.66-1.47 (m, 2H), 1.22 (d, J=6.3 Hz, 6H); [M+H]=381.09.

Example 421

3-[1-(Pyridazin-4-yl)-1H 4H 5H 6H-pyrrolo[3,4-c]pyrazole-5-carbonyl]-4-{[(2S)-1 1 1-trifluoropropan-2-yl]oxy}benzonitrile

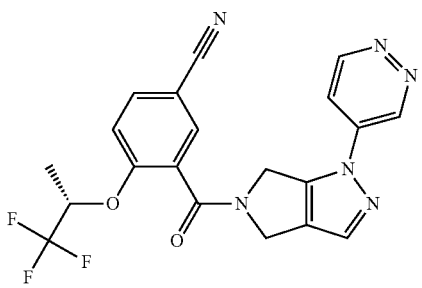 [SMILES: C[C@H](Oc1ccc(C#N)cc1C(=O)N1Cc2cnn(-c3ccnnc3)c2C1)C(F)(F)F]

¹H NMR (400 MHz, DMSO-d₆) δ=9.64-9.44 (m, 1H), 9.30-9.16 (m, 1H), 8.00 (ddd, J=2.2, 6.4, 8.7 Hz, 1H), 7.92-7.81 (m, 2H), 7.75-7.67 (m, 1H), 7.56 (dd, J=2.0, 9.0 Hz, 1H), 5.62-5.42 (m, 1H), 5.17 (s, 1H), 4.86 (d, J=9.4 Hz, 1H), 4.60 (br s, 1H), 4.28 (q, J=12.1 Hz, 1H), 1.40 (d, J=6.7 Hz, 3H); [M+H]=429.16.

Example 422

4-(Propan-2-yloxy)-3-[2-(pyridazin-4-yl)-2H 4H 5H 6H-pyrrolo[3,4-c]pyrazole-5-carbonyl]benzonitrile

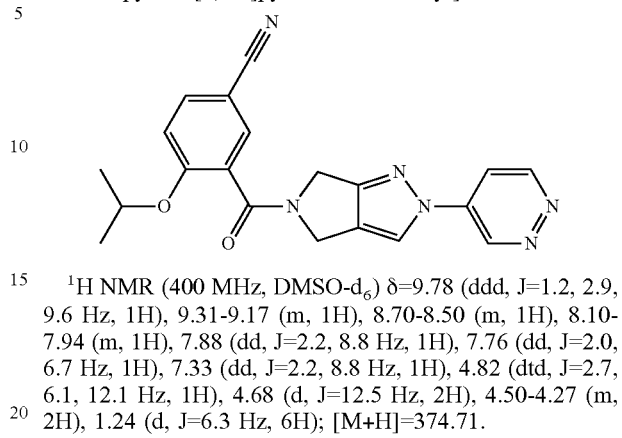

¹H NMR (400 MHz, DMSO-d₆) δ=9.78 (ddd, J=1.2, 2.9, 9.6 Hz, 1H), 9.31-9.17 (m, 1H), 8.70-8.50 (m, 1H), 8.10-7.94 (m, 1H), 7.88 (dd, J=2.2, 8.8 Hz, 1H), 7.76 (dd, J=2.0, 6.7 Hz, 1H), 7.33 (dd, J=2.2, 8.8 Hz, 1H), 4.82 (dtd, J=2.7, 6.1, 12.1 Hz, 1H), 4.68 (d, J=12.5 Hz, 2H), 4.50-4.27 (m, 2H), 1.24 (d, J=6.3 Hz, 6H); [M+H]=374.71.

Example 423

3-[2-(Pyridazin-4-yl)-2H 4H 5H 6H-pyrrolo[3,4-c]pyrazole-5-carbonyl]-4-{[(2S)-1 1 1-trifluoropropan-2-yl]oxy}benzonitrile

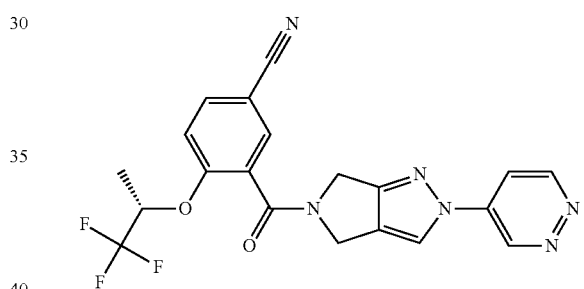

¹H NMR (400 MHz, DMSO-d₆) δ=9.78 (ddd, J=1.0, 2.9, 10.2 Hz, 1H), 9.24 (ddd, J=1.0, 2.1, 6.0 Hz, 1H), 8.72-8.49 (m, 1H), 8.06-7.95 (m, 2H), 7.88 (dd, J=2.2, 7.6 Hz, 1H), 7.55 (dd, J=2.7, 9.0 Hz, 1H), 5.52 (td, J=6.3, 12.5 Hz, 1H), 4.68 (d, J=12.9 Hz, 2H), 4.54-4.24 (m, 2H), 1.40 (d, J=6.3 Hz, 3H); [M+H]=429.05.

Example 424

3-(2-{Imidazo[1 2-a]pyridin-7-yl}-2H 4H 5H 6H-pyrrolo[3,4-c]pyrazole-5-carbonyl)-4-(propan-2-yloxy)benzonitrile

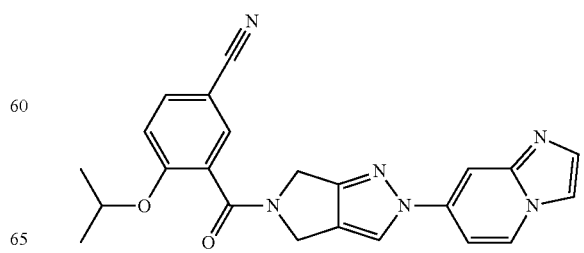

¹H NMR (400 MHz, DMSO-d₆) δ=8.67-8.59 (m, 1H), 8.54-8.28 (m, 1H), 7.95-7.91 (m, 2H), 7.90-7.84 (m, 1H), 7.76 (dd, J=2.2, 4.9 Hz, 1H), 7.57 (d, J=1.2 Hz, 1H), 7.49 (ddd, J=2.2, 7.3, 15.2 Hz, 1H), 7.33 (d, J=9.0 Hz, 1H), 4.90-4.75 (m, 1H), 4.67 (d, J=8.6 Hz, 2H), 4.37 (d, J=19.2 Hz, 2H), 1.24 (d, J=5.9 Hz, 6H); [M+H]=413.13.

Example 425

3-(2-{Imidazo[1 2-a]pyridin-7-yl}-2H 4H 5H 6H-pyrrolo[3,4-c]pyrazole-5-carbonyl)-4-{[(2S)-1 1 1-trifluoropropan-2-yl]oxy}benzonitrile

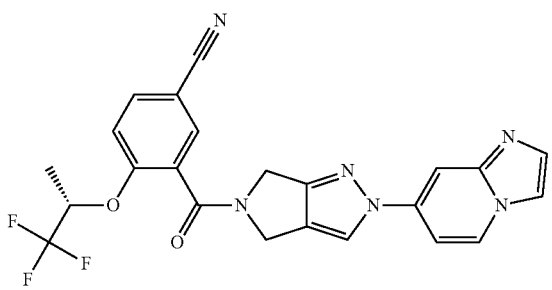 [SMILES: C[C@H](Oc1ccc(C#N)cc1C(=O)N1Cc2cn(-c3ccn4ccnc4c3)nc2C1)C(F)(F)F]

¹H NMR (400 MHz, DMSO-d₆) δ=8.66-8.60 (m, 1H), 8.55-8.38 (m, 1H), 7.98 (dd, J=2.2, 8.8 Hz, 1H), 7.95-7.91 (m, 2H), 7.89 (dd, J=2.0, 5.5 Hz, 1H), 7.60-7.42 (m, 3H), 5.64-5.45 (m, 1H), 4.67 (d, J=9.0 Hz, 2H), 4.50-4.21 (m, 2H), 1.41 (d, J=6.3 Hz, 3H); [M+H]=467.16.

Example 426

2-(Cyclobutylmethyl)-5-[2-(3-fluorophenyl)-5-methanesulfonylbenzoyl]-2H 4H 5H 6H-pyrrolo[3,4-c]pyrazole

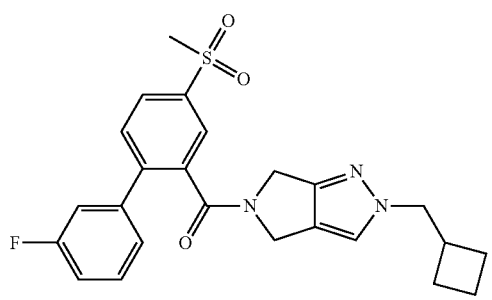 [SMILES: CS(=O)(=O)c1ccc(-c2cccc(F)c2)c(C(=O)N2Cc3cn(CC4CCC4)nc3C2)c1]

¹H NMR (400 MHz, DMSO-d₆) δ=8.13-7.97 (m, 2H), 7.80 (dd, J=4.5, 8.0 Hz, 1H), 7.55-7.30 (m, 4H), 7.29-7.18 (m, 1H), 4.39 (hr s, 2H), 4.03 (dd, J=2.7, 7.4 Hz, 4H), 3.31 (d, J=1.6 Hz, 4H), 2.64 (qd, J=7.5, 14.8 Hz, 1H), 2.07-1.42 (m, 6H); [M+H]=454.28.

Example 427

5-[2-(3-Fluorophenyl)-5-methanesulfonylbenzoyl]-2-(2-methylpropyl)-2H 4H 5H 6H-pyrrolo[3,4-c]pyrazole

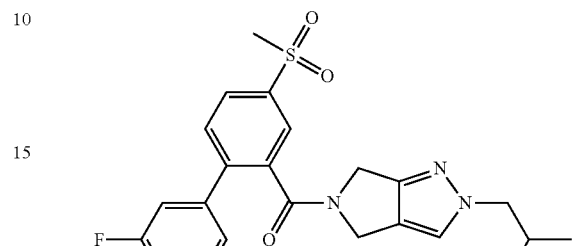

¹H NMR (400 MHz, DMSO-d₆) δ=8.13-7.98 (m, 2H), 7.81 (dd, J=4.3, 8.2 Hz, 1H), 7.56-7.31 (m, 4H), 7.29-7.16 (m, 1H), 4.40 (hr s, 2H), 4.02 (hr s, 2H), 3.82 (dd, J=2.5, 7.2 Hz, 2H), 2.09-1.91 (m, 1H), 0.77 (dd, J=2.7, 6.7 Hz, 6H); [M+H]=441.93.

Example 428

1-{2-[2-(Cyclobutylmethyl)-2H 4H 5H 6H-pyrrolo[3,4-c]pyrazole-5-carbonyl]-4-(ethanesulfonyl)phenyl}-4 4-difluoropiperidine

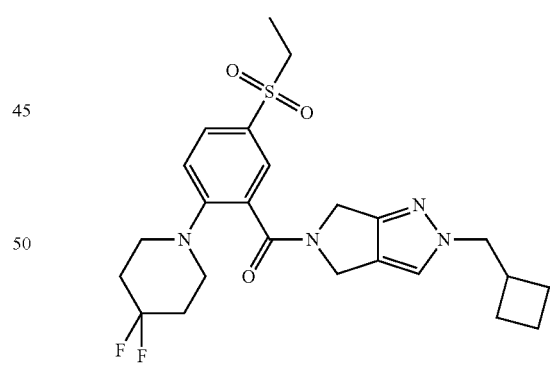

¹H NMR (400 MHz, DMSO-d₆) δ=7.80 (td, J=2.2, 8.6 Hz, 1H), 7.70-7.62 (m, 1H), 7.60-7.44 (m, 1H), 7.29 (d, J=8.6 Hz, 1H), 4.57 (hr s, 2H), 4.49-4.16 (m, 2H), 4.08 (dd, J=3.1, 7.4 Hz, 2H), 3.26-3.20 (m, 2H), 2.69 (qd, J=7.5, 15.2 Hz, 1H), 2.06-1.86 (m, 6H), 1.86-1.63 (m, 4H), 1.08 (dt, J=1.6, 7.4 Hz, 3H); [M+H]=493.27.

Example 429

4 4-Difluoro-1-(4-methanesulfonyl-2-{2-[(2S)-2-methylbutyl]-2H 4H 5H 6H-pyrrolo[3,4-c]pyrazole-5-carbonyl}phenyl)piperidine

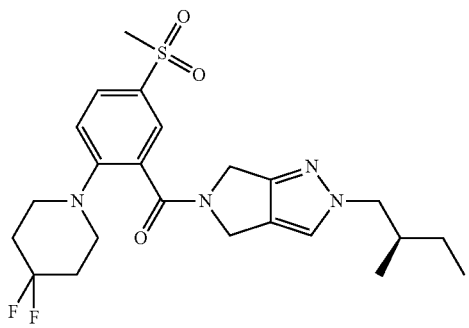 [SMILES: CC[C@@H](C)Cn1cc2c(n1)CN(C(=O)c1cc(S(C)(=O)=O)ccc1N1CCC(F)(F)CC1)C2]

$^1$H NMR (400 MHz, DMSO-d$_6$) δ=7.89-7.81 (m, 1H), 7.72 (d, J=2.3 Hz, 1H), 7.62-7.44 (m, 1H), 7.29 (d, J=9.0 Hz, 1H), 4.59 (br s, 2H), 4.36 (br s, 2H), 4.03-3.79 (m, 2H), 3.18 (d, J=2.7 Hz, 3H), 2.03-1.78 (m, 5H), 1.36-1.20 (m, 1H), 1.18-1.00 (m, 1H), 0.94-0.65 (m, 6H); [M+H]=481.34.

Example 430

1-(2-{2-Cyclopentyl-2H 4H 5H 6H-pyrrolo[3,4-c]pyrazole-5-carbonyl}-4-methanesulfonylphenyl)-4 4-difluoropiperidine

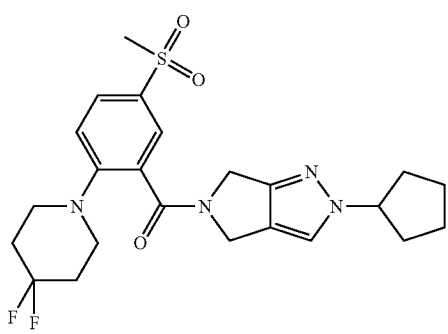 [SMILES: CS(=O)(=O)c1ccc(N2CCC(F)(F)CC2)c(C(=O)N2Cc3cn(C4CCCC4)nc3C2)c1]

$^1$H NMR (400 MHz, DMSO-d$_6$) δ=7.85 (qd, J=1.3, 8.6 Hz, 1H), 7.71 (d, J=2.3 Hz, 1H), 7.66-7.47 (m, 1H), 7.35-7.24 (m, 1H), 4.74-4.54 (m, 3H), 4.48-4.08 (m, 2H), 3.18 (d, J=2.7 Hz, 3H), 2.17-1.44 (m, 12H); [M+H]=479.29.

Example 431

1-{2-[2-(Cyclobutylmethyl)-2H 4H 5H 6H-pyrrolo[3,4-c]pyrazole-5-carbonyl]-4-methanesulfonylphenyl}-4 4-difluoropiperidine

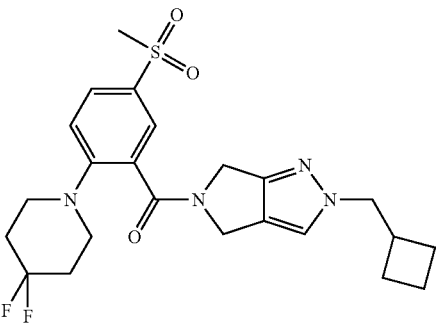 [SMILES: CS(=O)(=O)c1ccc(N2CCC(F)(F)CC2)c(C(=O)N2Cc3cn(CC4CCC4)nc3C2)c1]

$^1$H NMR (400 MHz, DMSO-d$_6$) δ=7.85 (td, J=2.1, 8.8 Hz, 1H), 7.72 (d, J=2.3 Hz, 1H), 7.60-7.43 (m, 1H), 7.29 (d, J=8.6 Hz, 1H), 4.58 (br s, 2H), 4.51-4.17 (m, 2H), 4.08 (dd, J=3.3, 7.2 Hz, 2H), 3.18 (d, J=2.3 Hz, 3H), 2.77-2.63 (m, 1H), 2.07-1.60 (m, 10H); [M+H]=479.29.

Example 432

4 4-Difluoro-1-{4-methanesulfonyl-2-[2-(2-methylpropyl)-2H 4H 5H 6H-pyrrolo[3,4-c]pyrazole-5-carbonyl]phenyl}piperidine

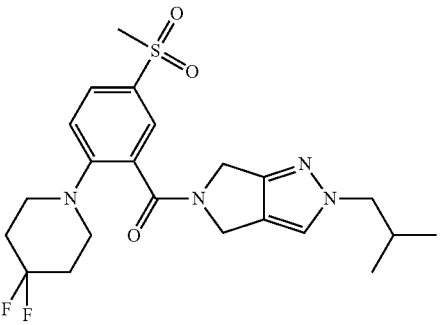 [SMILES: CC(C)Cn1cc2c(n1)CN(C(=O)c1cc(S(C)(=O)=O)ccc1N1CCC(F)(F)CC1)C2]

$^1$H NMR (400 MHz, DMSO-d$_6$) δ=7.85 (td, J=2.1, 8.8 Hz, 1H), 7.72 (d, J=2.3 Hz, 1H), 7.61-7.43 (m, 1H), 7.29 (d, J=8.6 Hz, 1H), 4.59 (br s, 2H), 4.41 (br s, 2H), 3.87 (dd, J=2.0, 7.0 Hz, 2H), 3.18 (d, J=2.3 Hz, 3H), 2.19-1.83 (m, 5H), 0.80 (dd, J=3.1, 6.7 Hz, 6H); [M+H]=467.28.

Example 433

4 4-Difluoro-1-{4-methanesulfonyl-2-[2-(propan-2-yl)-2H 4H 5H 6H-pyrrolo[3,4-c]pyrazole-5-carbonyl]phenyl}piperidine

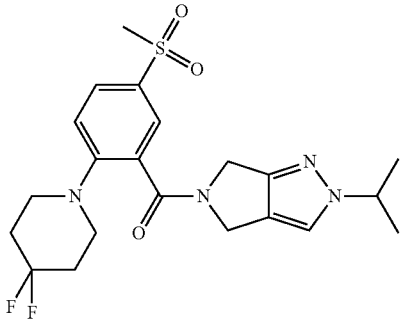 [SMILES: CC(C)n1cc2c(n1)CN(C(=O)c1cc(S(C)(=O)=O)ccc1N1CCC(F)(F)CC1)C2]

$^1$H NMR (400 MHz, DMSO-d$_6$) δ=7.85 (td, J=2.1, 8.8 Hz, 1H), 7.71 (d, J=2.3 Hz, 1H), 7.66-7.48 (m, 1H), 7.29 (d, J=8.6 Hz, 1H), 4.59 (br s, 2H), 4.47 (dtd, J=4.3, 6.7, 13.3 Hz, 1H), 4.33 (br s, 2H), 3.18 (d, J=3.1 Hz, 3H), 2.06-1.87 (m, 4H), 1.37 (dd, J=4.3, 6.7 Hz, 6H); [M+H]=453.18.

Example 434

2-(2-Fluoro-2-methylpropyl)-5-[2-(3-fluorophenyl)-5-methanesulfonylbenzoyl]-2H 4H 5H 6H-pyrrolo[3,4-c]pyrazole

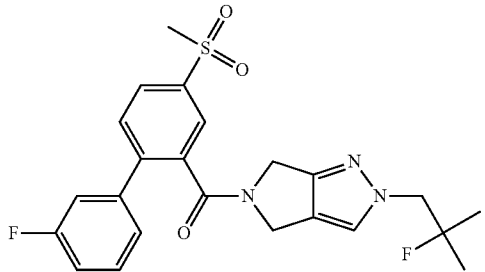 [SMILES: CC(C)(F)Cn1cc2c(n1)CN(C(=O)c1cc(S(C)(=O)=O)ccc1-c1cccc(F)c1)C2]

$^1$H NMR (400 MHz, DMSO-d$_6$) δ=8.12-7.99 (m, 2H), 7.81 (dd, J=4.3, 8.2 Hz, 1H), 7.57-7.41 (m, 1H), 7.40-7.29 (m, 3H), 7.24 (t, J=8.6 Hz, 1H), 4.42 (br s, 2H), 4.31-4.14 (m, 2H), 4.03 (br s, 1H), 3.31 (d, J=1.6 Hz, 3H), 1.32-1.10 (m, 6H); [M+H]=459.94.

Example 435

5-{5-Methanesulfonyl-2-[(3-methyloxetan-3-yl)methoxy]benzoyl}-2-phenyl-2H 4H 5H 6H-pyrrolo[3,4-c]pyrazole

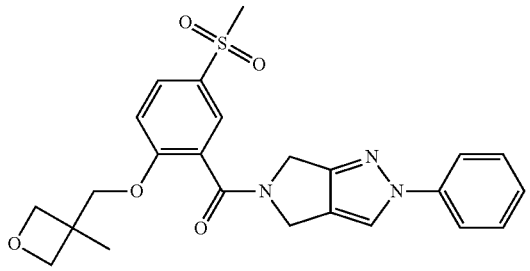 [SMILES: CC1(COc2ccc(S(C)(=O)=O)cc2C(=O)N2Cc3cn(-c4ccccc4)nc3C2)COC1]

$^1$H NMR (400 MHz, DMSO-d$_6$) δ=8.38-8.20 (m, 1H), 8.01-7.95 (m, 1H), 7.84 (dd, J=2.3, 4.3 Hz, 1H), 7.81-7.73 (m, 2H), 7.49-7.39 (m, 3H), 7.31-7.24 (m, 1H), 4.65 (d, J=6.3 Hz, 2H), 4.43-4.33 (m, 4H), 4.23 (d, J=1.2 Hz, 2H), 4.17 (dd, J=5.9, 6.7 Hz, 2H), 3.21 (s, 3H), 1.22 (d, J=2.0 Hz, 3H); [M+H]=468.27.

Example 436

2-(2-Fluorophenyl)-5-{5-methanesulfonyl-2-[(3-methyloxetan-3-yl)methoxy]benzoyl}-2H 4H 5H 6H-pyrrolo[3,4-c]pyrazole

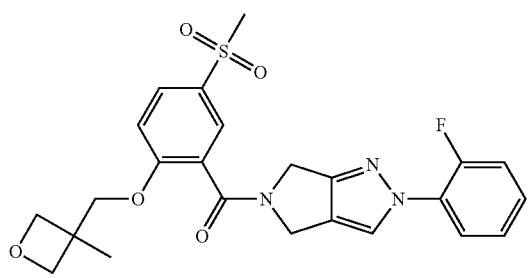 [SMILES: CC1(COc2ccc(S(C)(=O)=O)cc2C(=O)N2Cc3cn(-c4ccccc4F)nc3C2)COC1]

$^1$H NMR (400 MHz, DMSO-d$_6$) δ=8.07-7.91 (m, 2H), 7.84 (dd, J=2.3, 4.3 Hz, 1H), 7.80-7.67 (m, 1H), 7.49-7.29 (m, 4H), 4.65 (d, J=9.4 Hz, 2H), 4.43-4.34 (m, 4H), 4.23 (d, J=2.7 Hz, 2H), 4.18 (t, J=6.1 Hz, 2H), 3.21 (s, 3H), 1.23 (d, J=2.0 Hz, 3H); [M+H]=486.2.

Example 437

5-{5-Methanesulfonyl-2-[(3-methyloxetan-3-yl)methoxy]benzoyl}-2-(3-methylphenyl)-2H 4H 5H 6H-pyrrolo[3,4-c]pyrazole

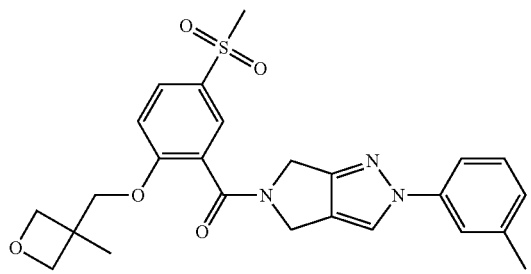 [SMILES: Cc1cccc(-n2cc3c(n2)CN(C(=O)c2cc(S(C)(=O)=O)ccc2OCC2(C)COC2)C3)c1]

$^1$H NMR (400 MHz, DMSO-d$_6$) δ=8.35-8.18 (m, 1H), 7.98 (dd, J=2.3, 8.6 Hz, 1H), 7.84 (dd, J=2.3, 3.9 Hz, 1H), 7.66-7.51 (m, 2H), 7.41 (dd, J=1.6, 9.0 Hz, 1H), 7.33 (dt, J=1.6, 7.8 Hz, 1H), 7.12-7.06 (m, 1H), 4.64 (d, J=4.7 Hz, 2H), 4.37 (dt, J=5.3, 6.2 Hz, 4H), 4.23 (d, J=1.6 Hz, 2H), 4.16 (t, J=6.3 Hz, 2H), 3.21 (s, 3H), 2.35 (d, J=3.1 Hz, 3H), 1.22 (d, J=2.0 Hz, 3H); [M+H]=482.14.

Example 438

2-[2-Fluoro-3-(trifluoromethyl)phenyl]-5-{5-methanesulfonyl-2-[(3-methyloxetan-3-yl)methoxy]benzoyl}-2H 4H 5H 6H-pyrrolo[3,4-c]pyrazole

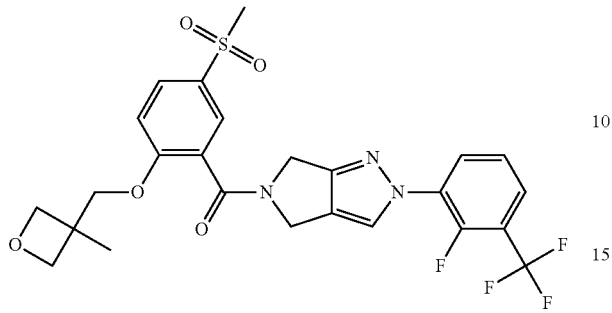

¹H NMR (400 MHz, DMSO-d$_6$) δ=8.18-7.95 (m, 3H), 7.85 (dd, J=2.3, 3.9 Hz, 1H), 7.79 (t, J=6.8 Hz, 1H), 7.54 (dt, J=4.7, 8.0 Hz, 1H), 7.42 (dd, J=2.7, 9.0 Hz, 1H), 4.67 (d, J=10.6 Hz, 2H), 4.45-4.34 (m, 4H), 4.26-4.15 (m, 4H), 3.24-3.17 (m, 3H), 1.23 (d, J=2.0 Hz, 3H); [M+H]=554.54.

Example 439

2-(5-Chloro-2-fluorophenyl)-5-{5-methanesulfonyl-2-[(3-methyloxetan-3-yl)methoxy]benzoyl}-2H 4H 5H 6H-pyrrolo[3,4-c]pyrazole

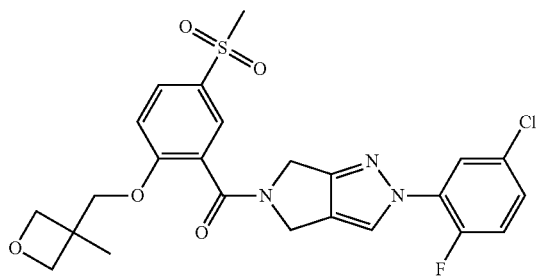 [SMILES: CC1(COc2ccc(S(C)(=O)=O)cc2C(=O)N2Cc3cn(-c4cc(Cl)ccc4F)nc3C2)COC1]

¹H NMR (400 MHz, DMSO-d$_6$) δ=8.13-7.96 (m, 2H), 7.89-7.76 (m, 2H), 7.57-7.39 (m, 3H), 4.65 (d, J=11.3 Hz, 2H), 4.42 (s, 1H), 4.39-4.34 (m, 3H), 4.23 (d, J=3.1 Hz, 2H), 4.17 (t, J=6.1 Hz, 2H), 3.21 (d, J=1.2 Hz, 3H), 1.22 (d, J=2.3 Hz, 3H); [M+H]=520.18.

Example 440

2-(4-Fluorophenyl)-5-{5-methane sulfonyl-2-[(3-methyloxetan-3-yl)methoxy]benzoyl}-2H 4H 5H 6H-pyrrolo[3,4-c]pyrazole

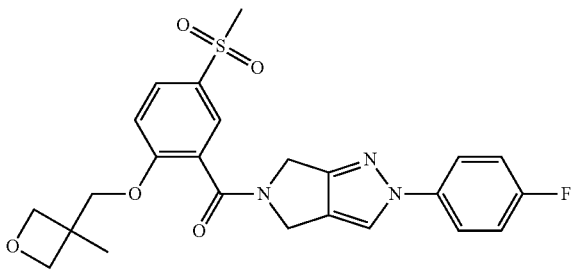 [SMILES: CC1(COc2ccc(S(C)(=O)=O)cc2C(=O)N2Cc3cn(-c4ccc(F)cc4)nc3C2)COC1]

¹H NMR (400 MHz, DMSO-d$_6$) δ=8.35-8.18 (m, 1H), 8.01-7.96 (m, 1H), 7.86-7.76 (m, 3H), 7.41 (dd, J=2.2, 8.8 Hz, 1H), 7.31 (dt, J=1.6, 8.8 Hz, 2H), 4.64 (d, J=5.9 Hz, 2H), 4.41-4.34 (m, 4H), 4.23 (s, 2H), 4.16 (t, J=6.1 Hz, 2H), 3.21 (s, 3H), 1.22 (d, J=1.6 Hz, 3H); [M+H]=486.24.

Example 441

2-(2-Fluoro-3-methylphenyl)-5-{5-methanesulfonyl-2-[(3-methyloxetan-3-yl)methoxy]benzoyl}-2H 4H 5H 6H-pyrrolo[3,4-c]pyrazole

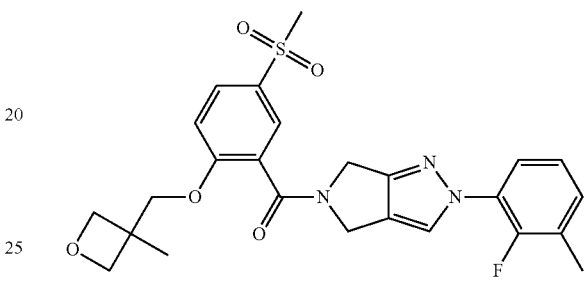

¹H NMR (400 MHz, DMSO-d$_6$) δ=8.05-7.89 (m, 2H), 7.84 (dd, J=2.5, 4.5 Hz, 1H), 7.59-7.46 (m, 1H), 7.41 (dd, J=2.5, 8.8 Hz, 1H), 7.32-7.26 (m, 1H), 7.24-7.15 (m, 1H), 4.65 (d, J=7.4 Hz, 2H), 4.42-4.34 (m, 4H), 4.23 (d, J=2.0 Hz, 2H), 4.20-4.14 (m, 2H), 3.21 (s, 3H), 2.30 (t, J=2.2 Hz, 3H), 1.23 (d, J=2.3 Hz, 3H); [M+H]=500.26.

Example 442

2-(2-Fluoro-5-methylphenyl)-5-{5-methanesulfonyl-2-[(3-methyloxetan-3-yl)methoxy]benzoyl}-2H 4H 5H 6H-pyrrolo[3,4-c]pyrazole

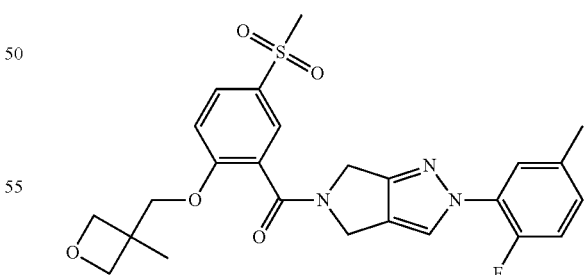

¹H NMR (400 MHz, DMSO-d$_6$) δ=8.05-7.88 (m, 2H), 7.84 (dd, J=2.3, 3.5 Hz, 1H), 7.62-7.48 (m, 1H), 7.42 (dd, J=1.6, 8.6 Hz, 1H), 7.31 (ddd, J=2.7, 8.5, 11.4 Hz, 1H), 7.22-7.15 (m, 1H), 4.65 (d, J=8.6 Hz, 2H), 4.44-4.32 (m, 4H), 4.23 (d, J=3.5 Hz, 2H), 4.17 (t, J=5.5 Hz, 2H), 3.21 (d, J=1.2 Hz, 3H), 2.32 (d, J=6.7 Hz, 3H), 1.22 (d, J=2.0 Hz, 3H); [M+H]=500.23.

Example 443

3-[2-(Pyridin-4-yl)-2H 4H 5H 6H-pyrrolo[3,4-c]pyrazole-5-carbonyl]-4-{[(2S)-1 1 1-trifluoropropan-2-yl]oxy}benzonitrile

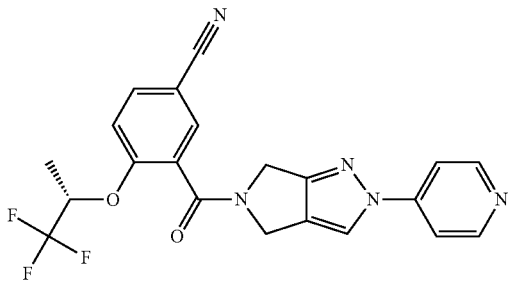 [SMILES: C[C@H](Oc1ccc(C#N)cc1C(=O)N1Cc2cn(-c3ccncc3)nc2C1)C(F)(F)F]

$^1$H NMR (400 MHz, DMSO-d$_6$) δ=8.65-8.43 (m, 3H), 7.98 (td, J=1.0, 9.8 Hz, 1H), 7.88 (dd, J=2.2, 7.2 Hz, 1H), 7.85-7.73 (m, 2H), 7.54 (dd, J=2.2, 8.8 Hz, 1H), 5.52 (td, J=6.3, 12.5 Hz, 1H), 4.66 (d, J=10.2 Hz, 2H), 4.49-4.18 (m, 2H), 1.40 (d, J=6.3 Hz, 3H); [M+H]=428.71.

Example 444

4-(Propan-2-yloxy)-3-[1-(2 2 2-trifluoroethyl)-1H 4H 5H 6H-pyrrolo[3,4-c]pyrazole-5-carbonyl]benzonitrile

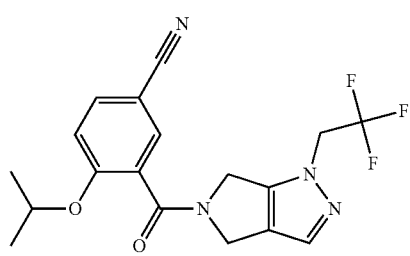 [SMILES: CC(C)Oc1ccc(C#N)cc1C(=O)N1Cc2cnn(CC(F)(F)F)c2C1]

$^1$H NMR (400 MHz, DMSO-d$_6$) δ=7.91-7.82 (m, 1H), 7.82-7.67 (m, 1H), 7.62-7.42 (m, 1H), 7.37-7.21 (m, 1H), 5.26-5.01 (m, 2H), 4.80 (dtd, J=2.9, 5.9, 12.2 Hz, 1H), 4.71-4.50 (m, 2H), 4.40-4.17 (m, 2H), 1.29-1.14 (m, 6H); [M+H]=379.1.

Example 445

5-[2-(3-Fluorophenyl)-5-methanesulfonylbenzoyl]-1-(2 2 2-trifluoroethyl)-1H 4H 5H 6H-pyrrolo[3,4-c]pyrazole

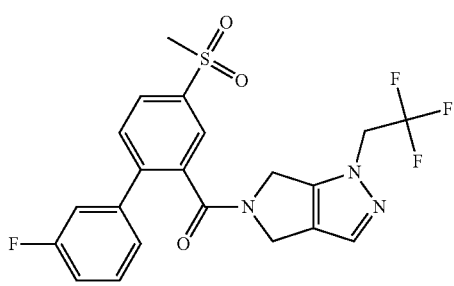 [SMILES: CS(=O)(=O)c1ccc(-c2cccc(F)c2)c(C(=O)N2Cc3cnn(CC(F)(F)F)c3C2)c1]

$^1$H NMR (400 MHz, DMSO-d$_6$) δ=8.12-8.00 (m, 2H), 7.81 (dd, J=6.3, 7.8 Hz, 1H), 7.68-7.51 (m, 1H), 7.51-7.44 (m, 1H), 7.39-7.31 (m, 2H), 7.31-7.18 (m, 1H), 5.06 (q, J=9.0 Hz, 2H), 4.43 (br s, 2H), 4.07 (d, J=16.4 Hz, 2H), 3.41-3.30 (m, 3H); [M+H]=468.19.

Example 446

1-{Imidazo[1 2-a]pyridin-5-yl}-5-(5-methanesulfonyl-2-{[(2S)-1 1 1-trifluoropropan-2-yl]oxy}benzoyl)-1H 4H 5H 6H-pyrrolo[3,4-c]pyrazole

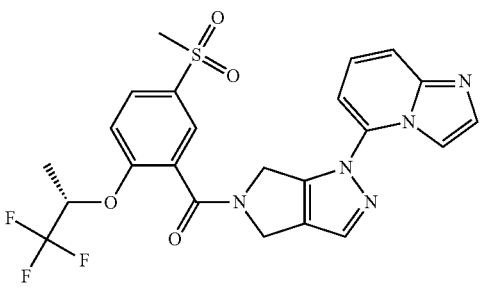 [SMILES: C[C@H](Oc1ccc(S(C)(=O)=O)cc1C(=O)N1Cc2cnn(-c3cccc4nccn34)c2C1)C(F)(F)F]

$^1$H NMR (400 MHz, DMSO-d$_6$) δ=8.76-8.53 (m, 1H), 8.10-7.84 (m, 3H), 7.79-7.63 (m, 1H), 7.63-7.50 (m, 2H), 7.47-7.33 (m, 1H), 7.26 (dd, J=2.3, 7.4 Hz, 1H), 5.54 (qd, J=6.6, 13.2 Hz, 1H), 5.23-4.72 (m, 2H), 4.72-4.22 (m, 2H), 3.24 (s, 3H), 1.59-1.28 (m, 3H); [M+H]=520.6.

Example 447

4-(Propan-2-yloxy)-3-[2-(pyridin-4-yl)-2H 4H 5H 6H-pyrrolo[3,4-c]pyrazole-5-carbonyl]benzonitrile

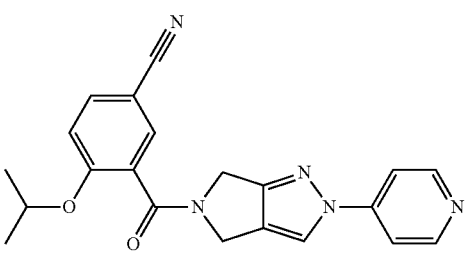 [SMILES: CC(C)Oc1ccc(C#N)cc1C(=O)N1Cc2cn(-c3ccncc3)nc2C1]

$^1$H NMR (400 MHz, DMSO-d$_6$) δ=8.63-8.55 (m, 2H), 8.54-8.35 (m, 1H), 7.94-7.70 (m, 4H), 7.33 (dd, J=2.0, 9.0 Hz, 1H), 4.82 (dtd, J=2.5, 6.1, 12.2 Hz, 1H), 4.66 (d, J=9.8 Hz, 2H), 4.46-4.26 (m, 2H), 1.24 (d, J=6.3 Hz, 6H); [M+H]=374.6.

Example 448

5-[2-(3-Fluorophenyl)-5-methanesulfonylbenzoyl]-2-(oxan-4-yl)-2H 4H 5H 6H-pyrrolo[3,4-c]pyrazole

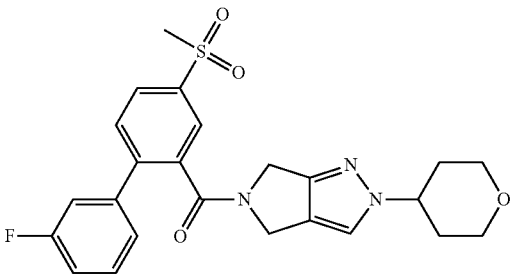 [SMILES: CS(=O)(=O)c1ccc(-c2cccc(F)c2)c(C(=O)N2Cc3cn(C4CCOCC4)nc3C2)c1]

$^1$H NMR (400 MHz, DMSO-$d_6$) δ=8.10-8.04 (m, 1H), 8.02 (t, J=2.0 Hz, 1H), 7.81 (dd, J=4.5, 8.4 Hz, 1H), 7.63-7.45 (m, 2H), 7.41-7.31 (m, 2H), 7.28-7.20 (m, 1H), 4.41 (br s, 2H), 4.32 (td, J=8.0, 15.3 Hz, 1H), 4.03 (d, J=13.7 Hz, 2H), 3.96-3.82 (m, 2H), 3.44-3.35 (m, 2H), 3.31 (d, J=2.0 Hz, 3H), 1.97-1.80 (m, 4H); [M+H]=470.17.

Example 449

2-(Cyclopropylmethyl)-5-[2-(3-fluorophenyl)-5-methanesulfonylbenzoyl]-2H 4H 5H 6H-pyrrolo[3,4-c]pyrazole

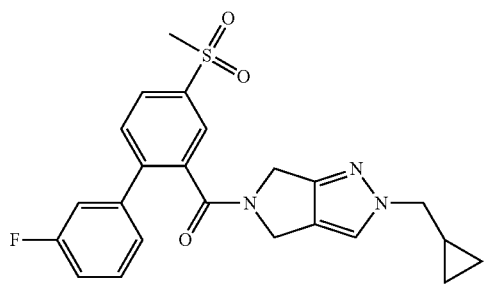 [SMILES: CS(=O)(=O)c1ccc(-c2cccc(F)c2)c(C(=O)N2Cc3cn(CC4CC4)nc3C2)c1]

$^1$H NMR (400 MHz, DMSO-$d_6$) δ=8.11-8.00 (m, 2H), 7.81 (dd, J=4.1, 8.4 Hz, 1H), 7.59-7.41 (m, 2H), 7.40-7.30 (m, 2H), 7.30-7.20 (m, 1H), 4.41 (br s, 2H), 4.02 (br s, 2H), 3.87 (dd, J=2.7, 7.0 Hz, 2H), 3.50-3.05 (m, 3H), 3.50-3.05 (m, 13H), 1.20-1.09 (m, 1H), 0.58-0.38 (m, 2H), 0.38-0.16 (m, 2H); [M+H]=440.29.

Example 450

3-[2-(Cyclopropylmethyl)-2H 4H 5H 6H-pyrrolo[3,4-c]pyrazole-5-carbonyl]-4-(propan-2-yloxy)benzonitrile

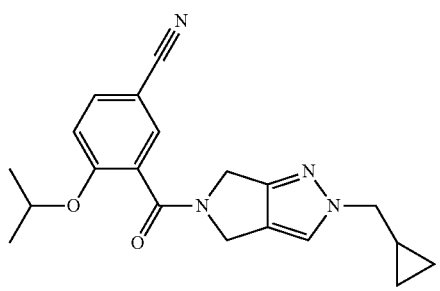 [SMILES: CC(C)Oc1ccc(C#N)cc1C(=O)N1Cc2cn(CC3CC3)nc2C1]

$^1$H NMR (400 MHz, DMSO-$d_6$) δ=7.85 (dd, J=2.2, 8.8 Hz, 1H), 7.73 (dd, J=2.2, 6.1 Hz, 1H), 7.64-7.45 (m, 1H), 7.31 (d, J=8.6 Hz, 1H), 4.80 (dtd, J=3.7, 6.0, 12.1 Hz, 1H), 4.53 (s, 2H), 4.22 (d, J=9.0 Hz, 2H), 3.92 (dd, J=1.2, 7.0 Hz, 2H), 1.32-1.11 (m, 7H), 0.55-0.42 (m, 2H), 0.37-0.27 (m, 2H); [M+H]=351.18.

Example 451

3-[2-(Cyclopropylmethyl)-2H 4H 5H 6H-pyrrolo[3,4-c]pyrazole-5-carbonyl]-4-{[(2S)-1 1 1-trifluoropropan-2-yl]oxy}benzonitrile

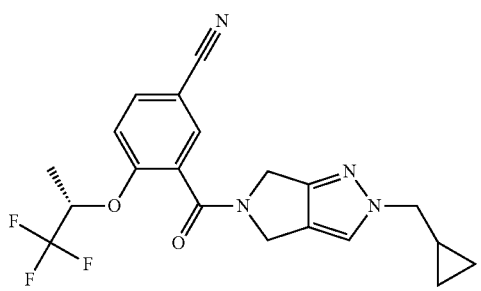 [SMILES: C[C@H](Oc1ccc(C#N)cc1C(=O)N1Cc2cn(CC3CC3)nc2C1)C(F)(F)F]

$^1$H NMR (400 MHz, DMSO-$d_6$) δ=7.96 (dd, J=2.2, 8.8 Hz, 1H), 7.85 (dd, J=2.2, 7.6 Hz, 1H), 7.65-7.47 (m, 2H), 5.50 (td, J=6.3, 12.5 Hz, 1H), 4.53 (s, 2H), 4.35-4.11 (m, 2H), 3.92 (d, J=7.0 Hz, 2H), 1.39 (d, J=6.7 Hz, 3H), 1.19 (dt, J=5.1, 7.8 Hz, 1H), 0.57-0.44 (m, 2H), 0.38-0.25 (m, 2H); [M+H]=405.11.

Example 452

1-(Cyclopropylmethyl)-5-[2-(3-fluorophenyl)-5-methanesulfonylbenzoyl]-1H 4H 5H 6H-pyrrolo[3,4-c]pyrazole

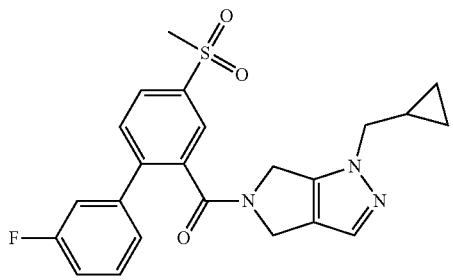 [SMILES: CS(=O)(=O)c1ccc(-c2cccc(F)c2)c(C(=O)N2Cc3cnn(CC4CC4)c3C2)c1]

$^1$H NMR (400 MHz, DMSO-$d_6$) δ=8.14-7.98 (m, 2H), 7.87-7.76 (m, 1H), 7.50 (dt, J=6.3, 8.2 Hz, 1H), 7.42-7.22 (m, 3H), 7.21-7.00 (m, 1H), 4.60 (br s, 1H), 4.37 (br s, 1H), 4.18 (br s, 1H), 3.99 (br s, 1H), 3.94-3.72 (m, 2H), 3.32 (d, J=1.2 Hz, 3H), 1.26-0.93 (m, 1H), 0.58-0.42 (m, 1H), 0.42-0.23 (m, 2H), 0.23-0.10 (m, 1H); [M+H]=440.3.

Example 453

2-[(2 2-Difluorocyclopropyl)methyl]-5-[2-(3-fluorophenyl)-5-methanesulfonylbenzoyl]-2H 4H 5H 6H-pyrrolo[3,4-c]pyrazole

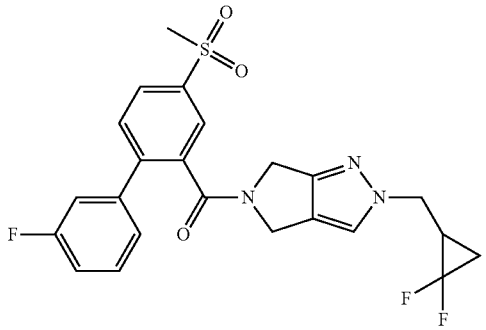 [SMILES: CS(=O)(=O)c1ccc(-c2cccc(F)c2)c(C(=O)N2Cc3cn(CC4CC4(F)F)nc3C2)c1]

¹H NMR (400 MHz, DMSO-d₆) δ=8.17-7.96 (m, 2H), 7.81 (dd, J=4.7, 8.2 Hz, 1H), 7.64-7.42 (m, 2H), 7.42-7.16 (m, 3H), 4.41 (br s, 2H), 4.16 (br s, 2H), 4.03 (br s, 1H), 2.26-2.06 (m, 2H), 1.62 (br s, 1H), 1.43 (br s, 1H); [M+H]=476.2.

Example 454

1-[(2 2-Difluorocyclopropyl)methyl]-5-[2-(3-fluorophenyl)-5-methanesulfonylbenzoyl]-1H 4H 5H 6H-pyrrolo[3,4-c]pyrazole

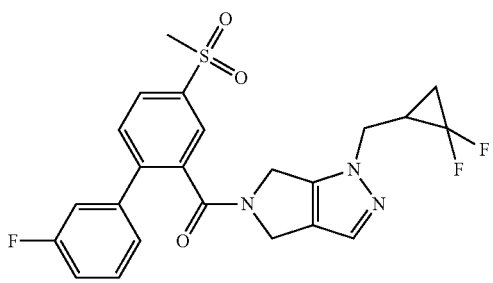 [SMILES: CS(=O)(=O)c1ccc(-c2cccc(F)c2)c(C(=O)N2Cc3cnn(CC4CC4(F)F)c3C2)c1]

¹H NMR (400 MHz, DMSO-d₆) δ=8.25-7.97 (m, 2H), 7.82 (dd, J=8.0, 11.9 Hz, 1H), 7.49 (d, J=8.2 Hz, 1H), 7.42-6.95 (m, 3H), 4.90-3.76 (m, 6H), 3.31-3.18 (m, 3H), 2.26-1.98 (m, 1H), 1.79-1.17 (m, 3H); [M+H]=476.17.

Example 455

2-[(2 2-Difluorocyclopropyl)methyl]-5-(5-methanesulfonyl-2-{[(2S)-1 1 1-trifluoropropan-2-yl]oxy}benzoyl)-2H 4H 5H 6H-pyrrolo[3,4-c]pyrazole

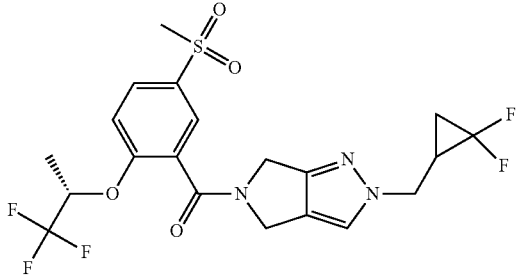 [SMILES: C[C@H](Oc1ccc(S(C)(=O)=O)cc1C(=O)N1Cc2cn(CC3CC3(F)F)nc2C1)C(F)(F)F]

¹H NMR (400 MHz, DMSO-d₆) δ=7.98 (dd, J=2.3, 8.6 Hz, 1H), 7.87 (dd, J=2.3, 4.7 Hz, 1H), 7.69-7.48 (m, 2H), 5.52 (dt, J=2.0, 6.3 Hz, 1H), 4.56 (s, 2H), 4.34-4.13 (m, 4H), 3.22 (s, 3H), 2.31-2.08 (m, 1H), 1.75-1.56 (m, 1H), 1.53-1.31 (m, 4H); [M+H]=494.18.

Example 456

3-{2-[(2 2-Difluorocyclopropyl)methyl]-2H 4H 5H 6H-pyrrolo[3,4-c]pyrazole-5-carbonyl}-4-(propan-2-yloxy)benzonitrile

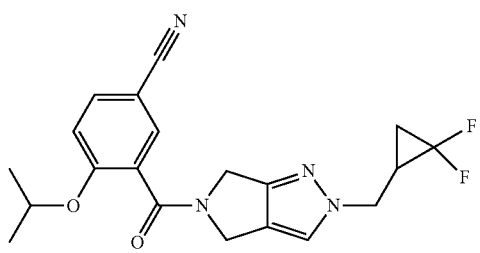 [SMILES: CC(C)Oc1ccc(C#N)cc1C(=O)N1Cc2cn(CC3CC3(F)F)nc2C1]

¹H NMR (400 MHz, DMSO-d₆) δ=7.85 (dd, J=2.3, 8.6 Hz, 1H), 7.79-7.69 (m, 1H), 7.68-7.47 (m, 1H), 7.31 (d, J=8.6 Hz, 1H), 4.93-4.73 (m, 1H), 4.54 (br s, 2H), 4.23 (d, J=11.7 Hz, 4H), 2.29-2.08 (m, 1H), 1.64 (dd, J=3.7, 7.6 Hz, 1H), 1.56-1.35 (m, 1H), 1.22 (d, J=5.9 Hz, 6H); [M+H]=387.09.

Example 457

3-{2-[(2 2-Difluorocyclopropyl)methyl]-2H 4H 5H 6H-pyrrolo[3,4-c]pyrazole-5-carbonyl}-4-{[(2S)-1 1 1-trifluoropropan-2-yl]oxy}benzonitrile

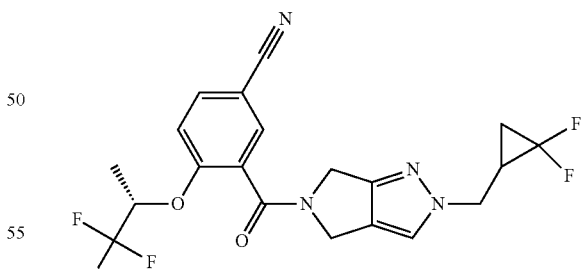

¹H NMR (400 MHz, DMSO-d₆) δ=7.96 (dd, J=2.2, 8.8 Hz, 1H), 7.91-7.77 (m, 1H), 7.71-7.43 (m, 2H), 6.98 (br s, 2H), 5.67-5.40 (m, 1H), 4.54 (br s, 2H), 4.38-4.00 (m, 4H), 2.29-2.08 (m, 1H), 1.64 (br s, 1H), 1.55-1.26 (m, 4H); [M+H]=441.10.

Example 458

3-[1-(Oxan-4-yl)-1H 4H 5H 6H-pyrrolo[3,4-c]pyrazole-5-carbonyl]-4-{[(2S)-1 1 1-trifluoropropan-2-yl]oxy}benzonitrile

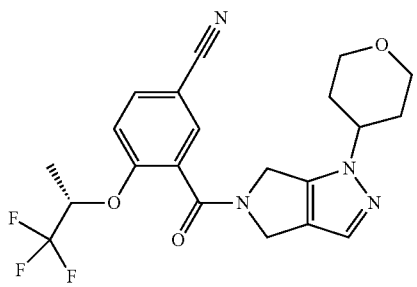 [SMILES: C[C@H](Oc1ccc(C#N)cc1C(=O)N1Cc2cnn(C3CCOCC3)c2C1)C(F)(F)F]

¹H NMR (400 MHz, DMSO-d₆) δ=8.00-7.92 (m, 1H), 7.86 (dd, J=2.2, 3.7 Hz, 1H), 7.53 (dd, J=5.5, 9.0 Hz, 1H), 7.36-7.17 (m, 1H), 5.59-5.43 (m, 1H), 4.78-4.46 (m, 2H), 4.46-4.21 (m, 2H), 4.21-4.06 (m, 1H), 4.03-3.78 (m, 2H), 3.52-3.31 (m, 3H), 2.04-1.69 (m, 4H), 1.40 (dd, J=2.7, 6.3 Hz, 3H); [M+H]=435.24.

Example 459

3-[2-(2-Cyclobutylpyridin-4-yl)-2H 4H 5H 6H-pyrrolo[3,4-c]pyrazole-5-carbonyl]-4-(propan-2-yloxy)benzonitrile

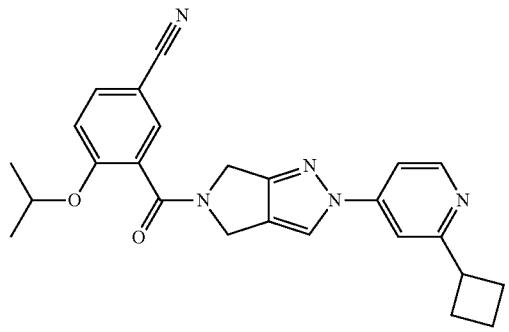 [SMILES: CC(C)Oc1ccc(C#N)cc1C(=O)N1Cc2cn(-c3ccnc(C4CCC4)c3)nc2C1]

¹H NMR (400 MHz, DMSO-d₆) δ=8.61-8.42 (m, 2H), 7.92-7.84 (m, 1H), 7.76 (dd, J=2.2, 7.2 Hz, 1H), 7.69-7.57 (m, 2H), 7.33 (dd, J=1.8, 8.8 Hz, 1H), 4.82 (dtd, J=2.3, 6.1, 12.1 Hz, 1H), 4.66 (d, J=8.6 Hz, 2H), 4.36 (d, J=18.4 Hz, 2H), 3.67 (dquin, J=3.1, 8.6 Hz, 1H), 2.39-2.18 (m, 4H), 2.08-1.92 (m, 2H), 1.90-1.73 (m, 1H), 1.23 (d, J=5.9 Hz, 6H); [M+H]=428.71.

Example 460

3-[2-(2-Cyclobutylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile

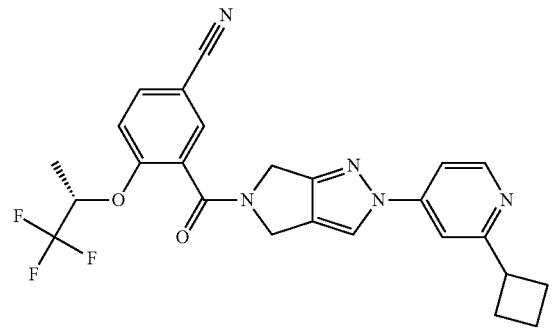 [SMILES: C[C@H](Oc1ccc(C#N)cc1C(=O)N1Cc2cn(-c3ccnc(C4CCC4)c3)nc2C1)C(F)(F)F]

¹H NMR (400 MHz, DMSO-d₆) δ=8.61-8.43 (m, 2H), 7.98 (dd, J=2.2, 8.8 Hz, 1H), 7.88 (dd, J=2.2, 7.6 Hz, 1H), 7.71-7.48 (m, 3H), 5.52 (td, J=6.3, 12.5 Hz, 1H), 4.66 (d, J=8.6 Hz, 2H), 4.44-4.23 (m, 2H), 3.67 (dquin, J=2.5, 8.6 Hz, 1H), 2.38-2.19 (m, 4H), 2.10-1.92 (m, 1H), 1.90-1.74 (m, 1H), 1.40 (d, J=6.3 Hz, 3H); [M+H]=482.1.

Example 461

2-[(3 3-Difluorocyclobutyl)methyl]-5-[5-methanesulfonyl-2-(propan-2-yloxy)benzoyl]-2H 4H 5H 6H-pyrrolo[3,4-c]pyrazole

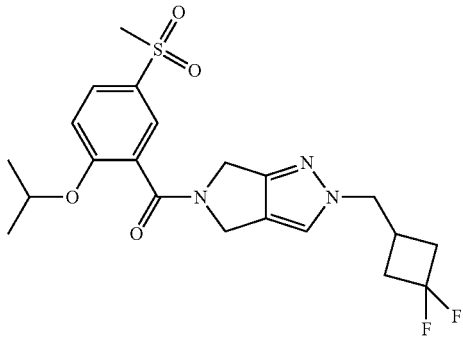 [SMILES: CC(C)Oc1ccc(S(C)(=O)=O)cc1C(=O)N1Cc2cn(CC3CC(F)(F)C3)nc2C1]

¹H NMR (400 MHz, DMSO-d₆) δ=7.90 (dd, J=2.7, 8.6 Hz, 1H), 7.76 (dd, J=2.5, 3.3 Hz, 1H), 7.66-7.50 (m, 1H), 7.41-7.31 (m, 1H), 4.88-4.75 (m, 1H), 4.55 (s, 2H), 4.34-4.09 (m, 4H), 3.18 (d, J=0.8 Hz, 3H), 2.70-2.51 (m, 3H), 2.45-2.26 (m, 2H), 1.24 (d, J=6.3 Hz, 6H); [M+H]=454.09.

Example 462

3-{2-[(3 3-Difluorocyclobutyl)methyl]-2H 4H 5H 6H-pyrrolo[3,4-c]pyrazole-5-carbonyl}-4-{[(2S)-1 1 1-trifluoropropan-2-yl]oxy}benzonitrile

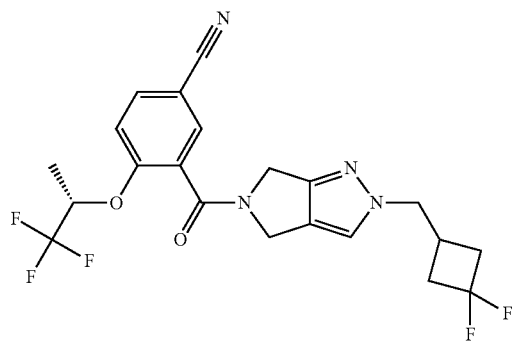 [SMILES: C[C@H](Oc1ccc(C#N)cc1C(=O)N1Cc2cn(CC3CC(F)(F)C3)nc2C1)C(F)(F)F]

¹H NMR (400 MHz, DMSO-d₆) δ=8.00-7.91 (m, 1H), 7.85 (dd, J=2.2, 7.6 Hz, 1H), 7.69-7.42 (m, 2H), 5.59-5.41 (m, 1H), 4.52 (s, 2H), 4.33-4.06 (m, 4H), 2.70-2.51 (m, 3H), 2.46-2.25 (m, 2H), 1.38 (d, J=6.3 Hz, 3H); [M+H]=455.27.

Example 463

2-[(3 3-Difluorocyclobutyl)methyl]-5-(5-methanesulfonyl-2-{[(2S)-1 1 1-trifluoropropan-2-yl]oxy}benzoyl)-2H 4H 5H 6H-pyrrolo[3,4-c]pyrazole

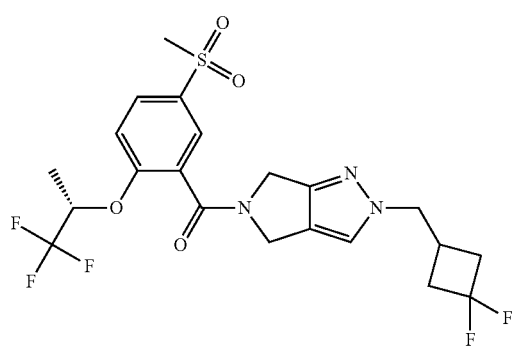 [SMILES: C[C@H](Oc1ccc(S(C)(=O)=O)cc1C(=O)N1Cc2cn(CC3CC(F)(F)C3)nc2C1)C(F)(F)F]

¹H NMR (400 MHz, DMSO-d₆) δ=7.97 (dd, J=2.3, 9.0 Hz, 1H), 7.87 (dd, J=2.3, 4.7 Hz, 1H), 7.67-7.51 (m, 2H), 5.51 (dt, J=2.5, 6.4 Hz, 1H), 4.54 (s, 2H), 4.34-4.03 (m, 4H), 3.22 (d, J=0.8 Hz, 3H), 2.69-2.52 (m, 3H), 2.45-2.26 (m, 2H), 1.40 (d, J=6.3 Hz, 3H); [M+H]=508.32.

Example 464

2-[(3 3-Difluorocyclobutyl)methyl]-5-[2-(3-fluorophenyl)-5-methanesulfonylbenzoyl]-2H 4H 5H 6H-pyrrolo[3,4-c]pyrazole

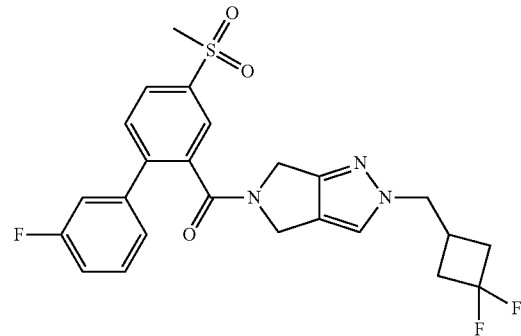 [SMILES: CS(=O)(=O)c1ccc(-c2cccc(F)c2)c(C(=O)N2Cc3cn(CC4CC(F)(F)C4)nc3C2)c1]

¹H NMR (400 MHz, DMSO-d₆) δ=8.10-8.01 (m, 2H), 7.80 (dd, J=4.1, 8.4 Hz, 1H), 7.59-7.45 (m, 2H), 7.39-7.31 (m, 2H), 7.28-7.20 (m, 1H), 4.40 (br s, 2H), 4.15 (d, J=4.7 Hz, 2H), 4.01 (br s, 2H), 2.70-2.50 (m, 3H), 2.45-2.28 (m, 2H); [M+H]=490.19.

Example 465

5-[5-(5-Cyano-2-{[(2S)-1 1 1-trifluoropropan-2-yl]oxy}benzoyl)-2H 4H 5H 6H-pyrrolo[3,4-c]pyrazol-2-yl]pyridine-2-carbonitrile

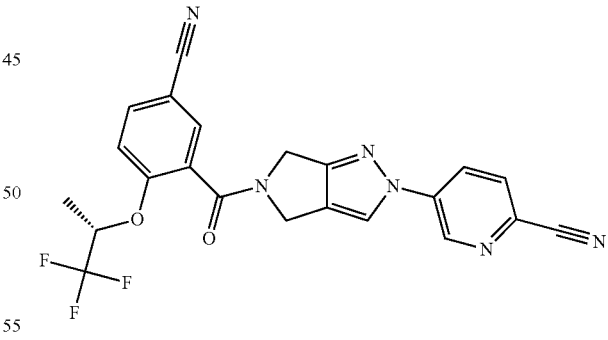

¹H NMR (400 MHz, DMSO-d₆) δ=9.29-9.20 (m, 1H), 8.64-8.48 (m, 1H), 8.46-8.34 (m, 1H), 8.20-8.13 (m, 1H), 8.03-7.96 (m, 1H), 7.88 (dd, J=2.2, 7.2 Hz, 1H), 7.54 (dd, J=2.7, 9.0 Hz, 1H), 5.52 (td, J=6.4, 12.6 Hz, 1H), 4.68 (d, J=11.3 Hz, 2H), 4.50-4.25 (m, 2H), 1.40 (d, J=6.3 Hz, 3H); [M+H]=453.00.

Example 466

5-{5-[5-Cyano-2-(propan-2-yloxy)benzoyl]-2H 4H 5H 6H-pyrrolo[3,4-c]pyrazol-2-yl}pyridine-2-carbonitrile

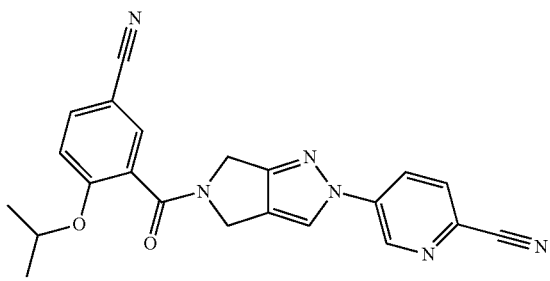 [SMILES: CC(C)Oc1ccc(C#N)cc1C(=O)N1Cc2cn(-c3ccc(C#N)nc3)nc2C1]

$^1$H NMR (400 MHz, DMSO-d$_6$) δ=9.24 (td, J=1.5, 10.3 Hz, 1H), 8.63-8.46 (m, 1H), 8.40 (ddd, J=2.7, 8.6, 12.5 Hz, 1H), 8.16 (td, J=1.2, 8.6 Hz, 1H), 7.88 (dd, J=2.3, 8.6 Hz, 1H), 7.76 (dd, J=2.2, 6.5 Hz, 1H), 7.33 (dd, J=2.2, 8.8 Hz, 1H), 4.82 (dtd, J=2.5, 6.0, 12.1 Hz, 1H), 4.68 (d, J=11.3 Hz, 2H), 4.45-4.33 (m, 2H), 1.23 (d, J=5.9 Hz, 6H); [M+H]=399.1.

Example 467

4-[5-(5-Cyano-2-{[(2S)-1 1 1-trifluoropropan-2-yl]oxy}benzoyl)-2H 4H 5H 6H-pyrrolo[3,4-c]pyrazol-2-yl]pyridine-2-carbonitrile

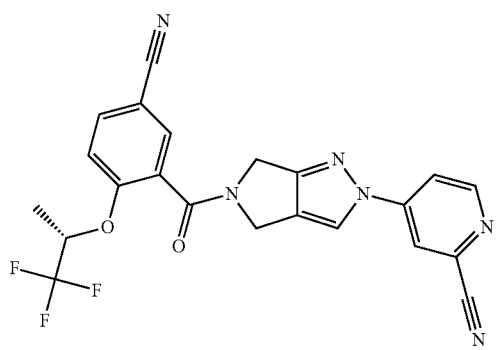 [SMILES: C[C@H](Oc1ccc(C#N)cc1C(=O)N1Cc2cn(-c3ccnc(C#N)c3)nc2C1)C(F)(F)F]

$^1$H NMR (400 MHz, DMSO-d$_6$) δ=8.77-8.73 (m, 1H), 8.65-8.51 (m, 1H), 8.51-8.43 (m, 1H), 8.16-8.06 (m, 1H), 7.99 (dd, J=2.2, 8.8 Hz, 1H), 7.88 (dd, J=2.3, 7.0 Hz, 1H), 7.55 (dd, J=2.3, 9.0 Hz, 1H), 5.59-5.45 (m, 1H), 4.67 (d, J=10.6 Hz, 2H), 4.51-4.22 (m, 3H), 1.40 (d, J=6.3 Hz, 3H); [M+H]=453.0.

Example 468

4-{5-[5-Cyano-2-(propan-2-yloxy)benzoyl]-2H 4H 5H 6H-pyrrolo[3,4-c]pyrazol-2-yl}pyridine-2-carbonitrile

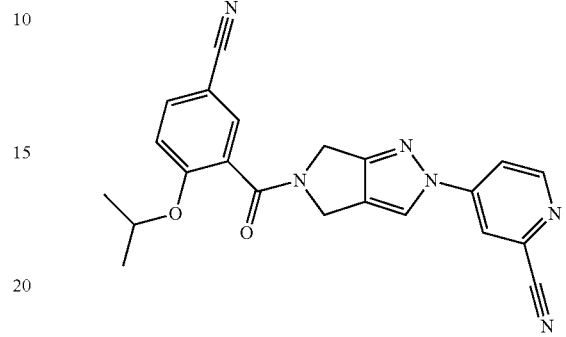

$^1$H NMR (400 MHz, DMSO-d$_6$) δ=8.79-8.71 (m, 1H), 8.65-8.50 (m, 1H), 8.47 (dd, J=2.3, 14.5 Hz, 1H), 8.17-8.05 (m, 1H), 7.91-7.84 (m, 1H), 7.76 (dd, J=2.2, 6.1 Hz, 1H), 7.33 (dd, J=2.2, 8.8 Hz, 1H), 4.82 (dtd, J=3.1, 6.1, 12.1 Hz, 1H), 4.74-4.60 (m, 2H), 4.44-4.33 (m, 2H), 1.23 (d, J=6.3 Hz, 6H); [M+H]=399.1.

Example 469

2-(4 4-Difluorocyclohexyl)-5-[2-(3-fluorophenyl)-5-methanesulfonylbenzoyl]-2H 4H 5H 6H-pyrrolo[3,4-c]pyrazole

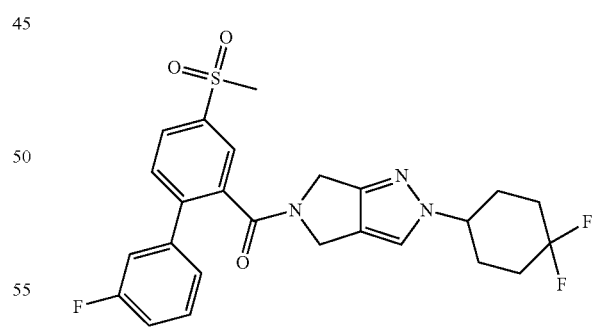

$^1$H NMR (400 MHz, DMSO-d$_6$) δ=8.07 (qd, J=1.0, 8.2 Hz, 1H), 8.04-8.00 (m, 1H), 7.81 (dd, J=4.5, 8.0 Hz, 1H), 7.62-7.45 (m, 2H), 7.39-7.31 (m, 2H), 7.28-7.21 (m, 1H), 4.32 (dd, J=5.1, 9.4 Hz, 1H), 4.03 (d, J=16.4 Hz, 3H), 2.16-1.86 (m, 8H); [M+H]=504.2.

Example 470

2-(4 4-Difluorocyclohexyl)-5-[5-methanesulfonyl-2-(propan-2-yloxy)benzoyl]-2H 4H 5H 6H-pyrrolo[3,4-c]pyrazole

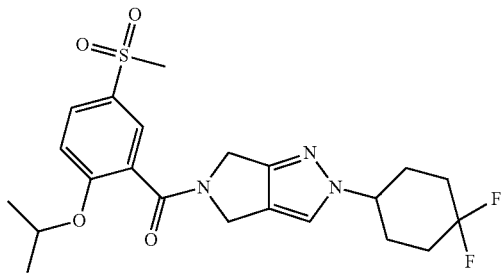 [SMILES: CC(C)Oc1ccc(S(C)(=O)=O)cc1C(=O)N1Cc2cn(C3CCC(F)(F)CC3)nc2C1]

¹H NMR (400 MHz, DMSO-d₆) δ=7.90 (dd, J=2.5, 8.8 Hz, 1H), 7.76 (dd, J=2.3, 3.9 Hz, 1H), 7.69-7.53 (m, 1H), 7.38-7.33 (m, 1H), 4.81 (dtd, J=2.7, 6.0, 12.2 Hz, 1H), 4.55 (s, 2H), 4.44-4.31 (m, 1H), 4.24 (d, J=12.1 Hz, 2H), 3.18 (s, 3H), 2.19-1.83 (m, 8H), 1.25 (d, J=6.3 Hz, 6H); [M+H]=468.1.

Example 471

2-(4 4-Difluorocyclohexyl)-5-(5-methanesulfonyl-2-{[(2S)-1 1 1-trifluoropropan-2-yl]oxy}benzoyl)-2H 4H 5H 6H-pyrrolo[3,4-c]pyrazole

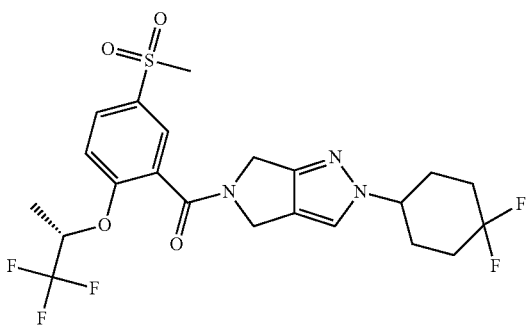 [SMILES: C[C@H](Oc1ccc(S(C)(=O)=O)cc1C(=O)N1Cc2cn(C3CCC(F)(F)CC3)nc2C1)C(F)(F)F]

¹H NMR (400 MHz, DMSO-d₆) δ=8.01-7.94 (m, 1H), 7.86 (dd, J=2.3, 4.7 Hz, 1H), 7.70-7.53 (m, 2H), 5.52 (td, J=6.4, 12.6 Hz, 1H), 4.55 (s, 2H), 4.37 (br s, 1H), 4.30-4.15 (m, 2H), 3.22 (d, J=0.8 Hz, 3H), 2.19-1.87 (m, 8H), 1.41 (d, J=6.3 Hz, 3H); [M+H]=522.0.

Example 472

3-[2-(4 4-Difluorocyclohexyl)-2H 4H 5H 6H-pyrrolo[3,4-c]pyrazole-5-carbonyl]-4-{[(2S)-1 1 1-trifluoropropan-2-yl]oxy}benzonitrile

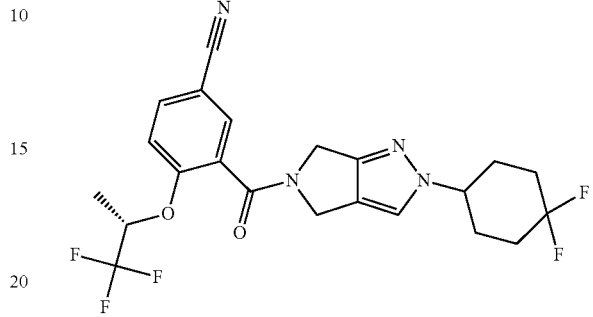

¹H NMR (400 MHz, DMSO-d₆) δ=7.99-7.93 (m, 1H), 7.84 (dd, J=2.2, 6.8 Hz, 1H), 7.69-7.54 (m, 1H), 7.52 (dd, J=2.0, 9.0 Hz, 1H), 5.50 (td, J=6.3, 12.5 Hz, 1H), 4.53 (s, 2H), 4.42-4.31 (m, 1H), 4.29-4.10 (m, 2H), 2.19-1.92 (m, 8H), 1.39 (d, J=6.3 Hz, 3H); [M+H]=469.1.

Examples 473-477 were prepared in a manner analogous to Example 4 with the appropriated starting material substitutions.

Example 473

3-[2-(4-Fluorophenyl)-3-methyl-2H 4H 5H 6H 7H-pyrazolo[4,3-c]pyridine-5-carbonyl]-2-methoxy-4-[(1 1 1-trifluoropropan-2-yl)oxy]benzonitrile

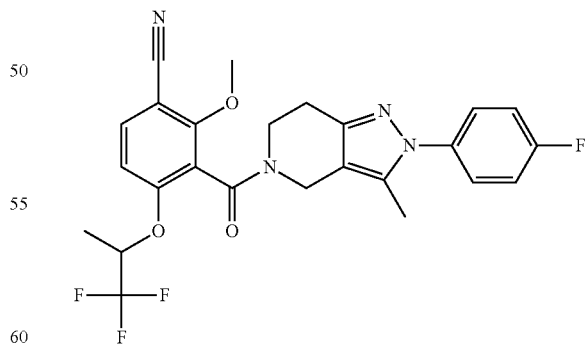

¹H NMR (400 MHz, CDCl₃) δ=7.58-7.49 (m, 1H), 7.37-7.22 (m, 1H), 7.18-6.98 (m, 2H), 6.91-6.77 (m, 1H), 6.77-6.61 (m, 1H), 5.21-4.43 (m, 2H), 4.39-3.96 (m, 4H), 3.93 (s, 1H), 3.72-3.28 (m, 1H), 2.92-2.60 (m, 2H), 2.05-1.94 (m, 3H), 1.49-1.35 (m, 3H); [M+H]=503.29.

Example 474

3-[1-(4-Fluorophenyl)-7 7-dimethyl-1H 4H 5H 6H 7H-pyrazolo[4,3-c]pyridine-5-carbonyl]-2-methoxy-4-[(1 1 1-trifluoropropan-2-yl)oxy]benzonitrile

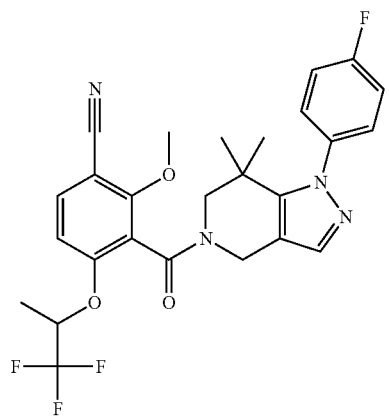 [SMILES: COc1c(C#N)ccc(OC(C)C(F)(F)F)c1C(=O)N1Cc2cnn(-c3ccc(F)cc3)c2C(C)(C)C1]

$^1$H NMR (400 MHz, CDCl$_3$) δ=7.68-7.57 (m, 1H), 7.50 (s, 0.4H), 7.42-7.32 (m, 2H), 7.30 (s, 0.6H), 7.21-7.11 (m, 2H), 6.83-6.70 (m, 1H), 5.01 (d, J=16.4 Hz, 0.5H), 4.86-4.70 (m, 1H), 4.68-4.58 (m, 0.5H), 4.29-4.22 (m, 1H), 4.13-4.07 (m, 3H), 4.01 (d, J=12.9 Hz, 0.5H), 3.83-3.61 (m, 1H), 3.46 (d, J=12.5 Hz, 0.5H), 1.55-1.47 (m, 2H), 1.39 (d, J=6.7 Hz, 1H), 1.30-1.23 (m, 1H), 1.23-1.08 (m, 5H), 517.33.

Example 475

3-[2-(4-Fluorophenyl)-2H 4H 5H 6H 7H-pyrazolo[4,3-c]pyridine-5-carbonyl]-2-methoxy-4-[(1-methylcyclopropyl)methoxy]benzonitrile

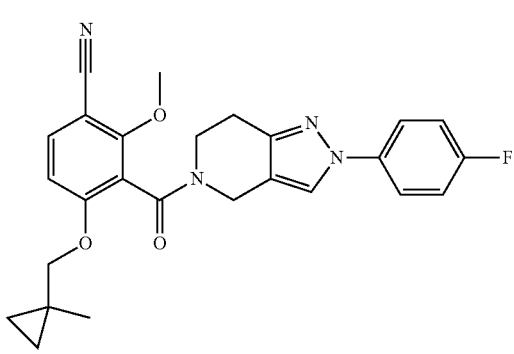 [SMILES: COc1c(C#N)ccc(OCC2(C)CC2)c1C(=O)N1CCc2nn(-c3ccc(F)cc3)cc2C1]

$^1$H NMR (400 MHz, CDCl$_3$) δ=7.50 (s, 1H), 7.43-7.27 (m, 3H), 6.98-6.85 (m, 2H), 6.52-6.32 (m, 1H), 4.79-4.63 (m, 1H), 4.23-4.09 (m, 2H), 3.85 (d, J=11.3 Hz, 3H), 3.74-3.51 (m, 2H), 3.47-3.30 (m, 2H), 2.84-2.56 (m, 2H), 0.93-0.72 (m, 3H), 0.33-0.08 (m, 4H); [M+H]=461.29.

Example 476

3-[2-(4-Fluorophenyl)-2H 4H 5H 6H 7H-pyrazolo[4,3-c]pyridine-5-carbonyl]-2-methoxy-4-{[1-(trifluoromethyl)cyclopropyl]methoxy}benzonitrile

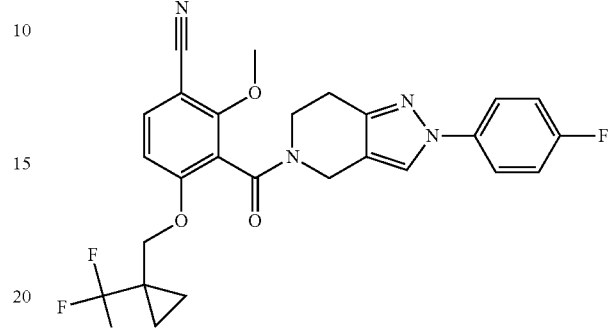

$^1$H NMR (400 MHz, CDCl$_3$) δ=7.70 (s, 1H), 7.65-7.48 (m, 3H), 7.13 (q, J=7.96 Hz, 2H), 6.86-6.71 (m, 1H), 5.19-4.64 (m, 1H), 4.50-4.22 (m, 2H), 4.19-4.05 (m, 1H), 4.01-3.76 (m, 3H), 3.69-3.43 (m, 1H), 3.04-2.65 (m, 2H), 1.18-0.77 (m, 5H); [M+H]=515.20.

Example 477

2-(4-Fluorophenyl)-5-{5-methanesulfonyl-2-[(1 1 1-trifluoro-2-methylpropan-2-yl)oxy]benzoyl}-2H 4H 5H 6H-pyrrolo[3,4-c]pyrazole

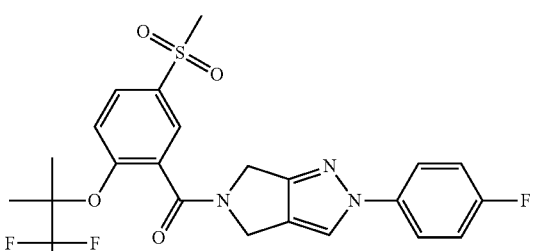

$^1$H NMR (400 MHz, CDCl$_3$) δ=8.04-7.96 (m, 2H), 7.71-7.53 (m, 3H), 7.36 (d, J=8.6 Hz, 1H), 7.20-7.10 (m, 2H), 4.82 (d, J=16.4 Hz, 2H), 4.61-4.32 (m, 2H), 3.10 (d, J=2.3 Hz, 3H), 1.50 (s, 6H); [M+H]=512.12.

Examples 478-482 were prepared in a manner analogous to Example 6 with the appropriated starting material substitutions.

Example 478

2-Chloro-3-[2-(4-fluorophenyl)-2H 4H 5H 6H 7H-pyrazolo[4,3-c]pyridine-5-carbonyl]-N-methyl-4-[(1 1 1-trifluoropropan-2-yl)oxy]benzamide

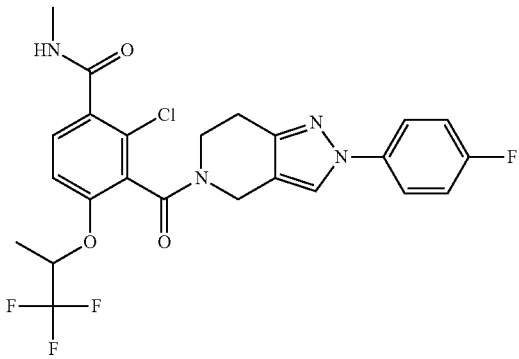

$^1$H NMR (400 MHz, CDCl$_3$) δ=7.70-7.37 (m, 4H), 7.06 (q, J=7.70 Hz, 2H), 6.97-6.82 (m, 1H), 6.15 (br s, 1H), 5.11-4.50 (m, 2H), 4.36-4.20 (m, 1H), 4.19-3.81 (m, 1H), 3.61-3.38 (m, 1H), 3.06 (q, J=7.04 Hz, 1H), 3.00-2.86 (m, 4H), 2.86-2.67 (m, 1H), 1.41 (t, J=5.67 Hz, 2H); [M+H]=525.22

Example 479

1-{3-[2-(4-Fluorophenyl)-2H 4H 5H 6H 7H-pyrazolo[4,3-c]pyridine-5-carbonyl]-2-methoxy-4-[(1 1 1-trifluoropropan-2-yl)oxy]benzoyl}azetidine

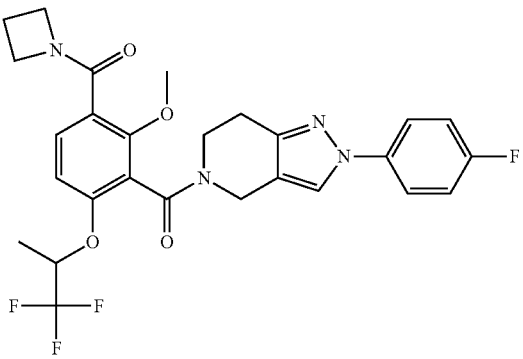 [SMILES: COc1c(C(=O)N2CCC2)ccc(OC(C)C(F)(F)F)c1C(=O)N1CCc2nn(-c3ccc(F)cc3)cc2C1]

$^1$H NMR (400 MHz, CDCl$_3$) δ=7.75-7.46 (m, 3H), 7.46-7.35 (m, 1H), 7.21-7.04 (m, 2H), 6.87-6.62 (m, 1H), 5.21-4.52 (m, 2H), 4.36 (s, 1H), 4.32-3.89 (m, 5H), 3.89-3.70 (m, 3H), 3.68-3.42 (m, 1H), 3.07-2.68 (m, 3H), 2.46-2.18 (m, 2H), 1.53-1.19 (m, 3H); [M+H]=547.28.

Example 480

3-[2-(4-Fluorophenyl)-2H 4H 5H 6H 7H-pyrazolo[4,3-c]pyridine-5-carbonyl]-2-methoxy-N-methyl-4-[(1 1 1-trifluoropropan-2-yl)oxy]benzamide

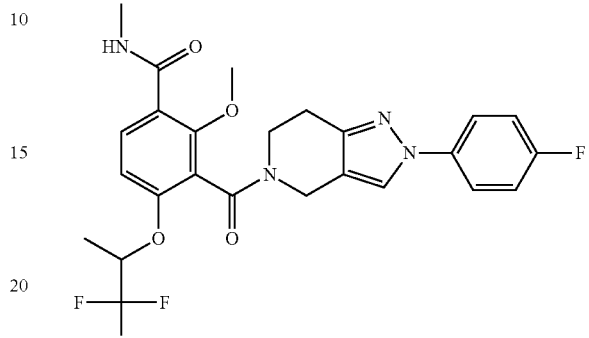

$^1$H NMR (400 MHz, CDCl$_3$) δ=7.76-7.46 (m, 4H), 7.13 (q, J=9.13 Hz, 2H), 6.93-6.73 (m, 1H), 5.27-4.52 (m, 2H), 4.37 (d, J=2.74 Hz, 1H), 4.24-4.01 (m, 1H), 3.97-3.74 (m, 3H), 3.69-3.39 (m, 1H), 3.13-2.92 (m, 4H), 2.84 (t, J=5.87 Hz, 1H), 1.54-1.20 (m, 3H); [M+H]=521.24.

Example 481

1-{3-[2-(4-Fluorophenyl)-2H 4H 5H 6H 7H-pyrazolo[4,3-c]pyridine-5-carbonyl]-4-[(1 1 1-trifluoropropan-2-yl)oxy]benzoyl}azetidine

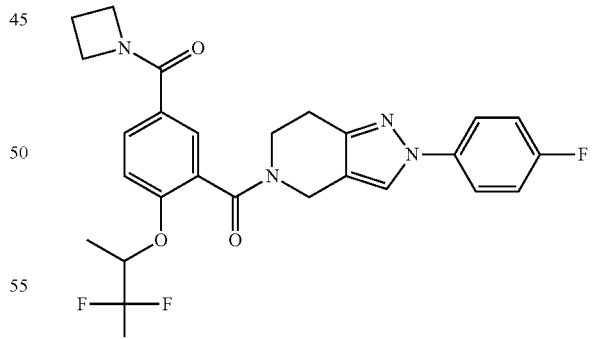

$^1$H NMR (400 MHz, CDCl$_3$) δ=7.80-7.42 (m, 5H), 7.21-6.85 (m, 3H), 5.21-4.59 (m, 2H), 4.46-4.05 (m, 5H), 3.98-3.35 (m, 1H), 3.07-2.65 (m, 3H), 2.46-2.25 (m, 2H), 1.59-1.30 (m, 3H); [M+H]=517.26.

Example 482

3-[2-(4-Fluorophenyl)-2H 4H 5H 6H 7H-pyrazolo[4,3-c]pyridine-5-carbonyl]-N-methyl-4-[(1 1 1-trifluoropropan-2-yl)oxy]benzamide

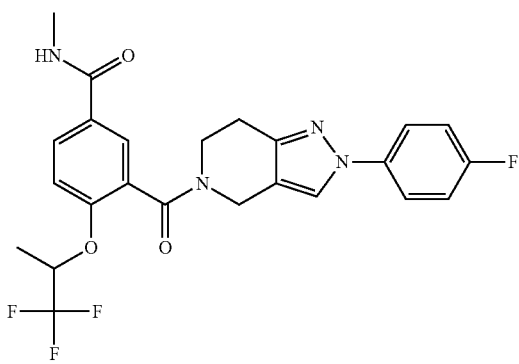 [SMILES: CNC(=O)c1ccc(OC(C)C(F)(F)F)c(C(=O)N2CCc3nn(-c4ccc(F)cc4)cc3C2)c1]

$^1$H NMR (400 MHz, CDCl$_3$) δ=7.94-7.82 (m, 1H), 7.78-7.41 (m, 4H), 7.21-6.88 (m, 3H), 6.42-6.17 (m, 1H), 5.18-4.54 (m, 2H), 4.49-4.24 (m, 1H), 4.23-3.74 (m, 1H), 3.67-3.43 (m, 2H), 3.09-2.66 (m, 4H), 1.58-1.30 (m, 3H); [M+H]=491.25.

Examples 483-484 were prepared in a manner analogous to Example 7 with the appropriated starting material substitutions.

Example 483

3-[2-(4-Fluorophenyl)-2H 4H 5H 6H 7H-pyrazolo[4,3-c]pyridine-5-carbonyl]-2-methoxy-4-[(1 1 1-trifluoropropan-2-yl)oxy]benzamide

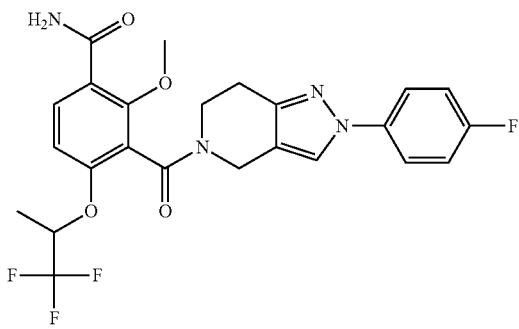 [SMILES: COc1c(C(N)=O)ccc(OC(C)C(F)(F)F)c1C(=O)N1CCc2nn(-c3ccc(F)cc3)cc2C1]

$^1$H NMR (400 MHz, CDCl$_3$) δ=8.11 (ddd, J=1.76, 6.75, 8.71 Hz, 1H), 7.69-7.35 (m, 4H), 7.11-6.97 (m, 2H), 6.89-6.69 (m, 1H), 5.80 (d, J=7.43 Hz, 1H), 5.16-4.55 (m, 2H), 4.40-4.09 (m, 1H), 3.90-3.73 (m, 3H), 3.64-3.34 (m, 1H), 3.04-2.85 (m, 1H), 2.78 (t, J=5.67 Hz, 1H), 1.49-1.20 (m, 4H); [M+H]=507.27.

Example 484

2-Chloro-3-[2-(4-fluorophenyl)-2H 4H 5H 6H-pyrrolo[3,4-c]pyrazole-5-carbonyl]-4-[(1 1 1-trifluoropropan-2-yl)oxy]benzamide

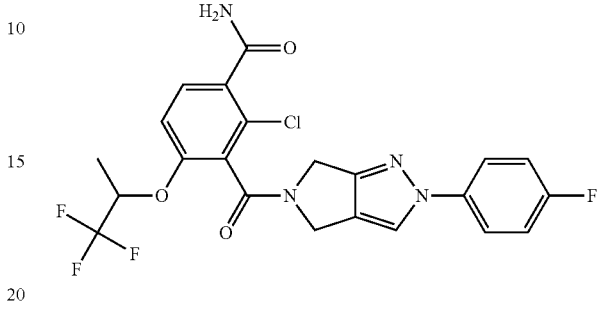

$^1$H NMR (400 MHz, CDCl$_3$) δ=7.97-7.67 (m, 2H), 7.66-7.51 (m, 2H), 7.21-7.09 (m, 2H), 7.08-6.94 (m, 1H), 6.34 (br s, 1H), 5.91 (br s, 1H), 5.00-4.68 (m, 3H), 4.49-4.26 (m, 2H), 1.54-1.41 (m, 3H); [M+H]=497.22

Examples 485-493 were prepared in a manner analogous to Example 4 with the appropriated starting material substitutions.

Example 485

4-Cyclopentyl-2-methoxy-3-{2-phenyl-2H 4H 5H 6H 7H-pyrazolo[4,3-c]uyridine-5-carbonyl}benzonitrile

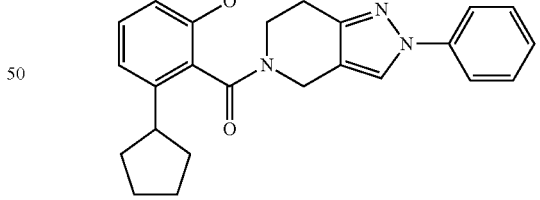

$^1$H NMR (400 MHz, CDCl$_3$) δ=7.82-7.28 (m, 6H), 7.15 (dd, J=8.2, 14.9 Hz, 1H), 5.10-4.81 (m, 1H), 4.56-4.19 (m, 1H), 4.03 (d, J=15.7 Hz, 3H), 3.86 (ddd, J=5.7, 7.5, 13.0 Hz, 1H), 3.62-3.41 (m, 1H), 3.14-2.66 (m, 3H), 2.26-2.02 (m, 1H), 2.00-1.37 (m, 8H); [M+H]=427.29

Example 486

4-Cyclopentyl-3-[2-(4-fluorophenyl)-2H 4H 5H 6H 7H-pyrazolo[4,3-c]pyridine-5-carbonyl]-2-methoxy-benzonitrile

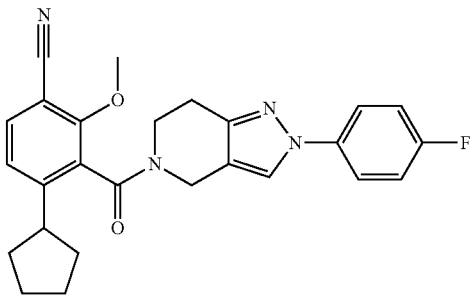 [SMILES: COc1c(C#N)ccc(C2CCCC2)c1C(=O)N1CCc2nn(-c3ccc(F)cc3)cc2C1]

¹H NMR (400 MHz), CDCl₃) δ=7.76-7.44 (m, 4H), 7.22-7.05 (m, 3H), 5.08-4.78 (m, 1H), 4.50-4.19 (m, 1H), 4.12-3.83 (m, 3H), 3.83-3.41 (m, 1H), 3.21-2.65 (m, 4H), 2.21-1.34 (m, 8 H); [M+H]=445.30

Example 487

4-(3-Fluorooxetan-3-yl)-2-methoxy-3-{2-phenyl-2H 4H 5H 6H 7H-pyrazolo[4,3-c]pyridine-5-carbonyl}benzonitrile

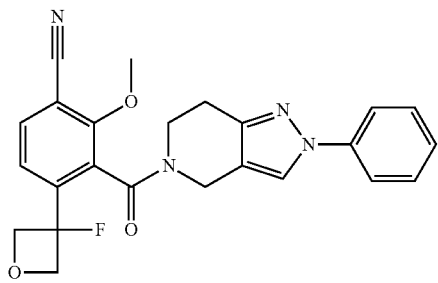 [SMILES: COc1c(C#N)ccc(C2(F)COC2)c1C(=O)N1CCc2nn(-c3ccccc3)cc2C1]

¹H NMR (400 MHz, DMSO-d₆) δ=8.45-8.08 (m, 1H), 8.03 (dd, J=5.3, 8.0 Hz, 1H), 7.84-7.69 (m, 2H), 7.60 (dd, J=8.2, 13.7 Hz, 1H), 7.52-7.39 (m, 2H), 7.32-7.21 (m, 1H), 5.54-5.21 (m, 1H), 4.94-4.63 (m, 4H), 4.42-4.12 (m, 2H), 3.93 (d, J=16.0 Hz, 3H), 3.75 (td, J=6.4, 13.1 Hz, 1H), 2.93-2.60 (m, 2 H); [M+H]=433.3.

Example 488

4-Cyclobutyl-2-methoxy-3-{2-phenyl-2H 4H 5H 6H 7H-pyrazolo[4,3-c]pyridine-5-carbonyl}benzonitrile

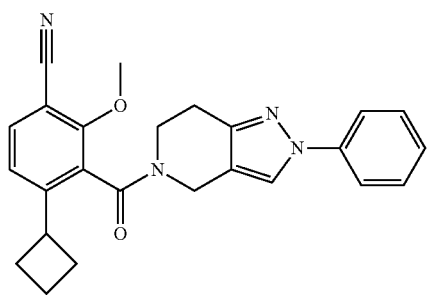 [SMILES: COc1c(C#N)ccc(C2CCC2)c1C(=O)N1CCc2nn(-c3ccccc3)cc2C1]

¹H NMR (400 MHz, DMSO-d₆) δ=8.50-8.04 (m, 1H), 7.95-7.61 (m, 3H), 7.55-7.33 (m, 3H), 7.27 (q, J=7.6 Hz, 1H), 5.07-4.08 (m, 3H), 4.01-3.77 (m, 4H), 2.94-2.55 (m, 3H), 2.27-2.05 (m, 3H), 2.02-1.50 (m, 3 H); [M+H]=413.3

Example 489

4-(1-Fluorocyclobutyl)-3-[2-(4-fluorophenyl)-2H 4H 5H 6H 7H-pyrazolo[4,3-c]pyridine-5-carbonyl]-2-methoxybenzonitrile

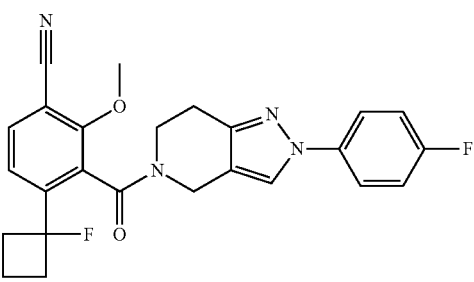

¹H NMR (400 MHz, CDCl₃) δ=7.77-7.44 (m, 4H), 7.26-7.18 (m, 1H), 7.12 (q, J=9.3 Hz, 2H), 5.15-4.66 (m, 1H), 4.35-4.12 (m, 1H), 4.03 (d, J=18.0 Hz, 3H), 3.61-3.35 (m, 1H), 2.97 (t, J=5.9 Hz, 1H), 2.88-2.41 (m, 6H), 2.11 (d, J=9.4 Hz, 1H), 1.90-1.72 (m, 1H); [M+H]=449.3.

Example 490

4-(1-Fluorocyclopentyl)-2-methoxy-3-{2-phenyl-2H 4H 5H 6H 7H-pyrazolo[4,3-c]pyridine-5-carbonyl}benzonitrile

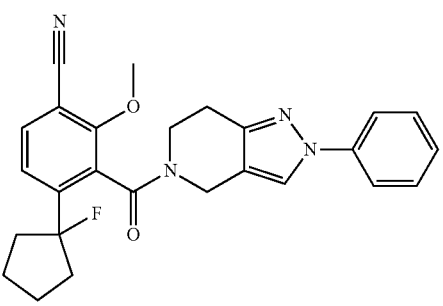 [SMILES: COc1c(C#N)ccc(C2(F)CCCC2)c1C(=O)N1CCc2nn(-c3ccccc3)cc2C1]

¹H NMR (400 MHz, CDCl₃) δ=7.82-7.51 (m, 4H), 7.43 (q, J=7.6Hz, 3H), 7.17-7.05 (m, 1H), 5.14-4.62 (m, 1H), 4.45-4.10 (m, 1H), 4.08-3.97 (m, 4H), 3.61-3.36 (m, 1H), 3.06-2.75 (m, 2H), 2.55-2.04 (m, 3H), 2.01-1.72 (m, 5H); [M+H]=445.3

Example 491

4-(1-Fluorocyclopentyl)-3-[2-(4-fluorophenyl)-2H 4H 5H 6H 7H-pyrazolo[4,3-c]pyridine-5-carbonyl]-2-methoxybenzonitrile

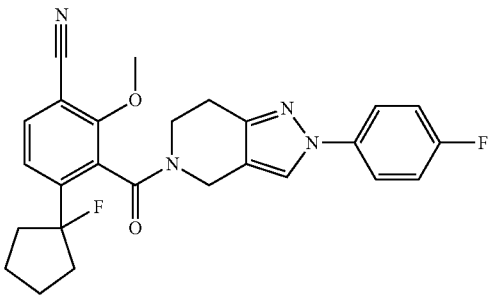 [SMILES: COc1c(C#N)ccc(C2(F)CCCC2)c1C(=O)N1CCc2nn(-c3ccc(F)cc3)cc2C1]

$^1$H NMR (400 MHz, CDCl$_3$) δ=7.83-7.45 (m, 4H), 7.13 (q, J=8.0Hz, 3H), 5.15-4.59 (m, 1H), 4.39-4.22 (m, 1H), 4.18-3.92 (m, 4H), 3.65-3.33 (m, 1H), 3.03-2.72 (m, 2H), 2.56-2.09 (m, 3H), 2.02-1.71 (m, 5H); [M+H]=463.3

Example 492

4-(4-Fluorooxan-4-yl)-3-[2-(4-fluorophenyl)-2H 4H 5H 6H 7H-pyrazolo[4,3-c]pyridine-5-carbonyl]-2-methoxybenzonitrile

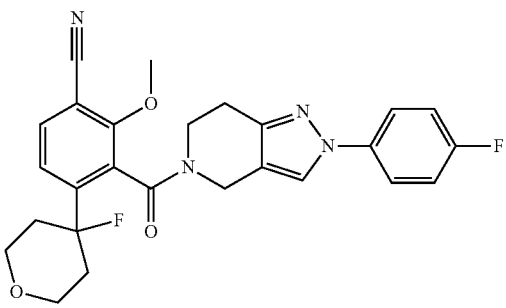 [SMILES: COc1c(C#N)ccc(C2(F)CCOCC2)c1C(=O)N1CCc2nn(-c3ccc(F)cc3)cc2C1]

$^1$H NMR (400 MHz, CDCl$_3$) δ=7.81-7.43 (m, 4H), 7.13 (q, J=8.3 Hz, 3H), 5.13-4.59 (m, 1H), 4.42-4.14 (m, 1H), 4.09-3.99 (m, 3H), 3.97-3.64 (m, 5H), 3.60-3.38 (m, 1H), 3.08-2.75 (m, 2H), 2.56-2.23 (m, 2H), 2.08-1.68 (m, 2H); [M+H]=479.3.

Example 493

3-[2-(4-Fluorophenyl)-2H 4H 5H 6H 7H-pyrazolo[4,3-c]pyridine-5-carbonyl]-2-methoxy-4-(1-methoxycyclobutyl)benzonitrile

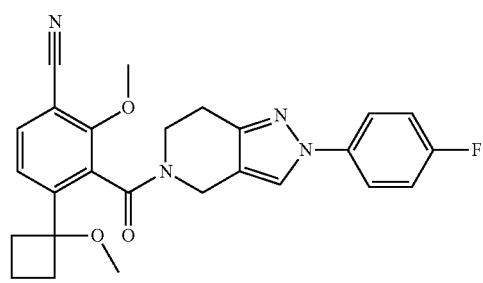 [SMILES: COc1c(C#N)ccc(C2(OC)CCC2)c1C(=O)N1CCc2nn(-c3ccc(F)cc3)cc2C1]

$^1$H NMR (400 MHz, CDCl$_3$) δ=7.78-7.43 (m, 4H), 7.23-7.05 (m, 3H), 5.26-4.44 (m, 1H), 4.35-4.19 (m, 1H), 4.06-3.96 (m, 3H), 3.95-3.82 (m, 1H), 3.60-3.27 (m, 1H), 3.13-2.77 (m, 5H), 2.60-2.25 (m, 4H), 2.09-1.87 (m, 1H), 1.80-1.66 (m, 1H); [M+H]=461.3.

Examples 494-495 were prepared in a manner analogous to Example 10 with the appropriated starting material substitutions.

Example 494

4-Cyclopentyl-3-[2-(4-fluorophenyl)-2H 4H 5H 6H-pyrrolo[3,4-c]pyrazole-5-carbonyl]-2-methoxybenzonitrile

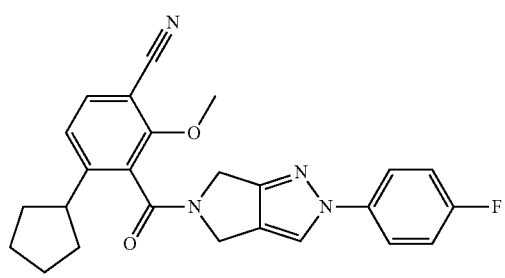 [SMILES: COc1c(C#N)ccc(C2CCCC2)c1C(=O)N1Cc2cn(-c3ccc(F)cc3)nc2C1]

$^1$H NMR (400 MHz, DMSO-d$_6$) δ=8.39-8.13 (m, 1H), 7.89-7.71 (m, 3H), 7.44-7.22 (m, 3H), 4.81-4.65 (m, 2H), 4.31 (t, J=13.7 Hz, 1H), 4.16 (dd, J=13.5, 18.2 Hz, 1H), 3.94 (d, J=2.0 Hz, 3H), 3.06-2.85 (m, 1H), 2.05-1.85 (m, 2H), 1.83-1.65 (m, 2H), 1.65-1.41 (m, 4H); [M+H]=431.3.

Example 495

4-Cyclopentyl-3-[2-(5-fluoropyridin-3-yl)-2H 4H 5H 6H-pyrrolo[3,4-c]pyrazole-5-carbonyl]-2-methoxybenzonitrile

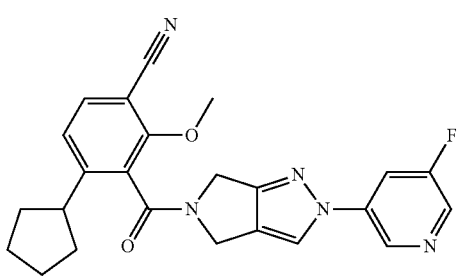 [SMILES: COc1c(C#N)ccc(C2CCCC2)c1C(=O)N1Cc2cn(-c3cncc(F)c3)nc2C1]

$^1$H NMR (400 MHz, CDCl$_3$) δ=8.75 (s, 1H), 8.42 (dd, J=2.5, 4.5 Hz, 1H), 7.86-7.64 (m, 2H), 7.63-7.53 (m, 1H), 7.23-7.15 (m, 1H), 5.30 (s, 1H), 4.89 (dd, J=3.7, 15.8 Hz, 2H), 4.54-4.41 (m, 1H), 4.30-4.17 (m, 1H), 4.09 (d, J=3.5 Hz, 2H), 3.13-2.94 (m, 1H), 2.17 (d, J=7.0 Hz, 1H), 2.02-1.90 (m, 1H), 1.81 (d, J=6.3 Hz, 2H), 1.73-1.51 (m, 5H); [M+H]=432.1.

Examples 496-546 were prepared in a manner analogous to Example 3 with the appropriated starting material substitutions.

Example 496

3 3-Difluoro-1-(4-methanesulfonyl-2-{2-phenyl-2H 4H 5H 6H 7H-pyrazolo[4,3-c]pyridine-5-carbonyl}phenyl)pyrrolidine

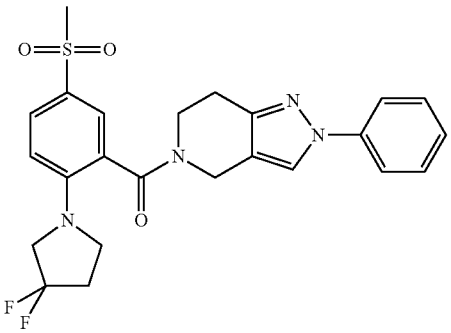 [SMILES: CS(=O)(=O)c1ccc(N2CCC(F)(F)C2)c(C(=O)N2CCc3nn(-c4ccccc4)cc3C2)c1]

$^1$H NMR (400 MHz, CDCl$_3$) δ=7.85-7.80 (m, 1H), 7.79 (s, 0.6H), 7.72 (dd, J=2.3, 8.6 Hz, 1H), 7.68-7.55 (m, 2.4H), 7.44 (q, J=8 Hz, 2H), 7.32-7.26 (m, 1H), 6.75 (t, J=10 Hz, 1H), 5.05-4.72 (m, 1H), 4.63-4.43 (m, 2H), 3.97-3.27 (m, 6H), 3.01 (s, 3H), 2.99-2.78 (m, 1H), 2.51-2.30 (m, 2H); [M+H]=487.33.

Example 497

5-[2-(2 2-Dimethylpropoxy)-5-methanesulfonylbenzoyl]-2-phenyl-2H 4H 5H 6H 7H-pyrazolo[4,3-c]pyridine

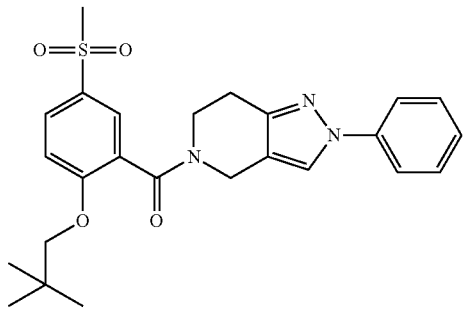 [SMILES: CC(C)(C)COc1ccc(S(C)(=O)=O)cc1C(=O)N1CCc2nn(-c3ccccc3)cc2C1]

$^1$H NMR (400 MHz, CDCl$_3$) δ=7.94 (ddd, J=2.3, 6.0, 8.5 Hz, 1H), 7.84 (t, J=2.2 Hz, 1H), 7.76 (s, 0.6H), 7.67-7.59 (m, 1H), 7.59-7.51 (m, 1.4H), 7.48-7.37 (m, 2H), 7.26 (q, J=8 Hz, 1H), 7.05 (dd, J=8.8, 12.3 Hz, 1H), 5.13-4.69 (m, 1H), 4.37 (q, J=16 Hz, 1H), 4.23-4.01 (m, 1H), 3.83-3.51 (m, 3H), 3.03 (s, 3H), 3.01-2.98 (m, 1H), 2.83-2.78 (m, 1H), 0.95 (s, 4.5H), 0.86 (s, 4.5H); [M+H]=468.36.

Example 498

1-(4-Methanesulfonyl-2-{2-phenyl-2H 4H 5H 6H 7H-pyrazolo[4,3-c]pyridine-5-carbonyl}phenyl)pyrrolidine

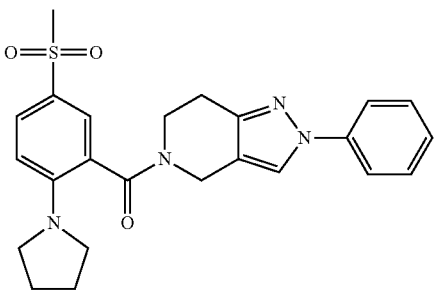 [SMILES: CS(=O)(=O)c1ccc(N2CCCC2)c(C(=O)N2CCc3nn(-c4ccccc4)cc3C2)c1]

$^1$H NMR (400 MHz, CDCl$_3$) δ=7.78 (s, 0.5H), 7.73 (ddd, J=2.3, 6.7, 9.0 Hz, 1H), 7.68-7.58 (m, 3.5H), 7.43 (q, J=8 Hz, 2H), 7.27 (q, J=8 Hz, 1H), 6.73 (t, J=8.4 Hz, 1H), 5.01-4.74 (m, 1H), 4.68-4.44 (m, 2H), 3.83-3.54 (m, 2H), 3.54-3.37 (m, 2H), 3.29-3.18 (m, 1H), 3.14-3.04 (m, 1H), 3.00 (s, 1.5H), 2.99 (s, 1.5H), 2.99-2.96 (m, 1H), 2.01-1.79 (m, 4H); [M+H]=451.37.

Example 499

1-(4-Methanesulfonyl-2-{2-phenyl-2H 4H 5H 6H 7H-pyrazolo[4,3-c]pyridine-5-carbonyl}phenyl)azetidine

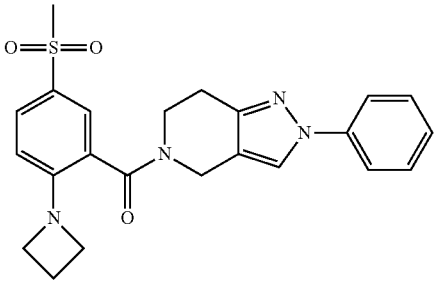 [SMILES: CS(=O)(=O)c1ccc(N2CCC2)c(C(=O)N2CCc3nn(-c4ccccc4)cc3C2)c1]

$^1$H NMR (400 MHz, CDCl$_3$) δ=7.77 (s, 0.4H), 7.76-7.69 (m, 1H), 7.67-7.62 (m, 1H), 7.60 (s, 0.6H), 7.45 (q, J=8 Hz, 2H), 7.32-7.22 (m, 2H), 6.45 (dd, J=8.6, 11.0 Hz, 1H), 4.94-4.77 (m, 1H), 4.69-4.38 (m, 2H), 4.14-4.06 (m, 2H), 3.92 (q, J=7.8 Hz, 1H), 3.85-3.76 (m, 1H), 3.76-3.67 (m, 1H), 3.65 (t, J=5.9 Hz, 1H), 3.00 (s, 3H), 2.99-2.96 (m, 1H), 2.43-2.21 (m, 2H); [M+H]=437.34.

Example 500

5-[2-(Cyclopropylmethoxy)-5-methanesulfonylbenzoyl]-2-phenyl-2H 4H 5H 6H 7H-pyrazolo[4,3-c]pyridine

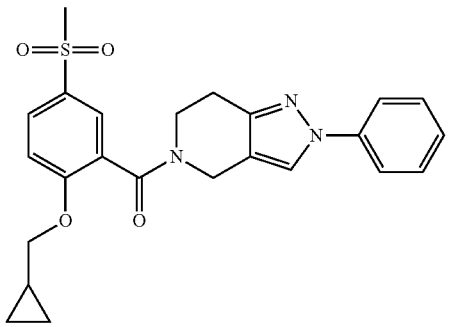 [SMILES: CS(=O)(=O)c1ccc(OCC2CC2)c(C(=O)N2CCc3nn(-c4ccccc4)cc3C2)c1]

¹H NMR (400 MHz, CDCl₃) δ=7.98-7.90 (m, 1H), 7.90-7.84 (m, 1H), 7.78 (s, 1H), 7.69-7.55 (m, 2H), 7.51-7.37 (m, 2H), 7.32-7.26 (m, 1H), 7.09-6.94 (m, 1H), 5.09-4.76 (m, 1H), 4.48-4.23 (m, 1H), 4.07-3.41 (m, 4H), 3.10-3.04 (m, 3H), 3.04-2.97 (m, 1H), 1.29-1.16 (m, 1H), 1.09-0.89 (m, 1H), 0.69-0.57 (m, 1H), 0.55-0.40 (m, 1H), 0.37-0.28 (m, 1H), 0.25-0.04 (m, 1H); [M+H]=452.3.

Example 501

2-Chloro-3-[1-(4-fluorophenyl)-1H 4H 5H 6H 7H-pyrazolo[4,3-c]pyridine-5-carbonyl]-4-[(1 1 1-trifluoropropan-2-yl)oxy]benzonitrile

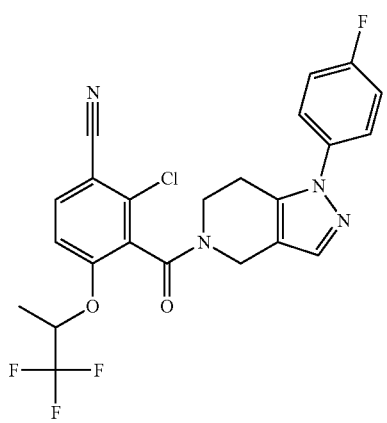 [SMILES: CC(Oc1ccc(C#N)c(Cl)c1C(=O)N1CCc2c(cnn2-c2ccc(F)cc2)C1)C(F)(F)F]

¹H NMR (400 MHz, CDCl₃) δ=7.71 (dd, J=2.7, 8.6 Hz, 1H), 7.63-7.32 (m, 3H), 7.22-7.08 (m, 2H), 7.07-6.82 (m, 1H), 5.16-4.51 (m, 2H), 4.43-4.16 (m, 2H), 3.66-3.25 (m, 1H), 3.13-2.65 (m, 2H), 1.51 (dd, J=3.1, 6.3 Hz, 3 H); [M+H]=493.21.

Example 502

2-Chloro-4-(4 4-difluoropiperidin-1-yl)-3-{2-phenyl-2H 4H 5H 6H 7H-pyrazolo[4,3-c]pyridine-5-carbonyl}benzonitrile

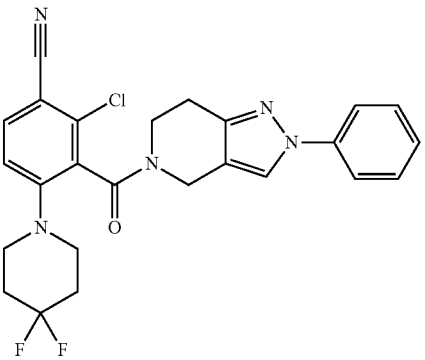 [SMILES: N#Cc1ccc(N2CCC(F)(F)CC2)c(C(=O)N2CCc3nn(-c4ccccc4)cc3C2)c1Cl]

¹H NMR (400 MHz), CDCl₃) δ=7.85-7.53 (m, 4H), 7.51-7.39 (m, 2H), 7.34-7.19 (m, 1H), 7.03 (dd, J=8.6, 14.5 Hz, 1H), 5.09-4.79 (m, 1H), 4.37-4.19 (m, 1H), 3.84 (ddd, J=5.9, 7.8, 13.3 Hz, 1H), 3.63-3.23 (m, 3H), 3.18-3.01 (m, 2H), 3.00-2.74 (m, 2H), 2.02-1.71 (m, 4H); [M+H]=482.26.

Example 503

2-Chloro-4-(2 2-dimethylpropoxy)-3-{2-phenyl-2H 4H 5H 6H 7H-pyrazolo[4,3-c]pyridine-5-carbonyl}benzonitrile

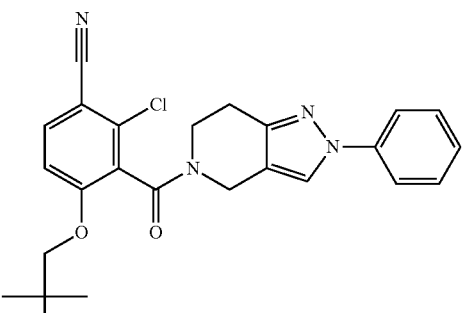

¹H NMR (400 MHz), CDCl₃) δ=7.84-7.61 (m, 2H), 7.59 (d, J=5.5 Hz, 2H), 7.45 (q, J=8.2 Hz, 2H), 7.35-7.21 (m, 1H), 6.91 (dd, J=8.8, 14.3 Hz, 1H), 5.10-4.75 (m, 1H), 4.51-4.28 (m, 1H), 3.95 (td, J=6.4, 13.1 Hz, 1H), 3.78-3.44 (m, 3H), 3.11-2.76 (m, 2H), 1.00-0.74 (m, 9H); [M+H]=449.28.

Example 504

2-Chloro-4-(cyclopropylmethoxy)-3-{2-phenyl-2H 4H 5H 6H 7H-pyrazolo[4,3-c]pyridine-5-carbonyl}benzonitrile

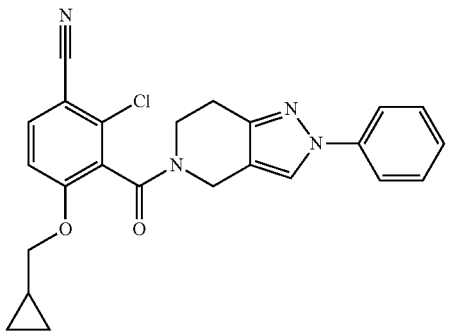 [SMILES: N#Cc1ccc(OCC2CC2)c(C(=O)N2CCc3nn(-c4ccccc4)cc3C2)c1Cl]

$^1$H NMR (400 MHz), CDCl$_3$) δ=7.82-7.52 (m, 4H), 7.42 (q, J=7.3 Hz, 2H), 7.32-7.13 (m, 1H), 7.00-6.60 (m, 1H), 5.14-4.65 (m, 1H), 4.51-4.22 (m, 1H), 4.01-3.76 (m, 2H), 3.70 (dd, J=7.0, 9.8 Hz, 1H), 3.56 (t, J=5.9, Hz, 1H), 3.19-2.94 (m, 1H), 2.88 (t, J=5.7 Hz, 1H), 1.20-0.88 (m, 1H), 0.55 (d, J=7.4 Hz, 1H), 0.45 (tdd, J=4.7, 8.9, 13.3 Hz, 1H), 0.28 (br s, 1H), 0.20-0.05 (m, 1H); [M+H]=433.26.

Example 505

2-Chloro-4-(morpholin-4-yl)-3-{2-phenyl-2H 4H 5H 6H 7H-pyrazolo[4,3-c]pyridine-5-carbonyl}benzonitrile

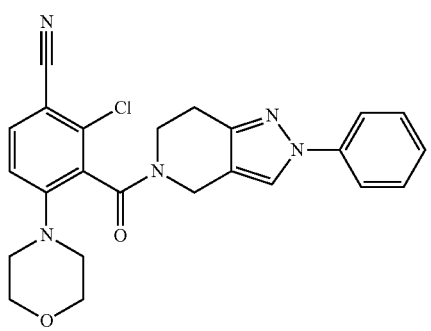 [SMILES: N#Cc1ccc(N2CCOCC2)c(C(=O)N2CCc3nn(-c4ccccc4)cc3C2)c1Cl]

$^1$H NMR (400 MHz), CDCl$_3$) δ=7.84-7.53 (m, 3H), 7.45 (q, J=8.09 Hz, 2H), 7.34-7.22 (m, 2H), 6.98 (dd, J=8.61, 12.91 Hz, 1H), 5.08-4.74 (m, 1H), 4.49 (dt, J=5.04, 13.01 Hz, 1H), 4.28 (s, 1H), 3.91-3.53 (m, 4H), 3.53-3.27 (m, 3H), 3.13-2.99 (m, 1H), 2.98-2.74 (m, 3H); [M+H]=448.25.

Example 506

2-Chloro-4-[(3-methyloxetan-3-yl)methoxy]-3-{2-phenyl-2H 4H 5H 6H 7H-pyrazolo[4,3-c]pyridine-5-carbonyl}benzonitrile

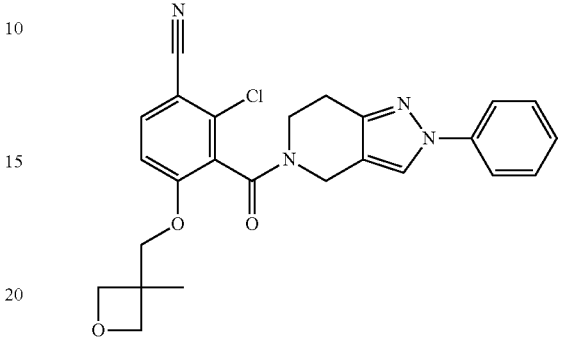

$^1$H NMR (400 MHz), CDCl$_3$) δ=7.75-7.47 (m, 4H), 7.37 (q, J=8.48 Hz, 2H), 7.25-7.14 (m, 1H), 6.90 (dd, J=8.61, 19.17 Hz, 1H), 5.02-4.69 (m, 1H), 4.51-4.20 (m, 4H), 4.20-3.85 (m, 4H), 3.77-3.38 (m, 1H), 2.98-2.68 (m, 2H), 1.25-1.12 (m, 3H); [M+H]=463.22.

Example 507

2-Chloro-4-[(1-methylcyclopropyl)methoxy]-3-{2-phenyl-2H 4H 5H 6H 7H-pyrazolo[4,3-c]pyridine-5-carbonyl}benzonitrile $^1$H NMR (400 MHz), CDCl$_3$) δ=7.80 (s, 1H), 7.71-7.55 (m, 3H), 7.44 (q, J=7.69 Hz, 2H), 7.35-7.22 (m, 1H), 7.04-6.67 (m, 1H), 4.96 (s, 1H), 4.58-4.28 (m, 1H), 3.96-3.73 (m, 2H), 3.72-3.48 (m, 2H), 3.08-2.83 (m, 2H), 1.13-0.90 (m, 3H), 0.56-0.07 (m, 4H); [M+H]=447.19.

Example 508

2-Chloro-3-[2-(4-fluorophenyl)-2H 4H 5H 6H 7H-pyrazolo[4,3-c]pyridine-5-carbonyl]-4-[(1-methylcyclopropyl)methoxy]benzonitrile

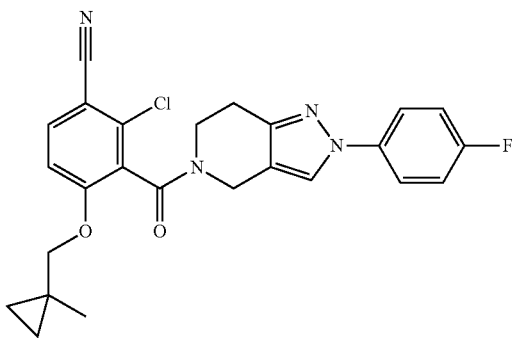 [SMILES: CC1(COc2ccc(C#N)c(Cl)c2C(=O)N2CCc3nn(-c4ccc(F)cc4)cc3C2)CC1]

$^1$H NMR (400 MHz), CDCl$_3$) δ=7.78-7.36 (m, 4H), 7.21-7.00 (m, 2H), 6.93-6.72 (m, 1H), 5.06-4.78 (m, 1H), 4.55-4.23 (m, 1H), 3.95-3.71 (m, 2H), 3.71-3.44 (m, 2H), 3.15-2.60 (m, 2H), 1.15-0.87 (m, 3H), 0.58-0.10 (m, 4H); [M+H]=465.21.

Example 509

2-Chloro-3-[2-(4-fluorophenyl)-2H 4H 5H 6H 7H-pyrazolo[4,3-c]pyridine-5-carbonyl]-4-{[1-(trifluoromethyl)cyclopropyl]methoxy}benzonitrile

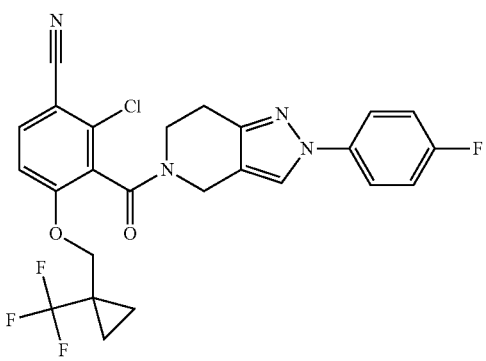 [SMILES: N#Cc1ccc(OCC2(C(F)(F)F)CC2)c(C(=O)N2CCc3nn(-c4ccc(F)cc4)cc3C2)c1Cl]

$^1$H NMR (400 MHz), CDCl$_3$) δ=7.76-7.65 (m, 1H), 7.64-7.49 (m, 2H), 7.21-7.07 (m, 2H), 6.96-6.82 (m, 1H), 5.19-4.65 (m, 1H), 4.50 (d, J=10.2 Hz, 1H), 4.43-4.31 (m, 1H), 4.23-4.01 (m, 1H), 3.83 (t, J=10.4 Hz, 1H), 3.67-3.41 (m, 1H), 3.10-2.96 (m, 1H), 2.95-2.76 (m, 1H), 1.26 (t, J=7.0, 1H), 1.16-0.99 (m, 2H), 0.97-0.65 (m, 2H); [M+H]=519.22.

Example 510

4-(4 4-Difluoropiperidin-1-yl)-3-[2-(4-fluorophenyl)-2H 4H 5H 6H-pyrrolo[3,4-c]pyrazole-5-carbonyl]-2-methoxybenzonitrile

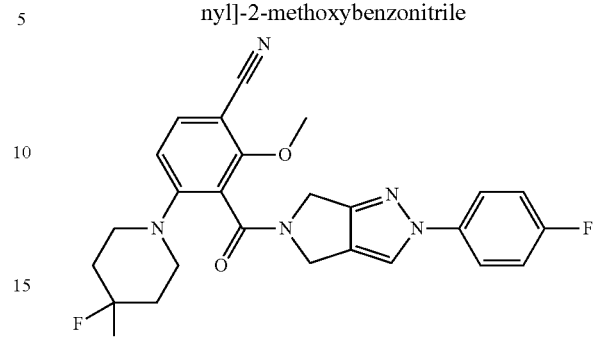

$^1$H NMR (400MHz, CDCl$_3$) δ=7.74-7.51 (m, 4H), 7.15 (dt, J=3.1, 8.6 Hz, 2H), 6.82 (dd, J=2.0, 8.6 Hz, 1H), 4.98-4.70 (m, 2H), 4.45-4.28 (m, 2H), 4.14-3.99 (m, 3H), 3.61-3.46 (m, 2H), 3.28-2.99 (m, 2H), 2.01 (qt, J=6.5, 13.2 Hz, 4H); [M+H]=482.40.

Example 511

4-(2 2-Dimethylpropoxy)-3-[2-(4-fluorophenyl)-2H 4H 5H 6H-pyrrolo[3,4-clnyrazole-5-carbonyl]-2-methoxybenzonitrile

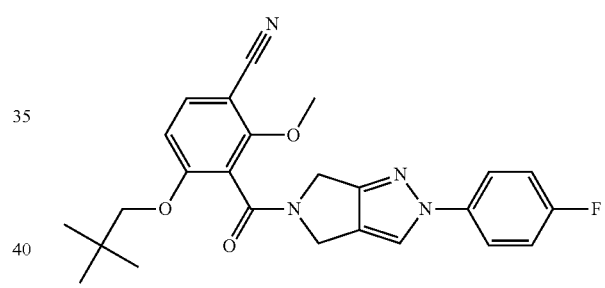

$^1$H NMR (400 MHz, CDCl$_3$) δ=7.73-7.47 (m, 3H), 7.19-7.07 (m, 1H), 6.72 (dd, J=2.2, 8.8 Hz, 1H), 4.96-4.74 (m, 2H), 4.51-4.30 (m, 2H), 4.10 (d, J=1.6 Hz, 2H), 3.75-3.59 (m, 2H), 0.94 (d, J=3.9 Hz, 9H); [M+H]=449.42.

Example 512

3-[2-(4-Fluorophenyl)-2H 4H 5H 6H-pyrrolo[3,4-c]pyrazole-5-carbonyl]-2-methoxy-4-[(1-methylcyclopropyl)methoxy]benzonitrile

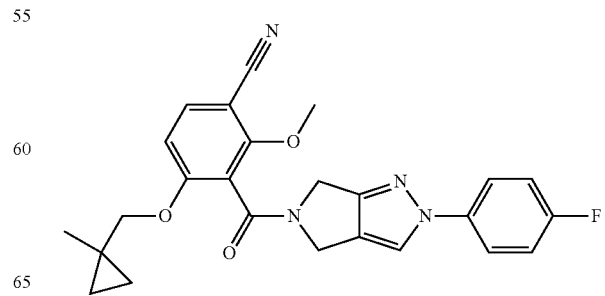

¹H NMR (400 MHz, CDCl₃) δ=7.74-7.51 (m, 4H), 7.14 (ddd, J=3.1, 8.0, 9.2 Hz, 2H), 6.67 (dd, J=2.0, 8.6 Hz, 1H), 4.97-4.78 (m, 2H), 4.49-4.34(m, 2H), 4.10 (d, J=1.6 Hz, 3H), 3.83 (s, 2H), 1.09 (d, J=5.5 Hz, 3H), 0.57-0.28 (m, 4H); [M+H]=447.29.

Example 513

4-(Cyclopentyloxy)-3-[2-(4-fluorophenyl)-2H 4H 5H 6H-pyrrolo[3,4-c]pyrazole-5-carbonyl]-2-methoxybenzonitrile

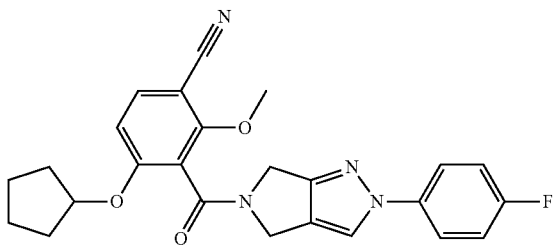 [SMILES: COc1c(C#N)ccc(OC2CCCC2)c1C(=O)N1Cc2cn(-c3ccc(F)cc3)nc2C1]

¹H NMR (400 MHz, CDCl₃) δ=7.72-7.52 (m, 4H), 7.20-7.10 (m, 2H), 6.74 (d, J=8.6 Hz, 1H), 4.94-4.74 (m, 3H), 4.47-4.25 (m, 2H), 4.09 (d, J=1.6 Hz, 3H), 2.03-1.41 (m, 9H); [M+H]=447.06.

Example 514

4-(3 3-Difluoropyrrolidin-1-yl)-3-[2-(4-fluorophenyl)-2H 4H 5H 6H-pyrrolo[3,4-c]pyrazole-5-carbonyl]-2-methoxybenzonitrile

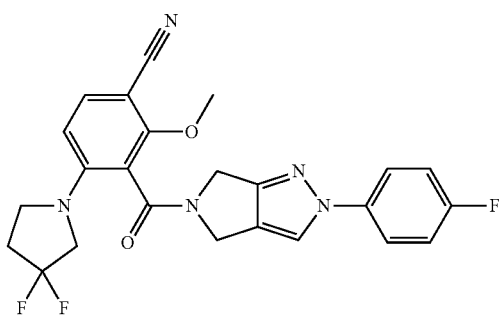 [SMILES: COc1c(C#N)ccc(N2CCC(F)(F)C2)c1C(=O)N1Cc2cn(-c3ccc(F)cc3)nc2C1]

¹H NMR (400 MHz, CDCl₃) δ=7.73-7.54 (m, 3H), 7.46 (dd, J=3.7, 8.8 Hz, 1H), 7.21-7.08 (m, 2H), 6.42 (dd, J=6.8, 8.8 Hz, 1H), 4.98-4.68 (m, 2H), 4.55 (dd, J=1.8, 13.9 Hz, 1H), 4.46-4.36 (m, 1H), 4.05 (d, J=3.9 Hz, 3H), 4.01-3.89 (m, 1H), 3.83-3.70 (m, 1H), 3.64-3.49 (m, 2H), 2.54-2.30 (m, 2H); [M+H]=468.42.

Example 515

3-[2-(4-Fluorophenyl)-2H 4H 5H 6H-pyrrolo[3,4-c]pyrazole-5-carbonyl]-2-methoxy-4-(propan-2-yloxy)benzonitrile

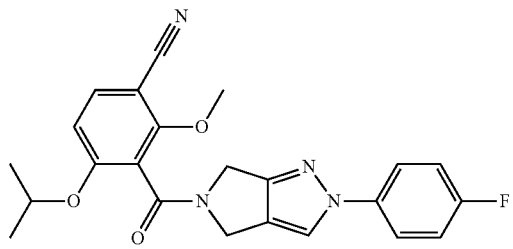 [SMILES: COc1c(C#N)ccc(OC(C)C)c1C(=O)N1Cc2cn(-c3ccc(F)cc3)nc2C1]

¹H NMR (400 MHz, CDCl₃) δ=7.75-7.49 (m, 4H), 7.14 (ddd, J=3.1, 8.1, 9.1 Hz, 2H), 6.74 (d, J=9.0 Hz, 1H), 4.97-4.75 (m, 2H), 4.64 (dtd, J=2.0, 6.1, 12.1 Hz, 1H), 4.48-4.27 (m, 2H), 4.09 (d, J=2.0 Hz, 3H), 1.41-1.27 (m, 6H); [M+H]=421.11.

Example 516

3-[2-(4-Fluorophenyl)-2H 4H 5H 6H-pyrrolo[3,4-c]pyrazole-5-carbonyl]-2-methoxy-4-[(1 1 1-trifluoro-2-methylpropan-2-yl)oxy]benzonitrile

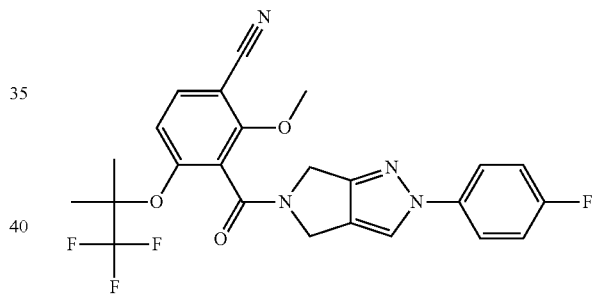

¹H NMR (400 MHz, CDCl₃) δ=7.79-7.47 (m, 4H), 7.21-7.09 (m, 2H), 6.99 (dd, J=3.3, 8.8 Hz, 1H), 4.92-4.69 (m, 2H), 4.51-4.30 (m, 2H), 4.13 (s, 3H), 1.54-1.47 (m, 6H); [M+H]=489.21.

Example 517

3-[2-(4-Fluorophenyl)-2H 4H 5H 6H-pyrrolo[3,4-c]pyrazole-5-carbonyl]-4-[(1-fluoropropan-2-yl)oxy]-2-methoxybenzonitrile

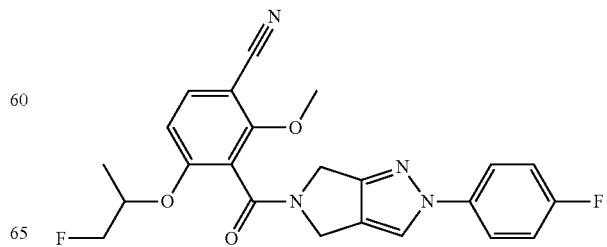

¹H NMR (400 MHz, CDCl₃) δ=7.72-7.51 (m, 4H), 7.19-7.10 (m, 2H), 6.86-6.74 (m, 1H), 4.94-4.67 (m, 3H), 4.61-4.28 (m, 4H), 4.15-4.06 (m, 3H), 1.41-1.28 (m, 3H); [M+H]=439.1.

Example 518

3-[2-(4-Fluorophenyl)-2H 4H 5H 6H-pyrrolo[3,4-c]pyrazole-5-carbonyl]-2-methoxy-4-(pentan-3-yloxy)benzonitrile

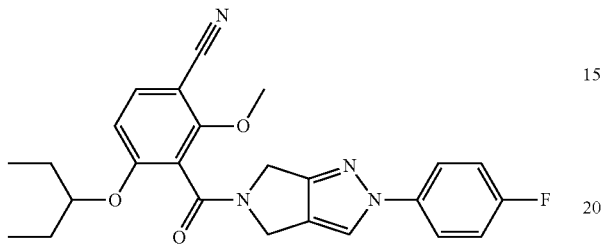

¹H NMR (400 MHz, CDCl₃) δ=7.72-7.51 (m, 4H), 7.18-7.09 (m, 2H), 6.76-6.67 (m, 1H), 4.95-4.71 (m, 2H), 4.48-4.29 (m, 2H), 4.24 (dt, J=2.3, 5.9 Hz, 1H), 4.10 (d, J=1.6 Hz, 3H), 1.77-1.60 (m, 4H), 1.01-0.83 (m, 6H); [M+H]=449.08.

Example 519

3-[2-(4-Fluorophenyl)-2H 4H 5H 6H-pyrrolo[3,4-c]pyrazole-5-carbonyl]-2-methoxy-4-(oxetan-3-yloxy)benzonitrile

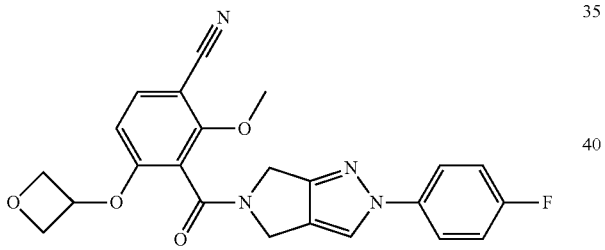

¹H NMR (400 MHz, CDCl₃) δ=7.76-7.54 (m, 4H), 7.20-7.10 (m, 2H), 6.29 (dd, J=3.3, 8.8 Hz, 1H), 5.33-5.20 (m, 1H), 5.03-4.91 (m, 2H), 4.88 (d, J=18.0 Hz, 2H), 4.81-4.58 (m, 2H), 4.54-4.31 (m, 2H), 4.22-4.02 (m, 3H); [M+H]=435.13.

Example 520

4-(2 2-Difluoroethoxy)-3-[2-(4-fluorophenyl)-2H 4H 5H 6H-pyrrolo[3,4-c]pyrazole-5-carbonyl]-2-methoxybenzonitrile

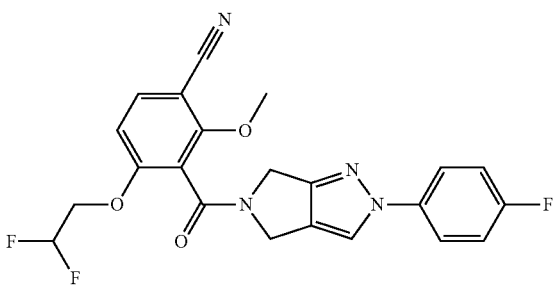 [SMILES: COc1c(C#N)ccc(OCC(F)F)c1C(=O)N1Cc2cn(-c3ccc(F)cc3)nc2C1]

¹H NMR (400 MHz, CDCl₃) δ=7.72-7.49 (m, 4H), 7.21-7.09 (m, 2H), 6.76 (d, J=8.6 Hz, 1H), 6.23-5.86 (m, 1H), 4.95-4.77 (m, 2H), 4.50-4.22 (m, 4H), 4.12 (d, J=2.0 Hz, 3H); [M+H]=442.9.

Example 521

3-[2-(4-Fluorophenyl)-2H 4H 5H 6H-pyrrolo[3,4-c]pyrazole-5-carbonyl]-2-methoxy-4-(pentan-2-yloxy)benzonitrile

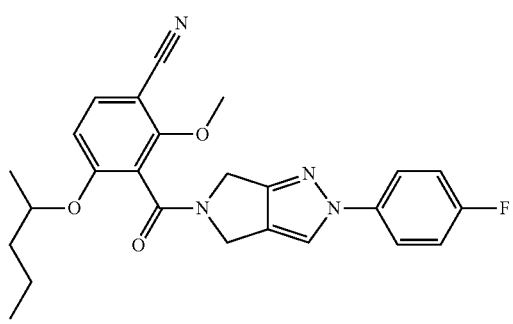 [SMILES: CCCC(C)Oc1ccc(C#N)c(OC)c1C(=O)N1Cc2cn(-c3ccc(F)cc3)nc2C1]

¹H NMR (400 MHz, CDCl₃) δ=7.71-7.52 (m, 4H), 7.19-7.09 (m, 2H), 6.72 (dd, J=2.5, 8.8 Hz, 1H), 4.94-4.74 (m, 2H), 4.53-4.26 (m, 4H), 4.09 (dd, J=1.0, 1.8 Hz, 3H), 1.78-1.23 (m, 12H), 0.96-0.74 (m, 3H); [M+H]=449.27.

Example 522

3-[2-(4-Fluorophenyl)-2H 4H 5H 6H-pyrrolo[3,4-c]pyrazole-5-carbonyl]-2-methoxy-4-(2-methylpropoxy)benzonitrile

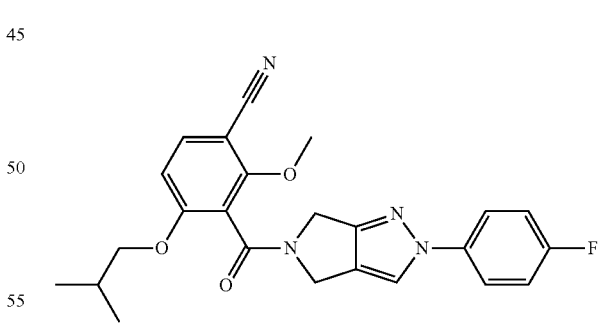

¹H NMR (400 MHz, CDCl₃) δ=7.71-7.51 (m, 4H), 7.20-7.10 (m, 2H), 6.73 (dd, J=2.0, 8.6 Hz, 1H), 4.95-4.76 (m, 2H), 4.48-4.30 (m, 2H), 4.10 (d, J=2.0 Hz, 3H), 3.92-3.74 (m, 2H), 2.16-1.97 (m, 1H), 1.02-0.85 (m, 6H); [M+H]=435.17.

Example 523

3-[2-(4-Fluorophenyl)-2H 4H 5H 6H-pyrrolo[3,4-c]pyrazole-5-carbonyl]-2-methoxy-4-[(3-methylbutan-2-yl)oxy]benzonitrile

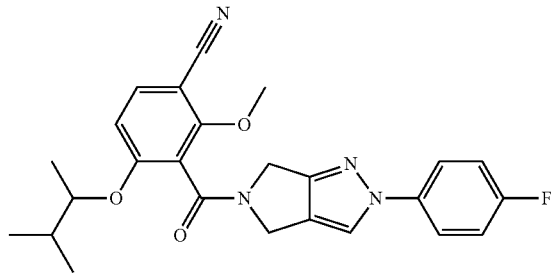 [SMILES: COc1c(C#N)ccc(OC(C)C(C)C)c1C(=O)N1Cc2cn(-c3ccc(F)cc3)nc2C1]

¹H NMR (400 MHz, CDCl₃) δ=7.71-7.52 (m, 4H), 7.19-7.10 (m, 2H), 6.76-6.67 (m, 1H), 4.93-4.74 (m, 2H), 4.46-4.22 (m, 3H), 4.10 (d, J=1.6 Hz, 3H), 1.98-1.82 (m, 1H), 1.33-1.18 (m, 3H), 1.02-0.77 (m, 6H); [M+H]=449.1.

Example 524

4-(1-Cyclopropylethoxy)-3-[2-(4-fluorophenyl)-2H 4H 5H 6H-pyrrolo[3,4-c]pyrazole-5-carbonyl]-2-methoxybenzonitrile

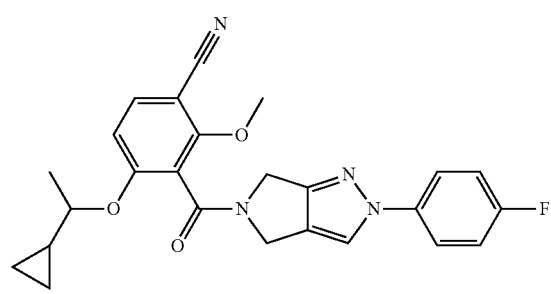 [SMILES: COc1c(C#N)ccc(OC(C)C2CC2)c1C(=O)N1Cc2cn(-c3ccc(F)cc3)nc2C1]

¹H NMR (400 MHz, CDCl₃) δ=7.74-7.49 (m, 4H), 7.19-7.07 (m, 2H), 6.76-6.59 (m, 1H), 5.00-4.74 (m, 2H), 4.55-4.28 (m, 2H), 4.20-4.04 (m, 3H), 4.03-3.85 (m, 1H), 1.46-1.29 (m, 3H), 1.19-0.95 (m, 1H), 0.66-0.17 (m, 4H); [M+H]=447.29.

Example 525

3-[2-(4-Fluorophenyl)-2H 4H 5H 6H-pyrrolo[3,4-c]pyrazole-5-carbonyl]-2-methoxy-4-(1-methylcyclopropoxy)benzonitrile

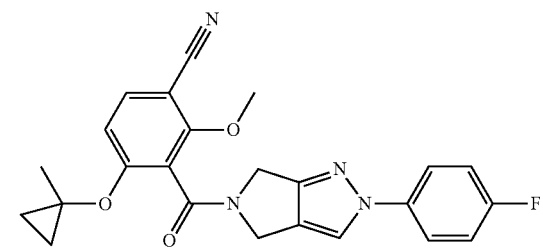 [SMILES: COc1c(C#N)ccc(OC2(C)CC2)c1C(=O)N1Cc2cn(-c3ccc(F)cc3)nc2C1]

¹H NMR (400 MHz, CDCl₃) δ=7.73-7.52 (m, 4H), 7.20-7.05 (m, 3H), 4.84 (d, J=18.8 Hz, 2H), 4.45-4.21 (m, 2H), 4.12-4.03 (m, 3H), 1.57 (s, 3H), 1.10-0.91 (m, 2H), 0.83-0.64 (m, 2H); [M+H]=433.15.

Example 526

4-(2 2-Dimethylpropoxy)-3-[2-(4-fluorophenyl)-2H 4H 5H 6H-pyrrolo[3,4-c]pyrazole-5-carbonyl]benzonitrile

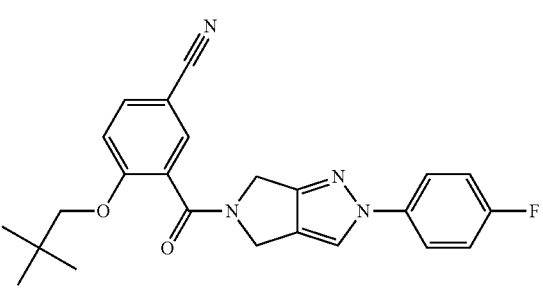 [SMILES: CC(C)(C)COc1ccc(C#N)cc1C(=O)N1Cc2cn(-c3ccc(F)cc3)nc2C1]

¹H NMR (400 MHz, CDCl₃) δ=7.72-7.51 (m, 5H), 7.19-7.10 (m, 2H), 7.02 (dd, J=3.5, 8.6 Hz, 1H), 4.85 (d, J=18.0 Hz, 2H), 4.43 (br s, 2H), 3.71 (d, J=2.7 Hz, 2H), 0.95 (d, J=2.7 Hz, 9H); [M+H]=419.09.

Example 527

4-(2 2-Difluoroethoxy)-3-[2-(4-fluorophenyl)-2H 4H 5H 6H-pyrrolo[3,4-c]pyrazole-5-carbonyl]benzonitrile

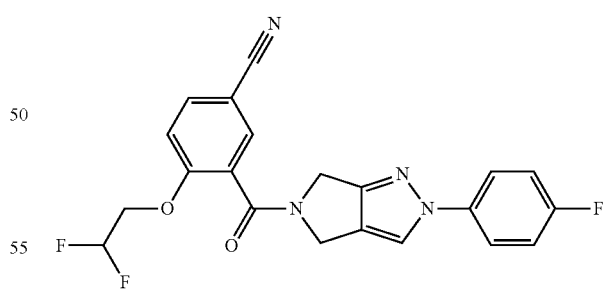

¹H NMR (400 MHz, CDCl₃) δ=7.77-7.72 (m, 1H), 7.69 (dd, J=1.4, 2.2 Hz, 1H), 7.63-7.53 (m, 3H), 7.15 (ddd, J=2.9, 8.2, 9.2 Hz, 2H), 7.07 (dd, J=2.3, 8.6 Hz, 1H), 6.26-5.88 (m, 2H), 4.85 (d, J=16.4 Hz, 2H), 4.44 (d, J=7.0 Hz, 2H), 4.33 (dt, J=4.1, 12.8 Hz, 2H); [M+H]=413.5.

Example 528

3-[2-(4-Fluorophenyl)-2H 4H 5H 6H-pyrrolo[3,4-c]pyrazole-5-carbonyl]-4-(2 2 2-trifluoroethoxy)benzonitrile

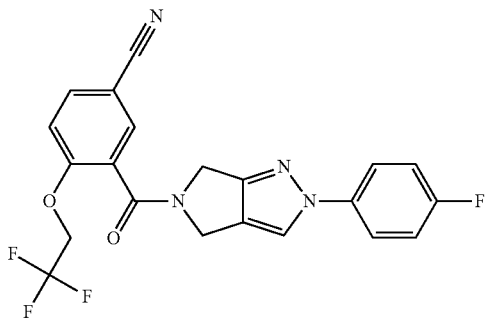 [SMILES: N#Cc1ccc(OCC(F)(F)F)c(C(=O)N2Cc3cn(-c4ccc(F)cc4)nc3C2)c1]

¹H NMR (400 MHz, CDCl₃) δ=7.79-7.73 (m, 1H), 7.73-7.68 (m, 1H), 7.66-7.50 (m, 3H), 7.21-7.03 (m, 3H), 4.85 (d, J=16.4 Hz, 2H), 4.51 (dq, J=2.7, 7.8 Hz, 2H), 4.44 (d, J=6.7 Hz, 2H); [M+H]=431.33.

Example 529

3-[2-(4-Fluorophenyl)-2H 4H 5H 6H-pyrrolo[3,4-c]pyrazole-5-carbonyl]-4-(propan-2-yloxy)benzonitrile

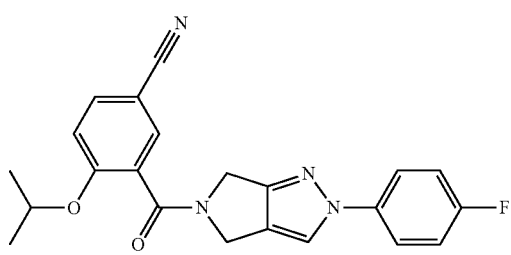 [SMILES: CC(C)Oc1ccc(C#N)cc1C(=O)N1Cc2cn(-c3ccc(F)cc3)nc2C1]

¹H NMR (400 MHz, CDCl₃) δ=7.71-7.53 (m, 5H), 7.20-7.09 (m, 2H), 7.03 (d, J=8.6 Hz, 1H), 4.84 (d, J=17.2 Hz, 2H), 4.69 (dtd, J=3.9, 6.1, 12.1 Hz, 1H), 4.45 (d, J=12.5 Hz, 2H), 1.36 (d, J=6.3 Hz, 6H); [M+H]=391.24.

Example 530

3-[2-(4-Fluorophenyl)-2H 4H 5H 6H-pyrrolo[3,4-c]pyrazole-5-carbonyl]-4-{[(2S)-1 1 1-trifluoropropan-2-yl]oxy}benzonitrile

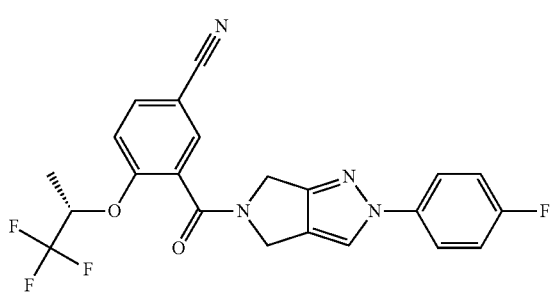 [SMILES: C[C@H](Oc1ccc(C#N)cc1C(=O)N1Cc2cn(-c3ccc(F)cc3)nc2C1)C(F)(F)F]

¹H NMR (400 MHz, CDCl₃) δ=7.76-7.71 (m, 1H), 7.71-7.67 (m, 1H), 7.63-7.54 (m, 2H), 7.20-7.06 (m, 3H), 4.93-4.72 (m, 3H), 4.52-4.34 (m, 2H), 1.53 (d, J=6.3 Hz, 3H); [M+H]=445.24.

Example 531

4-(Cyclopropylmethoxy)-3-[2-(4-fluorophenyl)-2H 4H 5H 6H-pyrrolo[3,4-c]pyrazole-5-carbonyl]benzonitrile

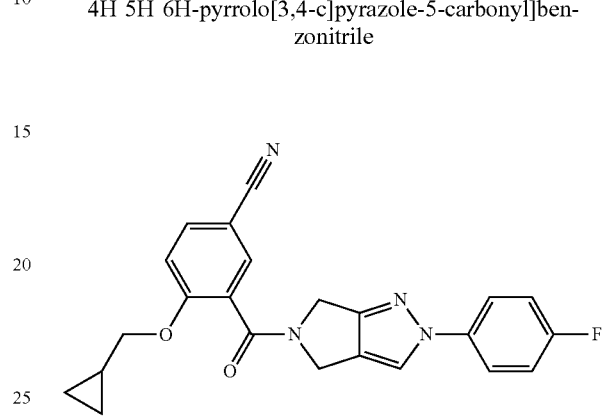

¹H NMR (400 MHz, CDCl₃) δ=7.75-7.52 (m, 5H), 7.15 (dt, J=2.3, 8.6 Hz, 2H), 7.01 (dd, J=2.7, 8.6 Hz, 1H), 4.86 (d, J=17.6 Hz, 2H), 4.49 (d, J=12.1 Hz, 2H), 3.97 (d, J=7.0 Hz, 2H), 1.23 (dq, J=5.5, 7.2 Hz, 1H), 0.66-0.53 (m, 2H), 0.39-0.22 (m, 2H); [M+H]=403.36.

Example 532

3-[2-(4-Fluorophenyl)-2H 4H 5H 6H-pyrrolo[3,4-c]pyrazole-5-carbonyl]-4-[(1 1 1-trifluoro-2-methylpropan-2-yl)oxy]benzonitrile

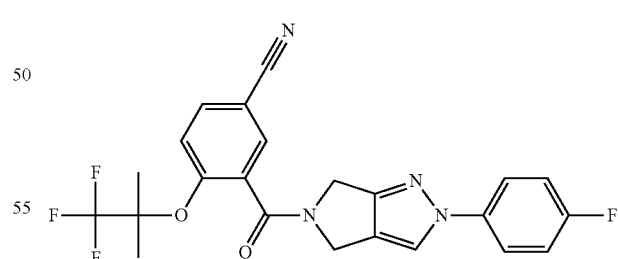

¹H NMR (400 MHz, CDCl₃) δ=7.76-7.67 (m, 2H), 7.63-7.53 (m, 2H), 7.29 (d, J=8.6 Hz, 1H), 7.20-7.08 (m, 2H), 5.04-4.20 (m, 4H), 1.47 (d, J=1.2 Hz, 6H); [M+H]=459.3.

Example 533

3-[2-(5-Fluoro-6-methylpyridin-2-yl)-2H 4H 5H 6H-pyrrolo[3,4-c]pyrazole-5-carbonyl]-2-methoxy-4-(2 2 2-trifluoroethoxy)benzonitrile

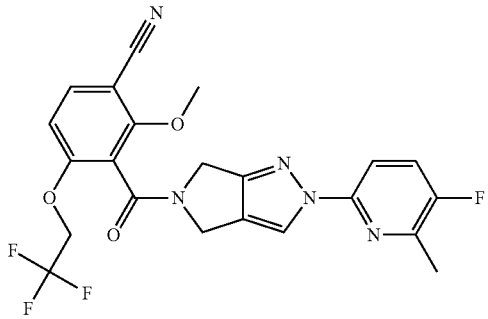 [SMILES: COc1c(C#N)ccc(OCC(F)(F)F)c1C(=O)N1Cc2cn(-c3ccc(F)c(C)n3)nc2C1]

$^1$H NMR (400 MHz, CDCl$_3$) δ=8.43-8.18 (m, 1H), 7.78-7.56 (m, 2H), 7.43 (td, J=8.6, 13.0 Hz, 1H), 6.77 (dd, J=2.0, 8.6 Hz, 1H), 4.98-4.71 (m, 2H), 4.56-4.24 (m, 4H), 4.20-3.95 (m, 3H), 2.61-2.39 (m, 3H); [M+H]=476.17.

Example 534

4-(2 2-Difluoroethoxy)-3-[2-(5-fluoro-6-methylpyridin-2-yl)-2H 4H 5H 6H-pyrrolo[3,4-c]pyrazole-5-carbonyl]-2-methoxybenzonitrile

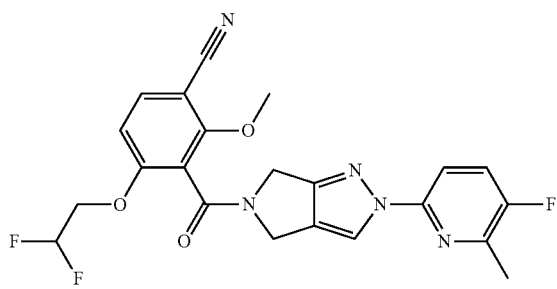 [SMILES: COc1c(C#N)ccc(OCC(F)F)c1C(=O)N1Cc2cn(-c3ccc(F)c(C)n3)nc2C1]

$^1$H NMR (400 MHz, CDCl$_3$) δ=8.42-8.13 (m, 1H), 7.77-7.57 (m, 2H), 7.43 (td, J=8.5, 12.8 Hz, 1H), 6.76 (d, J=9.0 Hz, 1H), 6.24-5.82 (m, 1H), 4.93-4.75 (m, 2H), 4.50-4.22 (m, 4H), 4.12 (d, J=1.2 Hz, 3H), 2.61-2.39 (m, 3H); [M+H]=458.23.

Example 535

3-[2-(5-Fluoro-6-methylpyridin-2-yl)-2H 4H 5H 6H-pyrrolo[3,4-c]pyrazole-5-carbonyl]-2-methoxy-4-(propan-2-yloxy)benzonitrile

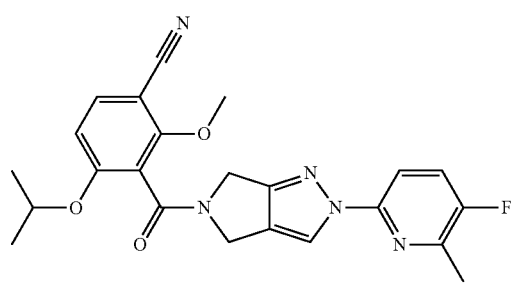 [SMILES: COc1c(C#N)ccc(OC(C)C)c1C(=O)N1Cc2cn(-c3ccc(F)c(C)n3)nc2C1]

$^1$H NMR (400 MHz, CDCl$_3$) δ=8.40-8.19 (m, 1H), 7.78-7.53 (m, 2H), 7.43 (td, J=8.6, 12.9 Hz, 1H), 6.73 (d, J=9.0 Hz, 1H), 4.83 (d, J=17.2 Hz, 2H), 4.64 (td, J=6.1, 12.1 Hz, 1H), 4.47-4.27 (m, 2H), 4.09 (s, 3H), 2.64-2.32 (m, 3H), 1.46-1.16 (m, 6H); [M+H]=436.4.

Example 536

3-[2-(5-Fluoro-6-methylpyridin-2-yl)-2H 4H 5H 6H-pyrrolo[3,4-c]pyrazole-5-carbonyl]-2-methoxy-4-[(3-methyloxetan-3-yl)methoxy]benzonitrile

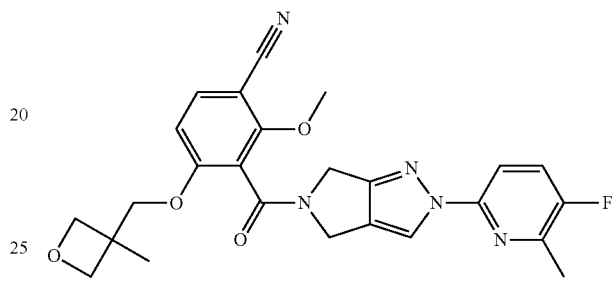

$^1$H NMR (400 MHz, CDCl$_3$) δ=8.42-8.13 (m, 1H), 7.85-7.54 (m, 2H), 7.42 (td, J=8.3, 13.9 Hz, 1H), 6.89-6.64 (m, 1H), 4.97-4.72 (m, 2H), 4.65-4.23 (m, 6H), 4.23-3.91 (m, 5H), 2.64-2.36 (m, 3H), 1.30 (s, 3H); [M+H]=478.11.

Example 537

3-[2-(5-Fluoro-6-methylpyridin-2-yl)-2H 4H 5H 6H-pyrrolo[3,4-c]pyrazole-5-carbonyl]-2-methoxy-4-(oxetan-3-yloxy)benzonitrile

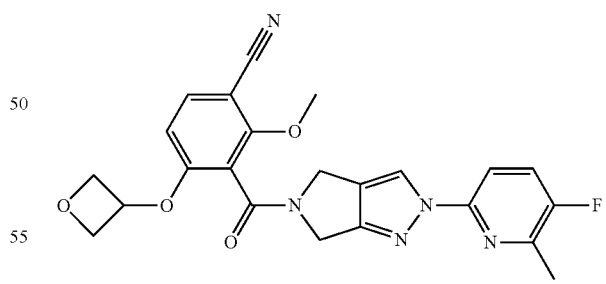

$^1$H NMR (400 MHz, CDCl$_3$) δ=8.48-8.15 (m, 1H), 7.87-7.36 (m, 3H), 6.28 (d, J=9.0 Hz, 1H), 5.37-5.22 (m, 1H), 5.04-4.61 (m, 6H), 4.58-4.28 (m, 2H), 4.11 (d, J=2.0 Hz, 3H), 2.67-2.34 (m, 3H); [M+H]=450.1.

Example 538

4-[(3-Methyloxetan-3-yl)methoxy]-3-[2-(2-methyl-pyridin-4-yl)-2H 4H 5H 6H-pyrrolo[3,4-c]pyrazole-5-carbonyl]benzonitrile

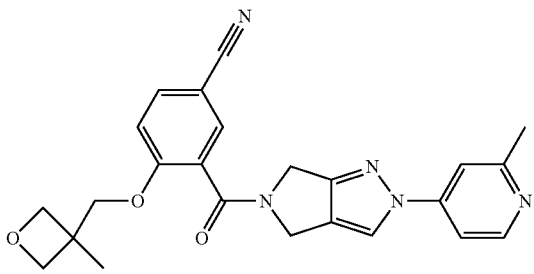 [SMILES: Cc1cc(-n2cc3c(n2)CN(C(=O)c2cc(C#N)ccc2OCC2(C)COC2)C3)ccn1]

$^1$H NMR (400 MHz, DMSO-d$_6$) δ=8.56-8.35 (m, 2H), 7.94 (ddd, J=1.0, 2.1, 8.7 Hz, 1H), 7.81 (dd, J=2.2, 6.1 Hz, 1H), 7.69 (dd, J=2.2, 19.0 Hz, 1H), 7.60 (ddd, J=2.2, 5.5, 14.7 Hz, 1H), 7.36 (dd, J=2.7, 8.6 Hz, 1H), 4.63 (d, J=7.4 Hz, 2H), 4.48-4.25 (m, 4H), 4.24-4.06 (m, 4H), 1.19 (d, J=2.7 Hz, 3H); [M+H]=430.27.

Example 539

3-[2-(2-Methylpyridin-4-yl)-2H 4H 5H 6H-pyrrolo[3,4-c]pyrazole-5-carbonyl]-4-(2 2 2-trifluoroethoxy)benzonitrile

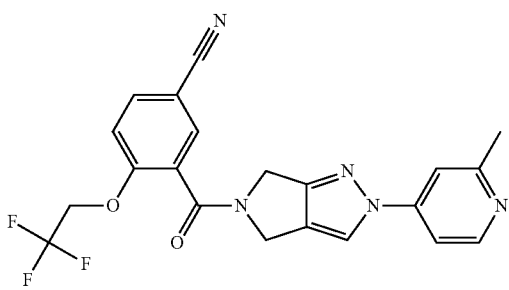 [SMILES: Cc1cc(-n2cc3c(n2)CN(C(=O)c2cc(C#N)ccc2OCC(F)(F)F)C3)ccn1]

$^1$H NMR (400 MHz, DMSO-d$_6$) δ=8.74-8.55 (m, 2H), 8.18-7.97 (m, 3H), 7.88 (dd, J=2.3, 7.0 Hz, 1H), 7.46 (dd, J=4.9, 8.8 Hz, 1H), 5.08-4.94 (m, 2H), 4.70 (d, J=12.9 Hz, 2H), 4.55-4.26 (m, 3H), 2.64 (d, J=2.3 Hz, 3H); [M+H]=427.72.

Example 540

4-(Cyclopropylmethoxy)-3-[2-(2-methylpyridin-4-yl)-2H 4H 5H 6H-pyrrolo[3,4-c]pyrazole-5-carbonyl]benzonitrile

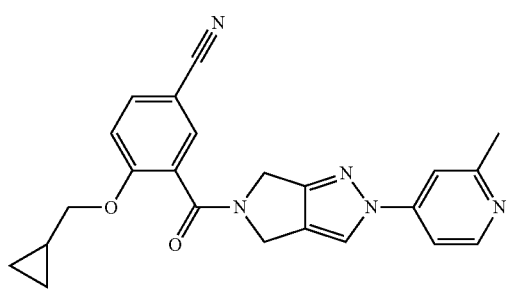 [SMILES: Cc1cc(-n2cc3c(n2)CN(C(=O)c2cc(C#N)ccc2OCC2CC2)C3)ccn1]

$^1$H NMR (400 MHz, CDCl$_3$) δ=8.54 (dd, J=2.2, 5.7 Hz, 1H), 7.89-7.72 (m, 1H), 7.71-7.63 (m, 2H), 7.58-7.46 (m, 1H), 7.40 (d, J=5.5 Hz, 1H), 7.06-6.99 (m, 1H), 4.87 (d, J=16.0 Hz, 2H), 4.51 (d, J=12.1 Hz, 2H), 3.98 (dd, J=2.0, 7.0 Hz, 2H), 2.66 (s, 3H), 1.32-1.12 (m, 1H), 0.70-0.45 (m, 2H), 0.41-0.19 (m, 2H); [M+H]=400.24.

Example 541

4-(4 4-Difluoropiperidin-1-yl)-3-[2-(2-methylpyridin-4-yl)-2H 4H 5H 6H-pyrrolo[3,4-c]pyrazole-5-carbonyl]benzonitrile

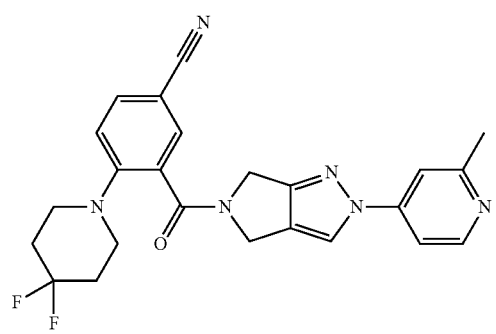 [SMILES: Cc1cc(-n2cc3c(n2)CN(C(=O)c2cc(C#N)ccc2N2CCC(F)(F)CC2)C3)ccn1]

$^1$H NMR (400 MHz, CDCl$_3$) δ=8.55 (dd, J=1.6, 5.9 Hz, 1H), 7.92-7.71 (m, 1H), 7.70-7.59 (m, 2H), 7.55-7.37 (m, 2H), 7.10 (dd, J=3.9, 8.6 Hz, 1H), 5.04-4.20 (m, 4H), 3.35 (br s, 4H), 2.67 (br s, 3H), 2.14-1.91 (m, 4H); [M+H]=449.2.

Example 542

3-[2-(2-Methylpyridin-4-yl)-2H 4H 5H 6H-pyrrolo[3,4-c]pyrazole-5-carbonyl]-4-[(1 1 1-trifluoro-2-methylpropan-2-yl)oxy]benzonitrile

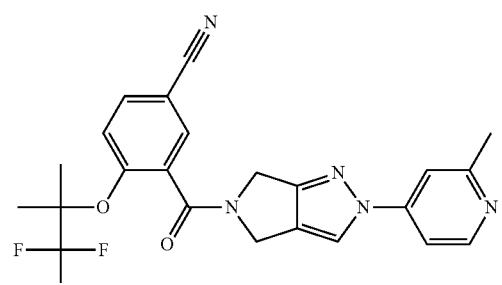

$^1$H NMR (400 MHz, CDCl$_3$) δ=8.53 (dd, J=2.5, 5.7 Hz, 1H), 7.89-7.67 (m, 3H), 7.49 (dd, J=1.8, 13.5 Hz, 1H), 7.42-7.32 (m, 1H), 7.29 (d, J=8.2 Hz, 1H), 4.98-4.27 (m, 4H), 2.63 (d, J=2.3 Hz, 3H), 1.47 (s, 6H); [M+H]=455.99.

Example 543

3-[2-(2-Ethylpyridin-4-yl)-2H 4H 5H 6H-pyrrolo[3,4-c]pyrazole-5-carbonyl]-4-(2 2 2-trifluoroethoxy)benzonitrile

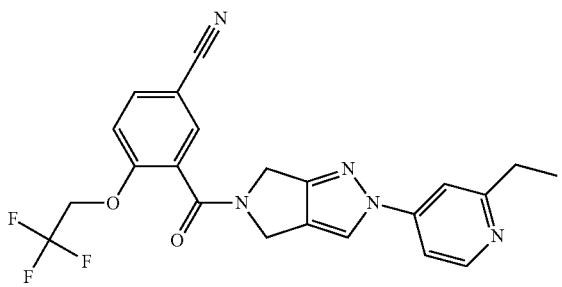 [SMILES: CCc1cc(-n2cc3c(n2)CN(C(=O)c2cc(C#N)ccc2OCC(F)(F)F)C3)ccn1]

$^1$H NMR (400 MHz, CDCl$_3$) δ=8.56 (dd, J=1.6, 5.5 Hz, 1H), 7.93-7.71 (m, 3H), 7.52 (dd, J=2.0, 19.6 Hz, 1H), 7.39 (d, J=5.1 Hz, 1H), 7.09 (d, J=8.6 Hz, 1H), 4.86 (d, J=16.0 Hz, 2H), 4.59-4.39 (m, 4H), 2.92 (dq, J=2.5, 7.6 Hz, 2H), 1.37 (dt, J=3.5, 7.6 Hz, 3H); [M+H]=442.6.

Example 544

4-(Cyclopropylmethoxy)-3-[2-(2-ethylpyridin-4-yl)-2H 4H 5H 6H-pyrrolo[3,4-c]pyrazole-5-carbonyl]benzonitrile

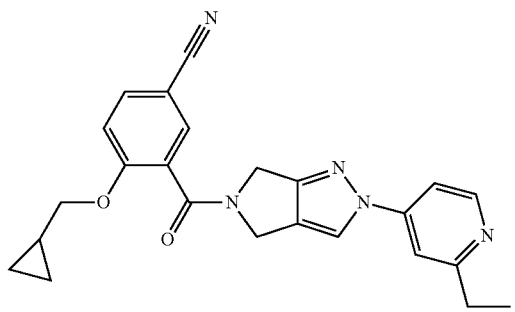 [SMILES: CCc1cc(-n2cc3c(n2)CN(C(=O)c2cc(C#N)ccc2OCC2CC2)C3)ccn1]

$^1$H NMR (400 MHz, CDCl$_3$) δ=8.57 (dd, J=1.6, 5.9 Hz, 1H), 7.92-7.73 (m, 1H), 7.73-7.63 (m, 2H), 7.62-7.50 (m, 1H), 7.44 (d, J=2.7 Hz, 1H), 7.03 (dd, J=3.1, 8.6 Hz, 1H), 4.87 (d, J=16.0 Hz, 2H), 4.51 (d, J=13.7 Hz, 2H), 3.98 (dd, J=2.2, 6.8 Hz, 2H), 2.96 (q, J=7.7 Hz, 2H), 1.38 (dt, J=3.5, 7.6 Hz, 3H), 1.29-1.14 (m, 1H), 0.65-0.53 (m, 2H), 0.34-0.28 (m, 2H); [M+H]=414.2.

Example 545

4-(2 2-Difluoroethoxy)-3-[2-(2-ethylpyridin-4-yl)-2H 4H 5H 6H-pyrrolo[3,4-c]pyrazole-5-carbonyl]benzonitrile

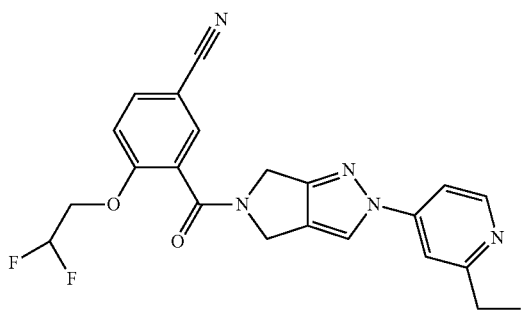 [SMILES: CCc1cc(-n2cc3c(n2)CN(C(=O)c2cc(C#N)ccc2OCC(F)F)C3)ccn1]

$^1$H NMR (400 MHz, CDCl$_3$) δ=8.56 (dd, J=1.6, 5.5 Hz, 1H), 7.91-7.67 (m, 3H), 7.52 (dd, J=2.2, 19.0 Hz, 1H), 7.39 (d, J=5.9 Hz, 1H), 7.07 (dd, J=2.3, 8.6 Hz, 1H), 6.32-5.87 (m, 2H), 4.86 (d, J=15.7 Hz, 2H), 4.46 (d, J=8.2 Hz, 2H), 4.33 (dt, J=3.9, 12.7 Hz, 2H), 2.92 (dq, J=2.7, 7.6 Hz, 2H), 1.37 (dt, J=3.7, 7.5 Hz, 3H); [M+H]=424.6.

Example 546

4-(4 4-Difluoropiperidin-1-yl)-3-[2-(2-ethylpyridin-4-yl)-2H 4H 5H 6H-pyrrolo[3,4-c]pyrazole-5-carbonyl]benzonitrile

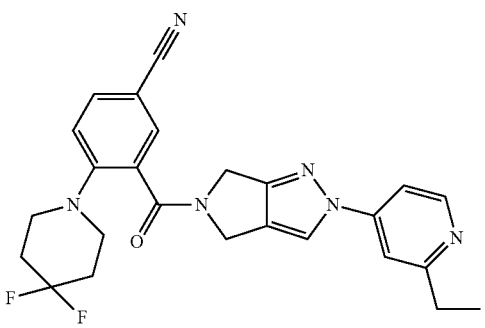 [SMILES: CCc1cc(-n2cc3c(n2)CN(C(=O)c2cc(C#N)ccc2N2CCC(F)(F)CC2)C3)ccn1]

$^1$H NMR (400 MHz, CDCl$_3$) δ=8.58 (dd, J=1.4, 5.7 Hz, 1H), 7.94-7.73 (m, 1H), 7.71-7.60 (m, 2H), 7.61-7.49 (m, 1H), 7.42 (d, J=5.5 Hz, 1H), 7.10 (dd, J=3.9, 8.6 Hz, 1H), 4.86 (br s, 2H), 4.47 (br s, 2H), 3.36 (br s, 4H), 3.10-2.84 (m, 2H), 2.09-1.95 (m, 4H), 1.38 (dt, J=3.9, 7.6 Hz, 3H); [M+H]=463.36.

Examples 547-574 were prepared in a manner analogous to Example 8 with the appropriated starting material substitutions.

Example 547

5-{2-[2-(2-Fluorophenyl)-2H 4H 5H 6H-pyrrolo[3,4-c]pyrazole-5-carbonyl]-4-methanesulfonylphenyl}-2-(trifluoromethyl)pyridine

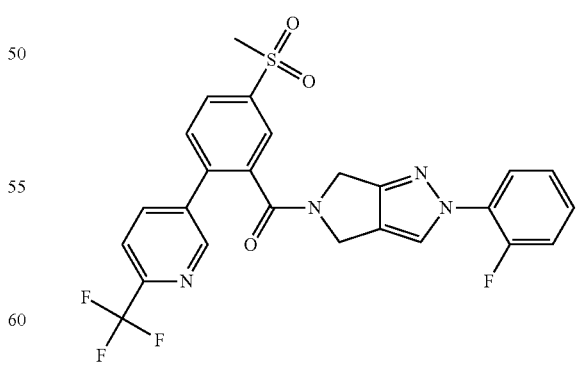

$^1$H NMR (400 MHz, CDCl$_3$) δ=8.88 (dd, J=2.2, 6.1 Hz, 1H), 8.22-8.08 (m, 3H), 7.83-7.67 (m, 4H), 7.28 (dd, J=2.2, 5.7 Hz, 1H), 7.25-7.17 (m, 2H), 4.71 (d, J=14.9 Hz, 2H), 4.19 (s, 2H), 3.15 (d, J=1.2 Hz, 3H); [M+H]=531.4.

Example 548

5-Fluoro-2-{5-[2-(5-fluoropyridin-3-yl)-5-methanesulfonylbenzoyl]-2H 4H 5H 6H-pyrrolo[3,4-c]pyrazol-2-yl}pyridine

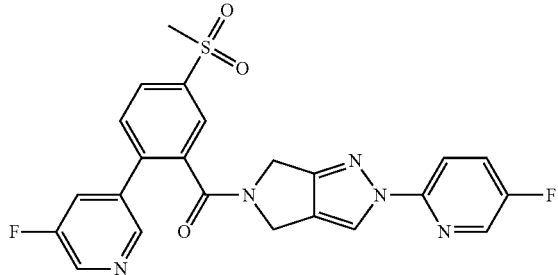 [SMILES: CS(=O)(=O)c1ccc(-c2cncc(F)c2)c(C(=O)N2Cc3cn(-c4ccc(F)cn4)nc3C2)c1]

¹H NMR (400 MHz, CDCl₃) δ=8.64-8.57 (m, 1H), 8.53 (d, J=2.7 Hz, 1H), 8.21 (dd, J=2.7, 5.9 Hz, 1H), 8.17-8.11 (m, 3H), 7.92-7.76 (m, 1H), 7.74-7.65 (m, 2H), 7.56-7.46 (m, 1H), 4.69 (d, J=11.7 Hz, 2H), 4.13 (d, J=4.3 Hz, 2H), 3.14 (s, 3H); [M+H]=482.5.

Example 549

5-Fluoro-2-{5-[5-methanesulfonyl-2-(5-methylpyridin-3-yl)benzoyl]-2H 4H 5H 6H-pyrrolo[3,4-c]pyrazol-2-yl}pyridine

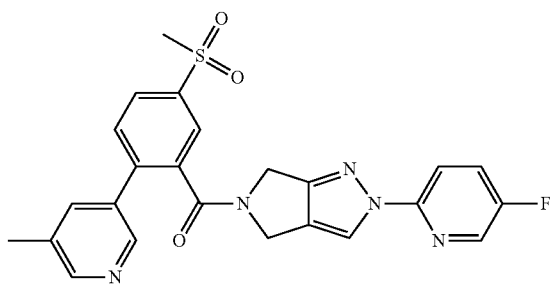 [SMILES: Cc1cncc(-c2ccc(S(C)(=O)=O)cc2C(=O)N2Cc3cn(-c4ccc(F)cn4)nc3C2)c1]

¹H NMR (400 MHz, CDCl₃) δ=8.61 (br s, 1H), 8.48 (br s, 1H), 8.20 (dd, J=3.1, 5.1 Hz, 1H), 8.11 (d, J=1.2 Hz, 2H), 7.90-7.65(m, 3H), 7.57-7.42 (m, 2H), 4.66 (d, J=11.0 Hz, 2H), 4.09 (br s, 2H), 3.13 (s, 3H), 2.39 (s, 3H); [M+H]=478.5.

Example 550

4-(2-Fluorophenyl)-3-[2-(5-fluoropyridin-3-yl)-2H 4H 5H 6H-pyrrolo[3,4-c]pyrazole-5-carbonyl]benzonitrile

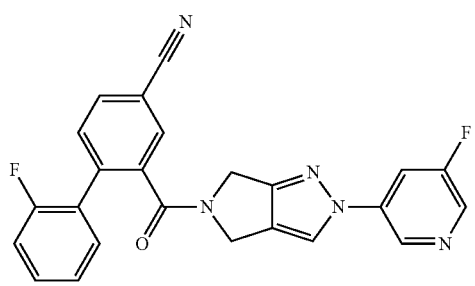 [SMILES: N#Cc1ccc(-c2ccccc2F)c(C(=O)N2Cc3cn(-c4cncc(F)c4)nc3C2)c1]

¹H NMR (400 MHz, DMSO-d₆) δ=8.97 (d, J=5.5 Hz, 1H), 8.58-8.34 (m, 2H), 8.18 (d, J=4.3 Hz, 2H), 8.05 (d, J=7.8 Hz, 1H), 7.70 (br s, 1H),7.50-7.35 (m, 2H), 7.33-7.17 (m, 2H), 4.61-4.31 (m, 4H); [M+H]=428.4.

Example 551

4-(3-Fluorophenyl)-3-[2-(5-fluoropyridin-3-yl)-2H 4H 5H 6H-pyrrolo[3,4-c]pyrazole-5-carbonyl]benzonitrile

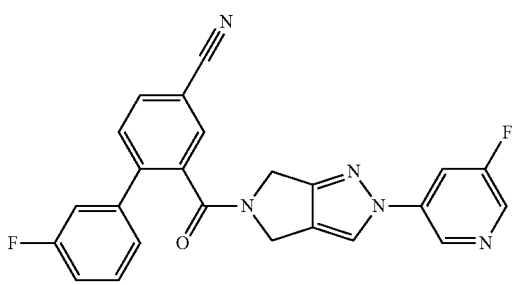 [SMILES: N#Cc1ccc(-c2cccc(F)c2)c(C(=O)N2Cc3cn(-c4cncc(F)c4)nc3C2)c1]

¹H NMR (400 MHz, DMSO-d₆) δ=8.98-8.85 (m, 1H), 8.50 (d, J=2.3 Hz, 1H), 8.47-8.29 (m, 1H), 8.14 (tdd, J=2.4, 10.4, 16.8 Hz, 1H), 8.08-7.99 (m, 2H), 7.80-7.68 (m, 1H), 7.54-7.42 (m, 1H), 7.39-7.28(m, 2H), 7.28-7.19(m, 1H), 4.52 (d, J=11.7 Hz, 2H), 4.23 (d, J=13.7 Hz, 2H); [M+H]=428.4.

Example 552

4-(5-Fluoropyridin-3-yl)-3-[2-(5-fluoropyridin-3-yl)-2H 4H 5H 6H-pyrrolo[3,4-c]pyrazole-5-carbonyl]benzonitrile

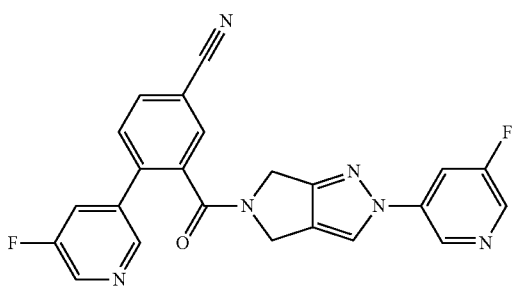 [SMILES: N#Cc1ccc(-c2cncc(F)c2)c(C(=O)N2Cc3cn(-c4cncc(F)c4)nc3C2)c1]

¹H NMR (400 MHz, DMSO-d₆) δ=8.95 (dd, J=1.2, 11.3 Hz, 1H), 8.61 (t, J=2.3 Hz, 1H), 8.55-8.49 (m, 2H), 8.48-8.34 (m, 1H), 8.23-8.12 (m,2H), 8.10 (td, J=1.6, 8.2 Hz, 1H), 7.91-7.84 (m, 1H), 7.82 (dd, J=3.3, 8.0 Hz, 1H), 4.54 (d, J=11.3 Hz, 2H), 4.45-4.33 (m, 2H); [M+H]=429.4.

Example 553

3-[2-(5 4H 5H 6H-pyrrolo[3,4-c]pyrazole-5-carbonyl]-4-(pyridin-3-yl)benzonitrile

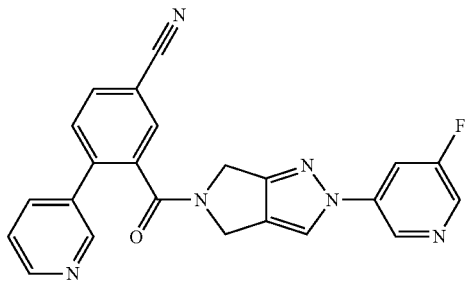 [SMILES: N#Cc1ccc(-c2cccnc2)c(C(=O)N2Cc3cn(-c4cncc(F)c4)nc3C2)c1]

¹H NMR (400 MHz, DMSO-d₆) δ=8.94 (d, J=11.3 Hz, 1H), 8.67 (br s, 1H), 8.70-8.56 (m, 1H), 8.58 (br s, 1H), 8.50 (d, J=2.3 Hz, 1H), 8.46-8.30 (m, 1H), 8.20-8.13 (m, 1H), 8.13-8.04 (m, 2H), 7.89 (t, J=7.4 Hz, 1H), 7.79 (dd, J=5.1, 7.8 Hz, 1H), 7.54-7.42 (m, 2H), 4.52 (d, J=11.7 Hz, 2H), 4.30 (d, J=20.0 Hz, 2H); [M+H]=411.4.

Example 554

4-(2-Fluorophenyl)-3-[2-(2-methylpyridin-4-yl)-2H 4H 5H 6H-pyrrolo[3,4-c]pyrazole-5-carbonyl]benzonitrile

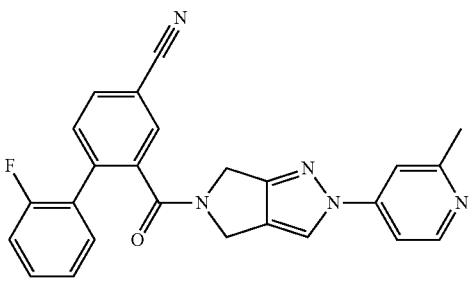 [SMILES: Cc1cc(-n2cc3c(n2)CN(C(=O)c2cc(C#N)ccc2-c2ccccc2F)C3)ccn1]

¹H NMR (400 MHz, DMSO-d₆) δ=8.50 (s, 1H), 8.49-8.41 (m, 1H), 8.17 (dd, J=1.6, 4.7 Hz, 1H), 8.04 (dd, J=1.8, 8.0 Hz, 1H), 7.75 (d, J=14.1 Hz, 1H), 7.72-7.63 (m, 2H), 7.46-7.36 (m, 2H), 7.30-7.22 (m, 2H), 4.50 (d, J=9.8 Hz, 2H), 4.44 (d, J=14.5 Hz, 2H), 2.53-2.50 (m, 3H); [M+H]=424.4.

Example 555

(2-(2-Fluorophenyl)pyrrolo[3,4-c]pyrazol-5(2H,4H,6H)-yl)(5-(methylsulfonyl)-2-(pyridin-3-yl)phenyl)methanone

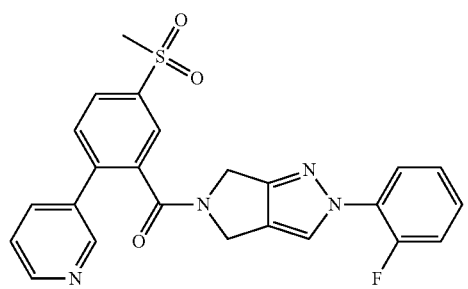 [SMILES: CS(=O)(=O)c1ccc(-c2cccnc2)c(C(=O)N2Cc3cn(-c4ccccc4F)nc3C2)c1]

¹H NMR (400 MHz, CDCl₃) δ=8.81 (br s, 1H), 8.66 (br s, 1H), 8.20-8.08 (m, 2H), 7.98 (t, J=8.6 Hz, 1H), 7.81-7.68 (m, 2H), 7.57 (d, J=2.3 Hz, 1H), 7.46-7.36 (m, 1H), 7.25-7.16 (m, 2H), 4.69 (d, J=14.1 Hz, 2H), 4.10 (s, 2H), 3.14 (s, 1H); [M+H]=463.5.

Example 556

4-(5-Fluoropyridin-3-yl)-3-[2-(2-methylpyridin-4-yl)-2H 4H 5H 6H-pyrrolo[3,4-c]pyrazole-5-carbonyl]benzonitrile

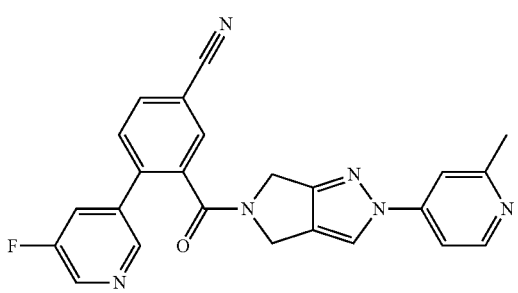 [SMILES: Cc1cc(-n2cc3c(n2)CN(C(=O)c2cc(C#N)ccc2-c2cncc(F)c2)C3)ccn1]

¹H NMR (400 MHz, DMSO-d₆) δ=8.61 (t, J=2.5 Hz, 1H), 8.54-8.50 (m, 1H), 8.49-8.37 (m, 2H), 8.18-8.14 (m, 1H), 8.12-8.07 (m, 1H), 7.91-7.84 (m, 1H), 7.82 (dd, J=2.9, 8.0 Hz, 1H), 7.68 (dd, J=2.2, 16.6 Hz, 1H), 7.58 (ddd, J=1.8, 5.6, 12.6 Hz, 1H), 4.53 (d, J=10.2 Hz, 2H), 4.46-4.32 (m, 2H), 2.49-2.49 (m, 3H); [M+H]=425.4.

Example 557

4-(3-Fluorophenyl)-3-[2-(oxan-4-yl)-2H 4H 5H 6H-pyrrolo[3,4-c]pyrazole-5-carbonyl]benzonitrile

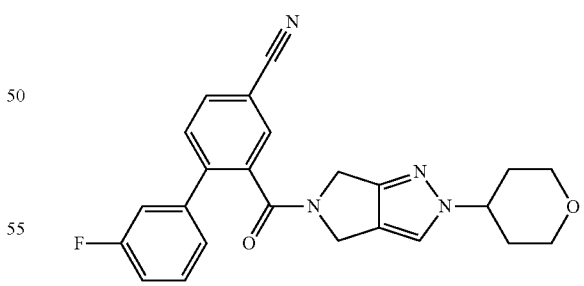

¹H NMR (400 MHz, CD₃OD) δ=7.99-7.89 (m, 2H), 7.79-7.69 (m, 1H), 7.57-7.40 (m, 2H), 7.40-7.25 (m, 2H), 7.20-7.07 (m, 1H), 4.50 (br s, 2H), 4.32 (dtt, J=2.3, 5.3, 10.6 Hz, 1H), 4.19-3.91 (m, 4H), 3.51 (II, J=2.8, 11.5 Hz, 2H), 2.06-1.91 (m, 4H); [M+H]=417.27.

Example 558

4-(3-Methylphenyl)-3-[2-(oxan-4-yl)-2H 4H 5H 6H-pyrrolo[3,4-c]pyrazole-5-carbonyl]benzonitrile

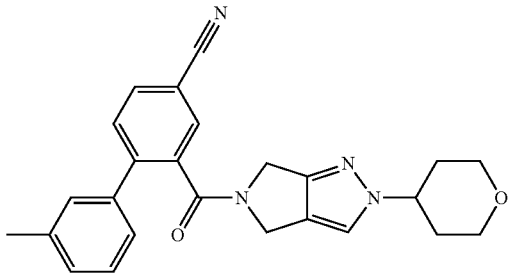 [SMILES: Cc1cccc(-c2ccc(C#N)cc2C(=O)N2Cc3cn(C4CCOCC4)nc3C2)c1]

$^1$H NMR (400 MHz, CD$_3$OD) δ=7.95-7.89 (m, 1H), 7.88 (d, J=1.6 Hz, 1H), 7.74-7.69 (m, 1H), 7.46-7.35 (m, 2H), 7.32 (dt, J=1.4, 3.0 Hz, 2H), 7.26-7.19 (m, 1H), 4.67-4.39 (m, 2H), 4.35-4.25 (m, 1H), 4.09-3.84 (m, 4H), 3.51 (tt, J=2.9, 11.5 Hz, 2H), 2.35 (s, 3H), 2.07-1.89 (m, 4H); [M+H]=413.16.

Example 559

2-(2-Fluorophenyl)-5-[2-(2-fluorophenyl)-5-methanesulfonylbenzoyl]-2H 4H 5H 6H-pyrrolo[3,4-c]pyrazole

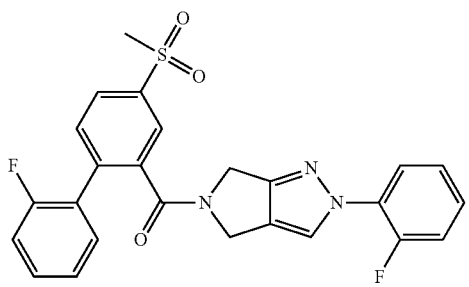 [SMILES: CS(=O)(=O)c1ccc(-c2ccccc2F)c(C(=O)N2Cc3cn(-c4ccccc4F)nc3C2)c1]

$^1$H NMR (400 MHz, DMSO-d$_6$) δ=8.17 (d, J=2.0 Hz, 1H), 8.09 (td, J=1.5, 8.3 Hz, 1H), 8.02-7.92 (m, 1H), 7.79-7.75 (m, 1H), 7.74-7.67 (m, 1H), 7.49-7.36 (m, 5H), 7.35-7.26 (m, 3H), 4.51 (d, J=10.2 Hz, 2H), 4.44-4.33 (m, 2H), 3.35 (d, J=3.1 Hz, 3H); [M+H]=480.5.

Example 560

2-(2-Fluorophenyl)-5-[2-(3-fluorophenyl)-5-methanesulfonylbenzoyl]-2H 4H 5H 6H-pyrrolo[3,4-c]pyrazole

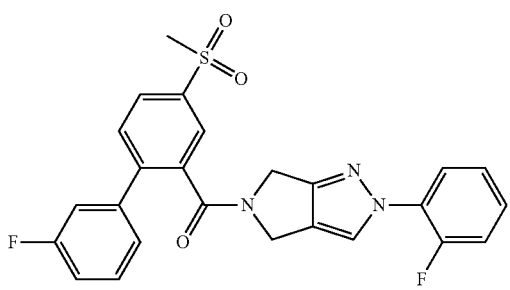 [SMILES: CS(=O)(=O)c1ccc(-c2cccc(F)c2)c(C(=O)N2Cc3cn(-c4ccccc4F)nc3C2)c1]

$^1$H NMR (400 MHz, DMSO-d$_6$) δ=8.11-7.99 (m, 2H), 7.87-7.81 (m, 1H), 7.69 (dtd, J=1.8, 7.9, 19.5 Hz, 1H), 7.55-7.20 (m, 8H), 4.53 (d, J=11.7 Hz, 2H), 4.27-4.09 (m, 2H), 3.33 (d, J=1.2 Hz, 3H); [M+H]=480.5.

Example 561

3-Fluoro-5-{2-[2-(2-fluorophenyl)-2H 4H 5H 6H-pyrrolo[3,4-c]pyrazole-5-carbonyl]-4-methanesulfonylphenyl}pyridine

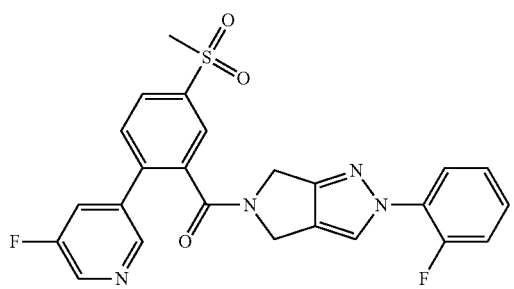 [SMILES: CS(=O)(=O)c1ccc(-c2cncc(F)c2)c(C(=O)N2Cc3cn(-c4ccccc4F)nc3C2)c1]

$^1$H NMR (400 MHz, DMSO-d$_6$) δ=8.63 (t, J=2.5 Hz, 1H), 8.56 (d, J=1.6 Hz, 1H), 8.17 (d, J=2.0 Hz, 1H), 8.13 (td, J=1.9, 7.9 Hz, 1H), 8.03-7.86 (m, 3H), 7.75-7.65 (m, 1H), 7.48-7.29 (m, 3H), 4.55 (d, J=12.1 Hz, 2H), 4.41-4.25 (m, 2H), 3.35 (d, J=2.7 Hz, 3H); [M+H]=481.5.

Example 562

4-(3 5-Difluorophenyl)-3-[2-(2-methylpyridin-4-yl)-2H 4H 5H 6H-pyrrolo[3,4-c]pyrazole-5-carbonyl]benzonitrile

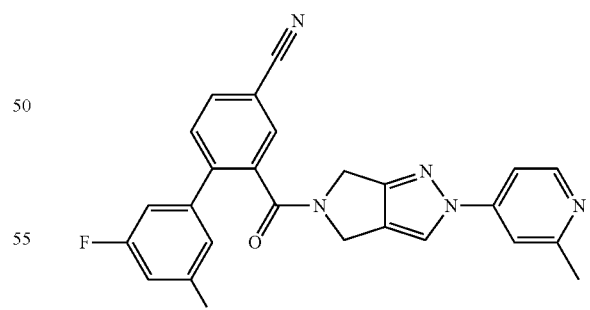

$^1$H NMR (400 MHz, DMSO-d$_6$) δ=8.47 (d, J=10.2 Hz, 1H), 8.44-8.36 (m, 1H), 8.09 (dd, J=1.6, 3.5 Hz, 1H), 8.08-8.04 (m, 1H), 7.77 (dd, J=3.7, 8.0 Hz, 1H), 7.67 (dd, J=2.3, 16.0 Hz, 1H), 7.58 (ddd, J=2.3, 5.6, 12.4 Hz, 1H), 7.30 (ddd, J=2.5, 6.8, 11.7 Hz, 1H), 7.24-7.17 (m, 2H), 4.53 (d, J=10.6 Hz, 2H), 4.40-4.24 (m, 2H), 3.31-3.31 (m, 3H); [M+H]=442.4.

Example 563

3-{5-[2-(3 5-Difluorophenyl)-5-methanesulfonyl-benzoyl]-2H 4H 5H 6H-pyrrolo[3,4-c]pyrazol-2-yl}-5-fluoropyridine

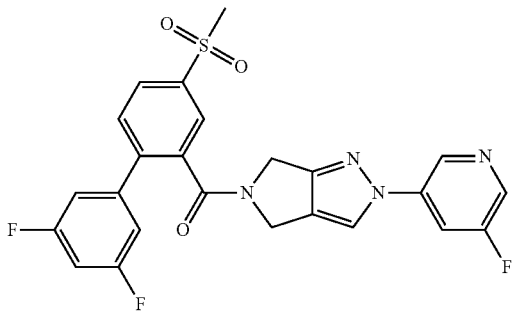 [SMILES: CS(=O)(=O)c1ccc(-c2cc(F)cc(F)c2)c(C(=O)N2Cc3cn(-c4cncc(F)c4)nc3C2)c1]

$^1$H NMR (400 MHz, DMSO-d$_6$) δ=8.94 (d, J=9.8 Hz, 1H), 8.51 (d, J=2.3 Hz, 1H), 8.47-8.33 (m, 1H), 8.20-8.13 (m, 1H), 8.11 (qt, J=2.2, 4.3 Hz, 2H), 7.87-7.82 (m, 1H), 7.36-7.28 (m, 1H), 7.25 (t, J=6.5 Hz, 2H), 4.56 (d, J=10.6 Hz, 2H), 4.33-4.19 (m, 2H), 3.33 (s, 3H); [M+H]=499.6.

Example 564

4-(3-Methylphenyl)-3-[2-(2-methylpyridin-4-yl)-2H 4H 5H 6H-pyrrolo[3,4-c]pyrazole-5-carbonyl]benzonitrile

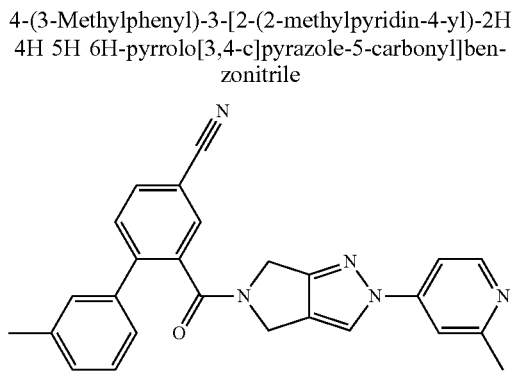

$^1$H NMR (400 MHz, DMSO-d$_6$) δ=8.46-8.30 (m, 2H), 8.03-7.97 (m, 2H), 7.74-7.69 (m, 1H), 7.64 (dd, J=1.8, 14.7 Hz, 1H), 7.55 (ddd, J=2.2, 5.7, 11.3 Hz, 1H), 7.34-7.25 (m, 3H), 7.19 (d, J=7.8 Hz, 1H), 4.50 (br s, 2H), 4.12 (br s, 2H), 3.31-3.31 (m, 3H), 2.29 (s, 3H); [M+H]=420.7.

Example 565

3-[2-(2-Methylpyridin-4-yl)-2H 4H 5H 6H-pyrrolo[3,4-c]pyrazole-5-carbonyl]-4-[3-(trifluoromethyl)phenyl]benzonitrile

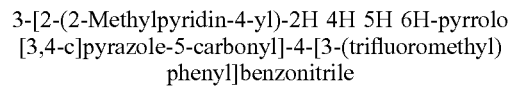

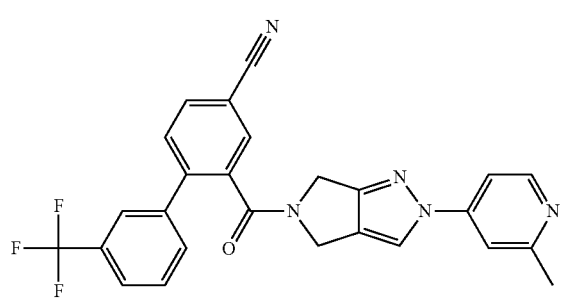 [SMILES: Cc1cc(-n2cc3c(n2)CN(C(=O)c2cc(C#N)ccc2-c2cccc(C(F)(F)F)c2)C3)ccn1]

$^1$H NMR (400 MHz, DMSO-d$_6$) δ=8.48-8.34 (m, 2H), 8.13-8.04 (m, 2H), 7.84-7.73 (m, 4H), 7.71-7.62 (m, 2H), 7.56 (dd, J=6.7, 13.3 Hz, 1H), 4.48 (d, J=9.4 Hz, 2H), 4.27 (d, J=13.3 Hz, 2H), 3.31-3.31 (m, 3H); [M+H]=474.6.

Example 566

5-Fluoro-2-[5-(5-methanesulfonyl-2-phenylbenzoyl)-2H 4H 5H 6H-pyrrolo[3,4-c]pyrazol-2-yl]pyridine

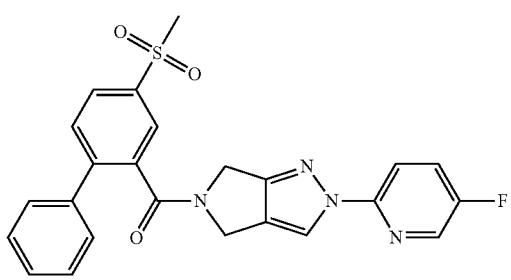 [SMILES: CS(=O)(=O)c1ccc(-c2ccccc2)c(C(=O)N2Cc3cn(-c4ccc(F)cn4)nc3C2)c1]

$^1$H NMR (400 MHz, CDCl$_3$) δ=8.23-8.04 (m, 3H), 7.88-7.73 (m, 1H), 7.73-7.68 (m, 1H), 7.61-7.55 (m, 2H), 7.54-7.34 (m, 4H), 4.65 (br s, 2H), 3.99 (br s, 2H), 3.13 (s, 3H); [M+H]=463.0.

Example 567

4-{5-[5-(Ethanesulfonyl)-2-phenylbenzoyl]-2H 4H 5H 6H-pyrrolo[3,4-c]pyrazol-2-yl}-2-methylpyridine

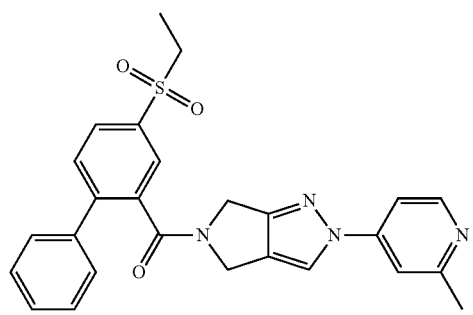 [SMILES: CCS(=O)(=O)c1ccc(-c2ccccc2)c(C(=O)N2Cc3cn(-c4ccnc(C)c4)nc3C2)c1]

$^1$H NMR (400 MHz, CDCl$_3$) δ=8.49 (br s, 1H), 8.08-8.00 (m, 2H), 7.76-7.68 (m, 2H), 7.58 (br s, 2H), 7.47-7.31 (m, 5H), 4.66 (br s, 2H), 4.00 (br s, 2H), 3.25-3.13 (m, 2H), 2.62 (br s, 3H), 1.40-1.31 (m, 3H); [M+H]=473.6.

Example 568

4-{5-[5-(Ethanesulfonyl)-2-(3-fluorophenyl)benzoyl]-2H 4H 5H 6H-pyrrolo[3,4-c]pyrazol-2-yl}-2-methylpyridine

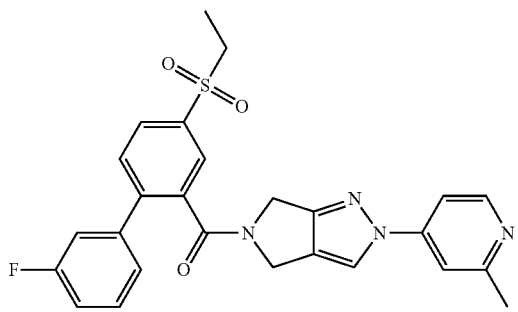 [SMILES: CCS(=O)(=O)c1ccc(-c2cccc(F)c2)c(C(=O)N2Cc3cn(-c4ccnc(C)c4)nc3C2)c1]

¹H NMR (400 MHz, CDCl₃) δ=8.51 (dd, J=2.9, 5.7 Hz, 1H), 8.08-8.02 (m, 2H), 7.80-7.62 (m, 2H), 7.49 (d, J=18.8 Hz, 1H), 7.46-7.27 (m, 4H), 7.10 (t, J=7.8 Hz, 1H), 4.67 (d, J=13.3 Hz, 2H), 4.05 (br s, 2H), 3.20 (q, J=7.2 Hz, 2H), 2.67 (d, J=3.5 Hz, 3H), 1.36 (dt, J=1.2, 7.4 Hz, 3H); [M+H]=491.6.

Example 569

4-{5-[2-(3 5-Difluorophenyl)-5-(ethanesulfonyl)benzoyl]-2H 4H 5H 6H-pyrrolo[3,4-c]pyrazol-2-yl}-2-methylpyridine

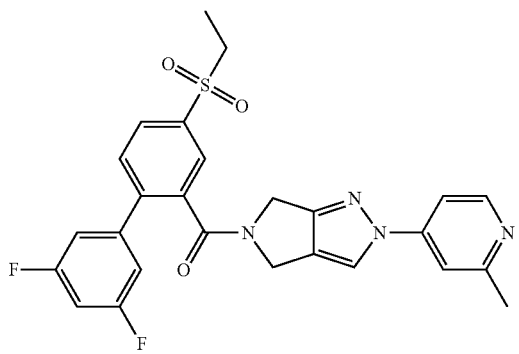 [SMILES: CCS(=O)(=O)c1ccc(-c2cc(F)cc(F)c2)c(C(=O)N2Cc3cn(-c4ccnc(C)c4)nc3C2)c1]

¹H NMR (400 MHz, DMSO-d₆) δ=8.58-8.41 (m, 2H), 8.09-8.04 (m, 2H), 7.85 (dd, J=5.5, 8.2 Hz, 2H), 7.78 (br s, 1H), 7.36-7.19 (m, 3H), 4.56 (d, J=11.7 Hz, 2H), 4.32-4.21 (m, 2H), 3.46-3.41 (m, 2H), 2.55 (d, J=2.7 Hz, 3H), 1.15 (t, J=6.8 Hz, 3H); [M+H]=509.5.

Example 570

3-{5[5-(Ethanesulfonyl)-2-phenylbenzoyl]-2H 4H 5H 6H-pyrrolo[3,4-c]pyrazol-2-yl}-5-fluoropyridine

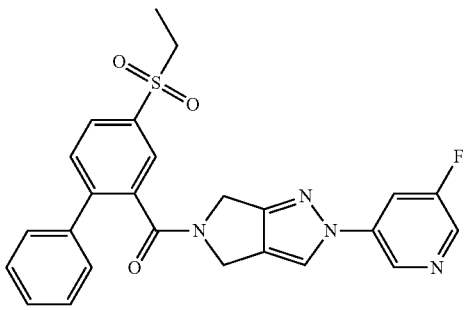 [SMILES: CCS(=O)(=O)c1ccc(-c2ccccc2)c(C(=O)N2Cc3cn(-c4cncc(F)c4)nc3C2)c1]

¹H NMR (400 MHz, DMSO-d₆) δ=8.91 (d, J=7.8 Hz, 1H), 8.49 (s, 1H), 8.43-8.27 (m, 1H), 8.17-8.09 (m, 1H), 8.07-8.02 (m, 1H), 8.00 (s, 1H), 7.81 (dd, J=4.1, 8.0 Hz, 1H), 7.57-7.52 (m, 2H), 7.49-7.37 (m, 3H), 4.52 (br s, 2H), 4.09 (br s, 2H), 3.41 (q, J=7.2 Hz, 2H), 1.16 (t, J=7.4 Hz, 3H); [M+H]=477.5.

Example 571

3-{5-[5-(Ethanesulfonyl)-2-(3-fluorophenyl)benzoyl]-2H 4H 5H 6H-pyrrolo[3,4-c]pyrazol-2-yl}-5-fluoropyridine

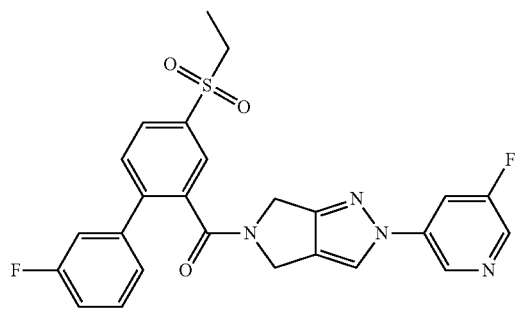 [SMILES: CCS(=O)(=O)c1ccc(-c2cccc(F)c2)c(C(=O)N2Cc3cn(-c4cncc(F)c4)nc3C2)c1]

¹H NMR (400 MHz, DMSO-d₆) δ=8.93 (d, J=8.2 Hz, 1H), 8.50 (d, J=2.0 Hz, 1H), 8.45-8.30 (m, 1H), 8.14 (tdd, J=2.2, 10.5, 12.9 Hz, 1H), 8.07-8.02 (m, 2H), 7.84 (dd, J=5.1, 7.8 Hz, 1H), 7.53-7.45 (m, 1H), 7.41-7.33 (m, 2H), 7.28-7.21 (m, 1H), 4.54 (d, J=11.0 Hz, 2H), 4.18 (d, J=19.2 Hz, 2H), 3.47-3.37 (m, 2H), 1.20-1.10 (m, 3H); [M+H]=495.6.

Example 572

3-{5-[2-(3 5-Difluorophenyl)-5-(ethanesulfonyl)benzoyl]-2H 4H 5H 6H-pyrrolo[3,4-c]pyrazol-2-yl}-5-fluoropyridine

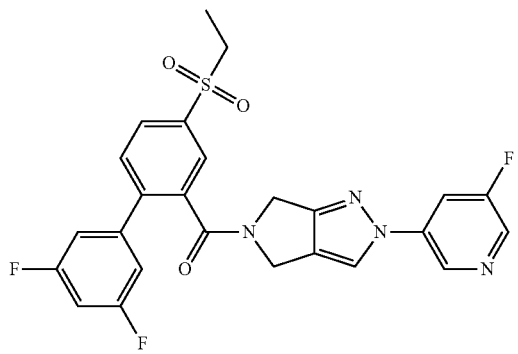 [SMILES: CCS(=O)(=O)c1ccc(-c2cc(F)cc(F)c2)c(C(=O)N2Cc3cn(-c4cncc(F)c4)nc3C2)c1]

$^{1}$H NMR (400 MHz, DMSO-d$_{6}$) δ=8.94 (d, J=8.6 Hz, 1H), 8.51 (d, J=2.3 Hz, 1H), 8.48-8.33 (m, 1H), 8.15 (tdd, J=2.3, 10.5, 13.0 Hz, 1H), 8.09-8.03 (m, 2H), 7.87-7.82 (m, 1H), 7.37-7.29 (m, 1H), 7.28-7.22 (m, 2H), 4.55 (d, J=10.6 Hz, 2H), 4.33-4.19 (m, 2H), 3.48-3.39 (m, 2H), 1.15 (t, J=7.4 Hz, 3H); [M+H]=513.5.

Example 573

5-{5-Methanesulfonyl-2-[(1 1 1-trifluoropropan-2-yl)oxy]benzoyl}-3-phenyl-2H 4H 5H 6H 7H-pyrazolo[4,3-c]pyridine

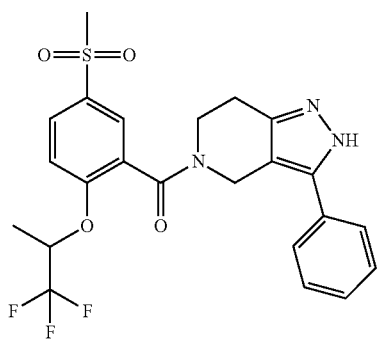 [SMILES: CC(Oc1ccc(S(C)(=O)=O)cc1C(=O)N1CCc2n[nH]c(-c3ccccc3)c2C1)C(F)(F)F]

The title compound was prepared in a manner analogous to Example 1, with the appropriate starting material and reagent substitutions. $^{1}$H NMR (400 MHz, DMSO-d$_{6}$) δ=12.62 (br s, 1H), 8.37 (s, 1H), 8.0 (br m, 1H), 7.79 (m, 2H), 7.51-7.41 (m, 4H), 4.68 (m, 1H), 4.46 (br s, 2H), 3.84 (t, J=7.0 Hz, 2H), 3.32 (s, 3H), 2.96 (t, J=7.0 Hz, 2H), 1.40 (d, J=6.9 Hz, 3H); [M+H]=494.5.

Example 574

2-(4-Fluorophenyl)-5-[5-methanesulfonyl-2-(2-methylpropoxy)benzoyl]-2H 4H 5H 6H-pyrrolo[3,4-c]pyrazole

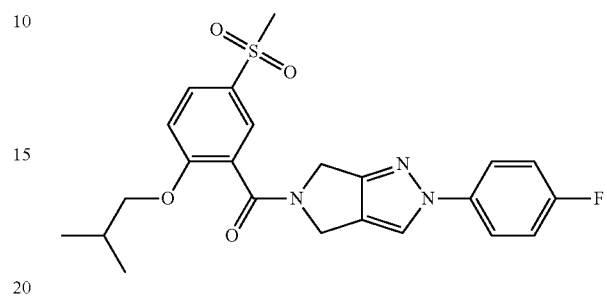

The title compound was prepared in a manner analogous to Intermediate 32, from (2-fluoro-5-(methylsulfonyl)phenyl)(2-(4-fluorophenyl)pyrrolo[3,4-c]pyrazol-5(2H,4H, 6H)-yl)methanone and 2-methylpropan-1-ol. Rotamers observed: $^{1}$H NMR (400 MHz, DMSO-d$_{6}$) δ=8.35-8.18 (m, 2H), 7.95 (dd, J=2.3, 9.0 Hz, 1H), 7.85-7.76 (m, 3H), 7.39-7.28 (m, 3H), 4.66 (d, J=6.3 Hz, 2H), 4.36 (d, J=17.6 Hz, 2H), 3.94 (dd, J=3.9, 6.3 Hz, 2H), 3.20 (s, 3H), 1.96 (tt, J=6.5, 13.1 Hz, 1H), 0.86 (dd, J=1.6, 6.7 Hz, 5H); [M+H]=458.38.

Examples 575-577 were prepared in a manner analogous to Example 4, with the appropriate starting material and reagent substitutions.

Example 575

3-[1-(2 4-Difluorophenyl)-1H 4H 5H 6H 7H-pyrazolo[4,3-c]pyridine-5-carbonyl]-2-methoxy-4-[(1 1 1-trifluoropropan-2-yl)oxy]benzonitrile

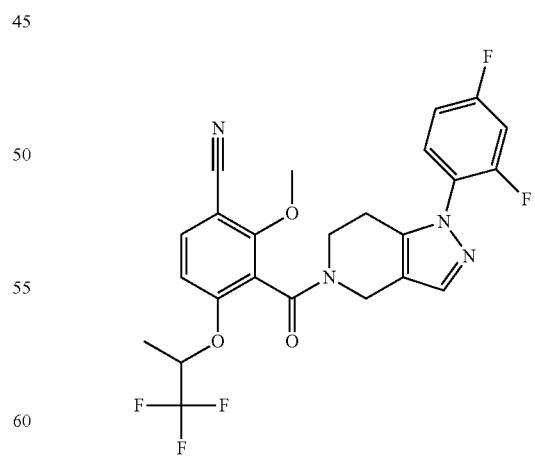

$^{1}$H NMR (400 MHz), CDCl$_{3}$) δ=7.69-7.36 (m, 3H), 7.10-6.92 (m, 2H), 6.84-6.56 (m, 1H), 5.04-4.62 (m, 2H), 4.36-4.24 (m, 1H), 4.15-4.00 (m, 3H), 3.51-3.41 (m, 1H), 2.78-2.58 (m, 3H), 1.53-1.42 (m, 3 H); [M+H]=507.24.

Example 576

3-[2-(4-Fluorophenyl)-3-(trifluoromethyl)-2H 4H 5H 6H 7H-pyrazolo[4,3-c]pyridine-5-carbonyl]-2-methoxy-4-[(1 1 1-trifluoropropan-2-yl)oxy]benzonitrile

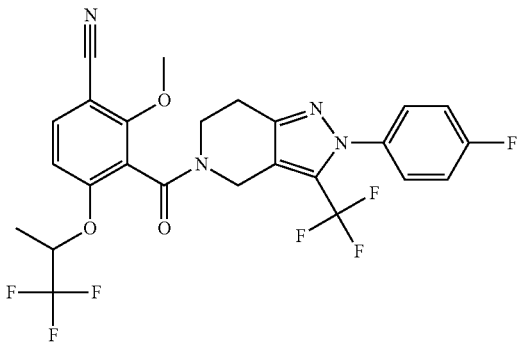 [SMILES: COc1c(C#N)ccc(OC(C)C(F)(F)F)c1C(=O)N1CCc2nn(-c3ccc(F)cc3)c(C(F)(F)F)c2C1]

$^1$H NMR (400 MHz), CDCl$_3$) δ=7.62 (d, J=8.6, 1H), 7.51-7.33 (m, 2H), 7.23-7.08 (m, 2H), 6.89-6.62 (m, 1H), 5.29-4.60 (m, 2H), 4.54-4.31 (m, 1H), 4.23-3.96 (m, 3H), 3.80-3.39 (m, 2H), 3.06-2.72 (m, 2H), 1.57-1.38 (m, 3 H); [M+H]=557.27.

Example 577

3-[1-(4-Fluorophenyl)-3-(trifluoromethyl)-1H 4H 5H 6H 7H-pyrazolo[4,3-c]pyridine-5-carbonyl]-2-methoxy-4-[(1 1 1-trifluoropropan-2-yl)oxy]benzonitrile

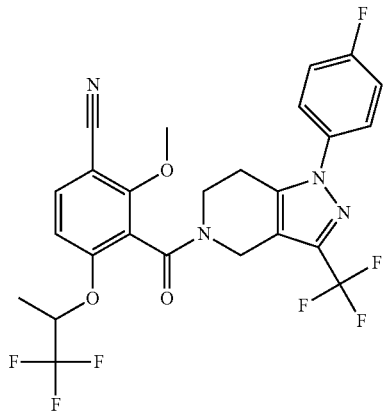 [SMILES: COc1c(C#N)ccc(OC(C)C(F)(F)F)c1C(=O)N1CCc2c(c(C(F)(F)F)nn2-c2ccc(F)cc2)C1]

$^1$H NMR (400 MHz), CDCl$_3$) δ=7.63 (dd, J=2.9, 8.8 Hz, 1H), 7.52-7.36 (m, 2H), 7.25-7.04 (m, 2H), 6.86-6.58 (m, 1H), 5.32-4.59 (m, 2H), 4.58-4.23 (m, 1H), 4.22-3.98 (m, 3H), 3.78-3.25 (m, 2H), 3.18-2.64 (m, 2H), 1.56-1.39 (m, 2H), 1.18 (d, J=6.3 Hz, 1H); [M+H]=557.30.

BIOLOGICAL EXAMPLES

Glycine Transporter 1 (GlyT1) Uptake Assay

A scintillation proximity assay (SPA) was used to measure the uptake of [$^{14}$C]-glycine in HEK293 cells stably expressing human GlyT1c and in cultured primary rat cortical neurons (Williams J B., et al., 2003, *Anal. Biochem.*, 321(1), 31-37).

Human GlyT1c Assay

HEK293 cells stably expressing hGlyT1c were plated onto 96-well Cytostar plates at a density of 4.5×10$^4$ cells per well in 100 μL of growth media (DMEM containing 10% fetal bovine serum) and incubated overnight in a 37° C., 10% CO$_2$ incubator. The following day, stock compounds in 10 mM DMSO were serially diluted in DMSO and 2× compound solutions were prepared by diluting compound again (1:100) in HBSS. Growth media was removed from the plate and 30 μL of 2× compound solution was added Immediately after, 30 μL of 15 μM [$^{14}$C] glycine in HBSS was added and plates were sealed and allowed to incubate at room temperature for 2 hours. Plates were then read on a MicroBeta plate counter (Perkin Elmer). Dose-response data for tested compounds were analyzed and curves were fit using a four parameter logistic fit to determine IC$_{50}$ values.

Rat Primary Cortical Neuron Assay

Primary rat cortical neurons were harvested from rat E18 pups and plated onto poly-D-lysine-coated 96-well Cytostar plates at a density of 3.5×10$^4$ cells per well in 100 μL of astrocyte media (MEM media with 20 mM glucose, 1× penicillin/streptomycin, and 10% fetal bovine serum) and incubated at 37° C. in a 5% CO$_2$ environment. Twenty-four hours later, media was replaced with 200 μL of neuronal media (BME media with 20 mM glucose, 1 mM sodium pyruvate, 2 mM GlutaMAX, 1× penicillin/streptomycin, 1% horse serum, and B27 supplement) and the cells were cultured for an additional 5 days in a 37° C., 5% CO$_2$ incubator. The following day, stock compounds in 10 mM DMSO were serially diluted in DMSO and 2× compound solutions were prepared by diluting compound again (1:100) in HBSS. Neuronal media was removed from the plate and 30 μL of 2× compound solution was added Immediately after, 30 μL of 25 μM [$^{14}$C] glycine in HBSS supplemented with 5 mM L-Alanine and 5 mM HEPES was added and plates were sealed and allowed to incubate at room temperature for 2 hours. Plates were then read on a MicroBeta plate counter (Perkin Elmer). Dose-response data for tested compounds were analyzed and curves were fit using a four parameter logistic fit to determine IC$_{50}$ values.

| GlyT1 (pIC$_{50}$) | Example Number |
|---|---|
| >7 | 1, 2, 3, 8, 9, 11, 16, 17, 18, 19, 27, 29, 30, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 75, 76, 77, 78, 79, 80, 82, 83, 84, 85, 100, 101, 102, 103, 104, 105, 106, 107, 108, 109, 110, 111, 112, 113, 114, 115, 116, 117, 119, 120, 121, 122, 123, 124, 125, 126, 127, 128, 129, 130, 131, 132, 133, 134, 135, 136, 137, 138, 139, 140, 141, 142, 143, 146, 147, 148, 149, 150, 151, 152, 153, 154, 156, 170, 176, 185, 198, 209, 210, 213, 215, 218, 219, 220, 226, 227, 231, 234, 235, 236, 242, 243, 244, 245, 246, 247, 248, 249, 250, 252, 253, 254, 261, 262, 263, 264, 266, 267, 268, 269, 270, 272, 273, 274, 275, 276, 277, 278, 279, 283, 284, 287, 288, 289, 290, 291, 293, 295, 296, 297, 298, 300, 301, 302, 303, 304, 305, 308, 309, 310, 311, 312, 313, 314, 316, 317, 318, 319, 320, 321, 322, 323, 324, 325, 326, 327, 328, 329, 331, 332, 334, 338, 341, 343, 350, 353, 355, 356, 357, 358, 359, 360, 362, 363, 364, 367, 368, 369, 374, 375, 376, 377, 380, 381, 397, 398, 399, 400, 403, 404, 405, 406, 407, 409, 410, 412, 413, 415, 417, 423, 426, 427, 428, 429, 430, 431, 432, 435, 437, 440, 443, 446, 447, 448, 449, 453, 455, 459, 460, 461, 463, 464, 469, 470, 471, 478, 479, 484, 485, 486, 490, 491, 494, 495, 510, 511, 512, 513, 514, 515, 516, 517, 518, 519, 520, 522, 523, 524, 525, 526, 533, 535, 540, 541, 542, 546, 549, 556, 559, 560, 561, 563, 566, 567, 568, 569, 570, 571, 574, 575, 576 |

-continued

| GlyT1 (pIC$_{50}$) | Example Number |
|---|---|
| 6-7 | 4, 10, 12, 14, 15, 20, 21, 22, 23, 24, 25, 26, 28, 31, 33, 74, 81, 86, 87, 88, 89, 90, 91, 92, 98, 99, 118, 155, 162, 163, 164, 166, 167, 169, 171, 173, 175, 177, 179, 187, 188, 189, 190, 193, 194, 195, 196, 201, 202, 204, 205, 206, 207, 211, 212, 214, 216, 217, 221, 222, 225, 228, 229, 230, 232, 233, 237, 238, 240, 241, 251, 256, 257, 258, 259, 260, 265, 271, 280, 281, 282, 285, 286, 292, 294, 299, 306, 307, 315, 330, 333, 335, 336, 337, 339, 340, 342, 344, 345, 346, 347, 348, 349, 351, 352, 361, 370, 371, 372, 373, 378, 382, 386, 389, 390, 391, 393, 395, 396, 401, 402, 408, 411, 414, 416, 418, 419, 420, 421, 422, 425, 433, 434, 436, 438, 439, 441, 442, 444, 445, 450, 451, 456, 457, 462, 465, 466, 467, 468, 472, 480, 482, 488, 489, 492, 496, 497, 501, 502, 503, 507, 508, 509, 521, 528, 529, 530, 531, 532, 534, 536, 537, 539, 543, 544, 545, 547, 552, 553, 555, 557, 562, 572, 577 |
| 5-6 | 7, 13, 93, 94, 95, 96, 97, 145, 159, 160, 161, 165, 168, 172, 174, 180, 181, 182, 184, 186, 191, 192, 199, 200, 203, 208, 223, 224, 239, 255, 354, 365, 366, 383, 384, 385, 388, 394, 424, 452, 454, 474, 476, 483, 487, 493, 498, 500, 504, 505, 506, 527, 538, 548, 550, 551, 554, 564, 565, 573 |
| <5 | 5, 6, 144, 157, 158, 178, 183, 197, 379, 387, 392, 458, 473, 475, 477, 481, 499, 558 |

The present disclosure will be further illustrated by the following biological examples. These examples are understood to be exemplary only and are not intended to limit the scope of the invention disclosed herein.

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present invention, as will be understood by those of ordinary skill in the art. These assays can be directed towards the evaluation of, without limitation, hippocampus-, cortex-, and/or amygdala-dependent memory formation or cognitive performance.

Biological Example 1

Effect of GlyT1 Inhibitors on Contextual Memory
Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, Behav. Neurosci. 1984, 98, 269-277; Fanselow, Behav. Neurosci. 1984, 98, 79-95; and Phillips and LeDoux, Behav. Neurosci. 1992, 106, 274-285).

Contextual conditioning has been extensively used to investigate the neural substrates mediating fear-motivated learning (e.g., Phillips and LeDoux, Behav. Neurosci. 1992, 106, 274-285; Kim et al., Behav. Neurosci. 1993, 107, 1093-1098; and Bourtchouladze et al., Learn. Mein. 1998, 5, 365-374). Studies in mice and rats provided evidence for functional interaction between hippocampal and nonhippocampal systems during contextual conditioning training (e.g., Maren et al., Behav. Brain Res. 1997, 88, 261-274; Maren et al., Neurobiol. Learn. Mem. 1997, 67, 142-149; and Frankland et al., Behav. Neurosci. 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning, as well as strain and genetic background differences in mice (e.g., Bourtchouladze et al., Cell 1994, 79, 59-68; Bourtchouladze et al., Learn Mem. 1998, 5, 365-374; Kogan et al., Current Biology 1997, 7, 1-11; Silva et al., Current Biology 1996, 6, 1509-1518; Abel et al., Cell 1997, 88, 615-626; Giese et al., Science 1998, 279, 870-873; Logue et al., Neuroscience 1997, 80, 1075-1086; Chen et al., Behav. Neurosci. 1996,110, 1177-1180; and Nguyen et al., Learn Mem. 2000, 7, 170-179).

Because robust learning can be triggered with a few minutes training session, contextual conditioning has been especially useful to study the biology of temporally distinct processes of short- and long-term memory (e.g., Kim et al., Behav. Neurosci. 1993, 107, 1093-1098; Bourtchouladze et al., Cell 1994, 79, 59-68; Abel et al., Cell 1997, 88, 615-626; Logue et al., Behav. Neurosci. 1997, 111, 104-113; Bourtchouladze et al., Learn. Mem.

1998, 5, 365-374; and Nguyen et al., Learn. Mem. 2000, 7, 170-179). As such, contextual conditioning provides an excellent model to evaluate the effects of novel drug compounds on hippocampal-dependent memory formation.

Procedures

Previous investigations have established that training with 1× or 2× CS-US pairings induces sub-maximal (weak) memory in wild-type mice (e.g., U.S.2009/0053140; Tully et al., Nat. Rev. Drug Discov. 2003, 2, 267-77; and Bourtchouladze et al. Learn. Mem. 1998, 5, 365-374). Such sub-maximal memory is facilitated by augmenting CREB, while inhibition of CREB impairs maximal memory induced with 5× CS-US pairings (Barad et al. Proc Natl Acad Sci. 1998, 95, 15020-15025; Peters et al. Genes Brain Behav. 2009, 8, 320-329). Accordingly, contextual conditioning in this study was performed as described by Barad et al. Proc Natl Acad Sci. 1998, 95, 15020-15025 and Peters et al. Genes Brain Behav. 2009, 8, 320-329. Young-adult (10-12 weeks old) C57BL/6 male mice or Long-Evans male rats were used. Mice and rats were group-housed in standard laboratory and maintained on a 12:12 light-dark cycle. The experiments were always conducted during the light phase of the cycle. With the exception of testing times, the animals had ad libidum access to food and water. To assess contextual memory, a modified contextual fear conditioning task originally developed for evaluation of memory in CREB knock-out mice was used (Bourtchouladze et al., 1994). Training sessions comprised a baseline period in the conditioning chamber (Med Associates, Inc.) followed by presentation of unconditioned stimuli (1-5 footshocks each at 0.2-1.0 mA for 2-sec) spaced at 60-sec intervals. Thirty seconds following the last shock, the animal was returned to its home cage. One to 7 days later, the animals were returned to the chamber and freezing behavior was scored. Freezing (complete immobility except respiration) was scored by Video Freeze software (Med Associates, Inc.) over an 8 minute test period. Treatment with cognition enhancers is expected to significantly increase freezing when compared to controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate post-hoc tests using GraphPad Prism software package.

Results

Exemplary compounds were found to enhance contextual memory in the fear conditioning assay. Significant enhancing effects were seen at several concentrations, including 0.01 mg/kg, 0.03 mg/kg, 0.1 mg/kg, 1 mg/kg, and 3 mg/kg.

Biological Example 2

Effect of GlyT1 Inhibitors on Novel Object Recognition

Rationale

Novel Object Recognition (NOR) is an assay of recognition learning and memory retrieval, it takes advantage of the spontaneous preference of rodents to investigate a novel object compared with a familiar one. It is an ethologically relevant task, which in contrast to fear conditioning, does not result from negative reinforcement (foot shock) (e.g., Ennaceur and Delacour, *Behav. Brain Res.* 1988, 31, 47-59).

The NOR test has been employed extensively to assess the potential cognitive-enhancing properties of novel compounds derived from high-throughput screening. In object recognition, the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., *Proc. Natl. Acad. Sci. USA* 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, *Behav. Brain Res.* 1998, 97, 107-113; Teng et al., *J. Neurosci.* 2000, 20, 3853-3863; Mumby, *Brain Res.* 2001, 127, 159-181; Eichenbaum et al., *Annu. Rev. Neurosci.* 2007, 30, 127-152; Squire et al., *Nat. Rev. Neurosci.* 2007, 8, 872-883; and Vann and Alabasser, *Curr. Opin. Neurobiol.* 2011, 21, 440-445). Hence, object recognition provides an excellent behavioral model to evaluate drug-compound effects on cognitive tasks associated with function of the hippocampus and cortex.

Procedures

Object recognition was tested in young rats using the following protocol. Animals were briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 hrs later.

For novel object recognition, one object was replaced with one that is novel. All combinations and locations of objects were used in a balanced manner to reduce potential biases attributable to preference for particular locations or objects. Training and test trials were recorded and scored by video-tracking software (e.g. Noldus Ethovision). An animal was scored as exploring an object when its head was oriented toward the object within a distance of 1-2 cm (rat) or when its nose was touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., *Proc. Natl. Acad. Sci. USA* 2003, /00, 10518-10522). In each experiment, the experimenter was unaware (blind) to the treatment of the subjects during training and testing. Data were analyzed by one-way ANOVA with appropriate post-hoc tests using GraphPad Prism or JMP software package.

Results

Exemplary compounds of Formula (I) were found to significantly enhance 24 hour memory for NOR in rats. Significant effects were seen at several concentrations, including 0.03 mg/kg, 0.1 mg/kg, 1 mg/kg and 3 mg/kg.

The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound of Formula I:

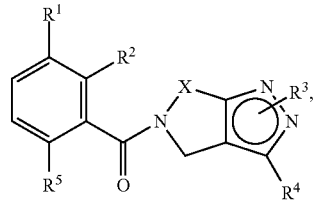

(I), or pharmaceutically acceptable salts thereof, wherein $R^1$ is selected from the group consisting of: —$CO_2H$, —C(O)N($R^a$)$_2$, —$SO_2$($C_{1-4}$alkyl), —$SO_2CH_2$($C_{3-6}$cycloalkyl), —CN,

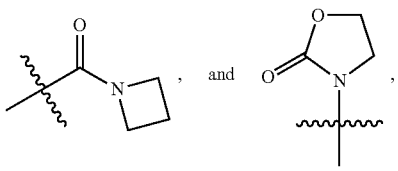

where each $R^a$ is independently —H, or —$C_{1-3}$alkyl;
$R^2$ is selected from the group consisting of: —H, halo, —$C_{1-3}$alkyl, —$C_{1-3}$haloalkyl, —$C_{1-3}$alkoxy, and —CN;
$R^3$ is selected from the group consisting of:
(a) —H, —$C_{1-6}$alkyl, —$C_{1-6}$haloalkyl, —($C_{1-3}$alkyl)$_{0-1}C_{3-6}$cycloalkyl, or —($C_{1-3}$alkyl)$_{0-1}$heterocycloalkyl;
(b) benzyl or phenyl, wherein the phenyl is unsubstituted or substituted with one to three members each independently selected from the group consisting of: halo, —$C_{1-4}$alkyl, —$C_{1-4}$haloalkyl, —$C_{1-6}$alkoxy, and —CN; and
(c) monocyclic five or six membered heteroaryl ring containing one to three nitrogen members, unsubstituted or substituted with one to three members each independently selected from the group consisting of: —$C_{1-6}$alkyl, —$C_{1-6}$haloalkyl, —$C_{1-3}$alkoxy, —$C_{1-3}$haloalkoxy, —$C_{3-6}$cycloalkyl, and —CN;
$R^4$ is selected from the group consisting of: —H, —F, —$C_{1-4}$alkyl, —$C_{1-4}$haloalkyl, —$C_{1-4}$alkoxy, —OH, phenyl, and 4-trifluoromethylphenyl;
$R^5$ is selected from the group consisting of:
(a) —$C_{1-6}$alkyl, —$C_{1-6}$haloalkyl, —O$C_{1-6}$alkyl or —O$C_{1-6}$haloalkyl;
(b) —($C_{1-3}$alkyl)$_{0-1}C_{3-6}$cycloalkyl, —($C_{1-3}$alkyl)$_{0-1}$heterocycloalkyl, —O($C_{1-3}$alkyl)$_{0-1}C_{3-6}$cycloalkyl, —O($C_{1-3}$alkyl)$_{0-1}$heterocycloalkyl, or —O($C_{1-3}$haloalkyl)$_{0-1}C_{3-6}$cycloalkyl, wherein each cycloalkyl member is unsubstituted or substituted with one to three members independently selected from the group consisting of: -D, —F, —O$C_{1-3}$alkyl, and —$C_{1-4}$haloalkyl, wherein each heterocycloalkyl member is a four, five, or six membered monocyclic ring, unsubstituted or substituted with one to three members each independently —F, or —$C_{1-6}$alkyl; and
(c) phenyl or pyridyl, each unsubstituted or substituted with one to three members each independently selected from the group consisting of: halo, —$C_{1-6}$alkyl, and $C_{1-6}$haloalkyl;
X is —($CR^b$)$_{1-2}$—; and
each $R^b$ is independently —H, or —$C_{1-3}$alkyl.

2. The compound of claim 1, wherein $R^1$ is —OCH$_3$, —CO$_2$H, —C(O)NH$_2$, —C(O)NHCH$_3$, —C(O)N(CH$_3$)$_2$, —SO$_2$CH$_3$, —SO$_2$CH$_2$CH$_3$, —SO$_2$CH(CH$_3$)$_2$, —SO$_2$CH$_2$cyclopropyl, —CN,

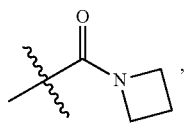

or oxazolidin-2-one, or
$R^1$ is —SO$_2$($C_{1-4}$alkyl) or —CN, or $R^1$ is —SO$_2$CH$_3$ or —CN.

3. The compound of claim 1, $R^2$ is —H, —Cl, —F or —OCH$_3$, or $R^2$ is —H, —OCH$_3$ or —Cl.

4. The compound of claim 1, wherein $R^3$ is —H, —CH$_3$, —CH(CH$_3$)$_2$, —CH$_2$CH(CH$_3$)$_2$, —CH$_2$CH$_2$CH$_2$OCH$_3$, (2S)-2-methylbutyl, —CH$_2$CF$_3$, —CH$_2$CF(CH$_3$)$_2$, (2,2-difluorocyclopropyl)methyl, 3,3-difluorocyclobutyl)methyl, cyclopentyl, cyclohexyl, cyclopropylmethyl, cyclobutylmethyl, cyclopentylmethyl, 4,4-difluorocyclohexyl, oxan-4-yl, oxan-4-ylmethyl or oxolan-3-ylmethyl, or $R^3$ is phenyl, benzyl or pyridyl unsubstituted or substituted with one to three members independently selected from the group consisting of: halo, —$C_{1-4}$alkyl, —$C_{1-4}$haloalkyl, —$C_{1-4}$alkoxy, and —CN, or $R^3$ is phenyl, benzyl, 2-fluorophenyl, 3-fluorophenyl, 4-fluorophenyl, 3-(trifluoromethyl)phenyl, 4-(trifluoromethyl)phenyl, 2,4-difluorophenyl, 2-methylphenyl, 3-methylphenyl, 3-methoxyphenyl, 4-methoxyphenyl, 4-cyanophenyl, 2,4-difluoro-3-methylphenyl, 2,5-difluorophenyl, 3,4-difluorophenyl, 3-(difluoromethyl)-4-fluorophenyl, 2-chloro-3-fluorophenyl, 5-chloro-2-fluorophenyl, 3-chloro-2-fluorophenyl, 2-fluoro-3-(trifluoromethyl)phenyl, 2-fluoro-3-methylphenyl, or 2-fluoro-5-methylphenyl, or $R^3$ is phenyl, 2-fluorophenyl, 4-fluorophenyl, 3-methylphenyl, 2,5-difluorophenyl, 2-fluoro-3-(trifluoromethyl)phenyl, 2-fluoro-3-methylphenyl, 2-cyclopropylpyridin-4-yl, 2-methylpyridin-4-yl, 2-ethylpyridin-4-yl, 5-fluoropyridin-3-yl, 5-methylpyridin-2-yl, or 5-fluoropyridin-2-yl, or $R^3$ is 1,2-dimethyl-1H-imidazol-4-yl, 1-methyl-1H-imidazol-4-yl, 1-methyl-1H-pyrazol-3-yl, 1-methyl-1H-pyrazol-4-yl, 2-(propan-2-yloxy)pyridin-4-yl, 2-(trifluoromethyl)pyridin-4-yl, 2,6-dimethylpyridin-4-yl, 2-cyclobutylpyridin-4-yl, 2-cyclopropylpyridin-4-yl, 2-ethoxypyridin-4-yl, 2-ethylpyridin-4-yl, 2-methoxypyridin-4-yl, 2-methylpyridin-4-yl, 3,5-difluoropyridin-2-yl, 3-fluoropyridin-2-yl, 3-fluoropyridin-4-yl, 3-methylpyridin-2-yl, 4-methylpyridin-2-yl, 5-(trifluoromethyl)pyridin-2-yl, 5-chloropyridin-2-yl, 5-fluoro-2-methoxypyridin-3-yl, 5-fluoro-2-methylpyridin-3-yl, 5-fluoro-3-methylpyridin-2-yl, 5-fluoro-4-methylpyridin-2-yl, 5-fluoro-4-methylpyridin-3-yl, 5-fluoro-6-methoxypyridin-3-yl, 5-fluoro-6-methylpyridin-2-yl, 5-fluoro-6-methylpyridin-3-yl, 5-fluoropyridin-2-yl, 5-fluoropyridin-3-yl, 5-methylpyridin-2-yl, 6-(trifluoromethyl)pyridin-3-yl, 6-methoxypyridin-2-yl, 6-methylpyridin-2-yl, 6-methylpyridin-3-yl, pyridazin-4-yl, pyridin-2-yl, pyridin-3-yl, pyridin-4-yl, pyridine-2-carbonitrile, or trimethyl-1H-pyrazol-4-yl, or $R^3$ is phenyl, 2-fluorophenyl, 4-fluorophenyl, 3-methylphenyl, 2,5-difluorophenyl, 2-fluoro-3-(trifluoromethyl)phenyl, 2-fluoro-3-methylphenyl, 2-cyclopropylpyridin-4-yl, or 2-ethylpyridin-4-yl.

5. The compound of claim 1, wherein $R^4$ is —H, —CH$_3$, —CF$_3$, —$C_{1-3}$alkoxy, phenyl, or 4-trifluoromethylphenyl, or $R^4$ is —H.

6. The compound of claim 1, wherein $R^5$ is —CH$_2$CH(CH$_3$)$_3$, —CF(CH$_2$CH$_3$)$_2$, —OCH$_2$C(CH$_3$)$_3$, —OCH(CH$_3$)$_2$, —OCH(CH$_2$CH$_3$)$_2$, —OCH$_2$CF$_3$, —OCH$_2$CHF$_2$, —OCH(CH$_3$)(CH$_2$F), —OCH(CH$_3$)(CHF$_2$), —OCH(CH$_3$)(CF$_3$), [(2S)-1,1,1-trifluoropropan-2-yl]oxy, —OC(CH$_3$)$_2$(CF$_3$), (3-methylbutan-2-yl)oxy, pentan-2-yloxy, —OCH$_2$cyclopropyl, (1-methyl cyclopropyl)methoxy, 1-cyclopropylethoxy, 1-methylcyclopropoxy, cyclopentyloxy, (3-methyloxetan-3-yl)methoxy, oxetan-3-yloxy, or [1-(trifluoromethyl)cyclopropyl]methoxy, or R⁵ is —OCH(CH₃)₂, —OCH₂C(CH₃)₃, —OCH(CH₃)(CF₃), or [(2S)-1,1,1-trifluoropropan-2-yl]oxy, or R⁵ is cyclobutyl, cyclopentyl, 1-deuterocyclohexyl, 1-methoxycyclobutyl, 1-fluorocyclobutyl, 1-fluorocyclopentyl, or 1,4,4-trifluorocyclohexyl, or R⁵ is 3-fluorooxetan-3-yl, 4-fluorooxan-4-yl, azetidine, pyrrolidine, 3,3-difluoropyrrolidine, piperidine, 4,4-difluoropiperidin-1-yl, or morpholin-4-yl, or R⁵ is phenyl, 2-fluorophenyl, 3-fluorophenyl, 3-methylphenyl, 3-(trifluoromethyl)phenyl, 3,5-difluorophenyl, pyridine, 2-(trifluoromethyl)pyridine, or 5-fluoropyridin-3-yl, or R⁵ is —OCH(CH₃)₂, —OCH₂C(CH₃)₃, —OCH(CH₃)(CF₃), or [(2S)-1,1,1-trifluoropropan-2-yl]oxy, cyclopentyl or 3-fluorophenyl.

7. The compound of claim 1, wherein X is —CH₂CH₂—, or CH₂(CH₃)₂—, or X is —CH₂—.

8. The compound of claim 1, wherein R¹ is —SO₂(C₁₋₃alkyl), or —CN, R³ is phenyl, or pyridyl unsubstituted or substituted with one to three members independently selected from the group consisting of: halo, —C₁₋₄alkyl, —C₁₋₄haloalkyl, —C₁₋₄alkoxy, and —CN, R⁵ is —OCH(CH₃)₂, —OCH₂C(CH₃)₃, —OCH(CH₃)(CF₃), [(2S)-1,1,1-trifluoropropan-2-yl]oxy, cyclopentyl, 3,5-difluorophenyl, and 3-fluorophenyl, and X is —CH₂—.

9. The compound of claim 1 having the structure of Formula (Ia):

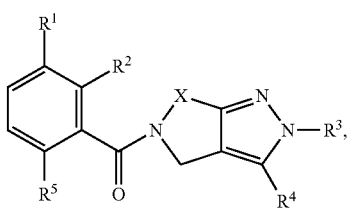

(Ia)

or pharmaceutically acceptable salts thereof.

10. The compound of claim 1 having the structure of Formula (Ib):

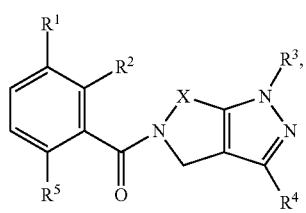

(Ib)

or pharmaceutically acceptable salts thereof.

11. A compound selected from the group consisting of:
(2-(4-Fluorophenyl)pyrrolo[3,4-c]pyrazol-5(2H,4H,6H)-yl)(2-isopropoxy-5-(methylsulfonyl)phenyl)methanone;
(2-(3,4-Difluorophenyl)pyrrolo[3,4-c]pyrazol-5(2H,4H,6H)-yl)(2-isopropoxy-5-(methylsulfonyl)phenyl)methanone;
3-(2-(2-Methylpyridin-4-yl)-2,4,5,6-tetrahydropyrrolo[3,4-c]pyrazole-5-carbonyl)-4-(neopentyloxy)benzonitrile;
2-Chloro-3-(2-(4-fluorophenyl)-2,4,5,6-tetrahydropyrrolo[3,4-c]pyrazole-5-carbonyl)-4-((1,1,1-trifluoropropan-2-yl)oxy)benzoic acid;
4-(3-Fluorophenyl)-3-[2-(2-methylpyridin-4-yl)-2H 4H 5H 6H-pyrrolo[3,4-c]pyrazole-5-carbonyl]benzonitrile;
4-((1,1-Difluoropropan-2-yl)oxy)-3-(2-(4-fluorophenyl)-2,4,5,6-tetrahydropyrrolo[3,4-c]pyrazole-5-carbonyl)benzonitrile;
4-(3,3-Dimethylbutyl)-3-(2-(4-fluorophenyl)-2,4,5,6-tetrahydropyrrolo[3,4-c]pyrazole-5-carbonyl)-2-methoxybenzonitrile;
4-[(1 1-Difluoropropan-2-yl)oxy]-3-[2-(4-fluorophenyl)-2H 4H 5H 6H-pyrrolo[3,4-c]pyrazole-5-carbonyl]-2-methoxybenzonitrile;
3-[2-(5-Fluoropyridin-2-yl)-2H 4H 5H 6H-pyrrolo[3,4-c]pyrazole-5-carbonyl]-2-methoxy-4-(1 4 4-trifluorocyclohexyl)benzonitrile;
2-Chloro-3-[2-(2-methoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile;
2-Chloro-3-[2-(2-methylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;
2-Methoxy-3-[2-(2-methylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;
2-Chloro-3-[2-(6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;
4-(1-Fluorocyclobutyl)-2-methoxy-3-[2-(6-methylpyridin-2-yl)-2H 4H 5H 6H-pyrrolo[3,4-c]pyrazole-5-carbonyl]benzonitrile;
4-(4-Fluorooxan-4-yl)-2-methoxy-3-[2-(6-methylpyridin-2-yl)-2H 4H 5H 6H-pyrrolo[3,4-c]pyrazole-5-carbonyl]benzonitrile;
2-Chloro-3-[2-(6-methylpyridin-2-yl)-2H 4H 5H 6H-pyrrolo[3,4-c]pyrazole-5-carbonyl]-4-(2 2 2-trifluoroethoxy)benzonitrile;
4-(1-Fluorocyclobutyl)-3-[2-(5-fluoropyridin-3-yl)-2H 4H 5H 6H-pyrrolo[3,4-c]pyrazole-5-carbonyl]-2-methoxybenzonitrile;
4-(4-Fluorooxan-4-yl)-3-[2-(5-fluoropyridin-3-yl)-2H 4H 5H 6H-pyrrolo[3,4-c]pyrazole-5-carbonyl]-2-methoxybenzonitrile;
2-Chloro-3-[2-(5-fluoropyridin-3-yl)-2H 4H 5H 6H-pyrrolo[3,4-c]pyrazole-5-carbonyl]-4-(2 2 2-trifluoroethoxy)benzonitrile;
4-(1-Fluorocyclobutyl)-3-[2-(4-fluorophenyl)-2H 4H 5H 6H-pyrrolo[3,4-c]pyrazole-5-carbonyl]-2-methoxybenzonitrile;
4-(4-Fluorooxan-4-yl)-3-[2-(4-fluorophenyl)-2H 4H 5H 6H-pyrrolo[3,4-c]pyrazole-5-carbonyl]-2-methoxybenzonitrile;
2-Chloro-3-[2-(4-fluorophenyl)-2H 4H 5H 6H-pyrrolo[3,4-c]pyrazole-5-carbonyl]-4-(2 2 2-trifluoroethoxy)benzonitrile;
3-[2-(4-Fluorophenyl)-2H 4H 5H 6H-pyrrolo[3,4-c]pyrazole-5-carbonyl]-2-methoxy-4-(2 2 2-trifluoroethoxy)benzonitrile;
2-Chloro-3-[2-(5-fluoropyridin-3-yl)-2H 4H 5H 6H-pyrrolo[3,4-c]pyrazole-5-carbonyl]-4-{[(2R)-1 1 1-trifluoropropan-2-yl]oxy}benzonitrile;
2-Chloro-3-[2-(3-methylpyridin-2-yl)-2H 4H 5H 6H-pyrrolo[3,4-c]pyrazole-5-carbonyl]-4-{[(2R)-1 1 1-trifluoropropan-2-yl]oxy}benzonitrile;
2-Chloro-3-[2-(5-fluoropyridin-2-yl)-2H 4H 5H 6H-pyrrolo[3,4-c]pyrazole-5-carbonyl]-4-{[(2R)-1 1 1-trifluoropropan-2-yl]oxy}benzonitrile;

5-(5-Methanesulfonyl-2-{[(2S)-1 1 1-trifluoropropan-2-yl]oxy}benzoyl)-2-(2-methylphenyl)-2H 4H 5H 6H-pyrrolo[3,4-c]pyrazole;

5-(5-Methanesulfonyl-2-{[(2S)-1 1 1-trifluoropropan-2-yl]oxy}benzoyl)-2-(3-methylphenyl)-2H 4H 5H 6H-pyrrolo[3,4-c]pyrazole;

2-(3-Chloro-4-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(4-Fluoro-3-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(3 4-Difluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(2 4-Difluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

5-[5-Methanesulfonyl-2-(2-methylpropoxy)benzoyl]-2-(3-methylphenyl)-2H 4H 5H 6H-pyrrolo[3,4-c]pyrazole;

5-[5-(Ethanesulfonyl)-2-{[(2S)-1 1 1-trifluoropropan-2-yl]oxy}benzoyl]-2-phenyl-2H 4H 5H 6H-pyrrolo[3,4-c]pyrazole;

5-[5-(Ethanesulfonyl)-2-{[(2S)-1 1 1-trifluoropropan-2-yl]oxy}benzoyl]-2-(4-fluorophenyl)-2H 4H 5H 6H-pyrrolo[3,4-c]pyrazole;

2-(2-Fluoro-3-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-[2-Fluoro-3-(trifluoromethyl)phenyl]-5-(5-methanesulfonyl-2-{[(2S)-1 1 1-trifluoropropan-2-yl]oxy}benzoyl)-2H 4H 5H 6H-pyrrolo[3,4-c]pyrazole;

5-(5-Methanesulfonyl-2-{[(2S)-1 1 1-trifluoropropan-2-yl]oxy}benzoyl)-2-[3-(trifluoromethyl)phenyl]-2H 4H 5H 6H-pyrrolo[3,4-c]pyrazole;

5-[5-Methanesulfonyl-2-(propan-2-yloxy)benzoyl]-2-phenyl-2H 4H 5H 6H-pyrrolo[3,4-c]pyrazole;

2-[2-Fluoro-3-(trifluoromethyl)phenyl]-5-[5-methanesulfonyl-2-(propan-2-yloxy)benzoyl]-2H 4H 5H 6H-pyrrolo[3,4-c]pyrazole;

5-[5-Methanesulfonyl-2-(propan-2-yloxy)benzoyl]-2-[3-(trifluoromethyl)phenyl]-2H 4H 5H 6H-pyrrolo[3,4-c]pyrazole;

5-[2-(2 2-Dimethylpropoxy)-5-methanesulfonylbenzoyl]-2-phenyl-2H 4H 5H 6H-pyrrolo[3,4-c]pyrazole;

5-[2-(2 2-Dimethylpropoxy)-5-methanesulfonylbenzoyl]-2-[2-fluoro-3-(trifluoromethyl)phenyl]-2H 4H 5H 6H-pyrrolo[3,4-c]pyrazole;

5-[2-(2 2-Dimethylpropoxy)-5-methanesulfonylbenzoyl]-2-[3-(trifluoromethyl)phenyl]-2H 4H 5H 6H-pyrrolo[3,4-c]pyrazole;

5-[5-Methanesulfonyl-2-(2-methylpropoxy)benzoyl]-2-phenyl-2H 4H 5H 6H-pyrrolo[3,4-c]pyrazole;

2-[2-Fluoro-3-(trifluoromethyl)phenyl]-5-[5-methanesulfonyl-2-(2-methylpropoxy)benzoyl]-2H 4H 5H 6H-pyrrolo[3,4-c]pyrazole;

5-[5-Methanesulfonyl-2-(2-methylpropoxy)benzoyl]-2-[3-(trifluoromethyl)phenyl]-2H 4H 5H 6H-pyrrolo[3,4-c]pyrazole;

4 4-Difluoro-1-(4-methanesulfonyl-2-{2-phenyl-2H 4H 5H 6H-pyrrolo[3,4-c]pyrazole-5-carbonyl}phenyl)piperidine;

4-Difluoro-1-(4-methanesulfonyl-2-{2-[3-(trifluoromethyl)phenyl]-2H 4H 5H 6H-pyrrolo[3,4-c]pyrazole-5-carbonyl}phenyl)piperidine;

4 4-Difluoro-1-{2-[2-(4-fluorophenyl)-2H 4H 5H 6H-pyrrolo[3,4-c]pyrazole-5-carbonyl]-4-methanesulfonylphenyl}piperidine;

2-(2-Fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(2 4-Difluoro-3-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(5-Chloro-2-fluorophenyl)-5-(5-methanesulfonyl-2-{[(2S)-1 1 1-trifluoropropan-2-yl]Oxy}benzoyl)-2H 4H 5H 6H-pyrrolo[3,4-c]pyrazole;

2-(2-Fluorophenyl)-5-[5-methanesulfonyl-2-(propan-2-yloxy)benzoyl]-2H 4H 5H 6H-pyrrolo[3,4-c]pyrazole;

2-(2 4-Difluoro-3-methylphenyl)-5-[5-methanesulfonyl-2-(propan-2-yloxy)benzoyl]-2H 4H 5H 6H-pyrrolo[3,4-c]pyrazole;

2-(5-Chloro-2-fluorophenyl)-5-[5-methanesulfonyl-2-(propan-2-yloxy)benzoyl]-2H 4H 5H 6H-pyrrolo[3,4-c]pyrazole;

5-[2-(2 2-Dimethylpropoxy)-5-methanesulfonylbenzoyl]-2-(2-fluorophenyl)-2H 4H 5H 6H-pyrrolo[3,4-c]pyrazole;

2-(2 4-Difluoro-3-methylphenyl)-5-[2-(2 2-dimethylpropoxy)-5-methanesulfonylbenzoyl]-2H 4H 5H 6H-pyrrolo[3,4-c]pyrazole;

2-(5-Chloro-2-fluorophenyl)-5-[2-(2 2-dimethylpropoxy)-5-methanesulfonylbenzoyl]-2H 4H 5H 6H-pyrrolo[3,4-c]pyrazole;

2-(2-Fluorophenyl)-5-[5-methanesulfonyl-2-(2-methylpropoxy)benzoyl]-2H 4H 5H 6H-pyrrolo[3,4-c]pyrazole;

2-(2 4-Difluoro-3-methylphenyl)-5-[5-methanesulfonyl-2-(2-methylpropoxy)benzoyl]-2H 4H 5H 6H-pyrrolo[3,4-c]pyrazole;

2-(5-Chloro-2-fluorophenyl)-5-[5-methanesulfonyl-2-(2-methylpropoxy)benzoyl]-2H 4H 5H 6H-pyrrolo[3,4-c]pyrazole;

4 4-Difluoro-1-{2-[2-(2-fluorophenyl)-2H 4H 5H 6H-pyrrolo[3,4-c]pyrazole-5-carbonyl]-4-methanesulfonylphenyl}piperidine;

1-{2-[2-(2 4-Difluoro-3-methylphenyl)-2H 4H 5H 6H-pyrrolo[3,4-c]pyrazole-5-carbonyl]-4-methanesulfonylphenyl}-4 4-difluoropiperidine;

1-{2-[2-(5-Chloro-2-fluorophenyl)-2H 4H 5H 6H-pyrrolo[3,4-c]pyrazole-5-carbonyl]-4-methanesulfonylphenyl}-4 4-difluoropiperidine;

5-[5-(Ethanesulfonyl)-2-{[(2S)-1 1 1-trifluoropropan-2-yl]oxy}benzoyl]-2-(3-methylphenyl)-2H 4H 5H 6H-pyrrolo[3,4-c]pyrazole;

5-[5-(Ethanesulfonyl)-2-(propan-2-yloxy)benzoyl]-2-phenyl-2H 4H 5H 6H-pyrrolo[3,4-c]pyrazole;

5-[5-(Ethanesulfonyl)-2-(propan-2-yloxy)benzoyl]-2-(2-fluorophenyl)-2H 4H 5H 6H-pyrrolo[3,4-c]pyrazole;

2-[3-(Difluoromethyl)-4-fluorophenyl]-5-(5-methanesulfonyl-2-{[(2S)-1 1 1-trifluoropropan-2-yl]oxy}benzoyl)-2H 4H 5H 6H-pyrrolo[3,4-c]pyrazole;

2-[3-(Difluoromethyl)-4-fluorophenyl]-5-[5-methanesulfonyl-2-(propan-2-yloxy)benzoyl]-2H 4H 5H 6H-pyrrolo[3,4-c]pyrazole;

2-[3-(Difluoromethyl)-4-fluorophenyl]-5-[2-(2 2-dimethylpropoxy)-5-methanesulfonylbenzoyl]-2H 4H 5H 6H-pyrrolo[3,4-c]pyrazole;

5-[5-(Ethanesulfonyl)-2-{[(2S)-1 1 1-trifluoropropan-2-yl]oxy}benzoyl]-2-(2-fluoro-3-methylphenyl)-2H 4H 5H 6H-pyrrolo[3,4-c]pyrazole;

2-[3-(Difluoromethyl)-4-fluorophenyl]-5-[5-(ethanesulfonyl)-2-{[(2S)-1 1 1-trifluoropropan-2-yl]oxy}benzoyl]-2H 4H 5H 6H-pyrrolo[3,4-c]pyrazole;
5-[5-(Ethanesulfonyl)-2-{[(2S)-1 1 1-trifluoropropan-2-yl]oxy}benzoyl]-2-(2-fluorophenyl)-2H 4H 5H 6H-pyrrolo[3,4-c]pyrazole;
2-(2 4-Difluorophenyl)-5-[5-(ethanesulfonyl)-2-(propan-2-yloxy)benzoyl]-2H 4H 5H 6H-pyrrolo[3,4-c]pyrazole;
2-[3-(Difluoromethyl)-4-fluorophenyl]-5-[5-(ethanesulfonyl)-2-(propan-2-yloxy)benzoyl]-2H 4H 5H 6H-pyrrolo[3,4-c]pyrazole;
5-[5-(Ethanesulfonyl)-2-(propan-2-yloxy)benzoyl]-2-(3-methylphenyl)-2H 4H 5H 6H-pyrrolo[3,4-c]pyrazole;
5-[5-(Ethanesulfonyl)-2-(propan-2-yloxy)benzoyl]-2-(4-fluorophenyl)-2H 4H 5H 6H-pyrrolo[3,4-c]pyrazole;
5-[5-Methanesulfonyl-2-(propan-2-yloxy)benzoyl]-2-(3-methylphenyl)-2H 4H 5H 6H-pyrrolo[3,4-c]pyrazole;
2-[2-Fluoro-3-(trifluoromethyl)phenyl]-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-(2-Fluoro-3-methylphenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-(2-Fluorophenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-(3-Methylphenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-Phenyl-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-(4-Fluorophenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-(3 4-Difluorophenyl)-5-[5-(propane-2-sulfonyl)-2-{[(2S)-1 1 1-trifluoropropan-2-yl]oxy}benzoyl]-2H 4H 5H 6H-pyrrolo[3,4-c]pyrazole;
2-[2-Fluoro-3-(trifluoromethyl)phenyl]-5-[2-(propan-2-yloxy)-5-(propane-2-sulfonyl)benzoyl]-2H 4H 5H 6H-pyrrolo[3,4-c]pyrazole;
2-(2-Fluoro-3-methylphenyl)-5-[2-(propan-2-yloxy)-5-(propane-2-sulfonyl)benzoyl]-2H 4H 5H 6H-pyrrolo[3,4-c]pyrazole;
2-(2-Fluorophenyl)-5-[2-(propan-2-yloxy)-5-(propane-2-sulfonyl)benzoyl]-2H 4H 5H 6H-pyrrolo[3,4-c]pyrazole;
2-(3-Methylphenyl)-5-[2-(propan-2-yloxy)-5-(propane-2-sulfonyl)benzoyl]-2H 4H 5H 6H-pyrrolo[3,4-c]pyrazole;
2-Phenyl-5-[2-(propan-2-yloxy)-5-(propane-2-sulfonyl)benzoyl]-2H 4H 5H 6H-pyrrolo[3,4-c]pyrazole;
2-(4-Fluorophenyl)-5-[2-(propan-2-yloxy)-5-(propane-2-sulfonyl)benzoyl]-2H 4H 5H 6H-pyrrolo[3,4-c]pyrazole;
2-(3 4-Difluorophenyl)-5-[2-(propan-2-yloxy)-5-(propane-2-sulfonyl)benzoyl]-2H 4H 5H 6H-pyrrolo[3,4-c]pyrazole;
3-{5-[2-(4 4-Difluoropiperidin-1-yl)-5-methanesulfonylbenzoyl]-2H 4H 5H 6H-pyrrolo[3,4-c]pyrazol-2-yl}-5-fluoropyridine;
4-{5-[2-(4 4-Difluoropiperidin-1-yl)-5-methanesulfonylbenzoyl]-2H 4H 5H 6H-pyrrolo[3,4-c]pyrazol-2-yl}-2-methylpyridine;
5-[5-Methanesulfonyl-2-(2 2 2-trifluoroethoxy)benzoyl]-2-phenyl-2H 4H 5H 6H-pyrrolo[3,4-c]pyrazole;
2-(4-Fluorophenyl)-5-[5-methanesulfonyl-2-(2 2 2-trifluoroethoxy)benzoyl]-2H 4H 5H 6H-pyrrolo[3,4-c]pyrazole;
2-(2-Fluorophenyl)-5-[5-methanesulfonyl-2-(2 2 2-trifluoroethoxy)benzoyl]-2H 4H 5H 6H-pyrrolo[3,4-c]pyrazole;
5-[5-Methanesulfonyl-2-(2 2 2-trifluoroethoxy)benzoyl]-2-(3-methylphenyl)-2H 4H 5H 6H-pyrrolo[3,4-c]pyrazole;
2-(2-Fluoro-3-methylphenyl)-5-[5-methanesulfonyl-2-(2 2 2-trifluoroethoxy)benzoyl]-2H 4H 5H 6H-pyrrolo[3,4-c]pyrazole;
5-Fluoro-2-{5-[2-(3-fluorophenyl)-5-methanesulfonylbenzoyl]-2H 4H 5H 6H-pyrrolo[3,4-c]pyrazol-2-yl}pyridine;
3-Fluoro-5-{5-[2-(3-fluorophenyl)-5-methanesulfonylbenzoyl]-2H 4H 5H 6H-pyrrolo[3,4-c]pyrazol-2-yl}pyridine;
4-{5-[2-(3-Fluorophenyl)-5-methanesulfonylbenzoyl]-2H 4H 5H 6H-pyrrolo[3,4-c]pyrazol-2-yl}-2-methylpyridine;
4-Difluoro-1-{4-methanesulfonyl-2-[2-(3-methylphenyl)-2H 4H 5H 6H-pyrrolo[3,4-c]pyrazole-5-carbonyl]phenyl}piperidine;
4-{5-[2-(4 4-Difluoropiperidin-1-yl)-5-(ethanesulfonyl)benzoyl]-2H 4H 5H 6H-pyrrolo[3,4-c]pyrazol-2-yl}-2-methylpyridine;
3-{5-[2-(4 4-Difluoropiperidin-1-yl)-5-(ethanesulfonyl)benzoyl]-2H 4H 5H 6H-pyrrolo[3,4-c]pyrazol-2-yl}-5-fluoropyridine;
4-{5-[5-(Ethanesulfonyl)-2-{[(2S)-1 1 1-trifluoropropan-2-yl]oxy}benzoyl]-2H 4H 5H 6H-pyrrolo[3,4-c]pyrazol-2-yl}-2-methylpyridine;
3-{5-[5-(Ethanesulfonyl)-2-{[(2S)-1 1 1-trifluoropropan-2-yl]oxy}benzoyl]-2H 4H 5H 6H-pyrrolo[3,4-c]pyrazol-2-yl}-5-fluoropyridine;
5-Fluoro-2-{5-[5-methanesulfonyl-2-(piperidin-1-yl)benzoyl]-2H 4H 5H 6H-pyrrolo[3,4-c]pyrazol-2-yl}pyridine;
3-Fluoro-5-{5-[5-methanesulfonyl-2-(piperidin-1-yl)benzoyl]-2H 4H 5H 6H-pyrrolo[3,4-c]pyrazol-2-yl}pyridine;
4-{5-[5-Methanesulfonyl-2-(piperidin-1-yl)benzoyl]-2H 4H 5H 6H-pyrrolo[3,4-c]pyrazol-2-yl}-2-methylpyridine;
5-[2-(Cyclopropylmethoxy)-5-methanesulfonylbenzoyl]-2-phenyl-2H 4H 5H 6H-pyrrolo[3,4-c]pyrazole;
5-[2-(Cyclopropylmethoxy)-5-methanesulfonylbenzoyl]-2-(2-fluorophenyl)-2H 4H 5H 6H-pyrrolo[3,4-c]pyrazole;
2-{5-[2-(4 4-Difluoropiperidin-1-yl)-5-methanesulfonylbenzoyl]-2H 4H 5H 6H-pyrrolo[3,4-c]pyrazol-2-yl}-5-fluoropyridine;
2-(2 5-Difluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;
2-(2-Fluoro-5-methylphenyl)-5-(5-methanesulfonyl-2-{[(2S)-1 1 1-trifluoropropan-2-yl]oxy}benzoyl)-2H 4H 5H 6H-pyrrolo[3,4-c]pyrazole;
1-{2-[2-(2 5-Difluorophenyl)-2H 4H 5H 6H-pyrrolo[3,4-c]pyrazole-5-carbonyl]-4-methanesulfonylphenyl}-4 4-difluoropiperidine;
4 4-Difluoro-1-{2-[2-(2-fluoro-5-methylphenyl)-2H 4H 5H 6H-pyrrolo[3,4-c]pyrazole-5-carbonyl]-4-methanesulfonylphenyl}piperidine;

2-(2 5-Difluorophenyl)-5-[5-(ethanesulfonyl)-2-{[(2S)-1 1 1-trifluoropropan-2-yl]oxy}benzoyl]-2H 4H 5H 6H-pyrrolo[3,4-c]pyrazole;

5-[5-(Ethanesulfonyl)-2-{[(2S)-1 1 1-trifluoropropan-2-yl]oxy}benzoyl]-2-(2-fluoro-5-methylphenyl)-2H 4H 5H 6H-pyrrolo[3,4-c]pyrazole;

1-{2-[2-(2 5-Difluorophenyl)-2H 4H 5H 6H-pyrrolo[3,4-c]pyrazole-5-carbonyl]-4-(ethanesulfonyl)phenyl}-4 4-difluoropiperidine;

1-[4-(Ethanesulfonyl)-2-[2-(2-fluoro-5-methylphenyl)-2H 4H 5H 6H-pyrrolo[3,4-c]pyrazole-5-carbonyl]phenyl]-4 4-difluoropiperidine;

2-(2 5-Difluorophenyl)-5-[5-methanesulfonyl-2-(propan-2-yloxy)benzoyl]-2H 4H 5H 6H-pyrrolo[3,4-c]pyrazole;

2-(2-Fluoro-5-methylphenyl)-5-[5-methanesulfonyl-2-(propan-2-yloxy)benzoyl]-2H 4H 5H 6H-pyrrolo[3,4-c]pyrazole;

4-{5-[2-(4 4-Difluoropiperidin-1-yl)-5-methanesulfonylbenzoyl]-2H 4H 5H 6H-pyrrolo[3,4-c]pyrazol-2-yl}-2-ethylpyridine;

4-{5-[2-(4 4-Difluoropiperidin-1-yl)-5-(ethanesulfonyl)benzoyl]-2H 4H 5H 6H-pyrrolo[3,4-c]pyrazol-2-yl}-2-ethylpyridine;

2-Ethyl-4-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]pyridine;

4-{5-[5-(Ethanesulfonyl)-2-{[(2S)-1 1 1-trifluoropropan-2-yl]oxy}benzoyl]-2H 4H 5H 6H-pyrrolo[3,4-c]pyrazol-2-yl}-2-ethylpyridine;

2-{5-[2-(4 4-Difluoropiperidin-1-yl)-5-(ethanesulfonyl)benzoyl]-2H 4H 5H 6H-pyrrolo[3,4-c]pyrazol-2-yl}-5-fluoropyridine;

5-[2-(Cyclopropylmethoxy)-5-methanesulfonylbenzoyl]-2-(2-fluoro-5-methylphenyl)-2H 4H 5H 6H-pyrrolo[3,4-c]pyrazole;

5-[2-(Cyclopropylmethoxy)-5-methanesulfonylbenzoyl]-2-(2 5-difluorophenyl)-2H 4H 5H 6H-pyrrolo[3,4-c]pyrazole;

5-[2-(Cyclopropylmethoxy)-5-methanesulfonylbenzoyl]-2-[2-fluoro-3-(trifluoromethyl)phenyl]-2H 4H 5H 6H-pyrrolo[3,4-c]pyrazole;

5-[2-(Cyclopropylmethoxy)-5-methanesulfonylbenzoyl]-2-(2-fluoro-3-methylphenyl)-2H 4H 5H 6H-pyrrolo[3,4-c]pyrazole;

5-[2-(Cyclopropylmethoxy)-5-methanesulfonylbenzoyl]-2-(3-methylphenyl)-2H 4H 5H 6H-pyrrolo[3,4-c]pyrazole;

3-{5-[2-(3-Fluorophenyl)-5-methanesulfonylbenzoyl]-2H 4H 5H 6H-pyrrolo[3,4-c]pyrazol-2-yl}pyridine;

4-{5-[2-(3-Fluorophenyl)-5-methanesulfonylbenzoyl]-2H 4H 5H 6H-pyrrolo[3,4-c]pyrazol-2-yl}pyridine;

2-Ethyl-4-{5-[2-(3-fluorophenyl)-5-methanesulfonylbenzoyl]-2H 4H 5H 6H-pyrrolo[3,4-c]pyrazol-2-yl}pyridine;

5-(5-Cyclopropylmethanesulfonyl-2-{[(2S)-1 1 1-trifluoropropan-2-yl]oxy}benzoyl)-2-phenyl-2H 4H 5H 6H-pyrrolo[3,4-c]pyrazole;

5-(5-Cyclopropylmethanesulfonyl-2-{[(2S)-1 1 1-trifluoropropan-2-yl]oxy}benzoyl)-2-(3-methylphenyl)-2H 4H 5H 6H-pyrrolo[3,4-c]pyrazole;

2-(3-Chloro-2-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(2-Chloro-3-fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

2-(3-Chloro-2-fluorophenyl)-5-[5-methanesulfonyl-2-(propan-2-yloxy)benzoyl]-2H 4H 5H 6H-pyrrolo[3,4-c]pyrazole;

2-(2-Chloro-3-fluorophenyl)-5-[5-methanesulfonyl-2-(propan-2-yloxy)benzoyl]-2H 4H 5H 6H-pyrrolo[3,4-c]pyrazole;

2-(3-Chloro-2-fluorophenyl)-5-[5-(ethanesulfonyl)-2-{[(2S)-1 1 1-trifluoropropan-2-yl]oxy}benzoyl]-2H 4H 5H 6H-pyrrolo[3,4-c]pyrazole;

2-(2-Chloro-3-fluorophenyl)-5-[5-(ethanesulfonyl)-2-{[(2S)-1 1 1-trifluoropropan-2-yl]oxy}benzoyl]-2H 4H 5H 6H-pyrrolo[3,4-c]pyrazole;

2-{5-[2-(3-Fluorophenyl)-5-methanesulfonylbenzoyl]-2H 4H 5H 6H-pyrrolo[3,4-c]pyrazol-2-yl}pyridine;

5-[2-(Cyclopropylmethoxy)-5-methanesulfonylbenzoyl]-1-methyl-1H 4H 5H 6H-pyrrolo[3,4-c]pyrazole;

5-[2-(Cyclopropylmethoxy)-5-methanesulfonylbenzoyl]-1-[3-(trifluoromethyl)phenyl]-1H 4H 5H 6H-pyrrolo[3,4-c]pyrazole;

3-[2-(5-Fluoropyridin-2-yl)-2H 4H 5H 6H-pyrrolo[3,4-c]pyrazole-5-carbonyl]-2-methoxy-4-[(1 1 1-trifluoropropan-2-yl)oxy]benzonitrile;

2-Chloro-3-[2-(5-fluoropyridin-2-yl)-2H 4H 5H 6H-pyrrolo[3,4-c]pyrazole-5-carbonyl]-4-[(1 1 1-trifluoropropan-2-yl)oxy]benzonitrile;

3-[1-(5-Fluoropyridin-2-yl)-1H 4H 5H 6H-pyrrolo[3,4-c]pyrazole-5-carbonyl]-2-methoxy-4-[(1 1 1-trifluoropropan-2-yl)oxy]benzonitrile;

2-Chloro-3-[2-(5-fluoropyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoropyridin-2-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Methoxy-3-[2-(pyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(pyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(4-Fluorophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(4-fluorophenyl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoropyridin-3-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

3-[2-(5-Fluoropyridin-2-yl)-2H 4H 5H 6H-pyrrolo[3,4-c]pyrazole-5-carbonyl]-4-[(1 1 1-trifluoropropan-2-yl)oxy]benzonitrile;

2-Chloro-3-[2-(5-fluoropyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-{2-[6-(trifluoromethyl)pyridin-3-yl]-2H 4H 5H 6H-pyrrolo[3,4-c]pyrazole-5-carbonyl}-4-{[(2S)-1 1 1-trifluoropropan-2-yl]oxy}benzonitrile;

2-Chloro-3-{2-[6-(trifluoromethyl)pyridin-3-yl]-2H 4H 5H 6H-pyrrolo[3,4-c]pyrazole-5-carbonyl}4-{[(2S)-1 1 1-trifluoropropan-2-yl]oxy}benzonitrile;

4-(1-Fluorocyclobutyl)-3-[2-(5-fluoropyridin-2-yl)-2H 4H 5H 6H-pyrrolo[3,4-c]pyrazole-5-carbonyl]-2-methoxybenzonitrile;

4-(4-Fluorooxan-4-yl)-3-[2-(5-fluoropyridin-2-yl)-2H 4H 5H 6H-pyrrolo[3,4-c]pyrazole-5-carbonyl]-2-methoxybenzonitrile;

3-[2-(5-Fluoropyridin-2-yl)-2H 4H 5H 6H-pyrrolo[3,4-c]pyrazole-5-carbonyl]-2-methoxy-4-(2 2 2-trifluoroethoxy)benzonitrile;

3-[2-(3-Fluoropyridin-2-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(3-fluoropyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(pyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(pyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(6-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(6-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(3-fluorophenyl)-2H 4H 5H 6H-pyrrolo[3,4-c]pyrazole-5-carbonyl]-4-{[(2S)-1 1 1-trifluoropropan-2-yl]oxy}benzonitrile;

3-[2-(3-Fluorophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(2-fluorophenyl)-2H 4H 5H 6H-pyrrolo[3,4-c]pyrazole-5-carbonyl]-4-{[(2S)-1 1 1-trifluoropropan-2-yl]oxy}benzonitrile;

3-[2-(2-Fluorophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(6-methoxypyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(6-methoxypyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(2-methoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

2-Methoxy-3-[2-(5-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(1-methyl-1H-pyrazol-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(1 2-Dimethyl-1H-imidazol-4-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

3-[1-(1 2-Dimethyl-1H-imidazol-4-yl)-1H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(1 2-dimethyl-1H-imidazol-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(4-Cyanophenyl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

3-[1-(4-Cyanophenyl)-1H 4H 5H 6H-pyrrolo[3,4-c]pyrazole-5-carbonyl]-2-methoxy-4-{[(2S)-1 1 1-trifluoropropan-2-yl]oxy}benzonitrile;

2-Methoxy-3-{2-[5-(trifluoromethyl)pyridin-2-yl]-2H 4H 5H 6H-pyrrolo[3,4-c]pyrazole-5-carbonyl}-4-{[(2S)-1 1 1-trifluoropropan-2-yl]oxy}benzonitrile;

2-Chloro-3-{2-[5-(trifluoromethyl)pyridin-2-yl]-2H 4H 5H 6H-pyrrolo[3,4-c]pyrazole-5-carbonyl}-4-{[(2S)-1 1 1-trifluoropropan-2-yl]oxy}benzonitrile;

2-Chloro-3-[2-(2-methylpyridin-4-yl)-2H 4H 5H 6H-pyrrolo[3,4-c]pyrazole-5-carbonyl]-4-{[(2R)-1 1 1-trifluoropropan-2-yl]oxy}benzonitrile;

2-Methoxy-3-[2-(2-methylpyridin-4-yl)-2H 4H 5H 6H-pyrrolo[3,4-c]pyrazole-5-carbonyl]-4-{[(2R)-1 1 1-trifluoropropan-2-yl]oxy}benzonitrile;

3-[2-(5-Fluoropyridin-3-yl)-2H 4H 5H 6H-pyrrolo[3,4-c]pyrazole-5-carbonyl]-2-methoxy-4-{[(2R)-1 1 1-trifluoropropan-2-yl]oxy}benzonitrile;

3-[2-(5-Fluoropyridin-2-yl)-2H 4H 5H 6H-pyrrolo[3,4-c]pyrazole-5-carbonyl]-2-methoxy-4-{[(2R)-1 1 1-trifluoropropan-2-yl]oxy}benzonitrile;

2-Methoxy-3-[2-(1-methyl-1H-pyrazol-3-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(1-methyl-1H-imidazol-4-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(1-methyl-1H-pyrazol-3-yl)-2H 4H 5H 6H-pyrrolo[3,4-c]pyrazole-5-carbonyl]-4-{[(2S)-1 1 1-trifluoropropan-2-yl]oxy}benzonitrile;

2-Chloro-3-[1-(1-methyl-1H-imidazol-4-yl)-1H 4H 5H 6H-pyrrolo[3,4-c]pyrazole-5-carbonyl]-4-{[(2S)-1 1 1-trifluoropropan-2-yl]oxy}benzonitrile;

2-Chloro-3-[2-(5-fluoro-6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-6-methylpyridin-2-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

3-[1-(5-Fluoro-6-methylpyridin-2-yl)-1H 4H 5H 6H-pyrrolo[3,4-c]pyrazole-5-carbonyl]-2-methoxy-4-{[(2S)-1 1 1-trifluoropropan-2-yl]oxy}benzonitrile;

3-[2-(5-Fluoro-3-methylpyridin-2-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(5-fluoro-3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

2-(4-Fluorophenyl)-5-(3-methanesulfonyl-2-methoxy-6-{[(2S)-1 1 1-trifluoropropan-2-yl]oxy}benzoyl)-2H 4H 5H 6H-pyrrolo[3,4-c]pyrazole;

5-Fluoro-2-[5-(3-methanesulfonyl-2-methoxy-6-{[(2S)-1 1 1-trifluoropropan-2-yl]oxy}benzoyl)-2H 4H 5H 6H-pyrrolo[3,4-c]pyrazol-2-yl]pyridine;

5-Fluoro-2-(5-{5-methanesulfonyl-2-[(1 1 1-trifluoropropan-2-yl)oxy]benzoyl}-2H 4H 5H 6H-pyrrolo[3,4-c]pyrazol-2-yl)pyridine;

2-(4-Fluorophenyl)-5-{5-methanesulfonyl-2-[(1 1 1-trifluoropropan-2-yl)oxy]benzoyl}-2H 4H 5H 6H-pyrrolo[3,4-c]pyrazole;

2-Chloro-3-[2-(5-fluoro-4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-4-methylpyridin-2-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Methoxy-4-{[(2S)-1 1 1-trifluoropropan-2-yl]oxy}-3-[2-(trimethyl-1H-pyrazol-4-yl)-2H 4H 5H 6H-pyrrolo[3,4-c]pyrazole-5-carbonyl]benzonitrile;

2-Chloro-4-{[(2S)-1 1 1-trifluoropropan-2-yl]oxy}-3-[2-(trimethyl-1H-pyrazol-4-yl)-2H 4H 5H 6H-pyrrolo[3,4-c]pyrazole-5-carbonyl]benzonitrile;

2-Methoxy-3-[2-(2-methylpyridin-4-yl)-2H 4H 5H 6H-pyrrolo[3,4-c]pyrazole-5-carbonyl]-4-(2 2 2-trifluoroethoxy)benzonitrile;

2-Methoxy-3-[1-(2-methyl pyridin-4-yl)-1H 4H 5H 6H-pyrrolo[3,4-c]pyrazole-5-carbonyl]-4-{[(2S)-1 1 1-trifluoropropan-2-yl]oxy}benzonitrile;

2-Chloro-3-[1-(2-methylpyridin-4-yl)-1H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoropyridin-3-yl)-2H 4H 5H 6H-pyrrolo[3,4-c]pyrazole-5-carbonyl]-2-methoxy-4-(2 2 2-trifluoroethoxy)benzonitrile;

3-[2-(3-Fluoropyridin-2-yl)-2H 4H 5H 6H-pyrrolo[3,4-c]pyrazole-5-carbonyl]-2-methoxy-4-(2 2 2-trifluoroethoxy)benzonitrile;

3-[2-(5-Fluoro-2-methoxypyridin-3-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

2-Chloro-3-[2-(5-fluoro-2-methoxypyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

3-[1-(5-Fluoro-6-methoxypyridin-3-yl)-1H 4H 5H 6H-pyrrolo[3,4-c]pyrazole-5-carbonyl]-2-methoxy-4-{[(2S)-1 1 1-trifluoropropan-2-yl]oxy}benzonitrile;

3-[2-(5-Fluoro-6-methoxypyridin-3-yl)-2H 4H 5H 6H-pyrrolo[3,4-c]pyrazole-5-carbonyl]-2-methoxy-4-{[(2S)-1 1 1-trifluoropropan-2-yl]oxy}benzonitrile;

4-(Cyclopropylmethoxy)-3-[2-(4-fluorophenyl)-2H 4H 5H 6H-pyrrolo[3,4-c]pyrazole-5-carbonyl]-2-methoxybenzonitrile;

4-(Cyclopropylmethoxy)-3-[2-(5-fluoropyridin-2-yl)-2H 4H 5H 6H-pyrrolo[3,4-c]pyrazole-5-carbonyl]-2-methoxybenzonitrile;

4-(Cyclopropylmethoxy)-3-[2-(5-fluoropyridin-3-yl)-2H 4H 5H 6H-pyrrolo[3,4-c]pyrazole-5-carbonyl]-2-methoxybenzonitrile;

4-(2 2-Dimethylpropoxy)-3-[2-(5-fluoropyridin-2-yl)-2H 4H 5H 6H-pyrrolo[3,4-c]pyrazole-5-carbonyl]-2-methoxybenzonitrile;

4-(2 2-Dimethylpropoxy)-3-[2-(5-fluoropyridin-3-yl)-2H 4H 5H 6H-pyrrolo[3,4-c]pyrazole-5-carbonyl]-2-methoxybenzonitrile;

2-Methoxy-3-{2-phenyl-2H 4H 5H 6H-pyrrolo[3,4-c]pyrazole-5-carbonyl}-4-{[(2S)-1 1 1-trifluoropropan-2-yl]oxy}benzonitrile;

2-Methoxy-3-{2-phenyl-2H 4H 5H 6H-pyrrolo[3,4-c]pyrazole-5-carbonyl}-4-(propan-2-yloxy)benzonitrile;

3-[2-(5-Fluoropyridin-2-yl)-2H 4H 5H 6H-pyrrolo[3,4-c]pyrazole-5-carbonyl]-2-methoxy-4-(propan-2-yloxy)benzonitrile;

3-[2-(5-Fluoropyridin-3-yl)-2H 4H 5H 6H-pyrrolo[3,4-c]pyrazole-5-carbonyl]-2-methoxy-4-(propan-2-yloxy)benzonitrile;

2-Methoxy-3-[2-(6-methylpyridin-2-yl)-2H 4H 5H 6H-pyrrolo[3,4-c]pyrazole-5-carbonyl]-4-(propan-2-yloxy)benzonitrile;

2-Chloro-3-{2-phenyl-2H 4H 5H 6H-pyrrolo[3,4-c]pyrazole-5-carbonyl}-4-{[(2S)-1 1 1-trifluoropropan-2-yl]oxy}benzonitrile;

2-Methoxy-3-[2-(2-methylpyridin-4-yl)-2H 4H 5H 6H-pyrrolo[3,4-c]pyrazole-5-carbonyl]-4-(propan-2-yloxy)benzonitrile;

4-(2 2-Difluoroethoxy)-2-methoxy-3-{2-phenyl-2H 4H 5H 6H-pyrrolo[3,4-c]pyrazole-5-carbonyl}benzonitrile;

4-(2 2-Difluoroethoxy)-3-[2-(5-fluoropyridin-2-yl)-2H 4H 5H 6H-pyrrolo[3,4-c]pyrazole-5-carbonyl]-2-methoxybenzonitrile;

4-(2 2-Difluoroethoxy)-3-[2-(5-fluoropyridin-3-yl)-2H 4H 5H 6H-pyrrolo[3,4-c]pyrazole-5-carbonyl]-2-methoxybenzonitrile;

4-(2 2-Difluoroethoxy)-2-methoxy-3-[2-(6-methylpyridin-2-yl)-2H 4H 5H 6H-pyrrolo[3,4-c]pyrazole-5-carbonyl]benzonitrile;

4-(2 2-Difluoroethoxy)-2-methoxy-3-[2-(2-methylpyridin-4-yl)-2H 4H 5H 6H-pyrrolo[3,4-c]pyrazole-5-carbonyl]benzonitrile;

3-{2-Phenyl-2H 4H 5H 6H-pyrrolo[3,4-c]pyrazole-5-carbonyl}-4-(propan-2-yloxy)benzonitrile;

3-[2-(5-Fluoropyridin-2-yl)-2H 4H 5H 6H-pyrrolo[3,4-c]pyrazole-5-carbonyl]-4-(propan-2-yloxy)benzonitrile;

3-[2-(5-Fluoropyridin-3-yl)-2H 4H 5H 6H-pyrrolo[3,4-c]pyrazole-5-carbonyl]-4-(propan-2-yloxy)benzonitrile;

3-[2-(2-Methylpyridin-4-yl)-2H 4H 5H 6H-pyrrolo[3,4-c]pyrazole-5-carbonyl]-4-(propan-2-yloxy)benzonitrile;

3-[2-(6-Methylpyridin-2-yl)-2H 4H 5H 6H-pyrrolo[3,4-c]pyrazole-5-carbonyl]-4-(propan-2-yloxy)benzonitrile;

3-[2-(5-Fluoro-6-methylpyridin-2-yl)-2H 4H 5H 6H-pyrrolo[3,4-c]pyrazole-5-carbonyl]-4-(propan-2-yloxy)benzonitrile;

2-(4-Fluorophenyl)-5-(5-methanesulfonyl-2-{[(2S)-1 1 1-trifluoropropan-2-yl]oxy}benzoyl)-2H 4H 5H 6H-pyrrolo[3,4-c]pyrazole;

5-[2-(2 2-Dimethylpropoxy)-5-methanesulfonylbenzoyl]-2-(4-fluorophenyl)-2H 4H 5H 6H-pyrrolo[3,4-c]pyrazole;

3-[2-(5-Fluoropyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoropyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(6-Methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-6-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-3-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(4-Methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-4-methylpyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(Pyridin-2-yl)-2H 4H 5H 6H-pyrrolo[3,4-c]pyrazole-5-carbonyl]-4-{[(2S)-1 1 1-trifluoropropan-2-yl]oxy}benzonitrile;

5-(2-Cyclopentyl-5-methanesulfonylbenzoyl)-2-(4-fluorophenyl)-2H 4H 5H 6H-pyrrolo[3,4-c]pyrazole;

3-[2-(5-Fluoro-6-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-4-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(2-Methylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(5-Fluoro-2-methylpyridin-3-yl)-2H 4H 5H 6H-pyrrolo[3,4-c]pyrazole-5-carbonyl]-4-{[(2S)-1 1 1-trifluoropropan-2-yl]oxy}benzonitrile;

5-(5-Methanesulfonyl-2-{[(2S)-1 1 1-trifluoropropan-2-yl]oxy}benzoyl)-2-phenyl-2H 4H 5H 6H-pyrrolo[3,4-c]pyrazole;

4-[5-(5-Methanesulfonyl-2-{[(2S)-1 1 1-trifluoropropan-2-yl]oxy}benzoyl)-2H 4H 5H 6H-pyrrolo[3,4-c]pyrazol-2-yl]-2-methylpyridine;

2-[5-(5-Methanesulfonyl-2-{[(2S)-1 1 1-trifluoropropan-2-yl]oxy}benzoyl)-2H 4H 5H 6H-pyrrolo[3,4-c]pyrazol-2-yl]-4-methylpyridine;

3-Fluoro-5-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]pyridine;

5-Fluoro-2-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]-4-methylpyridine;

2-[5-(5-Methanesulfonyl-2-{[(2S)-1 1 1-trifluoropropan-2-yl]oxy}benzoyl)-2H 4H 5H 6H-pyrrolo[3,4-c]pyrazol-2-yl]-6-methylpyridine;

5-Fluoro-2-[5-(5-methanesulfonyl-2-{[(2S)-1 1 1-trifluoropropan-2-yl]oxy}benzoyl)-2H 4H 5H 6H-pyrrolo[3,4-c]pyrazol-2-yl]-3-methylpyridine;

3-Fluoro-6-[5-(5-methane sulfonyl-2-{[(2S)-1 1 1-trifluoropropan-2-yl]oxy}benzoyl)-2H 4H 5H 6H-pyrrolo[3,4-c]pyrazol-2-yl]-2-methylpyridine;

1-{2-[2-(4-Fluorophenyl)-2H 4H 5H 6H-pyrrolo[3,4-c]pyrazole-5-carbonyl]-4-methanesulfonylphenyl}piperidine;

3-[2-(2-Methoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[1-(2-Methoxypyridin-4-yl)-1H 4H 5H 6H-pyrrolo[3,4-c]pyrazole-5-carbonyl]-4-{[(2S)-1 1 1-trifluoropropan-2-yl]oxy}benzonitrile;

3-[1-(2-Methoxypyridin-4-yl)-1H 4H 5H 6H-pyrrolo[3,4-c]pyrazole-5-carbonyl]-4-(propan-2-yloxy)benzonitrile;

3-[2-(2-Ethylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(2-Ethylpyridin-4-yl)-2H 4H 5H 6H-pyrrolo[3,4-c]pyrazole-5-carbonyl]-4-(propan-2-yloxy)benzonitrile;

3-[2-(2-Methoxypyridin-4-yl)-2H 4H 5H 6H-pyrrolo[3,4-c]pyrazole-5-carbonyl]-4-(propan-2-yloxy)benzonitrile;

3-[2-(2-Ethoxypyridin-4-yl)-2H 4H 5H 6H-pyrrolo[3,4-c]pyrazole-5-carbonyl]-4-(propan-2-yloxy)benzonitrile;

3-[2-(2-Ethoxypyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

3-{2-[2-(Propan-2-yloxy)pyridin-4-yl]-2H 4H 5H 6H-pyrrolo[3,4-c]pyrazole-5-carbonyl}-4-{[(2S)-1 1 1-trifluoropropan-2-yl]oxy}benzonitrile;

4-(Propan-2-yloxy)-3-{2-[2-(propan-2-yloxy)pyridin-4-yl]-2H 4H 5H 6H-pyrrolo[3,4-c]pyrazole-5-carbonyl}benzonitrile;

3-{2-[2-(Propan-2-yl)pyridin-4-yl]-2H 4H 5H 6H-pyrrolo[3,4-c]pyrazole-5-carbonyl}-4-(propan-2-yloxy)benzonitrile;

3-{2-[2-(Propan-2-yl)pyridin-4-yl]-2H 4H 5H 6H-pyrrolo[3,4-c]pyrazole-5-carbonyl}-4-{[(2S)-1 1 1-trifluoropropan-2-yl]oxy}benzonitrile;

4-(1-Fluorocyclopentyl)-2-methoxy-3-[2-(2-methylpyridin-4-yl)-2H 4H 5H 6H-pyrrolo[3,4-c]pyrazole-5-carbonyl]benzonitrile;

4-(1-Fluorocyclopentyl)-3-[2-(5-fluoropyridin-3-yl)-2H 4H 5H 6H-pyrrolo[3,4-c]pyrazole-5-carbonyl]-2-methoxybenzonitrile;

3-[2-(2-Fluoro-2-methylpropyl)-2H 4H 5H 6H-pyrrolo[3,4-c]pyrazole-5-carbonyl]-4-{[(2S)-1 1 1-trifluoropropan-2-yl]oxy}benzonitrile;

3-[1-(2-Fluoro-2-methylpropyl)-1H 4H 5H 6H-pyrrolo[3,4-c]pyrazole-5-carbonyl]-4-{[(2S)-1 1 1-trifluoropropan-2-yl]oxy}benzonitrile;

3-[2-(2 6-Dimethylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(2 6-Dimethylpyridin-4-yl)-2H 4H 5H 6H-pyrrolo[3,4-c]pyrazole-5-carbonyl]-4-(propan-2-yloxy)benzonitrile;

3-{2-Benzyl-2H 4H 5H 6H-pyrrolo[3,4-c]pyrazole-5-carbonyl}-4-{[(2S)-1 1 1-trifluoropropan-2-yl]oxy}benzonitrile;

3-{1-Benzyl-1H 4H 5H 6H-pyrrolo[3,4-c]pyrazole-5-carbonyl}-4-{[(2S)-1 1 1-trifluoropropan-2-yl]oxy}benzonitrile;

3-[1-(Propan-2-yl)-1H 4H 5H 6H-pyrrolo[3,4-c]pyrazole-5-carbonyl]-4-{[(2S)-1 1 1-trifluoropropan-2-yl]oxy}benzonitrile;

3-[2-(Propan-2-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(2-Methylpropyl)-2H 4H 5H 6H-pyrrolo[3,4-c]pyrazole-5-carbonyl]-4-{[(2S)-1 1 1-trifluoropropan-2-yl]oxy}benzonitrile;

3-[1-(2-Methylpropyl)-1H 4H 5H 6H-pyrrolo[3,4-c]pyrazole-5-carbonyl]-4-{[(2S)-1 1 1-trifluoropropan-2-yl]oxy}benzonitrile;

3-{1-Cyclopentyl-1H 4H 5H 6H-pyrrolo[3,4-c]pyrazole-5-carbonyl}-4-{[(2S)-1 1 1-trifluoropropan-2-yl]oxy}benzonitrile;

3-{2-Cyclopentyl-2H 4H 5H 6H-pyrrolo[3,4-c]pyrazole-5-carbonyl}-4-{[(2S)-1 1 1-trifluoropropan-2-yl]oxy}benzonitrile;

3-[2-(2 4-Difluorophenyl)-2H 4H 5H 6H-pyrrolo[3,4-c]pyrazole-5-carbonyl]-4-(propan-2-yloxy)benzonitrile;

3-[2-(2 4-Difluorophenyl)-2H 4H 5H 6H-pyrrolo[3,4-c]pyrazole-5-carbonyl]-4-{[(2S)-1 1 1-trifluoropropan-2-yl]oxy}benzonitrile;

3-[1-(3-Methoxypropyl)-1H 4H 5H 6H-pyrrolo[3,4-c]pyrazole-5-carbonyl]-4-{[(2S)-1 1 1-trifluoropropan-2-yl]oxy}benzonitrile;

3-[2-(3-Methoxypropyl)-2H 4H 5H 6H-pyrrolo[3,4-c] pyrazole-5-carbonyl]-4-{[(2S)-1 1 1-trifluoropropan-2-yl]oxy}benzonitrile;

3-[1-(Oxan-4-ylmethyl)-1H 4H 5H 6H-pyrrolo[3,4-c] pyrazole-5-carbonyl]-4-{[(2S)-1 1 1-trifluoropropan-2-yl]oxy}benzonitrile;

3-[2-(2-Fluoro-3-methylphenyl)-2H 4H 5H 6H-pyrrolo[3,4-c]pyrazole-5-carbonyl]-4-{[(2S)-1 1 1-trifluoropropan-2-yl]oxy}benzonitrile;

3-[2-(Oxan-4-ylmethyl)-2H 4H 5H 6H-pyrrolo[3,4-c] pyrazole-5-carbonyl]-4-{[(2S)-1 1 1-trifluoropropan-2-yl]oxy}benzonitrile;

3-[2-(2-Fluorophenyl)-2H 4H 5H 6H-pyrrolo[3,4-c]pyrazole-5-carbonyl]-4-{[(2S)-1 1 1-trifluoropropan-2-yl]oxy}benzonitrile;

2-Benzyl-5-(5-methanesulfonyl-2-{[(2S)-1 1 1-trifluoropropan-2-yl]oxy}benzoyl)-2H 4H 5H 6H-pyrrolo[3,4-c]pyrazole;

5-(5-Methanesulfonyl-2-{[(2S)-1 1 1-trifluoropropan-2-yl]oxy}benzoyl)-2-(2-methylpropyl)-2H 4H 5H 6H-pyrrolo[3,4-c]pyrazole;

5-[5-Methanesulfonyl-2-(propan-2-yloxy)benzoyl]-2-(2-methylpropyl)-2H 4H 5H 6H-pyrrolo[3,4-c]pyrazole;

3-[2-(Cyclobutylmethyl)-2H 4H 5H 6H-pyrrolo[3,4-c] pyrazole-5-carbonyl]-4-{[(2S)-1 1 1-trifluoropropan-2-yl]oxy}benzonitrile;

3-{2-Cyclohexyl-2H 4H 5H 6H-pyrrolo[3,4-c]pyrazole-5-carbonyl}-4-{[(2S)-1 1 1-trifluoropropan-2-yl]oxy}benzonitrile;

2-Cyclohexyl-5-[5-methanesulfonyl-2-(propan-2-yloxy) benzoyl]-2H 4H 5H 6H-pyrrolo[3,4-c]pyrazole;

3-[2-(2-Cyclopropylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

3-[2-(2-Cyclopropylpyridin-4-yl)-2H 4H 5H 6H-pyrrolo[3,4-c]pyrazole-5-carbonyl]-4-(propan-2-yloxy)benzonitrile;

2-Cyclopentyl-5-[5-methanesulfonyl-2-(propan-2-yloxy) benzoyl]-2H 4H 5H 6H-pyrrolo[3,4-c]pyrazole;

2-Cyclopentyl-5-(5-methanesulfonyl-2-{[(2S)-1 1 1-trifluoropropan-2-yl]oxy}benzoyl)-2H 4H 5H 6H-pyrrolo[3,4-c]pyrazole;

3-[2-(Oxan-4-yl)-2H 4H 5H 6H-pyrrolo[3,4-c]pyrazole-5-carbonyl]-4-(propan-2-yloxy)benzonitrile;

2-(Cyclobutylmethyl)-5-(5-methanesulfonyl-2-{[(2S)-1 1 1-trifluoropropan-2-yl]Oxy}benzoyl)-2H 4H 5H 6H-pyrrolo[3,4-c]pyrazole;

2-(Cyclobutylmethyl)-5-[5-methanesulfonyl-2-(propan-2-yloxy)benzoyl]-2H 4H 5H 6H-pyrrolo[3,4-c]pyrazole;

3-[2-(Cyclobutylmethyl)-2H 4H 5H 6H-pyrrolo[3,4-c] pyrazole-5-carbonyl]-4-(propan-2-yloxy)benzonitrile;

3-[2-(Oxan-4-yl)-2H 4H 5H 6H-pyrrolo[3,4-c]pyrazole-5-carbonyl]-4-{[(2S)-1 1 1-trifluoropropan-2-yl]oxy}benzonitrile;

2-(Cyclopentylmethyl)-5-(5-methanesulfonyl-2-{[(2S)-1 1 1-trifluoropropan-2-yl]oxy}benzoyl)-2H 4H 5H 6H-pyrrolo[3,4-c]pyrazole;

3-[2-(Cyclopentylmethyl)-2H 4H 5H 6H-pyrrolo[3,4-c] pyrazole-5-carbonyl]-4-{[(2S)-1 1 1-trifluoropropan-2-yl]oxy}benzonitrile;

2-Cyclopentyl-5-[5-(ethanesulfonyl)-2-(propan-2-yloxy) benzoyl]-2H 4H 5H 6H-pyrrolo[3,4-c]pyrazole;

3-{2-[(2S)-2-Methylbutyl]-2H 4H 5H 6H-pyrrolo[3,4-c] pyrazole-5-carbonyl}-4-(propan-2-yloxy)benzonitrile;

2-Cyclopentyl-5-[5-(ethanesulfonyl)-2-{[(2S)-1 1 1-trifluoropropan-2-yl]oxy}benzoyl]-2H 4H 5H 6H-pyrrolo[3,4-c]pyrazole;

3-{2-[(2S)-2-Methylbutyl]-2H 4H 5H 6H-pyrrolo[3,4-c] pyrazole-5-carbonyl}-4-{[(2S)-1 1 1-trifluoropropan-2-yl]oxy}benzonitrile;

3-[2-(Oxolan-3-ylmethyl)-2H 4H 5H 6H-pyrrolo[3,4-c] pyrazole-5-carbonyl]-4-{[(2S)-1 1 1-trifluoropropan-2-yl]oxy}benzonitrile;

3-[2-(Oxolan-3-ylmethyl)-2H 4H 5H 6H-pyrrolo[3,4-c] pyrazole-5-carbonyl]-4-(propan-2-yloxy)benzonitrile;

3-[1-(Pyridazin-4-yl)-1H 4H 5H 6H-pyrrolo[3,4-c]pyrazole-5-carbonyl]-4-{[(2S)-1 1 1-trifluoropropan-2-yl] oxy}benzonitrile;

4-(Propan-2-yloxy)-3-[2-(pyridazin-4-yl)-2H 4H 5H 6H-pyrrolo[3,4-c]pyrazole-5-carbonyl]benzonitrile;

3-[2-(Pyridazin-4-yl)-2H 4H 5H 6H-pyrrolo[3,4-c]pyrazole-5-carbonyl]-4-{[(2S)-1 1 1-trifluoropropan-2-yl] oxy}benzonitrile;

3-(2-{Imidazo[1 2-c]pyridin-7-yl}-2H 4H 5H 6H-pyrrolo[3,4-c]pyrazole-5-carbonyl)-4-(propan-2-yloxy)benzonitrile;

3-(2-{Imidazo[1 2-c]pyridin-7-yl}-2H 4H 5H 6H-pyrrolo[3,4-c]pyrazole-5-carbonyl)-4-{[(2S)-1 1 1-trifluoropropan-2-yl]oxy}benzonitrile;

2-(Cyclobutylmethyl)-5-[2-(3-fluorophenyl)-5-methanesulfonylbenzoyl]-2H 4H 5H 6H-pyrrolo[3,4-c]pyrazole;

5-[2-(3-Fluorophenyl)-5-methanesulfonylbenzoyl]-2-(2-methylpropyl)-2H 4H 5H 6H-pyrrolo[3,4-c]pyrazole;

1-{2-[2-(Cyclobutylmethyl)-2H 4H 5H 6H-pyrrolo[3,4-c]pyrazole-5-carbonyl]-4-(ethanesulfonyl)phenyl}-4 4-difluoropiperidine;

4 4-Difluoro-1-(4-methane sulfonyl-2-{2-[(2S)-2-methylbutyl]-2H 4H 5H 6H-pyrrolo[3,4-c]pyrazole-5-carbonyl}phenyl)piperidine;

1-(2-{2-Cyclopentyl-2H 4H 5H 6H-pyrrolo[3,4-c]pyrazole-5-carbonyl}-4-methanesulfonylphenyl)-4 4-difluoropiperidine;

1-{2-[2-(Cyclobutylmethyl)-2H 4H 5H 6H-pyrrolo[3,4-c]pyrazole-5-carbonyl]-4-methanesulfonylphenyl}-4 4-difluoropiperidine;

4-Difluoro-1-{4-methanesulfonyl-2-[2-(2-methylpropyl)-2H 4H 5H 6H-pyrrolo[3,4-c]pyrazole-5-carbonyl] phenyl}piperidine;

4 4-Difluoro-1-{4-methanesulfonyl-2-[2-(propan-2-yl)-2H 4H 5H 6H-pyrrolo[3,4-c]pyrazole-5-carbonyl] phenyl}piperidine;

2-(2-Fluoro-2-methylpropyl)-5-[2-(3-fluorophenyl)-5-methanesulfonylbenzoyl]-2H 4H 5H 6H-pyrrolo[3,4-c] pyrazole;

5-{5-Methanesulfonyl-2-[(3-methyloxetan-3-yl) methoxy]benzoyl}-2-phenyl-2H 4H 5H 6H-pyrrolo[3, 4-c]pyrazole;

2-(2-Fluorophenyl)-5-{5-methanesulfonyl-2-[(3-methyloxetan-3-yl)methoxy]benzoyl}-2H 4H 5H 6H-pyrrolo [3,4-c]pyrazole;

5-{5-Methanesulfonyl-2-[(3-methyloxetan-3-yl) methoxy]benzoyl}-2-(3-methylphenyl)-2H 4H 5H 6H-pyrrolo[3,4-c]pyrazole;

2-[2-Fluoro-3-(trifluoromethyl)phenyl]-5-{5-methanesulfonyl-2-[(3-methyloxetan-3-yl)methoxy]benzoyl}-2H 4H 5H 6H-pyrrolo[3,4-c]pyrazole;

2-(5-Chloro-2-fluorophenyl)-5-{5-methanesulfonyl-2-[(3-methyloxetan-3-yl)methoxy]benzoyl}-2H 4H 5H 6H-pyrrolo[3,4-c]pyrazole;

2-(4-Fluorophenyl)-5-{5-methanesulfonyl-2-[(3-methyl-oxetan-3-yl)methoxy]benzoyl}-2H 4H 5H 6H-pyrrolo[3,4-c]pyrazole;

2-(2-Fluoro-3-methylphenyl)-5-{5-methanesulfonyl-2-[(3-methyloxetan-3-yl)methoxy]benzoyl}-2H 4H 5H 6H-pyrrolo[3,4-c]pyrazole;

2-(2-Fluoro-5-methylphenyl)-5-{5-methanesulfonyl-2-[(3-methyloxetan-3-yl)methoxy]benzoyl}-2H 4H 5H 6H-pyrrolo[3,4-c]pyrazole;

3-[2-(Pyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

4-(Propan-2-yloxy)-3-[1-(2 2 2-trifluoroethyl)-1H 4H 5H 6H-pyrrolo[3,4-c]pyrazole-5-carbonyl]benzonitrile;

5-[2-(3-Fluorophenyl)-5-methanesulfonylbenzoyl]-1-(2 2 2-trifluoroethyl)-1H 4H 5H 6H-pyrrolo[3,4-c]pyrazole;

1-{Imidazo[1 2-a]pyridin-5-yl}-5-(5-methanesulfonyl-2-{[(2S)-1 1 1-trifluoropropan-2-yl]oxy}benzoyl)-1H 4H 5H 6H-pyrrolo[3,4-c]pyrazole;

4-(Propan-2-yloxy)-3-[2-(pyridin-4-yl)-2H 4H 5H 6H-pyrrolo[3,4-c]pyrazole-5-carbonyl]benzonitrile;

5-[2-(3-Fluorophenyl)-5-methanesulfonylbenzoyl]-2-(oxan-4-yl)-2H 4H 5H 6H-pyrrolo[3,4-c]pyrazole;

2-(Cyclopropylmethyl)-5-[2-(3-fluorophenyl)-5-methanesulfonylbenzoyl]-2H 4H 5H 6H-pyrrolo[3,4-c]pyrazole;

3-[2-(Cyclopropylmethyl)-2H 4H 5H 6H-pyrrolo[3,4-c]pyrazole-5-carbonyl]-4-(propan-2-yloxy)benzonitrile;

3-[2-(Cyclopropylmethyl)-2H 4H 5H 6H-pyrrolo[3,4-c]pyrazole-5-carbonyl]-4-{[(2S)-1 1 1-trifluoropropan-2-yl]oxy}benzonitrile;

1-(Cyclopropylmethyl)-5-[2-(3-fluorophenyl)-5-methanesulfonylbenzoy]-1H 4H 5H 6H-pyrrolo[3,4-c]pyrazole;

2-[(2 2-Difluorocyclopropyl)methyl]-5-[2-(3-fluorophenyl)-5-methanesulfonylbenzoyl]-2H 4H 5H 6H-pyrrolo[3,4-c]pyrazole;

1-[(2 2-Difluorocyclopropyl)methyl]-5-[2-(3-fluorophenyl)-5-methanesulfonylbenzoyl]-1H 4H 5H 6H-pyrrolo[3,4-c]pyrazole;

2-[(2 2-Difluorocyclopropyl)methyl]-5-(5-methanesulfonyl-2-{[(2S)-1 1 1-trifluoropropan-2-yl]Oxy}benzoyl)-2H 4H 5H 6H-pyrrolo[3,4-c]pyrazole;

3-{2-[(2 2-Difluorocyclopropyl)methyl]-2H 4H 5H 6H-pyrrolo[3,4-c]pyrazole-5-carbonyl]-4-(propan-2-yloxy)benzonitrile;

3-{2-[(2 2-Difluorocyclopropyl)methyl]-2H 4H 5H 6H-pyrrolo[3,4-c]pyrazole-5-carbonyl}-4-{[(2S)-1 1 1-trifluoropropan-2-yl]oxy}benzonitrile;

3-[1-(Oxan-4-yl)-1H 4H 5H 6H-pyrrolo[3,4-c]pyrazole-5-carbonyl]-4-{[(2S)-1 1 1-trifluoropropan-2-yl]oxy}benzonitrile;

3-[2-(2-Cyclobutylpyridin-4-yl)-2H 4H 5H 6H-pyrrolo[3,4-c]pyrazole-5-carbonyl]-4-(propan-2-yloxy)benzonitrile;

3-[2-(2-Cyclobutylpyridin-4-yl)-2H 4H 5H 6H-pyrrolo[3,4-c]pyrazole-5-carbonyl]-4-{[(2S)-1 1 1-trifluoropropan-2-yl]oxy}benzonitrile;

2-[(3 3-Difluorocyclobutyl)methyl]-5-[5-methanesulfonyl-2-(propan-2-yloxy)benzoyl]-2H 4H 5H 6H-pyrrolo[3,4-c]pyrazole;

3-{2-[(3 3-Difluorocyclobutyl)methyl]-2H 4H 5H 6H-pyrrolo[3,4-c]pyrazole-5-carbonyl-}4-{[(2S)-1 1 1-trifluoropropan-2-yl]oxy}benzonitrile;

2-[(3 3-Difluorocyclobutyl)methyl]-5-(5-methanesulfonyl-2-{[(2S)-1 1 1-trifluoropropan-2-yl]oxy}benzoyl)-2H 4H 5H 6H-pyrrolo[3,4-c]pyrazole;

2-[(3 3-Difluorocyclobutyl)methyl]-5-[2-(3-fluorophenyl)-5-methanesulfonylbenzoyl]-2H 4H 5H 6H-pyrrolo[3,4-c]pyrazole;

5-[5-(5-Cyano-2-{[(2S)-1 1 1-trifluoropropan-2-yl]oxy}benzoyl)-2H 4H 5H 6H-pyrrolo[3,4-c]pyrazol-2-yl]pyridine-2-carbonitrile;

5-{5-[5-Cyano-2-(propan-2-yloxy)benzoyl]-2H 4H 5H 6H-pyrrolo[3,4-c]pyrazol-2-yl}pyridine-2-carbonitrile;

4-[5-(5-Cyano-2-{[(2S)-1 1 1-trifluoropropan-2-yl]oxy}benzoyl)-2H 4H 5H 6H-pyrrolo[3,4-c]pyrazol-2-yl]pyridine-2-carbonitrile;

4-{5-[5-Cyano-2-(propan-2-yloxy)benzoyl]-2H 4H 5H 6H-pyrrolo[3,4-c]pyrazol-2-yl}pyridine-2-carbonitrile;

2-(4 4-Difluorocyclohexyl)-5-[2-(3-fluorophenyl)-5-methanesulfonylbenzoyl]-2H 4H 5H 6H-pyrrolo[3,4-c]pyrazole;

2-(4 4-Difluorocyclohexyl)-5-[5-methanesulfonyl-2-(propan-2-yloxy)benzoyl]-2H 4H 5H 6H-pyrrolo[3,4-c]pyrazole;

2-(4 4-Difluorocyclohexyl)-5-(5-methanesulfonyl-2-{[(2S)-1 1 1-trifluoropropan-2-yl]Oxy}benzoyl)-2H 4H 5H 6H-pyrrolo[3,4-c]pyrazole;

3-[2-(4 4-Difluorocyclohexyl)-2H 4H 5H 6H-pyrrolo[3,4-c]pyrazole-5-carbonyl]-4-{[(2S)-1 1 1-trifluoropropan-2-yl]oxy}benzonitrile;

2-(4-Fluorophenyl)-5-{5-methanesulfonyl-2-[(1 1 1-trifluoro-2-methylpropan-2-yl)oxy]benzoyl}-2H 4H 5H 6H-pyrrolo[3,4-c]pyrazole;

2-Chloro-3-[2-(4-fluorophenyl)-2H 4H 5H 6H-pyrrolo[3,4-c]pyrazole-5-carbonyl]-4-[(1 1 1-trifluoropropan-2-yl)oxy]benzamide;

4-Cyclopentyl-3-[2-(4-fluorophenyl)-2H 4H 5H 6H-pyrrolo[3,4-c]pyrazole-5-carbonyl]-2-methoxybenzonitrile;

4-Cyclopentyl-3-[2-(5-fluoropyridin-3-yl)-2H 4H 5H 6H-pyrrolo[3,4-c]pyrazole-5-carbonyl]-2-methoxybenzonitrile;

4-(4 4-Difluoropiperidin-1-yl)-3-[2-(4-fluorophenyl)-2H 4H 5H 6H-pyrrolo[3,4-c]pyrazole-5-carbonyl]-2-methoxybenzonitrile;

4-(2 2-Dimethylpropoxy)-3-[2-(4-fluorophenyl)-2H 4H 5H 6H-pyrrolo[3,4-c]pyrazole-5-carbonyl]-2-methoxybenzonitrile;

3-[2-(4-Fluorophenyl)-2H 4H 5H 6H-pyrrolo[3,4-c]pyrazole-5-carbonyl]-2-methoxy-4-[(1-methylcyclopropyl)methoxy]benzonitrile;

4-(Cyclopentyloxy)-3-[2-(4-fluorophenyl)-2H 4H 5H 6H-pyrrolo[3,4-c]pyrazole-5-carbonyl]-2-methoxybenzonitrile;

4-(3 3-Difluoropyrrolidin-1-yl)-3-[2-(4-fluorophenyl)-2H 4H 5H 6H-pyrrolo[3,4-c]pyrazole-5-carbonyl]-2-methoxybenzonitrile;

3-[2-(4-Fluorophenyl)-2H 4H 5H 6H-pyrrolo[3,4-c]pyrazole-5-carbonyl]-2-methoxy-4-(propan-2-yloxy)benzonitrile;

3-[2-(4-Fluorophenyl)-2H 4H 5H 6H-pyrrolo[3,4-c]pyrazole-5-carbonyl]-2-methoxy-4-[(1 1 1-trifluoro-2-methylpropan-2-yl)oxy]benzonitrile;

3-[2-(4-Fluorophenyl)-2H 4H 5H 6H-pyrrolo[3,4-c]pyrazole-5-carbonyl]-4-[(1-fluoropropan-2-yl)oxy]-2-methoxybenzonitrile;

3-[2-(4-Fluorophenyl)-2H 4H 5H 6H-pyrrolo[3,4-c]pyrazole-5-carbonyl]-2-methoxy-4-(pentan-3-yloxy)benzonitrile;

3-[2-(4-Fluorophenyl)-2H 4H 5H 6H-pyrrolo[3,4-c]pyrazole-5-carbonyl]-2-methoxy-4-(oxetan-3-yloxy)benzonitrile;

4-(2 2-Difluoroethoxy)-3-[2-(4-fluorophenyl)-2H 4H 5H 6H-pyrrolo[3,4-c]pyrazole-5-carbonyl]-2-methoxybenzonitrile;
3-[2-(4-Fluorophenyl)-2H 4H 5H 6H-pyrrolo[3,4-c]pyrazole-5-carbonyl]-2-methoxy-4-(pentan-2-yloxy)benzonitrile;
3-[2-(4-Fluorophenyl)-2H 4H 5H 6H-pyrrolo[3,4-c]pyrazole-5-carbonyl]-2-methoxy-4-(2-methylpropoxy)benzonitrile;
3-[2-(4-Fluorophenyl)-2H 4H 5H 6H-pyrrolo[3,4-c]pyrazole-5-carbonyl]-2-methoxy-4-[(3-methylbutan-2-yl)oxy]benzonitrile;
4-(1-Cyclopropylethoxy)-3-[2-(4-fluorophenyl)-2H 4H 5H 6H-pyrrolo[3,4-c]pyrazole-5-carbonyl]-2-methoxybenzonitrile;
3-[2-(4-Fluorophenyl)-2H 4H 5H 6H-pyrrolo[3,4-c]pyrazole-5-carbonyl]-2-methoxy-4-(1-methylcyclopropoxy)benzonitrile;
4-(2 2-Dimethylpropoxy)-3-[2-(4-fluorophenyl)-2H 4H 5H 6H-pyrrolo[3,4-c]pyrazole-5-carbonyl]benzonitrile;
4-(2 2-Difluoroethoxy)-3-[2-(4-fluorophenyl)-2H 4H 5H 6H-pyrrolo[3,4-c]pyrazole-5-carbonyl]benzonitrile;
3-[2-(4-Fluorophenyl)-2H 4H 5H 6H-pyrrolo[3,4-c]pyrazole-5-carbonyl]-4-(2 2 2-trifluoroethoxy)benzonitrile;
3-[2-(4-Fluorophenyl)-2H 4H 5H 6H-pyrrolo[3,4-c]pyrazole-5-carbonyl]-4-(propan-2-yloxy)benzonitrile;
3-[2-(4-Fluorophenyl)-2H 4H 5H 6H-pyrrolo[3,4-c]pyrazole-5-carbonyl]-4-{[(2S)-1 1 1-trifluoropropan-2-yl]oxy}benzonitrile;
4-(Cyclopropylmethoxy)-3-[2-(4-fluorophenyl)-2H 4H 5H 6H-pyrrolo[3,4-c]pyrazole-5-carbonyl]benzonitrile;
3-[2-(4-Fluorophenyl)-2H 4H 5H 6H-pyrrolo[3,4-c]pyrazole-5-carbonyl]-4-[(1 1 1-trifluoro-2-methylpropan-2-yl)oxy]benzonitrile;
3-[2-(5-Fluoro-6-methylpyridin-2-yl)-2H 4H 5H 6H-pyrrolo[3,4-c]pyrazole-5-carbonyl]-2-methoxy-4-(2 2 2-trifluoroethoxy)benzonitrile;
4-(2 2-Difluoroethoxy)-3-[2-(5-fluoro-6-methylpyridin-2-yl)-2H 4H 5H 6H-pyrrolo[3,4-c]pyrazole-5-carbonyl]-2-methoxybenzonitrile;
3-[2-(5-Fluoro-6-methylpyridin-2-yl)-2H 4H 5H 6H-pyrrolo[3,4-c]pyrazole-5-carbonyl]-2-methoxy-4-(propan-2-yloxy)benzonitrile;
3-[2-(5-Fluoro-6-methylpyridin-2-yl)-2H 4H 5H 6H-pyrrolo[3,4-c]pyrazole-5-carbonyl]-2-methoxy-4-[(3-methyloxetan-3-yl)methoxy]benzonitrile;
3-[2-(5-Fluoro-6-methylpyridin-2-yl)-2H 4H 5H 6H-pyrrolo[3,4-c]pyrazole-5-carbonyl]-2-methoxy-4-(oxetan-3-yloxy)benzonitrile;
4-[(3-Methyloxetan-3-yl)methoxy]-3-[2-(2-methylpyridin-4-yl)-2H 4H 5H 6H-pyrrolo[3,4-c]pyrazole-5-carbonyl]benzonitrile;
3-[2-(2-Methyl pyridin-4-yl)-2H 4H 5H 6H-pyrrolo[3,4-c]pyrazole-5-carbonyl]-4-(2 2 2-trifluoroethoxy)benzonitrile;
4-(Cyclopropylmethoxy)-3-[2-(2-methylpyridin-4-yl)-2H 4H 5H 6H-pyrrolo[3,4-c]pyrazole-5-carbonyl]benzonitrile;
4-(4 4-Difluoropiperidin-1-yl)-3-[2-(2-methylpyridin-4-yl)-2H 4H 5H 6H-pyrrolo[3,4-c]pyrazole-5-carbonyl]benzonitrile;
3-[2-(2-Methylpyridin-4-yl)-2H 4H 5H 6H-pyrrolo[3,4-c]pyrazole-5-carbonyl]-4-[(1 1 1-trifluoro-2-methylpropan-2-yl)oxy]benzonitrile;

3-[2-(2-Ethylpyridin-4-yl)-2H 4H 5H 6H-pyrrolo[3,4-c]pyrazole-5-carbonyl]-4-(2 2 2-trifluoroethoxy)benzonitrile;
4-(Cyclopropylmethoxy)-3-[2-(2-ethylpyridin-4-yl)-2H 4H 5H 6H-pyrrolo[3,4-c]pyrazole-5-carbonyl]benzonitrile;
4-(2 2-Difluoroethoxy)-3-[2-(2-ethylpyridin-4-yl)-2H 4H 5H 6H-pyrrolo[3,4-c]pyrazole-5-carbonyl]benzonitrile;
4-(4 4-Difluoropiperidin-1-yl)-3-[2-(2-ethylpyridin-4-yl)-2H 4H 5H 6H-pyrrolo[3,4-c]pyrazole-5-carbonyl]benzonitrile;
5-{2-[2-(2-Fluorophenyl)-2H 4H 5H 6H-pyrrolo[3,4-c]pyrazole-5-carbonyl]-4-methanesulfonylphenyl}-2-(trifluoromethyl)pyridine;
5-Fluoro-2-{5-[2-(5-fluoropyridin-3-yl)-5-methanesulfonylbenzoyl]-2H 4H 5H 6H-pyrrolo[3,4-c]pyrazol-2-yl}pyridine;
5-Fluoro-2-{5-[5-methanesulfonyl-2-(5-methylpyridin-3-yl)benzoyl]-2H 4H 5H 6H-pyrrolo[3,4-c]pyrazol-2-yl}pyridine;
4-(2-Fluorophenyl)-3-[2-(5-fluoropyridin-3-yl)-2H 4H 5H 6H-pyrrolo[3,4-c]pyrazole-5-carbonyl]benzonitrile;
4-(3-Fluorophenyl)-3-[2-(5-fluoropyridin-3-yl)-2H 4H 5H 6H-pyrrolo[3,4-c]pyrazole-5-carbonyl]benzonitrile;
4-(5-Fluoropyridin-3-yl)-3-[2-(5-fluoropyridin-3-yl)-2H 4H 5H 6H-pyrrolo[3,4-c]pyrazole-5-carbonyl]benzonitrile;
3-[2-(5-Fluoropyridin-3-yl)-2H 4H 5H 6H-pyrrolo[3,4-c]pyrazole-5-carbonyl]-4-(pyridin-3-yl)benzonitrile;
4-(2-Fluorophenyl)-3-[2-(2-methylpyridin-4-yl)-2H 4H 5H 6H-pyrrolo[3,4-c]pyrazole-5-carbonyl]benzonitrile;
(2-(2-Fluorophenyl)pyrrolo[3,4-c]pyrazol-5(2H,4H,6H)-yl)(5-(methylsulfonyl)-2-(pyridin-3-yl)phenyl)methanone;
4-(5-Fluoropyridin-3-yl)-3-[2-(2-methylpyridin-4-yl)-2H 4H 5H 6H-pyrrolo[3,4-c]pyrazole-5-carbonyl]benzonitrile;
4-(3-Fluorophenyl)-3-[2-(oxan-4-yl)-2H 4H 5H 6H-pyrrolo[3,4-c]pyrazole-5-carbonyl]benzonitrile;
4-(3-Methylphenyl)-3-[2-(oxan-4-yl)-2H 4H 5H 6H-pyrrolo[3,4-c]pyrazole-5-carbonyl]benzonitrile;
2-(2-Fluorophenyl)-5-[2-(2-fluorophenyl)-5-methanesulfonylbenzoyl]-2H 4H 5H 6H-pyrrolo[3,4-c]pyrazole;
2-(2-Fluorophenyl)-5-[2-(3-fluorophenyl)-5-methanesulfonylbenzoyl]-2H 4H 5H 6H-pyrrolo[3,4-c]pyrazole;
3-Fluoro-5-{2-[2-(2-fluorophenyl)-2H 4H 5H 6H-pyrrolo[3,4-e]pyrazole-5-carbonyl]-4-methanesulfonylphenyl}pyridine;
4-(3 5-Difluorophenyl)-3-[2-(2-methylpyridin-4-yl)-2H 4H 5H 6H-pyrrolo[3,4-c]pyrazole-5-carbonyl]benzonitrile;
3-{5-[2-(3 5-Difluorophenyl)-5-methanesulfonylbenzoyl]-2H 4H 5H 6H-pyrrolo[3,4-c]pyrazol-2-yl}-5-fluoropyridine;
4-(3-Methylphenyl)-3-[2-(2-methylpyridin-4-yl)-2H 4H 5H 6H-pyrrolo[3,4-c]pyrazole-5-carbonyl]benzonitrile;
3-[2-(2-Methylpyridin-4-yl)-2H 4H 5H 6H-pyrrolo[3,4-c]pyrazole-5-carbonyl]-4-[3-(trifluoromethyl)phenyl]benzonitrile;
5-Fluoro-2-[5-(5-methane sulfonyl-2-phenylbenzoyl)-2H 4H 5H 6H-pyrrolo[3,4-c]pyrazol-2-yl]pyridine;

4-{5-[5-(Ethanesulfonyl)-2-phenylbenzoyl]-2H 4H 5H 6H-pyrrolo[3,4-c]pyrazol -2-yl}-2-methylpyridine;

4-{5-[5-(Ethanesulfonyl)-2-(3-fluorophenyl)benzoyl]-2H 4H 5H 6H-pyrrolo[3,4-c]pyrazol-2-yl}-2-methylpyridine;

4-{5-[2-(3 5-Difluorophenyl)-5-(ethanesulfonyl)benzoyl]-2H 4H 5H 6H-pyrrolo[3,4-c]pyrazol-2-yl}-2-methylpyridine;

3-{5-[5-(Ethanesulfonyl)-2-phenylbenzoyl]-2H 4H 5H 6H-pyrrolo[3,4-c]pyrazol-2-yl}-5-fluoropyridine;

3-{5-[5-(Ethanesulfonyl)-2-(3-fluorophenyl)benzoyl]-2H 4H 5H 6H-pyrrolo[3,4-c]pyrazol-2-y}-5-fluoropyridine;

3-{5-[2-(3 5-Difluorophenyl)-5-(ethanesulfonyl)benzoyl]-2H 4H 5H 6H-pyrrolo[3,4-c]pyrazol-2-yl}-5-fluoropyridine;

2-(4-Fluorophenyl)-5-[5-methanesulfonyl-2-(2-methylpropoxy)benzoyl]-2H 4H 5H 6H-pyrrolo[3,4-c]pyrazole; and pharmaceutically acceptable salts thereof.

12. A compound selected from the group consisting of:

3-(2-(4-Fluorophenyl)-4,5,6,7-tetrahydro-2H-pyrazolo[4,3-c]pyridine-5-carbonyl)-2-methoxy-4-((1,1,1-trifluoropropan-2-yl)oxy)benzonitrile;

1-{2-Chloro-3-[2-(4-fluorophenyl)-2H 4H 5H 6H 7H-pyrazolo[4,3-c]pyridine-5-carbonyl]-4-[(1 1 1-trifluoropropan-2-yl)oxy]benzoyl}azetidine;

3-(2-(4-Fluorophenyl)-4,5,6,7-tetrahydro-2H-pyrazolo[4,3-c]pyridine-5-carbonyl)-4-((1,1,1-trifluoropropan-2-yl)oxy)benzamide;

3-[2-(5-Fluoropyridin-2-yl)-2H 4H 5H 6H 7H-pyrazolo[4,3-c]pyridine-5-carbonyl]-2-methoxy-4-(1 4 4-trifluorocyclohexyl)benzonitrile;

2-Methoxy-3-[2-(pyridin-3-yl)-2H 4H 5H 6H 7H-pyrazolo[4,3-c]pyridine-5-carbonyl]-4-(1 4 4-trifluorocyclohexyl)benzonitrile;

4-(4-Fluorooxan-4-yl)-3-[2-(5-fluoropyridin-2-yl)-2H 4H 5H 6H 7H-pyrazolo[4,3-c]pyridine-5-carbonyl]-2-methoxybenzonitrile;

2-Chloro-3-[2-(5-fluoropyridin-3-yl)-2H 4H 5H 6H 7H-pyrazolo[4,3-c]pyridine-5-carbonyl]-4-[(1 1 1-trifluoropropan-2-yl)oxy]benzonitrile;

3-[2-(5-Fluoropyridin-3-yl)-2H 4H 5H 6H 7H-pyrazolo[4, 3-c]pyridine-5-carbonyl]-2-methoxy-4-[(1 1 1-trifluoropropan-2-yl)oxy]benzonitrile;

2-Chloro-3-[2-(pyridin-4-yl)-2H 4H 5H 6H 7H-pyrazolo[4, 3-c]pyridine-5-carbonyl]-4-(2 2 2-trifluoroethoxy)benzonitrile;

2-Methoxy-3-[2-(pyridin-4-yl)-2H 4H 5H 6H 7H-pyrazolo[4,3-c]pyridine-5-carbonyl]-4-(2 2 2-trifluoroethoxy)benzonitrile;

5-[2-(Cyclopropylmethoxy)-5-methanesulfonylbenzoyl]-1-methyl-1H 4H 5H 6H 7H-pyrazolo[4, 3-c]pyridine;

5-[2-(Cyclopropylmethoxy)-5-methanesulfonylbenzoyl]-1-[3-(trifluoromethyl)phenyl]-1H 4H 5H 6H 7H-pyrazolo[4,3-c]pyridine;

5-{5-Methanesulfonyl-2-[(1 1 1-trifluoropropan-2-yl)oxy]benzoyl}-1-methyl-1H 4H 5H 6H 7H-pyrazolo[4, 3-c]pyridine;

5-{5-Methanesulfonyl-2-[(1 1 1-trifluoropropan-2-yl)oxy]benzoyl}-1-[3-(trifluoromethyl)phenyl]-1H 4H 5H 6H 7H-pyrazolo[4,3-c]pyridine;

5-{5-Methanesulfonyl-2-[(1 1 1-trifluoropropan-2-yl)oxy]benzoyl}-2-phenyl-2H 4H 5H 6H 7H-pyrazolo[4, 3-c]pyridine;

5-{5-Methanesulfonyl-2-[(1 1 1-trifluoropropan-2-yl)oxy]benzoyl}-1-phenyl-1H 4H 5H 6H 7H-pyrazolo[4, 3-c]pyridine;

1-{4-Methanesulfonyl-2-[1-phenyl-3-(trifluoromethyl)-1H 4H 5H 6H 7H-pyrazolo[4,3-c]pyridine-5-carbonyl]phenyl}piperidine;

1-(4-Methanesulfonyl-2-{3-methyl-1-phenyl-1H 4H 5H 6H 7H-pyrazolo[4,3-c]pyridine-5-carbonyl}phenyl)piperidine;

1-(4-Methanesulfonyl-2-{3-methyl-2-phenyl-2H 4H 5H 6H 7H-pyrazolo[4, 3-c]pyridine-5-carbonyl}phenyl)piperidine;

5-{5-Methanesulfonyl-2-[(1 1 1-trifluoropropan-2-yl)oxy]benzoyl}-1-phenyl-3-(trifluoromethyl)-1H 4H 5H 6H 7H-pyrazolo[4,3-c]pyridine;

4-Cyclopentyl-3-{2-phenyl-2H 4H 5H 6H 7H-pyrazolo[4, 3-c]pyridine-5-carbonyl}benzonitrile;

5-(2-Cyclopentyl-5-methanesulfonylbenzoyl)-2-phenyl-2H 4H 5H 6H 7H-pyrazolo[4,3-c]pyridine;

3-(4-Cyclopentyl-3-{2-phenyl-2H 4H 5H 6H 7H-pyrazolo[4,3-c]pyridine-5-carbonyl}phenyl)-1 3-oxazolidin-2-one;

3-(3-{2-Phenyl-2H 4H 5H 6H 7H-pyrazolo[4,3-c]pyridine-5-carbonyl}-4-[(1 1 1-trifluoropropan-2-yl)oxy]phenyl)-1 3-oxazolidin-2-one;

4-[(1-²H)Cyclopentyl]-3-{2-phenyl-2H 4H 5H 6H 7H-pyrazolo[4, 3-c]pyridine-5-carbonyl}benzonitrile;

4-Cyclobutyl-3-{2-phenyl-2H 4H 5H 6H 7H-pyrazolo[4, 3-c]pyridine-5-carbonyl}benzonitrile;

4-Cyclopentyl-2-fluoro-3-{2-phenyl-2H 4H 5H 6H 7H-pyrazolo[4, 3-c]pyridine-5-carbonyl}benzonitrile;

2-Methoxy-3-{2-phenyl-2H 4H 5H 6H 7H-pyrazolo[4,3-c]pyridine-5-carbonyl}-4-[(1 1 1-trifluoropropan-2-yl)oxy]benzonitrile;

2-Chloro-3-[2-(4-fluorophenyl)-2H 4H 5H 6H 7H-pyrazolo[4,3-c]pyridine-5-carbonyl]-4-[(1 1 1-trifluoropropan-2-yl)oxy]benzonitrile;

2-Fluoro-4-(3-fluorooxetan-3-yl)-3-{2-phenyl-2H 4H 5H 6H 7H-pyrazolo[4, 3-c]pyridine-5-carbonyl}benzonitrile;

2-Chloro-3-[1-(2 4-difluorophenyl)-1H 4H 5H 6H 7H-pyrazolo[4,3-c]pyridine-5-carbonyl]-4-[(1 1 1-trifluoropropan-2-yl)oxy]benzonitrile;

4-Cyclobutyl-2-fluoro-3-{2-phenyl-2H 4H 5H 6H 7H-pyrazolo[4,3-c]pyridine-5-carbonyl}benzonitrile;

3-[2-(4-Fluorophenyl)-2H 4H 5H 6H 7H-pyrazolo[4,3-c]pyridine-5-carbonyl]-4-[(1 1 1-trifluoropropan-2-yl)oxy]benzonitrile;

2-Chloro-3-[1-methyl-3-(trifluoromethyl)-1H 4H 5H 6H 7H-pyrazolo[4,3-c]pyridine-5-carbonyl]-4-[(1 1 1-trifluoropropan-2-yl)oxy]benzonitrile;

2-Chloro-3-{1H 4H 5H 6H 7H-pyrazolo[4,3-c]pyridine-5-carbonyl}-4-[(1 1 1-trifluoropropan-2-yl)oxy]benzonitrile;

2-Chloro-3-[3-ethoxy-2-(4-fluorophenyl)-2H 4H 5H 6H 7H-pyrazolo[4,3-c]pyridine-5-carbonyl]-4-[(1 1 1-trifluoropropan-2-yl)oxy]benzonitrile;

2-Chloro-3-[1-(4-fluorophenyl)-7 7-dimethyl-1H 4H 5H 6H 7H-pyrazolo[4,3-c]pyridine-5-carbonyl]-4-[(1 1 1-trifluoropropan-2-yl)oxy]benzonitrile;

2-Chloro-3-[2-methyl-3-(trifluoromethyl)-2H 4H 5H 6H 7H-pyrazolo[4,3-c]pyridine-5-carbonyl]-4-[(1 1 1-trifluoropropan-2-yl)oxy]benzonitrile;

2-Fluoro-4-(1-fluorocyclopentyl)-3-{2-phenyl-2H 4H 5H 6H 7H-pyrazolo[4,3-c]pyridine-5-carbonyl}benzonitrile;

2-Fluoro-4-(1-fluorocyclopentyl)-3-[2-(4-fluorophenyl)-2H 4H 5H 6H 7H-pyrazolo[4,3-c]pyridine-5-carbonyl]benzonitrile;

2-Chloro-3-[2-(4-fluorophenyl)-3-methyl-2H 4H 5H 6H 7H-pyrazolo[4,3-c]pyridine-5-carbonyl]-4-[(1 1 1-trifluoropropan-2-yl)oxy]benzonitrile;

2-Chloro-3-[1-(4-fluorophenyl)-3-methyl-1H 4H 5H 6H 7H-pyrazolo[4,3-c]pyridine-5-carbonyl]-4-[(1 1 1-trifluoropropan-2-yl)oxy]benzonitrile;

2-Chloro-3-[2-(4-fluorophenyl)-7 7-dimethyl-2H 4H 5H 6H 7H-pyrazolo[4, 3-c]pyridine-5-carbonyl]-4-[(1 1 1-trifluoropropan-2-yl)oxy]benzonitrile;

3-[2-(4-Fluorophenyl)-7 7-dimethyl-2H 4H 5H 6H 7H-pyrazolo[4,3-c]pyridine-5-carbonyl]-2-methoxy-4-[(1 1 1-trifluoropropan-2-yl)oxy]benzonitrile;

2-Chloro-3-{2-phenyl-2H 4H 5H 6H 7H-pyrazolo[4,3-c]pyridine-5-carbonyl}-4-[(1 1 1-trifluoropropan-2-yl)oxy]benzonitrile;

3-[2-(2 4-Difluorophenyl)-2H 4H 5H 6H 7H-pyrazolo[4, 3-c]pyridine-5-carbonyl]-2-methoxy-4-[(1 1 1-trifluoropropan-2-yl)oxy]benzonitrile;

3-{1-Benzyl-1H 4H 5H 6H 7H-pyrazolo[4,3-c]pyridine-5-carbonyl}-2-chloro-4-[(1 1 1-trifluoropropan-2-yl)oxy]benzonitrile;

2-Chloro-3-[2-(4-fluorophenyl)-2H 4H 5H 6H 7H-pyrazolo[4,3-c]pyridine-5-carbonyl]-4-[(1 1 1-trifluoropropan-2-yl)oxy]benzamide;

2-Chloro-3-[2-(4-fluorophenyl)-3-hydroxy-2H 4H 5H 6H 7H-pyrazolo[4,3-c]pyridine-5-carbonyl]-4-[(1 1 1-trifluoropropan-2-yl)oxy]benzonitrile;

2-(4-Fluorophenyl)-5-{3-methanesulfonyl-2-methoxy-6-[(1 1 1-trifluoropropan-2-yl)oxy]benzoyl}-2H 4H 5H 6H 7H-pyrazolo[4,3-c]pyridine;

2-Fluoro-4-(4-fluorooxan-4-yl)-3-[2-(4-fluorophenyl)-2H 4H 5H 6H 7H-pyrazolo[4,3-c]pyridine-5-carbonyl]benzonitrile;

2-Chloro-3-[2-(4-fluorophenyl)-2H 4H 5H 6H 7H-pyrazolo[4,3-c]pyridine-5-carbonyl]-N N-dimethyl-4-[(1 1 1-trifluoropropan-2-yl)oxy]benzamide;

2-Chloro-3-[2-(5-fluoropyridin-2-yl)-2H 4H 5H 6H 7H-pyrazolo[4,3-c]pyridine-5-carbonyl]-4-[(1 1 1-trifluoropropan-2-yl)oxy]benzonitrile;

3-[2-(5-Fluoropyridin-2-yl)-2H 4H 5H 6H 7H-pyrazolo[4,3-c]pyridine-5-carbonyl]-2-methoxy-4-[(1 1 1-trifluoropropan-2-yl)oxy]benzonitrile;

2-Chloro-3-{2-methyl-2H 4H 5H 6H 7H-pyrazolo[4,3-c]pyridine-5-carbonyl}-4-[(1 1 1-trifluoropropan-2-yl)oxy]benzonitrile;

2-Methoxy-3-{2-methyl-2H 4H 5H 6H 7H-pyrazolo[4,3-c]pyridine-5-carbonyl}-4-[(1 1 1-trifluoropropan-2-yl)oxy]benzonitrile;

2-Chloro-3-[2-(3-methoxyphenyl)-2H 4H 5H 6H 7H-pyrazolo[4,3-c]pyridine-5-carbonyl]-4-[(1 1 1-trifluoropropan-2-yl)oxy]benzonitrile;

2-Chloro-3-[2-(4-methoxyphenyl)-2H 4H 5H 6H 7H-pyrazolo[4,3-c]pyridine-5-carbonyl]-4-[(1 1 1-trifluoropropan-2-yl)oxy]benzonitrile;

2-Methoxy-3-[2-(4-methoxyphenyl)-2H 4H 5H 6H 7H-pyrazolo[4,3-c]pyridine-5-carbonyl]-4-[(1 1 1-trifluoropropan-2-yl)oxy]benzonitrile;

4-(3-Fluoropentan-3-yl)-3-[2-(4-fluorophenyl)-2H 4H 5H 6H 7H-pyrazolo[4, 3-c]pyridine-5-carbonyl]-2-methoxybenzonitrile;

3-[1-(5-Fluoropyridin-2-yl)-1H 4H 5H 6H 7H-pyrazolo[4,3-c]pyridine-5-carbonyl]-2-methoxy-4-[(1 1 1-trifluoropropan-2-yl)oxy]benzonitrile;

2-Chloro-3-[1-(5-fluoropyridin-2-yl)-1H 4H 5H 6H 7H-pyrazolo[4,3-c]pyridine-5-carbonyl]-4-[(1 1 1-trifluoropropan-2-yl)oxy]benzonitrile;

2-Chloro-3-[2-(pyridin-3-yl)-2H 4H 5H 6H 7H-pyrazolo[4,3-c]pyridine-5-carbonyl]-4-[(1 1 1-trifluoropropan-2-yl)oxy]benzonitrile;

4-(1-Fluorocyclobutyl)-3-[2-(5-fluoropyridin-2-yl)-2H 4H 5H 6H 7H-pyrazolo[4,3-c]pyridine-5-carbonyl]-2-methoxybenzonitrile;

2-Methoxy-3-[2-(pyridin-3-yl)-2H 4H 5H 6H 7H-pyrazolo[4,3-c]pyridine-5-carbonyl]-4-[(1 1 1-trifluoropropan-2-yl)oxy]benzonitrile;

2-Chloro-3-{1-cyclohexyl-1H 4H 5H 6H 7H-pyrazolo[4,3-c]pyridine-5-carbonyl}-4-[(1 1 1-trifluoropropan-2-yl)oxy]benzonitrile;

3-{1-Cyclohexyl-1H 4H 5H 6H 7H-pyrazolo[4,3-c]pyridine-5-carbonyl}-2-methoxy-4-[(1 1 1-trifluoropropan-2-yl)oxy]benzonitrile;

2-Chloro-3-[2-(pyridin-2-yl)-2H 4H 5H 6H 7H-pyrazolo[4,3-c]pyridine-5-carbonyl]-4-[(1 1 1-trifluoropropan-2-yl)oxy]benzonitrile;

2-Methoxy-3-[2-(pyridin-2-yl)-2H 4H 5H 6H 7H-pyrazolo[4,3-c]pyridine-5-carbonyl]-4-[(1 1 1-trifluoropropan-2-yl)oxy]benzonitrile;

2-Methoxy-3-[1-(pyridin-3-yl)-1H 4H 5H 6H 7H-pyrazolo[4,3-c]pyridine-5-carbonyl]-4-[(1 1 1-trifluoropropan-2-yl)oxy]benzonitrile;

2-Chloro-3-[2-(pyridin-4-yl)-2H 4H 5H 6H 7H-pyrazolo[4,3-c]pyridine-5-carbonyl]-4-[(1 1 1-trifluoropropan-2-yl)oxy]benzonitrile;

2-Methoxy-3-[2-(pyridin-4-yl)-2H 4H 5H 6H 7H-pyrazolo[4,3-c]pyridine-5-carbonyl]-4-[(1 1 1-trifluoropropan-2-yl)oxy]benzonitrile;

2-Methoxy-3-[1-(oxan-4-yl)-1H 4H 5H 6H 7H-pyrazolo[4,3-c]pyridine-5-carbonyl]-4-[(1 1 1-trifluoropropan-2-yl)oxy]benzonitrile;

2-Chloro-3-[2-(5-fluoropyridin-2-yl)-2H 4H 5H 6H 7H-pyrazolo[4,3-c]pyridine-5-carbonyl]-4-{[(2S)-1 1 1-trifluoropropan-2-yl]oxy}benzonitrile;

2-Chloro-3-[2-(4-fluorophenyl)-2H 4H 5H 6H 7H-pyrazolo[4,3-c]pyridine-5-carbonyl]-4-(2 2 2-trifluoroethoxy)benzonitrile;

2-Chloro-3-[2-(5-fluoropyridin-2-yl)-2H 4H 5H 6H 7H-pyrazolo[4,3-c]pyridine-5-carbonyl]-4-(2 2 2-trifluoroethoxy)benzonitrile;

3-[2-(5-Fluoropyridin-2-yl)-2H 4H 5H 6H 7H-pyrazolo[4,3-c]pyridine-5-carbonyl]-2-methoxy-4-{[(2S)-1 1 1-trifluoropropan-2-yl]oxy}benzonitrile;

2-Chloro-3-[2-(2-methylpyridin-4-yl)-2H 4H 5H 6H 7H-pyrazolo[4,3-c]pyridine-5-carbonyl]-4-[(1 1 1-trifluoropropan-2-yl)oxy]benzonitrile;

2-Methoxy-3-[2-(2-methylpyridin-4-yl)-2H 4H 5H 6H 7H-pyrazolo[4,3-c]pyridine-5-carbonyl]-4-[(1 1 1-trifluoropropan-2-yl)oxy]benzonitrile;

2-Chloro-3-[2-(5-chloropyridin-2-yl)-2H 4H 5H 6H 7H-pyrazolo[4,3-c]pyridine-5-carbonyl]-4-[(1 1 1-trifluoropropan-2-yl)oxy]benzonitrile;

3-[2-(5-Chloropyridin-2-yl)-2H 4H 5H 6H 7H-pyrazolo[4,3-c]pyridine-5-carbonyl]-2-methoxy-4-[(1 1 1-trifluoropropan-2-yl)oxy]benzonitrile;

2-Chloro-3-[2-(5-fluoro-2-methoxypyridin-3-yl)-2H 4H 5H 6H 7H-pyrazolo[4,3-c]pyridine-5-carbonyl]-4-[(1 1 1-trifluoropropan-2-yl)oxy]benzonitrile;

3-[2-(5-Fluoro-2-methoxypyridin-3-yl)-2H 4H 5H 6H 7H-pyrazolo[4,3-c]pyridine-5-carbonyl]-2-methoxy-4-[(1 1 1-trifluoropropan-2-yl)oxy]benzonitrile;

2-Chloro-3-[2-(3 5-difluoropyridin-2-yl)-2H 4H 5H 6H 7H-pyrazolo[4,3-c]pyridine-5-carbonyl]-4-[(1 1 1-trifluoropropan-2-yl)oxy]benzonitrile;

3-[2-(3 5-Difluoropyridin-2-yl)-2H 4H 5H 6H 7H-pyrazolo[4,3-c]pyridine-5-carbonyl]-2-methoxy-4-[(1 1 1-trifluoropropan-2-yl)oxy]benzonitrile;

2-Methoxy-3-[2-(pyridin-3-yl)-2H 4H 5H 6H 7H-pyrazolo[4,3-c]pyridine-5-carbonyl]-4-{[(2S)-1 1 1-trifluoropropan-2-yl]oxy}benzonitrile;

2-Methoxy-3-{2-[6-(trifluoromethyl)pyridin-3-yl]-2H 4H 5H 6H 7H-pyrazolo[4,3-c]pyridine-5-carbonyl}-4-{[(2S)-1 1 1-trifluoropropan-2-yl]oxy}benzonitrile;

2-Chloro-3-{2-[6-(trifluoromethyl)pyridin-3-yl]-2H 4H 5H 6H 7H-pyrazolo[4,3-c]pyridine-5-carbonyl}-4-{[(2S)-1 1 1-trifluoropropan-2-yl]oxy}benzonitrile;

2-Chloro-3-{2-[(trifluoromethyl)pyridin-4-yl]-2H 4H 5H 6H 7H-pyrazolo[4,3-c]pyridine-5-carbonyl}-4-{[(2S)-1 1 1-trifluoropropan-2-yl]oxy}benzonitrile;

2-Methoxy-3-2-[2-(trifluoromethyl)pyridin-4-yl]-2H 4H 5H 6H 7H-pyrazolo[4, 3-c]pyridine-5-carbonyl-4-{[(2S)-1 1 1-trifluoropropan-2-yl]oxy}benzonitrile;

2-Chloro-3-[2-(3-fluoropyridin-4-yl)-2H 4H 5H 6H 7H-pyrazolo[4,3-c]pyridine-5-carbonyl]-4-{[(2S)-1 1 1-trifluoropropan-2-yl]oxy}benzonitrile;

3-[2-(3-Fluoropyridin-4-yl)-2H 4H 5H 6H 7H-pyrazolo[4,3-c]pyridine-5-carbonyl]-2-methoxy-4-{[(2S)-1 1 1-trifluoropropan-2-yl]oxy}benzonitrile;

2-Chloro-3-{3-[4-(trifluoromethyl)phenyl]-1H 4H 5H 6H 7H-pyrazolo[4,3-c]pyridine-5-carbonyl}-4-{[(2S)-1 1 1-trifluoropropan-2-yl]oxy}benzonitrile;

2-Methoxy-3-{3-[4-(trifluoromethyl)phenyl]-1H 4H 5H 6H 7H-pyrazolo[4,3-c]pyridine-5-carbonyl}-4-{[(2S)-1 1 1-trifluoropropan-2-yl]oxy}benzonitrile;

3-[2-(4-Fluorophenyl)-3-methyl-2H 4H 5H 6H 7H-pyrazolo[4,3-c]pyridine-5-carbonyl]-2-methoxy-4-[(1 1 1-trifluoropropan-2-yl)oxy]benzonitrile;

3-[1-(4-Fluorophenyl)-7 7-dimethyl-1H 4H 5H 6H 7H-pyrazolo[4,3-c]pyridine-5-carbonyl]-2-methoxy-4-[(1 1 1-trifluoropropan-2-yl)oxy]benzonitrile;

3-[2-(4-Fluorophenyl)-2H 4H 5H 6H 7H-pyrazolo[4,3-c]pyridine-5-carbonyl]-2-methoxy-4-[(1-methylcyclopropyl)methoxy]benzonitrile;

3-[2-(4-Fluorophenyl)-2H 4H 5H 6H 7H-pyrazolo[4,3-c]pyridine-5-carbonyl]-2-methoxy-4-{[1-(trifluoromethyl)cyclopropyl]methoxy}benzonitrile;

2-Chloro-3-[2-(4-fluorophenyl)-2H 4H 5H 6H 7H-pyrazolo[4,3-c]pyridine-5-carbonyl]-N-methyl-4-[(1 1 1-trifluoropropan-2-yl)oxy]benzamide;

1-{3-[2-(4-Fluorophenyl)-2H 4H 5H 6H 7H-pyrazolo[4,3-c]pyridine-5-carbonyl]-2-methoxy-4-[(1 1 1-trifluoropropan-2-yl)oxy]benzoyl}azetidine;

3-[2-(4-Fluorophenyl)-2H 4H 5H 6H 7H-pyrazolo[4,3-c]pyridine-5-carbonyl]-2-methoxy-N-methyl-4-[(1 1 1-trifluoropropan-2-yl)oxy]benzamide;

1-{3-[2-(4-Fluorophenyl)-2H 4H 5H 6H 7H-pyrazolo[4,3-c]pyridine-5-carbonyl]-4-[(1 1 1-trifluoropropan-2-yl)oxy]benzoyl}azetidine;

3-[2-(4-Fluorophenyl)-2H 4H 5H 6H 7H-pyrazolo[4,3-c]pyridine-5-carbonyl]-N-methyl-4-[1 1 1-trifluoropropan-2-yl)oxy]benzamide;

3-[2-(4-Fluorophenyl)-2H 4H 5H 6H 7H-pyrazolo[4,3-c]pyridine-5-carbonyl]-2-methoxy-4-[(1 1 1-trifluoropropan-2-yl)oxy]benzamide;

4-Cyclopentyl-2-methoxy-3-{2-phenyl-2H 4H 5H 6H 7H-pyrazolo[4,3-c]pyridine-5-carbonyl}benzonitrile;

4-Cyclopentyl-3-[2-(4-fluorophenyl)-2H 4H 5H 6H 7H-pyrazolo[4,3-c]pyridine-5-carbonyl]-2-methoxybenzonitrile;

4-(3-Fluorooxetan-3-yl)-2-methoxy-3-{2-phenyl-2H 4H 5H 6H 7H-pyrazolo[4,3-c]pyridine-5-carbonyl}benzonitrile;

4-Cyclobutyl-2-methoxy-3-{2-phenyl-2H 4H 5H 6H 7H-pyrazolo[4,3-c]pyridine-5-carbonyl}benzonitrile;

4-(1-Fluorocyclobutyl)-3-[2-(4-fluorophenyl)-2H 4H 5H 6H 7H-pyrazolo[4,3-c]pyridine-5-carbonyl]-2-methoxybenzonitrile;

4-(1-Fluorocyclopentyl)-2-methoxy-3-{2-phenyl-2H 4H 5H 6H 7H-pyrazolo[4,3-c]pyridine-5-carbonyl}benzonitrile;

4-(1-Fluorocyclopentyl)-3-[2-(4-fluorophenyl)-2H 4H 5H 6H 7H-pyrazolo[4,3-c]pyridine-5-carbonyl]-2-methoxybenzonitrile;

4-(4-Fluorooxan-4-yl)-3-[2-(4-fluorophenyl)-2H 4H 5H 6H 7H-pyrazolo[4,3-c]pyridine-5-carbonyl]-2-methoxybenzonitrile;

3-[2-(4-Fluorophenyl)-2H 4H 5H 6H 7H-pyrazolo[4,3-c]pyridine-5-carbonyl]-2-methoxy-4-(1-methoxycyclobutyl)benzonitrile;

3 3-Difluoro-1-(4-methanesulfonyl-2-{2-phenyl-2H 4H 5H 6H 7H-pyrazolo[4,3-c]pyridine-5-carbonyl}phenyl)pyrrolidine;

5-[2-(2 2-Dimethylpropoxy)-5-methanesulfonylbenzoyl]-2-phenyl-2H 4H 5H 6H 7H-pyrazolo[4,3-c]pyridine;

1-(4-Methanesulfonyl-2-{2-phenyl-2H 4H 5H 6H 7H-pyrazolo[4,3-c]pyridine-5-carbonyl}phenyl)pyrrolidine;

1-(4-Methanesulfonyl-2-{2-phenyl-2H 4H 5H 6H 7H-pyrazolo[4,3-c]pyridine-5-carbonyl}phenyl)azetidine;

5-[2-(Cyclopropylmethoxy)-5-methanesulfonylbenzoyl]-2-phenyl-2H 4H 5H 6H 7H-pyrazolo[4,3-c]pyridine;

2-Chloro-3-[1-(4-fluorophenyl)-1H 4H 5H 6H 7H-pyrazolo[4,3-c]pyridine-5-carbonyl]-4-[(1 1 1-trifluoropropan-2-yl)oxy]benzonitrile;

2-Chloro-4-(4 4-difluoropiperidin-1-yl)-3-{2-phenyl-2H 4H 5H 6H 7H-pyrazolo[4,3-c]pyridine-5-carbonyl}benzonitrile;

2-Chloro-4-(2 2-dimethylpropoxy)-3-{2-phenyl-2H 4H 5H 6H 7H-pyrazolo[4,3-c]pyridine-5-carbonyl}benzonitrile;

2-Chloro-4-(cyclopropylmethoxy)-3-{2-phenyl-2H 4H 5H 6H 7H-pyrazolo[4,3-c]pyridine-5-carbonyl}benzonitrile;

2-Chloro-4-(morpholin-4-yl)-3-{2-phenyl-2H 4H 5H 6H 7H-pyrazolo[4,3-c]pyridine-5-carbonyl}benzonitrile;

2-Chloro-4-[(3-methyloxetan-3-yl)methoxy]-3-{2-phenyl-2H 4H 5H 6H 7H-pyrazolo[4,3-c]pyridine-5-carbonyl}benzonitrile;

2-Chloro-4-[(1-methylcyclopropyl)methoxy]-3-{2-phenyl-2H 4H 5H 6H 7H-pyrazolo[4,3-c]pyridine-5-carbonyl}benzonitrile;

2-Chloro-3-[2-(4-fluorophenyl)-2H 4H 5H 6H 7H-pyrazolo[4,3-c]pyridine-5-carbonyl]-4-[(1-methylcyclopropyl)methoxy]benzonitrile;

2-Chloro-3-[2-(4-fluorophenyl)-2H 4H 5H 6H 7H-pyrazolo[4,3-c]pyridine-5-carbonyl]-4-{[1-(trifluoromethyl)cyclopropyl]methoxy}benzonitrile;

5-{5-Methanesulfonyl-2-[(1 1 1-trifluoropropan-2-yl)oxy]benzoyl}-3-phenyl-2H 4H 5H 6H 7H-pyrazolo[4, 3-c]pyridine;

3-[1-(2 4-Difluorophenyl)-1H 4H 5H 6H 7H-pyrazolo[4, 3-c]pyridine-5-carbonyl]-2-methoxy-4-[(1 1 1-trifluoropropan-2-yl)oxy]benzonitrile;

3-[2-(4-Fluorophenyl)-3-(trifluoromethyl)-2H 4H 5H 6H 7H-pyrazolo[4,3-c]pyridine-5-carbonyl]-2-methoxy-4-[(1 1 1-trifluoropropan-2-yl)oxy]benzonitrile;

3-[1-(4-Fluorophenyl)-3-(trifluoromethyl)-1H 4H 5H 6H 7H-pyrazolo[4,3-c]pyridine-5-carbonyl]-2-methoxy-4-[(1 1 1-trifluoropropan-2-yl)oxy]benzonitrile; and pharmaceutically acceptable salts thereof.

13. A pharmaceutical composition comprising: a pharmaceutically acceptable excipient; and an effective amount of at least one compound of claim 1.

14. A pharmaceutical composition comprising: a pharmaceutically acceptable excipient; and an effective amount of at least one compound of claim 9.

15. A pharmaceutical composition comprising: a pharmaceutically acceptable excipient; and an effective amount of at least one compound of claim 10.

16. A pharmaceutical composition comprising: a pharmaceutically acceptable excipient; and an effective amount of at least one compound of claim 11.

17. A pharmaceutical composition comprising: a pharmaceutically acceptable excipient; and an effective amount of at least one compound of claim 12.

18. A method of treating a neurological disorder, comprising administering to a subject in need thereof an effective amount of at least one compound of claim 1,
wherein the neurological disorder is selected from the group consisting of: a central nervous system (CNS) disorder, a developmental disorder; a schizophrenia spectrum or psychotic disorder; a depressive disorder; an anxiety disorder; an obsessive-compulsive disorder; a dissociative disorder; a disruptive, impulse-control, or conduct disorder; a trauma- or stressor-related disorder; a feeding or eating disorder; a sleep-wake disorder; a sexual disorder; a substance-related or addictive disorder; and a personality disorder.

19. A method of treating a neurological disorder, comprising administering to a subject in need thereof an effective amount of at least one compound of claim 1, wherein the neurological disorder is an acquired disorder selected from the group consisting of delirium, dementia, an age-associated cognitive deficit, a trauma-dependent loss of function, and a cognitive impairment due to chemotherapy.

20. A method of treating pain or alcohol-dependence, comprising administering to a subject in need thereof an effective amount of at least one compound of claim 1.

* * * * *